US010806761B2

(12) United States Patent
Nakashima et al.

(10) Patent No.: US 10,806,761 B2
(45) Date of Patent: Oct. 20, 2020

(54) ONCOLYTIC HSV1 VECTOR AND METHODS OF USE

(71) Applicant: THE BRIGHAM AND WOMEN'S HOSPITAL, INC., Boston, MA (US)

(72) Inventors: Hiroshi Nakashima, Brookline, MA (US); Ennio Antonio Chiocca, Weston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 51 days.

(21) Appl. No.: 15/571,749

(22) PCT Filed: May 4, 2016

(86) PCT No.: PCT/US2016/030681

§ 371 (c)(1),
(2) Date: Nov. 3, 2017

(87) PCT Pub. No.: WO2010/179226

PCT Pub. Date: Nov. 10, 2016

(65) Prior Publication Data

US 2018/0133269 A1 May 17, 2018

Related U.S. Application Data

(60) Provisional application No. 62/156,447, filed on May 4, 2015.

(51) Int. Cl.

| | |
|---|---|
| ***A61K 35/763*** | (2015.01) |
| ***C12N 15/86*** | (2006.01) |
| ***C12Q 1/70*** | (2006.01) |
| ***C12N 7/00*** | (2006.01) |
| ***A61K 48/00*** | (2006.01) |
| ***A61K 31/675*** | (2006.01) |

(52) U.S. Cl.

CPC .......... *A61K 35/763* (2013.01); *A61K 31/675* (2013.01); *A61K 48/00* (2013.01); *C12N 7/00* (2013.01); *C12N 15/86* (2013.01); *C12Q 1/70* (2013.01); *C12N 2710/16621* (2013.01); *C12N 2710/16622* (2013.01); *C12N 2710/16632* (2013.01); *C12N 2710/16643* (2013.01); *C12N 2710/16671* (2013.01); *C12N 2830/008* (2013.01)

(58) Field of Classification Search

CPC .... A61K 35/763; A61K 31/675; A61K 48/00; A61P 25/00; A61P 35/00; A61P 43/00; C12N 15/86; C12N 7/00; C12N 2710/16621; C12N 2710/16622; C12N 2710/16632; C12N 2710/16643; C12N 2710/16671; C12N 2830/008; C12Q 1/70

See application file for complete search history.

(56) References Cited

U.S. PATENT DOCUMENTS

| | | | | |
|---|---|---|---|---|
| 5,728,379 A | 3/1998 | Martuza et al. | | |
| 6,897,057 B1 | 5/2005 | Chiocca et al. | | |
| 2007/0154456 A1 | 7/2007 | Bloom et al. | | |
| 2010/0272686 A1* | 10/2010 | Kaur ........................ | C12N 7/00 424/93.2 | |
| 2011/0177032 A1* | 7/2011 | Martuza .................. | C12N 7/00 424/93.2 | |

FOREIGN PATENT DOCUMENTS

| | | | | |
|---|---|---|---|---|
| WO | 2005103237 A1 | 11/2005 | | |
| WO | WO-2014078529 A1 * | 5/2014 | .............. | C12N 7/00 |

OTHER PUBLICATIONS

Broadley et al. "Side population is not necessary or sufficient for a cancer stem cell phenotype in glioblastoma multiforme." Stem Cells. Mar. 2011;29(3):452-61 (Year: 2011).*
Recombinant DNA Advisory Committee. Minutes of Meeting. Jun. 7-9, 2011. accessed from https://osp.od.nih.gov/wp-content/uploads/2013/11/RAC_Minutes_06-11.pdf. pp. 42-47 (Year: 2011).*
Kanai et al. "Combinatorial strategies for oncolytic herpes simplex virus therapy of brain tumors." CNS Oncol. Mar. 2013;2(2):129-42. (Year: 2013).*
Wakimoto et al. "Effects of innate immunity on herpes simplex virus and its ability to kill tumor cells." Gene Ther. Jun. 2003;10(11):983-90 (Year: 2003).*
Hendricks et al. "Novel delivery methods bypassing the blood-brain and blood-tumor barriers." Neurosurg Focus. Mar. 2015;38(3):E10. (Year: 2015).*
Sharma et al. "Receptor-Targeted Glial Brain Tumor Therapies." Int. J. Mol. Sci. 2018, 19(11), 3326 (Year: 2018).*
Chung et al., "B-myb promoter retargeting of herpes simplex virus γ34. 5 gene-mediated virulence toward tumor and cycling cells." Journal of Virology 73(9):7556-7564 (1999).
Kanai et al., "Effect of γ34. 5 Deletions on Oncolytic Herpes Simplex Virus Activity in Brain Tumors", Journal of Virology 86(8):4420-4431 (2012).
Nakamura et al., "Regulation of herpes simplex virus γ134.5 expression and oncolysis of diffuse liver metastases by Myb34. 5", The Journal of Clinical Investigation 109(7):871-882 (2002).
Ning et al., "Oncolytic herpes simplex virus-based strategies: toward a breakthrough in glioblastoma therapy." Frontiers in Microbiology 5(303):1-13 (2014).
Silva et al., "RNA interference inhibits herpes simplex virus type 1 isolated from saliva samples and mucocutaneous lesions", Brazilian Journal of Infectious Diseases 18(4):441-444 (2014).
Wong et al., "Targeted oncolytic herpes simplex viruses for aggressive cancers." Current Pharmaceutical Biotechnology 13(9):1786-1794 (2012).

(Continued)

*Primary Examiner* — Titilayo Moloye
(74) *Attorney, Agent, or Firm* — Nixon Peabody LLP; David S. Resnick; Teresa A. Ptashka

(57) ABSTRACT

Malignant tumors that are resistant to conventional therapies represent significant therapeutic challenges. An embodiment of the present invention provides a second generation oncolytic virus rQNestin34.5v2 with less toxicity that is more effective at selective killing target cells, such as tumor cells. In various embodiments presented herein, the oncolytic virus described herein is suitable for treatment of glioblastoma, as well as other cancers.

9 Claims, 23 Drawing Sheets

Specification includes a Sequence Listing.

(56) References Cited

OTHER PUBLICATIONS

Kambara et al. "An oncolytic HSV-1 mutant expressing ICP34. 5 under control of a nestin promoter increases of survival of animals even when symptomatic from a brain tumor." Cancer Research 65(7)2832-2839 (2005).
Kambara et al., "Cyclophosphamide allows for in vivo dose reduction of a potent oncolytic virus." Cancer Research 65(24)11255-11258 (2005).
Kasai et al., "Toxicology and biodistribution studies for MGH2. 1, an oncolytic virus that expresses two prodrug-activating genes, in combination with prodrugs." Molecular Therapy—Nucleic Acids 2:e113 (2013).

* cited by examiner

| Table 1- Toxicity of rQNestin34.5v.2 in Balb/c mice | | | | | | |
|---|---|---|---|---|---|---|
| **Experiment number** | **Virus** | **Mouse age** | **Route** | **Dose (Pfu)** | **Death/injected** | **Day of death** |
| 1 | rQNestin34.5v.2 | 8 weeks | intracranial | $10^7$ | 0/6 | |
| 1 | F strain | 8 weeks | intracranial | $10^5$ | 2/2 | Day 6 |
| 1 | PBS | 8 weeks | intracranial | - | 0/1 | |
| 2 | rQNestin34.5v.2 | 8 weeks | intrathecal | $10^7$ | 0/5 | |
| 3 | rQNestin34.5v.2 | 8 weeks | intracranial | $10^7$ | 1/22 | Day 3 |
| 4 | rQNestin34.5v.2 | 8 weeks | intrahepatic | $10^7$ | 0/10 | |
| 4 | F strain | 8 weeks | intrahepatic | $10^5$ | 0/4 | |
| 4 | PBS | 8 weeks | intrahepatic | | 0/5 | |
| 5 | rQNestin34.5v.2 | 8 weeks | intravenous | $10^7$ | 0/10 | |
| 5 | Fstrain | 8 weeks | intravenous | $10^5$ | 0/4 | |
| 5 | PBS | 8 weeks | intravenous | | 0/5 | |
| 6 | rQNestin34.5v.2 | 6 months | intracranial | $10^7$ | 0/5 | |
| 6 | F strain | 6 months | intracranial | $10^5$ | 3/5 | Days 7,8,12 |
| 6 | PBS | 6 months | intracranial | | 0/5 | |

Figure 8

SEQUENCE LISTING

<160> NUMBER OF SEQ ID NOS: 8

<210> SEQ ID NO 1
<211> LENGTH: 151249
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 1

```
ataacttcgt ataatgtatg ctatacgaag ttattaggtc cctcgacctg caggaaactc     60
tagtccggac ccgggaggcc tcctttgagg agtggctgcg atccaaggaa gtggccctgg    120
actttggcct gacggaaagg cttcgcgagc acgaagccca gctggtgatc ctggcccagg    180
ctctggacca ttacgactgt ctgatccaca gcacaccgca cacgctggtc gagcgggggc    240
tgcaatcggc cctgaagtat gaggagtttt acctaaagcg ctttggcggg cactacatgg    300
agtccgtctt ccagatgtac acccgcatcg ccggcttttt ggcctgccgg gccacgcgcg    360
gcatgcgcca catcgccctg ggcgagaggg ggtcgtggtg ggaaatgttc aagttctttt    420
tccaccgcct ctacgaccac cagatcgtac cgtcgacccc cgccatgctg aacctgggga    480
cccgcaacta ctacacctcc agctgctacc tggtaaaccc ccaggccacc acaaacaagg    540
cgaccctgcg ggccatcacc agcaacgtca gtgccatcct cgcccgcaac gggggcatcg    600
ggctatgcgt gcaggcgttt aacgactccg gccccgggac cgccagcgtc atgcccgccc    660
tcaaggtcct cgactcgctg gtggcggcgc acaacaaaga gagcgcgcgt ccgaccggcg    720
cgtgcgtgta cctggagccg tggcacaccg acgtgcgggc cgtgctccgg atgaaggggg    780
tcctcgccgg cgaagaggcc cagcgctgcg acaatatctt cagcgccctc tggatgccag    840
acctgttttt caagcgcctg attcgccacc tggacggcga gaagaacgtc acatggaccc    900
tgttcgaccg ggacaccagc atgtcgctcg ccgactttca cggggaggag ttcgagaagc    960
tctaccagca cctcgaggtc atggggttcg gcgagcagat acccatccag gagctggcct   1020
atggcattgt gcgcagtgcg gccacgaccg ggagcccctt cgtcatgttc aaagacgcgg   1080
tgaaccgcca ctacatctac gacacccagg gggcggccat cgccggctcc aacctctgca   1140
ccgagatcgt ccatccggcc tccaagcgat ccagtggggt ctgcaatctg ggaagcgtga   1200
atctggcccg atgcgtctcc aggcagacgt ttgactttgg gcggctccgc gacgccgtgc   1260
aggcgtgcgt gctgatggtg aacatcatga tcgacagcac gctacaaccc acgccccagt   1320
gcacccgcgg caacgacaac ctgcggtcca tgggaatcgg catgcagggc ctgcacacgg   1380
cctgcctgaa gctggggctg gatctggagt ctgccgaatt tcaggacctg aacaaacaca   1440
tcgccgaggt gatgctgctg tcggcgatga agaccagcaa cgcgctgtgc gttcgcgggg   1500
cccgtccctt caaccacttt aagcgcagca tgtatcgcgc cggccgcttt cactgggagc   1560
gctttccgga cgcccggccg cggtacgagg gcgagtggga gatgctacgc cagagcatga   1620
tgaaacacgg cctgcgcaac agccagtttg tcgcgctgat gcccaccgcc gcctcggcgc   1680
agatctcgga cgtcagcgag ggctttgccc ccctgttcac caacctgttt agcaaggtga   1740
cccgggacgg cgagacgctg cgccccaaca cgctcctgct aaaggaactg gaacgcacgt   1800
ttagcgggaa gcgcctcctg gaggtgatgg acagtctcga cgccaagcag tggtccgtgg   1860
cgcaggcgct cccgtgcctg gagcccaccc accccctccg gcgattcaag accgcgtttg   1920
actacgacca gaagttgctg atcgacctgt gtgcggaccg cgccccctac gtcgaccata   1980
gccaatccat gaccctgtat gtcacggaga aggcggacgg gaccctccca gcctccaccc   2040
tggtccgcct tctggtccac gcatataagc gcggactaaa aacagggatg tactactgca   2100
aggttcgcaa ggcgaccaac agcggggtct ttggcggcga cgacaacatt gtctgcacga   2160
gctgcgcgct gtgaccgaca aaccccctcc gcgccaggcc cgccgccact gtcgtcgccg   2220
```

-continued

```
tcccacgcgc tcccccgctg ccatggattc cgcggcccca gccctctccc ccgctctgac   2280
ggcccatacg ggccagagcg cgccggcgga cctggcgatc cagattccaa agtgccccga   2340
ccccgagagg tacttctaca cctcccagtg tcccgacatt aaccacctgc gctccctcag   2400
catccttaac cgctggctgg aaaccgagct tgttttcgtg ggggacgagg aggacgtctc   2460
caagctttcc gagggcgagc tcagctttta ccgcttcctc ttcgctttcc tgtcggccgc   2520
cgacgacctg gttacggaaa acctgggcgg cctctccggc ctgtttgagc agaaggacat   2580
tctccactac tacgtggagc aggaatgcat cgaagtcgta cactcgcgcg tgtacaacat   2640
catccagctg gtgctttttc acaacaacga ccaggcgcgc cgcgagtacg tggccggcac   2700
catcaaccac ccggccatcc gcgccaaggt ggactggttg gaagcgcggg tgcgggaatg   2760
cgcctccgtt ccggaaaagt tcattctcat gatcctcatc gagggcatct tttttgccgc   2820
ctcgtttgcc gccatcgcct accttcgcac caacaacctt ctgcgggtca cctgccagtc   2880
aaacgacctc atcagccggg acgaggccgt gcacacgacg gcctcgtgtt acatctacaa   2940
caactacctc ggcgggcacg ccaagccccc gcccgaccgc gtgtacgggc tgttccgcca   3000
ggcggtcgag atcgagatcg gatttatccg atcccaggcg ccgacggaca gccatatcct   3060
gagcccggcg gcgctggcgg ccatcgaaaa ctacgtgcga ttcagcgcgg atcgcctgtt   3120
gggccttatc cacatgaagc cactgttttc cgccccaccc cccgacgcca gctttccgct   3180
gagcctcatg tccaccgaca aacacaccaa tttttttcgag tgtcgcagca cctcctacgc   3240
cggggcggtc gtcaacgatc tgtgagggtc gcggcgcgct tctacccgtg tttgcccata   3300
ataaacctct gaaccaaact ttgggtctca ttgtgattct tgtcagggac gcggggggtgg   3360
gagaggataa aaggcggcgc aaaaagcagt aaccaggtcc ggccagattc tgagggcata   3420
ggataccata attttattgg tgggtcgttt gttcggggac aagcgcgctc gtctgacgtt   3480
tgggctactc gtcccagaat ttggccagga cgtccttgta gaacgcgggt ggggggggcct   3540
gggtccgcag ctgctccaga aacctgtcgg cgatatcagg ggccgtgata tgccgggtca   3600
cgatagatcg cgccaggttt tcgtcgcgga tgtcctggta gataggcagg cgtttcagaa   3660
gagtccacgg cccccgctcc ttggggccga taagcgatat gacgtactta atgtagcggt   3720
gttccaccag ctcggtgatg gtcatgggat cggggagcca gtccagggac tctggggcgt   3780
cgtggatgac gtggcgtcgc cggctggcca cataactgcg gtgctcttcc agcagctgcg   3840
cgttcgggac ctggacgagc tcgggcgggg tgagtatctc cgaggaggac gacctggggc   3900
cggggtggcc cccggtaacg tcccggggat ccagggggag gtcctcgtcg tcttcgtatc   3960
cgccggcgat ctgttgggtt agaatttcgg tccacgagac gcgcgtctcg gtgccgccgg   4020
tggccggcgg cagaggggggc ctggtttccg tggagcgcga gctggtgtgt tcccggcgga   4080
tggcccgccg ggtctgagag cgactcgggg gggtccagtg acattcgcgc agcacatcct   4140
ccacggaggc gtaggtgtta ttgggatgga ggtcggtgtg gcagcggaca aagagggcca   4200
ggaactgggg gtagctcatc ttaaagtact tcagtatatc gcgacagttg atcgtgggaa   4260
tgtagcaggc gctaatatcc aacacaatat cgcagcccat caacaggagg tcagtgtccg   4320
tggtgtacac gtacgcgacc gtgttggtgt gatagaggtt ggcgcaggca tcgtccgcct   4380
ccagctgacc cgagttaatg taggcgtacc ccagggcccg gagaacgcga atacagaaca   4440
gatgcgccag acgcagggcc ggcttcgagg gcgcggcgga cggcagcgcg gctccggacc   4500
cggccgtccc ccgggtcccc gaggccagag aggtgccgcg tcggcgcatg ttggaaaagg   4560
cagagctggg tctggagtcg gtgatggggg aaggcggtgg agaggcgtcc acgtcactgg   4620
```

cctcctcgtc cgtccggcac tgggccgtcg tgcgggccag gatggccttg gctccaaaca 4680
caaccggctc catacaattg accccgcgat cggtaacgaa gatggggaaa agggactttt 4740
gggtaaacac ttttaataag cgacagaggc agtgtagcgt aatggcctcg cggtcgtaac 4800
tggggtatcg gcgctgatat ttgaccacca acgtgtacat gacgttccac aggtccacgg 4860
caatgggggt gaagtacccg gccggggccc caaggccccg gcgcttgacc agatggtgtg 4920
tgtgggcaaa cttcatcatc ccgaacaaac ccatgtcagg tcgattgtaa ctgcggatcg 4980
gcctaactaa ggcgtggttg gtgcgacggt ccgggacacc cgagcctgtc tctctgtgta 5040
tggtgaccca gacaacaaca ccgacacaag aggacaataa tccgttaggg gacgctcttt 5100
ataatttcga tggcccaact ccacgcggat tggtgcagca ccctgcatgc gccggtgcgg 5160
gccaaccttc cccccgctca ttgcctcttc caaaagggtg tggcctaacg agctgggggc 5220
gtatttaatc aggctagcgc ggcgggcctg ccgtagtttc tggctcggtg agcgacggtc 5280
cggttgcttg ggtcccctgg ctgccatcaa aaccccaccc tcgcagcggc atacgccccc 5340
tccgcgtccc gcacccgaga ccccggcccg gctgccctca ccaccgaagc ccacctcgtc 5400
actgtggggt gttcccagcc cgcgttggga tgacggattc cctggcggt gtggcccccg 5460
cctcccacgt ggaggacgcg tcggacgcgt ccctcgggca gccggaggag ggggcgccct 5520
gccaggtggt cctgcagggc gccgagctta atggaatcct acaggcgttt gccccgctgc 5580
gcacgagcct tctggactcg cttctggtta tgggagaccg gggcatcctt atccataaca 5640
cgatctttgg ggagcaggtg ttcctgtccc tggaacactc gcaattcagt cggtatcgct 5700
ggcgcggacc cacggcggcg ttcctgtctc tcgtggacca gaagcgctcc ctcctgagcg 5760
tgtttcgcgc caaccagtac ccggacctac gtcgggtgga gttggcgatc acgggccagg 5820
ccccgtttcg cacgctggtt cagcgcatat ggacgacgac gtccgacggc gaggccgttg 5880
agctagccag cgagacgctg atgaagcgcg aactgacgag ctttgtggtg ctggttcccc 5940
agggaacccc cgacgttcag ttgcgcctga cgaggccgca gctcaccaag gtccttaacg 6000
cgaccggggc cgatagtgcc acgcccacca tgttcgagct cggggttaac ggcaaatttt 6060
ccgtgttcac cacgagtacc tgcgtcacat ttgctgcccg cgaggagggc gtgtcgtcca 6120
gcaccagcac ccaggtccag atcctgtcca acgcgctcac caaggcgggc caggcggccg 6180
ccaacgccaa gacggtgtac ggggaaaata cccatcgtac cttctctgtg gtcgtcgacg 6240
attgcagcat gcgggcggtg ctccggcgac tgcaggtcgc cgggggcacc ctcaagttct 6300
tcctcacgac ccccgtcccc agtctgtgcg tcaccgccac cggtcccaac gcggtatcgg 6360
cggtatttct cctgaaaccc cagaagattt gcctggactg gctgggtcat agccaggggt 6420
ctccttccgc cgggagctcg gcctcccggg cctctgggag cgagccaaca gacagccagg 6480
actccgcgtc ggacgcggtc agccacggcg atccggaaga cctcgatggc gctgcccggg 6540
cgggagaggc gggggcctcg tacgcctgtc cgatgccgtc gtcgaccacg cgggtcactc 6600
ccacgaccaa gcgggggcgc tcgggggcg aggatgcgca cgcggacacg gccctaaaga 6660
aacctaagac ggggtcgccc accgcacccc cgcccgcaga tccagtcccc ctggacacgg 6720
aggacgactc cgatgcggcg gacgggacag cggcccgtcc cgccgctcca gacgcccgaa 6780
gcggaagccg ttacgcgtgt tactttcgcg acctcccgac cggagaagca aaccccggcg 6840
ccttctccgc cttccggggg ggcccccaaa ccccgtctgg ttttggattc ccctgacggg 6900
gcggggcctt agcggccgcc caaccctcgc aacatcccgg ggttaatgta aataaacttg 6960

```
gtattgccca acactctccc gcgtgtcgcg tgtggttcat gtgtgtgcct ggcgccccca   7020
ccctcgggtt cgtgtatttc ctttccctgt ccttataaaa gccgtatgtg gggcgctgac   7080
ggaaccaccc cgcgtgccat cacggccaag gcgcgggatg ctccgcaacg acagccaccg   7140
ggccgcgtcc ccggaggacg gccagggacg ggtcgacgac ggacggccac acctcgcgtg   7200
cgtgggggcc ctggcgcggg ggttcatgca tatctggctt caggccgcca cgctgggttt   7260
tgcgggatcg gtcgttatgt cgcgcgggcc gtacgcgaat gccgcgtctg ggcgttcgc    7320
cgtcgggtgc gccgtgttgg gctttatgcg cgcgcccct ccctcgcgc ggcccaccgc     7380
gcggatatac gcctggctca aactggcggc cggtggagcg gcccttgttc tgtggagtct   7440
cggggagccc ggcacgcagc cgggggccct ggccccgggc ccggccaccc agtgcctggc   7500
gctgggcgcc gcctatgcgg cgctcctggt gctcgccgat gacgtctatc cgctctttct   7560
cctcgccccg gggcccctgt tcgtcggcac cctggggatg gtcgtcggcg ggctgacgat   7620
cggaggcagc gcgcgctact ggtggatcgg tgggcccgcc gcggccgccc tggccgcggc   7680
ggtgttggcg ggcccggggg cgaccaccgc cagggactgc ttctccaggg cgtgccccga   7740
ccaccgccgc gtctgcgtca tcgtcgcagg cgagtctgtt tcccgccgcc ccccggagga   7800
cccagagcga cccggggacc cagggccacc gtcccccccg acaccccaac gatcccaggg   7860
gccgccggcc gatgaggtcg caccggccgg ggtagcgcgg cccgaaaacg tctgggtgcc   7920
cgtggtcacc tttctggggg ctggcgcgct cgccgtcaag acggtgcgag aacatgcccg   7980
gggaacgccg ggcccgggcc tgccgctgtg gccccaggtg tttctcggag gccatgtggc   8040
ggtggccctg acggagctgt gtcaggcgct tgcgccctgg gaccttacgg acccgctgct   8100
gtttgttcac gccggactgc aggtcatcaa cctcgggttg gtgtttcggt tttccgaggt   8160
tgtcgtgtat gcggcgctag ggggtgccgt gtggatttcg ttggcgcagg tgctggggct   8220
ccggcgtcgc ctgcacagga aggaccccgg ggacggggcc cggttggcgg cgacgcttcg   8280
gggcctcttc ttctccgtgt acgcgctggg gtttggggtg ggggcgctgc tgtgccctcc   8340
ggggtcaacg ggcgggcggt cgggcgattg atatattttt caataaaagg cattagtccc   8400
gaagaccgcc ggtgtgtgat gatttcgcca taacacccaa accccggatg gggcccgggt   8460
ataaattccg gaaggggaca cgggctacct tcactaccga gggcgcttgg tcgggaggcc   8520
gcatcgaacg cacaccccca tccggtggtc cgtgtggagg tcgtttttca ttgcccggtc   8580
tcgctttgcc gggaacgcta gccgatccct cgcgaggggg aggcgtcggg catggccccg   8640
gggcgggtgg gccttgccgt ggtcctgtgg agcctggtgt ggctcggggc gggggtgtcc   8700
gggggctcgg aaactgcctc caccgggccc acgatcaccg cgggagcggt gacgaacgcg   8760
agcgaggccc ccacatcggg gtcccccggg tcagccgcca gcccggaggt caccccaca    8820
tcgaccccaa accccaacaa tgtcacacaa aaccaaacca cccccaccga gccggccagc   8880
cccccaacaa cccccaagcc cacctccaca cccaaaagcc cccccacgtc cacccccgac   8940
cccaaaccca agaacaacac cacccccgcc aagtcggacc gccccactaa accccccggg   9000
cccgtgtggt gcgaccgccg cgatttattg gcccggtacg gctcgcgggt gcagatccga   9060
tgccggtttc ggaattccac ccgcatggag ttccgcctcc agatatggcg ttactccatg   9120
ggtccgtccc ccccaatcgc tccggctccc gacctagagg aggtcctgac gaacatcacc   9180
gccccacccg gggactcct ggtgtacgac agcgccccca acctaacgga cccccacgtg    9240
ctctgggcgg agggggccgg cccgggcgcc gaccctccgt tgtattctgt caccgggccg   9300
ctgccgaccc agcggctgat tatcggcgag gtgacgcccg cgacccaggg aatgtattac   9360
```

-continued

```
ttggcctggg gccggatgga cagcccgcac gagtacggga cgtgggtgcg cgtccgcatg   9420
ttccgccccc cgtctctgac cctccagccc cacgcggtga tggagggtca gccgttcaag   9480
gcgacgtgca cggccgccgc ctactacccg cgtaaccccg tggagtttgt ctggttcgag   9540
gacgaccacc aggtgtttaa cccgggccag atcgacacgc agacgcacga gcacccccgac  9600
gggttcacca cagtctctac cgtgacctcc gaggctgtcg gcggccaggt ccccccgcgg   9660
accttcacct gccagatgac gtggcaccgc gactccgtga cgttctcgcg acgcaatgcc   9720
accgggctgg ccctggtgct gccgcggcca accatcacca tggaatttgg ggtccggcat   9780
gtggtctgca cggccggctg cgtccccgag ggcgtgacgt ttgcctggtt cctgggggac   9840
gacccctcac cggcggctaa gtcggccgtt acggcccagg agtcgtgcga ccgccccggg   9900
ctggctacgg tccggtccac cctgcccatt tcgtacgact acagcgagta catctgtcgg   9960
ttgaccggat atccggccgg gattcccgtt ctagagcacc acggcagtca ccagccccca  10020
cccagggacc ccaccgagcg gcaggtgatc gaggcgatcg agtgggtggg gattggaatc  10080
ggggttctcg cggcgggggt cctggtcgta acggcaatcg tgtacgtcgt ccgcacatca  10140
cagtcgcggc agcgtcatcg gcggtaacgc gagacccccc cgttaccttt ttaatatcta  10200
tatagtttgg tccccctcta tcccgcccac cgctgggcgc tataaagccg ccaccctctc  10260
ttccctcagg tcatccttgg tcgatcccga acgacacacg gcgtggagca aaacgcctcc  10320
ccctgagccg ctttcctacc agcgcaacgg catgcctctg cgggcatcgg aacacgccta  10380
ccggcccctg ggccccggga cacccccat gcgggctcgg ctccccgccg cggcctgggt   10440
tggcgtcggg accatcatcg ggggagttgt gatcattgcc gcgttggtcc tcgtgccctc  10500
gcgggcctcg tgggcacttt ccccatgcga cagcggatgg cacgagttca acctcgggtg  10560
catatcctgg gatccgaccc ccatggagca cgagcaggcg gtcggcggct gtagcgcccc  10620
ggcgaccctg atcccccgcg cggctgccaa acagctggcc gccgtcgcac gcgtccagtc  10680
ggcaagatcc tcgggctact ggtgggtgag cggagacggc attcgggcct gcctgcggct  10740
cgtcgacggc gtcggcggta ttgaccagtt ttgcgaggag cccgcccttc gcatatgcta  10800
ctatccccgc agtcccgggg gctttgttca gtttgtaact tcgacccgca acgcgctggg  10860
gctgccgtga ggcgcgtgta ctgcggtctg tctcgtctcc tcttctcccc ttccctcccc  10920
ctccgcatcc caggatcaca ccggccaacg agggttgggg ggtccggcac ggacccaaaa  10980
taataaacac acaatcacgt gcgataaaaa gaacacgcgg tcccctgtgg tgtttttggt  11040
tatttttatt aaatctcgtc gtcaaacagg gggaaagggg cgtggtctag cgacggcagc  11100
acgggtggag gcgttcaccg gctccggcgt ccttcgcgtt taagcttggt caggagggcg  11160
ctcagggcgg cgacgttggt cgggccgtcg ttggtcaggg cgttggctcg atggcgggcg  11220
aggacgggcg aggggctcaa cggcgggggc gggggcccgg tgcggcccgg gggggaaaat  11280
agggcggatc ccccccagtc gtacagggga ttttccgcct caatgtacgg ggaggccggc  11340
gctgcattcg ccgtgttcgc gcagacgttt tcgtagaccc gcatccatgg tatttcctcg  11400
tagacacgcc ccccgtcctc gctcacagtc tcgtatattg actcgtcgtc ctcgtagggg  11460
gcgtgccgtt cgcgggccga ggcggcgtgg gtggctttgc ggcgggcgtc gtcgtcgtcg  11520
tcgtcggccg tcagatacgt ggcttccatc tggtcgggtt ctccctccgg ggcgggtccc  11580
cacccccgtg gccgatcgag gctccccaga gacgcgcgcc ggacgaggag ggggcacgtc  11640
gccgccggcg gtcgcctgtc gggtcccgcg acgttacggg ccgggaggcg cgggggcacc  11700
```

-continued tcccccatgt gcgtgtaata cgtggccggc tgtgcggccg cagcgggggg ctcggcgacc 11760
gggtcgtccg catccggaag cgggggcgcc gcgccgtccg cgcggcgcct ccggaaccgc 11820
cgggtggccg cgggggtcga gtgtaggcga ggtcggggga ggggcggggg ctcgttgtcg 11880
cgccgcgccc gctgaatctt ttcccgacag gtcccacccc ccgcgcgatg ccccccgggg 11940
ccgcgggcca tgtcgtccgg gggaggcccc gcggaccacg tcgtccggcg agacgccacg 12000
agccgcagga tggactcgta gtggaacgac ggcgccccgc tgcggagcag atccgcggcc 12060
agggcggccc cgaaccaagc cttgatgctc aactccatcc gggcccagct gggggcggtc 12120
atcgtgggga acagggggggc ggtggtccga cagaaacgct cctggctgtc caccgcggcc 12180
cgcagatact cgttgttcag gctgtcggtg gcccagacgc cgtacccggt gagggtcgcg 12240
ttgatgatat actgggcgtg gtgatggacg atcgacagaa cctccaccgt ggatacgacg 12300
gtatccacgg tcccgtacgt accgccgctc cgcttgccgg tctgccacag gttggctagg 12360
cgcgtcaggt ggcccaggac gtcgctgacc gccgccctga gcgccatgca ctgcatggag 12420
ccggtcgtgc cgctgggacc ccggtccaga tggcgcgcga acgtttccgc gggcgcctcc 12480
gggctgccgc cgagcgggag gaaccggcga ttggagggac tcagccggtg gcatacgtgc 12540
ttgtctgtcg tccacagcat ccaggacgcc caccggtaca gcacggagac gtaggccagg 12600
agctcgttga gccgcagtgc ggtgtcggtg ctggggcggc ttgggtccgc cgggcgcata 12660
aagaacatgt actgctgaat ccgatggagg gcgtcgcgca ggccggccac ggtggcggcg 12720
tacttggccg ccgcggcccc gctcttgaac ggggtgcgcg ccagcagctt tggcgccagg 12780
gtgggccgca gcagcacgtg aaggctgggg tcgcagtcgc ccacggggtc ctcggggacg 12840
tccaggccgc tgggcaccac cgtctgcagg tacttccagt actgcgtgag gatggcgcgg 12900
ctcaactggc cgccggtgag ctccacctcg cccagcgcct gggtggcggc cgaagcgtag 12960
tgccggatgt actcgtagtg cgggtcgctg gcgagcccgt ccacgatcaa actctcggga 13020
accgtgttgt gttgccgcgc ggccaaccgg acgctgcgat cggtgcaggt cagaaacgcc 13080
ggctgcgcgt cgtcggagcg ctgccgcaag gcgcccacgg ccgcgctaag gagcccctcc 13140
ggggtgggga gcagacaccc gccgaagatg cgccgctcgg gaacgcccgc gttgtcgccg 13200
cggatcaggt tggcaggcgt caggcaccgc gccagccgca gggagctcgc gccgcgcgtc 13260
cggcgctgca tggtgacgcc cgttcggtcg ggacccgccg gtcggagtta tgccgcgtcc 13320
agggccatcg gggcgctttt tatcgggagg agcttatggg cgtggcgggc ctcccagccc 13380
ggtcgcgcgc ctccccgaca cgtgcgcccg cagggcggcg gccccctcgt ctcccatcag 13440
cagtttccta aactgggaca tgatgtccac cacgcggacc cgcgggccca acacggaccc 13500
gccgcttacg gggcgggggg ggaagggctc caggtccttg agaagaaagg cggggtctgc 13560
cgtcccggac acgggggccc ggggcgctga ggaggcgggg cgcagatcca cgtgctccgc 13620
ggccgcgcgg acgtccgccc agaacttggc gggggtggtg cgcgcgtaca ggggctgggt 13680
cgctcggagg acgcacgcgt agcgcagggg ggtgtatgtg cccacctcgg gggccgtgaa 13740
tcccccgtca aacgcggcca gtgtcacgca cgccaccacg gtgtcggcaa agcccagcag 13800
ccgctgcagg acgagcccgg cggccagaat ggcgcgcgtg gccgccgcgt cgtcccggcg 13860
ccggtgcgcg tccccgcacg cccgggcgta ctttaaggtc acggtcgcca gggccgtgtg 13920
cagcgcgtac accgcagcgc ccagcacggc gttgagcccg ctgttggcga gcagccggcg 13980
cgctgcggtg tcgcccagcg cctcgtgctc ggcccccacg accgcggggc ttcccagggg 14040
cagggcgcga aacagctcct cccgcgccac gtccgcaaag gcggggtggt gcacgtgcgg 14100
gtgcaggcgc gcccccacga ccaccgagag ccactggacc gtctgctccg ccatcaccgc 14160
cagcacatcc agcacgcgcc ccaggaaggc ggcctcccgc gtcaaaacgc accggacggc 14220
gtcgggattg aagcgggcga gcagggcccc ggtggccagg tacgtcatgc ggccggcata 14280
gcgggcggcc acgcgacagt cgcggtccag cagcgcgcgc accccgggcc agtacagcag 14340
ggaccccagc gagctgcgaa acaccgcggc gtcggggccg gattgggggg acactaaccc 14400
ccccgcgctc agtaacggca cggccgcggc cccgacggga cgcaacgccg tgaggctcgc 14460
gaactgccgc ctcagctcgg cagccctgtc gtccaggtcc gacccgcgcg cctctgcgtg 14520
aaggcgcgtc ccgcacaccc acccgttgat ggccagccgc acgacggcat ccgccaaaaa 14580
gctcatcgcc tgggcggggc tggtttttgt tcgacgatcc atcaggtcaa gaatcccatc 14640
gcccgtgata taccaggcca acgcctcgcc ctgctgcagg gtttggcgga aaaacaccgc 14700
ggggttgtcg gggaggcgaa agtgcatgac ccccacgcgc gataacccga acgcgctatc 14760
cggacacggg taaaacccgg ccggatgccc cagggctagg gcggagcgca cggactcgtc 14820
ccacacggca acctgagggg ccagtcgatc caacgggaat gccgccagga gctccgggcc 14880
cggcacgcgt ccctccagaa cctccacctt gggcggggaa cgggccccgc cgccgtcctc 14940
cggcccgacg tcttccgggt agtcgtcctc ctcgtactgc agctcctcta ggaacagcgg 15000
cgacggcgcc acccgcgaac cgccgacccg ccccaaaata gcccgcgcgt cgacgggacc 15060
caggtatccc ccctgccggg cctgcggagg accgcgggga acctcatcat catcgtccag 15120
gcgaccgcgc accgactggc tacgggccgc atcgggcccg gggcgctgcc gggacgctcg 15180
gcgatgggat gtgggcgggg cttccgacgc gcgccgtcgt cgggctcgcg ggccttcccg 15240
tcgacggcgc acgggcggct cgtcgcccgc catctcctcc agagcctcta gctcgctgtc 15300
gtcatccccg cggaacaccg cacgcaggta ccccatgaac cccaccccat cgcccgctgg 15360
ctcgtccgcc acgggcgagg cgcgggggcg ggtggatgcg cgcctcctac gccccgcggg 15420
ttcgcgagcc gacatggtgg cgatagacgc gggttatcgg atgtccgcta ccccccaaaa 15480
aagaaaaaga ccccacagcg cggatggagg ccggggtagg tgccgccgga ccccctcgcg 15540
atgggaatgg acgggagcga cggggccggc gcaaaaaacg cagtatctcc cgcgaaggct 15600
acccgccgcc ccagcccccg gccaaatgcg gaaacggtcc cgcgctctcg cctttatacg 15660
cgggccgccc tgcgacacaa tcacccgtcc gtggtttcga atctacacga caggcccgca 15720
gacgcggcta acacacacgc cggcaaccca gaccccagtg ggttggttgc gcggtcccgt 15780
ctcctggcta gttcttttcc ccaccaccaa ataatcagac gacaaccgca ggtttttgta 15840
atgtatgtgc tcgtgtttat tgtggatacg aaccggggac gggaggggaa aacccagacg 15900
ggggatgcgg gtccggtcgc gccccctacc caccgtactc gtcaattcca agggcatcgg 15960
taaacatctg ctcaaactcg aagtcggcca tatccagagc gccgtagggg gcggagtcgt 16020
ggggggtaaa tcccggaccc ggggaatccc cgtcccccaa catgtccaga tcgaaatcgt 16080
ctagcgcgtc ggcatgcgcc atcgccacgt cctcgccgtc taagtggagc tcgtccccca 16140
ggctgacatc ggtcgggggg gccgtcgaca gtctgcgcgt gtgtcccgcg gggagaaagg 16200
acaggcgcgg agccgccagc cccgcctctt cgggggcgtc gtcgtccggg agatcgagca 16260
ggccctcgat ggtagacccg taattgtttt tcgtacgcgc gcggctgtac gcgtgttccc 16320
gcatgaccgc ctcggagggc gaggtcgtga agctggaata cgagtccaac ttcgcccgaa 16380
tcaacaccat aaagtaccca gaggcgcggg cctggttgcc atgcagggtg ggaggggtcg 16440

-continued

```
tcaacggcgc ccctggctcc tccgtagccg cgctgcgcac cagcgggagg ttaaggtgct  16500
cgcgaatgtg gtttagctcc cgcagccggc gggcctcgat tggcactccc cggacggtga  16560
gcgctccgtt gacgaacatg aagggctgga acagacccgc caactgacgc cagctctcca  16620
ggtcgcaaca gaggcagtca aacaggtcgg gccgcatcat ctgctcggcg tacgcggccc  16680
ataggatctc gcgggtcaaa aatagataca aatgcaaaaa cagaacacgc gccagacgag  16740
cggtctctcg gtagtacctg tccgcgatcg tggcgcgcag catttctccc aggtcgcgat  16800
cgcgtccgcg catgtgcgcc tggcggtgca gctgccggac gctggcgcgc aggtaccggt  16860
acagggccga gcagaagttg gccaacacgg ttcgatagct ctcctcccgc gcccgtagct  16920
cggcgtggaa gaaacgagag agcgcttcgt agtagagccc gaggccgtcg cgggtggccg  16980
gaagcgtcgg gaaggccacg tcgccgtggg cgcgaatgtc gatttgggcg cgttcgggga  17040
cgtacgcgtc cccccattcc accacatcgc tgggcagcgt tgataggaat ttacactccc  17100
ggtacaggtc ggcgttggtc ggtaacgccg aaaacaaatc ctcgttccag gtatcgagca  17160
tggtacatag cgcggggccc gcgctaaagc ccaagtcgtc gaggagacgg ttaaagaggg  17220
cggcgggggg gacgggcatg ggcggggagg gcatgagctg ggcctggctc aggcgccccg  17280
ttgcgtacag cggaggggcc gccggggtgt ttttgggacc cccggccggg cggggggggtg  17340
gtggcgaagc gccgtccgcg tccatgtcgg caaacagctc gtcgaccaag aggtccattg  17400
ggtggggttg atacgggaaa gacgatatcg ggcttttgat gcgatcgtcc ccgcccgccc  17460
agagagtgtg ggacgcccga cggcgcggga agagaaaaac ccccaaacgc gttagaggac  17520
cggacggacc ttatgggggg aagtgggcag cgggaacccc gtccgttccc gaggaatgac  17580
agcccgtggt cgccaccccg catttaagca acccgcacgg gccgccccgt acctcgtgac  17640
ttccccccac attggctcct gtcacgtgaa ggcgaaccga gggcggctgt ccaacccacc  17700
ccccgccacc cagtcacggt ccccgtcgga ttgggaaaca aaggcacgca acgccaacac  17760
cgaatgaacc cctgttggtg ctttattgtc tgggtacgga agtttttcac tcgacgggcc  17820
gtctggggcg agaagcggag cgggctgggg ctcgaggtcg ctcggtgggg cgcgacgccg  17880
cagaacgccc tcgagtcgcc gtggccgcgt cgacgtcctg caccacgtct ggattcacca  17940
actcgttggc gcgctgaagc aggtttttgc cctcgcagac cgtcacgcgg atggtggtga  18000
tgccaaggag ttcgttgagg tcttcgtctg tgcgcggacg cgacatgtcc cagagctgga  18060
ccgccgccat ccgggcatgc atggccgcca ggcgcccgac cgcggcgcag aagacgcgct  18120
tgttaaagcc ggccacccgg ggggtccatg gcgcgtcggg gtttgggggg gcggtgctaa  18180
agtgcagctt tctggccagc ccctgcgcgg gtgtcttgga tcgggttggc gccgtcgacg  18240
cgggggcgtc tgggagtgcg gcggattctg gctgggccga tttcctgccg cgggtggtct  18300
ccgccgccgg ggccgcgggg gccttagtcg ccacccgctg ggttcggggg gcccgggggg  18360
cggtggtggg tgtgcgtccg gcccctccgg acccagcggg cggcggaggc gcccgcgcag  18420
gccccgggcc ggacaaaacc gccccggaaa cgggacgccg cgtccggggg acctccgggt  18480
gttcgtcgtc ttcggatgac gagcccccgt agagggcata atccgactcg tcgtactgga  18540
cgaaacggac ctcgcccctc gggcgcgcgc gtgtctgtag ggcgccacgg cgggaggtgg  18600
caggcggact atcgggactc gccatacatg aagacggggt gtagtacaga tcctcgtact  18660
catcgcgcgg aacctcccgc ggacccgact tcacggagcg gcgagaggtc atggttccac  18720
gaacacgcta gggtcggatg cgcggacaat taggcctggg ttcggacggc ggggggtggt  18780
gcaggtgtgg agaggtcgag cgataggggc ggcccgggag agaagagagg gtccgcaaaa  18840
```

```
cccactgggg atgcgtgagt ggccctctgt gggcggtggg ggagagtctt ataggaagtg  18900
catataacca caacccatgg gtctaaccaa tccccagggg ccaagaaaca gacacgcccc  18960
aaacggtctc ggtttccgcg aagaagggga agtcctggga caccctccac ccccacccct  19020
caccccacac agggcgggtt caggcgtgcc cggcagccag tagcctctgg cagatctgac  19080
agacgtgtgc gataatacac acgcccatcg aggccatgcc tacataaaag ggcaccaggg  19140
ccccgggggc agacatttgg ccagcgtttt gggtctcgca ccgcgcgccc ccgatcccat  19200
cgcgcccgcc ctcctcgccg ggcggctccc cgtgcgggcc cgcgtctccc gccgctaagg  19260
cgacgagcaa gacaaacaac aggcccgccc gacagaccct tctgggggg cccatcgtcc  19320
ctaacaggaa gatgagtcag tggggatccg gggcgatcct tgtccagccg gacagcttgg  19380
gtcgggggta cgatggcgac tggcacacgg ccgtcgctac tcgcgggggc ggagtcgtgc  19440
aactgaacct ggtcaacagg cgcgcggtgg cttttatgcc gaaggtcagc ggggactccg  19500
gatgggccgt cgggcgcgtc tctctggacc tgcgaatggc tatgccggct gacttttgtg  19560
cgattattca cgcccccgcg ctatccagcc cagggcacca cgtaatactg ggtcttatcg  19620
actcggggta ccgcggaacc gttatggccg tggtcgtagc gcctaaaagg acgcgggaat  19680
ttgcccccgg gaccctgcgg gtcgacgtga cgttcctgga catcctggcg acccccccgg  19740
ccctcaccaa gccgatttcc ctgcggcagt tcccgcaact ggcgcccccc cctccaaccg  19800
gggccgggat acgcgcagat ccttggttgg agggggcgct cggggaccca agcgtgactc  19860
cggccctacc ggcgcgacgc cgagggcggt ccctcgtcta tgccggcgag ctgacgccgg  19920
ttcagacgga acacggggac ggcgtacgag aagccatcgc cttccttcca aaacgcgagg  19980
aggatgccgg tttcgacatt gtcgtccgtc gcccggtcac cgtcccggca aacggcacca  20040
cggtcgtgca gccatccctc cgcatgctcc acgcggacgc cgggcccgcg gcctgttatg  20100
tgttggggcg gtcgtcgctc aacgcccgcg gcctcctggt cgttcctacg cgctggctcc  20160
ccgggcacgt atgtgcgttt gttgtttaca accttacggg ggttcctgtg accctcgagg  20220
ccggcgccaa ggtcgcccag ctcctggttg cgggggcgga cgctcttcct tggatccccc  20280
cggacaactt tcacgggacc aaagcgcttc gaaactaccc caggggtgtt ccggactcaa  20340
ccgccgaacc caggaacccg ccgctcttgg tgtttacgaa cgagtttgac gcggaggccc  20400
ccccgagcga gcgcgggacc gggggttttg gctctaccgg tatttagccc atagcttggg  20460
gttcgttccg ggcaataaaa aacgtttgta tctcatcttt cctgtgtgta gttgtttctg  20520
ttggaggcct gtgggtctat cacacccgcc cctccatccc acaaacacag aacacacggg  20580
ttggatgaaa acacgcattt attgacccaa aacacacgga gctgctcgag atgggccagg  20640
gcgaggtgcg gttggggagg ctgtaggtct gggaacggac acgcggggac acgattccgg  20700
tttggggtcc gggagggcgt cgccgtttcg ggcggcaggc gccagcgtaa cctccggggg  20760
cggcgtgtgg gggtgcccca aggagggcgc ctcggtcacc ccaagccccc ccaagcgggt  20820
tcccccggca accccgaagg cggagaggcc aagggcccgt tcggcgatgg ccacatcctc  20880
catgaccacg tcgctctcgg ccatgctccg aatagcctgg gagacgagca catccgcgga  20940
cttgtcagcc gcccccacgg acatgtacat ctgcaggatg gtggccatac acgtgtccgc  21000
caggcgccgc atcttgtcct gatgggccgc cacggccccg tcgatcgtgg gggcctcgag  21060
cccggggtgg tggcgcgcca gtcgttctag gttcaccatg caggcgtggt acgtgcgggc  21120
caaggcgcgg gccttcacga ggcgtcgggt gtcgtccagg gaccccaggg tgtcatcgag  21180
```

cgtgatgggg gcgggaagta gcgcgttaac gaccaccagg gcctcctgca gccgcggctc 21240
cgcctccgag ggcggaacgg ccgcgcggat catctcatat tgttcctcgg ggcgcgctcc 21300
ccagccacat atagccccga gaagagaagc catcgcgggc gggtactggc ccttgggcgc 21360
gcggacgcaa tggggcagga agacgggaac cgcggggaga ggcgggcggc cgggactccc 21420
gtggaggtga ccgcgcttta tgctaccgac gggtgcgtta ttacctcttc gatcgccctc 21480
ctcacaaact ctctactggg ggccgagccg gtttatatat tcagctacga cgcatacacg 21540
cacgatggcc gtgccgacgg gcccacggag caagacaggt tcgaagagag tcgggcgctc 21600
taccaagcgt cgggcgggct aaatggcgac tccttccgag taaccttttg tttattgggg 21660
acggaagtgg gtgggaccca ccaggcccgc gggcgaaccc gacccatgtt cgtctgtcgc 21720
ttcgagcgag cggacgacgt cgccgcgcta caggacgccc tggcgcacgg gaccccgcta 21780
caaccggacc acatcgccgc caccctggac gcggaggcca cgttcgcgct gcatgcgaac 21840
atgatcctgg ctctcaccgt ggccatcaac aacgccagcc cccgcaccgg acgcgacgcc 21900
gccgcggcgc agtatgatca gggcgcgtcc ctacgctcgc tcgtggggcg cacgtccctg 21960
ggacaacgcg gccttaccac gctatacgtc caccacgagg cgcgcgtgct ggccgcgtac 22020
cgcagggcgt attatggaag cgcgcagagt cccttctggt ttcttagcaa attcgggccg 22080
gacgaaaaaa gcctggtgct caccactcgg tactacctgc ttcaggccca gcgtctgggg 22140
ggcgcggggg ccacgtacga cctgcaggcc atcaaggaca tctgcgccac ctacgcgatt 22200
ccccacgccc cccgccccga caccgtcagc gccgcgtccc tgacctcgtt tgccgccatc 22260
acgcggttct gttgcacgag ccagtacgcc cgcggggccg cggcggccgg gtttccgctt 22320
tacgtggagc gccgtattgc ggccgacgtc cgcgagacca gtgcgctgga gaagttcata 22380
acccacgatc gcagttgcct gcgcgtgtcc gaccgtgaat tcattacgta catttacctg 22440
gcccattttg agtgtttcag ccccccgcgc ctagccacgc atcttcgggc cgtgacgacc 22500
cacgacccca accccgcggc caacacggag cagccctcgc ccctgggcag ggaggccgtg 22560
gaacaatttt tttgccacgt gcgcgcccaa ctgaatatcg gggagtacgt caaacacaac 22620
gtgacccccc gggagaccgt cctggatggc gatacggcca aggcctacct gcgcgctcgc 22680
acgtacgcgc ccggggccct gacgcccgcc cccgcgtatt gcggggccgt ggactccgcc 22740
accaaaatga tggggcgttt ggcggacgcc gaaaagctcc tggtccccgc cgggtggccc 22800
gcgtttgcgc ccgccagtcc cggggaggat acggcgggcg gcacgccgcc cccacagacc 22860
tgcggaatcg tcaagcgcct cctgagactg gccgccacgg aacaacagga caccacgccc 22920
ccggcgatcg cggcgcttat ccgtaatgcg gcggtgcaga ctcccctgcc cgtctaccgg 22980
atatccatgg tccccacggg acaggcattt gccgcgctgg cctgggacga ctggcccgc 23040
ataacgcggg acgctcgcct ggccgaagcg gtcgtgtccg ccgaagcggc ggcgcacccc 23100
gaccacggcg cgctgggcag gcggctcacg gatcgcatcc gcgcccaggg ccccgtgatg 23160
ccccctggcg gcctggatgc cggggggcag atgtacgtga atcgcaacga gatattcaac 23220
ggcgcgctgg caatcacaaa catcatcctg gatctcgaca tcgccctgaa ggagcccgtc 23280
ccctttcgcc ggctccacga ggccctgggc cactttaggc gcggggctct ggctgcggtt 23340
cagctcctgt ttcccgcggc ccgcgtggac cccgacgcat atccctgtta ttttttcaaa 23400
agcgcatgtc ggcccggccc ggcgtccgtg ggttccggca gcggactcgg caacgacgac 23460
gacggggact ggtttccctg ctacgacgac gccggtgatg aggagtgggc ggaggacccg 23520
ggcgccatgg acacatccca cgatccccg gacgacgagg ttgcctactt tgacctgtgc 23580

```
cacgaagtcg gccccacggc ggaacctcgc gaaacggatt cgcccgtgtg ttcctgcacc  23640
gacaagatcg gactgcgggt gtgcatgccc gtccccgccc cgtacgtcgt ccatggttct  23700
ctaacgatgc ggggggtggc acgggtcatc cagcaggcgg tgctgttgga ccgagatttt  23760
gtggaggcca tcgggagcta cgtaaaaaac ttcctgttga tcgatacggg ggtgtacgcc  23820
cacggccaca gcctgcgctt gccgtatttt gccaaaatcg cccccgacgg gcctgcgtgc  23880
ggaaggctgc tgccagtgtt tgtgatcccc cccgcctgca aagacgttcc ggcgtttgtc  23940
gccgcgcacg ccgacccgcg gcgcttccat tttcacgccc cgcccaccta tctcgcttcc  24000
ccccgggaga tccgtgtcct gcacagcctg ggtggggact atgtgagctt ctttgaaagg  24060
aaggcgtccc gcaacgcgct ggaacacttt gggcgacgcg agaccctgac ggaggtcctg  24120
ggtcggtaca acgtacagcc ggatgcgggg gggaccgtcg aggggttcgc atcggaactg  24180
ctggggcgga tagtcgcgtg catcgaaacc cactttcccg aacacgccgg cgaatatcag  24240
gccgtatccg tccggcgggc cgtcagtaag gacgactggg tcctcctaca gctagtcccc  24300
gttcgcggta ccctgcagca aagcctgtcg tgtctgcgct ttaagcacgg ccgggcgagt  24360
cgcgccacgg cgcggacatt cgtcgcgctg agcgtcgggg ccaacaaccg cctgtgcgtg  24420
tccttgtgtc agcagtgctt tgccgccaaa tgcgacagca accgcctgca cacgctgttt  24480
accattgacg ccggtacgcc atgctcgccg tccgttccct gcagcacctc tcaaccgtcg  24540
tcttgataac ggcgtacggc ctcgtgctcg tgtggtacac cgtcttcggt gccagtccgc  24600
tgcaccgatg tatttacgcg gtacgcccca ccggcaccaa caacgacacc gccctcgtgt  24660
ggatgaaaat gaaccagacc ctattgtttc tgggggcccc gacgcacccc cccaacgggg  24720
gctggcgcaa ccacgcccat atctgctacg ccaatcttat cgcgggtagg gtcgtgccct  24780
tccaggtccc acccgacgcc atgaatcgtc ggatcatgaa cgtccacgag gcagttaact  24840
gtctggagac cctatggtac acacgggtgc gtctggtggt cgtagggtgg ttcctgtatc  24900
tggcgttcgt cgccctccac caacgccgat gtatgtttgg tgtcgtgagt cccgcccaca  24960
agatggtggc cccggccacc tacctcttga actacgcagg ccgcatcgta tcgagcgtgt  25020
tcctgcagta cccctacacg aaaattaccc gcctgctctg cgagctgtcg gtccagcggc  25080
aaaacctggt tcagttgttt gagacggacc cggtcacctt cttgtaccac cgccccgcca  25140
tcggggtcat cgtaggctgc gagttgatgc tacgctttgt ggccgtgggt ctcatcgtcg  25200
gcaccgcttt catatcccgg ggggcatgtg caatcacata ccccctgttt ctgaccatca  25260
ccacctggtg ttttgtctcc accatcggcc tgacagagct gtattgtatt ctgcggcggg  25320
gcccggcccc caagaacgca gacaaggccg ccgccccggg gcgatccaag ggctgtcgg   25380
gcgtctgcgg gcgctgctgt tccatcatcc tctcgggcat cgcagtgcga ttgtgttata  25440
tcgccgtggt ggccggggtg gtgctcgtgg cgcttcacta cgagcaggag atccagaggc  25500
gcctgtttga tgtatgacgt cacatccagg ccggcggaaa ccggaacggc atatgcaaat  25560
tggaaactgt cctgtcttgg ggcccaccca cccgacgcgt catatgcaaa tgaaaatcgg  25620
tcccccgagg ccacgtgtag cctggatccc aacgaccccg cccatgggtc ccaattggcc  25680
gtcccgttac caagaccaac ccagccagca tatccacccc cgcccgggtc cccgcggaag  25740
cggaacggtg tatgtgatat gctaattaaa tacatgccac gtacttatgg tgtctgattg  25800
gtccttgtct gtgccggagg tggggcgggg gccccgcccg gggggcggaa cgaggagggg  25860
tttgggagag ccggccccgg caccacgggt ataaggacat ccaccacccg gccggtggtg  25920
```

gtgtgcagcc gtgttccaac cacggtcacg cttcggtgcc tctccccgat tcgggcccgg 25980
tcgctcgcta ccggtgcgcc accaccagag gccatatccg acaccccagc cccgacggca 26040
accgacagcc cggtcatggc gactgacatt gatatgctaa ttgacctcgg cctggacctc 26100
tccgacagcg atctggacga ggacccaccc gagccggcgg agagccgccg cgacgacctg 26160
gaatcggaca gcagcgggga gtgttcctcg tcggacgagg acatggaaga cccccacgga 26220
gaggacggac cggagccgat actcgacgcc gctcgcccgg cggtccgccc gtctcgtcca 26280
gaagaccccg gcgtacccag cacccagacg cctcgtccga cggagcggca gggccccaac 26340
gatcctcaac cagcgcccca cagtgtgtgg tcgcgcctcg ggcccggcg accgtcttgc 26400 tcccccgagc agcacggggg caaggtggcc cgcctccaac cccaccgac caaagcccag 26460 cctgcccgcg gcggacgccg cggcgtcgc aggggtcggg gtcgcggtgg tcccggggcc 26520
gccgatggtt tgtcggaccc ccgccggcgt gcccccagaa ccaatcgcaa cccgggggga 26580
ccccgccccg gggcggggtg gacggacggc cccggcgccc cccatggcga ggcgtggcgc 26640
ggaagtgagc agcccgaccc acccggaggc ccgcggacac ggggcgtgcg ccaagcaccc 26700
cccccgctaa tgacgctggc gattgccccc ccgcccgcgg acccccgcgc cccggccccg 26760
gagcgaaagg cgcccgccgc cgacaccatc gacgccacca cgcggttggt cctgcgctcc 26820
atctccgagc gcgcggcggt cgaccgcatc agcgagagct ttggccgcag cgcacaggtc 26880
atgcacgacc cctttggggg gcagccgttt cccgccgcga atagcccctg ggccccggtg 26940
ttggcgggcc aaggagggcc ctttgacgcc gagaccagac gggtctcctg ggaaaccttg 27000
gtcgcccacg gcccgagcct ctatcgcact tttgccggca atcctcgggc cgcatcgacc 27060
gccaaggcca tgcgcgactg cgtgctgcgc caagaaaatt tcatcgaggc gctggcctcc 27120
gccgacgaga cgctggcgtg gtgcaagatg tgcatccacc acaacctgcc gctgcgcccc 27180
caggacccca ttatcgggac ggccgcggct gtgctggata acctcgccac gcgcctgcgg 27240
ccctttctcc agtgctacct gaaggcgcga ggcctgtgcg gcctggacga actgtgttcg 27300
cggcggcgtc tggcggacat taaggacatt gcatccttcg tgtttgtcat tctggccagg 27360
ctcgccaacc gcgtcgagcg tggcgtcgcg gagatcgact acgcgaccct tggtgtcggg 27420
gtcggagaga agatgcattt ctacctcccc ggggcctgca tggcgggcct gatcgaaatc 27480
ctagacacac accgccagga gtgttcgagt cgtgtctgcg agttgacggc cagtcacatc 27540
gtcgcccccc cgtacgtgca cggcaaatat ttttattgca actccctgtt ttaggtacaa 27600
taaaaacaaa acatttcaaa caaatcgccc cacgtgttgt ccttctttgc tcatggccgg 27660
cggggcgtgg gtcacggcag atggcggggg tgggcccggc gtacggcctg ggtgggcgga 27720
gggaactaac ccaacgtata aatccgtccc cgctccaagg ccggtgtcat agtgccctta 27780
ggagcttccc gcccgggcgc atcccccctt ttgcactatg acagcgaccc ccctcaccaa 27840
cctgttctta cgggccccgg acataaccca cgtggccccc ccttactgcc tcaacgccac 27900
ctggcaggcc gaaacggcca tgcacaccag caaaacggac tccgcttgcg tggccgtgcg 27960
gagttacctg gtccgcgcct cctgtgagac cagcggcaca atccactgct ttttctttgc 28020
ggtatacaag gacacccacc acacccctcc gctgattacc gagctccgca actttgcgga 28080
cctggttaac cacccgccgg tcctacgcga actggaggat aagcgcgggg tgcggctgcg 28140
gtgtgcgcgg ccgtttagcg tcgggacgat taaggacgtc tctgggtccg gcgcgtcctc 28200
ggcgggagag tacacgataa acgggatcgt gtaccactgc cactgtcggt atccgttctc 28260
aaaaacatgc tggatggggg cctccgcggc cctacagcac ctgcgctcca tcagctccag 28320
cggcatggcc gcccgcgcgg cagagcatcg acgcgtcaag attaaaatta aggcgtgatc 28380
tccaaccccc ccatgaatgt gtgtaacccc ccaaaaaaat aaacagccgt aacccaatca 28440
aaccaggcgt ggtgtgagtt tgtggaccca aagccctcag agacaacgcg acaggccagt 28500
atggaccgtg atacttttat ttattaactc acaggggcgc ttaccgccac aggaatacca 28560
gaataatgac caccactatc gcgaccaccc caaatacagc atggcgcccc accacgccac 28620
aacagccctg tcgccggtat ggggcatgat cagacgagcc gcgagccgcg cgttgggccc 28680
tgtacagctc gcgcgaattg accctaggag gccgccacgc gcccgagttt tgcgttcgtc 28740
gctggtcgtc gggcgccaaa gccccggacg gctgttcggt cgaacgaacg gccacgacag 28800
tggcataggt tggggggtgg tccgacatag cctcggcgta cgtcgggagg cccgacaaga 28860
ggtcccttga gatgtcgggt ggggccacaa gcctggtttc cggaagaaac agggggggttg 28920
ccaataaccc gccagggcca aaactccggc gctgcgcacg tcgttcggcg cggcgccggg 28980
cgcgccgagc ggctcgctgg gcggcttggc gtgagcggcc ccgctccgac gcctcgccct 29040
ctccggagga ggttggcgga attggcacgg acgacagggg cccagcagag tacggtggag 29100
gtgggtccgt gggggtgtcc agatcaataa cgacaaacgg cccctcgttc ctaccagaca 29160
agctatcgta ggggggcggg ggatcagcaa acgcgttccc cgcgctccat agacccgcgt 29220
cgggttgcgc cgcctccgaa gccatggatg cgccccaaag ccacgactcc cgcgcgctag 29280
gtccttgggg taagggaaaa ggccctactc cccatccaag ccagccaagt taacgggcta 29340
cgccttcggg gatgggactg gcaccccggc ggattttgtt gggctggtac gcgttgccca 29400
accgagggcc gcgtccacgg gacgcgcctt ttataacccc gggggtcatt cccaacgatc 29460
acatgcaatc taactggctc ccctctcccc ccctctcccc tctccccccc tctcccctct 29520
cccccctct cccctctccc cccctctccc ctctccccc ctctcccctc tccccccctc 29580
tcccctctcc cccctctcc cctctcccc cctctcccct ctcccccct ctcccctctc 29640
cccccctctc ccctctcccc tctgctcttt ccccgtgaca cccgacgctg gggggcgtgg 29700
ctgccgggag gggccgcgga tgggcggggc ctacttggtt tcccgccccc cccccccgcc 29760
cccgaaccgc cccgccggcc ttgcccccct ttgatcccct gctaccccca acccgtgctg 29820
gtggtgcggg ttgggggggg agtgtgggcg ggggtgtgcg ggaggtgtcg gtggtggtgg 29880
tggtggtggt agtaggaatg gtggtgaggg ggggggggcg ctggttggtc aaaaaaggga 29940
gggacggggg ccggcagacc gacggcgaca acgctccccg gtggccgggt cgcggctctt 30000
acgagcggcc cggcccgcgc tcccaccccc cgggccgtgt ccttgctttc cccccgtctc 30060
cccccccccc gccttctcct cctcctcctc gtttttccaa accccgccca cccggcccgg 30120
cccggcccgg cccggcccgg ccaccgccgc ccacccaccc acctcgggag acccagcccc 30180
ggtcccccgt tccccggggg ccgttatctc cagcgccccg tccggcgcgc cgcccccgc 30240
cgctaaaccc catcccgccc ccgggacccc acatataagc ccccagccac acgcaagaac 30300
agacacgcag aacggctgtg tttatttaaa taaaccgatg tcggaataaa caaacacaaa 30360
cacccgcgac ggggggacgg aggggacgga gggagggggg tgacgggga cgggaacaga 30420
cacaccacaa aaaacaccca cccaccgaca cccccacccc agtctcctcg ccttctccca 30480
cccaccccac gcccccactg agcccggtcg atcgacgagc accccccgccc acgccccgc 30540
ccctgccccg gcgacccccg gcccgcacga tcccgacaac aataacaacc ccaacggaaa 30600
gcggcggggt gtgggggggg gcgaggaaca accgagggga acgggggatg gaaggacggg 30660
aagtggaagt cctgataccc atcctacacc cccctgcctt ccaccctccg gccccccgcg 30720
agtccacccg ccggccggct accgagaccg aacacggcgg ccgccgcagc cgccgcagcc 30780
gccgccgaca ccgcagagcc ggcgcgcgca cacacaagcg gcagaggcag aaaggcccag 30840
agtcattgtt tatgtggccg cgggccagca gacggcccgc gacacccccc ccccgcccgt 30900
gtgggtatcc ggccccccgc cccgcgccgg tccattaagg gcgcgcgtgc ccgcgagata 30960
tcaatccgtt aagtgctctg cagacagggg caccgcgccc ggaaatccat taggccgcag 31020
acgaggaaaa taaaattaca tcacctaccc acgtggtgct gtggcctgtt tttgctgcgt 31080
catctgagcc tttataaaag cgggggcgcg gccgtgccga tcgcgggtgg tgcgaaagac 31140
tttccgggcg cgtccgggtg ccgcggctct ccgggccccc ctgcagccgg ggcggccaag 31200
gggcgtcggc gacatcctcc ccctaagcgc cggccggccg ctggtctgtt ttttgttttc 31260
cccgtttcgg gggtgggggg ggttgcggtt tctgtttctt taacccgtct ggggtgtttt 31320
tcgttccgtc gccggaatgt ttcgttcgtc tgtcccctca cggggcgaag gccgcgtacg 31380
gcccgggacg agggggcccc cgaccgcggc ggtccgggcc ccgtccgggc ccgctcgccg 31440
gcacgcgacg cgaaaaaggc cccccggagg cttttccggg ttcccggccc ggggcctgag 31500
ataaacaatc ggggttaccg ccaacggccg gcccccgtgg cggcccggcc cggggccccg 31560
gcggacccaa ggggccccgg cccggggccc cacaacggcc cggcgcatgc gctgtggttt 31620 tttttttct cggtgttctg ccgggctcca tcgcctttcc tgttctcgct tctccccccc 31680
cccttcttca cccccagtac cctcctccct cccttcctcc cccgttatcc cactcgtcaa 31740
gggcgccccg gtgtggttca acaaagacgc cgcgtttcca ggtaggttag acacctgctt 31800
ctccccaata gagggggggg acccaaacga caggggggcgc cccagaggct aaggtcggcc 31860
acgccactcg cgggtgggct cgtgttacag cacaccagcc cgttcttttc ccccccctccc 31920 acccttagtc agactctgtt acttacccgt ccgaccacca actgcccccct tatctaaggg 31980 ccggctggaa gaccgccagg gggtcggccg gtgtcgctgt aacccccccac gccaatgacc 32040 cacgtactcc aagaaggcat gtgtcccacc ccgcctgtgt ttttgtgcct ggctctctat 32100
gcttgggtct tactgcctgg gggggggggag tgcgggggag ggggggtgtg gaaggaaatg 32160
cacggcgcgt gtgtaccccc cctaaagttg ttcctaaagc gaggatatgg aggagtggcg 32220
ggtgccgggg gaccggggtg atctctggca cgcgggggtg ggaagggtcg ggggaggggg 32280
gatggggtac cggcccacct ggccgacgcg ggtgcgcgtg cctctgcaca ccaaccccac 32340
gtcccccggc ggtctctaag aagcaccgcc cccccctcctt cataccaccg agcatgcctg 32400
ggtgtgggtt ggtaaccaac acgcccatcc cctcgtctcc tgtgattctc tggctgcacc 32460
gcattcttgt tttctaacta tgttcctgtt tctgtctccc cccccccac ccctccgccc 32520 caccccccaa cacccacgtc tgtggtgtgg ccgacccccct tttgggcgcc ccgtcccgcc 32580
ccgccacccc tcccgtcctt tgttgcccta tagtgtagtt aacccccccc gccctttgtg 32640
gcggccagag gccaggtcag tccgggcggg caggcgctcg cggaaactta acacccacac 32700
ccaacccact gtggttctgg ctccatgcca atggcaggat gctttcgggg atcggtggtc 32760
aggcagcccg ggccgcggct ctgtggttaa caccagagcc tgcccaacat ggcaccccca 32820
ctcccacgca cccccactcc cacgcacccc cactcccacg cacccccact cccacgcacc 32880
cccactccca cgcaccccca ctcccacgca cccccactcc cacgcacccc cactcccacg 32940
cacccccact cccacgcacc cccgagatcc atccaacaca gacagggaaa agatacaaaa 33000
gtaaaccttt atttcccaat agacagcaaa aatcccctga gttttttatt agggccaaca 33060
ctaaagaccc gctggtgtgt ggtgcccgtg tctttcactt ttcccctccc cgacacggat 33120
tggctggtgt agtgggcgcg gccagagacc acccagcgcc cgaccccccc ctccccacaa 33180
acacgggggg cgtcccttat tgttttccct cgtcccgggt cgacgccccc tgctccccgg 33240
accacgggtg ccgagaccgc aggctgcgga agtccagggc gcccactagg gtgccctggt 33300
cgaacagcat gttccccacg gggtcatcc agaggctgtt ccactccgac gcgggggccg 33360
tcgggtactc ggggggcatc acgtggttac ccgcggtctc ggggagcagg gtgcggcggc 33420
tccagccggg gaccgcggcc cgcagccggg tcgccatgtt tcccgtctgg tccaccagga 33480
ccacgtacgc cccgatgttc cccgtctcca tgtccaggat gggcaggcag tcccccgtga 33540
tcgtcttgtt cacgtaaggc gacagggcga ccacgctaga gacccccgag atgggcaggt 33600
agcgcgtgag gccgcccgcg ggggcggccc cggaagtctc cgcgtggcgc gtcttccggg 33660
cacacttcct cggcccccgc ggcccagaag cagcgcgggg gccgagggag gtttcctctt 33720
gtctccctcc cagggcaccg acggccccgc ccgaggaggc ggaagcggag gaggacgcgg 33780
ccccggcggc ggaagaggcg gcccccgcgg gagtcggggc cgaggaggaa gaggcagagg 33840
aggaagaggc ggaggccgcc gaggacgtca ggggggtccc gggcccaccc tggccgcgcc 33900
cccccggccc tgagtcggag ggggggtgcg tcgccgccct cttggcccct gccggcgcga 33960
ggggggacg cgtggactgg ggggaggggt tttcctggcc cgacccgcgc ctcttcctcg 34020
gacgcaccgc cgcctcctgc tcgacagagg cggcggaggg gagcgggggg gcgccggagg 34080
gggcggcgcc gcgggagggc ccgtgtccac cctccacgcc cggccccccc gagccgcgcg 34140
ccaccgtcgc acgcgcccgg cacagactct gttcttggtt cgcggcctga gccagggacg 34200
agtgcgactg gggcacacgg cgcgcgtccg cggggcgggc ggccggctcc gccccggggg 34260
ccggggcgcg ggggccgggc cccggaggcg gcgctcgcac gcacggggcc acggccgcgc 34320
gggggcgcgc gggtcccgac gcggccgagg acgcggtggg cccggggcgg ggggcggagc 34380
ctggcatggg cgccgcgggg ggcctgtggg gagaggccgg gggggagtcg ctgatcacta 34440
tggggtctct gttgtttgca agggggggcgg gtctgttgac aagggggccc gtccggcccc 34500
tcggccgccc cgcctccgct tcaacaaccc caaccccaac cccaaccccc ccggaggggc 34560
cagacgcccc ccgcggcgcc gcggctcgcg actggcggga gccgccgccg ccgctgctgt 34620
tggtggtggt gttggtgtta ctgctgccgt gtggcccgat gggcgccgag gggggcgctg 34680
tccgagccgc ggccggctgg ggggctgcgt gagacgcccc gcccgtcacg gggggcgcgg 34740
cggcgcctct gcgtgggggg gcgcggggcg tccggcgggg ggcgggcggt acgtagtctg 34800
ctgcaagaga caacgggggg cgcgatcagg ttacgccccc tcccaggccc tccctttccg 34860
cgcccgcccg cctattcctc cctccccccct cctcctcctc ctcccccagg gtcctcgccg 34920
cccccgcct caccgtcgtc caggtcgtcg tcatcctcgt ccgtggtggg ctcagggtgg 34980
gtgggcgaca gggccctcac cgtgtgcccc cccagggtca ggtaccgcgg ggcgaaccgc 35040
tgattgcccg tccagataaa gtccacggcc gtgcccgccc tgacggcctc ctcggcctcc 35100
atgcgggtct gggggtcgtt cacgatcggg atggtgctga acgacccgct gggcgtcacg 35160
cccactatca ggtacaccag cttggcgttg cacagcgggc aggtgttgcg caattgcatc 35220
caggttttca tgcacgggat gcagaagcgg tgcatgcacg ggaaggtgtc gcagcgcagg 35280
tggggcgcga tctcatccgt gcacacggcg cacacgtcgc cctcgtcgct ccccccgtcc 35340
tctcgagggg gggcgccccc gcaactgccg gggtcttcct cgcggggggg gctccccccc 35400

-continued

```
gagaccgccc ccccatccac gccctgcggc cccagcagcc ccgtctcgaa cagttccgtg  35460
tccgtgctgt ccgcctcgga ggcggagtcg tcgtcatggt ggtcggcgtc cccccgcccc  35520
cccacttcgg tctccgcctc agagtcgctg ctgtccggca ggtctcggtc gcagggaaac  35580
acccagacat ccggggcggg ctaaggggaa aaaagggggg cgggtaagaa tgggggggatt  35640
tcccgcgtca atcagcgccc acgagttccc cctctccccc ccccgcctca caaagtcctg  35700
ccccccctgct ggcctcggaa gagggggggag aaaggggtct gcaaccaaag gtggtctggg  35760
tccgtccttt ggatcccgac ccctcttctt ccctcttctc ccgccctcca gacgcaccgg  35820
agtcgggggt cccacggcgt cccccaaata tggcgggcgg ctcctcccca ccccccctaga  35880
tgcgtgtgag taagggggcc ctgcgtatga gtcagtgggg accacgcccc ctaacacggc  35940
gaccccggtc cttgtgtgtt tgttgtgggg gcgtgtctct gtgtatgagt caggggggtcc  36000
cacggcgacc ccgggccctg cgtctgagtc aaaggggcca tgtgtatgtg ttgggggggtc  36060
tgtatatata aagtcagggg gtcacatggc gacccccaac agggcgaccc cggtccctgt  36120
atatataggg tcaggggggtt ccgcgccccc taacatggcg cccccggtcc ctgtatatat  36180
agtgtcacgg ggttccacgc cccctaacat ggcgcccgcc cggctcccgt gtatgagtgg  36240
gggtccccca acatggcggc cggttccagt gtaagggtcg ggggtccccc aacatggcgc  36300
cccccaatat ggcgcccccc aatatggcgc cccagacatg gcgcccggcc cctcacctcg  36360
cgctgggggc ggccctcagg ccggcgggta ctcgctccgg ggcggggctc catgggggggtc  36420
gtatgcggct ggagggtcgc ggacggaggg tccctggggg tcgcaacgta ggcggggctt  36480
ctgtggtgat gcggagaggg ggcggcccga gtctgcctgg ctgctgcgtc tcgctccgag  36540
tgccgaggtg caaatgcgac cagactgtcg ggccagggct aacttatacc ccacgccttt  36600
cccctcccca aaggggcggc agtgacgatt cccccaatgg ccgcgcgtcc caggggaggc  36660
aggcccaccg cggggcggcc ccgtccccgg ggaccaaccc ggcgccccca aagaatatca  36720
ttagcatgca cggcccggcc cccgatttgg gggaccaacc cggtgtcccc caaagaaccc  36780
cattagcatg cccctcccac cgacgcaaca ggggcttggc ctgcgtcggt gccccggggc  36840
ttcccgcctt cccgaagaaa ctcattacca tacccggaac cccaggggac caatgcgggt  36900
tcattgagcg acccgcgggc caatgcgcga ggggccgtgt gttccgccaa aaaagcaatt  36960
agcataaccc ggaaccccag gggagtggtt acgcgcggcg cgggaggcgg ggaataccgg  37020
ggttgcccat taagggccgc gggaattgcc ggaagcggga agggcggccg gggccgccca  37080
ttaatgagtt tctaattacc ataccgggaa gcggaacaag ggttacctgg gactgtgcgg  37140
ttgggacggc gcccgtgggc ccgggcggcc gggggcggcg ggggccgcga tggcggcggc  37200
ggcgggccat ggagacagag agcgtgccgg ggtggtagag tttgacaggc aagcatgtgc  37260
gtgcagaggc gagtagtgct tgcctgtcta actcgctcgt ctcggccgcg gggggcccgg  37320
gctgccgccg ccgcgcttta aagggccgcg cgcgaccccc ggggggtgtg ttttgggggg  37380
ggcccgtttt cgctcctccc cccgctcctc cccccgctcc tccccccgct cctccccccg  37440
ctcctccccc cgctcctccc cccgctcctc cccccgctcc tccccccgct cctccccccg  37500
ctcctccccc cgctcctccc cccgctcctc cccccgctcc tccccccgct cctccccccg  37560
ctcctccccc cgctcctccc cccgctcctc cccccgctcc tccccccgct cccgcggccc  37620
cgcccccaac gcccgccgcg cgcgcgcacg ccgcccggac cgccgcccgc ctttttttgcg  37680
cgcgccccgc ccgcgggggg cccgggctgc cacaggtgta acaacacaca cggctcatcc  37740
acacgtcaca cgtcacgtca tccaccacac ctgcccacca acacaactca cagcgacaac  37800
```

```
tcaccgcgca acaactcctg ttcctcatcc acacgtcacc gcgcaccccc cgctcctcca  37860
gacgtccccc agcgcaacac gccgctcctg ctacacacca ccgccccctc cccagcccca  37920
gccctcccca gccccagccc tccccagccc cagccctccc cggccccagc cctccccggc  37980
cccagccctc cccggcccca gccctccccg gccccagccc tccccggccc cagccctccc  38040
cgccgcgtcc cgcgctccct cgggggggtt cgggcatctc tacctcagtg ccgccaatct  38100
caggtcagag atccaaaccc tccgggggcg cccgcgcacc accaccgccc ctcgccccct  38160
cccgcccctc gccccctccc gcccctcgcc ccctcccgcc cctcgccccc tcccgcccct  38220
cgccccctcc cgcccctcgc cccctcccgc ccctcgcccc ctcccgcccc tcgccccctc  38280
ccgcccctcg cccccctcccg cccctcgccc cctcccgccc ctcgccccct cccgcccctc  38340
gccccctccc gcccctcgcc ccctcccgcc cctcgccccc tcccgcccct cgccccctcc  38400
cgcccctcgc cccctcccgc ccctcgcccc ctcccgcccc tcgccccctc ccgcccctcg  38460
ccccctcccg cccctcaaat aaacaacgct actgcaaaac taaatcaggt cgttgtcgtt  38520
tattgtgtct tcgggtttcg caagcgcccc gccccgtccc ggcccgttac agcaccccgt  38580
ccccctcgaa cgcgccgccg tcgtcgtcgt cccaggcgcc ttcccagtcc acaacttccc  38640
gtcgcggggg cgtggccaag cccgcctccg cccccagcac ctccacggcc cccgccgccg  38700
ccagcacggt gccgctgcgg cccgtggccg aggcccagcg aatcccgggc aacgccggcg  38760
gcagggcccc cgggccgtcg tcgycgccgc gcagcaccag cggggggggcg tcgtcgtcgg  38820
gctccagcag ggcgcgggcg caaaagtccc tccgcggccc gcgccaccgg gccgggccgg  38880
cgcgcaccgc ctcgcgcccc agcgccacgt acacgggccg cagcggcgcg cccaggcccc  38940
agcgcgcgca ggcgcggtgc gagtgggcct cctcctcgca gaagtccggc gcgccgggcg  39000
ccatggcgtc ggtggtcccc gaggccgccg cccggccgtc cagcgccggc agcacggccc  39060
ggcggtactc gcgcggggac atgggcaccg gcgtgtccgg gccgaagcgc gtgcgcacgc  39120
ggtagcgcac gttgccgccg cggcacaggc gcagcggcgg cgcgtcgggg tacaggcgcg  39180
cgtgcgcggc ctccacgcgc gcgaagaccc ccgggccgaa cacgcggccc ggggccagca  39240
ccgtgcggcg caggtcccgc gccgccggcc agcgcacggc gcactgcacg gcgggcagca  39300
ggtcgcacgc caggtaggcg tgctgccgcg acaccgcggg cccgtcggcg ggccagtcgc  39360
aggcgcgcac ggtgttgacc acgatgagcc gccggtcgcc ggcgctggcg agcagcccca  39420
gaaactccac ggccccggcg aaggccaggt cccgcgtgga cagcagcagc acgccctgcg  39480
cgcccagcgc cgacacgtcg ggggcgccgg tccagttgcc cgcccaggcg gccgtgtccg  39540
gcccgcacag ccggttggcc agggccgcca gcaggcagga cagcccgccg cgctcggcgg  39600
accactccgg cggcccccc gaggccccgc cgccggccag gtcctcgccc ggcagcggcg  39660
agtacagcac caccacgcgc acgtcctcgg ggtcggggat ctggcgcatc caggccgcca  39720
tgcggcgcag cgggcccgag gcgcgcaggg ggccaaagag gcggccccg gcggccccgt  39780
gggggtgggg gttatcgtcg tcgtcgccgc cgccgcacgc ggcctgggcg gcgggggcgg  39840
gcccggcgca ccgcgcggcg atcgaggcca gggcccgcgg gtcaaacatg agggccggtc  39900
gccaggggac ggggaacagc gggtggtccg tgagctcggc cacggcgcgc ggggagcagt  39960
aggcctccag ggcggcggcc gcgggcgccg ccgtgtggct gggccccggg ggctgccgcc  40020
gccagccgcc cagggggtcg gggccctcgg cgggccggcg cgacacggcc acggggcgcg  40080
ggcgggcctg cgccgcggcg gcccggggcg ccgcgggctg ggcgggggcg ggctcgggcc  40140
```

-continued

```
ccgggggcgt ggagggggc gcgggcgcgg ggaggggggc gcgggcgtcc gagccggggg  40200
cgtccgcgcc gctcttcttc gtcttcgggg gtcgcgggcc gccgcctccg ggcggccggg  40260
ccgggccggg actcttgcgc ttgcgcccct cccgcggcgc ggcggaggcg gcggcggccg  40320
ccagcgcgtc ggcggcgtcc ggtgcgctgg cggccgccgc cagcaggggg cgcaggctct  40380
ggttctcaaa cagcaggtcc gcggcggcgg cggccgcgga gctcggcagg cgcgggtccc  40440
gcggcagcgc ggggcccagg gccccggcga ccaggctcac ggcgcgcacg gcggccacgg  40500
cggcctcgct gccgccggcc acgcgcaggt ccccgcgcag gcgcatgagc accagcgcgt  40560
cgcgcacgaa ccgcagctcg cgcagccacg cgcgcaggcg gggcgcgtcg gcgtgcggcg  40620
gcggcgggga agcggggccc gcgggtccct ccggccgcgg ggggctggcg ggccgggccc  40680
cggccagccc cgggacggcc gccaggtcgc cgtcgaagcc ctcggccagc gcctccagga  40740
tcccgcggca ggcggccagg cactccacgg ccacgcggcc ggcctgggcg cggcgcccgg  40800
cgtcgtcgtc ggcgtcggcg tggcgggcgg cgtcggggtc gtcgcccccc gcgggggagg  40860
cgggcgcggc ggacagccgc cccagggcgg cgaggatccc cgcggcgccg tacccggcgg  40920
gcaccgcgcg ctcgcccggt gcggcgacga cggcggcggc gaccccctcg tcatctgcgc  40980
cggcgccggg gctccccgcg gcccccgtca gcgccgcgtt ctcgcgcgcc aacaggggcg  41040
cgtaggcgcg gcgcaggctg gtcagcagga agcccttctg cgcgcggtcg tatcggcggc  41100
tcatggccac ggcggccgcc gcgtgcgcca ggccccagcc gaagcggccg gccgccatgg  41160
cgtagcccag gtggggcacg gcccgcgcca cgctgccggt gatgaaggag ctgctgttgc  41220
gcgcggcgcc cgagatccgg aagcaggcct ggtccagcgc cacgtccccg gggaccacgc  41280
gcgggttctg gagccacccc atggcctccg cgtccggggt gtacagcagc cgcgtgatca  41340
gggcgtactg ctgcgcggcg tcgcccagct cgggcgccca cacggccgcc ggggcgcccg  41400
aggcctcgaa ccggcgtcgc gcctcctccg cctcgggcgc cccccagagg cccgggcggc  41460
tgtcgcccag gccgccgtac agcacccgcc ccgggggcgg gggcccggcg ccgggccacg  41520
gctccccgct gacgtacccg tcgcgatagc gcgcgtagaa ggcgccggag gccgcgtcgg  41580
cgtccagctc gacccgccgg ggctgcccgg ccgtgaagcg gcccgtggcg tcgcggccgg  41640
ccaccgccgc gcgggcccgg cggcgctcga tgcggcccgc ggaggccgcg ggggtcctcg  41700
ccgccgcccg gggcttgggc gcggcctcgg agaggggggg tggcccgggc gggggcggcg  41760
tccgcccggg ggcttccggc gccgcgctcg acggaccccg cccgacggcc cgcgcctcgc  41820
gtgcgcggtc ggccgcgtcg ttgccgtcgt cgtcctcgtc ctcgtcggac gacgaggacg  41880
aagaggatgc ggacgacgag gacgaggacc cggagtccga cgaggtcgat gacgccgatg  41940
gccgccgccg gccgtgacga cgtctccgcg gcggctgggc cggcgggcgc ggcgacaggc  42000
ggtccgtggg gtccggatac gcgccgcgta gcggggcctc ccgtgcgcgg ccccgggccg  42060
gggcccggtc gccggcggcg tcggctgcgt cgtcgtactc gtccccgtca tcgtcgtcgg  42120
ctcgaaaggc gggggtccgg ggcggcgagg ccgcggggtc gggcgtcggg atcgtccgga  42180
cggcctcctc taccatggag gccagcaggg ccagctgtcg cggcgagacg gcgtccccgg  42240
cgtcctcgcc ggcgtcggtg cccgccgcgg gggccctccc gtcccgccgg gcgtcgtcga  42300
ggtcgtgggg gtggtcgggg tcgtggtcgg ggtcgtcccc gccctcctcc gtctccgcgc  42360
cccacccgag ggccccccgc tcgtcgcggt ctgggctcgg ggtgggcggc ggcccgtcgg  42420
tggggcccgg ggagccgggg cgctgcttgt tctccgacgc catcgccgat gcggggcgat  42480
cctccgggga tacggctgcg acggcggacg tagcacggta ggtcacctac ggactctcga  42540
```

```
tggggagggg gcgagaccca cggaccccga cgaccccccgc cgtcgacgcg gaactagcgc  42600
ggaccggtcg atgcttgggt gggaaaaagg acagggacgg ccgatccccc tcccgcgctt  42660
cgtccgcgta tcggcgtccc ggcgcggcga gcgtctgacg gtctgtctct ggcggtcccg  42720
cgtcgggtcg tggatccgtg tcggcagccg cgctccgtgt ggacgatcgg ggcgtcctcg  42780
ggctcatata gtcccagggg ccggcgggaa ggaggagcag cggaggccgc cggcccccccg  42840
ccccccaggc gggcccgccc cgaacggaat tccattatgc acgaccccgc cccgacgccg  42900
gcacgccggg ggcccgtggc cgcggcccgt tggtcgaacc cccggccccg cccatccgcg  42960
ccatctgcca tgggcggggc gcgagggcgg gtgggcccgc gccccgcccc gcatggcatc  43020
tcattaccgc ccgatccggt ggtttccgct tccgttccgc atgctaacga ggaacgggcc  43080
gggggcgggg cccgggcccc gacttcccgg ttcggcggta atgagatacg agccccgcgc  43140
gcccgttggc cgtccccggg cccccggtcc cgcccgccgg acgttgggac caacgggacg  43200
gcgggcggcc caagggccgc ccgccttgcc gccccccccat tggccggcgg gcgggaccgc  43260
cccaaggggg cggggccgcc gggtaaaaga agtgagaacg cgaagcgttc gcacttcgtc  43320
ccaatatata tatattatta gggcgaagtg cgagcactgg cgccgtgccc gactccgcgc  43380
cggccccggg ggcgggcccg ggcggcgggg ggcgggtctc tccggcgcac ataaaggccc  43440
ggcgcgaccg acgcccgcag acggcgccgg ccacgaacga cgggagcggc tgcggagcac  43500
gcggaccggg agcgggactc gcagagggcc gtcggagcgg acggcgtcgg catcgcgacg  43560
ccccggctcg ggatcgggat cgcatcggaa agggacacgc ggacaagacc cacccacccc  43620
acccacgaaa cacaggggac gcaccccggg ggcctccgac gacagaaacc caccggtccg  43680
cctttgtgca cgggtaagca ccttgggtgg gcggaggagg ggggacacgg gggcggagga  43740
ggggggacac gggggcggag gagggggggac gcgggggcgg aggagggggg acgcgggggc  43800
ggaggagggg ggacacgggg gcggaggagg gggctcaccc gcgttcgtgc cttcccgcag  43860
gaggaacgtc ctcgtcgagg cgaccggcgg cgaccgttgc gtggaccgct tcctgctcgt  43920
cgggcggggg gaagccactg tggtcctccg ggacgttttc tggatggccg acatttcccc  43980
aggcgctttt gcgccttgtg taaaagcgcg gcgtcccgct ctccgatccc cgcccctggg  44040
cacgcgcaag cgcaagcgcc cttcccgccc cctctcatcg gagtctgagg tagaatccga  44100
tacagccttg gagtctgagg tcgaatccga gacagcatcg gattcgaccg agtctgggga  44160
ccaggatgaa gccccccgca tcggtggccg tagggccccc cggaggcttg gggggcggtt  44220
ttttctggac atgtcggcgg aatccaccac ggggacggaa acggatgcgt cggtgtcgga  44280
cgaccccgac gacacatccg actggtctta tgacgacatt cccccacgac ccaagcgggc  44340
ccgggtaaac ctgcggctca cgagctctcc cgatcggcgg gatggggtta tttttcctaa  44400
gatggggcgg gtccggtcta cccgggaaac gcagccccgg gcccccaccc cgtcggcccc  44460
aagcccaaat gcaatgctac ggcgctcggt gcgccaggcc cagaggcgga gcagcgcacg  44520
atggaccccc gacctgggct acatgcgcca gtgtatcaat cagctgtttc gggtcctgcg  44580
ggtcgcccgg gacccccacg gcagtgccaa ccgcctgcgc cacctgatac gcgactgtta  44640
cctgatggga tactgccgag cccgtctggc cccgcgcacg tggtgccgtt tgctgcaggt  44700
gtccggcgga acctggggca tgcacctgcg caacaccata cgggaggtgg aggctcgatt  44760
cgacgccacc gcggaacccg tgtgcaagct tccttgtttg gagaccagac ggtacggccc  44820
ggagtgtgat cttagtaatc tcgagattca tctcagcgcg acaagcgatg atgaaatctc  44880
```

```
cgatgccacc gatctggagg ccgccggttc ggaccacacg ctcgcgtccc agtccgacac  44940
ggaggatgcc ccctccccg ttacgctgga aaccccagaa ccccgcgggt ccctcgctgt  45000
gcgtctggag gatgagtttg gggagtttga ctggacccccc caggagggct cccagccctg  45060
gctgtctgcg gtcgtggccg ataccagctc cgtggaacgc ccgggcccat ccgattctgg  45120
ggcgggtcgc gccgcagaag accgcaagtg tctggacggc tgccggaaaa tgcgcttctc  45180
caccgcctgc ccctatccgt gcagcgacac gtttctccgg ccgtgagtcc ggtcgccccg  45240
accccttgt atgtccccaa aataaaagac caaaatcaaa gcgtttgtcc cagcgtctta  45300
atggcgggaa gggcggagag aaacagacca cgcgtacatg gggggtgttt gggggtttat  45360
tgacatcggg gctacagggt ggtaaccgga tagcagatgt gaggaagtct gggccgttcg  45420
ccgcgaacgg cgatcagagg gtccgtttct tgcggaccac ggcccggtga tgtgggttgt  45480
tcgtctggga tctcgggcat gcccatacac gcacaacacg gacgccgcac cggatgggac  45540
gtcgtaaggg ggcctggggt agctgggtgg ggtttgtgca gagcaatcag ggaccgcagc  45600
cagcgcatac aatcgcgctc ccgtccgttt gtcccgggca gtaccacgcc gtactggtat  45660
tcgtaccggc tgagcagggt ctccaggggg tggttggggg ccgcggggaa cggggtccac  45720
gccacggtcc actcgggcaa aaaccgagtc ggcacggccc acggttctcc cacccacgcg  45780
tctggggtct tgatggcgat aaatcttacc ccgagccgga tttttgggc gtattcgaga  45840
aacggcacac acagatccgc cgcgcctacc acccacaagt ggtagaggcg agggggggctg  45900
ggttggtctc ggtgcagcag tcggaagcac gccacggcgt ccacgacctc ggtgctctcc  45960
aaggggctgt cctccgcaaa caggcccgtg gtggtgtttg gggggcagcg acaggaccta  46020
gtgcgcacga tcgggcgggt gggtttgggt aagtccatca gcggctcggc caaccgtcga  46080
aggttggccg gacgaacgac gaccggggta cccaggggtt ctgatgccaa aatgcggcac  46140
tgcctaagca ggaagctcca cagggccggg cttgcgtcga cggaagtccg ggcagggcg  46200
ttgttctggt caaggagggt cattacgttg acgacaacaa cgcccatgtt ggtatattac  46260
aggcccgtgt ccgatttggg gcacttgcag atttgtaagg ccacgcacgg cggggagaca  46320
ggccgacgcg gggctgctc taaaaattta agggccctac ggtccacaga cccgccttcc  46380
cgggggggcc cttggagcga ccggcagcgg aggcgtccgg gggaggggag ggtgatttac  46440
ggggggtag gtcagggggt gggtcgtcaa actgccgctc cttaaaaccc cggggcccgt  46500
cgttcggggt gctcgttggt tggcactcac ggtgcggcga atggcctgtc gtaagttttg  46560
tcgcgtttac gggggacagg gcaggaggaa ggaggaggcc gtcccgccgg agacaaagcc  46620
gtcccgggtg tttcctcatg gccccttttta taccccagcc gaggacgcgt gcctggactc  46680
cccgcccccg gagaccccca aaccttccca caccacacca cccggcgatg ccgagcgcct  46740
gtgtcatctg caggagatcc tggcccagat gtacggaaac caggactacc ccatagagga  46800
cgaccccagc gcggatgccg cggacgatgt cgacgaggac gccccggacg acgtggccta  46860
tccggaggaa tacgcagagg agcttttct gcccggggac gcgcccggtc cccttatcgg  46920
ggccaacgac cacatccctc ccccgtgtgg cgcatctccc cccggtatac gacgacgcag  46980
ccgggatgag attggggcca cgggatttac cgcggaagaa ctggacgcca tggacaggga  47040
ggcggctcga gccatcagcc gcggcggcaa gcccccctcg accatggcca agctggtgac  47100
tggcatgggc tttacgatcc acggagcgct caccccagga tcggaggggt gtgtctttga  47160
cagcagccac ccagattacc cccaacgggt aatcgtgaag gcggggtggt acacgagcac  47220
gagccacgag gcgcgactgc tgaggcgact ggaccacccc gcgatcctgc ccctcctgga  47280
```

cctgcatgtc gtctccgggg tcacgtgtct ggtcctcccc aagtaccagg ccgacctgta 47340
tacctatctg agtaggcgcc tgaacccgct gggacgcccg cagatcgcag cggtctcccg 47400
gcagctccta agcgccgttg actacattca ccgccagggc attatccacc gcgacattaa 47460
gaccgaaaat atttttatta acacccccga ggacatttgc ctgggggact ttggtgccgc 47520
gtgcttcgtg cagggttccc gatcaagccc cttcccctac ggaatcgccg gaaccatcga 47580
caccaacgcc cccgaggtcc tggccgggga tccgtatacc accaccgtcg acatttggag 47640
cgccggtctg gtgatcttcg agactgccgt ccacaacgcg tccttgttct cggccccccg 47700
cggccccaaa aggggcccgt gcgacagtca gatcacccgc atcatccgac aggcccaggt 47760
ccacgttgac gagttttccc cgcatccaga atcgcgcctc acctcgcgct accgctcccg 47820
cgcggccggg aacaatcgcc cgccgtacac ccgaccggcc tggacccgct actacaagat 47880
ggacatagac gtcgaatatc tggtttgcaa agccctcacc ttcgacggcg cgcttcgccc 47940
cagcgccgca gagctgcttt gtttgccgct gtttcaacag aaatgaccgc ccccaggggg 48000
cggtgctgtt tgcgggttgg cacaaaaaga ccccgacccg cgtctgtggt gtttttggca 48060
tcatgtcgcc gggcgccatg cgtgccgttg ttcccattat cccattcctt ttggttcttg 48120
tcggtgtatc gggggttccc accaacgtct cctccaccac ccaaccccaa ctccagacca 48180
ccggtcgtcc ctcgcatgaa gcccccaaca tgacccagac cggcaccacc gactctccca 48240
ccgccatcag ccttaccacg cccgaccaca cacccccccat gccaagtatc ggactggagg 48300
aggaggaaga ggaggagggg gccggggacg gcgaacatct tgaggggggga gatgggaccc 48360
gtgacaccct accccagtcc ccgggcccag ccttcccgtt ggctgaggac gtcgagaagg 48420
acaaacccaa ccgtcccgta gtcccatccc ccgatcccaa caactccccc gcgcgccccg 48480
agaccagtcg cccgaagaca ccccccacca ttatcgggcc gctggcaact cgccccacga 48540
cccgactcac ctcaaaggga cgacccttgg ttccgacgcc tcaacatacc ccgctgttct 48600
cgttcctcac tgcctccccc gccctggaca ccctcttcgt cgtcagcacc gtcatccaca 48660
ccttatcgtt tttgtgtatt ggtgcgatgg cgacacacct gtgtggcggt tggtccagac 48720
gcgggcgacg cacacaccct agcgtgcgtt acgtgtgcct gccgtccgaa cgcgggtagg 48780
gtatggggcg ggggatgggg agagcccaca cgcggaaagc aagaacaata aaggcggtgg 48840
tatctagttg atatgcatct ctgggtgttt ttggggtgtg gcggacgcgg ggcggtcatt 48900
ggacggggtg cagttaaata catgcccggg acccatgaag catgcgcgac ttccgggcct 48960
cggaacccac ccgaaacggc caacggacgt ctgagccagg cctggctatc cggagaaaca 49020
gcacacgact tggcgttctg tgtgtcgcga tgtctctgcg cgcagtctgg catctggggc 49080
ttttgggaag cctcgtgggg gctgttcttg ccgccaccca tcggggacct gcggccaaca 49140
caacggaccc cttaacacac gccccagtgt cccctcaccc cagccccctg gggggctttg 49200
ccgtccccct cgtagtcggt gggctgtgcg ccgtagtcct gggggcggcg tgtctgtttg 49260
agctcctgcg tcgtacgtgc cgcgggtggg ggcgttacca tccctacatg gacccagttg 49320
tcgtataatt cccccccccc ccccccttctc cgcatgggtg atgtcgggtc caaactcccg 49380
acaccaccag ctggcatggt ataaatcacc ggtgcgcccc ccaaaccatg tccggcaggg 49440
ggatgggggg gcgaatgcgg agggcaccca acaacaccgg gctaaccagg aaatccgtgg 49500
ccccggcccc caataaagat cgcggtagcc cggccgtgtg acactatcgt ccataccgac 49560
cacaccgacg aatcccctaa gggggagggg ccattttacg aggaggaggg gtataacaaa 49620
gtctgtcttt aaaaagcagg ggttagggag ttgttcggtc ataagcttca gcgcgaacga 49680
ccaactaccc cgatcatcag ttatccttaa ggtctctttt gtgtggtgcg ttccggtatg 49740
gggggggctg ccgccaggtt gggggccgtg attttgtttg tcgtcatagt gggcctccat 49800
ggggtccgcg gcaaatatgc cttggcggat gcctctctca agatggccga ccccaatcgc 49860
tttcgcggca aagaccttcc ggtcctggac cagctgaccg accctccggg ggtccggcgc 49920
gtgtaccaca tccaggcggg cctaccggac ccgttccagc cccccagcct cccgatcacg 49980
gtttactacg ccgtgttgga gcgcgcctgc cgcagcgtgc tcctaaacgc accgtcggag 50040
gccccccaga ttgtccgcgg ggcctccgaa gacgtccgga aacaacccta caacctgacc 50100
atcgcttggt ttcggatggg aggcaactgt gctatcccca tcacggtcat ggagtacacc 50160
gaatgctcct acaacaagtc tctgggggcc tgtcccatcc gaacgcagcc ccgctggaac 50220
tactatgaca gcttcagcgc cgtcagcgag gataacctgg ggttcctgat gcacgccccc 50280
gcgtttgaga ccgccggcac gtacctgcgg ctcgtgaaga taaacgactg gacggagatt 50340
acacagttta tcctggagca ccgagccaag ggctcctgta agtacgccct cccgctgcgc 50400
atcccccccgt cagcctgcct gtccccccag gcctaccagc aggggtgac ggtggacagc 50460
atcgggatgc tgccccgctt catccccgag aaccagcgca ccgtcgccgt atacagcttg 50520
aagatcgccg ggtggcacgg gcccaaggcc ccatacacga gcaccctgct gcccccggag 50580
ctgtccgaga cccccaacgc cacgcagcca gaactcgccc cggaagaccc cgaggattcg 50640
gccctcttgg aggaccccgt ggggacggtg gcgccgcaaa tcccaccaaa ctggcacata 50700
ccgtcgatcc aggacgccgc gacgccttac catcccccgg ccaccccgaa caacatgggc 50760
ctgatcgccg gcgcggtggg cggcagtctc ctggcagccc tggtcatttg cggaattgtg 50820
tactggatgc gccgccgcac tcaaaaagcc ccaaagcgca tacgcctccc ccacatccgg 50880
gaagacgacc agccgtcctc gcaccagccc ttgttttact agatacccccc ccttaatggg 50940
tgcggggggg tcaggtctgc ggggttggga tgggacctta actccatata aagcgagtct 51000
ggaagggggg aaaggcggac agtcgataag tcggtagcgg gggacgcgca cctgttccgc 51060
ctgtcgcacc cacagctttt tttgcgaacc gtcccgttcc gggatgccgt gccgcccgtt 51120
gcagggcctg gtgctcgtgg gcctctgggt ctgtgccacc agcctggttg tccgtggccc 51180
cacggtcagt ctggtatcaa actcatttgt ggacgccggg gccttggggc ccgacggcgt 51240
agtggaggaa gacctgctta ttctcgggga gcttcgcttt gtgggggacc aggtccccca 51300
caccacctac tacgatgggg tcgtagagct gtggcactac cccatgggac acaaatgccc 51360
acgggtcgtg catgtcgtca cggtgaccgc gtgcccacgt cgccccgccg tggctttcgc 51420
cctgtgtcgc gcgaccgaca gcactcacag ccccgcatat cccaccctgg agctgaatct 51480
ggcccaacag ccgcttttgc gggtccggag ggcgacgcgt gactatgccg gggtgtacgt 51540
gttacgcgta tgggtcgggg acgcaccaaa cgccagcctg tttgtcctgg ggatggccat 51600
agccgccgaa gggactctgg cgtacaacgg ctcggcccat ggctcctgcg acccgaaact 51660
gcttccgtat tcggccccgc gtctggcccc ggcgagcgta taccaacccg cccctaaccc 51720
ggcctccacc ccctcgacca ccacctccac cccctcgacc accatccccg ctccctcgac 51780
caccatcccc gctccccaag catcgaccac acccttcccc acgggagacc caaaacccca 51840
acctcacggg gtcaaccacg aacccccatc gaatgccacg cgagcgaccc gcgactcgcg 51900
atacgcgcta acggtgaccc agataatcca gatagccatc cccgcgtcca ttatagccct 51960
ggtgtttctg gggagctgta tttgctttat acacagatgt caacgccgct accgacgctc 52020

-continued

```
ccgccgcccg atttacaacc cccagatacc cactggcatc tcatgcgcgg tgaacgaagc  52080
ggccatggcc cgcctcggag ccgagctcaa atcgcatccg agcacccccc ccaaatcccg  52140
gcgccggtcg tcacgcacac caatgccctc cctgacggcc atcgccgaag agtcggagcc  52200
cgcgggggcg gctgggcttc cgacgccccc cgtggacccc acgacatcca ccccaacgcc  52260
tcccctgttg gtataggtcc acggccactg gccgggggca ccacataacc gaccgcagtc  52320
actgagttgg gaataaaccg gtattattta cctatatacg tgtatgtcca tttcttcccc  52380
ccccccccgg aaaccaaaga aggaaacaaa gaatggatgg gaggagttca ggaaaccggg  52440
gagagggccc gcggcgcatt taaggcgttg ttgtgttgac tttggctctt ctggcgggtt  52500
ggtgcggtgc tgtttgttgg gctcccattt tacccgaaga tcggctgcta tccccgggac  52560
atggatcgcg gggcggtggt ggggtttctt ctcggtgttt gtgttgtatc gtgcttggcg  52620
ggaacgccca aaacgtcctg gagacgggtg agtgtcggcg aggacgtttc gttgcttcca  52680
gctccggggc ctacggggcg cggcccgacc cagaaactac tatgggccgt ggaacccctg  52740
gatgggtgcg gcccccttaca cccgtcgtgg gtctcgctga tgccccccaa gcaggtgccc  52800
gagacggtcg tggatgcggc gtgcatgcgc gctccggtcc cgctggcgat ggcgtacgcc  52860
cccccggccc catctgcgac cgggggtcta cggacggact tcgtgtggca ggagcgcgcg  52920
gccgtggtta accggagtct ggttatttac ggggtccgag agacggacag cggcctgtat  52980
accctgtctg tgggcgacat aaaggacccg gctcgccaag tggcctcggt ggtcctggtg  53040
gtgcaaccgg ccccagttcc gaccccaccc ccgaccccag ccgattacga cgaggatgac  53100
aatgacgagg gcgaggacga aagtctagcc ggcactcccg ccagcgggac cccccggctc  53160
ccgcctcccc ccgccccccc gaggtcttgg cccagcgccc ccgaagtctc acacgtgcgt  53220
ggggtgaccg tgcgtatgga gactccggaa gctatcctgt tttcccccgg ggaggcgttt  53280
agcacgaacg tctccatcca tgccatcgcc cacgacgacc agacctacac catggacgtc  53340
gtctggttga ggttcgacgt gccgacctcg tgtgccgaga tgcgaatata cgaatcgtgt  53400
ctgtatcacc cgcagctccc agagtgtctg tccccggccg acgctccgtg cgccgcgagt  53460
acgtggacgt ctcgcctggc cgtccgcagc tacgcggggt gttccagaac aaaccccccg  53520
ccgcgctgtt cggccgaggc tcacatggag cccttcccgg ggctggcgtg gcaggcggcc  53580
tccgtcaatc tggagttccg ggacgcgtcc ccacaacact ccggcctgta tctgtgcgtg  53640
gtgtacgtca acgaccatat tcacgcatgg ggccacatta ccatcagcac cgcggcgcag  53700
taccggaacg cggtggtgga acagcccctc ccacagcgcg gcgcggattt ggccgagccc  53760
acccacccgc acgtcggggc ccctccccac gcgcccccaa cccacggcgc cctgcggtta  53820
ggggcggtga tgggggccgc cctgctgctg tctgcgctgg ggttgtcggt gtgggcgtgt  53880
atgacctgtt ggcgcaggcg tgcctggcgg gcggttaaaa gcagggcctc gggtaagggg  53940
cccacgtaca ttcgcgtggc cgacagcgag ctgtacgcgg actggagctc ggacagcgag  54000
ggagaacgcg accaggtccc gtggctggcc cccccggaga gacccgactc tccctccacc  54060
aatggatccg gctttgagat cttatcacca acggctccgt ctgtataccc ccgtagcgat  54120
gggcatcaat ctcgccgcca gctcacaacc tttggatccg gaaggcccga tcgccgttac  54180
tcccaggcct ccgattcgtc cgtcttctgg taaggcgccc catcccgagg ccccacgtcg  54240
gtcgccgaac tgggcgaccg ccggcgaggt ggacgtcgga gacgagctaa tcgcgatttc  54300
cgacgaacgc ggaccccccc gacatgaccg cccgcccctc gccacgtcga ccgcgccctc  54360
```

-continued gccacacccg cgacccccgg gctacacggc cgttgtctcc ccgatggccc tccaggctgt 54420
cgacgccccc tccctgtttg tcgcctggct ggccgctcgg tggctccggg gggcttccgg 54480
cctgggggcc gtcctgtgtg ggattgcgtg gtatgtgacg tcaattgccc gaggcgcata 54540
aagggccggt ggtccgccta gccgcagcaa attaaaaatc gtgagtcact gcgaccgcaa 54600
cttcccaccc ggagctttct tccggcctcg atgacgtccc ggctctccga tcccaactcc 54660
tcagcgcgat ccgacatgtc cgtgccgctt tatcccacgg cctcgccagt ttcggtcgaa 54720
gcctactact cggaaagcga agacgaggcg gccaacgact tcctcgtacg catgggccgc 54780
caacagtcgg tattaaggcg tcgacgcaga cgcacccgct gcgtcggcat ggtgatcgcc 54840
tgtctcctcg tggccgttct gtcgggcgga tttggggcgc tcctgatgtg gctgctccgc 54900
taaaagaccg catcgacacg cgcgtccttc ttgtcgtctc tcttcccccc catcaccccg 54960
caatttgcac ccagccttta actacattaa attgggttcg attggcaatg ttgtctcccg 55020
gttgattttt gggtgggtgg ggagtgggtg ggtggggagt gggtgggtgg ggagtgggtg 55080
ggtggggagt gggtgggtgg ggagtgggtg ggtggggagt gggtgggtgg ggagtgggtg 55140
ggtggggagt gggtgggtgg ggagtgggtg ggtggggagt ggcaaggaag aaacaagccc 55200
gaccaccaga cagaaaatgt aaccataccc aaaccgactc tgggggctgt ttgtggggtc 55260
ggaaccatag gatgaacaaa ccaccccgta cctcccgcac ccttgggtgc ggtggctcat 55320
cggcatctgt ccggtatggg ttgttcccca cccacttgcg ttcggacgtc ttagaatcat 55380
ggcggttttc tatgccgaca tcggttttct cccccgcaat aagacacgat gcgataaaat 55440
ctgtttgtga aatttattaa gggtacaaat tgccctagca caggggtggg gttagggccg 55500
ggtccccaca cccaaacgca ccaaacagat gcaggcagtg ggtcgagtac agccccgcgt 55560
acgaacacgt cgatgcgtgt gtcagacagc accagaaagc acaggccatc aacaggtcgt 55620
gcatatgtcg gtgggtttgg acgcgggggg ccatggtggt gataaagtta atggccgccg 55680
tccgccaggg ccacaggggc gacgtctctt ggttggcccg gagccactgg gtgtggacca 55740
gccgcgcgtg gcggcccaac atggcccctg tagccggggg cgggggatcg cgcacgtttg 55800
cagcgcacat gcgagacacc tcgaccacgg ttcggaagaa ggcccggtgg tccgcgggca 55860
acatcaccag gtgcgcaagc gcccgggcgt ccagagggta gagccctgag tcatccgagg 55920
ttggctcatc gcccgggtca tgccgcaagt gcgtgtgggt tgggcttccg gtgggcggga 55980
cgcgaaccgc ggtgtggagc cctacgcggg cccgagcgta cgctccatct tgtggggaga 56040
aggggtctgg gctcgccagg ggggcatact tgcccgggct atacagaccc gcgagccgta 56100
cgtggttcgc ggggggtgcg tggggtccgg ggctcccggg gaggccgggg ctcccgggga 56160
ggccggggct cccaccgggg ttgtcgtgga tccctggggt cacgcggtac cctggggtct 56220
ctgggagctc gcggtactct gggttcccta ggttctcggg gtggtcgcag aacccggggc 56280
tcccggggaa cacgcggtgt cctggggatt gttggcggtc ggacggcttc agatggcttc 56340
gagatcgtag tgtccgcacc gactcgtagt agacccgaat ctccacattg ccccgccgct 56400
tgatcattat caccccgttg cgggggtccg gagatcatgc gcgggtgtcc tcgaggtgcg 56460
tgaacacctc tggggtgcat gccggcggac ggcacgcctt ttaagtaaac atctgggtcg 56520
cccggcccaa ctggggccgg gggttgggtc tggctcatct cgagagccac ggggggaacc 56580
accctccgcc cagaaacttg ggcgatggtc gtacccggga ctcaacgggt taccggatta 56640
cggggactgt cggtcacggt cccgccggtt cttcgatgtg ccacacccaa ggatgcgttg 56700
ggggcgattt tgggcagcag cccgggagag cgcagcagag gacgctccgg gtcgtgcatg 56760
gcggttttgg ctgcctcccg gtcctcacgc cccctttat tgatctcatc gcgtacgtcg 56820
gcgtacgtcc tgggcccaac ccgcatgttg tccaggaagg tgtccgccat ttccagggcc 56880
cacgacatgc tcccccccga cgagcaggaa gcggtccacg caacggtcgc cgccggtcgc 56940
ctcgacgagg acgttcctcc tgcgggaagg cacgaacgcg ggtgagcccc ctcctccgcc 57000
cccgtgtccc ccctcctccg cccccgcgtc ccccctcctc cgcccccgcg tccccccctcc 57060
tccgcccccg cgtcccccct cctccgcccc cgcgtccccc ctcctccgcc cccgcgtccc 57120
ccctcctccg cccccgtgtc ccccctcctc cgcccaccca aggtgcttac ccgtgcacaa 57180
aggcggaccg gtgggtttct gtcgtcggag gcccccgggg tgcgtcccct gtgtttcgtg 57240
ggtggggtgg gtgggtcttt ccgcgtgtcc ctttccgatg cgatcccgat cccgagccgg 57300
ggcgtcgcga tgccgacgcc gtccgctccg acggccctct gcgagtcccg ctcccggtcc 57360
gcgtgctccg cagccgctcc cgtcgttcgt ggccggcgcc gtctgcgggc gtcggtcgcg 57420
ccgggccttt atgtgcgccg gagagacccg ccccccgccg cccgggcccg cccccggggc 57480
cggcgcggag tcgggcacgg cgccagtgct cgcacttcgc cctaataata tatatatatt 57540
gggacgaagt gcgaacgctt cgcgttctca cttcttttac ccggcggccc cgcccccttg 57600
gggcggtccc gcccgccggc caatgggggg gcggcaaggc gggcggccct tgggccgccc 57660
gccgtcccgt tggtcccaac gtccggcggg cgggaccggg ggcccgggga cggccaacgg 57720
gcgcgcgggg ctcgtatctc attaccgccg aaccgggaag tcggggcccg ggccccgccc 57780
ccggcccgtt cctcgttagc atgcggaacg gaagcggaaa ccaccggatc gggcggtaat 57840
gagatgccat gcggggcggg gcgcgggccc acccgccctc gcgccccgcc catggcagat 57900
ggcgcggatg ggcggggccg ggggttcgac caacgggccg cggccacggg cccccggcgt 57960
gccggcgtcg gggcggggtc gtgcataatg gaattccgtt cggggcgggc ccgcctgggg 58020
ggcgggggc cggcggcctc cgctgctcct ccttcccgcc ggcccctggg actatatgag 58080
cccgaggacg ccccgatcgt ccacacggag cgcggctgcc gacacggatc cacgacccga 58140
cgcgggaccg ccagagacag accgtcagac gctcgccgcg ccgggacgcc gatacgcgga 58200
cgaagcgcgg gagggggatc ggccgtccct gtccttttc ccacccaagc atcgaccggt 58260
ccgcgctagt tccgcgtcga cggcgggggt cgtcggggtc cgtgggtctc gccccctccc 58320
catcgagagt ccgtaggtga cctaccgtgc tacgtccgcc gtcgcagccg tatccccgga 58380
ggatcgcccc gcatcggcga tggcgtcgga gaacaagcag cgccccggct ccccgggccc 58440
caccgacggg ccgccgccca ccccgagccc agaccgcgac gagcgggggg ccctcgggtg 58500
gggcgcggag acggaggagg gcggggacga ccccgaccac gaccccgacc acccccacga 58560
cctcgacgac gcccggcggg acgggagggc ccccgcggcg ggcaccgacg ccggcgagga 58620
cgccggggac gccgtctcgc cgcgacagct ggccctgctg gcctccatgg tagaggaggc 58680
cgtccggacg atcccgacgc ccgaccccgc ggcctcgccg ccccggaccc ccgcctttcg 58740
agccgacgac gatgacgggg acgagtacga cgacgcagcc gacgccgccg gcgaccgggc 58800
cccggcccgg ggccgcgcac gggaggcccc gctacgcggc gcgtatccgg accccacgga 58860
ccgcctgtcg ccgcgcccgc cggcccagcc gccgcggaga cgtcgtcacg gccggcggcg 58920
gccatcggcg tcatcgacct cgtcggactc cgggtcctcg tcctcgtcgt ccgcatcctc 58980
ttcgtcctcg tcgtccgacg aggacgagga cgacgacggc aacgacgcgg ccgaccgcgc 59040
acgcgaggcg cgggccgtcg ggcggggtcc gtcgagcgcg gcgccggaag cccccgggcg 59100

-continued

```
gacgccgccc ccgcccgggc cacccccccct ctccgaggcc gcgcccaagc cccgggcggc  59160
ggcgaggacc cccgcggcct ccgcgggccg catcgagcgc cgccgggccc gcgcggcggt  59220
ggccggccgc gacgccacgg gccgcttcac ggccgggcag ccccggcggg tcgagctgga  59280
cgccgacgcg gcctccggcg ccttctacgc gcgctatcgc gacgggtacg tcagcgggga  59340
gccgtggccc ggcgccgggc ccccgccccc ggggcgggtg ctgtacggcg gcctgggcga  59400
cagccgcccg ggcctctggg gggcgcccga ggcggaggag gcgcgacgcc ggttcgaggc  59460
ctcgggcgcc ccggcggccg tgtgggcgcc cgagctgggc gacgccgcgc agcagtacgc  59520
cctgatcacg cggctgctgt acaccccgga cgcggaggcc atggggtggc tccagaaccc  59580
gcgcgtggtc cccggggacg tggcgctgga ccaggcctgc ttccggatct cgggcgccgc  59640
gcgcaacagc agctccttca tcaccggcag cgtggcgcgg gccgtgcccc acctgggcta  59700
cgccatggcg gccggccgct tcggctgggg cctggcgcac gcggcggccg ccgtggccat  59760
gagccgccga tacgaccgcg cgcagaaggg cttcctgctg accagcctgc gccgcgccta  59820
cgcgcccctg ttggcgcgcg agaacgcggc gctgacgggg gccgcgggga gccccggcgc  59880
cggcgcagat gacgaggggg tcgccgccgc cgccgccgcc gcaccgggcg agcgcgcggt  59940
gcccgccggg tacggcgccg cggggatcct cgccgccctg gggcggctgt ccgccgcgcc  60000
cgcctccccc gcggggggcg acgaccccga cgccgcccgc cacgccgacg ccgacgacga  60060
cgccgggcgc cgcgcccagg ccggccgcgt ggccgtggag tgcctggccg cctgccgcgg  60120
gatcctggag gcgctggccg agggcttcga cggcgacctg gcggccgtcc cggggctggc  60180
cggggcccgg cccgccagcc ccccgcggcc ggagggaccc gcgggccccg cttccccgcc  60240
gccgccgcac gccgacgcgc cccgcctgcg cgcgtggctg cgcgagctgc ggttcgtgcg  60300
cgacgcgctg gtgctcatgc gcctgcgcgg ggacctgcgc gtggccggcg gcagcgaggc  60360
cgccgtggcc gccgtgcgcg ccgtgagcct ggtcgccggg gccctgggcc ccgcgctgcc  60420
gcgggacccg cgcctgccga gctccgcggc cgccgccgcc gcggacctgc tgtttgagaa  60480
ccagagcctg cgccccctgc tggcggcggc ggccagcgca ccggacgccg ccgacgcgct  60540
ggcggccgcc gccgcctccg ccgcgccgcg ggaggggcgc aagcgcaaga gtcccggccc  60600
ggcccggccg cccggaggcg gcggcccgcg acccccgaag acgaagaaga gcggcgcgga  60660
cgcccccggc tcggacgccc gcgccccccct ccccgcgccc gcgcccccct ccacgccccc  60720
ggggcccgag cccgcccccg cccagcccgc ggcgccccgg gccgccgcgg cgcaggcccg  60780
cccgcgcccc gtggccgtgt cgcgccggcc cgccgagggc cccgaccccc tgggcggctg  60840
gcggcggcag cccccggggc ccagccacac ggcggcgccc gcggccgccg ccctggaggc  60900
ctactgctcc ccgcgcgccg tggccgagct cacggaccac ccgctgttcc ccgtcccctg  60960
gcgaccggcc ctcatgtttg acccgcgggc cctggcctcg atcgccgcgc ggtgcgccgg  61020
gcccgccccc gccgcccagg ccgcgtgcgg cggcggcgac gacgacgata acccccaccc  61080
ccacggggcc gccgggggcc gcctctttgg cccccctgcgc gcctcgggcc cgctgcgccg  61140
catggcggcc tggatgcgcc agatccccga ccccgaggac gtgcgcgtgg tggtgctgta  61200
ctcgccgctg ccgggcgagg acctggccgg cggcggggcc tcgggggggc cgccggagtg  61260
gtccgccgag cgcggcgggc tgtcctgcct gctggcggcc ctggccaacc ggctgtgcgg  61320
gccggacacg gccgcctggg cgggcaactg gaccggcgcc cccgacgtgt cggcgctggg  61380
cgcgcagggc gtgctgctgc tgtccacgcg ggacctggcc ttcgccgggg ccgtggagtt  61440
tctggggctg ctcgccagcg ccggcgaccg gcggctcatc gtggtcaaca ccgtgcgcgc  61500
```

```
ctgcgactgg cccgccgacg ggcccgcggt gtcgcggcag cacgcctacc tggcgtgcga  61560
cctgctgccc gccgtgcagt gcgccgtgcg ctggccggcg gcgcgggacc tgcgccgcac  61620
ggtgctggcc ccgggccgcg tgttcggccc gggggtcttc gcgcgcgtgg aggccgcgca  61680
cgcgcgcctg taccccgacg cgccgccgct gcgcctgtgc cgcggcggca acgtgcgcta  61740
ccgcgtgcgc acgcgcttcg gcccggacac gccggtgccc atgtccccgc gcgagtaccg  61800
ccgggccgtg ctgccggcgc tggacggccg ggcggcggcc tcggggacca ccgacgccat  61860
ggcgcccggc gcgccggact tctgcgagga ggaggcccac tcgcaccgcg cctgcgcgcg  61920
ctggggcctg ggcgcgccgc tgcggcccgt gtacgtggcg ctggggcgcg aggcggtgcg  61980
cgccggcccg gcccggtggc gcgggccgcg gagggacttt tgcgcccgcg ccctgctgga  62040
gcccgacgac gacgcccccc cgctggtgct gcgcggcgac gacgacggcc cgggggccct  62100
gccgccggcg ttgcccggga ttcgctgggc ctcggccacg ggccgcagcg gcaccgtgct  62160
ggcggcggcg ggggccgtgg aggtgctggg ggcggaggcg ggcttggcca cgcccccgcg  62220
acgggaagtt gtggactggg aaggcgcctg ggacgacgac gacggcggcg cgttcgaggg  62280
ggacggggtg ctgtaacggg ccgggacggg gcggggcgct tgcgaaaccc gaagacacaa  62340
taaacggcaa caacctgatt tagttttgca gtagcgttgt ttatttgagg ggcgggaggg  62400
ggcgaggggc gggagggggc gaggggcggg agggggcgag gggcgggagg gggcgagggg  62460
cgggaggggg cgaggggcgg gagggggcga ggggcgggag gggggcgaggg gcgggagggg  62520
gcgaggggcg ggagggggcg aggggcggga gggggcgagg ggcgggaggg ggcgaggggc  62580
gggagggggc gaggggcggg agggggcgag gggcgggagg gggcgagggg cgggaggggg  62640
cgaggggcgg gagggggcga ggggcgggag ggggcgaggg gcgggagggg gcgaggggcg  62700
ggagggggcg aggggcggtg gtggtgcgcg ggcgcccccg gagggtttgg atctctgacc  62760
tgagattggc ggcactgagg tagagatgcc cgaacccccc cgagggagcg cgggacgcgc  62820
cggggagggc tggggccggg gagggctggg gccggggagg gctggggccg gggagggctg  62880
gggccgggga gggctggggc cggggagggc tggggctggg gagggctggg gctggggagg  62940
gctggggctg gtggtgtgtg acaggagcgg cgtgttgcgc tgggggacgt ctggaggagc  63000
ggggggtgcg cggtgacgtg tggatgagga acaggagttg ttgcgcggtg agttgtcgct  63060
gtgagttgtg ttggtgggca ggtgtggtgg atgacgtgac gtgtgacgtg tggatgaggc  63120
gtgctctgtt ggtttcacct gtggcagccc gggcccccg cgggcggggc ggcgcgcaaa  63180
aaaggcgggc ggcggtccgg gcggcgtgcg cgcgcgcggc gggcgttggg ggcggggccg  63240
cgggagcggg gggaggagcg gggggaggag cggggggagg agcgrrggga ggagcggggg  63300
gaggagcggg gggaggagcg gggggaggag cggggggagg agcgggggga ggagcggggg  63360
gaggagcggg gggaggagcg gggggaggag cggggggagg agcgggggga ggagcggggg  63420
gaggagcggg gggaggagcg gggggaggag cggggggagg agcgaaaacg ggcccccccc  63480
saaacacacc ccccgggggt cgcgcgcggc cctttaaagc ggtggcggcg cagcccgggc  63540
cccccgcggg cgcgcgcgcg cgcaaaaaag gcgggcggcg gtccgggcgg cgtgcgcgcg  63600
cgcggcgggc gtggggggcg gggccgcggg agcgggggga ggagcggggg gaggagcggg  63660
gggaggagcg gggggaggag cggggggagg agcgggggga ggagcggggg gaggagcggg  63720
gggaggagcg gggggaggag cggggggagg agcgggggga ggagcggggg gaggagcggg  63780
gggaggagcg gggggaggag cggggggagg agcgggggga ggagcggggg gaggagcggg  63840
```

-continued

```
gggaggagcg aaaacgggcc ccccccaaaa cacaccccc gggggtcgcg cgcggccctt 63900
taaagcgggc ggcggcagcc cgggcccccc gcggccgaga cgagcgagtt agacaggcaa 63960
gcactactcg cctctgcacg cacatgcttg cctgtcaaac tctaccaccc cggcacgctc 64020
tctgtctcca tggcccgccg ccgccgccat cgcggccccc gccgcccccg gccgcccggg 64080
cccacgggcg ccgtcccaac cgcacagtcc caggtaaccc ttgttccgct tcccggtatg 64140
gtaattagaa actcattaat gggcggcccc ggccgccctt cccgcttccg gcaattcccg 64200
cggcccttaa tgggcaaccc cggtattccc cgcctcccgc gccgcgcgta accactcccc 64260
tggggttccg ggttatgcta attgcttttt tggcggaaca cacggcccct cgcgcattgg 64320
cccgcgggtc gctcaatgaa cccgcattgg tcccctgggg ttccgggtat ggtaatgagt 64380
ttcttcggga aggcgggaag ccccggggca ccgacgcagg ccaagcccct gttgcgtcgg 64440
tgggaggggc atgctaatgg ggttctttgg gggacaccgg gttggtcccc caaatcgggg 64500
gccgggccgt gcatgctaat gatattcttt gggggcgccg ggttggtccc cggggacggg 64560
gccgccccgc ggtgggcctg cctcccctgg gacgcgcggc cattggggga atcgtcactg 64620
ccgccccttt ggggagggga aaggcgtggg gtataagtta gccctggccc gacagtctgg 64680
tcgcatttgc acctcggcac tcggagcgag acgcagcagc caggcagact cgggccgccc 64740
cctctccgca tcaccacaga agccccgcct acgttgcgac ccccagggac cctccgtccg 64800
cgaccctcca gccgcatacg acccccatgg agccccgccc cggagcgagt acccgccggc 64860
ctgagggccg cccccagcgc gaggtgaggg gccgggcgcc atgtctgggg cgccatattg 64920
gggggcgcca tattgggggg cgccatgttg ggggaccccc gacccttaca ctggaaccgg 64980
ccgccatgtt gggggacccc cactcataca cgggagccgg gcgccatgtt ggggcgccat 65040
gttagggggc gtggaacccc gtgacactat atatacaggg accgggggcg ccatgttagg 65100
gggcgcggaa ccccctgacc ctatatatac agggaccggg gtcgccctgt tgggggtcgc 65160
catgtgaccc cctgacttta tatatacaga cccccccaaca catacacatg gcccctttga 65220
ctcagacgca gggcccgggg tcgccgtggg acccccctgac tcatacacag agacacgccc 65280
ccacaacaaa cacacaagga ccggggtcgc cgtgttaggg ggcgtggtcc ccactgactc 65340
atacgcaggg ccccccttact cacacgcatc tagggggggtg gggaggagcc gcccgccata 65400
tttgggggac gccgtgggac ccccgactcc ggtgcgtctg gagggcggga gaagagggaa 65460
gaagaggggt cgggatccaa aggacggacc cagaccacct ttggttgcag accccctttct 65520
ccccccctctt ccgaggccag caggggggca ggactttgtg aggcgggggg gggagagggg 65580
gaactcgtgg gcgctgattg acgcgggaaa tccccccatt cttacccgcc cccctttttt 65640
cccccttagcc cgccccggat gtctgggtgt ttccctgcga ccgagacctg ccggacagca 65700
gcgactctga ggcggagacc gaagtggggg ggcgggggga cgccgaccac catgacgacg 65760
actccgcctc cgaggcggac agcacggaca cggaactgtt cgagacgggg ctgctggggc 65820
cgcagggcgt ggatgggggg gcggtctcgg gggggagccc cccccgcgag gaagaccccg 65880
gcagttgcgg gggcgccccc cctcgagagg acggggggag cgacgagggc gacgtgtgcg 65940
ccgtgtgcac ggatgagatc gcgccccacc tgcgctgcga caccttcccg tgcatgcacc 66000
gcttctgcat cccgtgcatg aaaacctgga tgcaattgcg caacacctgc ccgctgtgca 66060
acgccaagct ggtgtacctg atagtgggcg tgacgcccag cgggtcgttc agcaccatcc 66120
cgatcgtgaa cgaccccccag acccgcatgg aggccgagga ggccgtcagg gcgggcacgg 66180
ccgtggactt tatctggacg ggcaatcagc ggttcgcccc gcggtacctg accctggggg 66240
```

```
ggcacacggt gagggccctg tcgcccaccc accctgagcc caccacggac gaggatgacg  66300
acgacctgga cgacggtgag gcgggggggc ggcgaggacc ctgggggagg aggaggagga  66360
gggggggaggg aggaataggc gggcgggga ggaaagggag ggcctgggag ggggcgtaac  66420
ctgatcgcgc cccccgttgt ctcttgcagc agactacgta ccgcccgccc cccgccggac  66480
gccccgcgcc cccccacgca gaggcgccgc cgcgcccccc gtgacgggcg gggcgtctca  66540
cgcagccccc cagccggccg cggctcggac agcgcccccc tcggcgccca tcgggccaca  66600
cggcagcagt aacaccaaca ccaccaccaa cagcagcggc ggcggcggct cccgccagtc  66660
gcgagccgcg gcgccgcggg gggcgtctgg cccctccggg ggggttgggg ttggggttgg  66720
ggttgttgaa gcggaggcgg ggcggccgag gggccggacg ggccccccttg tcaacagacc  66780
cgcccccctt gcaaacaaca gagaccccat agtgatcagc gactcccccc cggcctctcc  66840
ccacaggccc cccgcggcgc ccatgccagg ctccgccccc cgccccgggc ccaccgcgtc  66900
ctcggccgcg tcgggacccg cgcgcccccg cgcggccgtg gccccgtgcg tgcgagcgcc  66960
gcctccgggg cccggccccc gcgccccggc ccccggggcg gagccggccg cccgccccgc  67020
ggacgcgcgc cgtgtgcccc agtcgcactc gtccctggct caggccgcga accaagaaca  67080
gagtctgtgc cgggcgcgtg cgacggtggc gcgcggctcg ggggggccgg gcgtggaggg  67140
tggacacggg ccctcccgcg gcgccgcccc ctccggcgcc cccccgctcc cctccgccgc  67200
ctctgtcgag caggaggcgg cggtgcgtcc gaggaagagg cgcgggtcgg gccaggaaaa  67260
cccctccccc cagtccacgc gtcccccccct cgcgccggca ggggccaaga gggcggcgac  67320
gcaccccccc tccgactcag ggccgggggg gcgcggccag ggtgggcccg ggaccccccct  67380
gacgtcctcg gcggcctccg cctcttcctc ctctgcctct tcctcctcgg ccccgactcc  67440
cgcgggggcc gcctcttccg ccgccggggc cgcgtcctcc tccgcttccg cctcctcggg  67500
cggggccgtc ggtgccctgg gagggagaca agaggaaacc tccctcggcc cccgcgctgc  67560
ttctgggccg cgggggccga ggaagtgtgc ccggaagacg cgccacgcgg agacttccgg  67620
ggccgccccc gcgggcggcc tcacgcgcta cctgcccatc tcgggggtct ctagcgtggt  67680
cgccctgtcg ccttacgtga acaagacgat cacgggggac tgcctgccca tcctggacat  67740
ggagacgggg aacatcgggg cgtacgtggt cctggtggac cagacgggaa acatggcgac  67800
ccggctgcgg gccgcggtcc ccggctggag ccgccgcacc ctgctccccg agaccgcggg  67860
taaccacgtg atgccccccg agtacccgac ggcccccgcg tcggagtgga acagcctctg  67920
gatgaccccc gtggggaaca tgctgttcga ccagggcacc ctagtgggcg ccctggactt  67980
ccgcagcctg cggtctcggc acccgtggtc cggggagcag gggggcgtcga cccgggacga  68040
gggaaaacaa taagggacgc ccccccgtgtt tgtggggagg ggggggtcgg gcgctgggtg  68100
gtctctggcc gcgcccacta caccagccaa tccgtgtcgg ggaggggaaa agtgaaagac  68160
acgggcacca cacaccagcg ggtctttagt gttggcccta ataaaaaact caggggattt  68220
ttgctgtcta ttgggaaata aaggtttact tttgtatctt ttccctgtct gtgttggatg  68280
gatctcgggg gtgcgtggga gtgggggtgc gtgggagtgg gggtgcgtgg gagtgggggt  68340
gcgtgggagt gggggtgcgt gggagtgggg gtgcgtggga gtgggggtgc gtgggagtgg  68400
gggtgcgtgg gagtgggggt gcgtgggagt gggggtgcca tgttgggcag gctctggtgt  68460
taaccacaga gccgcggccc gggctgcctg accaccgatc cccgaaagca tcctgccatt  68520
ggcatggagc cagaaccaca gtgggttggg tgtgggtgtt aagtttccgc gagcgcctgc  68580
```

```
ccgcccggac tgacctggcc tctggccgcc acaaagggcg ggggggggtta actacactat  68640
agggcaacaa aggacgggag gggtggcggg gcgggacggg gcgcccaaaa gggggtcggc  68700
cacaccacag acgtgggtgt tggggggtgg ggcggagggg tgggggggggg ggagacagaa  68760
acaggaacat agttagaaaa caagaatgcg gtgcagccag agaatcacag gagacgaggg  68820
gatgggcgtg ttggttacca acccacaccc aggcatgctc ggtggtatga aggagggggg  68880
gcggtgcttc ttagagaccg ccgggggacg tggggttggt gtgcagaggc acgcgcaccc  68940
gcgcggccag gtgggccggt accccatccc ccctccccg acccttccca cccccgcgtg  69000
ccagagatca ccccggtccc ccggcacccg ccactcctcc atatcctcgc tttaggaaca  69060
actttagggg gggtacacac gcgccgtgca tttccttcca caccccccct cccccgcact  69120
cccccccccc cggcagtaag acccaagcat agagagccag gcacaaaaac acaggcgggg  69180
tgggacacat gccttcttgg agtacgtggg tcattggcgt ggggggttac agcgacaccg  69240
gccgaccccc tggcggtctt ccagccggcc cttagataag gggcagttg gtggtcggac  69300
gggtaagtaa cagagtctga ctaagggtgg gaggggggga aaagaacggg ctggtgtgct  69360
gtaacacgag cccacccgcg agtggcgtgg ccgaccttag cctctggggc gccccctgtc  69420
gtttgggtcc cccccctcta ttggggagaa gcaggtgtct aacctacctg gaaacgcggc  69480
gtctttgttg aaccacaccg gggcgccctt gacgagtggg ataacggggg aggaagggag  69540
ggaggagggt actgggggtg aagaaggggg gggggagaag cgagaacagg aaaggcgacg  69600
gagcccgaca aaacaccgag aaaaaaaaaa ccacagcgca tgcgccgggc cgttgtgggg  69660
ccccgggccg gggccccttg ggtccgccgg ggccccgggc cgggccgcca cgggggccgg  69720
ccgttggcgg taaccccgat tgtttatctc aggccccggg ccgggaaccc ggaaaagcct  69780
ccggggggcc tttttcgcgt cgcgtgccgg cgagcgggcc cggacggggc ccggaccgcc  69840
gcggtcgggg gccccctcgt cccgggccgt acgcggcctt cgccccgtga ggggacagac  69900
gaacgaaaca ttccggcgac ggaacgaaaa acaccccaga cgggttaaag aaacagaaac  69960
cgcaaccccc cccaccccg aaacggggaa aacaaaaaac agaccagcgg ccggccggcg  70020
cttaggggga ggatgtcgcc gacgcccctt ggccgccccg gctgcagggg ggcccggaga  70080
gccgcggcac ccggacgcgc ccggaaagtc tttcgcacca cccgcgatcg gcacggccgc  70140
gcccccgctt ttataaaggc tcagatgacg cagcaaaaac aggccacagc accacgtggg  70200
taggtgatgt aattttattt tcctcgtctg cggcctaatg gatttccggg cgcggtgccc  70260
ctgtctgcag agcacttaac ggattgatat ctcgcgggca cgcgcgccct taatggaccg  70320
gcgcggggcg gggggccgga tacccacacg ggcgggggg gggtgtcgcg ggccgtctgc  70380
tggcccgcgg ccacataaac aatgactctg ggcctttctg cctctgccgc ttgtgtgtgc  70440
gcgcgccggc tctgcggtgt cggcggcggc tgcggcggct gcggcggccg ccgtgttcgg  70500
tctcggtagc cggccggcgg gtggactcgc ggggggccgg agggtggaag gcaggggggt  70560
gtaggatggg tatcaggact tccacttccc gtccttccat cccccgttcc cctcggttgt  70620
tcctcgcccc ccccaacacc ccgccgcttt ccgttggggt tgttattgtt gtcgggatcg  70680
tgcgggccgg gggtcgccgg ggcaggggcg ggggcgtggg cgggggtgct cgtcgatcga  70740
ccgggctcag tgggggcgtg gggtgggtgg gagaaggcga ggagactggg gtgggggtgt  70800
cggtgggtgg ttgttttttg tggttgtttt tgtggctgtt cccgtccccc gtcacccccc  70860
tccctccgtc ccctccgtcc ccccgtcgcg ggtgtttgtg tttgtttatt ccgacatcgg  70920
tttatttaaa taaacacagc cgttctgcgt gtctgttctt gcgtgtggct gggggcttat  70980
```

-continued

```
atgtggggtc ccgggggcgg gatggggttt agcggcgggg ggcggcgcgc cggacggggc  71040
gctggagata acggcccccg gggaacgggg gaccggggct gggtctcccg aggtgggtgg  71100
gtgggcggcg gtggccgggc cgggccgggc cgggccgggc cgggtgggcg gggtttggaa  71160
aaacgaggag gaggaggaga aggagggggg gggggagacg gggggaaagc aaggacacgg  71220
cccggggggt gggagcgcgg gccgggccgc tcgtaagagc cgcgacccgg ccaccgggga  71280
gcgttgtcgc cgtcggtctg ccggcccccg tccctccctt ttttgaccaa ccagcgcccc  71340
ccccccccct caccaccatt cctactacca ccaccaccac caccaccgac acctcccgcg  71400
cacccccgcc cacatccccc cccaacccgc accacgagca cgggttgggg gtagcagggg  71460
atcaaagggg ggcaaggccg gcggggcggt tcgggggggg gggggggggg cgggagaccg  71520
agtaggcccc gcccatccgc ggcccctccc ggcagccacg ccccccagcg tcgggtgtca  71580
cggggaaaga gcagagggga gaggggagag ggggggagag gggagagggg gggagagggg  71640
agaggggggg agaggggaga gggggggaga ggggagaggg ggggagaggg gagagggggg  71700
gagaggggag aggggggggag aggggagagg gggggagagg ggagaggggg ggagggggag  71760
agaggggaga gggggtatat aaaccaacga aaagcgcggg aacggggata cggggcttgt  71820
gtggcacgac gtcgtggttg tgttactggg caaacacttg gggactgtag gtttctgtgg  71880
gtgccgaccc taggcgctat ggggattttg ggttgggtcg ggcttattgc cgttggggtt  71940
ttgtgtgtgc ggggggcctt gtcttcaacc gaatatgtta ttcggagtcg ggtggctcga  72000
gaggtggggg atatattaaa ggtgccttgt gtgccgctcc cgtctgacga tcttgattgg  72060
cgttacgaga ccccctcggc tataaactat gctttgatag acggtatatt tttgcgttat  72120
cactgtcccg gattggacac ggtcttgtgg gataggcatg cccagaaggc atattgggtt  72180
aaccccttttt tatttgtggc gggttttttg gaggacttga gtcaccccgc gtttcctgcc  72240
aacacccagg aaacagaaac gcgcttggcc ctttataaag agatacgcca ggcgctggac  72300
agtcgcaagc aggccgccag ccacacacct gtgaaggctg ggtgtgtgaa ctttgactat  72360
tcgcgcaccc gccgctgtgt agggcgacag gatttgggac ctaccaacgg aacgtctgga  72420
cggaccccgg ttctgccgcc ggacgatgaa gcgggcctgc agccgaagcc cctcaccacg  72480
ccgccgccca tcatcgccac gttggacccc accccgcgac gggacgccgc cgcaaaaagc  72540
agacgccgac gaccccactc ccggcgcatc taatgatgcc gcgacggaaa cccgtccggg  72600
ttcgggggc gaaccggccg cctgtcgctc gtcagggccg gcgggcgctc ctcgccgccc  72660
tagaggctgt cccgctggtg tgacgttttc ctcgtccgcg ccccccgacc ctcccatgga  72720
tttaacaaac ggggggggtgt cgcctgtggc gacctcggcg cctctggact ggaccacgtt  72780
tcggcgtgtg tttctgatcg acgacgcgtg gcggcccctg ttggagcctg agctggcgaa  72840
ccccttaacc gcccacctcc tgaccgaata taatcgtcgg tgccagaccg aagaggtgct  72900
gccgccgcgg gaggatgtgt tttcatggac tcgttattgc acccccgacg aggtgcgcgt  72960
ggttatcatc ggccaggacc catatcacca ccccggccag gcgcacggac ttgcgtttag  73020
cgtgcgcgcg aacgtgccgc ctcccctgag tcttcggaat gtcttggcgg ccgtcaagaa  73080
ctgttatccc gaggcacgga tgagcggcca cggttgcctg gaaaagtggg cgcgggacgg  73140
cgtcctgtta ctaaacacga ccctgaccgt caagcgcggg gcggcggcgt cccactctag  73200
aatcggttgg gaccgcttcg tgggcggagt tatccgccgg ttggccgcgc gccgccccgg  73260
cctggtgttt atgctctggg gcgcacatgc ccagaatgcc atcaggccgg accctcgggt  73320
```

ccattgcgtc ctcaagtttt cgcacccgtc gcccctctcc aaggttccgt tcggaacatg 73380
ccagcatttc ctcgtggcga atcgatatct cgagacccgg tcgatttcac ccatcgactg 73440
gtcggtttga aaggcatcga cgtccggggt tttcgtctgt gggggctttt gggtatttcc 73500
gatgaataaa gacggttaat ggttaaacct ctggtctcat acgggtcggt gatgtcgggc 73560
gtcgggggag agggagttcc ctctgtgctt gcgattctag cctcgtgggg ctggacgttc 73620
gacacgccaa accacgagtc agggatatcg ccagatacga ctcccgcaga ttccattcgg 73680
ggggccgctg tggcctcacc tgaccaacct ttacacgggg gcccggaacg ggaggccaca 73740
gcgccgtctt tctccccaac gcgcgcggat gacggcccgc cctgtaccga cgggccctac 73800
gtgacgtttg ataccctgtt tatggtgtcg tcgatcgacg aattagggcg tcgccagctc 73860
acggacacca tccgcaagga cctgcggttg tcgctggcca agtttagcat tgcgtgcacc 73920
aagacctcct cgttttcggg aaacgccccg cgccaccaca gacgcggggc gttccagcgc 73980
ggcacgcggg cgccgcgcag caacaaaagc cttcagatgt ttgtgttgtg caaacgcacc 74040
cacgccgctc gagtgcgaga gcagcttcgg gtcgttattc agtcccgcaa gccgcgcaag 74100
tattacacgt gatcttcgga cgggcggctc tgccccgccg tccccgtgtt cgtccacgag 74160
ttcgtctcgt ccgagccaat gcgcctccac cgagataacg tcatgctggc ctcgggggcc 74220
gagtaaccgc ccccccgcgc caccctcact gcccgtcgcg cgtgtttgat gttaataaat 74280
aacgcataaa tttggctggt tgtttgttgt ctttaatgga ccgcccgcaa ggggggggkg 74340
gcatttcagt gtcgggtgac gagcgcgatc cggccgggat cctaggaccc caaaagtttg 74400
tctgcgtatt ccagggcggg gctcagttga atctcccgca gcacctctac cagcaggtcc 74460
gcggtgggct ggagaaactc ggccgtcccg gggcaggcgg tcgtcggggg tggaggcgcg 74520
gcgcccaccc cgtgtgccgc gcctggcgtc tcctctgggg gcgacccgta aatggttgca 74580
gtgatgtaaa tggtgtccgc ggtccagacc acggtcaaaa tgccggccgt ggcgctccgg 74640
gcgctttcgc cgcgcgagga gctgacccag gagtcgaacg gatacgcgta catatgggcg 74700
tcccacccgc gttcgagctt ctggttgctg tcccggccta taaagcggta ggcacaaaat 74760
tcggcgcgac agtcgataat caccaacagc ccaatggggg tgtgttggat aacaacgcct 74820
ccgcgcggca ggcggtcctg gcgctcccgg ccccgtacca tgatcgcgcg ggtgccgtac 74880
tcaaaaacat gcaccacctg cgcggcgtcg ggcagtgcgc tggtcagcga ggccctggcg 74940
tggcataggc tatacgcgat ggtcgtctgt ggattggaca tctcgcggtg ggtagtgagt 75000
cccccgggcc gggttcggtg gaactgtaag gggacggcgg gttaatatac aatgaccacg 75060
ttcggatcgc gcagagccga tagtatgtgc ttactaatga cgtcatcgcg ctcgtggcgc 75120
tcccggagcg gatttaagtt catgcgaagg aattcggagg aggtggtgcg ggacatggcc 75180
acgtacgcgc tgttgaggcg caggttgccg ggcgtaaagc agatggcgac cttgtccagg 75240
ctaaggccct gggagcgcgt gatggtcatg gcaagcttgg agctgatgcc gtagtcggcg 75300
tttatggcca tggccagctc cgtagagtca atggactcga caaactcgct gatgttggtg 75360
ttgacgacgg acatgaagcc gtgttggtcc cgcaagacca cgtaaggcag gggggcctct 75420
tccagtaact cggccacgtt ggccgtcgcg tgccgcctcc gcagctcgtc cgcaaaggca 75480
aacacccgtg cgtacgtgta tcccatgagc gtataattgt ccgtctgcag ggcgacggac 75540
atcagccccc cgcgcggcga gccggtcagc atctcgcagc cccggaagat aacgttgtcc 75600
acgtacgtgc taaagggggc gccttcaaat gcctccccaa agagctcttg gaggattcgg 75660
aatctcccga ggaaggcccg cttcagcagc gcaaactggg tgtgaacggc ggcggtggtc 75720
tccggttccc cgggggtgta gtggcagtaa aacacgtcga gctgttgttc gtccagcccc 75780
gcgaaaataa cgtcgaggtc gtcgtcggga aaatcgtccg ggcccccgtc ccgcggcccc 75840
agttgcttaa aatcaaacgc acgctcgccg ggggcgcctg cgtcggccat taccgacgcc 75900
tgcgtcggca cccccgaaga tttggggcgc agagacagaa tctccgccgt tagttctccc 75960
atgcgggcgt aggcgagggt cctctgggtc gcatccaggc ccgggcgctg cagaaagttg 76020
taaaaggaga taagcccgct aaatatgagc cgcgacagga acctgtaggc aaactccacc 76080
gaagtctccc cctgagtctt tacaaagctg tcgtcacgca acactgcctc gaaggcccgg 76140
aacgtcccac taaacccaaa aaccagtttt cgcaggcgcg cggttaccgc gatctggctg 76200
ttgaggacgt aagtgacgtc gttgcgggcc acgaccagct gctgtttgct gtgcacctcg 76260
cagcgcatgt gccccgcgtc ctggtcctgg ctctgcgagt agttggtgat gcggctggcg 76320
ttggccgtga gccacttttc aatagtcagg ccgggctggt gtgtcagccg tcggtattcg 76380
tcaaactcct tgaccgacac gaacgtaagc acggggaggg tgaacacgac aaactccccc 76440
tcacgggtca ccttcaggta ggcgtggagc ttggccatgt acgcgctcac ctctttgtgg 76500
gaggagaaca accgcgtcca gccggggagg ttggcggggt tggtgatgta gttttccggg 76560
acgacgaagc gatccacgaa ctgcatgtgc tcctcggtga tgggtaggcc gtactccagc 76620
accttcatga ggttaccgaa ctcgtgctcg atgcaccgtt tgttgttaat aaaaatggcc 76680
cagctatacg agaggcgggc gtactcccgc agcgtgcggt tgcagatgag gtacgtgagc 76740
acgttctcgc tctggcggac ggaacaccgc agtttctggt gctcgaaggt cgactccagg 76800
gacgccgtct gtgtcggcga gcccacacac accaacacgg gccgcaggcg ggccgcgtac 76860
tggggggtgt ggtacagggc gttaatcatc caccagcaat acaccacggc cgtgaggagg 76920
tgacgcccaa ggagcccggc ctcgtcgatg acgatcacgt tgctgcgggt aaaggccggc 76980
agcgccccgt gggtggccgg ggccaaccgc gtcagggcgc cctcggccaa ccccagggtc 77040
cgttccaggg cggccagggc gcgaaactcg ttccgcgact cctcgccccc ggaggcggcc 77100
agggtgcgct tcgtgaggtc caaaatcacc tcccagtagt acgtcagatc tcgtcgctgc 77160
aggtcctcca gcgaggcggg gttgctggtc agggtgtacg ggtactgccc cagttgggcc 77220
tggacgtgat tcccgcgaaa cccaaattca tgaaagatgg tgttgatggg tcggctgaga 77280
aaggcgcccg agagtttggc gtacatgttt tgggccgcaa tgcgcgtggc gcccgtcacc 77340
acacagtcca agacctcgtt gattgtctgc acgcacgtgc tctttccgga gccagcgttg 77400
ccggtgataa gatacaccgc gaacggaaac tccctgaggg gcaggcctgc gggggactct 77460
aaggccgcca cgtcccggaa ccactgcaga cggggcactt gcgctccgtc gagctgttgt 77520
tgcgagagct ctcggatgcg cttaaggatt ggctgcaccc cgtgcataga cgtaaaattt 77580
aaaaaggcct cggccctccc tggaacggct ggtcggtccc cgggttgctg aaggtgcggc 77640
gggccgggtc tctgtccgtc tagctggcgc tccccgccgg ccgccgccat gaccgcacca 77700
cgctcgcggg cccccactac gcatgcgcgg ggggacacgg aagcgctgtg ctcccccgag 77760
gacggctggg taaaggttca ccccacccc ggtacgatgc tgttccgcga gattctccac 77820
gggcagctgg ggtataccga gggccagggg gtgtacaacg tcgtccggtc cagcgaggcg 77880
accacccggc agctgcaggc ggcgatcttt cacgcgctcc tcaacgccac cacttaccgg 77940
gacctcgagg cggactggct cggccacgtg gcggcccgcg gtctgcagcc ccaacggctg 78000
gttcgccggt acaggaacgc ccgggaggcg gatatcgccg ggtggccgga gcgggtgttc 78060

```
gacacgtggc ggaacacgct taggacgacg ctgctggact ttgcccacgg gttggtcgcc  78120
tgctttgcgc cgggcggccc gagcggcccg tcaagcttcc ccaaatatat cgactggctg  78180
acgtgcctgg ggctggtccc catattacgc aagcgacaag aagggggtgt gacgcagggt  78240
ctgagggcgt ttctcaagca gcacccgctg acccgccagc tggccacggt cgcggaggcc  78300
gcggagcgcg ccggccccgg gttttttgag ctggcgctgg ccttcgactc cacgcgcgtg  78360
gcggactacg accgcgtgta tatttactac aaccaccgcc ggggcgactg gctcgtgcga  78420
gaccccatca gcgggcagcg cggagaatgt ctggtgctgt ggcctccctt gtggaccggg  78480
gaccgtctgg tcttcgattc gcccgtacag cggctgtttc ccgagatcgt cgcgtgtcac  78540
tccctccggg aacacgcgca cgtctgccgg ctgcgcaata ccgcgtccgt caaggtgctg  78600
ctggggcgca agagcgacag cgagcgcggg gtggccggcg ccgcgcgggt cgttaacaag  78660
gtgttggggg aggacgacga gaccaaggcc gggtcggccg cctcgcgcct cgtgcggctt  78720
atcatcaaca tgaagggcat gcgccacgta ggcgacatta acgacactgt gcgtgcctac  78780
ctcgacgagg ccgggggggca cctgatagac gccccggccg tcgacggtac cctcccggga  78840
ttcggcaagg gcggaaacag ccgcgggtct gcgggccagg accagggggg gcgggcgccg  78900
cagcttcgcc aggccttccg cacggccgtg gttaacaaca tcaacggcgt gttggagggc  78960
tatataaata acctgtttgg aaccatcgag cgcctgcgcg agaccaacgc gggcctggcg  79020
acccagttgc aggagcgcga ccgcgagctc cggcgcgcaa catcgggggc cctggagcgc  79080
cagcagcgcg cggccgacct ggcggccgag tccgtgaccg ggggatgcgg cagccgccct  79140
gcgggggcgg acctgctccg ggccgactat gacattatcg acgtcagcaa gtccatggac  79200
gacgacacgt acgtcgccaa cagttttcag tacccgtaca tcccttcgta cgcccaggac  79260
ctggagcgcc tgtcgcgcct ctgggagcac gagctggtgc gctgtttcaa aattctgtgt  79320
caccgcaaca accagggcca agagacgtcg atctcgtact ccagcggggc gatcgccgca  79380
ttcgtcgccc cctactttga gtcagtgctt cgggcccccc gggtaggcgc gccatcacgg  79440
gctccgatgt catcctgggg gaggaggagt tatgggatgc ggtgtttaag aaaacccgcc  79500
tgcaaacgta cctgacagac atcgcggccc tgttcgtcgc ggacgtccag cacgcagcgc  79560
tgccccgcc cccctccccg gtcggcgccg atttccggcc cggcgcgtcc ccgcggggcc  79620
ggtccagatc gcggtcgccc ggaagaactg cgcgaggcgc gccggaccag ggcgggggca  79680
tcgggcaccg ggatggccgc cgcgacggcc gacgatgagg ggtcggccgc caccatcctc  79740
aaacaggcca tcgccgggga ccgcagcctg gtcgaggcgg ccgaggcgat tagccagcag  79800
acgctgctcc gcctggcctg cgaggtgcgc caggtcggcg accgccagcc gcggtttacc  79860
gccaccagca tcgcgcgcgt cgacgtcgcg cctgggtgcc ggttgcggtt cgttctggac  79920
gggagtcccg aggacgccta tgtgacgtcg gaggattact ttaagcgctg ctgcggccag  79980
tccagttatc gcggcttcgc ggtggcggtc ctgacggcca acgaggacca cgtgcacagc  80040
ctggccgtgc ccccccctcgt tctgctgcac cggttctccc tgttcaaccc cagggacctc  80100
ctggactttg agcttgcctg tctgctgatg tacctggaga actgcccccg aagccacgcc  80160
accccgtcga cctttgccaa ggttctggcg tggctcgggg tcgcgggtcg ccgcacgtcc  80220
ccattcgaac gcgttcgctg ccttttcctc cgcagttgcc actgggtcct aaacacactc  80280
atgttcatgg tgcacgtaaa accgttcgac gacgagttcg tcctgcccca ctggtacatg  80340
gcccggtacc tgctggccaa caacccgccc cccgttctct cggccctgtt ctgtgccacc  80400
ccgacaagct cctcattccg gctgccgggg ccgccccccc gctccgactg cgtggcctat  80460
```

aaccccgccg ggatcatggg gagctgctgg gcgtcggagg aggtgcgcgc gcctctggtc 80520
tattggtggc tttcggagac cccaaaacga cagacgtcgt cgctgtttta tcagttttgt 80580
tgaattttag gaaataaacc cggttttgtt tctgtggcct cccgacggat gcgcgtgtcc 80640
ttactccgtc ttggtgggtg ggtggctgtg tatggcgtcc catctgtgcg gggagggggg 80700
caagtcggca cgtattcgga cagactcaag cacacacggg ggagcgctct tgtctcaggg 80760
caatgttttt attggtcaaa ctcaggcaaa cagaaacgac atcttgtcgt caaagggata 80820
cacaaacttc ccccctcgc cccatactcc cgccagcacc ccggtaaaca ccaactcaat 80880
ctcgcgcagg atttcgcgca ggtgatgagc gcagtccacg ggggggagca caaggggccg 80940
cgggtataga tcgacgggga cgccgaccga ctccccgcct ccgggacaga cacgcacgac 81000
gcgccgccag tagtgctctg cgtccagcaa ggcgccgccg cggaaggcag tgggggcaa 81060
ggggtcgctg gcctcaaagg gggacacccg aacgctccag tactccgcgt ccaaccgttt 81120
attaaacgcg tccaagataa ggcggtcgca ggcgtcctcc ataaggcccc gggccgtgag 81180
tgcgtcctcc tccggcacgc ctgccgttgt caggcccagg acccgtcgca gcgtgtcgcg 81240
tacgaccccg gccgccgtgg tgtacgcggg cccgcggaga ggaaatcccc caagatggtc 81300
agtgttgtcg cgggagttcc agaaccacac tcccgcctgg ctccaggcga ctgcgtgggt 81360
gtagacgccc tcgagggcca ggcacagtgg gtgccgcagc cggaggccgt tggccctaag 81420
cacggctccc acggccgtct cgatggcccg ccgggcgtcc tcgatcaccc cggaagccgc 81480
atccgcgtct tgggggtcca cgttaaagac accccagaac gcacccccat cgcccccgca 81540
gaccgcgaac ttcaccgagc tggccgtctc ctcgatctgc aggcagacgg cggccattac 81600
cccacccagg agctgccgca gcgcagggca ggtgttgcac gtgtccggga ccaggcgctc 81660
caagacggcc ccggcccagg gctctgaggg agcggccacc accagcgcgt ccagtcttgc 81720
taggcccgtc cggccgtggg ggtccgccag cccgctcccc ccgaggtcgg ccagggccgc 81780
caggagctgg gcgcgaagtc cggggaagca aaaccgcgcc gtccagacgg gcccgacggc 81840
cgcgggcggg tctaacagtt ggatgatttt agtggcggga tgccaccgcg ccaccgcctc 81900
ccgcactgcg ggcaggaggc atccggctgc cgccgaggcc acgccgggcc aggctcgcgg 81960
ggggaggacg accctgaccc ccaccgcggg ccaggccccc aggagcgcgg cgtaagcggc 82020
cgcggccccg cgcaccaggt cccgtgccga ctcggccgtg gccggcacgg tgaacgtggg 82080
ccaacccgga aaccccagga cggcaaagta cgggacgggt cccccccgga cctcaaactc 82140
gggccccaga aaggcaaaga cgggggccag ggccccgggg gcggcgtgga ccgtggtatg 82200
ccactgccgg aaaagggcga cgagcgccgg cgcggagaac ttctcgccgg cgcttacaaa 82260
gtagtcgtaa tcgcggggca gcagcacccg tgccgtgact cgttgtgggt gcccgcgtgg 82320
ccgcaggccc acctcgcaca cctcgaccag gtccccgaac gcgccctcct tcttgatcgg 82380
cggaaacgca agagtctggt attcgcgcgc aaatagcgcg gttccggtgg tgatgttaac 82440
ggtcagcgaa gcggtggacg cgcactgggg ggtgtcgcga atggccgcca ggcgcgccca 82500
cgccagccgc gcgtcgggat gctcggcaac gcgcgccgcc agggccatag ggtcgatgtc 82560
aatgttggcc tccgcgacca ggagagcggc gcgaggggcg gcgggcgggc cccacgacgc 82620
tctctcaact ttcaccacca gtcccgtgcg tgggtccgag ccgatacgca gcgggggcgaa 82680
cagggccacc ggcccggtct ggtgctccag ggccgccagg acgcacgcgt acagcgcccg 82740
ccacagagtc gggttctcca ggggctccag cggggaggcg gccggcgtcg tcgcggcgcg 82800

-continued

```
ggcggccgcc acgacggcct ggacggagac gtccgcggag ccgtagaaat cccgcagctc  82860
cgtcgcggtg acggagacct ccgcaaagcg cgcgcgaccc tcccctgcgg cgttgcgaca  82920
tacaaaatac accagggcgt ggaagtactc gcgagcgcgg gggggcagcc ataccgcgta  82980
aagggtaatg gcgctgacgc tctcctccac ccacacgata tctgcggtgt ccatcgcacg  83040
gcccctaagg atcacgggcg gtctgtgggt cccatgctgc cgtgcctggc cgggcccggt  83100
gggttgcgga aaccggtgac gggggggggg cggtttttgg ggttggggtg ggaaacggcc  83160
cgggtccggg ggccaacttg gcccctcggt gcgttccggc aacagcgccg ccggtccgcg  83220
gacgaccacg taccgaacga gtgcggtccc gagacttata gggtgctaaa gttcaccgcc  83280
ccctgcatca tgggccaggc ctcggtgggg agctccgaca gcgccgcctc caggatgatg  83340
tcagcgttgg ggttggcgct ggatgagtgc gtgcgcaaac agcgccccca cgcgggcacg  83400
cgtagcttga agcgcgcgcc cgcaaactcc cgcttgtggg ccataagcag ggcgtacagc  83460
tgcctgtggg tccggcaggc gctgtggtcg atgtggtggg cgtccaacaa ccccacgatt  83520
gtctgtttgg tgaggttttt aacgcgcccc gccccgggaa acgtctgcgt gcttttggcc  83580
atctgcacgc caaacagttc gccccagatt atcttgaaca gcgccaccgc gtggtccgtc  83640
tcactaacgg acccgcgcgg gggacagccg cttagggcgt cggcgacgcg cttgacggct  83700
tcctccgaga gcagaagtcc gtcggttacg ttacagtggc ccagttcgaa caccagctgc  83760
atgtagcggt cgtagtgggg ggtcagcagg tccagcacgt catcggggcc gaaggtcctc  83820
ccagatcccc cggccgccga gtcccaatgc aggcgcgcgg ccatggtgct gcacaggcac  83880
aacagctccc agacaggggt tacgttcagg gtgggggca gggccacgag ctccagctct  83940
ccggtgacgt tgatcgtggg gatgacgccc gtggcgtagt ggtcatagat ccgccgaaat  84000
atggcgctgc tgcgggtggc catgggaacg cggagacagg cctccagcaa cgccaggtaa  84060
ataaaccgcg tgcgtcccat caggctgttg aggttgcgca tgagcgcgac aatttccgcc  84120
ggcgcgacat cggaccggag gtatttttcg acgaaaagac ccacctcctc cgtctcggcg  84180
gcctgggccg gcagcgacgc ctcgggatcc cggcaccgca gctcccgtag atcgcgctgg  84240
gccctgaggg cgtcgaaatg tacgccccgc aaaaacagac agaagtcctt tggggtcagg  84300
gtatcgtcgt gtccccagaa gcgcacgcgt atgcagttta gggtcagcag catgtgaagg  84360
atgttaaggc tgtccgagag acacgccagc gtgcatctct caaagtagtg tttgtaacgg  84420
aatttgttgt agatgcgcga cccccgcccc agcgacgtgt cgcatgccga cgcgtcacag  84480
cgccccttga accggcgaca cagcaggttt gtgacctggg agaactgcgc gggccactgg  84540
ccgcaggaac tgaccacgtg gttcaggagc atgggcgtaa agacgggctc cgagcgcgcc  84600
ccggagccgt ccatgtaaat cagtagctcc cccttgcgga gggtgcgcac ccgtcccagg  84660
gactggtaca cggacaccat gtccggtccg tagttcatgg gtttcacgta ggcgaacatg  84720
ccatcaaagt gcaggggatc gaagctgagg cccacggtta cgaccgtcgt gtatataacc  84780
acgcggtatt ggccccacgt ggtcacgtcc ccgagggggg tgagcgagtg aagcaacagc  84840
acgcggtccg taaactgacg gcagaaccgg gccacgatct ccgcgaagga gaccgtcgac  84900
gaaaaaatgc agatgttatc gcccccgcca aggcgcgctt ccagctcccc aaagaacgtg  84960
gccccccggg cgtccggaga ggcgtccgga gacgggccgc tcggcggccc gggcgggcgc  85020
agggcagcct gcaggagctc ggtccccaga cgcgggagaa acaggcaccg gcgcgccgaa  85080
aacccgggca tggcgtactc gccgaccacc acatgcacgt ttttttcgcc ccggagaccg  85140
cacaggaagt ccaccaactg cgcgttggcg gttgcgtcca tggcgatgat ccgaggacat  85200
```

gtgcgcagca ggcgtagcat taacgcatcc acgcggccca gttgctgcat cgttggcgaa 85260
tagagctggc ccagcgtcga cataacctcg tccagaacga ggacgtcgta gttgttcaga 85320
aggttggggc ccacgcgatg aaggctttcc acctggacga taagtcggtg gaaggggcgg 85380
tcgttcataa tgtaattggt ggatgagaag taggtgacaa agtcgaccag gcctgactca 85440
gcgaaccgcg tcgccagggt ctgggtaaaa ctccgacgac aggagacgac gagcacactc 85500
gtgtccggag agtggatcgc ttcccgcagc cagcggatca gcgcggtagt tttcccgac 85560
cccattggcg cgcggaccac agtcacgcac ctggccgtcg gggcgctcgc gttggggaag 85620
gtgacgggtc cgtgctgctg ccgctcgatc gttgttttcg ggtgaacccg gggcacccat 85680
tcggccaaat cccccccgta taacatccgc gctagcgata cgctcgacgt gtactgttcg 85740
cactcgtcgt ccccaatggg acgcccggcc cccagaggat cccccgactc cgcgcccccc 85800
acgaaaggca tgaccggggc gcggacggcg tggtgggtct ggtgtgtgca ggtggcgacg 85860
tttgtggtct ctgcggtctg cgtcacgggg ctcctcgtcc tggcctctgt gttccgggca 85920
cggtttccct gcttttacgc cacggcgagc tcttatgccg gggttaactc cacggccgag 85980
gtgcgcgggg gtgtagccgt gcccctcagg ttggacacgc agagccttgt gggcacttat 86040
gtaatcacgg ccgtattgtt gttggccgcg gccgtgtatg ccgtggtcgg cgccgtgacc 86100
tcccgctacg accgcgccct ggacgcgggc cgccgtctgg ctgcggcccg catggccatg 86160
ccgcacgcca cgctgatcgc cggaaacgtc tgctcttggt tgctgcagat caccgtcctg 86220
ctgctggccc atcgcatcag ccagctggcc cacctggttt acgtcctgca ctttgcgtgt 86280
ctggtgtatt ttgcggccca tttttgcacc agggggggtcc tgagcgggac gtatctgcgt 86340
caggtgcacg gcctgatgga gctggccccg acccatcatc gcgtcgtcgg cccggctcgc 86400
gccgtgctga caaacgcctt gctgttgggc gtcttcctgt gcacggccga cgccgcggta 86460
tccctgaata ccatcgccgc gttcaacttt aatttttcgg ccccgggcat gctcatctgc 86520
ctgaccgtgc tgttcgccat tctcgtcgta tcgctgttgt tggtggtcga gggggtgttg 86580
tgtcactacg tgcgcgtgtt ggtgggcccc cacctggggg ccgttgccgc cacgggcatc 86640
gtcggcctgg cctgcgagca ctattacacc aacggctact acgtggtgga gacgcagtgg 86700
ccgggggcac agacgggagt gcgcgtcgcc ctcgccctgg tcgccgcctt tgccctcggc 86760
atggccgtgc tccgctgcac ccgcgcctat ctgtatcaca ggcggcacca caccaaattt 86820
tttatgcgca tgcgcgacac gcgacaccgc gcacattccg ccctcaagcg cgtacgcagt 86880
tccatgcgcg gatcgcgaga cggccgccac aggcccgcgc ccggcagccc gcccgggatt 86940
cccgaatatg cggaagaccc ctacgcgatc tcatacggcg gccagctcga ccggtacgga 87000
gattccgacg gggagccgat ttacgacgag gtggcggacg accaaaccga cgtattgtac 87060
gccaagatac aacacccgcg gcacctgccc gacgacgagc ccatctatga caccgttggg 87120
gggtacgacc ccgagcccgc cgaggacccc gtgtacagca ccgtccgccg ttggtagctg 87180
tttggttccg ttttaataaa ccgtttgtgt ttaacccgac cgtggtgtat gtctggtgtg 87240
tggcgtccga tcccgttact atcaccgtcc cccccccccc tcaaccccgg cgattgtggg 87300
ttttttaaaa acgacacgcg tgcgaccgta tacagaacat tattttggtt tttattcgct 87360
atcggacatg gggggtggaa actgggtggc ggggcaggcg cctccggggg tccgccggtg 87420
agtgtggcgc gagggggggt ccgacgaacg caggcgcggt ctccccgggg cccgcgtaac 87480
cacgcgcata tccgggggca cgtagaaatt accttcctct tcggactcga tatccacgac 87540
gtcaaagtcg tgggcggtca gcgagacgac ctccccgtcg tcggtgatga ggacgttgtt 87600
tcggcagcag cagggccggg ccccggagaa cgagaggccc atagctcggc gagcgtgtcg 87660
tcgaacgcca ggcggctgct tcgctggatg gccttataga tctccggatc gatgcggacg 87720
ggggtaatga tcagggcgat cggaacggcc tggttcggga gaatggacgc cttgctgggt 87780
cctgcggccc cgagagcccc ggcgccgtcc tccaggcgga acgttacgcc ctcctccgcg 87840
ctggtgcggt gcctgccgat aaacgtcacc agatgcgggt ggggggggca gtcggggaag 87900
tggctgtcga gcacgtagcc ctgcaccaag atctgcttaa agttcgggtg gcgggggttc 87960
gcgaagacgg gctcgcggcg gaccagatcc ccggagctcc aggacacggg ggagatggtg 88020
tggcgtccga ggtcgggggc gccaaacaga agcacctccg agacaacgcc gctatttaac 88080
tccaccaagg cccgatccgc ggcggagcac cgcctttttt cgcccgaggc gtgggcctct 88140
gaccaggcct ggtcttgcgt gacgagagcc tcctccgggc cggggacgcg cccgggcgcg 88200
aagtatcgca cgctgggctt cgggatcgac cggataaatg cccggaacgc ctccggggac 88260
cggtgtgcca tcaagtcctc gtacgcggag gccgtggggt cgctggggtc catggggtcg 88320
aaagcgtact tggcccggca tttgacctcg taaaaggcca ggggggtctt ggggactggg 88380
gccaggtagc cgtgaatgtc ccgaggacag acgagaatat ccagggacgc cccgaccatc 88440
cccgtgtgac cgtccatgag gaccccacac gtatgcacgt tctcttcggc gaggtcgctg 88500
ggttcgtgga agataaagcg ccgcgtgtcg gcgccggcct cgccgccgtc gtccgcgcgg 88560
cccacgcagt agcgaaacag caggcttcgg gccgtcggct cgttcacccg cccgaacatc 88620
accgccgaag actgtacatc cggtcgcagg ctggcgttgt gcttcagcca ctggggcgag 88680
aaacacggac cctgggggcc ccagcggagg gtggatgcgg tcgtgaggcc ccgccggagc 88740
agggcccata gctggcagtc ggcctggttt tgcgtggccg cctcgtaaaa ccccatgagg 88800
ggccggggcg ccacggcgtc cgcggcggcc ggggggggcgc ggcgcgtcag gcgccatagg 88860
tgccggccga gtccgcggtc caccataccc gcctcctcga ggaccacggc cagggaacac 88920
agataatcca ggcgggccca gaggggaccg atggccagag gggcgcggac gccgcgcagc 88980
aacccgcgca ggtggcgctc gaacgtctcg gctagtatat gggagggcag cgcgttgggg 89040
atcaccgacg ccgaccacat agagtcaagg tccggggagt cgggatcggc gtccgggtcg 89100
cgggcgtggg tgcccccagg agatagcgga atgtccgggg tcggaggccc ggaggcgtca 89160
gaaagtgccg gcgacgcggc ccggggcttt tcgtctgcgg tgtcggtggc gtgctgatca 89220
cgtgggggt tatcgggcga atgggagctc gggtccacag ctgacgtcgt ctggggtggg 89280
gggggcaggg gacggaaggt ggttgtcagc ggaagactgt tagggcgggg gcgcttgggg 89340
gggctgtcgg ggccacgagg ggtgtcctcg gccagggccc agggacgctt agtcacggtg 89400
cgtcccggcg gacatgctgg gcctaccgtg gactccattt ccgagacgac gtggggggag 89460
cggtggttga gcgcgccgcc gggtgaacgc tgattctcac gacagcgcgt gccgcgcgca 89520
cgggttggtg tgatacaggc gggacaccag caccaggaga ggcttaagct cgggaggcag 89580
cgccaccgac gacagtatcg ccttgtgtgt gtgctggtaa tttatacacc gatccgtaaa 89640
cgcgcgccga atcttgggat tgcggaggtg gcgccggatg ccctctggga cgtcatacgc 89700
caggccgtgg gtgttggtct cggccgagtt gacaaacagg gctgggtgca gcacgcagcg 89760
ataggcgagc agggccaggg cgaagtccgg cgacagctgg ttgttgaaat actggtaacc 89820
gggaaaccgg gtcacgggta cgcccaggct cggggcgacg tacacgctaa ccaccaactc 89880
cagcagcgtc tggcccaggg cgtacaggtc aaccgctagc ccgacgtcgt gcttcaggcg 89940
gtggttggta aattcggccc gttcgttgtt aaggtatttc accaacagct ccgggggctg 90000
gttataccccg tgacccacca gggtgtgaaa gttggctgtg gttagggcgg tgggcatgcc 90060
aaacatccgg ggggacttga ggtccggctc ctggaggcaa aactgccccc gggcgatcgt 90120
ggagttggag ttgagggtga cgaggctaaa gtcggcgagg acggcccgcc ggagcgagac 90180
ggcgtccgac cgcagcatga cgaggatgtt ggcgcacttg atatccaggt ggctgatccc 90240
gcaggtggtg tttaaaaaca caacggcacg ggccagctcc gtgaagcact ggtggagggc 90300
cgtcgagacc gaggggtttg ttgtgcgcag ggacgccagt tggccgatat acttaccgag 90360
gtccatgtcg tacgcgggga acactatctg tcgttgttgc agcgagaacc cgaggggcgc 90420
gatgaagccg cggatgttgt gggtgcggcc ggcgcgtaga gcgcactccc cgaccaacag 90480
ggtcgcgatg agctcaacgg caaaccactc cttttccttt atggtcttaa cggcaagctt 90540
atgttcgcga atcagttgga cttcgccgta tcccccagac cccccgaagc ttcgggcccc 90600
ggggatctcg agggtcgtgt agtgtagggc ggggttgatg gcgaacacgg ggctgcatag 90660
cttgcggatg cgcgtgaggg tgaggatgtg cgagggggac gagggggggtg cggttaacgc 90720
cgcctgggat ctgcgcaggg gcgggcggtt cagtttggcc gccgtaccgg gcgcctcggg 90780
ggacgcgcgg cgatgagacg agcggctcat tcgccatcgg gatagtcccg cgcgaagccg 90840
ctcgcggagg ccggatcggt ggcggcaccc gtgggaggag cgggagacgg cggcgttctg 90900
gagagagggg ccgctggggc gcccggaggc cccatggggg ttggagtgta tgtaggatgc 90960
gagccaatcc ttgaaggacc gttggcgtgc accttggggg ctgaggttag ctgccacatg 91020
accagcaggt cgctgtctgc gggactcatc catccttcgg ccaggtcgcc gtctccccac 91080
agagaagcgt tggtcgctgc ctcctcgagt tgctcctcct ggtccgcaag acgatcgtcc 91140
acggcgtcca ggcgctcacc aagcgccgga tcgaggtacc gtcggtgtgc ggttagaaag 91200
tcacgacgcg ccgcttgctc ctccacgcga attttaacac aggtcgcgcg ctgtcgcatc 91260
atctctaagc gcgcgcggga ctttagccgc gcctccaatt ccaagtgggc cgcctttgca 91320
gccataaagg cgccaacaaa ccgaggatct tgggtgctga cgccctcccg gtgcagctgc 91380
agggtctggt ccttgtaaat ctcggctcgg aggtgcgtct cggccaggcg tcggcgcagg 91440
gccgcgtggg cggcatctcg gtccattccg ccaccctgcg ggcgacccgg gggtgctctg 91500
atagtctcgc gtgcccaagg cccgtgatcg gggtacttcg ccgccgcgac ccgccacccg 91560
gtgtgcgcga tgtttggtca gcagctggcg tccgacgtcc agcagtacct ggagcgcctc 91620
gagaaacaga ggcaacttaa ggtgggcgcg gacgaggcgt cggcgggcct cacaatgggc 91680
ggcgatgccc tacgagtgcc ctttttagat ttcgcgaccg cgacccccaa gcgccaccag 91740
accgtggtcc cgggcgtcgg gacgctccac gactgctgcg agcactcgcc gctcttctcg 91800
gccgtggcgc ggcggctgct gtttaatagc ctggtgccgg cgcaactaaa ggggcgtgat 91860
ttcgggggcg accacacggc caagctggaa ttcctggccc ccgagttggt acgggcggtg 91920
gcgcgactgc ggtttaagga gtgcgcgccg gcggacgtgg tgcctcagcg taacgcctac 91980
tatagcgttc tgaacacgtt tcaggccctc caccgctccg aagcctttcg ccagctggtg 92040
cactttgtgc gggactttgc ccagctgctt aaacctcctt ccgggcctcc agcctcacgg 92100
agaccacggg cccccccaaa aaacgggcca aggtggacgt ggccacccac ggccggacgt 92160
acggcacgct ggagctgttc caaaaaatga tccttatgca cgccacctac tttctggccg 92220
ccgtgctcct cggggaccac gcggagcagg tcaacacgtt cctgcgtctc gtgtttgaga 92280

-continued tccccctgtt tagcgacgcg gccgtgcgcc acttccgcca gcgcgccacc gtgtttctcg 92340
tcccccggcg ccacggcaag acctggtttc tggtgcccct catcgcgctg tcgctggcct 92400
cctttcgggg gatcaagatc ggctacacgg cgcacatccg caaggcgacc gagccggtgt 92460
ttgaggagat cgacgcctgc ctgcggggct ggttcggttc ggcccgagtg gaccacgtta 92520
aaggggaaac catctccttc tcgtttccgg acgggtcgcg cagtaccatc gtgtttgcct 92580
ccagccacaa cacaaacgta agtcctcttt tctttcgcat ggctctccca aggggccccg 92640
ggtcgacccg acccacaccc acccacccac atacacacac aaccagacgc gggaggaaag 92700
tctgccccgt gggcactgat ttttattcgg gatcgcttga ggaggcccgg gcaacggccc 92760
gggcaacggt ggggcaactc gtagcaaata ggcgactgat gtacgaagag aagacacaca 92820
ggcgccaccc ggcgctggtc ggggggatgt tgtccgcgcc gcaccgtccc ccgacgacct 92880
cttgcagacg gtccgtgatg caaggacggc ggggggcctg cagcagggtg accgtatcca 92940
cgggatggcc aaagagaagc ggacacaggc tagcatcccc ctggaccgcc agggtacact 93000
gggccatctt ggcccacaga cacggggcga cgcagggaca ggactccgtt acgacggagg 93060
agagccacag tgcgttggcg gaatcgatgt ggggcggcgg ggcgcaggac tcgcagcccc 93120
ccgggtggtt agtgatcctg gccaggagcc atcccagatg gcgggccctg cttcccggtg 93180
gacagagcga ccccaggtcg ctgtccatgg cccagcagta gatctggccg ctggggaggt 93240
gccaccaggc ccccgggccc aaggcgcagc acgcgcccgg ctccgggggg gtcttcgcgg 93300
ggaccagata cgcgccatcc agctcgccga ccactggctc ctccgcgagc tgttcggtgg 93360
ttgggtcggg ggtttcctcc ggggggggtgg ccgcccgtat gcgggcgaac gtgagggtgc 93420
acaggagcgg ggtcaggggg tgcgtcacgc tccggaggtg gacgatcgcg cagtagcggc 93480
gctcgcggtt aaagaaaaag agggcaaaga aggtgttcgg gggcaaccgc agcgccttgg 93540
ggcgcgtcag atacagaaaa atctcgcaga agagggcgcg cccggggtct gggttaggaa 93600
gggccacctg acacagaggc tcggtgagga ccgttagaca ccgaaagatc ttgagccgct 93660
cgtccgcccg aacgacgcgc cacacaaaga cggagttgac aatgcgcgcg atagagtcga 93720
cgtccgtccc caggtcgtcg actctgtcgc gcgtgccgcg agctccggcc cgggaatccg 93780
gccggggcaa ggtccccggg ggaccaggcg gcgccagggg ccgccggggt cccagctgcg 93840
ccatgccggg ggcgggggga gggcaaaccc cagaggcggg ggccaacggc gcggggagga 93900
gtggatgggc gaggtggccg ggggaaggcg cccgctagcg agaacggccg ttcccggacg 93960
acaccttgcg acaaaaccta aggacagcgg cccgcgcgac ggggtccgag aggctaaggt 94020
aggccgcgat gttaatggtg aacgcaaagc cgccgggaaa gacaactatg ccacagaggc 94080
ggcgattaaa ccccaggcag aggtaggcgt agctttcccc gggcaggtat tgctcgcaga 94140
ccctgcgtgg ggctgtggag gggacggcct ccatgaagcg acatttactc tgctcgcgtt 94200
tactgacgtc accatccatc gccacggcga ttggacgatt gttaagccgc agcgtgtctc 94260
cgcttgtgct gtagtagtca aaaacgtaat ggccgtcgga gtcggcaaag cgggccggga 94320
ggtcgtcgcc gagcgggacg acccgccgcc cccgaccgcc ccgtcccccc aggtgtgcca 94380
ggacggccag ggcatacgcg gtgtgaaaaa aggcgtcggg ggcggtcccc tcgacggcgc 94440
gcatcaggtt ctcgaggaga atggggaagc gcctggtcac ctcccccagc cacgcgcgtt 94500
ggtcggggcc aaagtcatag cgcaggcgct gtgagattcg cgggccgccc tgaagcgcgg 94560
cccggatggc ctggcccagg gcccggaggc acgccagatg tatgcgcgcg gtaaaggcga 94620
cctcggcggc gatgtcaaag ggcggcagga cggggcgcgg gtggcgcagg ggcacctcga 94680
gcgcgggaaa gcggagcagc agctccgcct gcccagcggg agacagctgg tgggggcgca 94740
cgacgcgttc tgcggcgcag gcctcggtca gggccgtggc cagcgccgag gacagcagcg 94800
gagggcgggc gcgtcgcccg ccccacgcca ctgagttctc gtaggagacg acgacgaagc 94860
gctgcttggt tccgtagtgg tggcgcagga ccacggagat agaacgacgg ctccacagcc 94920
agtccggccg gtcgccgccg gccagggctt cccatccgcg atccaaccac tcgaccagcg 94980
accgcggctt tgtggtacca ggggtaaggg ttagaacgtc gttcaggatg tcctcgcccc 95040
cgggcccgtg gggcgctggg gccacaaagc ggccccccgcc ggggggctcc agacccgcca 95100
gcaccgcatc tgcgtcagcc gcccccatgg cgccccccgct gacggcctgg tgaaccaggg 95160
cgccctggcg gagccccgat gcaacgccac aggccgcacg cccggtccga gcgcggaccg 95220
ggtggcggcg ggtgacgtcc tgcactgccc gctgaaccaa cgcgaggatc tcctcgttct 95280
cctgtgcgat ggacacgtcc tgggccgcgg tcgtgtcgcc gccgggggcc gtcagctgct 95340
cctccgggga gatggggggg tcggacgccc cgacgatggg cgggtctgcg ggcgcccccg 95400
cgtggggccg ggccaagggc tgcggacgcg gggacgcgct ttccccccaga cccatggaca 95460
ggtgggccgc ggcctccttc gcggccggcg gggcggcggc gccaagcaga gcgacgtagc 95520
ggcacaaatg ccgacagacg cgcatgatgc gcgtgctgtc ggccgcgtag cgcgtgttgg 95580
gggggacgag ctcgtcgtaa ctaaacagaa tcacgcgggc acagctcgcc cccgagcccc 95640
acgcgaggcg cagcgccgcc acggcgtacg ggtcatagac gccctgcgcg tcacacacca 95700
cgggcaggga gacgaacaac cccccggcgc tggacgcacg cggaaggagg ccagggtgtg 95760
ccggcacgac gggggccaga agctccccca ccgcatccgc gggcacgtag gcggcaaacg 95820
ccgtgcacca cggggtacag tcgccggtgg catgagcccg agtctggatt tcgacctgga 95880
agtttgcggc cgtcccgagt ccggggcggc cgcgcatcag ggcggccaga gggattcccg 95940
cggccgccag gcactcgctg gatatgatga cgtgaaccaa agacgagggc cgacccgggc 96000
cgtggccgag atcgtactgg acctcgttgg ccaagtgcgc gttcatggtt cggggtgggt 96060
gtgggtgtgt aggcgatgcg ggtcccccga gtccgcggga agggcgtggg tttggcgcgc 96120
gtatgcgtat tcgccaacgg aggcgtgcgt gcttatgcgc ggcgcgtttc ttctgtctcc 96180
agggaatccg aggccaggac tttaacctgc tctttgtcga cgaggccaac tttattcgcc 96240
cggatgcggt ccagacgatt atgggctttc tcaaccaggc caactgcaag attatcttcg 96300
tgtcgtccac caacaccggg aaggccagta cgagcttttt gtacaacctc cgcggggccg 96360
ccgacgagct tctcaacgtg gtgacctata tatgcgatga tcacatgccg agggtggtga 96420
cgcacacaaa cgccacggcc tgttcttgtt atatcctcaa caagcccgtt ttcatcacga 96480
tggacggggc ggttcgccgg accgccgatt tgtttctggc cgattccttc atgcaggaga 96540
tcatcggggg ccaggccagg gagaccggcg acgaccggcc cgttctgacc aagtctgcgg 96600
gggagcggtt tctgttgtac cgcccctcga ccaccaccaa cagcggcctc atggcccccg 96660
atttgtacgt gtacgtggat cccgcgttca cggccaacac ccgagcctcc gggaccggcg 96720
tcgctgtcgt cgggcggtac cgcgacgatt atatcatctt tgccctggag cactttttc 96780
tccgcgcgct cacgggctcg gcccccgccg acatcgcccg ctgcgtcgtc cacagtctga 96840
cgcaggtcct ggccctgcat cccggggcgt ttcgcggcgt ccgggtggcg gtcgagggaa 96900
atagcagcca ggactcggcc gtcgccatcg ccacgcacgt gcacacagag atgcaccgcc 96960
tactggcctc ggagggggcc gacgcgggct cgggccccga gcttctcttc taccactgcg 97020

-continued

```
agcctcccgg gagcgcggtg ctgtacccct ttttcctgct caacaaacag aagacgcccg  97080
cctttgaaca ctttattaaa aagtttaact ccgggggcgt catggcctcc caggagatcg  97140
tttccgcgac ggtgcgcctg cagaccgacc cggtcgagta tctgctcgag cagctgaata  97200
acctcaccga aaccgtctcc cccaacactg acgtccgtac gtattccgga aaacggaacg  97260
gcgcctcgga tgaccttatg gtcgccgtca ttatggccat ctaccttgcg gcccaggccg  97320
gacctccgca cacattcgct cccatcacac gcgtttcgtg agcgcccaat aaacacaccc  97380
aggtatgcta cgcacgacca cggtgtcgcc tgttaagggg ggggaagggg gtgttggcgg  97440
gaagcgtggg aacacggggg attctctcac gaccggcacc agtaccaccc ccctgtgaac  97500
acagaaaccc aacccaaatc ccataaacat acgacacaca ggcatatttt ggaatttctt  97560
gggtttttat ttatttaggt atgctggggt ttctccctgg atgcccaccc cccacccccc  97620
cgtgggtcta gccgggcctt agggatagcg tataacgggg gccatgtctc cggaccgcac  97680
aacggccgcg ccgtcaaagg tgcacacccg aaccacggga gccagggcca aggtgtctcc  97740
tagttggccc gcgtgggtca gccaggcgac gagcgcctcg taaagcggca gccttcgctc  97800
tccatcctgc accagggccg gggcttcggg gtgaatgagc tgggcggcct cccgcgtgac  97860
actctgcatc tgcaggagag cgttcacgta cccgtcctgg gcacttagcg caaagagccg  97920
ggggattagc gtaaggatga tggtggttcc ctccgtgatc gagtaaacca tgttaaggac  97980
cagcgatcgc agctcggcgt ttacgggacc gagttgttgg acgtccgcca gcagcgagag  98040
gcgactcccg ttgtagtaca gcacgttgag gtctggcagc cctccggggt ttctggggct  98100
ggggttcagg tcccggatgc ccctggccac gagccgcgcc acgatttcgc gcgccagggg  98160
cgatggaagc ggaacgggaa accgcaacgt gaggtccagc gaatccaggc gcacgtccgt  98220
cgcttggccc tcgaacacgg gcgggacgag gctgatgggg tccccgttac agagatctac  98280
gggggaggtg ttgcgaaggt taacggtgcc ggcgtgggtg aggcccacgt ccaggggggca  98340
ggcgacgatt cgcgtgggaa gcacccgggt gatgaccgcg gggaagcgcc ttcggtacgc  98400
cagcaacaac cccaacgtgt cgggactgac gcctccggag acgaaggatt cgtgcgccac  98460
gtcggccagc gtcagttgcc ggcggatggt cggcaggaat accacccgcc cttcgcagcg  98520
ctgcagcgcc gccgcatcgg ggcgcgagat gcccgagggt atcgcgatgt cagtttcaaa  98580
gccgtccgcc agcatggcgc cgatccacgc ggcagggagt gcagtggtgg ttcgggtggc  98640
gggaggagcg cggtgggggt cagcggcgta gcagagacgg gcgaccaacc tcgcatagga  98700
cggggggtgg gtcttagggg gttgggaggc gacagggacc ccagagcatg cgcggggagg  98760
tctgtcgggc ccagacgcac cgagagcgaa tccgtccacg gagtcccggt ctgggtttta  98820
tggggcccgg ccctcggaat cgcggcttgt cggcggggac aaagggggcg gggctagggg  98880
gcttgcggaa acagaagacg cgtgggataa aagaatcgca ctaccccaag gaagggcggg  98940
gcggtttatt acagagccag tcccttgagc ggggatgcgt catagacgag atactgcgcg  99000
aagtgggtct cccgcgcgtg ggcttccccg ttgcgggcgc tgcggaggag ggcggggtcg  99060
ctggcgcagg tgagcgggta ggcctcctga aacaggccac acgggtcctc cacgagttcg  99120
cggcaccccg gggggcgctt aaactgtacg tcgctggcgg cggtggccgt ggacaccgcc  99180
gaacccgtct ccacgatcag gcgctccagg cagcgatgtt tggcggcgat gtcggccgac  99240
gtaaagaact taaagcaggg gctgagcacc ggcgaggccc cgttgaggtg gtaggccccg  99300
ttatagagca ggtccccgta cgaaaatcgc tgcgacgccc acgggttggc cgtggccgca  99360
aaggcccggg acgggtcgct ctggccgtgg tcgtacatga gggcggtgac atccccctcc  99420
```

ttgtcccccg cgtaaacgcc cccggcggcg cgtccccggg ggttgcaggg ccggcggaag 99480
tagttgacgt cggtcgacac gggggtggcg ataaactcac acacggcgtc ctggccgtgg 99540
tccatccctg cgcgccgcgg cacctgggcg cacccgaaca cggggacggg ctgggccggc 99600
cccaggcggt ttcccgccac gaccgcgttc cgcaggtaca cggctgccgc gttgtccagg 99660
agagggggag ccccgcggcc caggtaaaag ttttggggaa ggttgcccat gtcggtgacg 99720
gggttgcgga cggttgccgt ggccacgacg gcggtgtagc ccacgcccag gtccacgttc 99780
ccgcgcggct gggtgagcgt gaagtttacc cccccgccag tttcgtgccg ggccacctgg 99840
agctggccca ggaagtacgc ctccgacgcg cgctccgaga acagcatgtt ctcagtcaca 99900
aagcggtcct gtcggacgac ggtgaaccca aacccgggat ggaggcccgt cttgagctga 99960
tgatgcaagg ccacgggact gatcttgaag taccccgcca tgagcgcgta ggtcagcgcg 100020
ttctccccgg ccgcgctctc gcggacgtgc tgcacgacgg gctgtcggat cgacgaaaag 100080
tagttggccc ccagagccgg ggggaccagg gggacctgcc gcgacaggtc gcgcagggcc 100140
ggggggaaat tgggcgcgtt cgccacgtgg tcggccccgg cgaacagcgc gttgacggga 100200
agggggtaaa aatagtcgcc attttggatg gtatggtcca gatgctgggg ggccatcagc 100260
aggattccgg cgtgcaacgc cccgtcgaat atgcgcatgt tggtggtgga cgcggtgttg 100320
gcgcccgcgt cgggcgccgc cgagcagagc agcgccgttg tgcgttcggc catgttgtgg 100380
gccagcacct gcagcgtgag catggcgggc ccgtccacta ccacgcgccc gttgtgaaac 100440
atggcgttga ccgtgttggc caccagattg gccgggtgca gggggtgcgc ggggtccgtc 100500
acggggtcgc tggggcactc ctcgccgggg gcgatctccg ggaccaccat gttctgcagg 100560
gtggcgtata cgcggtcgaa gcgaaccccc gcggtgcagc agcggccccg cgagaaggcg 100620
ggcaccatca cgtagtagta aatcttgtgg tgcacggtcc agtccgcccc ccggtgcggc 100680
cggtcatccg cggcgtccgc ggctcgggcc tgggtgttgt gcagcagctg gccgtcgttg 100740
cggttgaagt ccgcggtcgc cacgttacat gccgccgcgt acacggggtc gtggcccccc 100800
gcgctaaccc ggcagtcgcg atggcggtcc agggccgcgc gccgcatcag ggcgtcacag 100860
tcccacacga ggggtggcag cagcgccggg tctcgcatta ggtgattcag ctcggcttgc 100920
gcctgcccgc ccagctccgg gccggtcagg gtaaagtcat caaccagctg ggccagggcc 100980
tcgacgtgcg ccaccaggtc ccggtacacg gccatgcact cctcgggaag gtctcccccg 101040
aggtaggtca cgacgtacga gaccagcgag tagtcgttca cgaacgccgc gcaccgcgtg 101100
ttgttccagt agctggtgat gcactggaca acgagccggg ccagggcgca gaagacgtgc 101160
tcgctgccgt gtatggcggc ctgcagcagg taaaacaccg ccgggtagtt gcggtcgtcg 101220
aacgccccgc gaacggcggc gatggtggcg ggggccatgg cgtggcgtcc cacccccagc 101280
tccaggcccc gggcgtcccg gaacgccgcc ggacatagcg ccaggggcaa gttgccgttc 101340
accacgcgcc aggtggcctg gatctccccc gggccggccg ggggaacgtc cccccccggc 101400
agctccacgt cggccacccc cacgaagaag tcgaacgcgg ggtgcagctc aagagccagg 101460
ttggcgttgt cgggctgcat aaactgctcc ggggtcatct ggccttccgc gacccatcgg 101520
acccgcccgt gggccaggcg ctgcccccag gcgttcaaaa acagctgctg catgtctgcg 101580
gcggggccgg ccggggccgc cacgtacgcc ccgtacggat tggcggcttc gacggggtcg 101640
cggttaaggc ccccgaccgc cgcgtcaacg ttcatcagcg aagggtggca cacggtcccg 101700
atcgcgtgtt ccagagacag gcgcagcacc tggcggtcct tcccccaaaa aaacagctgg 101760

-continued cggggcggga aggcgcgggg atccgggtgg ccgggggcgg ggactaggtc cccggcgtgc 101820
gcggcaaacc gttccatgac cggattgaac aggcccaggg gcaggacgaa cgtcaggtcc 101880
atggcgccca ccagggggta gggaacgttg gtggcggcgt agatgcgctt ctccagggcc 101940
tccagaaaga ccagcttctc gccgatggac accagatccg cgcgcacgcg cgtcgtctgg 102000
ggggcgctct cgagctcgtc cagcgtctgc cggttcaggt cgagctgctc ctcctgcatc 102060
tccagcaggt ggcggcccac gtcgtccaga cttcgcacgg ccttgcccat cacgagcgcc 102120
gtgaccaggt tggccccgtt caggaccatc tcgccgtacg tcaccggcac gtcggcttcg 102180
gtgtcctcca ctttcaggaa ggactgcagg aggcgctgtt tgatcggggc tgtggtgact 102240
agcaccccgt cgaccggccg cccgcgcgtg tcggcatgcg tcagacgggg cacggccacg 102300
gagggctgcg tggccgtggt gaggtccacg agccaggcct cgacggcctc ccggcggtgg 102360
cccgccttgc ccaggaaaaa gctcgtctcg cagaagcttc gctttagctc ggcgaccagg 102420
gtcgcccggg ccaccctggt ggccaggcgg ccgttgtcca ggtatcgttg catcggcaac 102480
aacaaagcca ggggcggcgc cttttccagc agcacgtgca gcatctggtc ggccgtgccg 102540
cgctcaaacg ccccgaggac ggcctggacg ttgcgagcga gctgttggat ggcgcgcaac 102600
tggcgatgcg cgctgatacc cgtcccgtcc agggcctccc ccgtgagcag ggcgatggcc 102660
tcggtggcca ggctgaaggc ggcgttcagg gcccggcggt cgataatctt ggtcatgtaa 102720
ttgtgtgtgg gttgctcgat ggggtgcggg ccgtcgcggg caatcagcgg ctggtggacc 102780
tcgaactgta cgcgcccctc gttcatgtag gccagctccg gaaacttggt acacacgcac 102840
gccaccgaca acccgagctc cagaaagcgc acgagcgaca gggtgttgca atacgacccc 102900
agcagggcgt cgaactcgac gtcgtacagg ctgtttgcat cggagcgcac gcgggaaaaa 102960
aaatcgaaca ggcgtcgatg cgacgccacc tcgatcgtgc taaggaggga cccggtcggc 103020
accatggccg cggcataccg gtatcccgga gggtcgcggt tgggagcggc catagggtcg 103080
cgtggagatc ggctgtctct agcgatattg gcccggggag gctaagatcc accccaacgc 103140
ccggccaccc gtgtacgtgc ccgacggccc aaggtccacc gaaagacacg acggacccgg 103200
acccaaagag gcgggggatg ctgtgtgaga ggccgggtgt cggtcggggg ggaaaggcac 103260
cgggagaagg ctgcggcctc gttccaggag aacccagtgt ccccaacaga cccggggacg 103320
tgggatcccc ggccttatat accccccccc ccgccccacc cccgttagaa cgcgacgggt 103380
gcattcaaga tggccctggt ccaaaagcgt gccaggaaga aattggcaga ggcggcaaag 103440
ctgtccgccg ccgccaccca catcgaggcc ccggccacac aggctatccc cagggcccgt 103500
gtgcgcaggg gatcggtggg tggcagcatt tggttggtgg cgataaagtg gaaaagcccg 103560
tccggactga aggtctcgtg ggcggcggcg aacaaggcac acagggccgt gcctcccaaa 103620
aacatggaca tcccccaaaa cacgggcgcc gacaacggca gacgatccct cttgatgtta 103680
acgtacagga ggagcgcccg caccgcccac gtaacgtagt agccgacgat ggcggccagg 103740
atacaggccg gcgccaccac ccttccggtc agcccgtaat acatgcccgc tgccaccatc 103800
tccaacggct tcaggaccaa aaacgaccaa aggaacagaa tcacgcgctt tgaaaagacc 103860
ggctgggtat ggggcggaag acgcgagtat gccgaactga caaaaaaatc agaggtgccg 103920
tacgaggaca atgaaaactg ttcctccagc ggcagttctc cctcctcccc cccgaaggcg 103980
gcctcgtcga ccagatctcg atccaccaga ggaaggtcat cccgcatggt catggggtgt 104040
gcggtggagg tggggagacc gaaaccgcaa agggtcgctt acgtcagcag gatcccgaga 104100
tcaaagacac ccgggttctt gcacaaacac cacccgggtt gcatccgcgg aggcgagtgt 104160
tttgataagg ccgttccgcg ccttgatata acctttgatg ttgaccacaa aacccggaat 104220
ttacgcctac gccccaatgc ccacgcaaga tgaggtaggt aacccccccg tgggtgtgac 104280
gttgcgttta gttcattgga ggccaagggg aaaaatgggg tggggaggaa acggaaaacc 104340
cagtaggccg tgtcgggaac acgcccgggg ttgtcctcaa aaggcagggt ccatactacg 104400
gaagccgtcg ttgtattcga gacctgcctg tgcgacgcac gtcggggttg cctgtgtccg 104460
gttcggcccc caccgcgtgc ggcacgcacg aggacgagtc cgcgtgcttt attggcgttc 104520
caagcgttgc cctccagttt ctgttgtcgg tgttccccca tacccacgcc cacatccacc 104580
gtagggggcc tctgggccgt gttacgtcgc cgcccgcgat ggagcttagc tacgccacca 104640
ccatgcacta ccgggacgtt gtgttttacg tcacaacgga ccgaaaccgg gcctactttg 104700
tgtgcggggg gtgtgtttat tccgtggggc ggccgtgtgc ctcgcagccc ggggagattg 104760
ccaagtttgg tctggtcgtt cgagggacag gcccagacga ccgcgtggtc gccaactatg 104820
tacgaagcga actccgacaa cgcggcctgc aggacgtgcg tcccattggg gaggacgagg 104880
tgtttctgga cagcgtgtgt cttctaaacc cgaacgtgag ctccgagctg gatgtgatta 104940
acacgaacga cgtggaagtg ctggacgaat gtctggccga gtactgcacc tcgctgcgaa 105000
ccagcccggg tgtgctaata tccgggctgc gcgtgcgggc gcaagacaga atcatcgagt 105060
tgtttgaaca cccaacgata gtcaacgttt cctcgcactt tgtgtatacc ccgtccccat 105120
acgtgttcgc cctggcccag gcgcacctcc cccggctccc gagctcgctg gaggccctgg 105180
tgagcggcct gtttgacggc atccccgccc cacgccagcc acttgacgcc cacaacccgc 105240
gcacggatgt ggttatcacg ggccgccgcg ccccacgacc catcgccggg tcgggggcgg 105300
ggtcgggggg cgcgggcgcc aagcgggcca ccgtcagcga gttcgtgcaa gtcaaacaca 105360
ttgaccgcgt gggccccgct ggcgtttcgc cggcgcctcc gccaaacaac accgactcga 105420
gttccctggt gcccggggcc caggattccg ccccgcccgg ccccacgcta agggagctgt 105480
ggtgggtgtt ttatgccgca gaccgggcgc tggaggagcc ccgcgccgac tctggcctca 105540
cccgcgagga ggtacgtgcc gtacgtgggt tccgggagca ggcgtggaaa ctgtttggct 105600
ccgcgggggc cccgcgggcg tttatcgggg ccgcgttggg cctgagcccc ctccaaaagc 105660
tggccgttta ctactatatc atccaccgag agaggcgcct gtccccctc cccgcgctag 105720
tccggctcgt aggccggtac acacagcgcc acggcctgta cgtccctcgg cccgacgacc 105780
cagtcttggc cgatgccatc aacgggctgg ttcgcgacgc gctggcggcc ggaaccacag 105840
ccgagcagct cctcatgttc gaccttctcc ccccaaagga cgtgccggtg ggaagcgacg 105900
tgcaggccga cagcaccgct ctgctgcgct ttatagaatc gcaacgtctc gccgtccccg 105960
ggggggtgat ctcccccgag cacgtcgcgt accttggtgc gttcctgagc gtgctgtacg 106020
ctggccgcgg gcgcatgtcc gcagcaacgc acaccgcgcg gctgacaggg gtgacctccc 106080
tggtgctagc ggtgggtgac gtggaccgtc tttccgcgtt tgaccgcgga gcggcgggcg 106140
cggccagccg cacgcgggcc gccgggtacc tggatgtgct tcttaccgtt cgtctcgctc 106200
gctccaaaca cggacagtct gtgtaacaga ccccaataaa cgtatgtcgc taccacaccc 106260
ttgtgtgtca atggacgcct ctccgggggg gagagggaaa acaaagaggg gctgggggag 106320
cggcaccact ggggcctgaa caaacaaacc acagacacgg ttacagttta ttcggtcggg 106380
cggataaacg gccgaagcca cgccccctt attcgcgtct ccaaaaaaac gggacacttg 106440
tccggagaac ctttaggatg ccagccaggg cggcggtaat cataaccacg cccagcgcag 106500
aggcggccag aaacccgggc gcaattgcgg ccacgggctg cgtgtcaaag gctagcaaat 106560
gaatgacggt tccgtttgga aatagcaaca aggccgtgga cggcacgtcg ctcgaaaaca 106620
cgctcggggc gccctccgtc ggcccggcgg cgatttgctg ctgtgtgttg tccgtatcca 106680
ccagcaacac agacatgacc tccccggctg ggtgtagcg cataaacacg gcccccacga 106740
gccccaggtc gcgctggttt tgggtgcgca ccagccgctt ggactcgata tcccgggtgg 106800
agccttcgca tgtcgcggtg aggtaggtta ggaacagtgg gcgtcggacg tcgacgccgg 106860
tgagcttgta gccgatcccc cggggcagag gggagtgggt gacgacgtag ctggcgttgt 106920
gggtgatggg taccaggatc cgtggctcga cgttggcaga ctgccccccg caccgatgtg 106980
aggcctcagg gacgaaggcg cggatcaggg cgttgtagtg tgcccagcgc gtcagggtcg 107040
aggcgaggcc gtgggtctgc tgggccagga cttcgaccgg ggtctcggat cgggtggctt 107100
gagccagcgc gtccaggata aacacgctct cgtctagatc aaagcgcagg gaggccgcgc 107160
atggcgaaaa gtggtccgga agccaaaaga gggttttctg gtggtcggcc cgggccagcg 107220
cggtccggag gtcggcgttg gtcgctgcgg cgacgtcgga cgtacacagg gccgatgcta 107280
tcagaaggct ccggcgggcg cgttcccgct gcaccgccga ggggacgccc gccaagaacg 107340
gctgccggag gacagccgag gcgtaaaata gcgcccggtg gacgaccggg gtggtcagca 107400
cgcggccccc tagaaactcg gcatacaggg cgtcgatgag atgggctgcg ctgggcgcca 107460
ctgcgtcgta cgccgagggg ctatccagca cgaaggccag ctgatagccc agcgcgtgta 107520
atgccaagct ctgttcgcgc tccagaatct cggccaccag gtgctggagc cgagcctcta 107580
gctgcaggcg ggccgtggga tccaagactg acacattaaa aaacacagaa tccgcggcac 107640
agcccgcggc cccgcgggcg gccaacccgg caagcgcgcg cgagtgggcc aaaaagccta 107700
gcaggtcgga gaggcagacc gcgccgtttg cgtgggcggc gttcacgaaa gcaaaacccg 107760
acgtcgcgag cagccccgtt aggcgccaga agagaggggg gcgcgggccc tgctcggcgc 107820
ccgcgtcccc cgagaaaaac tccgcgtatg cccgcgacag gaactgggcg tagttcgtgc 107880
cctcctccgg gtagccgccc acgcggcgga gggcgtccag cgcggagccg ttgtcggccc 107940
gcgtcaggga ccctaggaca aagacccgat accgggggcc gcccgggggc ccgggaagag 108000
cccccggggg gttttcgtcc gcggggtccc cgacccgatc tagcgtctgg cccgcgggga 108060
ccaccatcac ttccaccgga gggctgtcgt gcatggatat cacgagcccc atgaattccc 108120
gcccgtagcg cgcgcgcacc agcgcggcat cgcacccgag caccagctcc cccgtcgtcc 108180
agatgcccac gggccacgtc gaggccgacg gggagaaata cacgtaccta cctggggatc 108240
tcaacaggcc ccgggtggcc aaccaggtcg tggacgcgtt gtgcaggtgc gtgatgtcca 108300
gctccgtcgt cgggtgccgc cgggccccaa ccggcggtcg ggggggcggt gtatcacgcg 108360
gcccgcttgg gtggctcgcc gtcgccacgt tgtctccccg cgggaacgtc agggcctcgg 108420
ggtcagggac ggccgaaaac gttacccagg cccgggaacg cagcaacacg gaggcgactg 108480
gattgtacaa gagaccctta aggggggcga ccgagggggg aggctgggcg gtcggctcga 108540
ccgtggtggg ggcgggcagg ctcgcgttcg ggggccggcc gagcaggtag gtcttcggga 108600
tgtaaagcag ctggccgggg tcccgcggaa actcggccgt ggtgaccaat acaaaacaaa 108660
agcgctcctc gtaccagcga agaaggggca gagatgccgt agtcaggttt agttcgtccg 108720
gcggcgccag aaatccgcgc ggtggttttt gggggtcggg ggtgtttggc agccacagac 108780
gcccggtgtt tgtgtcgcgc cagtacatgc ggtccatgcc caggccatcc aaaaaccatg 108840
ggtctgtctg ctcagtccag tcgtggacct gaccccacgc aacgcccaaa ataataaccc 108900
ccacgaacca taaaccattc cccatggggg accccgtccc taacccacgg ggcccgtggc 108960
tatggcaggg cttgccgccc cgacgttggc tgcgagccct gggccttcac ccgaacttgg 109020
ggggtggggt ggggaaaagg aagaaacgcg ggcgtattgg ccccaatggg gtctcggtgg 109080
ggtatcgaca gagtgccagc cctgggaccg aaccccgcgt ttatgaacaa acgacccaac 109140
acccgtgcgt tttattctgt ctttttattg ccgtcatagc gcgggttcct tccggtattg 109200
tctccttccg tgtttcagtt agcctccccc atctcccggg caaacgtgcg cgccaggtcg 109260
cagatcgtcg gtatggagcc gggggtggtg acgtgggtct ggaccatccc ggaggtaagt 109320
tgcagcaggg cgtcccggca gccggcgggc gattggtcgt aatccaggat aaagacgtgc 109380
atgggacgga ggcgtttggc caagacgtcc aaggcccagg caaacacgtt gtacaggtcg 109440
ccgttggggg ccagcaactc gggggcccga aacagggtaa ataacgtgtc cccgatatgg 109500
ggtcgtgggc ccgcgttgct ctggggctcg gcaccctggg gcggcacggc cgtccccgaa 109560
agctgtcccc aatcctcccg ccacgacccg ccgccctgca gataccgcac cgtattggca 109620
agcagcccgt aaacgcggcg aatcgcggcc agcatagcca ggtcaagccg ctcgccgggg 109680
cgctggcgtt tggccaggcg gtcgatgtgt ctgtcctccg gaagggcccc caacacgatg 109740
tttgtgccgg gcaaggtcgg cgggatgagg gccacgaacg ccagcacggc ctggggggtc 109800
atgctgccca taaggtatcg cgcggccggg tagcacagga gggcggcgat gggatggcgg 109860
tcgaagatga gggtgagggc cgggggcggg gcatgtgagc tcccagcctc ccccccgata 109920
tgaggagcca gaacggcgtc ggtcacggca taaggcatgc ccattgttat ctgggcgctt 109980
gtcattacca ccgccgcgtc cccggccgat atctcaccct ggtcgaggcg gtgttgtgtg 110040
gtgtagatgt tcgcgattgt ctcggaagcc cccagcacct gccagtaagt catcggctcg 110100
ggtacgtaga cgatatcgtc gcgcgaaccc agggccacca gcagttgcgt ggtggtggtt 110160
ttccccatcc cgtgaggacc gtctatataa acccgcagta gcgtgggcat tttctgctcc 110220
aggcggactt ccgtggcttc ttgctgccgg cgagggcgca acgccgtacg tcggttgcta 110280
tggccgcgag aacgcgcagc ctggtcgaac gcagacgcgt gttgatggca ggggtacgaa 110340
gccatacgcg cttctacaag gcgcttgccg aagaggtgcg ggagtttcac gccaccaaga 110400
tctgcggcac gctgttgacg ctgttaagcg ggtcgctgca gggtcgctcg gtgttcgagg 110460
ccacacgcgt caccttaata tgcgaagtgg acctgggacc gcgccgcccc gactgcatct 110520
gcgtgttcga attcgccaat gacaagacgc tgggcggggt ttgtgtcatc atagaactaa 110580
agacatgcaa atatatttct tccggggaca ccgccagcaa acgcgagcaa cgggccacgg 110640
ggatgaagca gctgcgccac tccctgaagc tcctgcagtc cctcgcgcct ccgggtgaca 110700
agatagtgta cctgtgcccc gtcctggtgt ttgtcgccca acggacgctc cgcgtcagcc 110760
gcgtgacccg gctcgtcccg cagaaggtct ccggtaatat caccgcagtc gtgcggatgc 110820
tccagagcct gtccacgtat acggtcccca tggagcctag gacccagcga gcccgtcgcc 110880
gccgcggcgg cgccgccggg gggtctgcga gcagaccgaa aaggtcacac tctggggcgc 110940
gcgacccgcc cgagtcagcg gcccgccaat taccacccgc cgaccaaacc cccgcctcca 111000
cggagggcgg gggggtgctt aagaggatcg cggcgctctt ctgcgtgccc gtggccacca 111060
agaccaaacc ccgagccgcc tccgaatgag agtgtttcgt tccttccccc tccccccgcg 111120
tcagacaaac cctaaccacc gcttaagcgg cccccgcgag gtccgaagac tcatttggat 111180
ccggcgggag ccacccgaca acagccccg ggttttccca cgccagacgc cggtccgctg 111240
tgccatcgcg ccccctcatc ccacccccca tcttgtcccc aaataaaaca aggtctggta 111300
attaggacaa cgaccgcagt tctcgtgtgt tattttcgct ctccgcctct cgcagatgga 111360
cccgtactgc ccatttgacg ctctggacgt ctgggaacac aggcgcttca tagtcgccga 111420
ttcccgaaac ttcatcaccc ccgagttccc ccgggacttt tggatgtcgc ccgtctttaa 111480
cctcccccgg gagacggcgg cggagcaggt ggtcgtccta caggcccagc gcacagcggc 111540
tgccgctgcc ctggagaacg ccgccatgca ggcggccgag ctccccgtcg atatcgagcg 111600
ccggttacgc ccgatcgaac ggaacgtgca caagatcgca ggcgccctgg aggcgctgga 111660
gacggcggcg gccgccgccg aagaggcgga tgccgcgcgc ggggatgagc cggcgggtgg 111720
gggcgacggg ggggcgcccc cgagtctggc cgtcgcggag atggaggtcc agatcgtgcg 111780
caacgacccg ccgctacgat acgacaccaa cctccccgtg gatctgctac acatggtgta 111840
cgcgggccgc ggggcgaccg gatcgtcggg ggtggtgttc gggacctggt accgcactat 111900
ccaggaccgc accatcacgg actttcccct gaccacccgc agtgccgact ttcgggacgg 111960
ccgtatgtcc aagaccttca tgacggcgct ggtactgtcc ctgcagtcgt gcggccggct 112020
gtatgtgggc cagcgccact attccgcctt cgagtgcgcc gtgttgtgtc tctacctgct 112080
gtaccgaaac acgcacgggg ccgccgacga tagcgaccgc gctccggtca cgttcgggga 112140
tctgctgggc cggctgcccc gctacctggc gtgcctggcc gcggtgatcg ggaccgaggg 112200
cggccggcca cagtaccgct accgcgacga caagctcccc aagacgcagt tcgcggccgg 112260
cgggggccgc tacgaacacg gagcgctggc gtcgcacatc gtgatcgcca cgctgatgca 112320
ccacggggtg ctcccggcgg ccccggggga cgtcccccgg gacgcgagca cccacgttaa 112380
ccccgacggc gtggcgcacc acgacgacat aaaccgcgcc gccgccgcgt tcctcagccg 112440
gggccacaac ctattcctgt gggaggacca gactctgctg cgggcaaccg cgaacaccat 112500
aacggccctg ggcgttatcc agcggctcct cgcgaacggc aacgtgtacg cggaccgcct 112560
caacaaccgc ctgcagctgg gcatgctgat ccccggagcc gtcccttcgg aggccatcac 112620
ccgtggggcc tccgggtccg actcgggggc catcaagagc ggagacaaca atctggaggc 112680
gctatgtgcc aattacgtgc ttccgctgta ccgggccgac ccggcggtcg agctgaccca 112740
gctgtttccc ggcctggccg ccctgtgtct tgacgcccag gcggggcggc cggtcgggtc 112800
gacgcggcgg gtggtggata tgtcatcggg ggcccgccag gcggcgctgg tgcgcctcac 112860
cgccctggaa ctcatcaacc gcacccgcac aaaccccacc cccgtggggg aggttatcca 112920
cgcccacgac gccctggcga tccaatacga acaggggctt ggcctgctgg cgcagcaggc 112980
acgcattggc ttgggctcca acaccaagcg tttctccgcg ttcaacgtta gcagcgacta 113040
cgacatgttg tactttttat gtctggggtt cattccacag tacctgtcgg cggtttagtg 113100
ggtggtgggc gagggggggag ggggcattag ggagaaagaa caagagcctc cgttgggttt 113160
tctttgtgcc tgtactcaaa aggtcatacc ccgtaaacgg cgggctccag tcccggcccg 113220
gcggttggcg tgaacgcaac ggcgggagct gggttagcgt ttagtttagc attcgctctc 113280
gcctttccgc ccgccccccg accgttgcgc cttttttttt ttcgtccacc aaagtctctg 113340
tgggtgcgcg catgacagcc gatgccccgg gagaccggat ggaggagccc ctgccagaca 113400
gggccgtgcc catttacgtg gctgggtttt tggccctgta tgacagcggg gactcgggcg 113460
agttggcatt ggatccggat acggtgcgtg cggccctgcc tccggataac ccactcccga 113520
ttaacgtgga ccaccgcgct ggctgcgagg tggggcgggt gctggccgtg gtcgacgacc 113580
cccgcgggcc gtttttgtg ggactgatcg cctgcgtgca actggagcgc gtcctcgaga 113640
cggccgccag cgctgcgatt ttcgagcgcc gcgggccgcc gctctcccgg gaggagcgcc 113700
tgttgtacct gatcaccaac tacctgccct cggtctccct ggccacaaaa cgcctggggg 113760
gcgaggcgca ccccgatcgc acgctgttcg cgcacgtcgc gctgtgcgcg atcgggcggc 113820
gcctcggcac tatcgtcacc tacgacaccg gtctcgacgc cgccatcgcg ccctttcgcc 113880
acctgtcgcc ggcgtctcgc gagggggcgc ggcgactggc cgccgaggcc gagctcgcgc 113940
tgtccggacg cacctgggcg cccggcgtgg aggcgctgac ccacacgctg ctttccaccg 114000
ccgttaacaa catgatgctg cgggaccgct ggagcctggt ggccgagcgg cggcggcagg 114060
ccgggatcgc cggacacacc tacctccagg cgagcgaaaa attcaaaatg tgggggcgg 114120 agcctgtttc cgcgccggcg cgcgggtata agaacggggc cccggagtcc acggacatac 114180
cgcccggctc gatcgctgcc gcgccgcagg gtgaccggtg cccaatcgtc cgtcagtgcg 114240
gggtcgcctc gcccccggta ctgcccccca tgaaccccgt tccggcatcg ggcaccccgg 114300
cccccgcgcc gcccggcgac gggagctacc tgtggatccc ggcctcccat tacaaccagc 114360
tcgtcgccgg ccacgccgcg ccccaacccc agccgcattc cgcgtttggt ttcccggctg 114420
cggcgggggc cgtggcctat gggcctcacg gcgcgggtct ttcccagcat taccctcccc 114480
acgtcgccca tcagtatccc ggggtgctgt tctcgggacc cagcccactc gaggcgcaga 114540
tagccgcgtt ggtgggggcc atagccgcgg accgccaggc gggcggtcag acggccgcgg 114600
gagaccctgg ggtccggggg tcgggaaagc gtcgccggta cgaggcgggg ccgtcggagt 114660
cctactgcga ccaggacgaa ccggacgcgg actacccgta ctaccccggg gaggctcgag 114720
gcgggccgcg cggggtcgac tctcggcgcg cggcccgcca gtctcccggg accaacgaga 114780
ccatcacggc gctgatgggg gcggtgacgt ctctgcagca ggaactggcg cacatgcggg 114840
ctcggaccag cgccccctat ggaatgtaca cgccggtggc gcactatcgc cctcaggtgg 114900
gggagccgga accaacaacg acccacccgg ccctttgtcc cccggaggcc gtgtatcgcc 114960
ccccaccaca cagcgccccc tacggtcctc cccagggtcc ggcgtcccat gcccccactc 115020
ccccgtatgc cccagctgcc tgcccgccag gcccgccacc gcccccatgt ccttccaccc 115080
agacgcgcgc ccctctaccg acggagcccg cgttcccccc cgccgccacc ggatcccaac 115140
cggaggcatc caacgcggag gccggggccc ttgtcaacgc cagcagcgca gcacacgtgg 115200
acgttgacac ggcccgcgcc gccgatttgt tcgtctctca gatgatgggg gcccgctgat 115260
tcgccccggt ctttggtacc atgggatgtc ttactgtata tctttttaaa taaaccaggt 115320
aataccaaat aagacccatt ggtgtatgtt ctttttttat tgggaggcgc gggtaggcgg 115380
gtagctttac aatgcaaaaa ccttcgacgt ggaggaaggc gtggggggggg ggaatcggca 115440 ctgaccaagg gggtccgttt tgtcacggga aaggaaagag gaaacaggcc gcggacaccc 115500
gggggagttt atgtgttccc ttttctttct tcccacacac acaaaaggcg taccaaacaa 115560
acaaaccaaa agatgcacat gcggtttaac acccgtggtt tttatttaca acaaaccccc 115620
cgtcacaggt cgtcctcgtc ggcgtcaccg tctttgttgg gaacttgggt gtagttggtg 115680
ttgcggcgct tgcgcatgac catgtcggtg accttggcgc tgagcagcgc gctcgtgccc 115740
ttcttcttgg ccttgtgttc cgtgcgctcc atggcagaca ccagggccat gtaccgtatc 115800
atctcccggg cctcggctag cttggcctcg tcaaagtcgc cgccctcctc gccctccccg 115860
gacgcgtccg ggttggtggg gttcttgagc tccttggtgg ttagcgggta cagggccttc 115920
atggggttgc tctgcagccg catgacgtag cgaaaggcga agaaagccgc cgccaggccg 115980

-continued gccaggacca acagacccac ggccagcgcc ccaaaggggt tggacatgaa ggaggacacg 116040
cccgacacgg ccgataccac gccgcccacg atgcccatca ccaccttgcc gaccgcgcgc 116100
cccaggtcgc ccatcccctc gaagaacgcg cccaggcccg cgaacatggc ggcgttggcg 116160
tcggcgtgga tgaccgtgtc gatgtcggcg aagcgcaggt cgtgcagctg gttgcggcgc 116220
tggacctccg tgtagtccag caggccgctg tccttgatct cgtggcgggt gtacacctcc 116280
agggggacaa actcgtgatc ctccagcatg gtgatgttga ggtcgatgaa ggtgctgacg 116340
gtggtgatgt cggcgcggct cagctggtgg gagtacgcgt actcctcgaa gtacacgtag 116400
cccccgccga aggtgaagta gcgccggtgt cccacggtgc acggctcgat cgcatcgcgc 116460
gtcagccgca gctcgttgtt ctcccccagc tgcccctcga ccaacgggcc ctggtcttcg 116520
taccgaaagc tgaccagggg gcggctgtag caggccccgg gccgcgagct gatgcgcatc 116580
gagttttgga cgatcacgtt gtccgcggcg accggcacgc acgtggagac ggccatcacg 116640
tcgccgagca tccgcgcgct cacccgccgg cccacggtgg ccgaggcgat ggcgttgggg 116700
ttcagcttgc gggcctcgtt ccacagggtc agctcgtgat tctgcagctc gcaccacgcg 116760
atggcaacgc ggcccaacat atcgttgaca tggcgctgta tgtggttgta cgtaaactgc 116820
agccgggcga actcgatgga ggaggtggtc ttgatgcgct ccacggacgc gttggcgctg 116880
gccccgggcg gcgggggcgt ggggtttggg ggcttgcggc tctgctctcg gaggtgttcc 116940
cgcacgtaca gctccgcgag cgtgttgctg agaaggggct ggtacgcgat cagaaaaccc 117000
ccattggcca ggtagtactg cggctggccc accttgatgt gcgtcgcgtt gtacctgcgg 117060
gcgaagatgc ggtccatggc gtcgcgggcg tccttgccga tgcagtcccc caggtccacg 117120
cgcgagagcg ggtactcggt caggttggtg gtgaaggtgg tggatatggc gtcggaggag 117180
aatcggaagg agccgccgta ctcggagcgc agcatctcgt ccacctcctg ccacttggtc 117240
atggtgcaga ccgacgggcg ctttggcacc cagtcccagg ccacggtgaa cttgggggtc 117300
gtgagcaggt tccgggtggt cggcgccgtg gcccgggcct tggtggtgag gtcgcgcgcg 117360
tagaagccgt caacctgctt gaagcggtcg gcggcgtagc tggtgtgttc ggtgtgcgac 117420
ccctcccggt agccgtaaaa cggggacatg tacacaaagt cgccagtcgc cagcacaaac 117480
tcgtcgtacg ggtacaccga gcgcgcgtcc acctcctcga cgatgcagtt taccgtcgtc 117540
ccgtaccggt ggaacgcctc cacccgcgag gggttgtact tgaggtcggt ggtgtgccag 117600
ccccggctcg tgcgggtcgc ggcgttggcc ggtttcagct ccatgtcggt ctcgtggtcg 117660
tcccggtgaa acgcggtggt ctccaggttg ttgcgcacgt acttggccgt ggaccgacag 117720 accccccttgg cgttgatctt gtcgatcacc tcctcgaagg ggacgggggc gcggtcctca 117780
aagatcccca taaactggga gtagcggtgg ccgaaccaca cctgcgaaac ggtgacgtct 117840
ttgtagtaca tggtggcctt gaacttgtac ggggcgatgt tctccttgaa gaccaccgcg 117900
atgccctccg tgtagttctg accctcgggc cgggtcgggc agcggcgcgg ctgctcgaac 117960
tgcaccaccg tggcgcccgt ggggggtggg cacacgtaaa agtttgcatc ggtgttctcc 118020
gccttgatgt cccgcaggtg ctcgcgcagg gtggcgtggc ccgcggcgac ggtcgcgttg 118080
tcgccggcgg ggcgcggcgg cggtgggggt ttcggttttt tgttcttctt cggtttcgtg 118140
tcccccgttg gggcggggcc aggggcgggc ggcgccggag tggcaggtcc cccgttcgcc 118200
gcctgggtcg cggccgcgac cccaggcgtg ccgggggaac tcggagccgc cgacgccacc 118260
aggaccccca gcgtcaaccc caagagcgcc catacgacga accaccggca cccccgcgcg 118320
ggggcgccct ggcgcatggc gggactacgg gggcccgtcg tgccccccgt caggtagcct 118380
gggggcgagg tgctggagga ccgagtagag gatcgagaaa acgtctcggt cgtagaccac 118440
gaccgaccgg gggccgatac agccgtcggg ggcgctctcg acgatggcca ccagcggaca 118500
gtcggagtcg tacgtgagat atacgccggg cgggtaacgg taacgacctt cggaggtcgg 118560
gcggctgcag tccgggcggc gcaactcgag ctccccgcac cggtagaccg aggcaaagag 118620
tgtggtggcg ataatcagct cgcgaatata tcgccaggcg gcgcgctgag tgggcgttat 118680
tccggaaatg ccgtcaaaac agtaaaacct ctgaaattcg ctgacggccc aatcagcacc 118740
cgagcccccc gcccccatga tgaaccgggc gagctcctcc ttcaggtgcg gcaggagccc 118800
cacgttctcg acgctgtaat acagcgcggt gttggggggc tgggcgaagc tgtgggtgga 118860
gtgatcaaag aggggcccgt tgacgagctc gaagaagcga tgggtgatgc tggggagcag 118920
ggccgggtcc acctggtgtc gcaggagaga cgctcgcatg aaccggtgcg cgtcgaacac 118980
gcccggcgcc gagcggttgt cgatgaccgt gcccgcgccc gccgtcaggg cgcagaagcg 119040
cgcgcgcgcc gcaaagccgt tggcgaccgc ggcgaacgtc gcgggcagca cctcgccgtg 119100
gacgctgacc cgcagcatct tctcgagctc cccgcgctgc tcgcggacgc agcgccccag 119160
gctggccaac gaccgcttcg tcaggcggtc cgcgtacagc cgccgtcgct cccgcacgtc 119220
cgcggccgct tgcgtggcga tgtcccccca cgtctcgggc ccctgccccc cgggcccgcg 119280
gcgacggtct tcgtcctcgc ccccgccccc gggagctccc aaccccCgtg cccCttcctc 119340
tacggcgaca cggtccccgt cgtcgtcggg gcccgcgccg cccttgggcg cgtccgccgc 119400
gccccccgcc cccatgcgcg ccagcacgcg acgcagcgcc tcctcgtcgc actgttcggg 119460
gctgacgagg cgccgcaaga gcggcgtcgt caggtggtgg tcgtagcacg cgcggatgag 119520
cgcctcgatc tgatcgtcgg gtgacgtggc ctgaccgccg attattaggg cgtccaccat 119580
atccagcgcc gccaggtggc tcccgaacgc gcgatcgaaa tgctccgccc gccgcccgaa 119640
cagcgccagt tccacggcca ccgcggcggt ctcctgctgc aactcgcgcc gcgccagcgc 119700
ggtcaggttg ctggcaaacg cgtccatggt ggtctggccg gcgcggtcgc cggacgcgag 119760
ccagaatcgc aattcgctga tggcgtacag gccgggcgtg gtggcctgaa acacgtcgtg 119820
cgcctccagc agggcgtcgg cctccttgcg gaccgagtcg ttctcgggcg acgggtgggg 119880
ctgcccgtcg ccccccgcgg tccgggccag cgcatggtcc aacacggaga gcgcccgcgc 119940
gcggtcggcg tccgacagcc cggcggcgtg gggcaggtac cgccgcagct cgttggcgtc 120000
cagccgcacc tgcgcctgct gggtgacgtg gttacagata cggtccgcca ggcggcgggc 120060
gatcgtcgcc ccctggttcg ccgtcacaca cagttcctcg aaacagaccg cgcaggggtg 120120
ggacgggtcg ctaagctccg gggggacgat aaggcccgac cccaccgccc ccaccataaa 120180
ctcccgaacg cgctccagcg cggcggtggc gccgcgcgag gggGtgatga ggtggcagta 120240
gtttagctgc tttagaaagt tctcgacgtc gtgcaggaaa cacagctcca tatggacggt 120300
cccgccatac gtatccagcc tgacccgttg gtgatacgga cagggtcggg ccaggcccat 120360
ggtctccgtg aaaaacaccg cgacgtctcc cgcggtcgcg aacgtctcca ggctgcccag 120420
gagccgctcg ccctcgcgcc acgcgtactc tagcagcaac tccagggtga ccgacagcgg 120480
ggtgagaaag gccccggcct gggcctccag gcccggcctc agacgacgcc gcagcgcccg 120540
cacctgaagc gcgttcagct tcagttgggg gagcttcccc cgtccgatgt gggggtcgca 120600
ccgccggagc agctctatct gaaacacata ggtctgcacc tgtccgagca gggctaacaa 120660
cttttgacgg gccacggtgg gctcggacac cggggcggcc atctcgcggc gccgatctgt 120720

-continued accgcggccg gagtatgcgg tggaccgagg cggtccgtac gctacccggc gtctggctga 120780
gccccggggt cccccctattc ggggcggcct cccgcgggcc cgccgaccgg caagccggga 120840
gtcggcggcg cgtgcgtttc tgttctattc ccagacaccg cggagaggaa tcacggcccg 120900
cccagagata tagacacgga acacaaacaa gcacggatgt cgtagcaata atttatttta 120960
cacacattcc ccgccccgcc ctaggttccc ccacccccca acccctcaca gcatatccaa 121020
cgtcaggtct cccttttttgt cggggggccc ctccccaaac gggtcatccc cgtggaacgc 121080
ccgtttgcgg ccggcaaatg ccggtcccgg ggcccccggg ccgccgaacg gcgtcgcgtt 121140
gtcgtcctcg cagccaaaat ccccaaagtt aaacacctcc ccgacgttgc cgagttggct 121200
gactagggcc tcggcctcgt gcgccacctc cagggccgcg tccgtcgacc actcgccgtt 121260
gccgcgctcc agggcacgtg cggtcagctc catcatctcc tcgcttaggt actcgtcctc 121320
caggagcgcc agccagtcct cgatctgcag ctgttgggtg cggggcccca ggcttttcac 121380
ggtcgccacg aacacgctac tggcgacggc cgccccgccc tcggagataa tgccccggag 121440
ctgctcgcac agcgagcttt cgtgcgctcc gccgccgagg ctcgaggccg cgcacacaaa 121500
cccggcccgg ggacaggcca ggacgaactt gcgggtgcgg tcaaaaataa ggagcgggca 121560
cgcgtttttg ccgcccatca ggctggccca gttcccggcc tgaaacacac ggtcgttgcc 121620
ggccatgccg tagtatttgc tgatgctcaa ccccaacacg accatggggc gtgccgccat 121680
gacgggccgc agcaggttgc agctggcgaa catggaggtc cacgcgcccg gatgcgcgtc 121740
cacggcgtcc atcagcgcgc gggccccggc ctccaggccc gccccgccct gcgcggacca 121800
cgcggccgcc gcctgcacgc tggggggacg gcgggacccc gcgatgatgg ccgtgagggt 121860
gttgatgaag tacgtcgagt gatcgcagta ccgcagaatc tggtttgcca tgtagtacat 121920
cgccagctcg ctcacgttgt tgggggccag gttaataaag ttgatcgcgc cgtagtccag 121980
ggaaaacttt ttaatgaacg cgatggtctc gatgtcctcg cgcgacagga gccgggcggg 122040
aagctggttg cgttggaggg ccgtccagaa ccactgcggg ttcggctggt tggaccccgg 122100
gggcttgccg ttggggaaga tggccgcgtg gaactgcttc agcagaaagc ccagcggtcc 122160
gaggaggatg tccacgcgct tgtcgggctt ctggtaggcg ctctggaggc tggcgacccg 122220
cgccttggcg gcctcggacg cgttggcgct cgcgcccgcg aacaacacgc ggctcttgac 122280
gcgcagctcc ttgggaaacc ccagggtcac gcgggcaacg tcgccctcga agctgctctc 122340
ggcgggggcc gtctggccgg ccgtcaggct gggggcgcag atagccgcac cctccgagag 122400
cgcgaccgtc agcgttttgg ccgacagaaa cccgttgtta aacatgtcca tcacgcgccg 122460
ccgcagcacc ggttggaatt gattgcgaaa gttgcgcccc tcgaccgact gcccggcgaa 122520
caccccgtgg cactggctca gggccaggtc ctggtacacg gcgaggttgg atcgccgccc 122580
gagaagctga agcagggggc acggcccgca cgcgtacggg tccagcgtca gggacatggc 122640
gtggttggcc tcgcccagac cgtcgcgaaa cttgaagttc ctcccctcca ccaggttgcg 122700
catcagctgc tccacctcgc ggtccacgac ctgcctgacg ttgttcacca ccgtatgcag 122760
ggcctcgcgg ttggtgatga tggtctccag ccgccccatg gccgtgggga ccgcctggtc 122820
cacgtactgc agggtctcga gttcggccat gacgcgctcg gtcgccgcgc ggtacgtctc 122880
ctgcatgatg gtccgggcgg tctcggatcc gtccgcgcgc ttcagggccg agaaggcggc 122940
gtagtttccc agcacgtcgc agtcgctgta catgctgttc atggtcccga agacgccgat 123000
ggctccgcgg gcggcgctgg cgaacttggg atggcgcgcc cggaggcgca tgagcgtcgt 123060
gtgtacgcag gcgtggcgcg tgtcgaaggt gcacaggtta cagggcacgt cggtctggtt 123120
ggagtccgcg acgtatcgaa acacgtccat ctcctggcgc ccgacgatca cgccgccgtc 123180
gcagcgctcc aggtaaaaca gcatcttggc cagcagcgcc ggggaaaacc cacacaacat 123240
ggccaggtgc tcgccggcaa attcctgggt tccgccgacg aggggcgcgg tgggccgacc 123300
ctcgaacccg ggcaccacgt gtccctcgcg gtccacctgt gggttggccg ccacgtgggt 123360
cccgggcacg aggaagaagc ggtaaaagga gggtttgctg tggtcctttg ggtccgccgg 123420
gccggcgtcg tccacctcgg tgagatggag ggccgagttg gtgctaaata ccatggcccc 123480
cacgagtccc gcggcgcgcg ccaggtacgc cccgacggcg ttggcgcggg ccgcggccgt 123540
gtcctggccc tcgaacagcg gccacgcgga gatgtcggtg ggcggctcgt caaagacggc 123600
catcgacacg atagactcga gggccagggc ggcatctccg gccatgacgg aggccaggcg 123660
ctgttcgaac ccgcccgcag ggcccttgcc gccgccgtca cgcccgcccc gcggggtctt 123720
accctggctg gcttcgaagg ccgtgaacgt aatgtcggcg gggagggcgg cgccctcgtg 123780
gttttcgtca aacgccaggt gggcggccgc gcgggccacg gcgtccacgt ttcggcatcg 123840
cagtgccacg gcggcgggtc ccacgaccgc ctcgaacagg aggcggtgga gggggcggtt 123900
aaaaaacgga agcgggtagg taaaattctc cccgatagat cggtggttgg cgttgaacgg 123960
ctctgcgatg acacggctaa aatccggcat gaacagctgc aacgggtaca cgggtatgcg 124020
gtgcacctcc gccccgccta tggttacctt gtccgagcct cccaggtgca gaaaggtgtt 124080
gttgatgcac acggcctcct tgaagccctc ggtaacgacc agatacagga gggcgcggtc 124140
cgggtccagg ccgaggcgct cacacagcgc ctccccgtc gtctcgtgtt tgaggtcgcc 124200
gggccggggg gtgtagtccg aaaagccaaa atggcggcgt gcccgctcgc agagtcgcgt 124260
caggttcggg gcctgggtgc tggggtccag gtgccggccg ccgtgaaaga cgtacacgga 124320
cgagctgtag tgcgagggcg tcagtttcag ggacaccgcg gtacccccga gccccgtcgt 124380
gcgagaaccc acgaccacgg ccacgttggc ctcaaagccg ctctccacgg tcaggcccac 124440
gaccaggggc gccacggcga cgtcggcatc gccgctgcgc gccgacagta acgccagaag 124500
ctcgatgcct tcggacggac acgcgcgagc gtacacgtat cccaggggcc cggggggac 124560
cttgatggtg gttgccgtct tgggctttgt ctccatgtcc ttctgtcaat cggtccgcga 124620
acggaggtaa tcccggcacg acgacggacg cccgacaagg tatgtctccc gagcgtcaaa 124680
atccgggggg gggcggcgac ggtcaagggg agggttggag accggggttg gggaatgaat 124740
ccctaccctt caccgacaac cccccgggta atcacggggt gccgatgaac cccggcggcc 124800
ggcaacgcgg ggtccctgcg agaggcacag atgcttacgg tcaggtgctc cgggtcgggt 124860
gcgtctggta tgcggttggt atatgtacac tttacctggg ggcgtgcctg gccgccccag 124920
cccctcccac gccccgcgcg tcatcagccg gtgggcgtgg ccgctattat aaaaaaagtg 124980
agaacgcgaa gcgttcgcac tttgtcctaa taatatatat attattagga caaagtgcga 125040
acgcttcgcg ttctcacttt ttttataata gcgcccacgc ccaccggcta cgtcacgctc 125100
ctgtcggccg ccggcggtcc ataagcccgg ccggccgggc cgacgcgaat aaaccgggcc 125160
gccggccggg gcgccgcgca gcagctcgcc gcccggatcc gccagacaaa caaggccctt 125220
gcacatgccg gcccgggcga gcctgggggt ccggtaattt tgccatccca cccaagcggc 125280
tttttgggtt tttctcttcc cccctcccca catcccccct ctttaggggt tcgggtggta 125340
acaaccgcga tgttttccgg tggcggcggc ccgctgtccc ccggaggaaa gtcggcggcc 125400
agggcggcgt ccgggttttt tgcgcccgcc ggccctcgcg gagccggccg gggacccccg 125460

-continued ccttgcttga ggcaaaactt ttacaacccc tacctcgccc cagtcgggac gcaacagaag 125520
ccgaccgggc caacccagcg ccatacgtac tatagcgaat gcgatgaatt tcgattcatc 125580
gccccgcggg tgctggacga ggatgccccc ccggagaagc gcgccggggt gcacgacggt 125640
cacctcaagc gcgcccccaa ggtgtactgc ggggggg acg agcgcgacgt cctccgcgtc 125700
gggtcgggcg gcttctggcc gcggcgctcg cgcctgtggg gcggcgtgga ccacgccccg 125760
gcggggttca accccaccgt caccgtcttt cacgtgtacg acatcctgga gaacgtggag 125820
cacgcgtacg catgcgcgcg gcccagttcc acgcgcggtt tatggacgcc atcacaccga 125880
cggggaccgt catcacgctc ctgggcctga ctccggaagg ccaccgggtg gccgttcacg 125940
tttacggcac gcggcagtac ttttacatga acaaggagga ggtcgacagg cacctacaat 126000
gccgcgcccc acgagatctc tgcgagcgca tggccgcggc cctgcgcgag tccccgggcg 126060
cgtcgttccg cggcatttcc gcggaccact tcgaggcgga ggtggtggag cgcaccgacg 126120
tgtactacta cgagacgcgc cccgctctgt tttaccgcgt ctacgtccga agcgggcgcg 126180
tgctgtcgta cctgtgcgac aacttctgcc cggccatcaa gaagtacgag ggtggggtcg 126240
acgccaccac ccggttcatc ctggacaacc ccgggttcgt caccttcggc tggtaccgtc 126300
tcaaaccggg ccggaacaac acgctagccc agccggcggc cccgatggcc ttcgggacat 126360
ccagcgacgt cgagtttaac tgtacggcgg acaacctggc catcgagggg ggcatgagcg 126420
acctaccggc atacaagctc atgtgcttcg atatcgaatg caaggcgggg ggggaggacg 126480
agctggcctt tccggtggcc gggcacccgg aggacctggt catccagata tcctgtctgc 126540
tctacgacct gtccaccacc gccctggagc acgtcctcct gttttcgctc ggttcctgcg 126600
acctccccga atcccacctg aacgagctgg cggccagggg cctgcccacg cccgtggttc 126660
tggaattcga cagcgaattc gagatgctgt tggccttcat gacccttgtg aaacagtacg 126720
gccccgagtt cgtgaccggg tacaacatca tcaacttcga ctggcccttc ttgctggcca 126780
agctgacgga catttacaag gtccccctgg acgggtacgg ccgcatgaac ggccggggcg 126840
tgtttcgcgt gtgggacata ggccagagcc acttccagaa gcgcagcaag ataaaggtga 126900
acggcatggt gaacatcgac atgtacggga ttataaccga caagatcaag ctctcgagct 126960
acaagctcaa cgccgtggcc gaagccgtcc tgaaggacaa gaagaaggac ctgagctatc 127020
gcgacatccc cgcctactac gccgccgggc ccacgcaacg cggggtgatc ggcgagtact 127080
gcatacagga ttccctgctg gtgggccagc tgttttttaa gtttttgccc catctggagc 127140
tctcggccgt cgcgcgcttg gcgggtatta acatcacccg caccatctac gacggccagc 127200
agatccgcgt ctttacgtgc ctgctgcgcc tggccgacca gaagggcttt attctgccgg 127260
acacccaggg gcgatttagg ggcgccgggg gggaggcgcc caagcgtccg gccgcagccc 127320
gggaggacga ggagcggcca gaggaggagg gggaggacga ggacgaacgc gaggagggcg 127380
ggggcgagcg ggagccggag ggcgcgcggg agaccgccgg ccggcacgtg gggtaccagg 127440
gggccagggt ccttgacccc acttccgggt ttcatgtgaa ccccgtggtg gtgttcgact 127500
ttgccagcct gtaccccagc atcatccagg cccacaacct gtgcttcagc acgctctccc 127560
tgagggccga cgcagtggcg cacctggagg cgggcaagga ctacctggag atcgaggtgg 127620
gggggcgacg gctgttcttc gtcaaggctc acgtgcgaga gagcctcctc agcatcctcc 127680
tgcgggactg gctcgccatg cgaaagcaga tccgctcgcg gattccccag agcagccccg 127740
aggaggccgt gctcctggac aagcaacagg ccgccatcaa ggtcgtgtgt aactcggttt 127800
acgggttcac gggagtgcag cacggactcc tgccgtgcct gcacgttgcc gcgacggtga 127860

-continued cgaccatcgg ccgcgagatg ctgctcgcga cccgcgagta cgtccacgcg cgctgggcgg 127920
ccttcgaaca gctcctggcc gatttcccgg aggcggccga catgcgcgcc cccgggccct 127980
attccatgcg catcatctac ggggacacgg actccatctt tgtgctgtgc cgcggcctca 128040
cggccgccgg gctgacggcc gtgggcgaca agatggcgag ccacatctcg cgcgcgctgt 128100
ttctgtcccc catcaaactc gagtgcgaaa agacgttcac caagctgctg ctgatcgcca 128160
agaaaaagta catcggcgtc atctacgggg gtaagatgct catcaagggc gtggatctgg 128220
tgcgcaaaaa caactgcgcg tttatcaacc gcacctccag ggccctggtc gacctgctgt 128280
tttacgacga taccgtatcc ggagcggccg ccgcgttagc cgagcgcccc gcagaggagt 128340
ggctggcgcg acccctgccc gagggactgc aggcgttcgg ggccgtcctc gtagacgccc 128400
atcggcgcat caccgacccg gagagggaca tccaggactt tgtcctcacc gccgaactga 128460
gcagacaccc gcgcgcgtac accaacaagc gcctggccca cctgacggtg tattacaagc 128520
tcatggcccg ccgcgcgcag gtcccgtcca tcaaggaccg gatcccgtac gtgatcgtgg 128580
cccagacccg cgaggtagag gagacggtcg cgcggctggc cgccctccgc gagctcgacg 128640
ccgccgcccc aggggacgag cccgcccccc ccgcggccct gccctccccg gccaagcgcc 128700
cccgggagac gccgttgcat gccgaccccc cgggaggcgc gtccaagccc cgcaagctgc 128760
tggtgtccga gctggccgag gatcccgcat acgccattgc ccacggcgtc gccctgaaca 128820
cggactatta cttctcccac ctgttggggg cggcgtgcgt gacattcaag gccctgtttg 128880
ggaataacgc caagatcacc gagagtctgt taaaaaggtt tattcccgaa gtgtggcacc 128940
ccccggacga cgtggccgcg cggctccggg ccgcagggtt cggggcggtg ggtgccggcg 129000
ctacggcgga ggaaactcgt cgaatgttgc atagagcctt tgatactcta gcatgagccc 129060
cccgtcgaag ctgatgtccc tcattttaca ataaatgtct gcggccgaca cggtcggaat 129120
ctccgcgtcc gtgggtttct ctgcgttgcg ccggaccacg agcacaaacg tgctctgcca 129180
cacgtgggcg acgaaccggt accccgggca cgcggtgagc atccggtcta tgagccggta 129240
gtgcaggtgg gcggacgtgc cgggaaagat gacgtacagc atgtggcccc cgtaagtggg 129300
gtccgggtaa aacaacagcc gcgggtcgca cgccccgcct ccgcgcagga tcgtgtggac 129360
gaaaaaaagc tcgggttggc caagaatccc ggccaagagg tcctggaggg gggcgttgtg 129420
gcggtcggcc aacacgacca aggaggccag gaaggcgcga tgctcgaata tcgtgttgat 129480
ctgctgcacg aaggccagga ttagggcctc gcggctggtg gcggcgaacc gcccgtctcc 129540
cgcgttgcac gcgggacagc aacccccgat gcctaggtag tagcccatcc cggagagggt 129600
caggcagttg tcggccacgg tctggtccag acagaagggc agcgagacgg gagtggtctt 129660
caccaggggc accgagagcg agcgcacgat ggcgatctcc tcggagggcg tctgggcgag 129720
ggcggcgaaa aggccccgat agcgctggcg ctcgtgtaaa cacagctcct gtttgcgggc 129780
gtgaggcggc aggctcttcc gggaggcccg acgcaccacg cccagagtcc cgccggccgc 129840
agaggagcgc gaccgccggc gctccttgcc gtgatagggc ccgggccggg agccgcggcg 129900
atgggggtcg gtgtcataca taggtacaca gggtgtgctc cagggacagg agcgagatcg 129960
agtggcgtct aagcagcgcg cccgcctcac ggacaaatgt ggcgagcgcg gtgggctttg 130020
gtacaaatac ctgatacgtc ttgaaggtgt agatgagggc acgcaacgct atgcagacac 130080
gcccctcgaa ctcgttcccg caggccagtt tggccttgtg gagcagcagc tcgtcgggat 130140
gggtggcggg gggatggccg aacagaaccc aggggtcaac ctccatctcc gtaatggcgc 130200
acatggggtc acagaacatg tgcttaaaga tggcctcggg ccccgcggcc cgaagcaggc 130260
tcacaaaccg gcccccgtcc ccgggctgcg tctcggggtc agcctcgagc tggtcgacga 130320
cgggtacgat acagtcgaag aggctcgtgt tgttttccga gtagcggacc acggaggccc 130380
ggagtctgcg cagggccagc cagtaagcac gcaccagtaa caggttacac agcaggcatt 130440
ctccgccggt gcgcccgcgc ccccggccgt gtttcagcac ggtggccatc agagggccca 130500
ggtcgaggtc gggctgggca tcgggttcgg taaactgcgc aaagcgcgga gccacgtcgc 130560
gcgtgcgtgc cccgcgatgc gcttcccagg actggcggac cgtggcgcga cgggcctccg 130620
cggcagcgcg cagctggggc cccgactccc agacggcggg ggtgccggcg aggagcagca 130680
ggaccagatc cgcgtacgcc cacgtatccg gcgactcctc cggctcgcgg tccccggcga 130740
ccgtctcgaa ttccccgttg cgagcggcgg cgcgcgtaca gcagctgtcc ccgcccccgc 130800
gccgaccctc cgtgcagtcc aggagacggg cgcaatcctt ccagttcatc agcgcggtgg 130860
tgagcgacgg ctgcgtgccg gatcccgccg accccgcccc ctcctcgccc ccggaggcca 130920
aggttccgat gagggcccgg gtggcagact gcgccaggaa cgagtagttg gagtactgca 130980
ccttggcggc tcccggggag ggcgagggct tgggttgctt ctgggcatgc cgcccgggca 131040
ccccgccgtc ggtacggaag cagcagtgga gaaaaaagtg ccggtggatg tcgtttatgg 131100
tgagggcaaa gcgtgcgaag gagccgacca gggtcgcctt cttggtgcgc agaaagtggc 131160
ggtccatgac gtacacaaac tcgaacgcgg ccacgaagat gctagcggcg cagtggggcg 131220
cccccaggca tttggcacag agaaacgcgt aatcggccac ccactgaggc gagaggcggt 131280
aggtttgctt gtacagctcg atggtgcggc agaccagaca gggccggtcc agcgcgaagg 131340
tgtcgatggc cgccgcggaa aagggcccgg tgtccaaaag cccctcccca cagggatccg 131400
ggggcgggtt gcggggtcct ccgcgcccgc ccgaaccccc tccgtcgccc gcccccccgc 131460
gggcccttga gggggcggtg accacgtcgg cggcgacgtc ctcgtcgagc gtaccgacgg 131520
gcggcacacc tatcacgtga ctggccgtca ggagctcggc gcagagagcc tcgttaagag 131580
ccaggaggct gggatcgaag gccacatacg cgcgctcgaa cgcccccgcc ttccagctgc 131640
tgccggggga ctcttcgcac accgcgacgc tcgccaggac cccgggggc gaagttgcca 131700 tggctgggcg ggaggggcgc acgcgccagc gaactttacg ggacacaatc cccgactgcg 131760
cgctgcggtc ccagaccctg gagagtctag acgcgcgcta cgtctcgcga gacggcgcgc 131820
atgacgcggc cgtctggttc gaggatatga cccccgccga gctggaggtt gtcttcccga 131880
ctacggacgc caagctgaac tacctgtcgc ggacgcagcg gctggcctcc ctcctgacgt 131940
acgccgggcc tataaaagcg cccgacgacg ccgccgcccc gcagaccccg gacaccgcgt 132000
gtgtgcacgg cgagctgctc gcccgcaagc gggaaagatt cgcggcggtc attaaccggt 132060
tcctggacct gcaccagatt ctgcggggct gacgcgcgtg ctgttgggcg ggacggttcg 132120
cgaacccttt ggtgggttta cgcgggcacg cacgctccca tcgcgggcgc catggcggga 132180
ctgggcaagc cctacaccgg ccacccaggt gacgccttcg agggtctcgt tcagcgaatt 132240
cggcttatcg tcccatctac gttgcggggc ggggacgggg aggcgggccc ctactctccc 132300
tccagcctcc cctccaggtg cgcctttcag tttcatggcc atgacgggtc cgacgagtcg 132360
tttcccatcg agtatgtact gcggcttatg aacgactggg ccgaggtccc gtgcaaccct 132420
tacctgcgca tacagaacac cggcgtgtcg gtgctgtttc aggggttttt tcatcgccca 132480
cacaacgccc ccgggggcgc gattacgcca gagcggacca atgtgatcct ggggtccacc 132540
gagacgacgg ggttgtccct cggcgacctg gacaccatca aggggcggct cggcctggat 132600
gcccggccga tgatggccag catgtggatc agctgctttg tgcgcatgcc ccgcgtgcag 132660
ctcgcgtttc ggttcatggg ccccgaagat gccggacgga cgagacggat cctgtgccgc 132720
gccgccgagc aggctattac ccgtcgccgc cgaacccggc ggtcccggga ggcgtacggg 132780
gccgaggccg ggctgggggt ggccggaacg ggtttccggg ccagggggga cggttttggc 132840
ccgctcccct tgttaaccca agggccctcc cgcccgtggc accaggccct gcggggtctt 132900
aagcacctac ggattggccc ccccgcgctc gttttggcgg cgggactcgt cctgggggcc 132960
gctatttggt gggtggttgg tgctggcgcg cgcctataaa aaaggacgca ccgccgccct 133020
aatcgccagt gcgttccgga cgccttcgcc ccacacagcc ctcccgaccg acaccccccat 133080
atcgcttccc gacctccggt cccgatggcg tcccgcaatt tcaccgcccc aacaccgtta 133140
ccaccgatag cgtccgggcg cttggcatgc gcgggctcgt cttggccacc aataactctc 133200
agtttatcat ggataacaac cacccacacc cccagggcac ccaaggggcc gtgcgggagt 133260
ttctccgcgg tcaggcggcg gcactgacgg accttggtct ggcccacgca aacaacacgt 133320
ttaccccgca gcctatgttc gcgggcgacg caccggccgc ctggttgcgg cccgcgtttg 133380
gcctgcggcg cacctattca ccttttgtcg ttcgagaacc ttcgacgccc gggaccccgt 133440
gaggcccagg gagttccttc tggggtgttt taatcaataa aagaccacac caacgcacga 133500
gccttgcgtt taatgtcgtg tttattcaag ggagtgggat agggttcgac ggttcgaaac 133560
ttaacacacc aaataatcga gcgcgtctag cccagtaaca tgcgcacgtg atgtaggctg 133620
gtcagcacgg cgtcgctgtg atgaagcagc gcccggcggg tccgctgtaa ctgctgttgt 133680
aggcggtaac aggcgcggat cagcaccgcc agggcgctac gaccggtgcg ttgcacgtag 133740
cgtcgcgaca gaactgcgtt tgccgatacg ggcgggggggc cgaattgtaa gcgcgtcacc 133800
tcttgggagt catcggcgga taacgcactg aatggttcgt tggttatggg ggagtgtggt 133860
tccccaggga gtgggtcgaa cgcctcggcc tcggaatccg agaggaacaa cgaggtggcg 133920
tcggagtctt cgtcgtcaga gacatacagg gtctgaagca gcgacacggg cggggggggta 133980
gcgtcgatgt gtagcgcgag ggaggatgcc cacgaagaca ccccagacaa ggagctgccc 134040
gtgcgtggat ttgtggaaga cgcggaagcc gggacggatg ggcggttttg cggtgcccgg 134100
aaccgaaccg ccggatactc cccgggtgct acatgcccgt tttggggctg gggttggggc 134160
tggggttggg gctggggttg gggctggggt tggggctggg gttggggctg gggttggggt 134220
tggggttggg gctggggttg gggttggggc tggggctggg gctggggctg gggctggggc 134280
tggggctggg gctggggctg gggctggggc tggggctggg gctggggctg gggctggggt 134340
tggggctggg gcgcggacag gcggctgacg gtcaaatgcc cccgggggcg cgcagatgtg 134400
gtgggcgtgg ccaccggctg ccgtgtagtg gggcggcggg aaaccgggcc tccgggcgta 134460
acaccgccct ccagcgtcaa gtatgtgggg ggcgggcctg acgtcggggg cggggtgacg 134520
ggttggaccg cgggaggcgg gggagaggga cctgcgggag aggatgaggt cggctcggcc 134580
gggttgcggc ctaaaacagg ggccgtgggg tcggcggggt cccagggtga agggagggat 134640
tcccgcgatt cggacagcga cgcgacagcg gggcgcgtaa ggcgccgctg cggcccgcct 134700
acgggaaccc tgggggggggt tggcgcggga cccgaggtta gcggggggcg gcggttttcg 134760
cccccgggca aaaccgtgcc ggttgcgacc gggggcggaa cgggatcgat agggagagcg 134820
ggagaagcct ggccggcgga ctggggaccg agcgggaggg gcacaccaga caccaaagcg 134880
tggggcgctg gctctggggg tttgggaggg gccgggggggc gcgcgaaatc ggtaaccggg 134940

-continued gcgaccgtgt cggggagggc aggcggccgc caaccctggg tggtcgcgga agcctgggtg 135000
gcgcgcgcca gggagcgtgc ccggcggtgt cggcgcgcgc gcgacccgga cgaagaagcg 135060
gtagaagcgc gggaggaggc ggggggcgg ggggcggtgg catcgggggg cgccggggaa 135120
ctttgggggg acggcaagcg ccggaagtcg tcgcgggggc ccacgggcgc cggccgcgtg 135180
ctttcggccg ggacgcccgg tcgtgcttcg cgagccgtga ctgccggccc agggggccgc 135240
ggtgcacact gggacgtggg gacggactga tcggcggtgg gcgaaagggg gtccggggca 135300
aggaggggcg cggggccgcc ggagtcgtca gacgcgagct cctccaggcc gtgaatccat 135360
gcccacatgc gaggggggac gggctcgccg ggggtggcgt cggtgaatag cgtgggggcc 135420
aggcttccgg gccccaacga gccctccgcc ccaacaaggt ccgccgggcc gggggtcggg 135480
ttcgggaccg aggggctctg gtcgtcgggg gcgcgctggt acaccggatg ccccgggaat 135540
agctcccccg acaggaggga ggcgtcgaac ggccgcccga ggatagctcg cgcgaggaag 135600
gggtcctcgt cggtggcgct cgcggcgagg acgtcctcgc cgcccaccac aaacgggagc 135660
tcctcggtgg cctcgctgcc aacaaaccgc acgtcggggg ggccgggggg gtccgggttt 135720
tcccacaaca ccgcgaccgg ggtcatggag atgtccacga gcaccaggca cggcgggccc 135780
cgggcgaggg gccgctcggc gatgagcgcg gacaggcgcg ggagctgtgc cgccagacac 135840
gcgttttcga tcgggttaag gtcggcgtgc aggaggcgga cggcccacgt ctcgatgtcg 135900
gacgacacgg catcgcgcaa ggcggcgtcc ggcccgcgag cgcgtgagtc aaacagcgtg 135960
aggcacagct ccagttccga ctcgcgggaa aaggccgtgg tgttgcggag cgccacgacg 136020
acgggcgcgc ccaggagcac tgccgccagc accaggtcca tggccgtaac gcgcgccgcg 136080
ggggtgcggt gggtggcggc ggccggcacg gcgacgtgct ggcccgtggg ccggtagagg 136140
gcgttggggg gagcgggggg tgacgcctcg cgcccccccg aggggctcag cgtctgccca 136200
gattccagac gcgcggtcag aagggcgtcg aaactgtcat actctgtgta gtcgtccgga 136260
aacatgcagg tccaaagagc ggccagcgcg gtgcttggga gacacatgcg cccgaggacg 136320
ctcaccgccg ccagcgcctg ggcgggactc agctttccca gcgcggcgcc gcgctcggtt 136380
cccagctcgg ggaccgagcg ccagggcgcc agggggtcgg tttcggacaa cttgccgcgg 136440
cgccagtctg ccagccgcgt gccgaacatg aggccccggg tcggagggcc tccggccgaa 136500
aacgctggca gcacgcggat gcgggcgtct ggatgcgggg tcaggcgctg cacgaatagc 136560
atggaatctg ctgcgttctg aaacgcacgg gggagggtga gatgcatgta ctcgtgttgg 136620
cggaccagat ccaggcgcca aaaggtgtaa atgtgttccg gggagctggc caccagcgcc 136680
accagcacgt cgttctcgtt aaaggaaacg cggtgcctag tggagctctg gggtccgagc 136740
ggcggccccg gggccgccgc gtcacccccc cattccagct gggcccagcg acacccaaac 136800
tcgcgcgtga gagtggtcgc gacgagggcg acgtagagct cggccgccgc atccatcgag 136860
gccccccatc tcgcctggcg gtggcgcaca aagcgtccga agagctgaaa gttggcggcc 136920
tgggcgtcgc tgagggccag ctgaaaccgg ttgatgacgg tgaggacgta catggccgtg 136980
acggtcgagg ccgactccag ggtgtccgtc ggaagcgggg ggcgaatgca tgccgcctcg 137040
ggacacatca gcagcgcgcc gagcttgtcg gtcacggccg ggaagcagag cgcgtactgc 137100
agtggcgttc catccgggac caaaaagctg gggcgaacg gcctatccag cgtactggtg 137160
gcctcgcgca gcaccagggg ccccgggcct ccgctcactc gcaggtacgc ctcgccccgg 137220
cggcgcagca tctgcgggtc ggcctcttgg ccgggtgggg cggacgcccg ggcgcgggcg 137280
tctagggcgc gaagatccac gagcaggggc gcgggcgcgg ccgccgcgcc cgcgcccgtc 137340
tggcctgtgg ccttggcgta cgcgctatat aagcccatgc ggcgttggat gagctcccgc 137400
gcgccccgga actcctccac cgcccatggg gccaggtccc cggccaccgc gtccaattcc 137460
gccaacaggc cccccagggt gtcaaagttc atctcccagg ccacccttgg caccacctcg 137520
tcccgcagcc gggcgctcag gtcggcgtgt tgggccacgc gccccccgag ctcctccacg 137580
gccccggccc gctcggcgct cttggcgccc aggacgccct ggtacttggc gggaaggcgc 137640
tcgtagtccc gctgggctcg cagccccgac acagtgttgg tggtgtcctg cagggcgcga 137700
agctgctcgc atgccgcgcg aaatccctcg ggcgatttcc aggccccccc gcgaacgcgg 137760
ccgaagcgac cccatacctc gtcccactcc gcctcggcct cctcgaaaga cctccgcagg 137820
gcctcgacgc ggcgacgggt gtcgaagagc gactgcaggc gcgcgccctg tcgcgtcagg 137880
aggcccgggc cgtcgccgct ggccgcgctt agcgggtgcg tctcaaaggt gcgctgggca 137940
tgttccaacc aggcgaccgc ctgcacgtcg agctcgcgcg ccttctccgt ctggtccaac 138000
agaatctcga cctgatccgc gatctcctcc gccgagcgcg cctggtccag cgtcttggcc 138060
acggtcgccg ggacggcaac caccttcagc agggtcttca gattggccag accctcggcc 138120
tcgagctggg cccggcgctc gcgcgcggcc agcacctccc gcaaccccgc cgtgacccgc 138180
tcggtggctt cggcgcgctg ctgtttggcg cgcaccacgg cgtccttggt atcggccagg 138240
tcctgtcggg tcacgaatgc gacgtagtcg gcgtacgccg tgtccttcac ggggctctgg 138300
tccacgcgct ccagcgccgc cacacacgcc accagcgcgt cctcgctcgg gcagggcagg 138360
gtgacccctg cccggacaag ctcggcggcc gccgccgggt cgttgcgcac cgcggatatc 138420
tcctccgcgg cggcggccag gtccagcgcc acgcttccga tcgcgcgccg cgcgtcggcc 138480
cggagggcgt ccaggcgatc gcggatatcc acgtactcgg cgtagccctt ttgaaaaaac 138540
ggcacgtact ggcgcagggc cggcacgccc cccaagtctt ccgacaggtg taggacggcc 138600
tcgtggtagt cgataaaccc gtcgttcacc tgggcccgct ccagcagccc ccccgcgagc 138660
cgcagaagcc gcgccagggg ctcggtgtcc acccgaaaca tgtcggcgta cgtgtcggcc 138720
gcggccccga aggccgcgct ccagtcgatg cggtgaatgg ctgcgagcgg ggggagcatg 138780
gggtggcgct ggttctcggg ggtgtatggg ttaaacgcaa gggccgtctc cagggcaagg 138840
gtcaccgcct tggcgttggt tcccagcgcc tgctcggccc gctttcggaa gtcccggggg 138900
ttgtagccgt gcgtgcccgc cagcgcctgc aggcgacgga gctcgaccac gtcaaactcg 138960
gcaccgcttt ccacgcggtc cagcacggcc tccacgtcgg cggcccagcg ctcgtggcta 139020
ctgcgggcgc gctgggccgc catcttctct ctgaggtcgg cggtggcggc ctcaagttcg 139080
tcggcgcggc gtcgcgtggc gccgatgacc tttcccagct cctgcagggc gcgcccgctg 139140
ggggagtggt ccccggccgt cccttcggcg tgcaacaggc ccccgaacct gccctcgtgg 139200
cccgcgaggc tttcccgcgc gccggtggtc gcgcgcgtcg cggcctggat cagggaggca 139260
tgctctccct ccggttggtt ggcggcccgg cgcacctgga cgacaaggtc ggcggcagcc 139320
gaccctaagg tcgtgagctg ggcgatggcc ccccgcgcgt ccagggccaa ccgagtcgcc 139380
ttgacgtatc ccgcggcgct gtcggccatg gccgctagga aggccagggg ggaggccggg 139440
tcgctggcgg ccgcgcccag ggccgtcact gcgtcgacca ggacgcggtg cgcccgcacg 139500
gccgcatcca ccgtcgacgc ggggtctgcc gtcgcgacgg cggcgctgcc ggcgttgatg 139560
gcgttcgaga cggcgtgggc tatgatcggg gcgtgatcgg cgaagaactg caagagaaac 139620
ggagtctcgg gggcgttggc gaacaggttc ttcagcacca ccacgaagct gggatgcaag 139680
ccggacagag ccgtcgccgt gtccggagtc gggtgctcca gggcatctcg gtactgcccc 139740
agcagccccc acatgtccgc ccgcagcgcc gccgtaacct ccgggggcgc cccccgaacg 139800
gcctcgggga ggtccgacca gcccgccggc agggaggccc gcagggtcgt caggacggcc 139860
ggacaggcct ttagccccac aaagtcaggg aggggccgca ggaccccctg gagtttgtgc 139920
aagaacttct cccgggcgtc gcgggccacc ttcgcccgct cccgcgctcc ctcgagcatt 139980
gcctccaggg agcgcgcgcg ctcccgcaaa cgggcacgcg catcgggggc gagctctgcc 140040
gtcagcttgg cggcatccat ggcccgcgcc tgccgcagcg cttcctcggc catgcgcgtg 140100
gcctctggcg acagcccgcc gtcgtcgggg tagggcgacg cgccgggcgc aggaacaaag 140160
gccgcgtcgc tgtccagctg ctggcccagg gccgcatcta gggcgtcgaa gcgccgcagc 140220
tcggccagac ccgagctgcg gcgcgcctgc tggtcgttaa tgtcgcggat gctgcgcgcc 140280
agctcgtcca gcggcttgcg ttctatcagc ccttggttgg cggcgtccgt caggacggag 140340
agccaggccg ccaggtcctc gggggcgtcc agcgtctggc cccgctgtat cagatcccgc 140400
aacaggatgg ccgtggggct ggtcgcgatc gggggcgggg cgggaatggc ggcgctctgc 140460
gcgatgtccc gcgtgtgctg gtcgaagaca ggcagggact ctagcagctg gaccacgggc 140520
acgacggcgg ccgaagccac gtgaaaccgg cggtcgttgt tgtcgctggc ctgcagagcc 140580
ttggcgctgt atacggcccc ccggtaaaag tactccttaa ccgcgccctc gatcgcccga 140640
cgggcctggg tccgcacctc ctccagccga acctgaacgg cctcggggcc caggggggggt 140700 gggcgcggag ccccctgcgg ggccgccccg gccggggcgg gcattacgcc gaggggcccg 140760
gcgtgctgtg agaccgcgtc gaccccgcga gcgagggcgt cgagggcctc gcgcatctgg 140820
cgatcctccg cctccaccct aatctcttcg ccacgggcaa atttggccag agcctggact 140880
ctatacagaa gcggttctgg gtgcgtcggg gtggcggggg caaaaagggt gtccgggtgg 140940
gcctgcgagc gctccagaag ccactcgccg aggcgtgtat acagattggc cggcggggcc 141000
gcgcgaagct gcagctccag gtccgcgagt tccccgtaaa aggcgtccgt ctcccgaatg 141060
acatccctag ccacaaggat cagcttcgcc agcgccaggc gaccgatcag agagttttcg 141120
tccagcacgt gctggacgag gggcagatgg gcggccacgt cggccaggct caggcgcgtg 141180
gaggccagaa agtcccccac ggccgttttc cggggcagca tgctcagggt aaactccagc 141240
agggcggcgg ccgggccggc caccccggcc tgggtgtgcg tccgggcccc gttctcgatg 141300
agaaaggcga ggacgcgttc aaagaaaaaa ataacacaga gctccagcag ccccggagaa 141360
gccggatacg gcgaccgtaa ggcgctgatg gtgagccgcg aacacgcggc gacctcgcgg 141420
gccagggcgg cggagcacgc ggtgaactta accgccgtgg cggccacgtt tgggtgggcc 141480
tcgaacagct gggcaaggtc tgcgcccggg ggctcgggtg agcggcgagt cttcagcgcc 141540
tcgagggcct gcgaggacgc cggaaccgtg ggcccgtcgt cctcgcccgc ctcggcgacc 141600
ggcggcccgg ccgggtcggg gggtgccgag gcgaggacag gctccggaac ggaggcgggg 141660
accgcggccc cgacgggggt tttgcctttg ggggtggatt tcttcttggt tttggcaggg 141720
ggggccgagc gtttcgtttt ctcccccgaa gtcaggtctt cgacgctgga aggcggagtc 141780
caggtgggtc ggcggcgctt gggaaggccg gccgagtagc gtgcccggtg ccgaccaacc 141840
gggacgacgc ccatctccag gacccgcatg tcgtcgtcat cttcttcggc cgcctctgcg 141900 gcgggggggct tgggggcgga gggaggcggt ggtgggatcg cggagggtgg gtcggcggag 141960
ggtgggtcgg cggagggggg atccgtgggt ggggtaccct tcagggccac cgcccataca 142020
tcgtcgggcg cccgattcgg gcgcttggcc tctggttttg ccgacggacc ggccgtcccc 142080
cgggatgtct cggaggccct gtcgtcgcga cgggcccggg tcggtggcgg cgactgggcg 142140
gctgtgggcg ggtggggccc cgtgcccccct accccctccc gggggcccac gccgacgcag 142200
ggctccccca ggcccgcgat ctcgccccgc agggggtgcg tgatggccac gcgccgttcg 142260
ctgaacgctt cgtcctgcag gtaagtctcg ctggccccgt aaagatgcag agccgcggcc 142320
gtcaagtccg caggagccgc gggttccggg cccgacggca cgaaaaacac catggctccc 142380
gcccaccgta cgtccgggcg atcgcgggtg taatacgtca ggtatggata catgtccccc 142440
gcccgcactt tggcgatgaa cgcgggggtg ccctccggaa ggccgtgcgg gtcaaaaagg 142500
tatgcggtgt cgccgtccct gaacaacccc atccctaggg ggccaatggt taggagcgtg 142560
tacgacaggg ggcgcagggc ccacgggccg gcgaagaacg tgtgtgcggg gcattgtgtc 142620
tccagcaggc ccgccgcggg ctccccgaag aagcccacct cgccgtatac gcgcgagaag 142680
acacagcgca gtccgccgcg cgcccctggg tactcgagga agttggggag ctcgacgatc 142740
gaacacatgc gcggcggccc agggcccgcg gtcgcgcgcg tccactcgcc cccctcgacc 142800
aaacaaccct cgatggcctc cgcggacaga acgtcgcgag ggcccacatc aaatatgagg 142860
ctgagaaagg acagcgacga gcgcatgcac gataccgacc cccccggctc caggtcgggc 142920
gcgaactggt tccgagcacc ggtgaccacg atgtcgcgat ccccccccgcg ttccatcgtg 142980
gagtgcggtg gggtgcccgc gatcatatgt gccctactgg ccagagaccc ggcctgttta 143040
tggaccggac ccccggggtt agtgttgttt ccgccaccca tgcccccgta ccatggcccc 143100
ggttcccctg attaggctac gagtcgcggt gatcgcttcc caaaaaccga gctgcgtttg 143160
tctgtcttga tctttccccc cccccccgcc cgcccgcaca ccataacacc gagaacaaca 143220
cacgggggtg ggcgtaacat aataaagctt tattggtaac tagttaacgg caagtccgtg 143280
ggtggcgcga cggtgtcctc cgggctcatc tcgtcgtcct cgacgggggt gttggaatga 143340
ggcgcccccct cgcggtccgc ctggcgtggg ccgtgcccat aggcctccgg cttctgtgcg 143400
tccatgggca taggcgcggg gagactgttt ccggcgtcgc ggacctccag gtccctggga 143460
gactccggtc cggctaacgg acgaaacgcg gaagcgcgaa acacgccgtc ggtgacccgc 143520
aggagctcgt tcatcagtaa ccaatccata ctcagcgtaa cggccagccc ctggcgagac 143580
agatccacgg aatccggaac cgcggtcgtc tggcccaggg ggccgaggct gtagtccccc 143640
caggccccta ggtcgcgacg gctcgtaagc acgacgcggt cggccgcggg gctttgcggg 143700
ggggcgtcct cgggcgcatg cgccattacc tctcggatgg ccgcggcgcg ctggtcggcc 143760
gagctgacca agggcgccac gaccacggcg cgctccgtct gcaggccctt ccacgtgtcg 143820
tggagttcct ggacaaactc ggccacgggc tcgggtcccg cggccgcgcg cgcggcttga 143880
tagcaggccg agagacgccg ccagcgcgct agaaactgac ccatgaagca aaacccgggg 143940
acctggtctc ccgacagcag cttcgacgcc cgggcgtgaa tgccggacac gacggacaga 144000
aacccgtgaa tttcgcgccg gaccacggcc agcacgttgt cctcgtgcga cacctgggcc 144060
gccagctcgt cgcacacccc caggtgcgcc gtggtttcgg tgatgacgga acgcaggctc 144120
gcgagggacg cgaccagcgc gcgcttggcg tcgtgataca tgctgcagta ctgactcacc 144180
gcgtccccca tggcctcggg gggccagggc cccaggcggt cgggcgtgtc cccgaccacc 144240
gcatacaggc ggcgcccgtc gctctcgaac cgacactcga aaaaggcgga gagcgtgcgc 144300
atgtgcagcc gcagcagcac gatggcgtcc tccagttggc gaatcagggg gtctgcgcgc 144360
tcggcgaggt cctgcagcac cccccgggcg gccagggcgt acatgctaat caacaggagg 144420
ctggtgccca cctcgggggg cgggggggc tgcagctgga ccaggggccg cagctgctcg 144480
acggcacccc tggagatcac gtacagctcc cggagcagct gctctatgtt gtcggccatc 144540
tgcatagtgg ggccgaggcc gccccgggcg gccggttcga ggagggtaat cagcgcgccc 144600
agtttggtgc gatggccctc gaccgtgggg agatagccca gcccaaagtc ccgggcccag 144660
gccaacacac gcagggcgaa ctcgaccggg cgtggaaggt aggccgcgct acacgtggcc 144720
ctcaacgcgt ccccgaccac cagggccaga acgtagggga cgaagcccgg gtcggcgagg 144780
acgttggggt gaatgccctc gagggcgggg aagcggatct gggtcgccgc ggccaggtgg 144840
acagaggggg cgtggctggg ctgcccgacg gggagaagcg cggacagcgg cgtggccggg 144900
gtggtggggg tgatgtccca gtgggtctga ccatacacgt cgatccagat gagcgccgtc 144960
tcgcggagaa ggctgggttg accggaacta aagcggcgct cggccgtctc aaactccccc 145020
acgagcgccc gccgcaggct cgccagatgt tccgtcggca cggccggacc catgatacgc 145080
gccagcgtct ggctcagaac gccccccgac aggccgaccg cctcgcagag ccgcccgtgc 145140
gtgtgctcgc tggcgccctg gacccgcctg aaagttttta cgtagttggc atagtacccg 145200
tattcccgcg ccagaccaaa cacgttcgac cccgcgaggg caatgcaccc aaagagctgc 145260
tggacttcgc cgagtccgtg gccggcgggc gtccgcgcgg ggacgcccgc cgccagaaac 145320
ccctccaggg ccgaaaggta gtgcgtgcag tgcgagggcg tgaacccagc gtcgatcagg 145380
gtgttgatca ccacggaggg cgaattggta ttctggatca acgtccacgt ctgctgcagc 145440
agagccaaca gccgctgctg ggcgccggcg gagggctgct ccccgagctg cagcaggctg 145500
gagacggcag gctggaagac tgccagtgcc gacgaactca ggaacggcac gtcgggatca 145560
aacacggcca cgtccgtccg cacgcgcgcc attagcgtcc ccgggggcgc acaggccgag 145620
cgcgggctga cgcggctgag ggccgtcgac acgcgcacct cctcgcggct gcgaaccatc 145680
ttgttggcct ccagtggcgg aatcattatg gccgggtcga tctcccgcac ggtgtgctga 145740
aactgcgcca acaggggcgg cgggaccaca gccccccgct cgggggtcgt caggtactcg 145800
tccaccaggg ccaacgtaaa gagggcccgt gtgaggggag tgagggtcgc gtcgtctatg 145860
cgctggaggt gcgccgagaa cagcgtcacc cgattactca ccagggccaa gaaccggagg 145920
ccctcttgca cgaacggggc ggggaagagc aggctgtacg ccggggtggt aaggttcgcg 145980
ctgggctgcc ccaacgggac cggcgccatc ttgagcgacg tctccccaag ggcctcgatg 146040
gaggtccgcg ggctcatggc caagcagctc ttggtgacgg tttgccagcg gtctatccac 146100
tccacggcgc actggcggac gcggaccggc cccagggccg ccgcggtcgc aggccggcgg 146160
aatccagcgc atgggacgtg tcggagccgg tgaccgcgag gatggtgtcc ttgatgacct 146220
ccatctcccg gaaggcctgg tcgggggcct cggggagagc caccaccaag cggtgtacga 146280
gcaacccggg gaggttctcg gccaagagcg ccgtctccgg aagcccgtgg gcccggtgga 146340
acgcgcacag gtgttccagc agcggccgcc agcatgcccg cgcgtctgcc ggggcgatgg 146400
ccgttcccga caacagaaac gccgccatgg cggcgcgcag cttggccgtg gccagaaacg 146460
ccgggtcgtc cgccccgttt gccgtctcgg ccgtgggggt tggcggttgg cgaaggccgg 146520
ctaggctcgc caataggcgc tgcataggtc cgtccgaggg cggaccggcg ggtgaggtcg 146580
tgacgacggg ggcctcggac gggagaccgc ggtctgccat gacgcccggc tcgcgtgggt 146640
gggggacagc gtagaccaac gacgagaccg ggcgggaatg actgtcgtgc gctgtaggga 146700
gcggcgaatt atcgatcccc tgcggccctc caggaacccc gcaggcgttg cgagtacccc 146760
gcgtcttcgc ggggtgttat acggccactt aagtcccggc atcccgttcg cggacccagg 146820
cccgggggat tgtccggatg tgcgggcagc ccggacggcg tgggttgcgg actttctgcg 146880
gggcggccca aatggccctt taaacgtgtg tatacggacg cgccgggcca gtcggccaac 146940
acaacccacc ggaggcggta gccgcgtttg gctgtggggt gggtggttcc gccttgtgtg 147000
agtgtccttt cgaccccccc cccccccctc ccccgggtct tgctaggtcg cgatctgtgg 147060
tcgcaatgaa gaccaatccg ctacccgcaa ccccttccgt gtggggcggg agtaccgtgg 147120
aactcccccc caccacacgc gataccgcgg ggcagggcct gcttcggcgc gtcctgcgcc 147180
ccccgatctc tcgccgcgac ggcccagtgc tccccagggg gtcgggaccc cggagggcgg 147240
ccagcacgct gtggttgctt ggcctggacg gcacagacgc gccccctggg gcgctgaccc 147300
ccaacgacga taccgaacag gccctggaca agatcctgcg gggcaccatg cgcggggggg 147360
cggccctgat cggctccccg cgccatcatc taacccgcca agtgatcctg acggatctgt 147420
gccaacccaa cgcggatcgt gccgggacgc tgcttctggc gctgcggcac cccgccgacc 147480
tgcctcacct ggcccaccag cgcgccccgc caggccggca gaccgagcgg ctgggcgagg 147540
cctggggcca gctgatggag gcgaccgccc tggggtcggg gcgagccgag agcgggtgca 147600
cgcgcgcggg cctcgtgtcg tttaacttcc tggtggcggc gtgtgccgcc tcgtacgacg 147660
cgcgcgacgc cgccgatgcg gtacgggccc acgtcacggc caactaccgc gggacgcggg 147720
tgggggcgcg cctggatcgt ttttccgagt gtctgcgcgc catggttcac acgcacgtct 147780
tcccccacga ggtcatgcgg tttttcgggg ggctggtgtc gtgggtcacc caggacgagc 147840
tagcgagcgt caccgccgtg tgcgccgggc cccaggaggc ggcgcacacc ggccacccgg 147900
gccggccccg ctcggccgtg atcctcccgg cgtgtgcgtt cgtggacctg gacgccgagc 147960
tggggctggg gggcccgggc gcggcgtttc tgtacctggt attcacttac cgccagcgcc 148020
gggaccagga gctgtgttgt gtgtacgtga tcaagagcca gctccccccg cgcgggttgg 148080
agccggccct ggagcggctg tttgggcgcc tccggatcac caacacgatt cacggcaccg 148140
aggacatgac gcccccggcc ccaaaccgaa accccgactt ccccctcgcg ggcctggccg 148200
ccaatcccca aaccccgcgt tgctcggctg gccaggtcac gaacccccag ttcgccgaca 148260
ggctgtaccg ctggcagccg gaccttcggg ggcgccccac cgcacgcacc tgtacgtacg 148320
ccgcctttgc agagctcggc atgatgcccg aggatagtcc ccgctgcctg caccgcaccg 148380
agcgctttgg ggcggtcagc gtccccgttg ttattctgga aggcgtggtg tggcgccccg 148440
gcgagtggcg ggcatgcgcg tgagcgtagc aaacgccccg cccacacaac gctccgcccc 148500
caaccccttc cccgctgtca ctcgtggttc gttgacccgg acgtccgcca aataaagcca 148560
ctgaaacccg aaacgcgagt gttgtaacgt cctttgggcg ggaggaagcc cgtatagcat 148620
acattatacg aagttatagc gcgaagttcc tattctctag aaagtatagg aacttcgaat 148680
tggtcgacgg atccaaccgc ggaagaccca ggccgcctcg ggtgtaacgt tagaccgagt 148740
tcgccgggcc ggctccgcgg gccagggccc gggcacgggc ctcgggcccc aggcacggcc 148800
cgatgaccgc ctcggcctcc gccacccggc gccggaaccg agcccggtcg gcccgctcgc 148860
gggcccacga gccgcggcgc gccaggcggg cggccgaggc ccagaccacc aggtggcgca 148920
cccggacgtg gggcgagaag cgcacccgcg tgggggtcgc gggggtcgcg ggggtcgcgg 148980
ggggcttcgg cgccccctcc ccgcccgcgc gtcgcaggcg caggcgcgcc aggtgctctg 149040
cggtgacgcg caggcggagg gcgaggcgcg gcggaaggcg gaaggggcgt gagggggggt 149100
gggaggggtt agccccgccc cccgggcccg cgccgggcgg tgggggccgg ggccgggggg 149160

```
cggcggcggt gggccgggcc tctggcgccg gctcgggcgg ggggctgtcc ggccagtcgt 149220

cgtcatcgtc gtcgtcggac gcggactcgg gaacgtggag ccactggcgc agcagcagcg 149280

aacaagaagg cgggggccca ctggcggggg gcggcggcgg ggcggccgcg ggcgcgctcc 149340

tgaccacggg ttccgagttg ggcgtggagg ttacctggga ctgtgcggtt gggacggcgc 149400

ccgtgggccc gggcggccgg gggcggcggg ggccgcgatg gcggcggcgg cgggccatga 149460

tcaagctcat ggcgccgcgc tctgcttctg gaaggctgcg ctccgcggcg tggatgctcc 149520

ggggaaagtt gcgctccgcg gcagggatgc tcctgggaag gttgcgctcc gcggcaggga 149580

tgctctgggg aaggctggtc ctggccgagg atcgggaacg cgccgctcgc tctgcttctc 149640

ttgtcttcgc ttgtctctgg atggaaccag atttggttct gagtagctgt cagcgtctgg 149700

tgacctgctc gccgccctgc gcctttaagg agtcttcacc ggccccgccc actctccgct 149760

gggccaatca gcgagccgga ggaggccttg gggccaggaa tcttccagca gtttcgcgtc 149820

tggtggagct tccccgcctc ccttgagtaa tcggagttgt gggttccgcc cttgtccaga 149880

actctccaga ggtttctggg gttcactgga gagtacggat tcctgagggg gagggtgtgg 149940

ggaagtgctg gtgctactag tgacactgtt gctatggcga cgcattacta aggcctgtgt 150000

ggaatggaca agaaagatca cctctagctc ggtgttgtgt acagtttgtt gtgatttgtg 150060

gggtttcgcc aactcgcaca gttctgaata tgggggttaa aggctaaaac ttaagggcta 150120

aaacttctcc ccgccaagtt taggagaccc agggagatgc ctgggggcgt gtccggtgac 150180

gtgatcctct ccaatcgcgt tacaatggca gtgctgcctc tgacctcatg gactaattta 150240

ggaactagag gctctgtccc agcacaggct caaagttgcc gggaggggcg gggtgggggg 150300

tgggggggac cccggctgct cagtttggat gttcctggag ctcggtaccc gcgatcgccc 150360

ctagaggatc tactagtcat atggataagc ctgggaacct cgtccaggtg tctgcaaccg 150420

agagttctca gcctccagca gagtcctggt ggggagtggg gagatagggt cagctccagc 150480

tgaggtagca tgtcctgcca ctgcaggatc aatctctatt gtgaccattg tcatataaaa 150540

gccacacagt catataccca cagatatata cttagccaac ccatatttga gacacaggga 150600

gaccccacat gcagattccc acagtcggag gcagggccaa atgaattgct aacacttata 150660

tcagactcct cagatcagtc tccgcctccc cacccaaggc caaggccgat gacctcatcc 150720

tctgggaggg aggccgattc tcatgctaat tattgccttt tgtccacact accatctgga 150780

gggcctaaga agggagggct cctcagggga agtgggaatt ctcaggctgt tcccagggga 150840

tggctctctc tctgccccca gagctggtaa cagacaaaag caaatgaatt cagctcccct 150900

tctccaaatc cttttcagac ctcaaacgcc agtggttaca ttcctcagag ctgcctggac 150960

ccttcccctc agaggactga ctggggctaa agccctcatc tcaggatcac aaactcttca 151020

gggatcggat ctcggcccgg gctagcacgc gtaagagctc ggtacctatc gatagagaaa 151080

tgttctggca cctgcacttg cactggggac agcctatttt gctagtttgt tttgtttcgt 151140

tttgttttga tggagagcgt atgttagtac tatcgattca cacaaaaaac caacacacag 151200

atgtaatgaa aataaagata ttttattgcg gcgatccgga acccttaat             151249
```

<210> SEQ ID NO 2
<211> LENGTH: 1540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
aaccctgaag agtttgtgat cctgagatga gggctttagc cccagtcagt cctctgaggg        60
gaagggtcca ggcagctctg aggaatgtaa ccactggcgt ttgaggtctg aaaaggattt       120
ggagaagggg agctgaattc atttgctttt gtctgttacc agctctgggg gcagagagag       180
agccatcccc tgggaacagc ctgagaattc ccacttcccc tgaggagccc tcccttctta       240
ggccctccag atggtagtgt ggacaaaagg caataattag catgagaatc ggcctccctc       300
ccagaggatg aggtcatcgg ccttggcctt gggtggggag gcggagactg atctgaggag       360
tctgatataa gtgttagcaa ttcatttggc cctgcctccg actgtgggaa tctgcatgtg       420
gggtctccct gtgtctcaaa tatgggttgg ctaagtatat atctgtgggt atatgactgt       480
gtggctttta tatgacaatg gtcacaatag agattgatcc tgcagtggca ggacatgcta       540
cctcagctgg agctgaccct atctccccac tccccaccag gactctgctg gaggctgaga       600
actctcggtt gcagacacct ggacgaggtt caggcttatc atatgactag tagatcctct       660
aggggcgatc gcgggtaccg agctccagga acatccaaac tgagcagccg gggtcccccc       720
caccccccac cccgcccctc ccggcaactt tgagcctgtg ctgggacaga gcctctagtt       780
cctaaattag tccatgaggt cagaggcagc actgccattg taacgcgatt ggagaggatc       840
acgtcaccgg acacgccccc aggcatctcc ctgggtctcc taaacttggc ggggagaagt       900
tttagccctt aagttttagc ctttaacccc catattcaga actgtgcgag ttggcgaaac       960
cccacaaatc acaacaaact gtacacaaca ccgagctaga ggtgatcttt cttgtccatt      1020
ccacacaggc cttagtaatg cgtcgccata gcaacagtgt cactagtagc accagcactt      1080
ccccacaccc tcccccctcag gaatccgtac tctccagtga accccagaaa cctctggaga      1140
gttctggaca agggcggaac ccacaactcc gattactcaa gggaggcggg gaagctccac      1200
cagacgcgaa actgctggaa gattcctggc cccaaggcct cctccggctc gctgattggc      1260
ccagcggaga gtgggcgggg ccggtgaaga ctccttaaag gcgcagggcg gcgagcaggt      1320
caccagacgc tgacagctac tcagaaccaa atctggttcc atccagagac aagcgaagac      1380
aagagaagca gagcgagcgg cgcgttcccg atcctcggcc aggaccagcc ttccccagag      1440
catccctgcc gcggagcgca accttcccag gagcatccct gccgcggagc gcaactttcc      1500
ccggagcatc cacgccgcgg agcgcagcct tccagaagca                            1540
```

<210> SEQ ID NO 3
<211> LENGTH: 1137
<212> TYPE: PRT
<213> ORGANISM: Human herpesvirus 1

<400> SEQUENCE: 3

```
Met Ala Ser Arg Pro Ala Ala Ser Ser Pro Val Glu Ala Arg Ala Pro
1               5                   10                  15

Val Gly Gly Gln Glu Ala Gly Gly Pro Ser Ala Ala Thr Gln Gly Glu
            20                  25                  30

Ala Ala Gly Ala Pro Leu Ala His Gly His His Val Tyr Cys Gln Arg
        35                  40                  45

Val Asn Gly Val Met Val Leu Ser Asp Lys Thr Pro Gly Ser Ala Ser
    50                  55                  60

Tyr Arg Ile Ser Asp Asn Asn Phe Val Gln Cys Gly Ser Asn Cys Thr
65                  70                  75                  80

Met Ile Ile Asp Gly Asp Val Val Arg Gly Arg Pro Gln Asp Pro Gly
                85                  90                  95
```

```
Ala Ala Ala Ser Pro Ala Pro Phe Val Ala Val Thr Asn Ile Gly Ala
            100                 105                 110

Gly Ser Asp Gly Gly Thr Ala Val Val Ala Phe Gly Gly Thr Pro Arg
        115                 120                 125

Arg Ser Ala Gly Thr Ser Thr Gly Thr Gln Thr Ala Asp Val Pro Thr
    130                 135                 140

Glu Ala Leu Gly Gly Pro Pro Pro Pro Pro Arg Phe Thr Leu Gly Gly
145                 150                 155                 160

Gly Cys Cys Ser Cys Arg Asp Thr Arg Arg Arg Ser Ala Val Phe Gly
                165                 170                 175

Gly Glu Gly Asp Pro Val Gly Pro Ala Glu Phe Val Ser Asp Asp Arg
            180                 185                 190

Ser Ser Asp Ser Asp Ser Asp Asp Ser Glu Asp Thr Asp Ser Glu Thr
        195                 200                 205

Leu Ser His Ala Ser Ser Asp Val Ser Gly Gly Ala Thr Tyr Asp Asp
    210                 215                 220

Ala Leu Asp Ser Asp Ser Ser Ser Asp Asp Ser Leu Gln Ile Asp Gly
225                 230                 235                 240

Pro Val Cys Arg Pro Trp Ser Asn Asp Thr Ala Pro Leu Asp Val Cys
                245                 250                 255

Pro Gly Thr Pro Gly Pro Gly Ala Asp Ala Gly Gly Pro Ser Ala Val
            260                 265                 270

Asp Pro His Ala Pro Thr Pro Glu Ala Gly Ala Gly Leu Ala Ala Asp
        275                 280                 285

Pro Ala Val Ala Arg Asp Asp Ala Glu Gly Leu Ser Asp Pro Arg Pro
    290                 295                 300

Arg Leu Gly Thr Gly Thr Ala Tyr Pro Val Pro Leu Glu Leu Thr Pro
305                 310                 315                 320

Glu Asn Ala Glu Ala Val Ala Arg Phe Leu Gly Asp Ala Val Asn Arg
                325                 330                 335

Glu Pro Ala Leu Met Leu Glu Tyr Phe Cys Arg Cys Ala Arg Glu Glu
            340                 345                 350

Thr Lys Arg Val Pro Pro Arg Thr Phe Gly Ser Pro Pro Arg Leu Thr
        355                 360                 365

Glu Asp Asp Phe Gly Leu Leu Asn Tyr Ala Leu Val Glu Met Gln Arg
    370                 375                 380

Leu Cys Leu Asp Val Pro Pro Val Pro Pro Asn Ala Tyr Met Pro Tyr
385                 390                 395                 400

Tyr Leu Arg Glu Tyr Val Thr Arg Leu Val Asn Gly Phe Lys Pro Leu
                405                 410                 415

Val Ser Arg Ser Ala Arg Leu Tyr Arg Ile Leu Gly Val Leu Val His
            420                 425                 430

Leu Arg Ile Arg Thr Arg Glu Ala Ser Phe Glu Glu Trp Leu Arg Ser
        435                 440                 445

Lys Glu Val Ala Leu Asp Phe Gly Leu Thr Glu Arg Leu Arg Glu His
    450                 455                 460

Glu Ala Gln Leu Val Ile Leu Ala Gln Ala Leu Asp His Tyr Asp Cys
465                 470                 475                 480

Leu Ile His Ser Thr Pro His Thr Leu Val Glu Arg Gly Leu Gln Ser
                485                 490                 495

Ala Leu Lys Tyr Glu Glu Phe Tyr Leu Lys Arg Phe Gly Gly His Tyr
            500                 505                 510
```

-continued

```
Met Glu Ser Val Phe Gln Met Tyr Thr Arg Ile Ala Gly Phe Leu Ala
        515                 520                 525

Cys Arg Ala Thr Arg Gly Met Arg His Ile Ala Leu Gly Arg Glu Gly
    530                 535                 540

Ser Trp Trp Glu Met Phe Lys Phe Phe Phe His Arg Leu Tyr Asp His
545                 550                 555                 560

Gln Ile Val Pro Ser Thr Pro Ala Met Leu Asn Leu Gly Thr Arg Asn
                565                 570                 575

Tyr Tyr Thr Ser Ser Cys Tyr Leu Val Asn Pro Gln Ala Thr Thr Asn
            580                 585                 590

Lys Ala Thr Leu Arg Ala Ile Thr Ser Asn Val Ser Ala Ile Leu Ala
        595                 600                 605

Arg Asn Gly Gly Ile Gly Leu Cys Val Gln Ala Phe Asn Asp Ser Gly
    610                 615                 620

Pro Gly Thr Ala Ser Val Met Pro Ala Leu Lys Val Leu Asp Ser Leu
625                 630                 635                 640

Val Ala Ala His Asn Lys Glu Ser Ala Arg Pro Thr Gly Ala Cys Val
                645                 650                 655

Tyr Leu Glu Pro Trp His Thr Asp Val Arg Ala Val Leu Arg Met Lys
            660                 665                 670

Gly Val Leu Ala Gly Glu Glu Ala Gln Arg Cys Asp Asn Ile Phe Ser
        675                 680                 685

Ala Leu Trp Met Pro Asp Leu Phe Phe Lys Arg Leu Ile Arg His Leu
    690                 695                 700

Asp Gly Glu Lys Asn Val Thr Trp Thr Leu Phe Asp Arg Asp Thr Ser
705                 710                 715                 720

Met Ser Leu Ala Asp Phe His Gly Glu Glu Phe Glu Lys Leu Tyr Gln
                725                 730                 735

His Leu Glu Val Met Gly Phe Gly Glu Gln Ile Pro Ile Gln Glu Leu
            740                 745                 750

Ala Tyr Gly Ile Val Arg Ser Ala Ala Thr Thr Gly Ser Pro Phe Val
        755                 760                 765

Met Phe Lys Asp Ala Val Asn Arg His Tyr Ile Tyr Asp Thr Gln Gly
    770                 775                 780

Ala Ala Ile Ala Gly Ser Asn Leu Cys Thr Glu Ile Val His Pro Ala
785                 790                 795                 800

Ser Lys Arg Ser Ser Gly Val Cys Asn Leu Gly Ser Val Asn Leu Ala
                805                 810                 815

Arg Cys Val Ser Arg Gln Thr Phe Asp Phe Gly Arg Leu Arg Asp Ala
            820                 825                 830

Val Gln Ala Cys Val Leu Met Val Asn Ile Met Ile Asp Ser Thr Leu
        835                 840                 845

Gln Pro Thr Pro Gln Cys Thr Arg Gly Asn Asp Asn Leu Arg Ser Met
    850                 855                 860

Gly Ile Gly Met Gln Gly Leu His Thr Ala Cys Leu Lys Leu Gly Leu
865                 870                 875                 880

Asp Leu Glu Ser Ala Glu Phe Gln Asp Leu Asn Lys His Ile Ala Glu
                885                 890                 895

Val Met Leu Leu Ser Ala Met Lys Thr Ser Asn Ala Leu Cys Val Arg
            900                 905                 910

Gly Ala Arg Pro Phe Asn His Phe Lys Arg Ser Met Tyr Arg Ala Gly
        915                 920                 925

Arg Phe His Trp Glu Arg Phe Pro Asp Ala Arg Pro Arg Tyr Glu Gly
```

```
    930                 935                 940

Glu Trp Glu Met Leu Arg Gln Ser Met Met Lys His Gly Leu Arg Asn
945                 950                 955                 960

Ser Gln Phe Val Ala Leu Met Pro Thr Ala Ala Ser Ala Gln Ile Ser
                965                 970                 975

Asp Val Ser Glu Gly Phe Ala Pro Leu Phe Thr Asn Leu Phe Ser Lys
            980                 985                 990

Val Thr Arg Asp Gly Glu Thr Leu  Arg Pro Asn Thr Leu  Leu Leu Lys
        995                 1000                 1005

Glu Leu  Glu Arg Thr Phe Ser  Gly Lys Arg Leu Leu  Glu Val Met
    1010                 1015                 1020

Asp Ser  Leu Asp Ala Lys Gln  Trp Ser Val Ala Gln  Ala Leu Pro
    1025                 1030                 1035

Cys Leu  Glu Pro Thr His Pro  Leu Arg Arg Phe Lys  Thr Ala Phe
    1040                 1045                 1050

Asp Tyr  Asp Gln Lys Leu Leu  Ile Asp Leu Cys Ala  Asp Arg Ala
    1055                 1060                 1065

Pro Tyr  Val Asp His Ser Gln  Ser Met Thr Leu Tyr  Val Thr Glu
    1070                 1075                 1080

Lys Ala  Asp Gly Thr Leu Pro  Ala Ser Thr Leu Val  Arg Leu Leu
    1085                 1090                 1095

Val His  Ala Tyr Lys Arg Gly  Leu Lys Thr Gly Met  Tyr Tyr Cys
    1100                 1105                 1110

Lys Val  Arg Lys Ala Thr Asn  Ser Gly Val Phe Gly  Gly Asp Asp
    1115                 1120                 1125

Asn Ile  Val Cys Met Ser Cys  Ala Leu
    1130                 1135


<210> SEQ ID NO 4
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

aaccctgaag agtttgtgat cctgagatga gggctttagc cccagtcagt cctctgaggg     60

gaagggtcca ggcagctctg aggaatgtaa ccactggcgt ttgaggtctg aaaaggattt    120

ggagaagggg agctgaattc atttgctttt gtctgttacc agctctgggg gcagagagag    180

agccatcccc tgggaacagc ctgagaattc ccacttcccc tgaggagccc tcccttctta    240

ggccctccag atggtagtgt ggacaaaagg caataattag catgagaatc ggcctccctc    300

ccagaggatg aggtcatcgg ccttggcctt gggtggggag gcggagactg atctgaggag    360

tctgatataa gtgttagcaa ttcatttggc cctgcctccg actgtgggaa tctgcatgtg    420

gggtctccct gtgtctcaaa tatgggttgg ctaagtatat atctgtgggt atatgactgt    480

gtggctttta tatgacaatg gtcacaatag agattgatcc tgcagtggca ggacatgcta    540

cctcagctgg agctgaccct atctccccac tccccaccag gactctgctg gaggctgaga    600

actctcggtt gcagacacct ggacgaggtt                                     630


<210> SEQ ID NO 5
<211> LENGTH: 910
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 5
caggcttatc atatgactag tagatcctct aggggcgatc gcgggtaccg agctccagga 60
acatccaaac tgagcagccg gggtcccccc caccccccac cccgcccctc ccggcaactt 120
tgagcctgtg ctgggacaga gcctctagtt cctaaattag tccatgaggt cagaggcagc 180
actgccattg taacgcgatt ggagaggatc acgtcaccgg acacgccccc aggcatctcc 240
ctgggtctcc taaacttggc ggggagaagt tttagccctt aagttttagc ctttaacccc 300
catattcaga actgtgcgag ttggcgaaac cccacaaatc acaacaaact gtacacaaca 360
ccgagctaga ggtgatcttt cttgtccatt ccacacaggc cttagtaatg cgtcgccata 420
gcaacagtgt cactagtagc accagcactt ccccacaccc tccccctcag gaatccgtac 480
tctccagtga accccagaaa cctctggaga gttctggaca agggcggaac ccacaactcc 540
gattactcaa gggaggcggg gaagctccac cagacgcgaa actgctggaa gattcctggc 600
cccaaggcct cctccggctc gctgattggc ccagcggaga gtgggcgggg ccggtgaaga 660
ctccttaaag gcgcagggcg gcgagcaggt caccagacgc tgacagctac tcagaaccaa 720
atctggttcc atccagagac aagcgaagac aagagaagca gagcgagcgg cgcgttcccg 780
atcctcggcc aggaccagcc ttccccagag catccctgcc gcggagcgca accttcccag 840
gagcatccct gccgcggagc gcaactttcc ccggagcatc cacgccgcgg agcgcagcct 900
tccagaagca 910

<210> SEQ ID NO 6
<211> LENGTH: 4772
<212> TYPE: DNA
<213> ORGANISM: Human herpesvirus 1

<400> SEQUENCE: 6
acaacaggtg ggtgctttgg aaacttgccg gtcgccgtgc tcctgtgagc ttgcgtccct 60
ccccggtttc ctttgcgctc ccgccttccg gacctgctct cgcctatctt ctttggctct 120
cggtgcgatt cgtcaggcag cggccttgtc gaatctcgac cccaccactc gccggacccg 180
ccgacgtccc ctctcgagcc cgccgaaacc cgccgcgtct gttgaaatgg ccagccgccc 240
agccgcatcc tctcccgtcg aagcgcgggc cccggttggg ggacaggagg ccggcggccc 300
cagcgcagcc acccaggggg aggccgccgg ggcccctctc gcccacggcc accacgtgta 360
ctgccagcga gtcaatggcg tgatggtgct ttccgacaag acgcccgggt ccgcgtccta 420
ccgcatcagc gatagcaact ttgtccaatg tggttccaac tgcaccatga tcatcgacgg 480
agacgtggtg cgcgggcgcc cccaggaccc gggggccgcg gcatcccccg ctcccttcgt 540
tgcggtgaca aacatcggag ccggcagcga cggcgggacc gccgtcgtgg cattcggggg 600
aaccccacgt cgctcggcgg ggacgtctac cggtacccag acggccgacg tccccaccga 660
ggcccttggg ggcccccctc ctcctccccg cttcaccctg ggtggcggct gttgttcctg 720
tcgcgacaca cggcgccgct ctgcggtatt cggggggggag ggggatccag tcggccccgc 780
ggagttcgtc tcggacgacc ggtcgtccga ttccgactcg gatgactcgg aggacacgga 840
ctcggagacg ctgtcacacg cctcctcgga cgtgtccggc ggggccacgt acgacgacgc 900
ccttgactcc gattcgtcat cggatgactc cctgcagata gatggccccg tgtgtcgccc 960
gtggagcaat gacaccgcgc ccctggatgt ttgccccggg acccccggcc cgggcgccga 1020
cgccggtggt ccctcagcgg tagacccaca cgcgccgacg ccagaggccg gcgctggtct 1080
tgcggccgat cccgccgtgg cccgggacga cgcggagggg ctttcggacc cccggccacg 1140
tctgggaacg ggcacggcct accccgtccc cctggaactc acgcccgaga acgcggaggc 1200
cgtggcgcgc tttctgggag atgccgtgaa ccgcgaaccc gcgctcatgc tggagtactt 1260
ttgccggtgc gcccgcgagg aaaccaagcg tgtccccccc aggacattcg gcagcccccc 1320
tcgcctcacg gaggacgact ttgggcttct caactacgcg ctcgtggaga tgcagcgcct 1380
gtgtctggac gttcctccgg tcccgccgaa cgcatacatg ccctattatc tcagggagta 1440
tgtgacgcgg ctggtcaacg ggttcaagcc gctggtgagc cggtccgctc gcctttaccg 1500
catcctgggg gttctggtgc acctgcggat ccggacccgg gaggcctcct ttgaggagtg 1560
gctgcgatcc aaggaagtgg ccctggattt tggcctgacg gaaaggcttc gcgagcacga 1620
agcccagctg gtgatcctgg cccaggctct ggaccattac gactgtctga tccacagcac 1680
accgcacacg ctggtcgagc gggggctgca atcggccctg aagtatgagg agttttacct 1740
aaagcgtttt ggcgggcact acatggagtc cgtcttccag atgtacaccc gcatcgccgg 1800
ctttttggcc tgccgggcca cgcgcggcat gcgccacatc gccctggggc gagaggggtc 1860
gtggtgggaa atgttcaagt tctttttcca ccgcctctac gaccaccaga tcgtaccgtc 1920
gacccccgcc atgctgaacc tggggacccg caactactac acctccagct gctacctggt 1980
aaacccccag gccaccacaa acaaggcgac cctgcgggcc atcaccagca acgtcagtgc 2040
catcctcgcc cgcaacgggg gcatcgggct atgcgtgcag gcgtttaacg actccggccc 2100
cgggaccgcc agcgtcatgc ccgccctcaa ggtccttgac tcgctggtgg cggcgcacaa 2160
caaagagagc gcgcgtccga ccggcgcgtg cgtgtacctg gagccgtggc acaccgacgt 2220
gcgggccgtg ctccggatga aggggtcct cgccggcgaa gaggcccagc gctgcgacaa 2280
tatcttcagc gccctctgga tgccagacct gtttttcaag cgcctgattc gccacctgga 2340
cggcgagaag aacgtcacat ggaccctgtt cgaccgggac accagcatgt cgctcgccga 2400
ctttcacggg gaggagttcg agaagctcta ccagcacctc gaggtcatgg ggttcggcga 2460
gcagataccc atccaggagc tggcctatgg cattgtgcgc agtgcggcca cgaccgggag 2520
ccccttcgtc atgttcaaag acgcggtgaa ccgccactac atctacgaca cccagggggc 2580
ggccatcgcc ggctccaacc tctgcaccga gatcgtccat ccggcctcca agcgatccag 2640
tggggtctgc aacctgggaa gcgtgaatct ggcccgatgc gtctccaggc agacgtttga 2700
ctttgggcgg ctccgcgacg ccgtgcaggc gtgcgtgctg atggtgaaca tcatgatcga 2760
cagcacgcta caacccacgc cccagtgcac ccgcggcaac gacaacctgc ggtccatggg 2820
aatcggcatg cagggcctgc acacggcctg cctgaagctg gggctggatc tggagtctgc 2880
cgaatttcag gacctgaaca aacacatcgc cgaggtgatg ctgctgtcgg cgatgaagac 2940
cagcaacgcg ctgtgcgttc gcggggcccg tcccttcaac cactttaagc gcagcatgta 3000
tcgcgccggc cgctttcact gggagcgctt tccggacgcc cggccgcggt acgagggcga 3060
gtgggagatg ctacgccaga gcatgatgaa acacggcctg cgcaacagcc agtttgtcgc 3120
gctgatgccc accgccgcct cggcgcagat ctcggacgtc agcgagggct ttgccccct 3180
gttcaccaac ctgttcagca aggtgacccg ggacggcgag acgctgcgcc ccaacacgct 3240
cctgctaaag gaactggaac gcacgtttag cgggaagcgc ctcctggagg tgatggacag 3300
tctcgacgcc aagcagtggt ccgtggcgca ggcgctcccg tgcctggagc ccacccaccc 3360
cctccggcga ttcaagaccg cgtttgacta cgaccagaag ttgctgatcg acctgtgtgc 3420
ggaccgcgcc ccctacgtcg accatagcca atccatgacc ctgtatgtca cggagaaggc 3480
ggacgggacc ctcccagcct ccaccctggt ccgccttctg gtccacgcat ataagcgcgg 3540
actaaaaaca gggatgtact actgcaaggt tcgcaaggcg accaacagcg gggtctttgg 3600
cggcgacgac aacattgtct gcatgagctg cgcgctgtga ccgacaaacc ccctccgcgc 3660
caggcccgcc gccactgtcg tcgccgtccc acgctctccc ctgctgccat ggattccgcg 3720
gccccagccc tctcccccgc tctgacggcc cttacgggcc agagcgcgac ggcggacctg 3780
gcgatccaga ttccaaagtg ccccgacccc gagaggtact tctacacctc ccagtgtccc 3840
gacattaacc acctgcgctc cctcagcatc cttaaccgct ggctggaaac cgagcttgtt 3900
ttcgtggggg acgaggagga cgtctccaag ctttccgagg gcgagctcag cttttaccgc 3960
ttcctcttcg ctttcctgtc ggccgccgac gacctggtta cggaaaacct gggcggcctc 4020
tccggcctgt ttgagcagaa ggacattctc cactactacg tggagcagga atgcatcgaa 4080
gtcgtacact cgcgcgtgta caacatcatc cagctggtgc ttttccacaa caacgaccag 4140
gcgcgccgcg agtacgtggc cggtaccatc aaccacccgg ccatccgcgc caaggtggac 4200
tggttggaag cgcgggtgcg ggaatgcgcc tccgttccgg aaaagttcat tctcatgatc 4260
ctcatcgagg gcatcttttt tgccgcctcg tttgccgcca tcgcctacct tcgcaccaac 4320
aaccttctgc gggtcacctg ccagtcaaac gacctcatca gccgggacga ggccgtgcac 4380
acgacggcct cgtgttacat ctacaacaac tacctcggcg ggcacgccaa gccccgccc 4440 gaccgcgtgt acgggctgtt ccgccaggcg gtcgagatcg agatcggatt tatccgatcc 4500
caggcgccga cggacagcca tatcctgagc ccggcggcgc tggcggccat cgaaaactac 4560
gtgcgattca gcgcggatcg cctgttgggc cttatccaca tgaagccact gttttccgcc 4620
ccaccccccg acgccagctt tccgctgagc ctcatgtcca ccgacaaaca caccaatttt 4680
ttcgagtgtc gcagcacctc ctacgccggg gcggtcgtca acgatctgtg agtgtcgcgg 4740
cgcgcttcta cccgtgtttg cccataataa ac 4772

<210> SEQ ID NO 7
<211> LENGTH: 1733
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
aataaagcca ctgaaacccg aaacgcgagt gttgtaacgt cctttgggcg ggaggaagcc 60
acaaaatgca aatgggatac atggaaggaa cacacccccg tgactcagga catcggtgtg 120
tccttttggg tttcactgaa actggcccgc gccccacccc tgcgcgatgt ggataaaaag 180
ccagcgcggg tggtttaggg taccacaggt gggtgctttg gaaacttgcc ggtcgccgtg 240
ctcctgtgag cttgcgtccc tccccggttt cctttgcgct cccgccttcc ggacctgctc 300
tcgcctactc ttctttggct ctcggtgcga ttcgtcaggc agcggccttg tcgaatctcg 360
accccaccac tcgccggacc cgccgacgtc ccctcagctt gcatgcctgc aggtcgagcc 420
cgccgaaacc cgccgcgtct gttgaaatgg ccagccgccc cgccgcatcc tctcccgtcg 480
aagcgcgggc cccggttggg ggacaggagg ccggcggccc cagcgcagcc acccaggggg 540
aggccgccgg ggcccctctc gcccgcggcc accacgtgta ctgccagcga gtcaatggcg 600

-continued

```
tgatggtgct ttccgacaag acgcccgggt ccgcgtccta ccgcatcagc gatagcaact    660

ttgtccaatg tggttccaac tgcaccatga tcatagacgg agacgtggtg cgcgggcgcc    720

cccaggaccc gggggccgcg gcatcccccg ctcccttcgt tgcggtgaca aacatcggag    780

ccggcagcga cggcgggacc gccgtcgtgg cattcggggg aaccccacgt cgctcggcgg    840

ggacgtctac cggtacccag acgaccgacg tccccaccga ggcccttggg ggcccccctc    900

ctcctccccg cttcaccctg ggtggcggct gttgttcctg tcgcgacaca cggcgccgct    960

ctgcggtatt cgggggggag ggggatcgat ccatcgccac catggtgagc aagggcgagg   1020

agctgttcac cggggtggtg cccatcctgg tcgagctgga cggcgacgta aacggccaca   1080

agttcagcgt gtccggcgag ggcgagggcg atgccaccta cggcaagctg accctgaagt   1140

tcatctgcac caccggcaag ctgcccgtgc cctggcccac cctcgtgacc accctgacct   1200

acggcgtgca gtgcttcagc cgctaccccg accacatgaa gcagcacgac ttcttcaagt   1260

ccgccatgcc cgaaggctac gtccaggagc gcaccatctt cttcaaggac gacggcaact   1320

acaagacccg cgccgaggtg aagttcgagg gcgacaccct ggtgaaccgc atcgagctga   1380

agggcatcga cttcaaggag gacggcaaca tcctggggca caagctggag tacaactaca   1440

acagccacaa cgtctatatc atggccgaca agcagaagaa cggcatcaag gtgaacttca   1500

agatccgcca caacatcgag gacggcagcg tgcagctcgc cgaccactac cagcagaaca   1560

cccccatcgg cgacggcccc gtgctgctgc ccgacaacca ctacctgagc acccagtccg   1620

ccctgagcaa agaccccaac gagaagcgcg atcacatggt cctgctggag ttcgtgaccg   1680

ccgccgggat cactctcggc atggacgagc tgtacaagta aagcggccga tcc          1733
```

<210> SEQ ID NO 8
<211> LENGTH: 1226
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
aataaagcca ctgaaacccg aaacgcgagt gttgtaacgt cctttgggcg ggaggaagcc     60

cgtatagcat acattatacg aagttatagc gcgaagttcc tattctctag aaagtatagg    120

aacttcaagc tttaaacttt tgccattctc accggattca gtcgtcactc atggtgattt    180

ctcacttgat aaccttattt ttgacgaggg gaaattaggc cgggaagccg atctcggctt    240

gaacgaattg ttaggtggcg gtacttgggt cgatatcaaa gtgcatcact tcttcccgta    300

tgcccaactt tgtatagaga gccactgcgg gatcgtcacc gtaatctgct tgcacgtaga    360

tcacataagc accaagcgcg ttggcctcat gcttgaggag attgatgagc gcggtggcaa    420

tgccctgcct ccggtgctcg ccggagactg cgagatcata gatatagatc tcactacgcg    480

gctgctcaaa cttgggcaga acgtaagccg cgagagcgcc aacaaccgct tcttggtcga    540

aggcagcaag cgcgatgaat gtcttactac ggagcaagtt cccgaggtaa tcggagtccg    600

gctgatgttg ggagtaggtg gctacgtctc cgaactcacg accgaaaaga tcaagagcag    660

cccgcatgga tttgacttgg tcagggccga gcctacatgt gcgaatgatg cccatacttg    720

agccacctaa ctttgtttta gggcgactgc cctgctgcgt aacatcgttg ctgctgcgta    780

acatcgttgc tgctccataa catcaaacat cgacccacgg cgtaacgcgc ttgctgcttg    840

gatgcccgag gcatagactg tacaaaaaaa cagtcataac aagccatgaa aaccgccact    900
```

-continued

```
gcgccgttac caccgctgcg ttcggtcaag gttctggacc agttgcgtga gcgcatacgc    960

tacttgcatt acagtttacg aaccgaacag gcttatgtca actgggttcg tgccttcatc   1020

cgtttccacg gtgtgcgtca cccggcaacc ttgggcagca gcgaagtcga ggcatttctg   1080

tcctggctgg cgaacgagcg caaggtttcg gtctccacgc atcgtcaggc attggcggcc   1140

ttgctgttct tctacggcaa ggtgctgtga ccgccgccgg gatcactctc ggcatggacg   1200

agctgtacaa gtaaagcggc cgatcc                                        1226
```

ONCOLYTIC HSV1 VECTOR AND METHODS OF USE

CROSS-REFERENCE TO RELATED APPLICATIONS

This Application is a 35 U.S.C. § 371 National Phase Entry Application of International Application No. PCT/US2016/030681 filed May 4 2016, which claims benefit under 35 U.S.C. § 119(e) of U.S. Provisional Application No. 62/156,447, filed May 4, 2015, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 21, 2016, is named 043214-084831-PCT SL.txt and is 221,995 bytes in size.

FIELD OF INVENTION

The present invention is directed compositions and methods of treating cancer of the brain in a patient using oncolytic herpes simplex virus 1 (HSV-1).

BACKGROUND

Many malignant tumors are intrinsically resistant to conventional therapies and represent significant therapeutic challenges, e.g. malignant gliomas and recurrent systemic solid tumors such as lung cancer. Malignant gliomas are the most abundant primary brain tumors, having an annual incidence of 6.4 cases per 100,000. These neurologically devastating tumors are the most common subtype of primary brain tumors and are one of the deadliest human cancers. In the most aggressive cancer manifestation, glioblastoma multiforme (GBM), median survival duration for patients is 14 months, despite maximum treatment efforts. Treatments for the most malignant, types of brain tumors (malignant glioma/glioblastoma multiforme, GBM) fail to provide long-lasting control with 50% of afflicted patients dying within 15 months from diagnosis, in spite of a variety of treatments such as surgery, radiation and chemotherapy. A variety of experimental treatments have been tried and tested. Because few good treatment options are available for many of these refractory tumors, the exploration of novel and innovative therapeutic approaches is important.

One area of experimental therapy has involved the use of oncolytic (tumor-killing) viruses, whose infection and replication into tumor cells has been engineered to be tumor-selective. Replication selective oncolytic viruses have shown great promise as anti-tumor agents for solid tumors. The viruses have been constructed genetically so that they are able to preferentially replicate within tumor cells, while being at least somewhat restricted in their ability to replicate in normal cells. The principal anti-tumor mechanism of oncolytic viruses is through a direct cytopathic effect as they propagate and spread from initially infected tumor cells to surrounding tumor cells, achieving a larger volume of distribution and anticancer effects.

Oncolytic herpes simplex viruses (HSVs) were initially designed and constructed for the treatment of brain tumors. Subsequently, they have been found to be effective in a variety of other human solid tumors, including breast, prostate, lung, ovarian, colon and liver cancers. The safety of oncolytic HSVs has also been extensively tested in mice and primates, which are extremely sensitive to HSV. One oncolytic HSV-1 mutant that has been studied as a glioma-specific therapeutic is rQNestin34.5 (Kambara et al. An oncolytic HSV-1 mutant expression ICP34.5 under control of a Nestin promoter increases survival of animals even when symptomatic from a brain tumor, (2005) *Cancer Res.* 65(7): 2832-2839).

Despite encouraging preclinical studies, results from early clinical trials have suggested that most of the current versions of oncolytic viruses, although acceptably safe, may only have limited anti-tumor activity on their own.

Considering the limited effective treatment options available for certain types of cancer, including certain types of brain cancer, there remains a need in the art for improved oncolytic viruses.

SUMMARY OF THE INVENTION

We have generated an improved oncolytic rQNestin34.5 HSV virus, a second generation virus referred to as rQNestin34.5.v2. The genetically modified HSV1 rQNestin34.5.v2 has been made glioma-selective by the following maneuvers: 1) one of the viral genes that encodes for a viral protein (ICP6) has been removed. Without this gene, HSV1 has to utilize factors within the infected cells to efficiently grow and replicate and we have shown that such factors are existent in cells that are mitotically active or that have a defect in a cellular gene (p16) that is missing in most gliomas; and 2) the two copies of the viral gene that encode for a protein (ICP34.5) needed for robust viral growth in an infected cell have also been removed and one copy was reinserted under control of a Nestin promoter that is also present selectively in gliomas in the adult human brain. These two maneuvers combined with the reduced toxicity due to lack of ICP6-EGFP fusion protein present in the first generation rQNestin34.5 (Kambara et al. An oncolytic HSV-1 mutant expression ICP34.5 under control of a Nestin promoter increases survival of animals even when symptomatic from a brain tumor, (2005) *Cancer Res.* 65(7): 2832-2839), allow this new HSV1 (designated as rQNestin34.5v.2) to be relatively selective in destroying gliomas and not normal brain cells. We have confirmed this in cultured cells and in animal models.

Accordingly, provided herein are tumor-selective oncolytic herpes viral vectors comprising: a) a deletion or inactivating mutation in both copies of the gene encoding γ34.5, b) an insertion of at least one copy of the HSV γ34.5 gene under the transcriptional control of a nestin promoter; and c) a deletion or inactivating mutation in the gene that encodes for the HSV viral protein ICP6, wherein the tumor-selective oncolytic herpes viral vector does not express green fluorescent protein. In one embodiment, the vector does not express ICP6-EGFP fusion protein present in the first generation HSV-1 vector rQNestin34.5. In one embodiment the tumor-selective oncolytic herpes viral vector does not comprise SEQ ID NO: 7. In one embodiment, the vector does not contain UL39 nucleic acid regulatory sequences (promoter and enhancer elements). In one embodiment, the vector does not contain a fusion protein of ICP6. In one embodiment, the at least one copy of the γ34.5 gene under the transcriptional control of a nestin promoter is inserted into UL39 gene that encodes for the large subunit of ribonucleotide reductase ICP6 (infected cell protein 6). In one embodiment, the nestin promoter comprises SEQ ID NO: 2 or a degenerate variant thereof. In one embodiment the tumor-selective oncolytic herpes viral vector comprises SEQ ID NO: 8.

Also provided is a tumor-selective oncolytic herpes viral vector that comprises the sequence of SEQ ID NO: 1, or a degenerate variant thereof.

Another aspect of the invention provides for a method of selectively killing intracranial tumor cells in a subject, comprising introducing into the vicinity of the tumor-selective oncolytic herpes viral vectors of the invention. We have determined that one additional maneuver allows rQNestin34.5v.2 to be highly effective in injected gliomas. Mammals are able to rapidly counteract HSV1 in the brain through their initial immune responses. Brain cells such as microglia and systemic cells such as NK cells and macrophages can blunt and effectively ensure that viral replication and its untoward consequences on normal brain does not occur. We have discovered that such innate initial host defenses also exist in the context of gliomas injected with rQNestin34.5v.2 that curtail the biodistribution of the virus within the tumor and limit its therapeutic effectiveness. In animal models, we have discovered that a single dose of cyclophosphamide, a commonly utilized agent that modulates the immune response, administered two days before rQNestin34.5v.2 significantly enhances viral biodistribution, replication and efficacy, effectively reducing the dose of virus required to produce a survival effect by two orders of magnitude.

Accordingly, in one embodiment, the method further comprises administration of cyclophoshamide (CPA). In certain embodiments, the CPA is administered, simultaneously with the HSV oncolytic vector. In certain embodiments the CPA is administered hours, days, or weeks before the administration of the HSV-1 oncolytic vector. In one embodiment, the CPA is administered two days before the oncolytic herpes viral vector.

In some embodiments, the tumor cells comprise a glioblastoma cell, or a cancer stem cell. In some embodiments, the subject to be treated is a mammal. In certain embodiments, the mammal is human.

Also provided are pharmaceutical compositions of the tumor-selective oncolytic herpes viral vectors of the invention described herein for use in the treatment of intracranial tumor cells in a subject. In various embodiments, tumor-selective oncolytic herpes viral vectors comprising: a) a deletion or inactivating mutation in both copies of the gene encoding g34.5; b) an insertion of at least one copy of the HSV γ34.5 gene under the transcriptional control of a. Nestin promoter; and c) a deletion or inactivating mutation in the gene that encodes for the HSV viral protein ICP6, wherein the tumor-selective oncolytic herpes viral vector does not express green fluorescent protein. In one embodiment, the vector does not express ICP6-EGFP fusion protein present in the first generation HSV-1 vector rQNestin34.5. In one embodiment the tumor-selective oncolytic herpes viral vector does not comprise SEQ ID NO: 7. In one embodiment, the vector does not contain UL39 nucleic acid regulatory sequences (promoter and enhancer elements). In one embodiment, the vector does not contain a fusion protein of ICP6. In one embodiment, the at least one copy of the γ34.5 gene under the transcriptional control of a nestin promoter is inserted into UL39 gene that encodes for the large subunit of ribonucleotide reductase ICP6 (infected cell protein 6). In one embodiment, the nestin promoter comprises SEQ II) NO: 2 or a degenerate variant thereof. In one embodiment the tumor-selective oncolytic herpes viral vector comprises SEQ ID NO: 8.

BRIEF DESCRIPTION OF THE DRAWINGS

Exemplary embodiments are illustrated in the referenced figures. It is intended that the embodiments and figures disclosed herein are to be considered illustrative rather than restrictive.

FIG. 8 is a table that summarizes the results of all experiments to date with Balb/c mice. Intracerebral injection of 107 pfus in either 8 week old or 6 month old mice was well tolerated (32/33, with one death at day 3 post-injection for unknown reasons)

FIG. 12A schematic of the toxicity studies in mice. FIG. 12B a graph showing survival rate vs time after injection of rQNestin34.5v.2 (v2-$1\times10^7$) and wild type HSV1 F strain.

FIG. 13A schematic of the preclinical studies in mice using CPA. FIG. 13B a graph showing survival rate vs time after injection of rQNestin34.5v.2 (v2-1×107) and wild type HSV1 F strain. CPA (300 mg/kg) was administered i.p., two days before intracranial inoculation of rQNestin34.5v2 (v2) at $10^6$ pfus (blue triangle with broken line), $3\times10^6$ pfus (light blue circle/line), or $10^7$ pfus (blue diamond/line). The numerator represents animal euthanized (due to veterinary criteria of toxicity) or found dead, while the denominator represents total number injected. F represents wild-type HSV1 F strain, injected at $10^3$ pfus (red cross/line). PBS represents intracranial vehicle injection. The experiment was terminated at day 62-63 with planned euthanasia of all surviving animals to harvest organs for toxicity/biodistribution analyses.

FIG. 17A shows GFAP immunohistochemistry with several positive astrocytes in the high power microphotograph. FIG. 17B shows that Nestin immunohistochemistry of a similar area is relatively negative. FIG. 17C shows Nestin immunohistochemistry of the subventricular zone (SVZ) (Arrows) was also negative (low power). FIG. 17D shows high power microphotograph of Nestin IHC of SVZ (arrows).

FIG. 18A—Low power; FIG. 18B—Mid-power; FIG. 18C—High power microphotograph.

FIG. 22A HUVEC; FIG. 22B U251; FIG. 22C U87ΔEGFR; FIG. 22D Gli36ΔEGFR.

DESCRIPTION OF THE INVENTION

Figure 1:
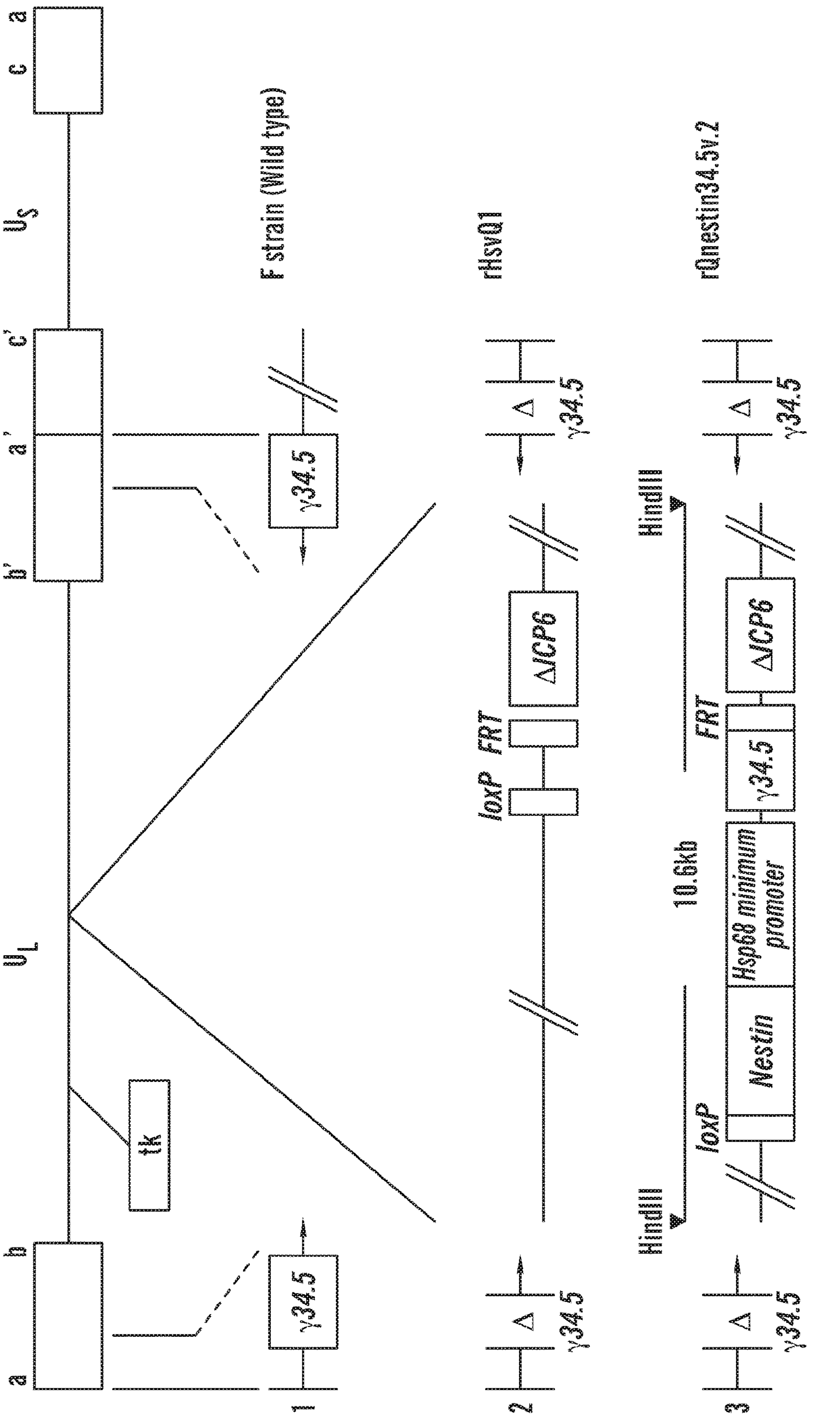
FIG. 1 is a schematic of rQNestin34v.2. Schematic maps of HSV strain F (wild-type), rHsvQ1 (double UL39-γ34.5 mutant), and rQNestin34.5. All strains contain the typical HSV-1 genome with its two unique segments (UL and US, respectively), each flanked by inverted repeat elements (ab and ca, respectively). The locations of diploid γ34.5 genes and of the thymidine kinase gene (tk) are shown in the top construct, representing wild-type F strain HSV. In the middle construct, UL39 (ICP6) has been deleted of its coding sequences and the deletions within γ1 34.5 are shown for rHsvQ1. These consist of a deletion of about 1,000 bp in the coding region. The bottom construct shows the site of recombination of the hybrid promoter (nestin enhancer and hsp68 minimum promoter)-γ1 34.5 expression cassette into the ICP6 loss, giving rise to the novel mutant oncolytic virus rQNestin34.5v.2. The approximate sizes of the HindIII fragment from rQNestin34.5 are provided (from Kambara et al., Cancer Res., 20051). rQNestin34.5v.2 was sequenced in its entirety to confirm its identity (SEQ ID NO: 1).

All references cited herein are incorporated by reference in their entirety as though fully set forth. Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. Definitions of common terms can be found in Singleton et al., *Dictionary of Microbiology and Molecular Biology* $3^{rd}$ ed., J. Wiley & Sons New York, N.Y. (2001); March, *Advanced Organic Chemistry Reactions, Mechanisms and Structure* $5^{th}$ ed., J. Wiley & Sons New York, N.Y. (2001); Michael Richard Green and Joseph Sambrook, *Molecular Cloning: A Laboratory Manual,* 4th ed., Cold Spring Harbor Laboratory Press, Cold Spring Harbor, N.Y., USA (2012); Davis et al., *Basic Methods in Molecular Biology*, Elsevier Science Publishing, Inc., New York, USA (2012); Jon Lorsch (ed.) *Laboratory Methods in Enzymology*: DNA, Elsevier, (2013); Frederick M. Ausubel (ed.), *Current Protocols in Molecular Biology* (CPMB), John Wiley and Sons, (2014); John E. Coligan (ed.), *Current Protocols in Protein Science* (CPPS), John Wiley and Sons, Inc., (2005); and Ethan M Shevach, Warren Strobe, (eds.) *Current Protocols in Immunology* (CPI) (John E. Coligan, ADA M Kruisbeek, David H Margulies, John Wiley and Sons, Inc., (2003); each of which provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

The term "mammal," as used herein, refers to a member of the class Mammalia, including, without limitation, humans, as well as nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like.

The term "vector," as used herein, refers to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both of which are incorporated herein by reference). Additionally, the techniques described herein and demonstrated in the referenced figures are also instructive with regard to effective vector construction.

The term "oncolytic HSV-1 vector" refers to a genetically engineered HSV-1 virus corresponding to at least a portion of the genome of HSV-1 that is capable of transducing a target cell, replicating, and being packaged into HSV-1 virions. The genetically engineered virus comprises deletions and or mutations and or insertions of nucleic acid that render the virus oncolytic such that the engineered virus replicates in- and kills-tumor cells by oncolytic activity. The virus may be attenuated or non-attenuated. The virus may or may not deliver a transgene—that differs from the HSV viral genome. In one embodiment, the oncolytic HSV-1 vector does not express a transgene to produce a protein foreign to the virus.

HSV-1 is a human neurotropic virus that is capable of infecting virtually all vertebrate cells. Natural infections follow either a lytic, replicative cycle or establish latency, usually in peripheral ganglia, where the DNA is maintained indefinitely in an episomal state. HSV-1 contains a double-stranded, linear DNA genome, 153 kilobases in length, which has been completely sequenced by McGeoch (McGeoch et al., *J. Gen. Virol.* 69: 1531 (1988); McGeoch et al., *Nucleic Acids Res* 14: 1727 (1986); McGeoch et al., *J. Mol. Biol.* 181: 1 (1985); *Perry and McGeoch, J. Gen. Virol.* 69:2831 (1988)). DNA replication and virion assembly occurs in the nucleus of infected cells. Late in infection, concatemeric viral DNA is cleaved into genome length molecules which are packaged into virions. In the CNS, herpes simplex virus spreads transneuronally followed by intraaxonal transport to the nucleus, either retrograde or anterograde, where replication occurs.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term "promoter," as used herein, refers to a nucleic acid sequence that regulates, either directly or indirectly, the transcription of a corresponding nucleic acid coding sequence to which it is operably linked. The promoter may function alone to regulate transcription, or, in some cases, may act in concert with one or more other regulatory sequences such as an enhancer or silencer to regulate transcription of the gene of interest. The promoter comprises a DNA regulatory sequence, wherein the regulatory sequence is derived from a gene, which is capable of binding RNA polymerase and initiating transcription of a downstream (3'-direction) coding sequence. A promoter generally comprises a sequence that functions to position the start site for RNA synthesis. The best-known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one can position the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. Depending on the promoter used, individual elements can function either cooperatively or independently to activate transcription. The promoters described herein may or may not be used in conjunction with an "enhancer," which refers to a cis-acting regulatory sequence involved in the transcriptional activation of a nucleic acid sequence, such as those for the genes, or portions or functional equivalents thereof, listed herein.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages may be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the beta-lactamase (penicillinase), lactose and tryptophan (trp) promoter systems. As demonstrated herein, in some embodiments, a nestin promoter is used to drive expression of the gene of interest. In addition to producing nucleic acid sequences of promoters and enhancers synthetically, sequences may be produced using recombinant cloning and/or nucleic acid amplification technology, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

A "gene," or a "sequence which encodes" a particular protein, is a nucleic acid molecule which is transcribed (in the case of DNA) and translated (in the case of mRNA) into a polypeptide in vitro or in vivo when placed under the control of one or more appropriate regulatory sequences. A gene of interest can include, but is no way limited to, cDNA from eukaryotic mRNA, genomic DNA sequences from eukaryotic DNA, and even synthetic DNA sequences. A transcription termination sequence will usually be located 3' to the gene sequence. Typically, a polyadenylation signal is provided to terminate transcription of genes inserted into a recombinant virus.

The term "polypeptide" or "protein," as used herein, means a polymer of amino acids joined in a specific sequence by peptide bonds. As used herein, the term "amino acid" refers to either the D or L stereoisomer form of the amino acid, unless otherwise specifically designated.

The term "transgene" refers to a particular nucleic acid sequence encoding a polypeptide or a portion of a polypeptide to be expressed in a cell into which the nucleic acid sequence is inserted. The term "transgene" is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been inserted; (3) a nucleic acid sequence that serves to add additional copies of the same (i.e., homologous) or a similar nucleic acid sequence naturally occurring in the cell into which it has been inserted; or (4) a silent naturally occurring or homologous nucleic acid sequence whose expression is induced in the cell into which it has been inserted. A "mutant form" or "modified nucleic acid" or "modified nucleotide" sequence means a sequence that contains one or more nucleotides that are different from the wild-type or naturally occurring sequence, i.e., the mutant nucleic acid sequence contains one or more nucleotide substitutions, deletions, and/or insertions. In some cases, the gene of interest may also include a sequence encoding a leader peptide or signal sequence such that the transgene product may be secreted from the cell.

As used herein, the term "transfection" refers to the uptake of foreign DNA by a mammalian cell. A cell has been "transfected" when exogenous DNA has been introduced inside the cell membrane. A number of transfection techniques are known in the art. See, Michael Richard Green and Joseph Sambrook, *Molecular Cloning: A Laboratory Manual,* 4th ed., Cold Spring Harbor Laboratory Press, Cold Spring Harbor, N.Y., USA (2012); Davis et al., *Basic Methods in Molecular Biology*, Elsevier Science Publishing, Inc., New York, USA (2012); Jon Lorsch (ed.) *Laboratory Methods in Enzymology: DNA, Elsevier*, (2013); Frederick M. Ausubel (ed.), *Current Protocols in Molecular Biology* (CPMB), John Wiley and Sons, (2014). Such techniques can be used to introduce one or more exogenous DNA moieties, such as a viral vector and other nucleic acid molecules, into suitable host cells. The term refers to both stable and transient uptake of the genetic material.

The term "oncolytic activity," as used herein, refers to cytotoxic effects in vitro and/or in vivo exerted on tumor cells without any appreciable or significant deleterious effects to normal cells under the same conditions. The cytotoxic effects under in vitro conditions are detected by various means as known in prior art, for example, by staining with a selective stain for dead cells, by inhibition of DNA synthesis, or by apoptosis. Detection of the cytotoxic effects under in vivo conditions is performed by methods known in the art.

A "biologically active" portion of a molecule, as used herein, refers to a portion of a larger molecule that can perform a similar function as the larger molecule. Merely by way of non-limiting example, a biologically active portion of a promoter is any portion of a promoter that retains the ability to influence gene expression, even if only slightly. Similarly, a biologically active portion of a protein is any portion of a protein which retains the ability to perform one or more biological functions of the full-length protein (e.g. binding with another molecule, phosphorylation, etc.), even if only slightly.

With the aforementioned preliminary descriptions and definitions in mind, additional background is provided herein below to provide context for the genesis and development of the inventive vectors, compositions and methods described herein.

Current mutant HSV-1 vectors that target malignant glioma are based on the two deletion mutant genes, ICP6 ($U_L39$ gene product), the large subunit of HSV-1 ribonucleotide reductase (RR), and ICP34.5 (34.5 gene product), a multifunctional protein that is also related to neurovirulence. While the lack of ICP6 restricts virus replication to non-dividing cells but allows replication to continue in cells with defects in the p16 tumor suppressor pathway, deletions of both $\gamma_2$ 34.5 genes suppresses HSV-1 encephalitis. This may be due to ICP34.5's facilitation of Beclin-1 autophagy function, essential for neurovirulence. Besides this autophagic inhibitory effect, ICP34.5 also counteracts a host defense mechanism triggered by viral infection. This mechanism activates PKR (double-stranded RNA protein kinase) that then phosphorylates the translation factor, eIF2$\alpha$, leading to translation inhibition. ICP34.5 directly binds and activates PP1 (protein phosphatase 1) that dephosphorylates eIF2a, allowing for viral mRNA translation to continue. Oncolytic HSV-1 with mutated γ34.5 genes (e.g. G207, 1716) has proven to be safe for administration in humans with gliomas in multiple clinical trials, but efficacy has been elusive, probably due to their limited viral replication. To overcome this limitation, an HSV1 was previously engineered, wherein the ICP34.5 gene is under the transcriptional control of the glioma stem cell promoter for nestin. rQNestin34.5 has exhibited increased efficacy in glioma models.

Nestin is an intermediate filament predominantly expressed in neural stems cells during embryogenesis, and is considered to be upregulated in glioma. A variety of primary tumors of the central nervous system (CNS) display elevated levels of nestin within tumor and/or endothelial cells. This transcriptionally driven oncolytic virus has shown efficient anti-tumor efficacy against CNS and neuroblastoma tumors in vitro and in vivo. Nestin gene sequence can be found in Genebank Gene ID: 10763, Chromosome 1—NC_000001.11 (156668763 . . . 156677397, complement).

The Herpes Gamma (γ) 34.5 Gene

Published results have demonstrated that at least one function of the herpes γ34.5 gene (which is alternatively known as the γ134.5 gene) is to preclude the host cell's response to viral infection, namely the triggering of host protein synthesis shutoff in an apoptotic-like response (Chou, J., et al., *Science* 250:1262-1266 (1990); Chou, J. and Roizman, *B., Proc. Natl. Acad. Sci. USA* 89:3266-3270 (1992); Chou, J., et al., *Proc. Natl. Acad. Sci. USA* 92:10516-10520 (1995)). A similar function is widespread among pathogenic viruses (Cosentino, G. P., et al., *Proc. Natl. Acad. Sci. USA* 92:9445-9449 (1995); Gale, M., Jr., et al., *Mol. Cell Biol.* 18:5208-5218 (1998); Katze, M. G., et al., *Trends Microbiol.* 3:75-78 (1995); Sharp, T. V., et al., *Nuc. Acids Res.* 21:4483-4490 (1993)).

While γ34.5 is nonessential for viral growth in culture in Vero cells, it enables the virus to spread in the central nervous system (CNS) of mice, and maps to a region of the HSV genome previously implicated in CNS replication (Markovitz, N. S., et al., *J. Virol.* 71:5560-5569 (1997); Centifanto-Fitzgerald, Y. M., et al., *J. Esp. Med* 155:475-489 (1982)). This may be due to the fact that the γ34.5-encoded protein inhibits the double-stranded RNA-dependent kinase (PKR). On exposure to double stranded RNA molecules, as seen commonly with viral infection, PKR phosphorylates the alpha subunit of elongation initiation factor eIF-2, resulting in inhibition of protein synthesis (Chou, J., et al., *Science* 250:1262-1266 (1990); Chou, J. and Roizman, *B., Proc. Natl. Acad. Sci USA* 89:3266-3270 (1992); Chou, J., et al., *J. Virol.* 68:8304-8311 (1994)). Infection of cells of neuronal origin with mutants incapable of expressing γ34.5 results in shut-off of cellular protein synthesis, with the resultant limitation of viral production.

In summary, in the presence of γ34.5, HSV will prevent apoptosis, thus allowing for production of progeny viruses. In its absence, the cell dies and the infecting HSV cannot generate progeny viruses. Thus, HSV infection/propagation throughout an organ is eliminated.

The nestin promoter/γ34.5 approach of the invention, thus allows for production of virus in cells that can use that promoter, but cells that cannot turn on the promoter will not propagate infection.

The herpes viral mutant of the invention comprises a deletion or inactivating mutation in both copies of the γ34.5 gene, wherein at least one copy of the γ34.5 gene is reintroduced under the control of a cell-specific or tumor-specific promoter.

As used herein, the term "deletion" is intended to mean the elimination of nucleic acids from a gene, such as the γ34.5 gene.

As used herein, the term "inactivating mutation" is intended to broadly mean a mutation or alteration to a gene wherein the expression of that gene is significantly decreased, or wherein the gene product is rendered nonfunctional, or its ability to function is significantly decreased.

The term "gene" encompasses both the regions coding the gene product as well as regulatory regions for that gene, such as a promoter or enhancer, unless otherwise indicated.

Ways to achieve such alterations include: (a) any method to disrupt the expression of the product of the gene or (b) any method to render the expressed gene nonfunctional. Numerous methods to disrupt the expression of a gene are known, including the alterations of the coding region of the gene, or its promoter sequence, by insertions, deletions and/or base changes. (See, Roizman, B. and Jenkins, F. J., *Science* 229: 1208-1214 (1985)).

We have generated an improved oncolytic rQNestin34.5 HSV virus, a second generation virus referred to as rQNestin34.5.v2. The genetically modified HSV1 rQNestin34.5.v2 has been made glioma-selective by the following maneuvers: 1) one of the viral genes that encodes for a viral protein (ICP6) has been removed. Without this gene, HSV1 has to utilize factors within the infected cells to efficiently grow and replicate and we have shown that such factors are existent in cells that are mitotically active or that have a defect in a cellular gene (p16) that is missing in most gliomas; and 2) the two copies of the viral gene that encode for a protein (ICP34.5) needed for robust viral growth in an infected cell have also been removed and one copy was reinserted under control of a Nestin promoter that is also present selectively in gliomas in the adult human brain. These two maneuvers thus allow this new HSV1 (designated as rQNestin34.5v.2) to be relatively selective in destroying gliomas and not normal brain cells and we have confirmed these statements in cultured cells and in animal models. In addition, there is lack of an ICP6-EGFP fusion protein present in the first generation rQNestin34.5 (Kambara et al. An oncolytic HSV-1 mutant expression ICP34.5 under control of a Nestin promoter increases survival of animals even when symptomatic from a brain tumor, (2005) *Cancer Res.* 65(7): 2832-2839), further removing a source of genomic instability and toxicity Accordingly, provided herein are tumor-selective oncolytic herpes viral vectors comprising: a) a deletion or inactivating mutation in both copies of the gene encoding γ35.5; b) an insertion of at least one copy of the HSV γ35.5 gene under the transcriptional control of a Nestin promoter; and c) a deletion or inactivating mutation in the gene that encodes for the HSV viral protein ICP6, wherein the tumor-selective oncolytic herpes viral vector does not express green fluorescent protein, e.g. ICP6-EGFP fusion protein present in the first generation HSV-1 vector rQNestin34.5.

In certain embodiments, the vector does not contain UL39 nucleic acid regulatory sequences (promoter and enhancer elements). In certain embodiments, the vector does not contain a fusion protein of ICP6.

In one embodiment, the at least one copy of the γ35.5 gene under the transcriptional control of a nestin promoter is inserted into UL39 gene that encodes for the large subunit of ribonucleotide reductase ICP6 (infected cell protein 6). In one embodiment, the nestin promoter comprises SEQ ID NO: 2 or a degenerate variant thereof. In one embodiment, a hybrid promoter comprising a nestin promoter and elements of heat shock protein 68 promoter is used (See Kambara et al. An oncolytic HSV-1 mutant expression ICP34.5 under control of a Nestin promoter increases survival of Animals even when symptomatic from a brain tumor, (2005) *Cancer Res.* 65(7): 2832-2839; and Kawaguchi et al. Nestin EGFP transgenic mice, visualization of the self-renewal and multipotentcy of CNS stem cells *Mol. Cell Neurosci*. (2001)17:259-273, incorporated by reference in their entirety).

In one embodiment, the tumor-selective oncolytic herpes viral vector comprises the sequence of SEQ ID NO: 1, or a degenerate variant thereof.

One of skill in the art would readily appreciate that a modified version of sequences disclosed herein could also be used, so long as it retains similar biological activity. Merely by way of non-limiting example, the nestin $2^{nd}$ intron sequence (enhancer) represented in SEQ ID NO: 4, and the hsp68 minimum promoter represented in SEQ ID NO: 5, could be used alone or combined when designing various constructs contemplated herein. In some embodiments, the nestin enhancer element may be operably linked to a heat shock protein 68 (hsp68) minimum promoter to drive the expression of γ34.5. In some embodiments, alternative or additional expression control sequences may be incorporated into the oncolytic expression vectors to initiate or influence the expression of any of the aforementioned nucleotide sequences of interest. Merely by way of non-limiting examples, the nestin promoter may incorporate microRNA target sequences. Examples of miR translational control sequences include, but are not limited to: miR128 or miR124 to differentiate glioma cells from normal neural cells.

In various embodiments, the present invention provides a method for treating a neoplastic disease in a subject. In certain embodiments, the method includes administering to the subject a therapeutically effective amount of an expression vector with oncolytic activity. In some embodiments, the cancer is brain cancer. Merely by way of non-limiting examples, the types of brain cancer that can be treated may include glioblastoma, anaplastic astrocytoma, astrocytoma, pilocytic astrocytoma, diffuse intrinsic pontine glioma, oligodendroglioma, anaplastic oligodendroglioma, mixed oligo-astrocytoma, and pendymoma. In some embodiments, cancer stem cells are treated with the inventive method. In some embodiments, the subject treated is a mammal. In certain embodiments, the subject treated is a human.

Methods of treating any of the neoplastic diseases described herein, including brain cancer, may include administration of the compounds of exemplary embodiments as a single active agent, or in combination with additional methods of treatment including, but not limited to, stem cell-based therapy, immunotherapy, radiation therapy, therapy with immunosuppressive agents, chemotherapeutic or anti-proliferative agents, including cytokines. The methods of treatment of the invention may be in parallel to, prior to, or following additional methods of treatment.

"Therapeutic benefit," as used herein, includes any decrease in cancer cell number, cancer cell proliferation rate, or metastasis. In some embodiments, the promoter used herein facilitates selective or increased expression of the associated gene of interest in one or more cancer cell type of interest, compared to a normal cell.

The term "operably linked," as used herein, refers to the arrangement of various nucleic acid molecule elements relative to each other such that the elements are functionally connected and are able to interact with each other. Such elements may include, without limitation, a promoter, an enhancer, a polyadenylation sequence, one or more introns and/or exons, and a coding sequence of a gene of interest to be expressed. The nucleic acid sequence elements, when operably linked, can act together to modulate the activity of one another, and ultimately may affect the level of expression of the gene of interest, including any of those encoded by the sequences described above.

One of skill in the art will understand that although specific sequences are provided herein, the nucleic acid molecules used in the inventive vectors, compositions and methods are not limited strictly to molecules including the sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. Rather, specific embodiments encompass nucleic acid molecules carrying modifications such as substitutions, small deletions, insertions, or inversions. Included in the invention are nucleic acid molecules, the nucleotide sequence of which is at least 95% identical (e.g., at least 96%, 97%, 98%, or 99% identical) to the nucleotide sequence shown as SEQ ID NOS: 1, 2, 3, 4, 5, 6, 7 and 8 in the Sequence Listing.

Also included in the invention is a nucleic acid molecule that has a nucleotide sequence which is a degenerate variant of a nucleic acid disclosed herein, e.g., SEQ ID NOS: 1, 2, 3, 4, 5, 6, 7, and 8. A sequential grouping of three nucleotides, a "codon," encodes one amino acid. Since there are 64 possible codons, but only 20 natural amino acids, most amino acids are encoded by more than one codon. This natural "degeneracy" or "redundancy" of the genetic code is well known in the art. It will thus be appreciated that the nucleic acid sequences shown in the Sequence Listing provide only an example within a large but definite group of nucleic acid sequences that will encode the polypeptides as described above.

Importantly, the vectors of the embodiments described herein may be useful for the introduction of additional genes in gene therapy. Thus, for example, the HSV vectors of this invention may contain one or more additional exogenous gene for the expression of a protein effective in regulating the cell cycle, such as p53, Rb, or mitosin, or a biologically active variant thereof, or in inducing cell death, such as the conditional suicide gene thymidine kinase, the latter must be used in conjunction with a thymidine kinase metabolite in order to be effective, or any other anti-tumor gene, such as for example a toxin.

When used pharmaceutically, oncolytic vector embodiments discussed herein can be combined with various pharmaceutically acceptable carriers. Suitable pharmaceutically acceptable carriers are well known to those of skill in the art. The compositions can then be administered therapeutically or prophylactically, in effective amounts, described in greater detail below.

As used herein, the term "therapeutically effective amount" is intended to mean the amount of vector which exerts oncolytic activity, causing attenuation or inhibition of tumor cell proliferation, leading to tumor regression. An effective amount will vary, depending upon the pathology or condition to be treated, by the patient and his or her status, and other factors well known to those of skill in the art. Effective amounts are easily determined by those of skill in the art. In some embodiments a therapeutic range is from $10^3$ to $10^{12}$ plaque forming units introduced once. In some embodiments a therapeutic dose in the aforementioned therapeutic range is administered at an interval from every day to every month via the intratumoral, intrathecal, convection-enhanced, intravenous or intra-arterial route.

Although certain routes of administration are provided in the foregoing description, according to the invention, any suitable route of administration of the vectors may be adapted, and therefore the routes of administration described above are not intended to be limiting. Routes of administration may including but are not limited to, intravenous, oral, buccal, intranasal, inhalation, topical application to a mucosal membrane or injection, including intratumoral, intradermal, intrathecal, intracisternal, intralesional or any other type of injection. Administration can be effected continuously or intermittently and will vary with the subject and the condition to be treated. One of skill in the art would readily appreciate that the various routes of administration described herein would allow for the inventive vectors or compositions to be delivered on, in, or near the tumor or targeted cancer cells. One of skill in the art would also readily appreciate that various routes of administration described herein will allow for the vectors and compositions described herein to be delivered to a region in the vicinity of the tumor or individual cells to be treated. "In the vicinity" can include any tissue or bodily fluid in the subject that is in sufficiently close proximity to the tumor or individual cancer cells such that at least a portion of the vectors or compositions administered to the subject reach their intended targets and exert their therapeutic effects.

Pharmaceutically acceptable carriers are well known in the art and include aqueous solutions such as physiologically buffered saline or other solvents or vehicles such as glycols, glycerol, vegetable oils (e.g., olive oil) or injectable organic esters. A pharmaceutically acceptable carrier can be used to administer the compositions of the invention to a cell in vitro or to a subject in vivo. A pharmaceutically acceptable carrier can contain a physiologically acceptable compound that acts, for example, to stabilize the composition or to increase the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the polypeptide.

Some embodiments of the technology describedHSF herein can be defined according to any of the following numbered paragraphs:

Paragraph 1. A tumor-selective oncolytic herpes viral vector, comprising:
- (a) a deletion or inactivating mutation in both copies of the gene encoding γ34.5, and
- (b) an insertion of at least one copy of the HSV γ34.5 gene under the transcriptional control of a Nestin promoter; and
- (c) a deletion or inactivating mutation in the gene that encodes for the HSV viral protein ICP6, wherein the tumor-selective oncolytic herpes viral vector does not express green fluorescent protein.

Paragraph 2. The tumor-selective oncolytic herpes viral vector of paragraph 1, wherein the vector does not contain UL39 nucleic acid regulatory sequences.

Paragraph 3. The tumor-selective oncolytic herpes viral vector of any of paragraphs 1-2, wherein the vector does not contain a fusion protein of ICP6.

Paragraph 4. The tumor-selective oncolytic herpes viral vector of any of paragraphs 1-3, wherein the at least one copy of the γ34.5 gene under the transcriptional control of a nestin promoter is inserted into UL39 gene that encodes for the large subunit of ribonucleotide reductase ICP6.

Paragraph 5. The oncolytic expression vector of any of paragraphs 1-4, wherein the nestin promoter comprises SEQ ID NO: 2 or a degenerate variant thereof.

Paragraph 6. The tumor-selective oncolytic herpes viral vector of paragraph 1, wherein the vector comprises the sequence of SEQ ID NO: 1 or a degenerate variant thereof.

Paragraph 7. A method for selectively killing intracranial tumor cells in a subject, comprising introducing into the vicinity of the tumor-selective oncolytic herpes viral vector of any of paragraphs 1-6.

Paragraph 8. The method of paragraph 7, further comprising the administration of cyclophoshamide (CPA).

Paragraph 9. The method of any of paragraphs 7-8, wherein the CPA is administered two days before the oncolytic herpes viral vector.

Paragraph 10. The method of any of paragraphs 7-9, wherein the tumor cells comprise a glioblastoma cell.

Paragraph 11. The method of any of paragraphs 7-10, wherein the tumor cells comprise a cancer stem cell.

Paragraph 12. The method of any of paragraphs 7-11, wherein the subject is a mammal.

Paragraph 13. The method of any of paragraphs 7-12, wherein the subject is a human.

Paragraph 14. A tumor-selective oncolytic herpes viral vector for use in the treatment of intracranial tumor cells in a subject, said tumor-selective oncolytic herpes viral vector comprising:
- (d) a deletion or inactivating mutation in both copies of the gene encoding γ34.5; and
- (e) an insertion of at least one copy of the HSV γ34.5 gene under the transcriptional control of a nestin promoter; and
- (f) a deletion or inactivating mutation in the gene that encodes for the HSV viral protein ICP6, wherein the tumor-selective oncolytic herpes viral vector does not express green fluorescent protein.

Paragraph 15. The tumor-selective oncolytic herpes viral vector of paragraph 14, wherein the vector does not contain UL39 nucleic acid regulatory sequences.

Paragraph 16. The tumor-selective oncolytic herpes viral vector of any of paragraphs 14-15, wherein the vector does not contain a fusion protein of ICP6.

Paragraph 17. The tumor-selective oncolytic herpes viral vector of any of paragraphs 14-16, wherein the at least one copy of the γ34.5 gene under the transcriptional control of a nestin promoter is inserted into UL39 gene that encodes for the large subunit of ribonucleotide reductase ICP6.

Paragraph 18. The oncolytic expression vector of any of paragraphs 14-17, wherein the nestin promoter comprises SEQ ID NO: 2 or a degenerate variant thereof.

Paragraph 19. The tumor-selective oncolytic herpes viral vector of any of paragraphs 14-18, wherein the vector comprises the sequence of SEQ ID NO: 1 or a degenerate variant thereof.

Paragraph 20. The tumor-selective oncolytic herpes viral vector of any of paragraphs 14-19, wherein the tumor cells comprise a glioblastoma cell.

Paragraph 21. The tumor-selective oncolytic herpes viral vector of any of paragraphs 14-20, wherein the tumor cells comprise a cancer stem cell.

Paragraph 22. The tumor-selective oncolytic herpes viral vector of any of paragraphs 14-21, wherein the subject is a mammal.

Paragraph 23. The tumor-selective oncolytic herpes viral vector of any of paragraphs 14-22, wherein the subject is a human.

Paragraph 24. The tumor-selective virus of any of paragraphs 1-23, wherein the vector does not comprise SEQ ID NO: 7.

Paragraph 25. The tumor-selective virus of any of paragraphs 1-23, wherein the vector comprises SEQ ID NO: 8.

Paragraph 26. The use of the tumor-selective virus of any of paragraphs 1-25 for selectively killing intracranial tumor cells in a subject.

Paragraph 27. The use of paragraph 26, wherein cyclophoshamide (CPA) is administered to the subject.

Paragraph 28. The use of any of paragraphs 26-27, wherein the CPA is administered two days before the oncolytic herpes viral vector.

Paragraph 29. The use of any of paragraphs 26-28, wherein the tumor cells comprise a glioblastoma cell.

Paragraph 30. The use of any of paragraphs 26-29, wherein the tumor cells comprise a cancer stem cell.

Paragraph 31. The use of any of paragraphs 26-30, wherein the subject is a mammal.

Paragraph 32. The use of any of paragraphs 26-31, wherein the subject is a human.

Paragraph 33. A tumor-selective oncolytic herpes viral vector that consists essentially of SEQ ID NO: 1.

EXAMPLES

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1 Generation of rQNestin34.5v.2 rQNestin34.5v.2 is a genetically engineered HSV1 (F strain derivative), designed to replicate in glioma cells and not normal cells in the brain or other tissues. HSV1 is present endemically in the human population primarily in a latent form within the sensory neurons of the trigeminal ganglia. The virus is approximately 152-158 kilobases, it is enveloped and measures 150 nm in diameter. The virus will infect and replicate in most, if not all, established human glioma cell lines, as well as freshly established gliomas from patients expanded under conditions that enrich for the "stem-like" glioma subpopulation. The following genetic modification were made to HSV1 F strain (e.g. commercially available form OriGene Technologies Inc. Rockville, Md. 20850 U.S.S) to generate rQNestin34.5v.2:

1—Both endogenous copies of the coding region of the viral gene encoding for ICP34.5 have been mostly removed;

2—A single copy of the ICP34.5 coding region was placed under control of a glioma-selective nestin promoter/enhancer sequence, providing glioma-selective expression of the ICP34.5 viral gene, allowing for more robust replication of the virus in nestin-expressing glioma vs. nestin-non expressing brain cells;

3—The viral ICP6 gene locus is also disrupted, restricting viral replication to glioma cells with defective p16 tumor suppressor pathway signaling (>90% of gliomas) or mitotic cells.

The schematic of rQNestin34.5v.2 is shown if FIG. 1. In infected cells, viral DNA remains extrachromosomal. The virus, upon entry in tumor cells will enter the lytic cycle, usually resulting in tumor cell lysis within 12-18 hours. Latency only occurs in trigeminal sensory neurons.

rQNestin34.5 v. 2 DNA was subjected to next generation sequencing on an Illumina GA IIe machine at the Microarray Core Facility Huntsman Cancer Institute University of Utah, the Sequence is provided in SEQ ID NO: 1.

The nestin-hsp68 minimum enhancer/promoter sequence are derived from the human nestin enhancer/promoter and the human hsp68 promoter fused together to provide specific transcriptional regulation to cells expressing nestin. Specific transcriptional regulation of ICP34.5 in the context of rQNestin was shown in the following set of experiments (Note: ICP34.5 expression in infected cells is leads to dephosphorylation of the translation factor eIF2a. Therefore, we would expect to see dephosphorylated eiF2a in glioma cells that express nestin, while cells that do not express nestin (HUVEC and human astrocytes) should have high levels of phosphor eiF2a, after viral infection).

Figure 2:
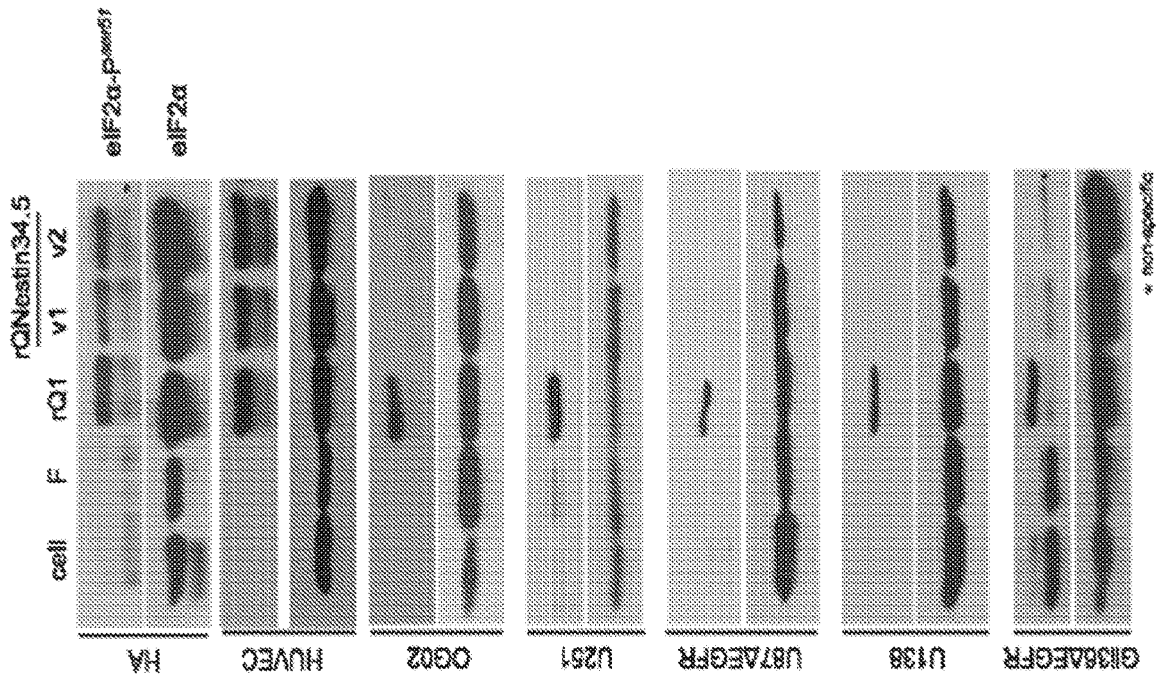
FIG. 2 are western blots of several glioma cells (U87dEGFR, U251, U138 and Gli36dEGFR) and freshly explanted glioma "stem-like" cells (GBM 02) and normal human astrocytes (HA) andendothelial cells (HUVEC) were infected with rQNestin 34.5 v.2 or parental rQNestin34.5 (v.1), control rQ1 virus, wild-type F strain or uninfected (cell). Lysates were then harvested and Western blots carried out to visualize total eiF2a and phospho-eiF2a (eiF2a-Pser51). X12 (another GSC) is not included but showed same results as OG02.

Several established glioma cell lines (U87dEGFR, U215, U138 and Gli36dEGFR), a freshly explanted glioma cell grown under conditions to enrich for the glioma "stem-like" cell subpopulation (GBM #02), normal human vein endothelial cells (HUVEC) and normal human astrocytes were infected with rQNestin34.5 v.2 or another rQNestin34.5 (v.1—that expressed GFP) (FIG. 2). In addition, rHSVQ1 (rQ1) (see e.g. US 20020110543 and Hirokazu Kambara et al. An Oncolytic HSV-1 Mutant Expressing ICP34.5 under Control of a Nestin Promoter Increases Survival of Animals even when Symptomatic from a Brain Tumor, Cancer Res Apr. 1, 2005, 65; 2832), an ICP34.5 deleted mutant, wild-type F strain virus, and uninfected cells were also used. Cell lysates were separated and Western blots for eIF2a vs. phosphor-eiF2a were then performed. In normal HUVEC cells and astrocytes, phospo-eiF2a was present, as expected, in rQNestin34.5, rQNestin34.5v.2, and rHSVQ1 virally-infected cells, showing that they functioned as ICP34.5 mutants, while no phosphor-eiF2a was observed in wild-type F strain infected cells. However, in all glioma cells, there was no phosphor-eiF2a detected in in rQNestin34.5 or rQNestin34.5v.2 infected cells, similar to wild-type F strain virus, while phosphor-eiF2a was still visible in rHSVQ1-infected cells. This data thus showed that rQNestin34.5v.2 functioned as an ICP34.5-defective virus in normal cells (HUVEC and astrocytes) unlike wild-type virus. However, in glioma cells, rQNestin34.5v.2 functioned as an ICP345.-positive virus, similar to wild-type virus. Quantitatively, there was clearly a >2-fold decrease in the levels of phosphorylated eiF2a in glioma cells infected with rQNestin34.5v.2 and parental rQNestin34.5 compared to control rHSVQ1 virus. Also, the levels of observed phosphorylated eIF2a in the rQNestin34.5v.2 and parental rQNestin34.5 infected glioma cells were >2-fold less than unphosphorylated eIF2a protein in the same cells.

Figure 3:
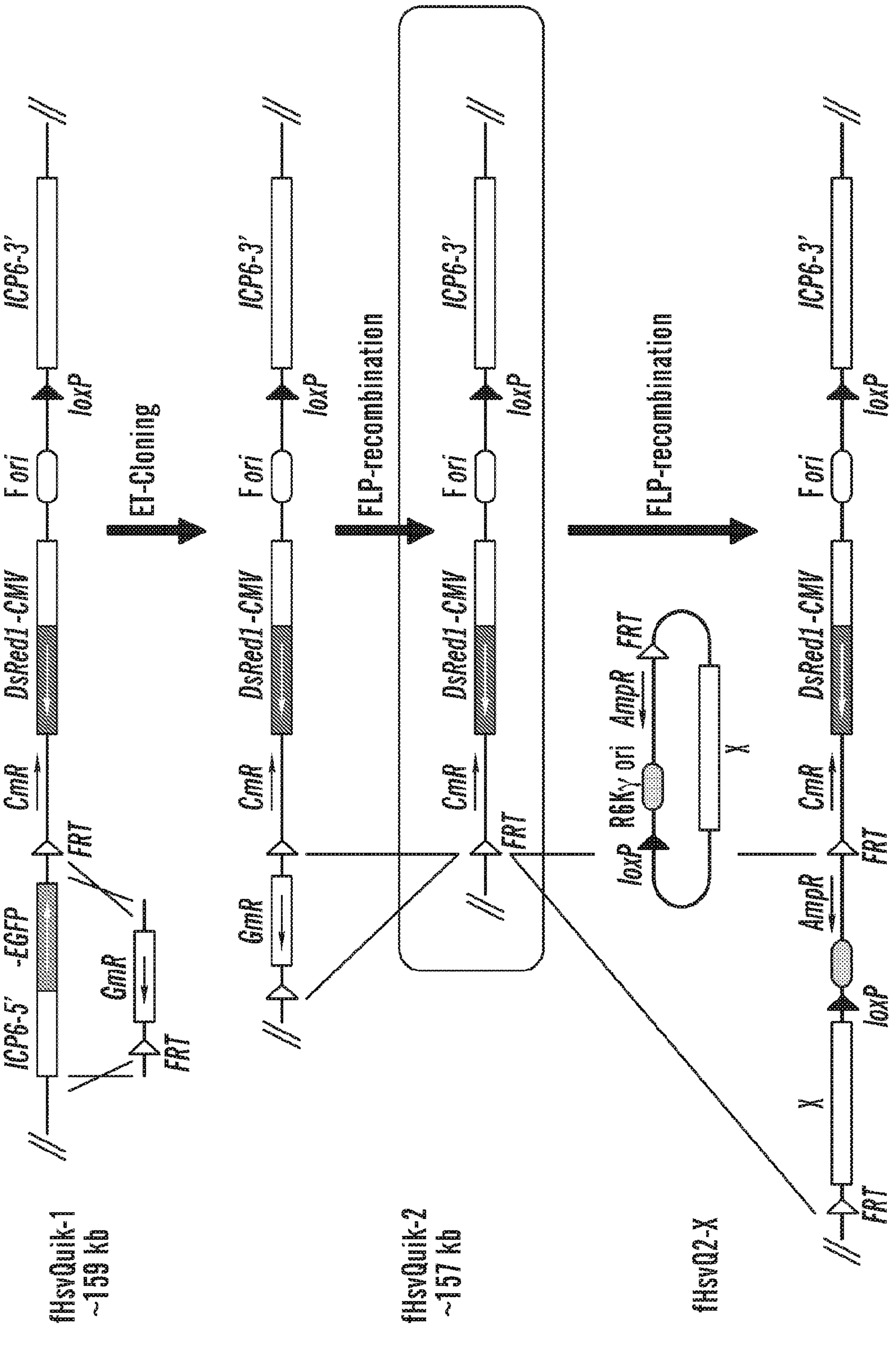
FIG. 3 is a schematic of the construction of the fHSVQ2-X series of bacterial artificial chromosomes (BAC) that contain the entire HSV1 genome with endogenous HSV1 ICP34.5 and ICP6 deletions and insertion of a large sequence utilized for transfer of exogenous sequences, such as the Nestin/hsp68 promoter/enhancer sequence (marked by X).

In the first series of steps, we had to modify fHSVQuik-1, the bacterial artificial chromosome (BAC) that contains the F strain HSV1 sequence with the deleted diploid ICP34.5 genes. The generation of fHSVQ1 was described in Terada et al. (Terada et al. Development of a rapid method to generate multiple oncolytic HSV vectors and their in vivo evaluation using synergenic mouse tumor models. *Gene Ther.* 13: 705-714, 2006). FIG. 3 shows that the modification of fHSVQuik-1 to remove the entire sequence of EGFP under control of the ICP6 promoter was accomplished by ET-cloning of a GmR selection marker at the site with removal of the ICP6 promoter-EGFP transcriptional cassette, followed by FLP-recombination and removal of the selectable marker to generate fHSVQuik-2. In order to transfer in the Nestin/hsp68 promoter/enhancer—ICP34.5 cassette into fHSVQuik-2, a transfer plasmid with this cassette (marked in X) is then recombined back into the same site using Flp-recombinatiion to give rise to fHsvQ2-X. When X is the Nestin/hsp68 promoter/enhancer—ICP34.5 cassette, it is designated as fHSVQ2-nestin34.5 (see FIG. 4)

Figure 4:
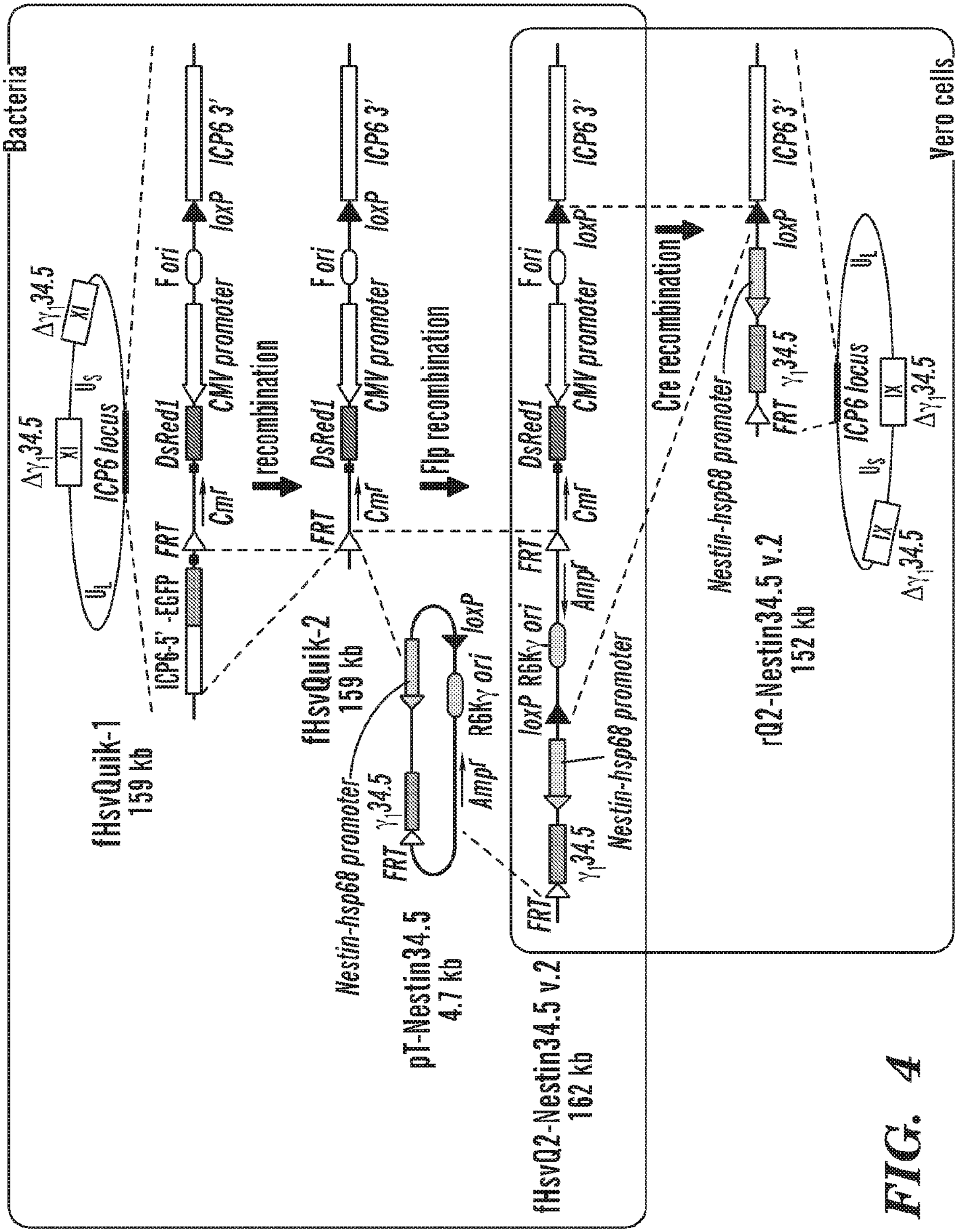
FIG. 4 is a schematic of the engineering of rQNestin34.5 v.2 (rQNestin34.5 lacking ICP6GFP). A bacterial artificial chromosome (BAC) containing the HSV1 genome lacking both copies of the HSV1 gene γ134.5, encoding for the viral protein ICP34.5 and with a large deletion of the viral gene for ICP6 (only some 3' sequence remains) was obtained (designated as fHSVQuick-2). A plasmid with the Nestin-promoter enhancer element upstream of a γ1 34.5 transgene (pT-Nestin34.5) is then recombined by site-specific recombination into the FRT locus by employing FLP. The BAC concatenate (fHSVQ2-Nestin34.5 v.2) is then purified from bacteria and electroporated in mammalian Vero cells in the presence of Cre recombinase to remove internal antibiotic resistance sites, fluorescent proteins sites, such as DSRed1, FRT site and F plasmid origin of replication. The viral genome will replicate in Vero cells, generating rQNestin34.5 v.2 virions. (see for example Terada et al. Development of a rapid method to generate multiple oncolytic HSV vectors and their in vivo evaluation using synergenic mouse tumor models. *Gene Ther.* 13: 705-714, 2006).

After generating fHSVQ2-nestin34.5 in bacteria, the entire BAC is purified and electroporated into mammalian Vero cells where Cre-Lox recombination is utilized to remove all BAC sequences (FIG. 4). The viral genome is now "free" to begin its own process of DNA replication, generating viral plaques that can be purified to generate rQNestin34.5v.2. The generated rQnestin34.5v.2 was identified by Southern blotting as possessing the desired genetic identity (data not shown). An isolate of rQNestin34.5v.2 was then sent to Diamyd, Inc. who proceeded with viral DNA isolation and transfection into their certified Vero derived Master Cell Bank (MCB) followed by expansion to obtain the final seed of rQNestin34.5v.2 employed for subsequent efficacy/toxicity experiments. This Viral Seed Stock (VSS) was subjected to a panel of validated assays in order to allow subsequent cGMP procedures moving toward large scale manufacturing of the vector for the clinical trial. The VSS tests performed under validated GLP conditions included; Sterility (including Bacteristasis and Fungistasis (B&F) immersion), Mycoplasma (Points to Consider), Endotoxin, Polymerase Chain Reaction (PCR) based Reverse Transcription (PBRT) assay, and quantitative PCR (QPCR) testing for the following adventitious agents: Porcine Circovirus 1 and 2; Adenovirus type 5; Adeno-Associated Virus types 1, 2, 3, 4, 6, 7, 8, 9, 10, and 11. The results of this testing panel document the suitability to advance with manufacturing.

Virus Production

Cell Thaw and Expansion. One or more vials of VeroD Master Cell Bank are thawed at 37° C. and the cells are transferred to a conical tube and pooled. The cells were vialed at $1.2\times10^7$ cell/mL/tube and viable recoveries have been ~$9.2\times10^6$ cell/tube. The cells were gradually diluted with complete medium and a sample is removed to obtain viable cell counts. The cells are plated to flasks at a density of 3.0-$5.0\times10^4$ cells/cm2.

The cells were incubated at 37° C., 7.5% $CO_2$ and examined periodically by phase microscopy for growth and visual evidence of microbial contamination. When the cells were ~80% confluent, the cells were passaged. Briefly, the complete medium is removed and PBS is added to rinse the cells. The PBS is removed and TryPLE Select is added to the flasks to dissociate the cells. The flasks are incubated at 37° C. for approximately 3-5 minutes or until the cells are detached. The cells were re-suspended in complete medium, pooled, counted and seeded into new flasks at a density between 2.0-$4.0\times10^4$ cells/$cm^2$. The cells were expanded to 16×10-layer Nunc Cell Factories and allowed to reach 1-2 days post confluence prior to infection. allowed to reach 1-2 days post confluence prior to infection.

Infection with rQNestin34.5v.2 Vector. When the cells have reached desired confluence, an example flask was treated with TryPLE Select and counted to estimate cell numbers. The rQNestin34.5v.2 Master Virus Bank vector inoculum was prepared by thawing the appropriate volume required to obtain an MOI=0.1. The cell factories were infected by an initial 1.5 hour adsorption period followed by incubation for the first day of infection in complete medium. After ~24 hours, the culture medium was removed and replaced with an equal volume of serum-free medium. The cell factories were placed in the incubator and the temperature is reduced to 33° C./7.5% CO2. The cultures were monitored daily and checked visually for percent cytopathic effect. The infection typically lasts for 4 days.

Crude Viral Harvest and Clarification. The infection was stopped by placing the cell factories in the biosafety cabinet and pooling the supernatant and cell debris into a sterile bag. The harvest sodium chloride level was increased to 0.45 M by the addition of a 5 M NaCl stock solution. The harvest was then mixed by hand for 20-30 minutes. The harvest was then aliqotted into 500 mL centrifuge tubes and the cell debris is removed by centrifugation at 1500×g. The supernatant was repooled into a sterile bag. After pre-treatment of a Sartopore clarification filter capsule with sterile water, the virus-containing supernatant was then pumped through the filter capsule into another sterile bag. The virus is followed by pumping sterile water to recover remaining virus in the capsule. The bag was mixed and the filtrate is stored overnight at 4° C.

The next day, the filtrate was warmed and adjusted to ~2 mM $MgCl_2$ by addition of 2 volumes of 3 mM $MgCl_2$ in sterile water. The diluted filtrate is mixed and Benzonase treatment is performed next. This is done by first diluting 100,000-200,000 U of the enzyme into dilution buffer and 7 sequential additions are injected at 5 minute intervals with continuous mixing over a 35 minute period.

Cation Exchange Column Chromatography. A BPG 100 column is packed with SP high performance resin and is sanitized with 0.5N NaOH. After sanitization, the column is equilibrated with wash buffer (PBS pH 7.0), strip buffer (1M NaCl-PBS pH 7.0), and wash buffer before loading benzonase treated virus. Conductivity, UV, and pH are monitored during the run.

The process bag containing the Benzonase treated filtrate was connected to the inlet using a tubing welder and the virus is loaded onto the column. The flow through was collected in a sterile bag. The virus capture step was followed by washing with PBS pH 7.0 until the UV absorbance returns to baseline. The pump was stopped and the process bag containing 0.45 M NaCl-PBS pH 7.0 was connected to the inlet. The outlet tubing was transferred to a sterile container in the biosafety cabinet. The buffer was pumped into the column and when the UV absorbance began to increase sharply, the column outlet was transferred to a new sterile container to collect the eluted virus. The collection was stopped after the UV absorbance returns to near baseline. This is the purified viral elute fraction. The process bag containing strip buffer is next connected to the inlet. The end of the outlet tubing is transferred into a sterile bottle to collect the strip fraction. The buffer is pumped through the column until UV absorbance reaches a peak and returns to near baseline. The elute is stored at 4° C. overnight.

Tangential Flow Filtration and Final Filtration. The tangential-flow filtration system is prepared by assembling the tubing and cartridge and sterilizing the system by autoclaving. The system is transferred to the biosafety cabinet and flushed with sterile PBS pH 7.0. An equal volume of sterile PBS pH 7.0 and the 0.45M virus elute fraction are added to the system reservoir and recirculated for 5-10 minutes. After this equilibration, the permeate collection pump is turned on and filtrate is collected at ~5 mL/minute. The system is run until the loaded volume is reduced by half. The retentate in the reservoir is diluted with PBS pH 7.0 to double the volume and continued to reconcentrate. This process is repeated while monitoring the conductivity of the permeate. When the permeate conductivity was within 10% of the diafiltering buffer (PBS pH 7.0) the product was allowed to concentrate to about 40 mL The retentate was recovered and filtered through a 0.45 um Millipack filter unit.

Final Formulation and Packaging. The terminal filtered virus stock was adjusted to 10% final volume with sterile glycerol and mixed well. The product was manually dispensed into cryovials for storage at a volume of 110 uL per vial. The tubes were labeled and stored at ≤−65° C.

Example 2 Preclinical Studies

Figure 5:
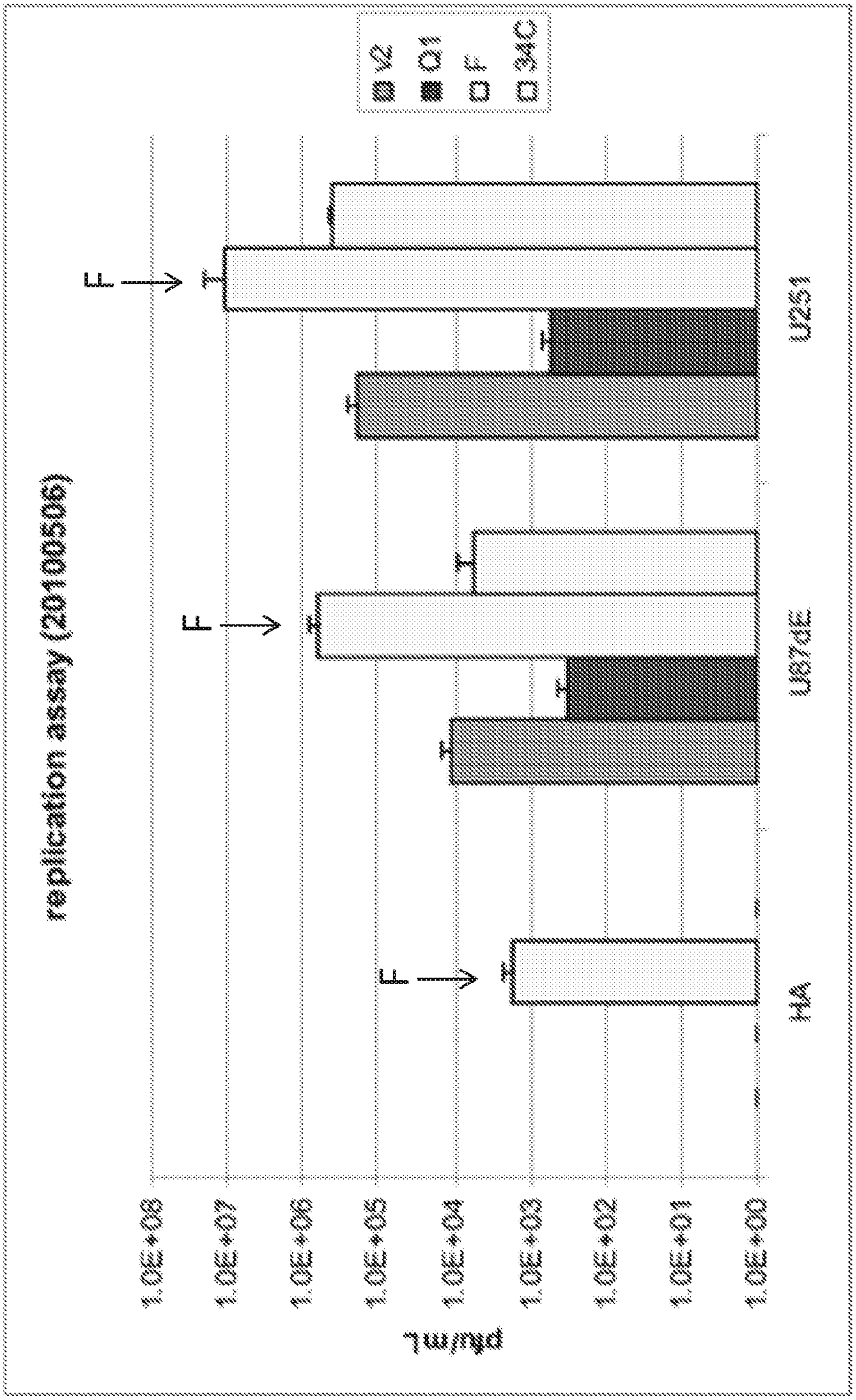
FIG. 5 is a graph depicting viral yields in human glioma cells and normal human astrocytes. Normal human astrocytes (HA) and human glioma cells, U87dEGFR (U87dE) and U251, were cultured in the presence of rQNestin34.5v.2 (v2), parental rHSVQ1 (Q1), wild-type F strain (F), and also another oncolytic viral construct unrelated to this project (34C). Viral yields were then assayed 3 days later.
Figure 6:
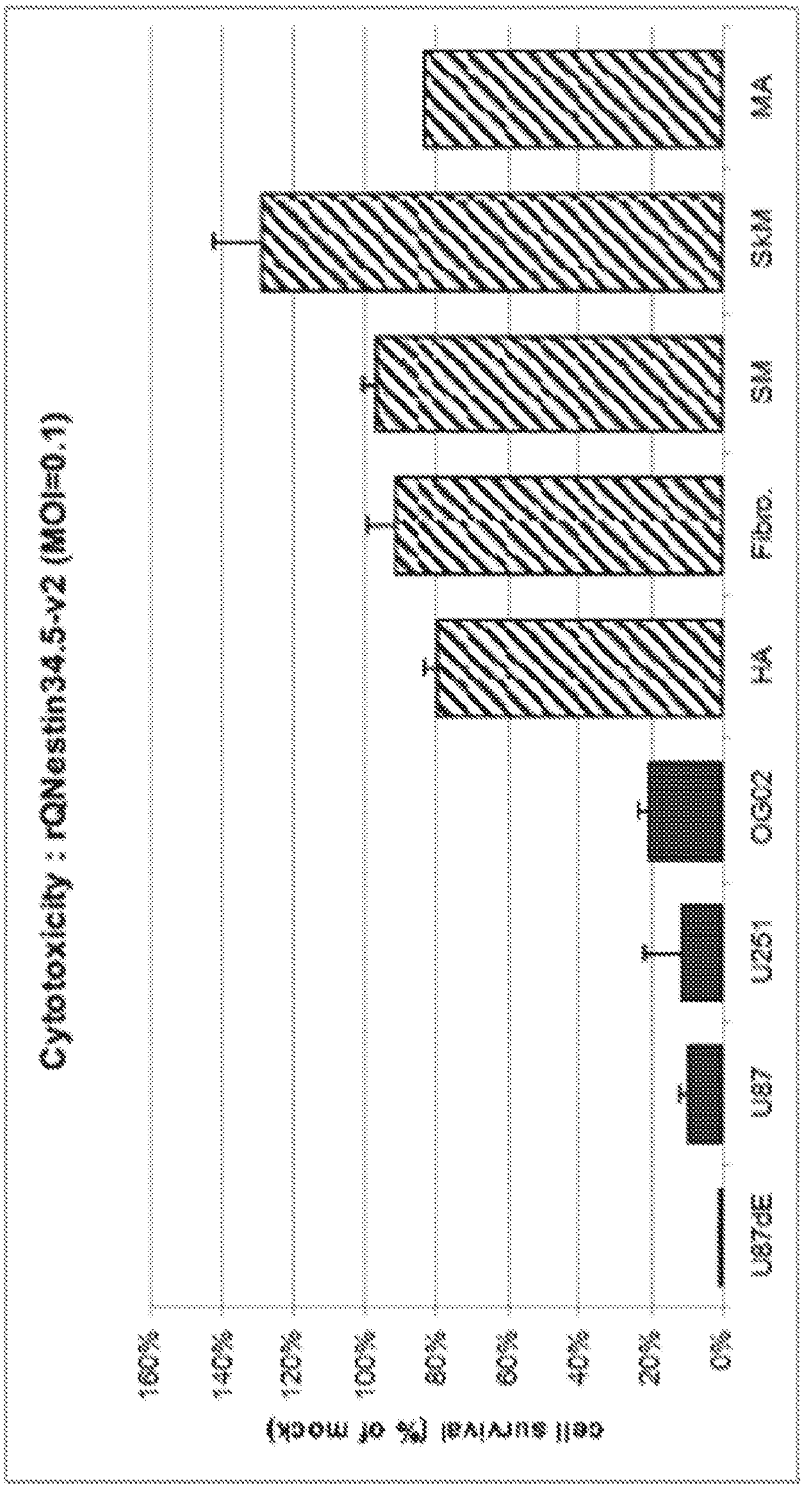
FIG. 6 is a graph depicting cell survival in various cells. rQNestin34.5v.2 was added to a panel of glioma cells, U87dEGFR (U87dEGFR), U87, U251 and OG02 and to a panel of normal cells, human astrocytes (HA), human fibroblasts (Fibro.), human smooth muscle (SM), human skeletal muscle cells (SkM) and mouse astrocytes (MA). Surviving cells were then counted 5 days later by Coulter counter enumeration

Three general sets of experiments were performed. In the first, in vitro studies utilizing glioma cell lines and normal human cells (particularly human astrocytes) are utilized as models to show the relative selectivity of rQNestin34.5 replication and cytotoxicity against the former and not the latter. In the second, a mouse athymic model of intracranial human glioma xenograft is used to show that a single intratumoral injection of rQNestin34.5v.2 leads to a significant prolongation of animal survival. Due to the lack of replication of the virus in syngeneic murine gliomas grown in C57/B6 mice, a suitable efficacy experiment in an immunocompetent animal model is not possible. Finally, intracranial injections of the agent in the brains HSV-susceptible Balb/c mice were performed to determine the degree of toxicity We first determined if rQNestin34.5v.2 replicated efficiently in human glioma cells vs. normal human astrocytes. The former express nestin while the latter do not (data not shown). FIG. 2 shows that nestin promoter activation of ICP34.5 in rQNestin34.5 infected glioma cells led to dephosphorylation of the translation factor eiF2a thus allowing for efficient translation of viral mRNAs in infected cells, similar to wild-type F strain, while ICP34.4-deleted HSV1 (such as Q1, aka rQ1, rHSVQ1) cannot do this. Therefore, one would expect in human glioma cells robust replication of rQNestin34.5v.2 similar to F strain, while Q1 should replicate poorly. FIG. 5 confirms this. Conversely, in normal human astrocytes (the predominant cell population in the brain, whose progenitor is thought to give rise to glioma) that do not express nestin, rQNestin34.5v.2 will not dephosphorylate eiF2a, leading to poor to nil viral replication, similar to other ICP34.5-deleted HSV1 such as Q1 (FIG. 5). Wild-type F strain HSV1 will still replicate though. In fact, As shown in FIG. 4, the yield of rQNestin34.5v.2 was at least 4 log units more in U87dEGFR and 5 log units more in U251 compared to that in human astrocytes (where it approached almost no virus obtained). We then tested the cytotoxicity of rQNestin34.5v.2 against a panel of human glioma cells and normal human cells. rQNestin34.5 v.2 was added to panels of gliomas cells and normal human and mouse cells to a MOI of 0.1 (FIG. 6). Five days later, surviving cells were counted. There were < or =20% of glioma cells alive and > or =80% normal cells alive at this time point. The sum of these experiments thus established the relative selectivity in replication and toxicity of rQNestin34.5v.2 against human glioma vs. normal cells.

Figure 7A:
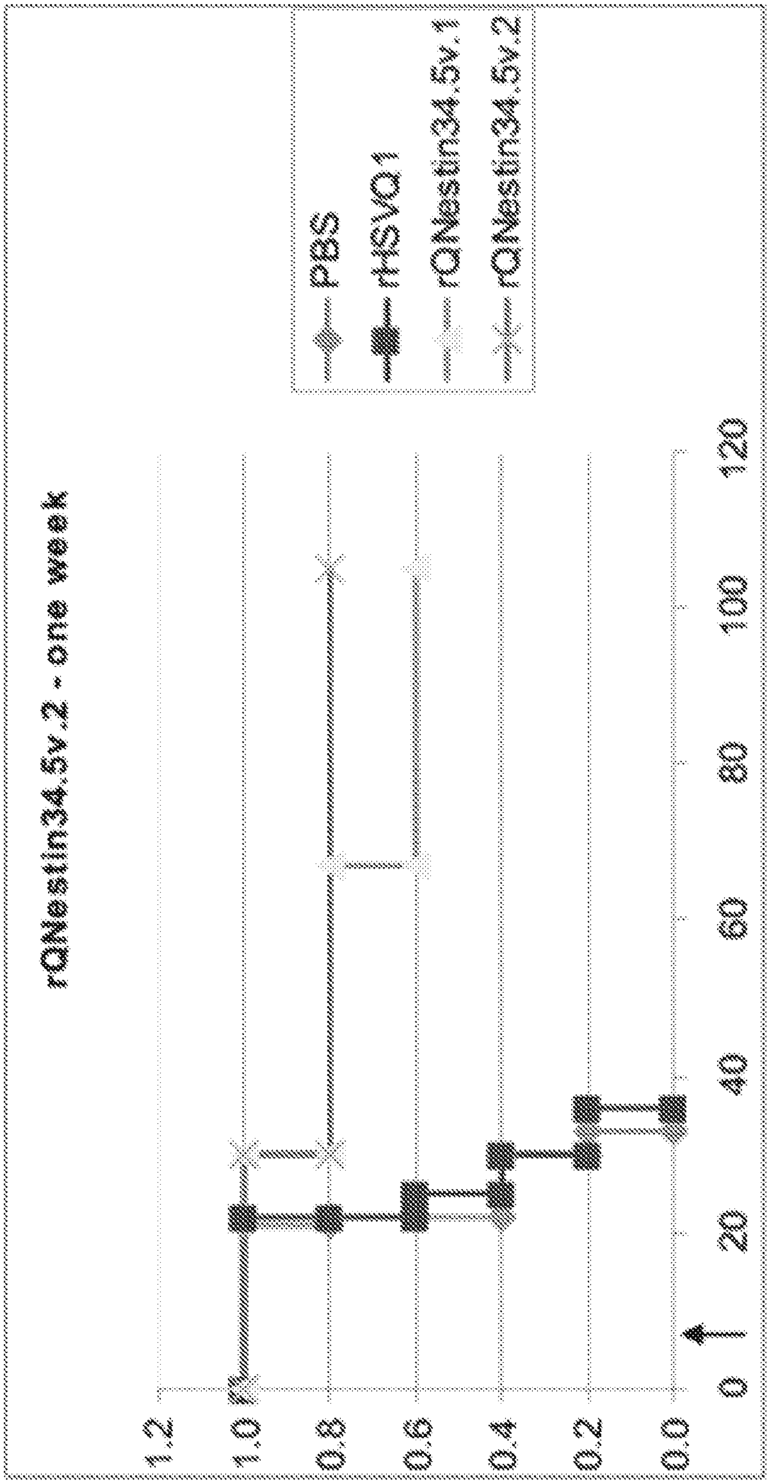
FIG. 7A is a graph showing mouse survival (y) over time (x). U87dEGFR glioma cells ($2\times10^5$) were implanted in the brain of 8 week old athymic mice. One week later, PBS, rHSVQ1, rQNestin34.5v.1 and rQNestin34.5v.2 ($3\times10^5$ pfu in 5 ul) were injected into the same location. Survival was then monitored.
Figure 7B:
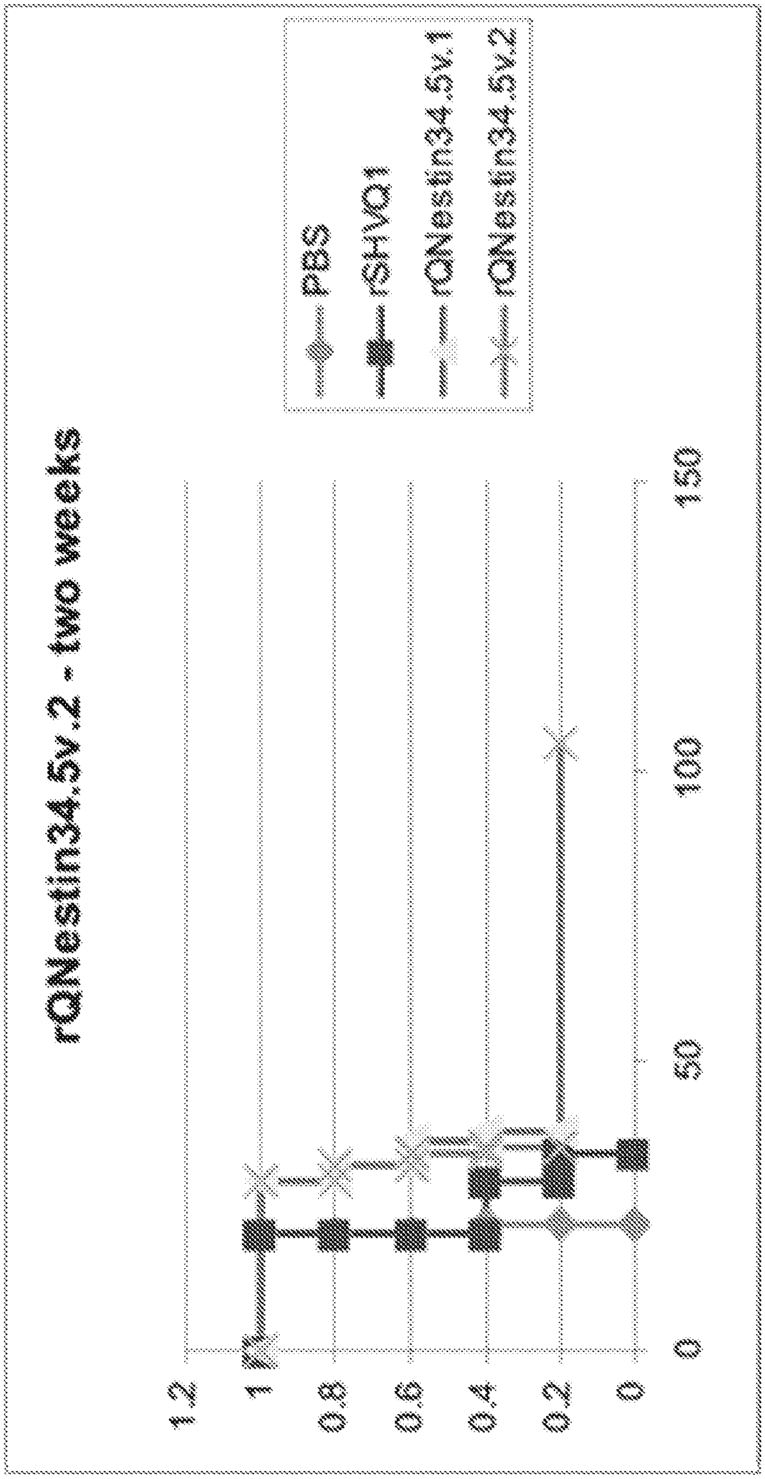
FIG. 7B is a graph showing mouse survival rate (y) over time (x). U87dEGFR glioma cells ($2\times10^5$) were implanted in the brain of 8 week old athymic mice. Two weeks later, PBS, rHSVQ1, rQNestin34.5v.1 and rQNestin34.5v.2 ($3\times10^5$ pfu in 5 ul) were injected into the same location. Survival was then monitored.

We then employed an orthotopic model of human glioma growth in athymic mice. For this, we utilized human U87dEGFR glioma cells that usually establish after a few days of intracerebral inoculation and lead to animal death by 3-4 weeks. In the first experiment, rQNestin34.5v.2 was inoculated seven days after tumor cell inhection (FIG. 7A), while in the second the virus was injected 14 days later, as animals become symptomatic from tumor growth (FIG. 7B). In both cases, the virus was injected at a dose of 3×105 pfus. In both, there was a significant increase in mouse survival, indicating that rQNestin34.5v.2 was an effective antiglioma agent in this mouse model.

Finally, we tested the relative safety of rQNestin34.5v.2 by direct intracerebral inoculation into the brains of Balb/c mice that are relatively sensitive to HSV-induced encephalitis/meningitis Table 1 in FIG. 8 summarizes the results of all experiments to date with Balb/c mice. Intracerebral injection of $10^7$ pfus in either 8 week old or 6 month old mice was well tolerated (32/33, with one death at day 3 post-injection for unknown reasons). In contrast, F strain caused death in 5/animals at 6, 6, 7, 8, and 12 days after injection. Intrathecal, intrahepatic and intravenous injections of rQNetsin34.5v.2 were also well tolerated without deaths at a dose of $10^7$ pfus, although F strain also did not cause death by these routes.

The sum of these experiments thus indicates that rQNestin34.5v.2 is selectively toxic for human glioma cells vs. normal cells including astrocytes, leads to a prolongation of survival in animal models of gliomas at a dose of $3\times10^5$ pfus, and 97% of Balb/c mice survive an intracranial injection at a dose of $10^7$ pfus, while less than 30% of mice survive an intracranial injection of wild-type F strain at a dose of $10^5$ pfus.

Brief Description of Cloning to Remove GFP Region

Figure 15:
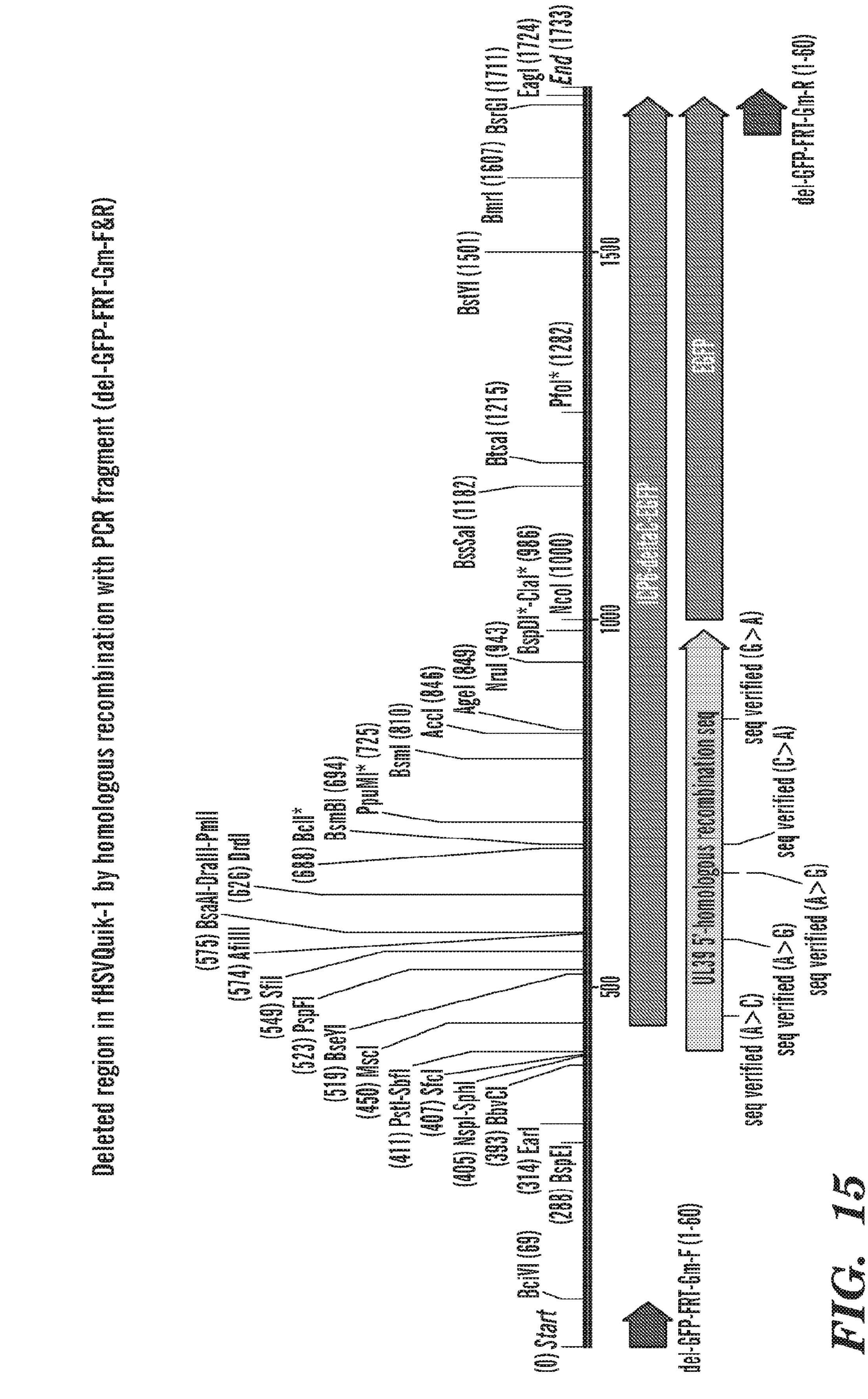
FIG. 15 shows a schematic of the deleted region in fHSVQuick-1 by homologous recombination with PCR fragment (del-GFP-FRT-Gm-F&R).
Figure 16:
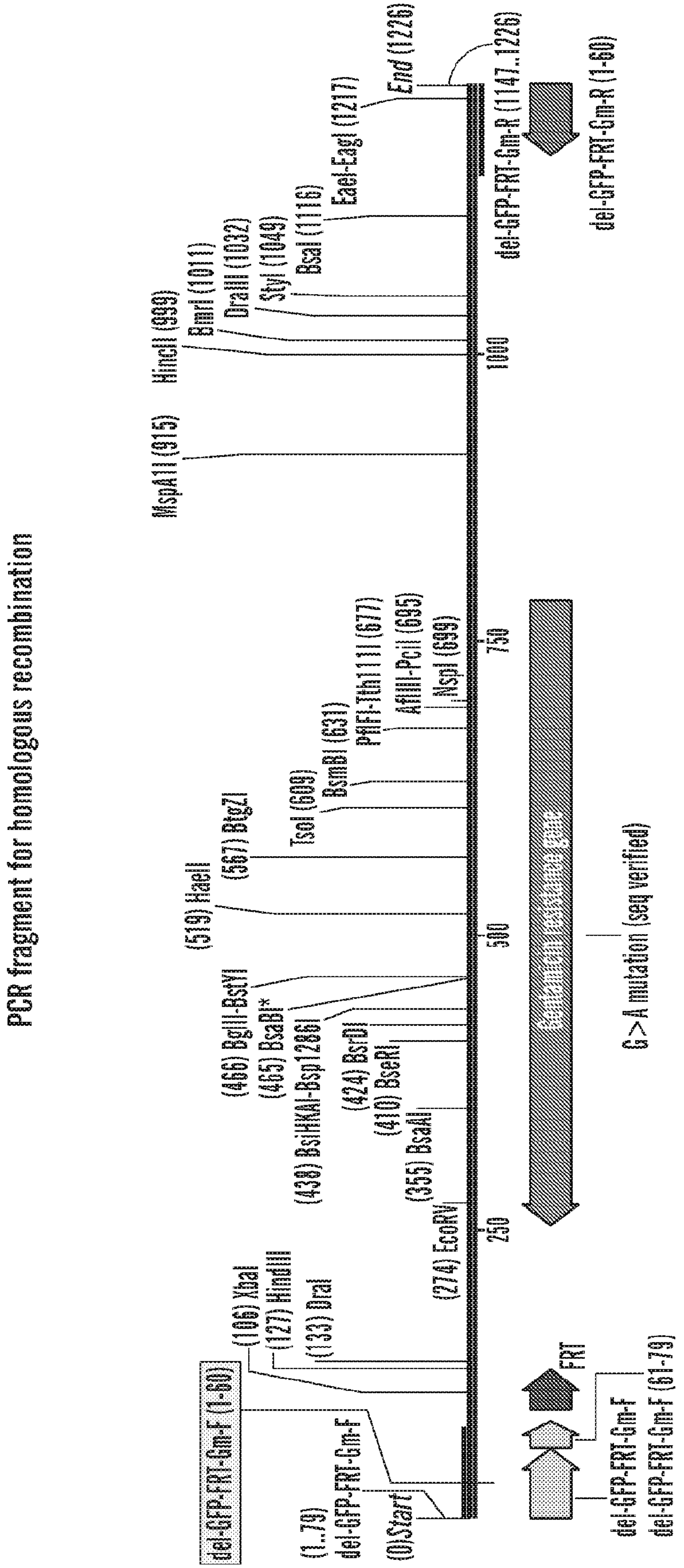
FIG. 16 shows a schematic of the PCR Fragment del-GFP-FRT-Gm-F&R used for homologous recombination.

We generated PCR-del-GFP-FRT-Gm-F&R DNA (SEQ ID NO: 8) by PCR amplification. We then performed homologous recombination of this PCR product with fHS-VQuik-1 BAC vector using ET-recombination technique, resulting in the replacement of FIG. 15 region schematic (SEQ ID NO: 7) to FIG. 16 schematic, sequence (SEQ ID NO: 8). We then Transformed Flp-T vector in *E. coli* containing above BAC vector to remove the region surrounded by two FRT sites, one of which locates in original fHSVQuik-1 BAC vector. This resultant vector is called fHSVQuik-2.

In Vivo Replication

Figure 9:
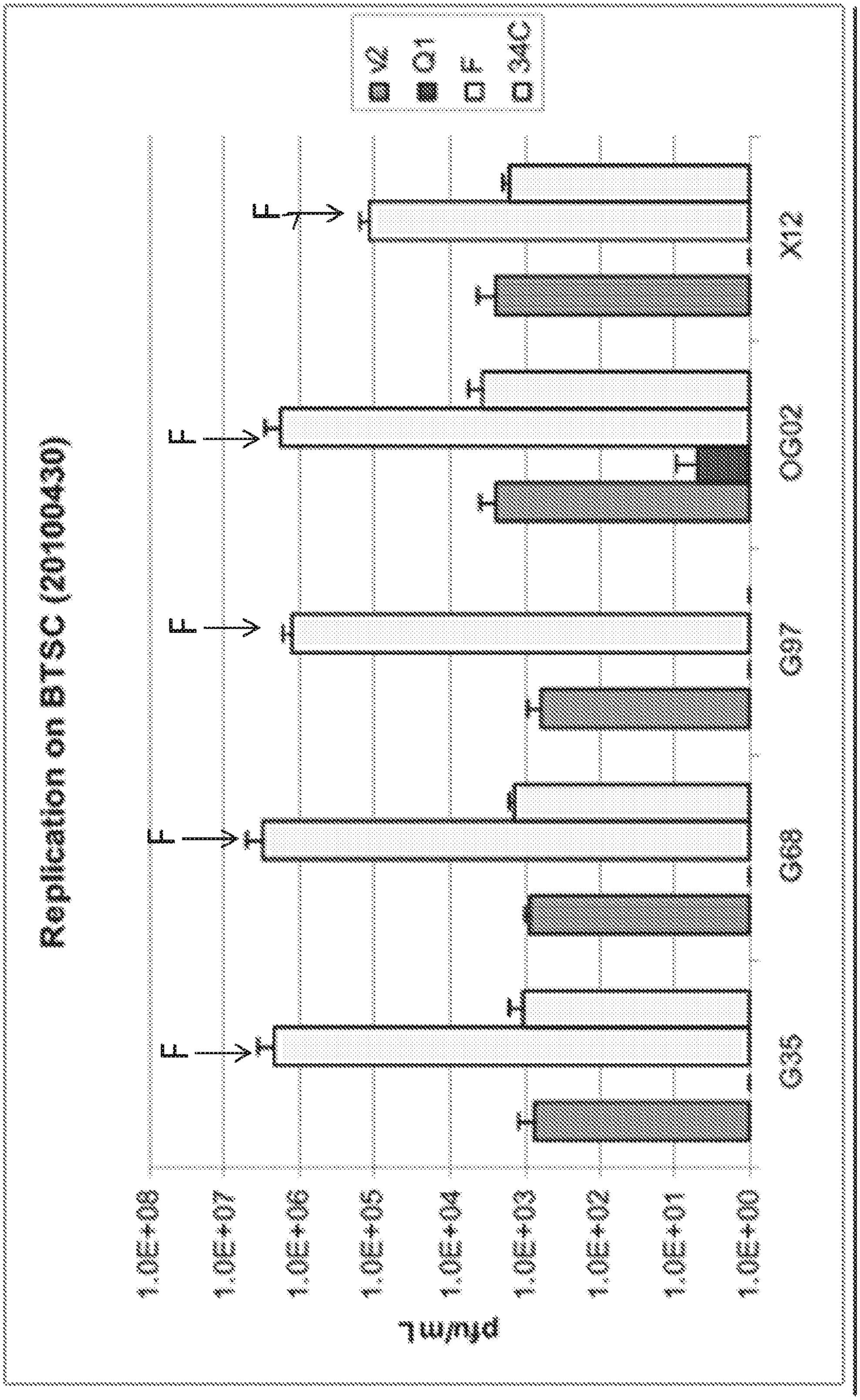
FIG. 9 is a graph showing replication of rQNestin34.5v.2 (v2) which was analyzed in 5 glioma stem cells (brain tumor initiating cells—BTIC) freshly generated from humans (G35, G68, G97, OG02, X12). HSVQ1 (Q1) an ICP34.5 deleted virus showed no or minimal replication. F (wild-type HSV) showed the most replication. 34C is an unrelated HSV recombinant HSV.

Replication of rQNestin34.5v.2 (v2) was analyzed in 5 glioma stem cells (brain tumor initiating cells—BTIC) freshly generated from humans (G35, G68, G97, OG02, X12). HSVQ1 (Q1) an ICP34.5 deleted virus showed no or minimal replication. F (wild-type HSV) showed the most replication. 34C is an unrelated HSV recombinant HSV. We utilize athymic mice (nu/nu) where implantable human glioma cells (human U87EGFR or Gli36dEGFR) are grown. This model has been widely utilized by us and others to monitor efficacy. These tumors reliably form in animal brains leading to their death within 3-4 weeks. These cells are histologically similar to human glioma cells and the tumors are highly vascular like the clinical tumors. The major difference is that they are not as invasive as the clinical gliomas. We have also shown efficacy in glioma cells freshly excised from humans with tumors and grown to enrich for the glioma stem-like cell population (FIG. 9).

Figure 10:
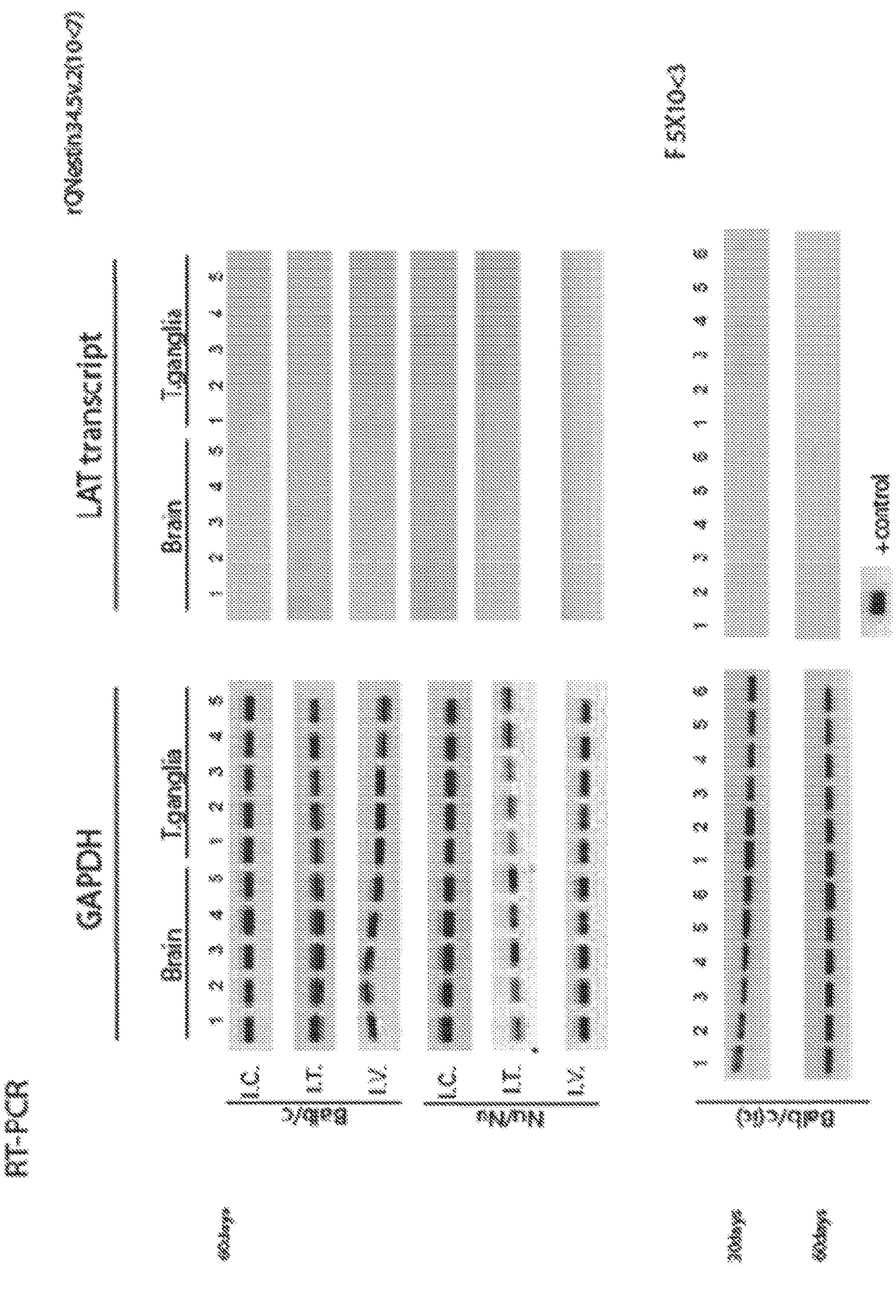
FIG. 10 shows RT-PCR for LAT transcript in mice treated with rQNestin34.5v.2 or F. The former was injected ic., i.t. or i.v., at a dose of $10^7$ pfus. 60 days later, RT-PCR in 6 different brains and 6 different trigeminal ganglia was performed for the LAT transcript (35 cycles). The positive control for the reaction consisted of glioma cells infected with rQNestin34.5v.2. F strain virus was injected i.c. and mice were sacrificed 30 or 60 days later to detect LAT.

Injected mice have been kept alive for at least 60 days. In addition, we have conducted biodistribution studies in athymic and Balb/c mice after intracerebral (i.c.), intravenous (i.v.) or intrathecal (i.t.) inoculation of rQNestin34.5v.2 or F (wild-type) HSv1 strain to detect a viral transcript (LAT) by RT-PCR, expressed during both lytic and latent phases of the viral life cycle. FIG. 10 shows that the transcript was not detectable in the brain or trigeminal ganglia of either Nu/nu or Balb/c mice 60 days after i.c., i.t. or i.c, routes of administration of $10^7$ pfus of rQNestin34.5v.2. In contrast, there were some faint bands in all tested brain and trigeminal ganglia samples at the 30 and 60 day time point after i.c. administration of $10^3$ pfus of F strain.

Figure 11:
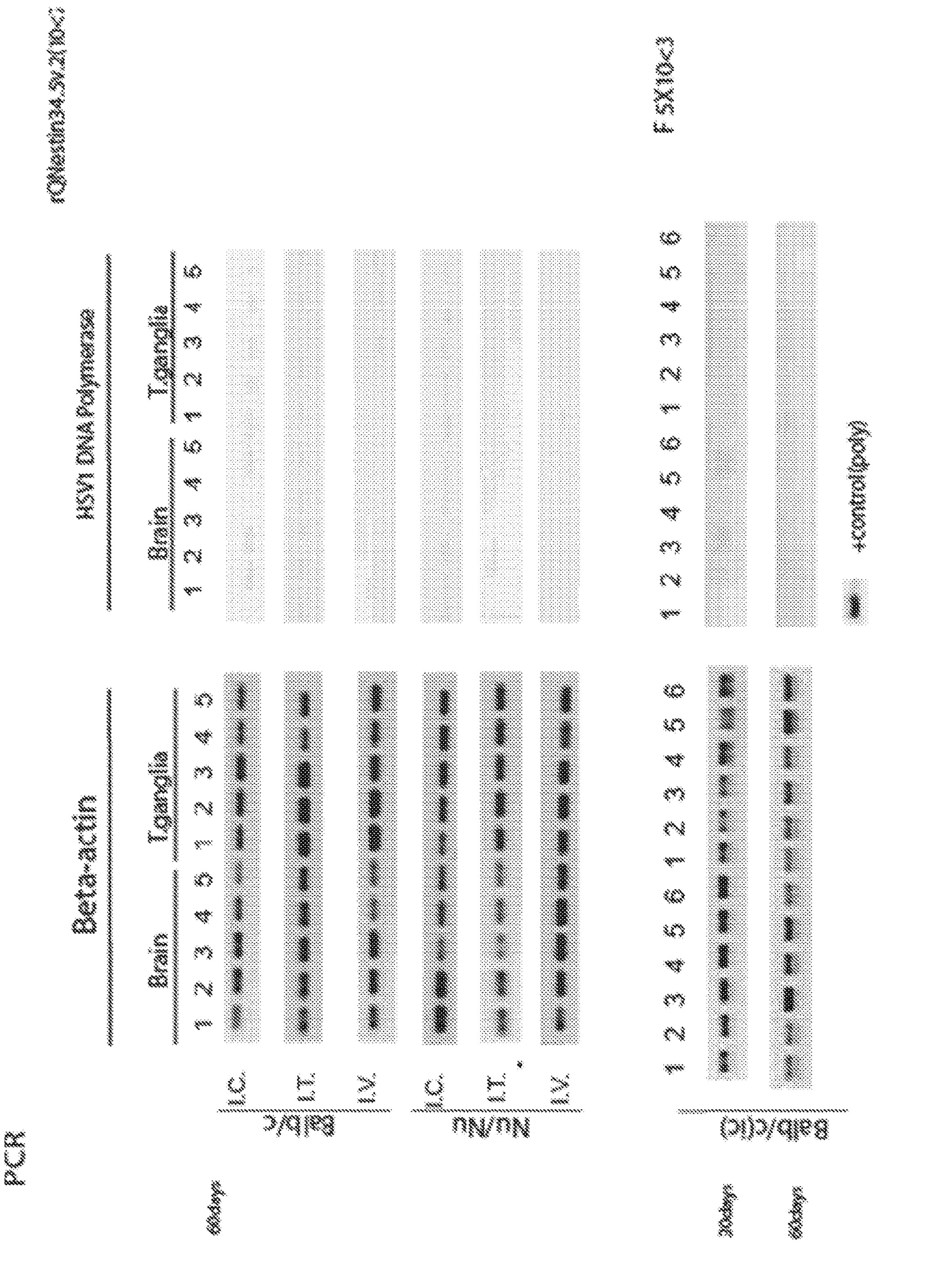
FIG. 11 shows PCR for DNA pol transcript in mice treated with rQNestin34.5v.2 or F. The former was injected ic., i.t. or i.v., at a dose of $10^7$ pfus. 60 days later, PCR in different brains and 5 different trigeminal ganglia was performed for the LAT transcript (35 cycles). The positive control for the reaction consisted of glioma cells infected with rQNestin34.5v.2. F strain virus was injected i.c. and mice were sacrificed 30 or 60 days later to detect DNA pol.
Figure 12A:
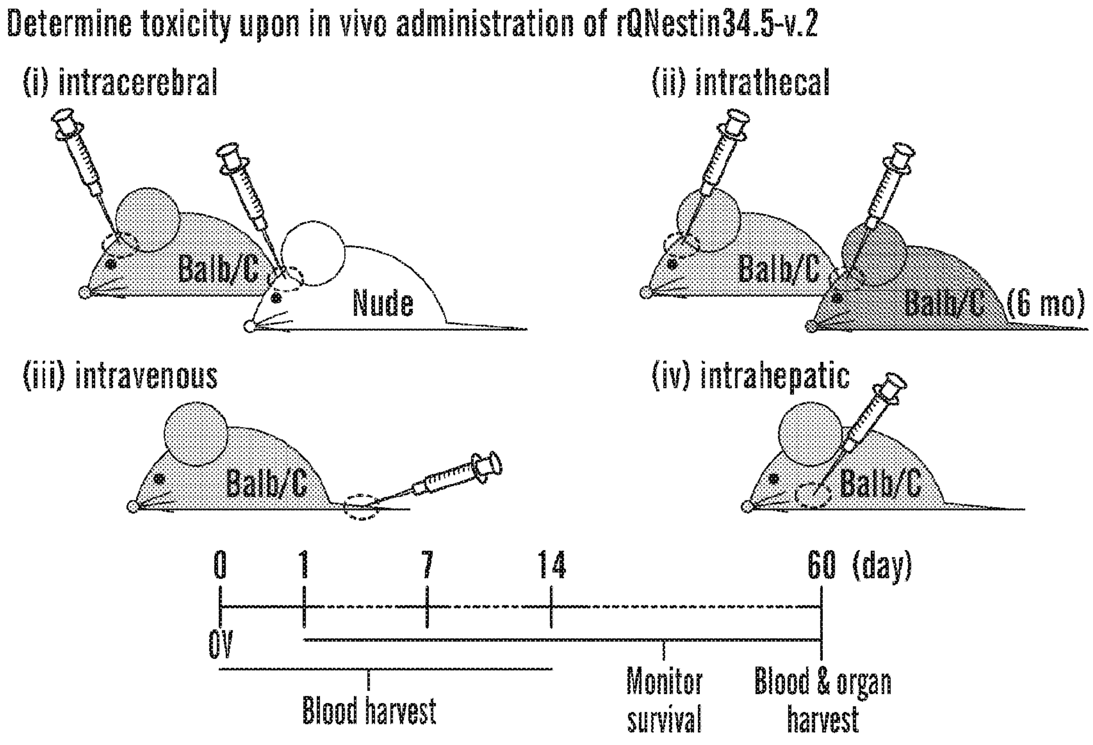
FIGS. 12A to 12B show a schematic and graph.
Figure 12B:
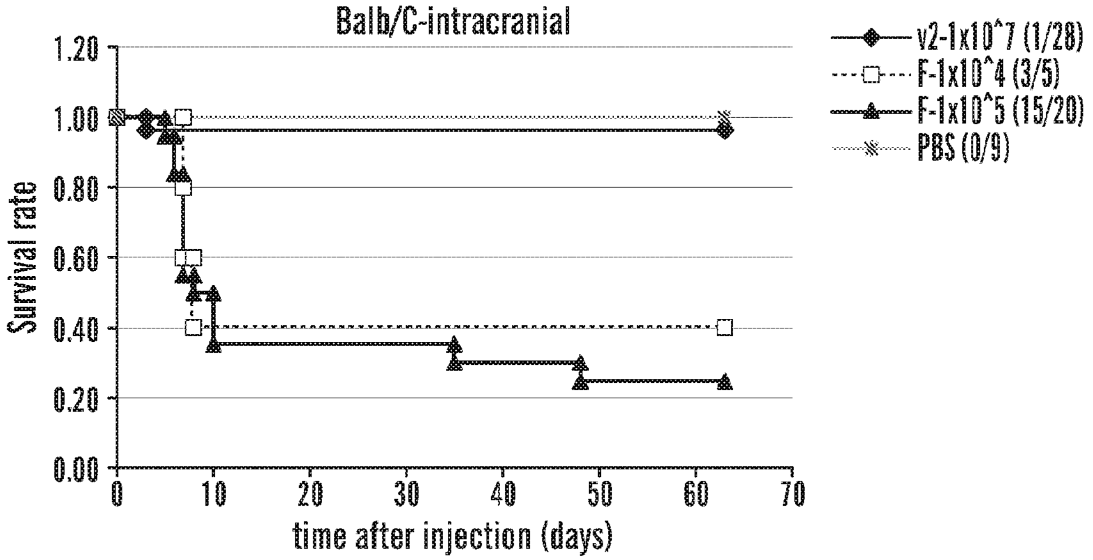
Figure 13A:
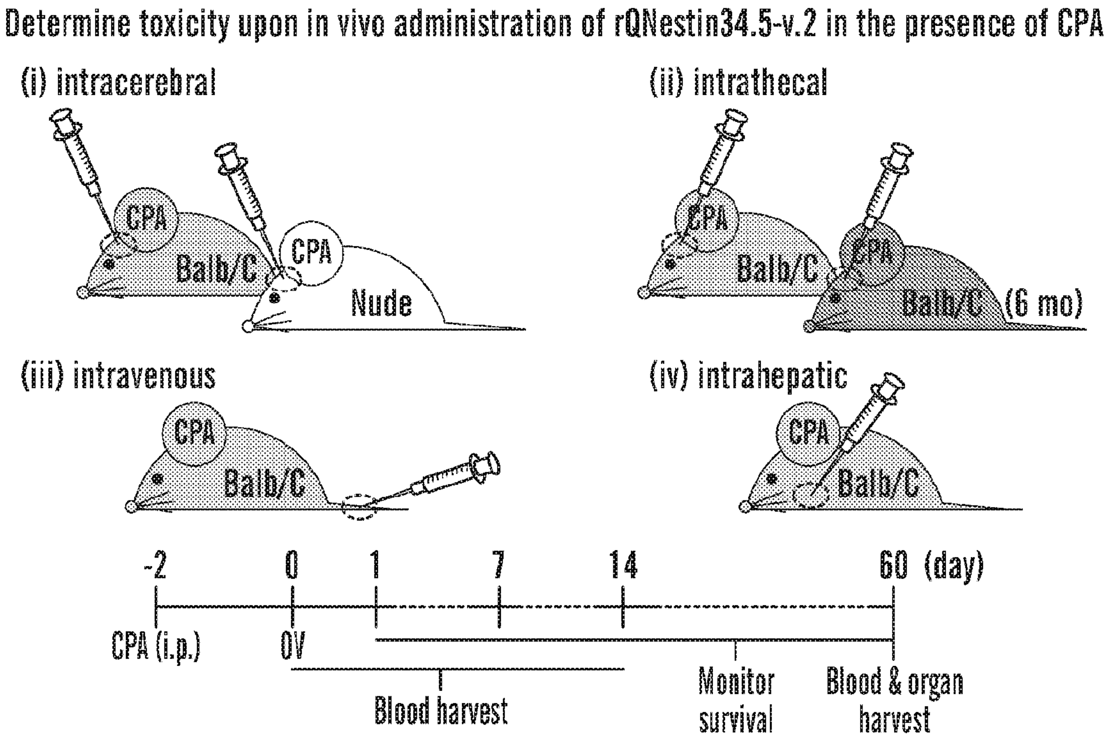
FIGS. 13A and 13B show a schematic and graph.
Figure 13B:
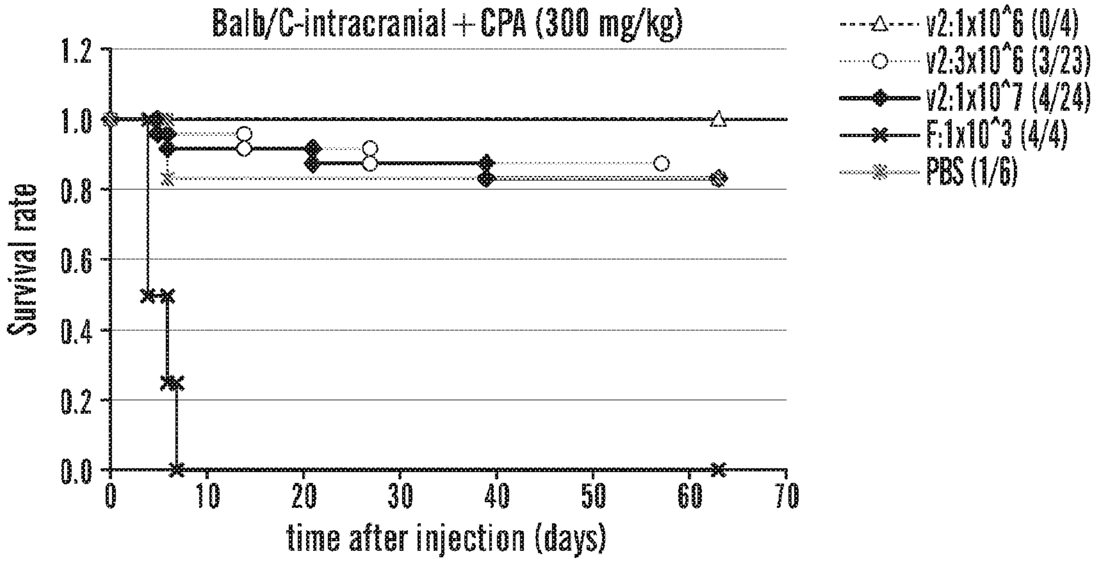
Figure 14:
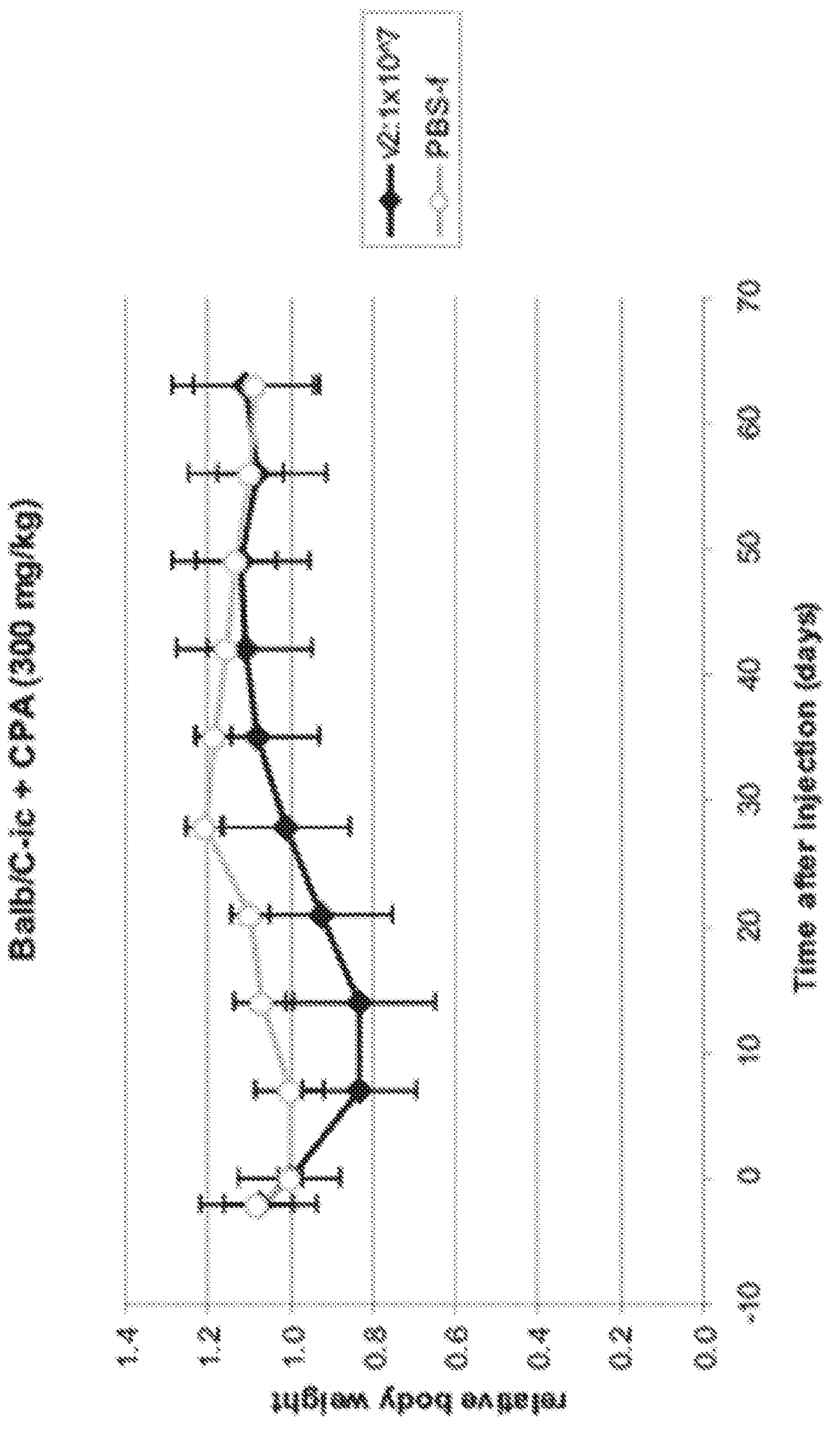
FIG. 14 shows a graph of the relative body weight over time after injection of the mice used in FIG. 13.

In addition, we performed PCR for the HSV DNA polymerase gene. FIG. 11 shows that copies of the gene were not detected in brains or trigeminal ganglia of mice after rQNetsin34.5v.2, indicating lack of active viral replication. In contrast, there was faint detection of DNA pol after injection of F strain, indicating some low level of DNA replication, particularly in brain.

Example 3 Utilization of a Nestin Transcriptional Enhancer/Promoter

Nestin expression in human brain adjacent to gliomas and in human brain after treatment.

Amongst the several levels of tumor cell selectivity for rQNestin34.5v.2, one of significance, the nestin transcriptional element is composed of the nestin-hsp minimum enhancer/promoter sequence, derived from a the second intron/enhancer of the rat nestin gene enhancer fused to the mouse hsp68 promoter to provide specific transcriptional regulation to cells expressing nestin, including human cells. This construct provides selective expression of the viral ICP34.5 gene to nestin-expressing cells in the brain. The presence or absence of nestin in human brain adjacent to a malignant glioma or in human brain after malignant glioma treatment was confirmed by Nestin IHC in human brain adjacent to gliomas and in human brain after treatment.

Figure 17:
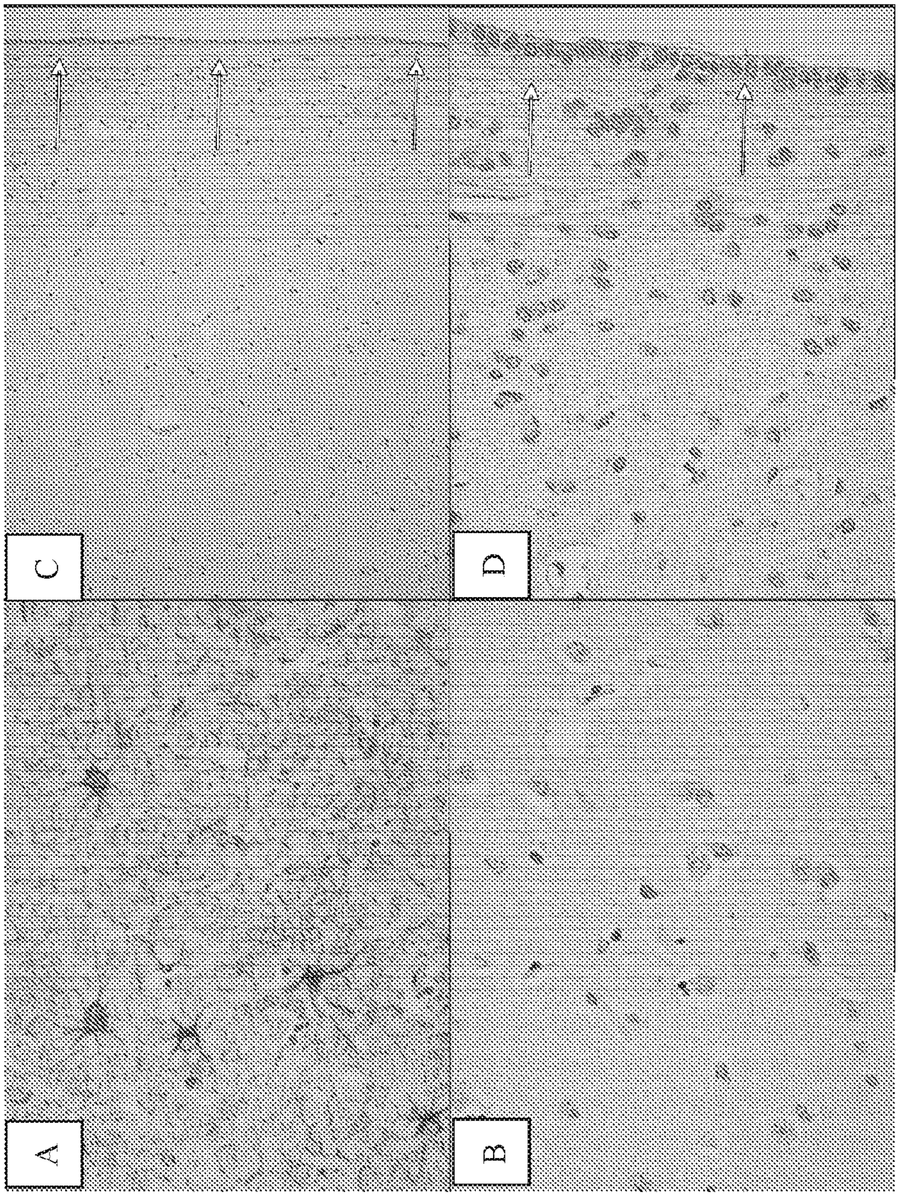
FIGS. 17A to 17D show Nestin expression in human brain adjacent to gliomas. The subject is a 50+ year old male with a MG. As part of the resection, brain adjacent to tumor and devoid of gross tumor was also resected up to the ventricle.
Figure 18:
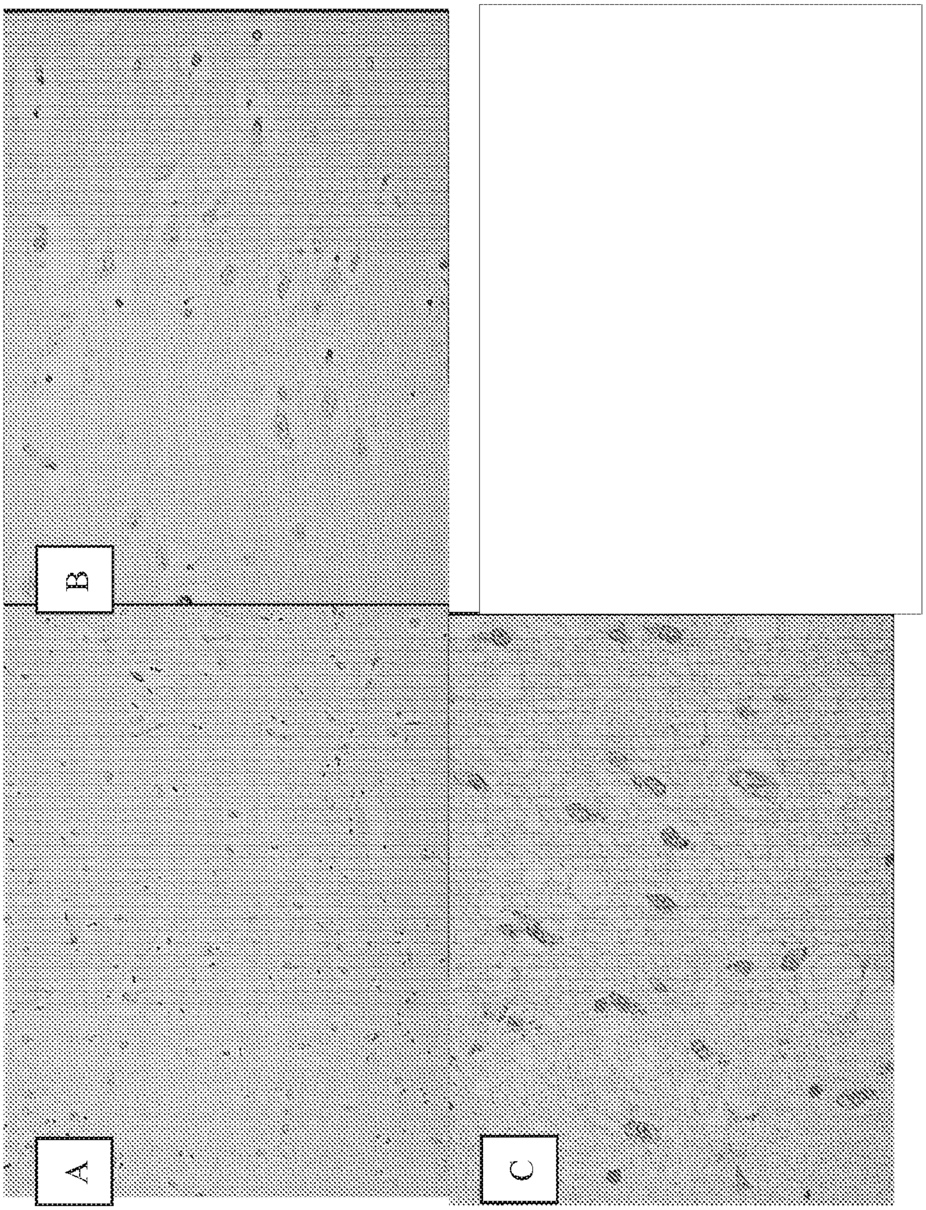
FIGS. 18A to 18C show Nestin expression in human brain after treatment. The subject was a 50+ year old male with a history of MG, who underwent surgery, radiation and chemotherapy. The patient passed away of causes other than tumor. At postmortem, there was no tumor in brain. Nestin IHC again showed little if any evidence of positivity within the white matter where the subject was treated for his tumor.

An adult male older than 50 years underwent resection of a malignant glioma at the Ohio State University Medical Center. As part of the resection, brain adjacent to tumor that was devoid of gross tumor was also resected up to the lateral ventricle. This brain was stained for expression of GFAP (FIG. 17A) and Nestin (FIG. 17B-17D) at the Ohio State University Medical Center Neuropathology Core. A second subject was also over 50 and had a malignant glioma resected and then underwent radiation and chemotherapy. He passed away from causes other than his tumor (FIG. 18). The primary antibody was Nestin from Millipore at a 1:500 dilution. Deparaffization and dehydration were performed as per routine. Antigen was exposed with standard heat-induced epitope retrieval methods. Slides were immersed in Target Retrieval Solution PH9 (DAKO) and microwaved until the solution came to a boil. Boiling was then carried out for 15 min with lower power. After cooling the solution for about 30 min, slides were rinsed in PBS. To inhibit internal peroxidase, slides were immerse in methanol with 0.3% H2O2 for 15 min and then rinses in PBS-T. Blocking was carried out for 1 h at room temperature, before applying the primary antibody to human Nestin (Millipore) 1:500 at 4° C. overnight. The secondary antibody was then applied at 1:500 dilution, followed by DAPI staining and mounting of sections on slides. At autopsy, brain showed little if any nestin immunoreactivity. There was no Nestin immunopositivity in brain or in cells of the ependyma/subependyma within the subventricular zone (SVZ), where neural stem cells usually reside. Therefore the evidence shows that a target population for a clinical trial (human adults with MG) exhibit little if any evidence for nestin expression in brain white matter where the MG usually resides or in the SVZ where neural stem cells are found. Instead, published evidence shows that the MG exhibits high levels of widespread nestin immunoreactivity.

Athymic Mice Studies Related to Nestin Expression in Brain.

Figure 19:
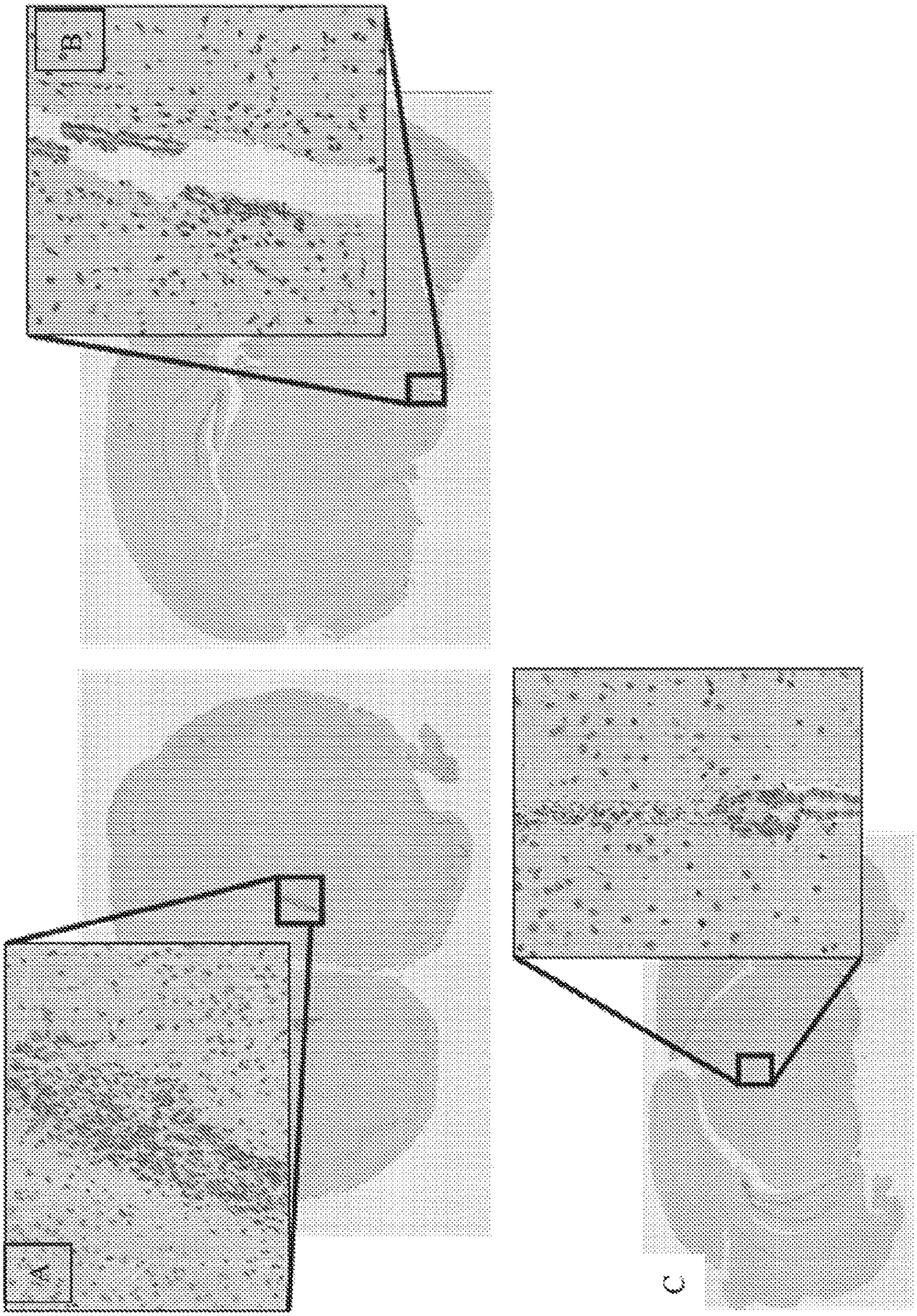
FIGS. 19A to 19C show nestin expression in the brains of athymic mice. The brain of this athymic mouse was inoculated with vehicle (PBS). At day 4, the mouse was euthanized and brain was harvested. Nestin IHC was performed. Positive nestin IHC is visualized in tanicytes (i.e. cells in ependymal layer of lateral ventricle (upper left panel, FIG. 19A) of third ventricle (upper right panel, FIG. 19B) and aqueduct (lower left panel, FIG. 19C). Each panel shows a low power microphotograph of the entire brain, with the boxed inset showing the high power one.

To determine whether there was nestin expression in the brains of athymic mice, since these were the species selected for efficacy and toxicology/biodistribution studies, male and female athymic mice (6-8 week of age) were inoculated intracerebrally with the agent, rQNestin34.5v.2. However, one control group of mice (group 1) was inoculated intracerebrally with vehicle (PBS) alone. At day 4 after this PBS inoculation, mice were euthanized per protocol for brain analyses. It was determined whether there was nestin expression in the brain of one of these mice. FIG. 19 shows nestin positive cells in tanicytes (ependymal cells) lining the lateral and third ventricle as well as the aqueduct. There was also nestin positivity in cells lining the fourth ventricle. The same experiment was performed with an animal from group 2 (preadministration of CPA followed by injection of PBS vehicle), to confirm the same pattern of nestin expression. In addition, nestin expression was seen in astrocytes around the needle tract, indicating up-regulation of nestin in reactive astrocytes in mice.

Example 4 In Vitro Characterization of rQNestin34.5v.2

Figure 20:
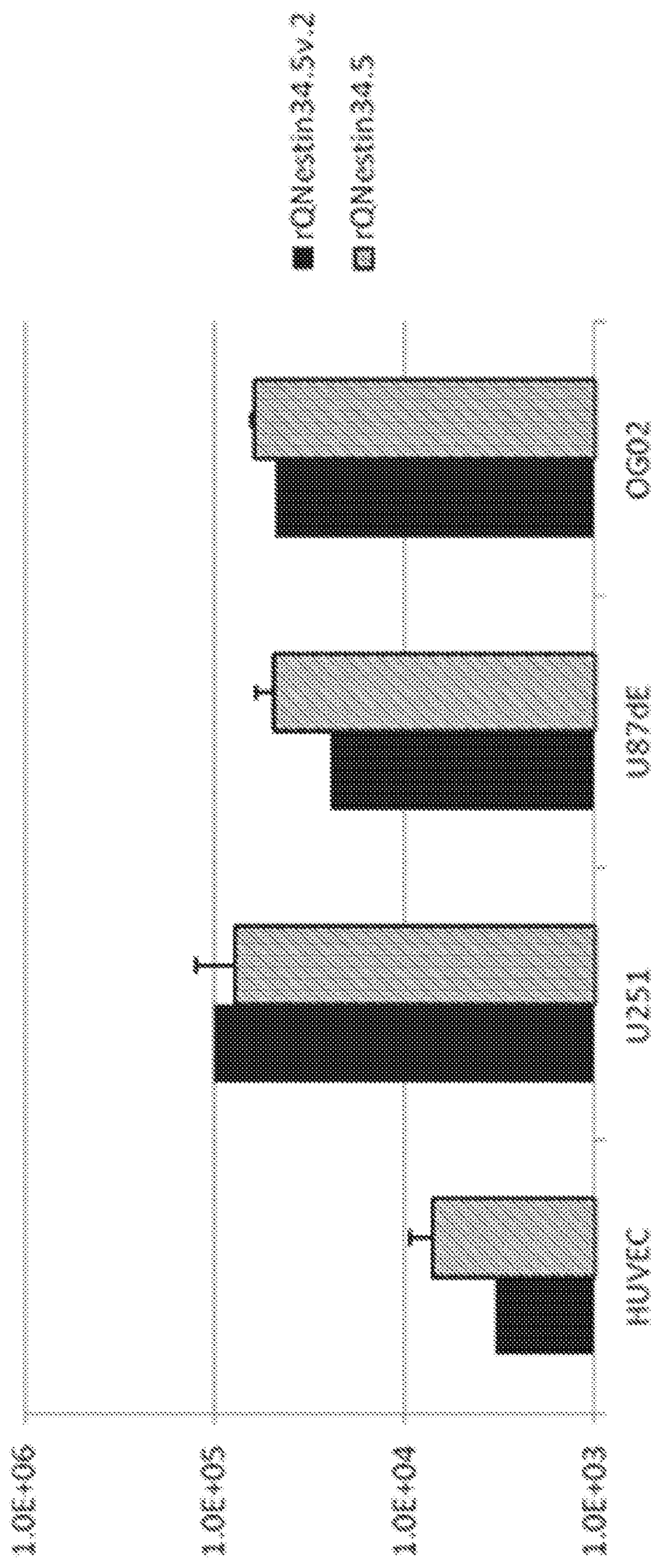
FIG. 20 shows bioequivalency of viral yields of rQNestin34.5v.2 and rQNestin in HUVEC cells and established U251, U87dEGFR glioma cells and OG02 glioma "stem-like" cells. The plot shows that the viral yield of rQnestin34.5v.2 was equivalent to that of rQNestin34.5 in 3 glioma cells, including a glioma stem-like cell and superior to that in HUVEC cells.
Figure 21:
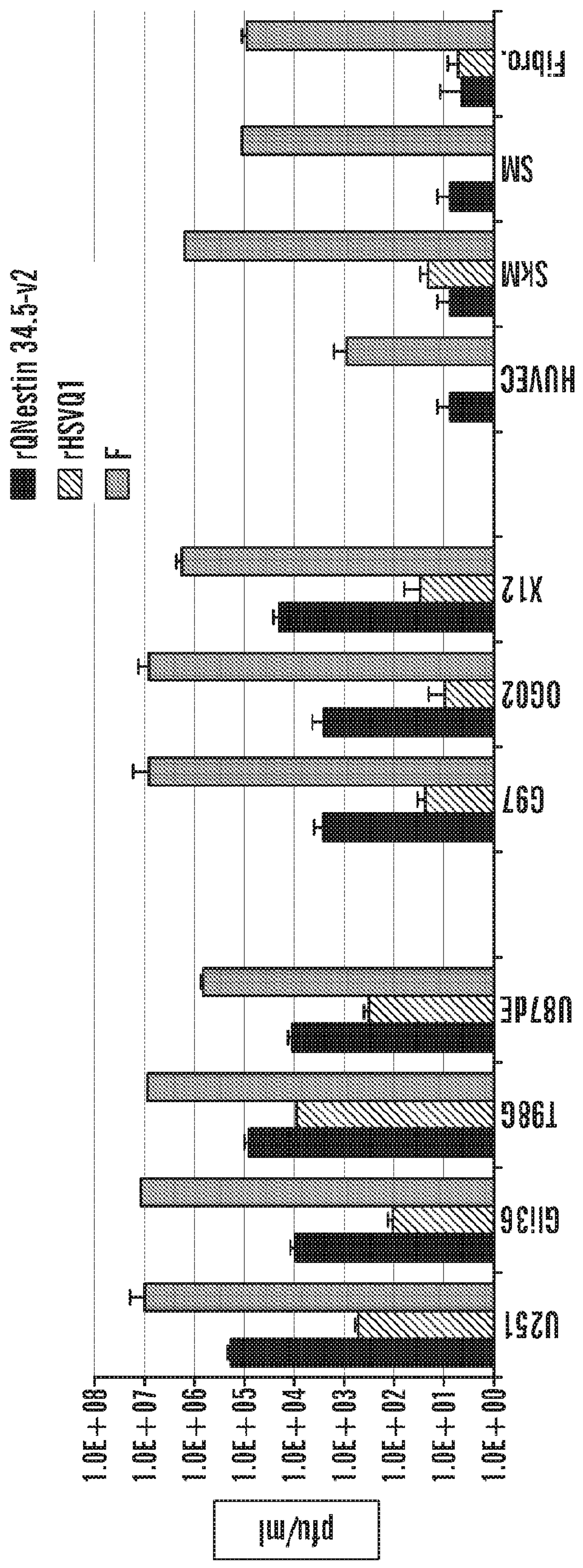
FIG. 21 shows plot of replication assay results comparing yields of rQNestin34.5v.2, control rHSVQ1 and wild-type F strain in 4 established glioma cell lines (U251, Gli36, T98G, and U87dE), 3 glioma stem-like cells (G97, OG02, X12) and 4 normal cells (HUVEC, Skeletal muscle-SKM, Smooth musckle-SM, and Fibroblasts). The plot shows that shows that rQNestin34.5v.2 replication was higher than that of the ICP34.5-negative rHSVQ1 in 4 established glioma cell lines and 3 primary gliomas grown under stem-like condition, but similar to rHSVQ1 in 4 normal cells. F strain replication was higher in all.

The viral yield of rQNestin34.5v.2. was determined. Cells ($2\times10^5$) were plated in 6-well plates. The following day, cells were infected with rQNestin34.5v.2 (v2), parental rHSVQ1 (Q1), or wild-type F strain (F) at MOI=0.1. One hour after infection, cells were washed with glycine saline solution (10 mM glycine, 137 mM NaCl, 24.1 mM KCl, 0.49 mM MgCl2. 0.68 mM CaCl2, pH 3) followed by PBS to remove unattached viruses and fresh medium were added. Cells were incubated for 3 days at 37° C. in an atmosphere containing 5% CO2. The cells and medium were collected, and subjected to three cycles of freeze/thaw with dry ice/Ethanol and 37° C. water bath. After pelleting cell debris by centrifugation (35000×g, 10 min., 4° C.), supernatant was transferred to new tubes and stored at −80° C. until titration. The titer of each sample was determined by conventional plaque assay with Vero cells. FIG. 20 shows that the viral yield of rQnestin34.5v.2 was equivalent to that of rQNestin34.5 in 3 glioma cells, including a glioma stem-like cell and superior to that in HUVEC cells. The replication potential of rQNestin34.5v.2. was determined in multiple cell lines. FIG. 21 shows that rQNestin34.5v.2 replication was higher than that of the ICP34.5-negative rHSVQ1 in 4 established glioma cell lines and 3 primary gliomas grown under stem-like condition, but similar to rHSVQ1 in 4 normal cells. F strain replication was higher in all.

Figure 22:
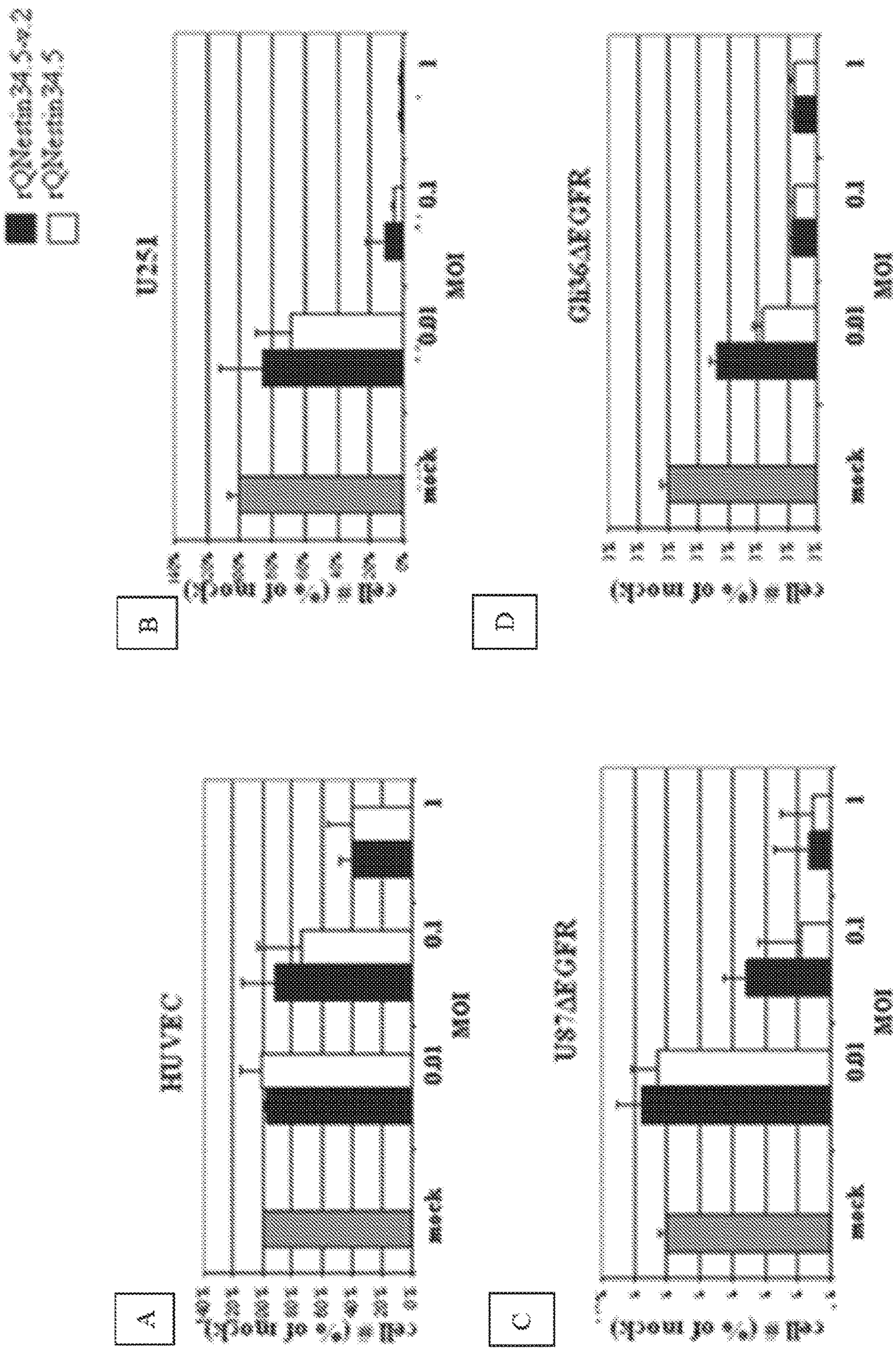
FIGS. 22A to 22D show cytotoxicity of rQNestin34.5 and QNestin34.5V.2 rQNestin34.5v.2 was equivalent to rQNestin34.5 in cytotoxicity at all tested MOIs against a panel of normal and glioma cells.

The cytotoxicity of rQnestin34.5v.2 was determined. rQNestin34.5v.2 was added to a panel of glioma cells, U87ΔEGFR (U87dE), U87, U251 and OG02 glioma "stem-like" cells and to a panel of normal cells, human astrocytes (HA), human fibroblasts (Fibro.), human smooth muscle (SM), human skeletal muscle cells (SkM) and mouse astrocytes (MA). Cells were seeded on 6-well plates in complete medium prepared by following manufacturer's instructions for normal primary cells, BTSC medium for primary glioma cells or DMEM supplemented with 2% FBS for glioma cell lines and allowed to adhere. The medium for normal cells were changed to basal medium a few hours after cell preparation. Next day, viruses were added at MOI=0.1. rQNestin34.5v.2 inactivated with UV radiation was used as mock control. One hour after infection, cells were washed with glycine saline solution (10 mM glycine, 137 mM NaCl, 24.1 mM KCl, 0.49 mM MgCl2. 0.68 mM CaCl2, pH 3) followed by PBS to remove unattached viruses and fresh medium were added. Cells were incubated at 37° C. in an atmosphere containing 5% CO2. Five days after infection virus cytotoxicity was measured as surviving cells counted with a Coulter counter (Beckman Coulter). FIG. 22 shows the cytotoxity of of rQnestin34.5v.2 and rQnestin34.5.

A clinical trial is planned that will be performed as a dose-escalation study. Clinical outcome will be asssesed (overall survival after injection, progression-free survival after injection), radiologic outcome (regression of tumor visualized on MRI), and tissue analysis of viral biodistribution studied. The trial will be performed as a dose-escalation, starting at $10^8$ pfus (1 ml volume, multiple injection sites). This dose was selected because $10^7$ pfus appeared to be safe in a mouse brain. Since a mouse brain weighs about 1 gram, while the human barin weighs 1500 grams, this would translate to a safe dose of $5\times10^{10}$ in a human. To further ensure safety, we thus will start by almost 3 logs less in humans. Dose-escalations will proceed by half—a −log up to $10^{10}$ pfus.

The maximum tolerated dose (MTD) will be defined as the dose one half-log order less than the dose level at which one-third of the patients have a dose limiting toxicity (DLT) of grade 3 or grade 4 (defined below) related to the administration of rQNestin34.5v.2. Cohorts of three patients will be administered with be escalated by half-log increments at each dose level until a dose limiting toxicity (DLT) is reached. If the MTD is not reached, the phase I dose will be the highest dose reached A DLT will consist of: 'Any Grade 4 or 5 toxicity on the Common Terminology Criteria for Adverse Events v4.0 (CTCAE) attributed to rQNestin34.5v.2, except for Grade 4 lymphocyte, neutrophil, white blood count decrease on the investigation category of CTCAE v4.0.' Grade 3 toxicity for encephalitis, encephalomyelitis, meningitis infections/infestations categories on CTCAE v4.0 attributed to rQNestin34.5v.2. ' Grade 3 toxicity for Nervous System disorder category on the CTCAE v4.0 relative to the changes from the pre-treatment neurological status attributed to rQNestin34.5v.2: ataxia, depressed level of consciousness, encephalopathy, extrapyramidal disorder, hydrocephalus, intracranial hemorrhage, leukoencephalopathy, myelitis, pyramidal tract syndrome, somnolence, stroke.' Grade 3 toxicity for Psychiatric disorder category on CTCAE v4.0 relative to changes from the pre-treatment status attributed to rQNestin34.5v.2: delirium, hallucinations, psychosis.

The first patient in each cohort will be observed for at least 10 days following injection with rQNestin34.5v.2 prior to the next patient being enrolled into the study protocol. If there is no DLT, then the second and third patient will be accrued at the same dose. Patients will only be enrolled into the next dose level if 1/3 DLT is not reached based on CTCAE v.4.

The determination of DLT and MTD will be separate for arm A and arm B since the gliomatous mass will have been largely resected in the former and not the latter and, thus, may lead to toxicities at different doses.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" or "consists essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

SEQUENCES

```
SEQ ID NO: 1 rQNestin34.5v.2Sequence, consensus
sequence_BreakPoint_151409
ATAACTTCGTATAATGTATGCTATACGAAGTTATTAGGTCCCTCGACCTGCAGGAAACTCTAGTCC
GGACCCGGGAGGCCTCCTTTGAGGAGTGGCTGCGATCCAAGGAAGTGGCCCTGGACTTTGGCCTGACGGAAAGGCTTC
GCGAGCACGAAGCCCAGCTGGTGATCCTGGCCCAGGCTCTGGACCATTACGACTGTCTGATCCACAGCACACCGCACA
CGCTGGTCGAGCGGGGGCTGCAATCGGCCCTGAAGTATGAGGAGTTTTACCTAAAGCGCTTTGGCGGGCACTACATGG
AGTCCGTCTTCCAGATGTACACCCGCATCGCCGGCTTTTTGGCCTGCCGGGCCACGCGCGGCATGCGCCACATCGCCC
TGGGGCGAGAGGGGTCGTGGTGGGAAATGTTCAAGTTCTTTTTCCACCGCCTCTACGACCACCAGATCGTACCGTCGA
CCCCCGCCATGCTGAACCTGGGGACCCGCAACTACTACACCTCCAGCTGCTACCTGGTAAACCCCCAGGCCACCACAA
ACAAGGCGACCCTGCGGGCCATCACCAGCAACGTCAGTGCCATCCTCGCCCGCAACGGGGGCATCGGGCTATGCGTGC
AGGCGTTTAACGACTCCGGCCCCGGGACCGCCAGCGTCATGCCCGCCCTCAAGGTCCTCGACTCGCTGGTGGCGGCGC
ACAACAAAGAGAGCGCGCGTCCGACCGGCGCGTGCGTGTACCTGGAGCCGTGGCACACCGACGTGCGGGCCGTGCTCC
GGATGAAGGGGGTCCTCGCCGGCGAAGAGGCCCAGCGCTGCGACAATATCTTCAGCGCCCTCTGGATGCCAGACCTGT
TTTTCAAGCGCCTGATTCGCCACCTGGACGGCGAGAAGAACGTCACATGGACCCTGTTCGACCGGGACACCAGCATGT
CGCTCGCCGACTTTCACGGGGAGGAGTTCGAGAAGCTCTACCAGCACCTCGAGGTCATGGGGTTCGGCGAGCAGATAC
CCATCCAGGAGCTGGCCTATGGCATTGTGCGCAGTGCGGCCACGACCGGGAGCCCCTTCGTCATGTTCAAAGACGCGG
TGAACCGCCACTACATCTACGACACCCAGGGGGCGGCCATCGCCGGCTCCAACCTCTGCACCGAGATCGTCCATCCGG
CCTCCAAGCGATCCAGTGGGGTCTGCAATCTGGGAAGCGTGAATCTGGCCCGATGCGTCTCCAGGCAGACGTTTGACT
TTGGGCGGCTCCGCGACGCCGTGCAGGCGTGCGTGCTGATGGTGAACATCATGATCGACAGCACGCTACAACCCACGC
CCCAGTGCACCCGCGGCAACGACAACCTGCGGTCCATGGGAATCGGCATGCAGGGCCTGCACACGGCCTGCCTGAAGC
TGGGGCTGGATCTGGAGTCTGCCGAATTTCAGGACCTGAACAAACACATCGCCGAGGTGATGCTGCTGTCGGCGATGA
AGACCAGCAACGCGCTGTGCGTTCGCGGGGCCCGTCCCTTCAACCACTTTAAGCGCAGCATGTATCGCGCCGGCCGCT
TTCACTGGGAGCGCTTTCCGGACGCCCGGCCGCGGTACGAGGGCGAGTGGGAGATGCTACGCCAGAGCATGATGAAAC
ACGGCCTGCGCAACAGCCAGTTTGTCGCGCTGATGCCCACCGCCGCCTCGGCGCAGATCTCGGACGTCAGCGAGGGCT
TTGCCCCCCTGTTCACCAACCTGTTTAGCAAGGTGACCCGGGACGGCGAGACGCTGCGCCCCAACACGCTCCTGCTAA
AGGAACTGGAACGCACGTTTAGCGGGAAGCGCCTCCTGGAGGTGATGGACAGTCTCGACGCCAAGCAGTGGTCCGTGG
CGCAGGCGCTCCCGTGCCTGGAGCCCACCCACCCCCTCCGGCGATTCAAGACCGCGTTTGACTACGACCAGAAGTTGC
TGATCGACCTGTGTGCGGACCGCGCCCCCTACGTCGACCATAGCCAATCCATGACCCTGTATGTCACGGAGAAGGCGG
ACGGGACCCTCCCAGCCTCCACCCTGGTCCGCCTTCTGGTCCACGCATATAAGCGCGGACTAAAAACAGGGATGTACT
ACTGCAAGGTTCGCAAGGCGACCAACAGCGGGGTCTTTGGCGGCGACGACAACATTGTCTGCACGAGCTGCGCGCTGT
GACCGACAAACCCCCTCCGCGCCAGGCCCGCCGCCACTGTCGTCGCCGTCCCACGCGCTCCCCCGCTGCCATGGATTC
CGCGGCCCCAGCCCTCTCCCCCGCTCTGACGGCCCATACGGGCCAGAGCGCGCCGGCGGACCTGGCGATCCAGATTCC
AAAGTGCCCCGACCCCGAGAGGTACTTCTACACCTCCCAGTGTCCCGACATTAACCACCTGCGCTCCCTCAGCATCCT
TAACCGCTGGCTGGAAACCGAGCTTGTTTTCGTGGGGGACGAGGAGGACGTCTCCAAGCTTTCCGAGGGCGAGCTCAG
CTTTTACCGCTTCCTCTTCGCTTTCCTGTCGGCCGCCGACGACCTGGTTACGGAAAACCTGGGCGGCCTCTCCGGCCT
GTTTGAGCAGAAGGACATTCTCCACTACTACGTGGAGCAGGAATGCATCGAAGTCGTACACTCGCGCGTGTACAACAT
```

-continued

| SEQUENCES |
| --- |
| CATCCAGCTGGTGCTTTTTCACAACAACGACCAGGCGCGCCGCGAGTACGTGGCCGGCACCATCAACCACCCGGCCAT<br>CCGCGCCAAGGTGGACTGGTTGGAAGCGCGGGTGCGGGAATGCGCCTCCGTTCCGGAAAAGTTCATTCTCATGATCCT<br>CATCGAGGGCATCTTTTTTGCCGCCTCGTTTGCCGCCATCGCCTACCTTCGCACCAACAACCTTCTGCGGGTCACCTG<br>CCAGTCAAACGACCTCATCAGCCGGGACGAGGCCGTGCACACGACGGCCTCGTGTTACATCTACAACAACTACCTCGG<br>CGGGCACGCCAAGCCCCCGCCCGACCGCGTGTACGGGCTGTTCCGCCAGGCGGTCGAGATCGAGATCGGATTTATCCG<br>ATCCCAGGCGCCGACGGACAGCCATATCCTGAGCCCGGCGGCGCTGGCGGCCATCGAAAACTACGTGCGATTCAGCGC<br>GGATCGCCTGTTGGGCCTTATCCACATGAAGCCACTGTTTTCCGCCCCACCCCCCGACGCCAGCTTTCCGCTGAGCCT<br>CATGTCCACCGACAAACACACCAATTTTTTCGAGTGTCGCAGCACCTCCTACGCCGGGGCGGTCGTCAACGATCTGTG<br>AGGGTCGCGGCGCGCTTCTACCCGTGTTTGCCCATAATAAACCTCTGAACCAAACTTTGGGTCTCATTGTGATTCTTG<br>TCAGGGACGCGGGGGTGGGAGAGGATAAAAGGCGGCGCAAAAAGCAGTAACCAGGTCCGGCCAGATTCTGAGGGCATA<br>GGATACCATAATTTTATTGGTGGGTCGTTTGTTCGGGGACAAGCGCGCTCGTCTGACGTTTGGGCTACTCGTCCCAGA<br>ATTTGGCCAGGACGTCCTTGTAGAACGCGGGTGGGGGGCCTGGGTCCGCAGCTGCTCCAGAAACCTGTCGGCGATAT<br>CAGGGGCCGTGATATGCCGGGTCACGATAGATCGCGCCAGGTTTTCGTCGCGGATGTCCTGGTAGATAGGCAGGCGTT<br>TCAGAAGAGTCCACGGCCCCCGCTCCTTGGGGCCGATAAGCGATATGACGTACTTAATGTAGCGGTGTTCCACCAGCT<br>CGGTGATGGTCATGGGATCGGGGAGCCAGTCCAGGGACTCTGGGGCGTCGTGGATGACGTGGCGTCGCCGGCTGGCCA<br>CATAACTGCGGTGCTCTTCCAGCAGCTGCGCGTTCGGGACCTGGACGAGCTCGGGCGGGGTGAGTATCTCCGAGGAGG<br>ACGACCTGGGGCCGGGGTGGCCCCCGGTAACGTCCCGGGGATCCAGGGGGAGGTCCTCGTCGTCTTCGTATCCGCCGG<br>CGATCTGTTGGGTTAGAATTTCGGTCCACGAGACGCGCGTCTCGGTGCCGCCGGTGGCCGGCGGCAGAGGGGGCCTGG<br>TTTCCGTGGAGCGCGAGCTGGTGTGTTCCCGGCGGATGGCCCGCCGGGTCTGAGAGCGACTCGGGGGGGTCCAGTGAC<br>ATTCGCGCAGCACATCCTCCACGGAGGCGTAGGTGTTATTGGGATGGAGGTCGGTGTGGCAGCGGACAAAGAGGGCCA<br>GGAACTGGGGGTAGCTCATCTTAAAGTACTTCAGTATATCGCGACAGTTGATCGTGGGAATGTAGCAGGCGCTAATAT<br>CCAACACAATATCGCAGCCCATCAACAGGAGGTCAGTGTCCGTGGTGTACACGTACGCGACCGTGTTGGTGTGATAGA<br>GGTTGGCGCAGGCATCGTCCGCCTCCAGCTGACCCGAGTTAATGTAGGCGTACCCCAGGGCCCGGAGAACGCGAATAC<br>AGAACAGATGCGCCAGACGCAGGGCCGGCTTCGAGGGCGCGGCGGACGGCAGCGCGGCTCCGGACCCGGCCGTCCCCC<br>GGGTCCCCGAGGCCAGAGAGGTGCCGCGTCGGCGCATGTTGGAAAAGGCAGAGCTGGGTCTGGAGTCGGTGATGGGGG<br>AAGGCGGTGGAGAGGCGTCCACGTCACTGGCCTCCTCGTCCGTCCGGCACTGGGCCGTCGTGCGGGCCAGGATGGCCT<br>TGGCTCCAAACACAACCGGCTCCATACAATTGACCCCGCGATCGGTAACGAAGATGGGGAAAAGGGACTTTTGGGTAA<br>ACACTTTTAATAAGCGACAGAGGCAGTGTAGCGTAATGGCCTCGCGGTCGTAACTGGGGTATCGGCGCTGATATTTGA<br>CCACCAACGTGTACATGACGTTCCACAGGTCCACGGCAATGGGGGTGAAGTACCCGGCCGGGGCCCCAAGGCCCCGGC<br>GCTTGACCAGATGGTGTGTGTGGGCAAACTTCATCATCCCGAACAAACCCATGTCAGGTCGATTGTAACTGCGGATCG<br>GCCTAACTAAGGCGTGGTTGGTGCGACGGTCCGGGACACCCGAGCCTGTCTCTCTGTGTATGGTGACCCAGACAACAA<br>CACCGACACAAGAGGACAATAATCCGTTAGGGGACGCTCTTTATAATTTCGATGGCCCAACTCCACGCGGATTGGTGC<br>AGCACCCTGCATGCGCCGGTGCGGGCCAACCTTCCCCCCGCTCATTGCCTCTTCCAAAAGGGTGTGGCCTAACGAGCT<br>GGGGGCGTATTTAATCAGGCTAGCGCGGCGGGCCTGCCGTAGTTTCTGGCTCGGTGAGCGACGGTCCGGTTGCTTGGG<br>TCCCCTGGCTGCCATCAAAACCCCACCCTCGCAGCGGCATACGCCCCCTCCGCGTCCCGCACCCGAGACCCCGGCCCG<br>GCTGCCCTCACCACCGAAGCCCACCTCGTCACTGTGGGGTGTTCCCAGCCCGCGTTGGGATGACGGATTCCCCTGGCG<br>GTGTGGCCCCCGCCTCCCACGTGGAGGACGCGTCGGACGCGTCCCTCGGGCAGCCGGAGGAGGGGGCGCCCTGCCAGG<br>TGGTCCTGCAGGGCGCCGAGCTTAATGGAATCCTACAGGCGTTTGCCCCGCTGCGCACGAGCCTTCTGGACTCGCTTC<br>TGGTTATGGGAGACCGGGGCATCCTTATCCATAACACGATCTTTGGGGAGCAGGTGTTCCTGTCCCTGGAACACTCGC<br>AATTCAGTCGGTATCGCTGGCGCGGACCCACGGCGGCGTTCCTGTCTCTCGTGGACCAGAAGCGCTCCCTCCTGAGCG<br>TGTTTCGCGCCAACCAGTACCCGGACCTACGTCGGGTGGAGTTGGCGATCACGGGCCAGGCCCCGTTTCGCACGCTGG<br>TTCAGCGCATATGGACGACGACGTCCGACGGCGAGGCCGTTGAGCTAGCCAGCGAGACGCTGATGAAGCGCGAACTGA<br>CGAGCTTTGTGGTGCTGGTTCCCCAGGGAACCCCCGACGTTCAGTTGCGCCTGACGAGGCCGCAGCTCACCAAGGTCC<br>TTAACGCGACCGGGGCCGATAGTGCCACGCCCACCATGTTCGAGCTCGGGGTTAACGGCAAATTTTCCGTGTTCACCA<br>CGAGTACCTGCGTCACATTTGCTGCCCGCGAGGAGGGCGTGTCGTCCAGCACCAGCACCCAGGTCCAGATCCTGTCCA<br>ACGCGCTCACCAAGGCGGGCCAGGCGGCCGCCAACGCCAAGACGGTGTACGGGGAAAATACCCATCGTACCTTCTCTG<br>TGGTCGTCGACGATTGCAGCATGCGGGCGGTGCTCCGGCGACTGCAGGTCGCCGGGGGCACCCTCAAGTTCTTCCTCA<br>CGACCCCCGTCCCCAGTCTGTGCGTCACCGCCACCGGTCCCAACGCGGTATCGGCGGTATTTCTCCTGAAACCCCAGA<br>AGATTTGCCTGGACTGGCTGGGTCATAGCCAGGGGTCTCCTTCCGCCGGGAGCTCGGCCTCCCGGGCCTCTGGGAGCG<br>AGCCAACAGACAGCCAGGACTCCGCGTCGGACGCGGTCAGCCACGGCGATCCGGAAGACCTCGATGGCGCTGCCCGGG<br>CGGGAGAGGCGGGGGCCTCGTACGCCTGTCCGATGCCGTCGTCGACCACGCGGGTCACTCCCACGACCAAGCGGGGGC<br>GCTCGGGGGGCGAGGATGCGCACGCGGACACGGCCCTAAAGAAACCTAAGACGGGGTCGCCCACCGCACCCCCGCCCG<br>CAGATCCAGTCCCCCTGGACACGGAGGACGACTCCGATGCGGCGGACGGGACAGCGGCCCGTCCCGCCGCTCCAGACG<br>CCCGAAGCGGAAGCCGTTACGCGTGTTACTTTCGCGACCTCCCGACCGGAGAAGCAAACCCCGGCGCCTTCTCCGCCT<br>TCCGGGGGGGCCCCCAAACCCCGTCTGGTTTTGGATTCCCCTGACGGGGCGGGGCCTTAGCGGCCGCCCAACCCTCGC<br>AACATCCCGGGGTTAATGTAAATAAACTTGGTATTGCCCAACACTCTCCCGCGTGTCGCGTGTGGTTCATGTGTGTGC<br>CTGGCGCCCCCACCCTCGGGTTCGTGTATTTCCTTTCCCTGTCCTTATAAAAGCCGTATGTGGGGCGCTGACGGAACC<br>ACCCCGCGTGCCATCACGGCCAAGGCGCGGATGCTCCGCAACGACAGCCACCGGGCCGCGTCCCCGGAGGACGGCCA<br>GGGACGGGTCGACGACGGACGGCCACACCTCGCGTGCGTGGGGGCCCTGGCGCGGGGGTTCATGCATATCTGGCTTCA<br>GGCCGCCACGCTGGGTTTTGCGGGATCGGTCGTTATGTCGCGCGGGCCGTACGCGAATGCCGCGTCTGGGGCGTTCGC<br>CGTCGGGTGCGCCGTGTTGGGCTTTATGCGCGCGCCCCCTCCCCTCGCGCGGCCCACCGCGCGGATATACGCCTGGCT<br>CAAACTGGCGGCCGGTGGAGCGGCCCTTGTTCTGTGGAGTCTCGGGGAGCCCGGCACGCAGCCGGGGGCCCTGGCCCC<br>GGGCCCGGCCACCCAGTGCCTGGCGCTGGGCGCCGCCTATGCGGCGCTCCTGGTGCTCGCCGATGACGTCTATCCGCT<br>CTTTCTCCTCGCCCCGGGGCCCCTGTTCGTCGGCACCCTGGGGATGGTCGTCGGCGGGCTGACGATCGGAGGCAGCGC<br>GCGCTACTGGTGGATCGGTGGGCCCGCCGCGGCCGCCCTGGCCGCGGCGGTGTTGGCGGGCCCGGGGGCGACCACCGC<br>CAGGGACTGCTTCTCCAGGGCGTGCCCCGACCACCGCCGCGTCTGCGTCATCGTCGCAGGCGAGTCTGTTTCCCGCCG<br>CCCCCCGGAGGACCCAGAGCGACCCGGGGACCCAGGGCCACCGTCCCCCCCGACACCCCAACGATCCCAGGGGCCGCC<br>GGCCGATGAGGTCGCACCGGCCGGGGTAGCGCGGCCCGAAAACGTCTGGGTGCCCGTGGTCACCTTTCTGGGGGCTGG<br>CGCGCTCGCCGTCAAGACGGTGCGAGAACATGCCCGGGGAACGCCGGGCCCGGGCCTGCCGCTGTGGCCCCAGGTGTT<br>TCTCGGAGGCCATGTGGCGGTGGCCCTGACGGAGCTGTGTCAGGCGCTTGCGCCCTGGGACCTTACGGACCCGCTGCT<br>GTTTGTTCACGCCGGACTGCAGGTCATCAACCTCGGGTTGGTGTTTCGGTTTTCCGAGGTTGTCGTGTATGCGGCGCT<br>AGGGGGTGCCGTGTGGATTTCGTTGGCGCAGGTGCTGGGGCTCCGGCGTCGCCTGCACAGGAAGGACCCCGGGGACGG<br>GGCCCGGTTGGCGGCGACGCTTCGGGGCCTCTTCTTCTCCGTGTACGCGCTGGGGTTTGGGGTGGGGGCGCTGCTGTG<br>CCCTCCGGGGTCAACGGGCGGGCGGTCGGGCGATTGATATATTTTTCAATAAAAGGCATTAGTCCCGAAGACCGCCGG<br>TGTGTGATGATTTCGCCATAACACCCAAACCCCGGATGGGGCCCGGGTATAAATTCCGGAAGGGGACACGGGCTACCT<br>TCACTACCGAGGGCGCTTGGTCGGGAGGCCGCATCGAACGCACACCCCCATCCGGTGGTCCGTGTGGAGGTCGTTTTT<br>CATTGCCCGGTCTCGCTTTGCCGGGAACGCTAGCCGATCCCTCGCGAGGGGGAGGCGTCGGGCATGGCCCCGGGGCGG |

-continued

| SEQUENCES |
|---|
| GTGGGCCTTGCCGTGGTCCTGTGGAGCCTGGTGTGGCTCGGGGCGGGGGTGTCCGGGGGCTCGGAAACTGCCTCCACC<br>GGGCCCACGATCACCGCGGGAGCGGTGACGAACGCGAGCGAGGCCCCCACATCGGGGTCCCCCGGGTCAGCCGCCAGC<br>CCGGAGGTCACCCCCACATCGACCCCAAACCCCAACAATGTCACACAAAACCAAACCACCCCCACCGAGCCGGCCAGC<br>CCCCCAACAACCCCCAAGCCCACCTCCACACCCAAAAGCCCCCCACGTCCACCCCCGACCCCAAACCCAAGAACAAC<br>ACCACCCCCGCCAAGTCGGACCGCCCCACTAAACCCCCCGGGCCCGTGTGGTGCGACCGCCGCGATTTATTGGCCCGG<br>TACGGCTCGCGGGTGCAGATCCGATGCCGGTTTCGGAATTCCACCCGCATGGAGTTCCGCCTCCAGATATGGCGTTAC<br>TCCATGGGTCCGTCCCCCCCAATCGCTCCGGCTCCCGACCTAGAGGAGGTCCTGACGAACATCACCGCCCCACCCGGG<br>GGACTCCTGGTGTACGACAGCGCCCCCAACCTAACGGACCCCCACGTGCTCTGGGCGGAGGGGGCCGGCCCGGGCGCC<br>GACCCTCCGTTGTATTCTGTCACCGGGCCGCTGCCGACCCAGCGGCTGATTATCGGCGAGGTGACGCCCGCGACCCAG<br>GGAATGTATTACTTGGCCTGGGGCCGGATGGACAGCCCGCACGAGTACGGGACGTGGGTGCGCGTCCGCATGTTCCGC<br>CCCCCGTCTCTGACCCTCCAGCCCCACGCGGTGATGGAGGGTCAGCCGTTCAAGGCGACGTGCACGGCCGCCGCCTAC<br>TACCCGCGTAACCCCGTGGAGTTTGTCTGGTTCGAGGACGACCACCAGGTGTTTAACCCGGGCCAGATCGACACGCAG<br>ACGCACGAGCACCCCGACGGGTTCACCACAGTCTCTACCGTGACCTCCGAGGCTGTCGGCGGCCAGGTCCCCCCGCGG<br>ACCTTCACCTGCCAGATGACGTGGCACCGCGACTCCGTGACGTTCTCGCGACGCAATGCCACCGGGCTGGCCCTGGTG<br>CTGCCGCGGCCAACCATCACCATGGAATTTGGGGTCCGGCATGTGGTCTGCACGGCCGGCTGCGTCCCCGAGGGCGTG<br>ACGTTTGCCTGGTTCCTGGGGGACGACCCCTCACCGGCGGCTAAGTCGGCCGTTACGGCCCAGGAGTCGTGCGACCGC<br>CCCGGGCTGGCTACGGTCCGGTCCACCCTGCCCATTTCGTACGACTACAGCGAGTACATCTGTCGGTTGACCGGATAT<br>CCGGCCGGGATTCCCGTTCTAGAGCACCACGGCAGTCACCAGCCCCCACCCAGGGACCCCACCGAGCGGCAGGTGATC<br>GAGGCGATCGAGTGGGTGGGGATTGGAATCGGGGTTCTCGCGGCGGGGGTCCTGGTCGTAACGGCAATCGTGTACGTC<br>GTCCGCACATCACAGTCGCGGCAGCGTCATCGGCGGTAACGCGAGACCCCCCCGTTACCTTTTTAATATCTATATAGT<br>TTGGTCCCCCTCTATCCCGCCCACCGCTGGGCGCTATAAAGCCGCCACCCTCTCTTCCCTCAGGTCATCCTTGGTCGA<br>TCCCGAACGACACACGGCGTGGAGCAAAACGCCTCCCCCTGAGCCGCTTTCCTACCAGCGCAACGGCATGCCTCTGCG<br>GGCATCGGAACACGCCTACCGGCCCCTGGGCCCCGGGACACCCCCCATGCGGGCTCGGCTCCCCGCCGCGGCCTGGGT<br>TGGCGTCGGGACCATCATCGGGGGAGTTGTGATCATTGCCGCGTTGGTCCTCGTGCCCTCGCGGGCCTCGTGGGCACT<br>TTCCCCATGCGACAGCGGATGGCACGAGTTCAACCTCGGGTGCATATCCTGGGATCCGACCCCCATGGAGCACGAGCA<br>GGCGGTCGGCGGCTGTAGCGCCCCGGCGACCCTGATCCCCCGCGCGGCTGCCAAACAGCTGGCCGCCGTCGCACGCGT<br>CCAGTCGGCAAGATCCTCGGGCTACTGGTGGGTGAGCGGAGACGGCATTCGGGCCTGCCTGCGGCTCGTCGACGGCGT<br>CGGCGGTATTGACCAGTTTTGCGAGGAGCCCGCCCTTCGCATATGCTACTATCCCCGCAGTCCCGGGGGCTTTGTTCA<br>GTTTGTAACTTCGACCCGCAACGCGCTGGGGCTGCCGTGAGGCGCGTGTACTGCGGTCTGTCTCGTCTCCTCTTCTCC<br>CCTTCCCTCCCCCTCCGCATCCCAGGATCACACCGGCCAACGAGGGTTGGGGGGTCCGGCACGGACCCAAAATAATAA<br>ACACACAATCACGTGCGATAAAAAGAACACGCGGTCCCCTGTGGTGTTTTTGGTTATTTTTATTAAATCTCGTCGTCA<br>AACAGGGGGAAAGGGGCGTGGTCTAGCGACGGCAGCACGGGTGGAGGCGTTCACCGGCTCCGGCGTCCTTCGCGTTTA<br>AGCTTGGTCAGGAGGGCGCTCAGGGCGGCGACGTTGGTCGGGCCGTCGTTGGTCAGGGCGTTGGCTCGATGGCGGGCG<br>AGGACGGGCGAGGGGCTCAACGGCGGGGGCGGGGGCCCGGTGCGGCCCGGGGGGGAAAATAGGGCGGATCCCCCCCAG<br>TCGTACAGGGGATTTTCCGCCTCAATGTACGGGGAGGCCGGCGCTGCATTCGCCGTGTTCGCGCAGACGTTTTCGTAG<br>ACCCGCATCCATGGTATTTCCTCGTAGACACGCCCCCCGTCCTCGCTCACAGTCTCGTATATTGACTCGTCGTCCTCG<br>TAGGGGGCGTGCCGTTCGCGGGCCGAGGCGGCGTGGGTGGCTTTGCGGCGGGCGTCGTCGTCGTCGTCGTCGGCCGTC<br>AGATACGTGGCTTCCATCTGGTCGGGTTCTCCCTCCGGGGCGGGTCCCCACCCCCGTGGCCGATCGAGGCTCCCCAGA<br>GACGCGCGCCGGACGAGGAGGGGGCACGTCGCCGCCGGCGGTCGCCTGTCGGGTCCCGCGACGTTACGGGCCGGGAGG<br>CGCGGGGGCACCTCCCCCATGTGCGTGTAATACGTGGCCGGCTGTGCGGCCGCAGCGGGGGGCTCGGCGACCGGGTCG<br>TCCGCATCCGGAAGCGGGGGCGCCGCGCCGTCCGCGCGGCGCCTCCGGAACCGCCGGGTGGCCGCGGGGGTCGAGTGT<br>AGGCGAGGTCGGGGGAGGGGCGGGGGCTCGTTGTCGCGCCGCGCCCGCTGAATCTTTTCCCGACAGGTCCCACCCCCC<br>GCGCGATGCCCCCCCGGGCCGCGGGCCATGTCGTCCGGGGGAGGCCCCGCGGACCACGTCGTCCGGCGAGACGCCACG<br>AGCCGCAGGATGGACTCGTAGTGGAACGACGGCGCCCCGCTGCGGAGCAGATCCGCGGCCAGGGCGGCCCCGAACCAA<br>GCCTTGATGCTCAACTCCATCCGGGCCCAGCTGGGGGCGGTCATCGTGGGGAACAGGGGGGCGGTGGTCCGACAGAAA<br>CGCTCCTGGCTGTCCACCGCGGCCCGCAGATACTCGTTGTTCAGGCTGTCGGTGGCCCAGACGCCGTACCCGGTGAGG<br>GTCGCGTTGATGATATACTGGGCGTGGTGATGGACGATCGACAGAACCTCCACCGTGGATACGACGGTATCCACGGTC<br>CCGTACGTACCGCCGCTCCGCTTGCCGGTCTGCCACAGGTTGGCTAGGCGCGTCAGGTGGCCCAGGACGTCGCTGACC<br>GCCGCCCTGAGCGCCATGCACTGCATGGAGCCGGTCGTGCCGCTGGGACCCCGGTCCAGATGGCGCGCGAACGTTTCC<br>GCGGGCGCCTCCGGGCTGCCGCCGAGCGGGAGGAACCGGCGATTGGAGGGACTCAGCCGGTGGCATACGTGCTTGTCT<br>GTCGTCCACAGCATCCAGGACGCCCACCGGTACAGCACGGAGACGTAGGCCAGGAGCTCGTTGAGCCGCAGTGCGGTG<br>TCGGTGCTGGGGCGGCTTGGGTCCGCCGGGCGCATAAAGAACATGTACTGCTGAATCCGATGGAGGGCGTCGCGCAGG<br>CCGGCCACGGTGGCGGCGTACTTGGCCGCCGCGGCCCCGCTCTTGAACGGGGTGCGCGCCAGCAGCTTTGGCGCCAGG<br>GTGGGCCGCAGCAGCACGTGAAGGCTGGGGTCGCAGTCGCCCACGGGGTCCTCGGGGACGTCCAGGCCGCTGGGCACC<br>ACCGTCTGCAGGTACTTCCAGTACTGCGTGAGGATGGCGCGGCTCAACTGGCCGCCGGTGAGCTCCACCTCGCCCAGC<br>GCCTGGGTGGCGGCCGAAGCGTAGTGCCGGATGTACTCGTAGTGCGGGTCGCTGGCGAGCCCGTCCACGATCAAACTC<br>TCGGGAACCGTGTTGTGTTGCCGCGCGGCCAACCGGACGCTGCGATCGGTGCAGGTCAGAAACGCCGGCTGCGCGTCG<br>TCGGAGCGCTGCCGCAAGGCGCCCACGGCCGCGCTAAGGAGCCCCTCCGGGGTGGGGAGCAGACACCCGCCGAAGATG<br>CGCCGCTCGGGAACGCCCGCGTTGTCGCCGCGGATCAGGTTGGCAGGCGTCAGGCACCGCGCCAGCCGCAGGGAGCTC<br>GCGCCGCGCGTCCGGCGCTGCATGGTGACGCCCGTTCGGTCGGGACCCGCCGGTCGGAGTTATGCCGCGTCCAGGGCC<br>ATCGGGGCGCTTTTTATCGGGAGGAGCTTATGGGCGTGGCGGGCCTCCCAGCCCGGTCGCGCGCCTCCCCGACACGTG<br>CGCCCGCAGGGCGGCGGCCCCCTCGTCTCCCATCAGCAGTTTCCTAAACTGGGACATGATGTCCACCACGCGGACCCG<br>CGGGCCCAACACGGACCCGCCGCTTACGGGGGCGGGGGGGAAGGGCTCCAGGTCCTTGAGAAGAAAGGCGGGGTCTGC<br>CGTCCCGGACACGGGGGCCCGGGGCGCTGAGGAGGCGGGGCGCAGATCCACGTGCTCCGCGGCCGCGCGGACGTCCGC<br>CCAGAACTTGGCGGGGGTGGTGCGCGCGTACAGGGGCTGGGTCGCTCGGAGGACGCACGCGTAGCGCAGGGGGGTGTA<br>TGTGCCCACCTCGGGGGCCGTGAATCCCCCGTCAAACGCGGCCAGTGTCACGCACGCCACCACGGTGTCGGCAAAGCC<br>CAGCAGCCGCTGCAGGACGAGCCCGGCGGCCAGAATGGCGCGCGTGGCCGCCGCGTCGTCCCGGCGCCGGTGCGCGTC<br>CCCGCACGCCCGGGCGTACTTTAAGGTCACGGTCGCCAGGGCCGTGTGCAGCGCGTACACCGCAGCGCCCAGCACGGC<br>GTTGAGCCCGCTGTTGGCGAGCAGCCGGCGCGCTGCGGTGTCGCCCAGCGCCTCGTGCTCGGCCCCCACGACCGCGGG<br>GCTTCCCAGGGGCAGGGCGCGAAACAGCTCCTCCCGCGCCACGTCCGCAAAGGCGGGGTGGTGCACGTGCGGGTGCAG<br>GCGCGCCCCCACGACCACCGAGAGCCACTGGACCGTCTGCTCCGCCATCACCGCCAGCACATCCAGCACGCGCCCCAG<br>GAAGGCGGCCTCCCGCGTCAAAACGCACCGGACGGCGTCGGGATTGAAGCGGGCGAGCAGGGCCCCGGTGGCCAGGTA<br>CGTCATGCGGCCGGCATAGCGGGCGGCCACGCGACAGTCGCGGTCCAGCAGCGCGCGCACCCCGGGCCAGTACAGCAG<br>GGACCCCAGCGAGCTGCGAAACACCGCGGCGTCGGGGCCGGATTGGGGGGACACTAACCCCCCCGCGCTCAGTAACGG<br>CACGGCCGCGGCCCCGACGGGACGCAACGCCGTGAGGCTCGCGAACTGCCGCCTCAGCTCGGCAGCCCTGTCGTCCAG<br>GTCCGACCCGCGCGCCTCTGCGTGAAGGCGCGTCCCGCACACCCACCCGTTGATGGCCAGCCGCACGACGGCATCCGC<br>CAAAAAGCTCATCGCCTGGGCGGGGCTGGTTTTTGTTCGACGATCCATCAGGTCAAGAATCCCATCGCCCGTGATATA |

-continued

| SEQUENCES |
|---|
| CCAGGCCAACGCCTCGCCCTGCTGCAGGGTTTGGCGGAAAAACACCGCGGGGTTGTCGGGGGAGGCGAAGTGCATGAC<br>CCCCACGCGCGATAACCCGAACGCGCTATCCGGACACGGGTAAAACCCGGCCGGATGCCCCAGGGCTAGGGCGGAGCG<br>CACGGACTCGTCCCACACGGCAACCTGAGGGGCCAGTCGATCCAACGGGAATGCCGCCAGGAGCTCCGGGCCCGGCAC<br>GCGTCCCTCCAGAACCTCCACCTTGGGCGGGGAACGGGCCCCGCCGCCGTCCTCCGGCCCGACGTCTTCCGGGTAGTC<br>GTCCTCCTCGTACTGCAGCTCCTCTAGGAACAGCGGCGACGGCGCCACCCGCGAACCGCCGACCCGCCCCAAAATAGC<br>CCGCGCGTCGACGGGACCCAGGTATCCCCCCTGCCGGGCCTGCGGAGGACCGCGGGGAACCTCATCATCATCGTCCAG<br>GCGACCGCGCACCGACTGGCTACGGGCCGCATCGGGCCCGGGGCGCTGCCGGGACGCTCGGCGATGGGATGTGGGCGG<br>GGCTTCCGACGCGCGCCGTCGTCGGGCTCGCGGGCCTTCCCGTCGACGGCGCACGGGCGGCTCGTCGCCCGCCATCTC<br>CTCCAGAGCCTCTAGCTCGCTGTCGTCATCCCCGCGGAACACCGCACGCAGGTACCCCATGAACCCCACCCCATCGCC<br>CGCTGGCTCGTCCGCCACGGGCGAGGCGCGGGGGCGGGTGGATGCGCGCCTCCTACGCCCCGCGGGTTCGCGAGCCGA<br>CATGGTGGCGATAGACGCGGGTTATCGGATGTCCGCTACCCCCCAAAAAAGAAAAAGACCCCACAGCGCGGATGGAGG<br>CCGGGGTAGGTGCCGCCGGACCCCCTCGCGATGGGAATGGACGGGAGCGACGGGGCCGGCGCAAAAAACGCAGTATCT<br>CCCGCGAAGGCTACCCGCCGCCCCAGCCCCCGGCCAAATGCGGAAACGGTCCCGCGCTCTCGCCTTTATACGCGGGCC<br>GCCCTGCGACACAATCACCCGTCCGTGGTTTCGAATCTACACGACAGGCCCGCAGACGCGGCTAACACACACGCCGGC<br>AACCCAGACCCCAGTGGGTTGGTTGCGCGGTCCCGTCTCCTGGCTAGTTCTTTTCCCCACCACCAAATAATCAGACGA<br>CAACCGCAGGTTTTTGTAATGTATGTGCTCGTGTTTATTGTGGATACGAACCGGGGACGGGAGGGGAAAACCCAGACG<br>GGGGATGCGGGTCCGGTCGCGCCCCCTACCCACCGTACTCGTCAATTCCAAGGGCATCGGTAAACATCTGCTCAAACT<br>CGAAGTCGGCCATATCCAGAGCGCCGTAGGGGGCGGAGTCGTGGGGGGTAAATCCCGGACCCGGGGAATCCCCGTCCC<br>CCAACATGTCCAGATCGAAATCGTCTAGCGCGTCGGCATGCGCCATCGCCACGTCCTCGCCGTCTAAGTGGAGCTCGT<br>CCCCCAGGCTGACATCGGTCGGGGGGGCCGTCGACAGTCTGCGCGTGTGTCCCGCGGGGAGAAAGGACAGGCGCGGAG<br>CCGCCAGCCCCGCCTCTTCGGGGGCGTCGTCGTCCGGGAGATCGAGCAGGCCCTCGATGGTAGACCCGTAATTGTTTT<br>TCGTACGCGCGCGGCTGTACGCGTGTTCCCGCATGACCGCCTCGGAGGGCGAGGTCGTGAAGCTGGAATACGAGTCCA<br>ACTTCGCCCGAATCAACACCATAAAGTACCCAGAGGCGCGGGCCTGGTTGCCATGCAGGGTGGGAGGGGTCGTCAACG<br>GCGCCCCTGGCTCCTCCGTAGCCGCGCTGCGCACCAGCGGGAGGTTAAGGTGCTCGCGAATGTGGTTTAGCTCCCGCA<br>GCCGGCGGGCCTCGATTGGCACTCCCCGGACGGTGAGCGCTCCGTTGACGAACATGAAGGGCTGGAACAGACCCGCCA<br>ACTGACGCCAGCTCTCCAGGTCGCAACAGAGGCAGTCAAACAGGTCGGGCCGCATCATCTGCTCGGCGTACGCGGCCC<br>ATAGGATCTCGCGGGTCAAAAATAGATACAAATGCAAAAACAGAACACGCGCCAGACGAGCGGTCTCTCGGTAGTACC<br>TGTCCGCGATCGTGGCGCGCAGCATTTCTCCCAGGTCGCGATCGCGTCCGCGCATGTGCGCCTGGCGGTGCAGCTGCC<br>GGACGCTGGCGCGCAGGTACCGGTACAGGGCCGAGCAGAAGTTGGCCAACACGGTTCGATAGCTCTCCTCCCGCGCCC<br>GTAGCTCGGCGTGGAAGAAACGAGAGAGCGCTTCGTAGTAGAGCCCGAGGCCGTCGCGGGTGGCCGGAAGCGTCGGGA<br>AGGCCACGTCGCCGTGGGCGCGAATGTCGATTTGGGCGCGTTCGGGGACGTACGCGTCCCCCCATTCCACCACATCGC<br>TGGGCAGCGTTGATAGGAATTTACACTCCCGGTACAGGTCGGCGTTGGTCGGTAACGCCGAAAACAAATCCTCGTTCC<br>AGGTATCGAGCATGGTACATAGCGCGGGGCCCGCGCTAAAGCCCAAGTCGTCGAGGAGACGGTTAAAGAGGGCGGCGG<br>GGGGGACGGGCATGGGCGGGGAGGGCATGAGCTGGGCCTGGCTCAGGCGCCCCGTTGCGTACAGCGGAGGGGCCGCCG<br>GGGTGTTTTTGGGACCCCCGGCCGGGCGGGGGGGTGGTGGCGAAGCGCCGTCCGCGTCCATGTCGGCAAACAGCTCGT<br>CGACCAAGAGGTCCATTGGGTGGGGTTGATACGGGAAAGACGATATCGGGCTTTTGATGCGATCGTCCCCGCCCGCCC<br>AGAGAGTGTGGGACGCCCGACGGCGCGGGAAGAGAAAAACCCCCAAACGCGTTAGAGGACCGGACGGACCTTATGGGG<br>GGAAGTGGGCAGCGGGAACCCCGTCCGTTCCCGAGGAATGACAGCCCGTGGTCGCCACCCCGCATTTAAGCAACCCGC<br>ACGGGCCGCCCCGTACCTCGTGACTTCCCCCCACATTGGCTCCTGTCACGTGAAGGCGAACCGAGGGCGGCTGTCCAA<br>CCCACCCCCCGCCACCCAGTCACGGTCCCCGTCGGATTGGGAAACAAAGGCACGCAACGCCAACACCGAATGAACCCC<br>TGTTGGTGCTTTATTGTCTGGGTACGGAAGTTTTTCACTCGACGGGCCGTCTGGGGCGAGAAGCGGAGCGGGCTGGGG<br>CTCGAGGTCGCTCGGTGGGGCGCGACGCCGCAGAACGCCCTCGAGTCGCCGTGGCCGCGTCGACGTCCTGCACCACGT<br>CTGGATTCACCAACTCGTTGGCGCGCTGAAGCAGGTTTTTGCCCTCGCAGACCGTCACGCGGATGGTGGTGATGCCAA<br>GGAGTTCGTTGAGGTCTTCGTCTGTGCGCGGACGCGACATGTCCCAGAGCTGGACCGCCGCCATCCGGGCATGCATGG<br>CCGCCAGGCGCCCGACCGCGGCGCAGAAGACGCGCTTGTTAAAGCCGGCCACCCGGGGGGTCCATGGCGCGTCGGGGT<br>TTGGGGGGGCGGTGCTAAAGTGCAGCTTTCTGGCCAGCCCCTGCGCGGGTGTCTTGGATCGGGTTGGCGCCGTCGACG<br>CGGGGGCGTCTGGGAGTGCGGCGGATTCTGGCTGGGCCGATTTCCTGCCGCGGGTGGTCTCCGCCGCCGGGGCCGCGG<br>GGGCCTTAGTCGCCACCCGCTGGGTTCGGGGGGCCCGGGGGGCGGTGGTGGGTGTGCGTCCGGCCCCTCCGGACCCAG<br>CGGGCGGCGGAGGCGCCCGCGCAGGCCCCGGGCCGGACAAAACCGCCCCGGAAACGGGACGCCGCGTCCGGGGGACCT<br>CCGGGTGTTCGTCGTCTTCGGATGACGAGCCCCCGTAGAGGGCATAATCCGACTCGTCGTACTGGACGAAACGGACCT<br>CGCCCCTCGGGCGCGCGCGTGTCTGTAGGGCGCCACGGCGGGAGGTGGCAGGCGGACTATCGGGACTCGCCATACATG<br>AAGACGGGGTGTAGTACAGATCCTCGTACTCATCGCGCGGAACCTCCCGCGGACCCGACTTCACGGAGCGGCGAGAGG<br>TCATGGTTCCACGAACACGCTAGGGTCGGATGCGCGGACAATTAGGCCTGGGTTCGGACGGCGGGGGGTGGTGCAGGT<br>GTGGAGAGGTCGAGCGATAGGGGCGGCCCGGGAGAGAAGAGAGGGTCCGCAAAACCCACTGGGGATGCGTGAGTGGCC<br>CTCTGTGGGCGGTGGGGGAGAGTCTTATAGGAAGTGCATATAACCACAACCCATGGGTCTAACCAATCCCCAGGGGCC<br>AAGAAACAGACACGCCCCAAACGGTCTCGGTTTCCGCGAAGAAGGGGAAGTCCTGGGACACCCTCCACCCCCACCCCT<br>CACCCCACACAGGGCGGGTTCAGGCGTGCCCGGCAGCCAGTAGCCTCTGGCAGATCTGACAGACGTGTGCGATAATAC<br>ACACGCCCATCGAGGCCATGCCTACATAAAAGGGCACCAGGGCCCCGGGGGCAGACATTTGGCCAGCGTTTTGGGTCT<br>CGCACCGCGCGCCCCCGATCCCATCGCGCCCGCCCTCCTCGCCGGGCGGCTCCCCGTGCGGGCCCGCGTCTCCCGCCG<br>CTAAGGCGACGAGCAAGACAAACAACAGGCCCGCCCGACAGACCCTTCTGGGGGGGCCCATCGTCCCTAACAGGAAGA<br>TGAGTCAGTGGGGATCCGGGGCGATCCTTGTCCAGCCGGACAGCTTGGGTCGGGGGTACGATGGCGACTGGCACACGG<br>CCGTCGCTACTCGCGGGGGCGGAGTCGTGCAACTGAACCTGGTCAACAGGCGCGCGGTGGCTTTTATGCCGAAGGTCA<br>GCGGGGACTCCGGATGGGCCGTCGGGCGCGTCTCTCTGGACCTGCGAATGGCTATGCCGGCTGACTTTTGTGCGATTA<br>TTCACGCCCCCGCGCTATCCAGCCCAGGGCACCACGTAATACTGGGTCTTATCGACTCGGGGTACCGCGGAACCGTTA<br>TGGCCGTGGTCGTAGCGCCTAAAAGGACGCGGGAATTTGCCCCCGGGACCCTGCGGGTCGACGTGACGTTCCTGGACA<br>TCCTGGCGACCCCCCCGGCCCTCACCAAGCCGATTTCCCTGCGGCAGTTCCCGCAACTGGCGCCCCCCCCTCCAACCG<br>GGGCCGGGATACGCGCAGATCCTTGGTTGGAGGGGGCGCTCGGGGACCCAAGCGTGACTCCGGCCCTACCGGCGCGAC<br>GCCGAGGGCGGTCCCTCGTCTATGCCGGCGAGCTGACGCCGGTTCAGACGGAACACGGGGACGGCGTACGAGAAGCCA<br>TCGCCTTCCTTCCAAAACGCGAGGAGGATGCCGGTTTCGACATTGTCGTCCGTCGCCCGGTCACCGTCCCGGCAAACG<br>GCACCACGGTCGTGCAGCCATCCCTCCGCATGCTCCACGCGGACGCCGGGCCCGCGGCCTGTTATGTGTTGGGGCGGT<br>CGTCGCTCAACGCCCGCGGCCTCCTGGTCGTTCCTACGCGCTGGCTCCCCGGGCACGTATGTGCGTTTGTTGTTTACA<br>ACCTTACGGGGGTTCCTGTGACCCTCGAGGCCGGCGCCAAGGTCGCCCAGCTCCTGGTTGCGGGGGCGGACGCTCTTC<br>CTTGGATCCCCCCGGACAACTTTCACGGGACCAAAGCGCTTCGAAACTACCCCAGGGGTGTTCCGGACTCAACCGCCG<br>AACCCAGGAACCCGCCGCTCTTGGTGTTTACGAACGAGTTTGACGCGGAGGCCCCCCCGAGCGAGCGCGGGACCGGGG<br>GTTTTGGCTCTACCGGTATTTAGCCCATAGCTTGGGGTTCGTTCCGGGCAATAAAAAACGTTTGTATCTCATCTTTCC<br>TGTGTGTAGTTGTTTCTGTTGGAGGCCTGTGGGTCTATCACACCCGCCCCTCCATCCCACAAACACAGAACACACGGG<br>TTGGATGAAAACACGCATTTATTGACCCAAAACACACGGAGCTGCTCGAGATGGGCCAGGGCGAGGTGCGGTTGGGGA |

-continued

| SEQUENCES |
| --- |
| GGCTGTAGGTCTGGGAACGGACACGCGGGGACACGATTCCGGTTTGGGGTCCGGGAGGGCGTCGCCGTTTCGGGCGGC<br>AGGCGCCAGCGTAACCTCCGGGGGCGGCGTGTGGGGGTGCCCCAAGGAGGGCGCCTCGGTCACCCCAAGCCCCCCCAA<br>GCGGGTTCCCCCGGCAACCCCGAAGGCGGAGAGGCCAAGGGCCCGTTCGGCGATGGCCACATCCTCCATGACCACGTC<br>GCTCTCGGCCATGCTCCGAATAGCCTGGGAGACGAGCACATCCGCGGACTTGTCAGCCGCCCCCACGGACATGTACAT<br>CTGCAGGATGGTGGCCATACACGTGTCCGCCAGGCGCCGCATCTTGTCCTGATGGGCCGCCACGGCCCCGTCGATCGT<br>GGGGGCCTCGAGCCCGGGGTGGTGGCGCGCCAGTCGTTCTAGGTTCACCATGCAGGCGTGGTACGTGCGGGCCAAGGC<br>GCGGGCCTTCACGAGGCGTCGGGTGTCGTCCAGGGACCCCAGGGTGTCATCGAGCGTGATGGGGGCGGGAAGTAGCGC<br>GTTAACGACCACCAGGGCCTCCTGCAGCCGCGGCTCCGCCTCCGAGGGCGGAACGGCCGCGCGGATCATCTCATATTG<br>TTCCTCGGGGCGCGCTCCCCAGCCACATATAGCCCCGAGAAGAGAAGCCATCGCGGGCGGGTACTGGCCCTTGGGCGC<br>GCGGACGCAATGGGGCAGGAAGACGGGAACCGCGGGGAGAGGCGGGCGGCCGGGACTCCCGTGGAGGTGACCGCGCTT<br>TATGCTACCGACGGGTGCGTTATTACCTCTTCGATCGCCCTCCTCACAAACTCTCTACTGGGGGCCGAGCCGGTTTAT<br>ATATTCAGCTACGACGCATACACGCACGATGGCCGTGCCGACGGGCCCACGGAGCAAGACAGGTTCGAAGAGAGTCGG<br>GCGCTCTACCAAGCGTCGGGCGGGCTAAATGGCGACTCCTTCCGAGTAACCTTTTGTTTATTGGGGACGGAAGTGGGT<br>GGGACCCACCAGGCCCGCGGGCGAACCCGACCCATGTTCGTCTGTCGCTTCGAGCGAGCGGACGACGTCGCCGCGCTA<br>CAGGACGCCCTGGCGCACGGGACCCCGCTACAACCGGACCACATCGCCGCCACCCTGGACGCGGAGGCCACGTTCGCG<br>CTGCATGCGAACATGATCCTGGCTCTCACCGTGGCCATCAACAACGCCAGCCCCCGCACCGGACGCGACGCCGCCGCG<br>GCGCAGTATGATCAGGGCGCGTCCCTACGCTCGCTCGTGGGGCGCACGTCCCTGGGACAACGCGGCCTTACCACGCTA<br>TACGTCCACCACGAGGCGCGCGTGCTGGCCGCGTACCGCAGGGCGTATTATGGAAGCGCGCAGAGTCCCTTCTGGTTT<br>CTTAGCAAATTCGGGCCGGACGAAAAAAGCCTGGTGCTCACCACTCGGTACTACCTGCTTCAGGCCCAGCGTCTGGGG<br>GGCGCGGGGGCCACGTACGACCTGCAGGCCATCAAGGACATCTGCGCCACCTACGCGATTCCCCACGCCCCCCGCCCC<br>GACACCGTCAGCGCCGCGTCCCTGACCTCGTTTGCCGCCATCACGCGGTTCTGTTGCACGAGCCAGTACGCCCGCGGG<br>GCCGCGGCGGCCGGGTTTCCGCTTTACGTGGAGCGCCGTATTGCGGCCGACGTCCGCGAGACCAGTGCGCTGGAGAAG<br>TTCATAACCCACGATCGCAGTTGCCTGCGCGTGTCCGACCGTGAATTCATTACGTACATTTACCTGGCCCATTTTGAG<br>TGTTTCAGCCCCCCGCGCCTAGCCACGCATCTTCGGGCCGTGACGACCCACGACCCCAACCCCGCGGCCAACACGGAG<br>CAGCCCTCGCCCCTGGGCAGGGAGGCCGTGGAACAATTTTTTTGCCACGTGCGCGCCCAACTGAATATCGGGGAGTAC<br>GTCAAACACAACGTGACCCCCCGGGAGACCGTCCTGGATGGCGATACGGCCAAGGCCTACCTGCGCGCTCGCACGTAC<br>GCGCCCGGGGCCCTGACGCCCGCCCCCGCGTATTGCGGGGCCGTGGACTCCGCCACCAAAATGATGGGGCGTTTGGCG<br>GACGCCGAAAAGCTCCTGGTCCCCCGCGGGTGGCCCGCGTTTGCGCCCGCCAGTCCCGGGGAGGATACGGCGGGCGGC<br>ACGCCGCCCCCACAGACCTGCGGAATCGTCAAGCGCCTCCTGAGACTGGCCGCCACGGAACAACAGGACACCACGCCC<br>CCGGCGATCGCGGCGCTTATCCGTAATGCGGCGGTGCAGACTCCCCTGCCCGTCTACCGGATATCCATGGTCCCCACG<br>GGACAGGCATTTGCCGCGCTGGCCTGGGACGACTGGGCCCGCATAACGCGGGACGCTCGCCTGGCCGAAGCGGTCGTG<br>TCCGCCGAAGCGGCGGCGCACCCCGACCACGGCGCGCTGGGCAGGCGGCTCACGGATCGCATCCGCGCCCAGGGCCCC<br>GTGATGCCCCCTGGCGGCCTGGATGCCGGGGGCAGATGTACGTGAATCGCAACGAGATATTCAACGGCGCGCTGGCA<br>ATCACAAACATCATCCTGGATCTCGACATCGCCCTGAAGGAGCCCGTCCCCTTTCGCCGGCTCCACGAGGCCCTGGGC<br>CACTTTAGGCGCGGGGCTCTGGCTGCGGTTCAGCTCCTGTTTCCCGCGGCCCGCGTGGACCCCGACGCATATCCCTGT<br>TATTTTTTCAAAAGCGCATGTCGGCCCGGCCCGGCGTCCGTGGGTTCCGGCAGCGGACTCGGCAACGACGACGACGGG<br>GACTGGTTTCCCTGCTACGACGACGCCGGTGATGAGGAGTGGGCGGAGGACCCGGGCGCCATGGACACATCCCACGAT<br>CCCCCGGACGACGAGGTTGCCTACTTTGACCTGTGCCACGAAGTCGGCCCCACGGCGGAACCTCGCGAAACGGATTCG<br>CCCGTGTGTTCCTGCACCGACAAGATCGGACTGCGGGTGTGCATGCCCGTCCCCGCCCCGTACGTCGTCCATGGTTCT<br>CTAACGATGCGGGGGGTGGCACGGGTCATCCAGCAGGCGGTGCTGTTGGACCGAGATTTTGTGGAGGCCATCGGGAGC<br>TACGTAAAAAACTTCCTGTTGATCGATACGGGGGTGTACGCCCACGGCCACAGCCTGCGCTTGCCGTATTTTGCCAAA<br>ATCGCCCCCGACGGGCCTGCGTGCGGAAGGCTGCTGCCAGTGTTTGTGATCCCCCCCGCCTGCAAAGACGTTCCGGCG<br>TTTGTCGCCGCGCACGCCGACCCGCGGCGCTTCCATTTTCACGCCCCGCCCACCTATCTCGCTTCCCCCCGGGAGATC<br>CGTGTCCTGCACAGCCTGGGTGGGGACTATGTGAGCTTCTTTGAAAGGAAGGCGTCCCGCAACGCGCTGGAACACTTT<br>GGGCGACGCGAGACCCTGACGGAGGTCCTGGGTCGGTACAACGTACAGCCGGATGCGGGGGGGACCGTCGAGGGGTTC<br>GCATCGGAACTGCTGGGGCGGATAGTCGCGTGCATCGAAACCCACTTTCCCGAACACGCCGGCGAATATCAGGCCGTA<br>TCCGTCCGGCGGGCCGTCAGTAAGGACGACTGGGTCCTCCTACAGCTAGTCCCCGTTCGCGGTACCCTGCAGCAAAGC<br>CTGTCGTGTCTGCGCTTTAAGCACGGCCGGGCGAGTCGCGCCACGGCGCGGACATTCGTCGCGCTGAGCGTCGGGGCC<br>AACAACCGCCTGTGCGTGTCCTTGTGTCAGCAGTGCTTTGCCGCCAAATGCGACAGCAACCGCCTGCACACGCTGTTT<br>ACCATTGACGCCGGTACGCCATGCTCGCCGTCCGTTCCCTGCAGCACCTCTCAACCGTCGTCTTGATAACGGCGTACG<br>GCCTCGTGCTCGTGTGGTACACCGTCTTCGGTGCCAGTCCGCTGCACCGATGTATTTACGCGGTACGCCCCACCGGCA<br>CCAACAACGACACCGCCCTCGTGTGGATGAAAATGAACCAGACCCTATTGTTTCTGGGGGCCCCGACGCACCCCCCCA<br>ACGGGGGCTGGCGCAACCACGCCCATATCTGCTACGCCAATCTTATCGCGGGTAGGGTCGTGCCCTTCCAGGTCCCAC<br>CCGACGCCATGAATCGTCGGATCATGAACGTCCACGAGGCAGTTAACTGTCTGGAGACCCTATGGTACACACGGGTGC<br>GTCTGGTGGTCGTAGGGTGGTTCCTGTATCTGGCGTTCGTCGCCCTCCACCAACGCCGATGTATGTTTGGTGTCGTGA<br>GTCCCGCCCACAAGATGGTGGCCCCGGCCACCTACCTCTTGAACTACGCAGGCCGCATCGTATCGAGCGTGTTCCTGC<br>AGTACCCCTACACGAAAATTACCCGCCTGCTCTGCGAGCTGTCGGTCCAGCGGCAAAACCTGGTTCAGTTGTTTGAGA<br>CGGACCCGGTCACCTTCTTGTACCACCGCCCCGCCATCGGGGTCATCGTAGGCTGCGAGTTGATGCTACGCTTTGTGG<br>CCGTGGGTCTCATCGTCGGCACCGCTTTCATATCCCGGGGGGCATGTGCAATCACATACCCCCTGTTTCTGACCATCA<br>CCACCTGGTGTTTTGTCTCCACCATCGGCCTGACAGAGCTGTATTGTATTCTGCGGCGGGGCCCGGCCCCCAAGAACG<br>CAGACAAGGCCGCCGCCCCGGGGCGATCCAAGGGGCTGTCGGGCGTCTGCGGGCGCTGCTGTTCCATCATCCTCTCGG<br>GCATCGCAGTGCGATTGTGTTATATCGCCGTGGTGGCCGGGGTGGTGCTCGTGGCGCTTCACTACGAGCAGGAGATCC<br>AGAGGCGCCTGTTTGATGTATGACGTCACATCCAGGCCGGCGGAAACCGGAACGGCATATGCAAATTGGAAACTGTCC<br>TGTCTTGGGGCCCACCCACCCGACGCGTCATATGCAAATGAAAATCGGTCCCCCGAGGCCACGTGTAGCCTGGATCCC<br>AACGACCCCGCCCATGGGTCCCAATTGGCCGTCCCGTTACCAAGACCAACCCAGCCAGCATATCCACCCCCGCCCGGG<br>TCCCCGCGGAAGCGGAACGGTGTATGTGATATGCTAATTAAATACATGCCACGTACTTATGGTGTCTGATTGGTCCTT<br>GTCTGTGCCGGAGGTGGGGCGGGGGCCCCGCCCGGGGGGCGGAACGAGGAGGGGTTTGGGAGAGCCGGCCCCGGCACC<br>ACGGGTATAAGGACATCCACCACCCGGCCGGTGGTGGTGTGCAGCCGTGTTCCAACCACGGTCACGCTTCGGTGCCTC<br>TCCCCGATTCGGGCCCGGTCGCTCGCTACCGGTGCGCCACCACCAGAGGCCATATCCGACACCCCAGCCCCGACGGCA<br>ACCGACAGCCCGGTCATGGCGACTGACATTGATATGCTAATTGACCTCGGCCTGGACCTCTCCGACAGCGATCTGGAC<br>GAGGACCCACCCGAGCCGGCGGAGAGCCGCCGCGACGACCTGGAATCGGACAGCAGCGGGGAGTGTTCCTCGTCGGAC<br>GAGGACATGGAAGACCCCCACGGAGAGGACGGACCGGAGCCGATACTCGACGCCGCTCGCCCGGCGGTCCGCCCGTCT<br>CGTCCAGAAGACCCCGGCGTACCCAGCACCCAGACGCCTCGTCCGACGGAGCGGCAGGGCCCCAACGATCCTCAACCA<br>GCGCCCCACAGTGTGTGGTCGCGCCTCGGGGCCCGGCGACCGTCTTGCTCCCCCGAGCAGCACGGGGGCAAGGTGGCC<br>CGCCTCCAACCCCCACCGACCAAAGCCCAGCCTGCCCGCGGCGGACGCCGCGGGCGTCGCAGGGGTCGGGGTCGCGGT<br>GGTCCCGGGGCCGCCGATGGTTTGTCGGACCCCCGCCGGCGTGCCCCCAGAACCAATCGCAACCCGGGGGGACCCCGC<br>CCCGGGGCGGGGTGGACGGACGGCCCCGGCGCCCCCCATGGCGAGGCGTGGCGCGGAAGTGAGCAGCCCGACCCACCC |

-continued

| SEQUENCES |
|---|
| GGAGGCCCGCGGACACGGGGCGTGCGCCAAGCACCCCCCCCGCTAATGACGCTGGCGATTGCCCCCCCGCCCGCGGAC<br>CCCCGCGCCCCGGCCCCGGAGCGAAAGGCGCCCGCCGCCGACACCATCGACGCCACCACGCGGTTGGTCCTGCGCTCC<br>ATCTCCGAGCGCGCGGCGGTCGACCGCATCAGCGAGAGCTTTGGCCGCAGCGCACAGGTCATGCACGACCCCTTTGGG<br>GGGCAGCCGTTTCCCGCCGCGAATAGCCCCTGGGCCCCGGTGTTGGCGGGCCAAGGAGGGCCCTTTGACGCCGAGACC<br>AGACGGGTCTCCTGGGAAACCTTGGTCGCCCACGGCCCGAGCCTCTATCGCACTTTTGCCGGCAATCCTCGGGCCGCA<br>TCGACCGCCAAGGCCATGCGCGACTGCGTGCTGCGCCAAGAAAATTTCATCGAGGCGCTGGCCTCCGCCGACGAGACG<br>CTGGCGTGGTGCAAGATGTGCATCCACCACAACCTGCCGCTGCGCCCCCAGGACCCCATTATCGGGACGGCCGCGGCT<br>GTGCTGGATAACCTCGCCACGCGCCTGCGGCCCTTTCTCCAGTGCTACCTGAAGGCGCGAGGCCTGTGCGGCCTGGAC<br>GAACTGTGTTCGCGGCGGCGTCTGGCGGACATTAAGGACATTGCATCCTTCGTGTTTGTCATTCTGGCCAGGCTCGCC<br>AACCGCGTCGAGCGTGGCGTCGCGGAGATCGACTACGCGACCCTTGGTGTCGGGGTCGGAGAGAAGATGCATTTCTAC<br>CTCCCCGGGGCCTGCATGGCGGGCCTGATCGAAATCCTAGACACACACCGCCAGGAGTGTTCGAGTCGTGTCTGCGAG<br>TTGACGGCCAGTCACATCGTCGCCCCCCCGTACGTGCACGGCAAATATTTTTATTGCAACTCCCTGTTTTAGGTACAA<br>TAAAAACAAAACATTTCAAACAAATCGCCCCACGTGTTGTCCTTCTTTGCTCATGGCCGGCGGGGCGTGGGTCACGGC<br>AGATGGCGGGGGTGGGCCCGGCGTACGGCCTGGGTGGGCGGAGGGAACTAACCCAACGTATAAATCCGTCCCCGCTCC<br>AAGGCCGGTGTCATAGTGCCCTTAGGAGCTTCCCGCCCGGGCGCATCCCCCCTTTTGCACTATGACAGCGACCCCCCT<br>CACCAACCTGTTCTTACGGGCCCCGGACATAACCCACGTGGCCCCCCCTTACTGCCTCAACGCCACCTGGCAGGCCGA<br>AACGGCCATGCACACCAGCAAAACGGACTCCGCTTGCGTGGCCGTGCGGAGTTACCTGGTCCGCGCCTCCTGTGAGAC<br>CAGCGGCACAATCCACTGCTTTTTCTTTGCGGTATACAAGGACACCCACCACACCCCTCCGCTGATTACCGAGCTCCG<br>CAACTTTGCGGACCTGGTTAACCACCCGCCGGTCCTACGCGAACTGGAGGATAAGCGCGGGGTGCGGCTGCGGTGTGC<br>GCGGCCGTTTAGCGTCGGGACGATTAAGGACGTCTCTGGGTCCGGCGCGTCCTCGGCGGGAGAGTACACGATAAACGG<br>GATCGTGTACCACTGCCACTGTCGGTATCCGTTCTCAAAAACATGCTGGATGGGGGCCTCCGCGGCCCTACAGCACCT<br>GCGCTCCATCAGCTCCAGCGGCATGGCCGCCCGCGCGGCAGAGCATCGACGCGTCAAGATTAAAATTAAGGCGTGATC<br>TCCAACCCCCCCATGAATGTGTGTAACCCCCCAAAAAAATAAACAGCCGTAACCCAATCAAACCAGGCGTGGTGTGAG<br>TTTGTGGACCCAAAGCCCTCAGAGACAACGCGACAGGCCAGTATGGACCGTGATACTTTTATTTATTAACTCACAGGG<br>GCGCTTACCGCCACAGGAATACCAGAATAATGACCACCACTATCGCGACCACCCCAAATACAGCATGGCGCCCCACCA<br>CGCCACAACAGCCCTGTCGCCGGTATGGGGCATGATCAGACGAGCCGCGAGCCGCGCGTTGGGCCCTGTACAGCTCGC<br>GCGAATTGACCCTAGGAGGCCGCCACGCGCCCGAGTTTTGCGTTCGTCGCTGGTCGTCGGGCGCCAAAGCCCCGGACG<br>GCTGTTCGGTCGAACGAACGGCCACGACAGTGGCATAGGTTGGGGGGTGGTCCGACATAGCCTCGGCGTACGTCGGGA<br>GGCCCGACAAGAGGTCCCTTGAGATGTCGGGTGGGGCCACAAGCCTGGTTTCCGGAAGAAACAGGGGGGTTGCCAATA<br>ACCCGCCAGGGCCAAAACTCCGGCGCTGCGCACGTCGTTCGGCGCGGCGCCGGGCGCGCCGAGCGGCTCGCTGGGCGG<br>CTTGGCGTGAGCGGCCCCGCTCCGACGCCTCGCCCTCTCCGGAGGAGGTTGGCGGAATTGGCACGGACGACAGGGGCC<br>CAGCAGAGTACGGTGGAGGTGGGTCCGTGGGGGTGTCCAGATCAATAACGACAAACGGCCCCTCGTTCCTACCAGACA<br>AGCTATCGTAGGGGGGCGGGGGATCAGCAAACGCGTTCCCCGCGCTCCATAGACCCGCGTCGGGTTGCGCCGCCTCCG<br>AAGCCATGGATGCGCCCCAAAGCCACGACTCCCGCGCGCTAGGTCCTTGGGGTAAGGGAAAAGGCCCTACTCCCCATC<br>CAAGCCAGCCAAGTTAACGGGCTACGCCTTCGGGGATGGGACTGGCACCCCGGCGGATTTTGTTGGGCTGGTACGCGT<br>TGCCCAACCGAGGGCCGCGTCCACGGGACGCGCCTTTTATAACCCCGGGGGTCATTCCCAACGATCACATGCAATCTA<br>ACTGGCTCCCCTCTCCCCCCCTCTCCCCTCTCCCCCCCTCTCCCCTCTCCCCCCCTCTCCCCTCTCCCCCCCTCTCCC<br>CTCTCCCCCCCTCTCCCCTCTCCCCCCCTCTCCCCTCTCCCCCCCTCTCCCCTCTCCCCCCCTCTCCCCTCTCCCCCC<br>CTCTCCCCTCTCCCCCCCTCTCCCCTCTCCCCTCTGCTCTTTCCCCGTGACACCCGACGCTGGGGGGCGTGGCTGCCG<br>GGAGGGGCCGCGGATGGGCGGGGCCTACTTGGTTTCCCGCCCCCCCCCCCCGCCCCCGAACCGCCCCGCCGGCCTTGC<br>CCCCCTTTGATCCCCTGCTACCCCCAACCCGTGCTGGTGGTGCGGGTTGGGGGGGGAGTGTGGGCGGGGGTGTGCGGG<br>AGGTGTCGGTGGTGGTGGTGGTGGTGGTAGTAGGAATGGTGGTGAGGGGGGGGGGGGCGCTGGTTGGTCAAAAAAGGGA<br>GGGACGGGGGCCGGCAGACCGACGGCGACAACGCTCCCCGGTGGCCGGGTCGCGGCTCTTACGAGCGGCCCGGCCCGC<br>GCTCCCACCCCCCGGGCCGTGTCCTTGCTTTCCCCCCGTCTCCCCCCCCCCCCGCCTTCTCCTCCTCCTCCTCGTTTTT<br>CCAAACCCCGCCCACCCGGCCCGGCCCGGCCCGGCCCGGCCCGGCCACCGCCGCCCACCCACCCACCTCGGGAGACCC<br>AGCCCCGGTCCCCCGTTCCCCGGGGGCCGTTATCTCCAGCGCCCCGTCCGGCGCGCCGCCCCCCGCCGCTAAACCCCA<br>TCCCGCCCCCGGGACCCCACATATAAGCCCCCAGCCACACGCAAGAACAGACACGCAGAACGGCTGTGTTTATTTAAA<br>TAAACCGATGTCGGAATAAACAAACACAAACACCCGCGACGGGGGGACGGAGGGGACGGAGGGAGGGGGGTGACGGGG<br>GACGGGAACAGACACACCACAAAAAACACCCACCCACCGACACCCCCACCCCAGTCTCCTCGCCTTCTCCCACCCACC<br>CCACGCCCCCACTGAGCCCGGTCGATCGACGAGCACCCCCGCCCACGCCCCCGCCCCTGCCCCGGCGACCCCCGGCCC<br>GCACGATCCCGACAACAATAACAACCCCAACGGAAAGCGGCGGGGTGTGGGGGGGGGCGAGGAACAACCGAGGGGAAC<br>GGGGGATGGAAGGACGGGAAGTGGAAGTCCTGATACCCATCCTACACCCCCCTGCCTTCCACCCTCCGGCCCCCCGCG<br>AGTCCACCCGCCGGCCGGCTACCGAGACCGAACACGGCGGCCGCCGCAGCCGCCGCAGCCGCCGCCGACACCGCAGAG<br>CCGGCGCGCGCACACACAAGCGGCAGAGGCAGAAAGGCCCAGAGTCATTGTTTATGTGGCCGCGGGCCAGCAGACGGC<br>CCGCGACACCCCCCCCCCGCCCGTGTGGGTATCCGGCCCCCCGCCCCGCGCCGGTCCATTAAGGGCGCGCGTGCCCGC<br>GAGATATCAATCCGTTAAGTGCTCTGCAGACAGGGGCACCGCGCCCGGAAATCCATTAGGCCGCAGACGAGGAAAATA<br>AAATTACATCACCTACCCACGTGGTGCTGTGGCCTGTTTTTGCTGCGTCATCTGAGCCTTTATAAAAGCGGGGGCGCG<br>GCCGTGCCGATCGCGGGTGGTGCGAAAGACTTTCCGGGCGCGTCCGGGTGCCGCGGCTCTCCGGGCCCCCCTGCAGCC<br>GGGGCGGCCAAGGGGCGTCGGCGACATCCTCCCCCTAAGCGCCGGCCGGCCGCTGGTCTGTTTTTTGTTTTCCCCGTT<br>TCGGGGGTGGGGGGGGTTGCGGTTTCTGTTTCTTTAACCCGTCTGGGGTGTTTTTCGTTCCGTCGCCGGAATGTTTCG<br>TTCGTCTGTCCCCTCACGGGGCGAAGGCCGCGTACGGCCCGGGACGAGGGGGCCCCCGACCGCGGCGGTCCGGGCCCC<br>GTCCGGGCCCGCTCGCCGGCACGCGACGCGAAAAAGGCCCCCCGGAGGCTTTTCCGGGTTCCCGGCCCGGGGCCTGAG<br>ATAAACAATCGGGGTTACCGCCAACGGCCGGCCCCCGTGGCGGCCCGGCCCGGGGCCCCGGCGGACCCAAGGGGCCCC<br>GGCCCGGGGCCCCACAACGGCCCGGCGCATGCGCTGTGGTTTTTTTTTTTCTCGGTGTTCTGCCGGGCTCCATCGCCT<br>TTCCTGTTCTCGCTTCTCCCCCCCCCCTTCTTCACCCCCAGTACCCTCCTCCCTCCCTTCCTCCCCCGTTATCCCACT<br>CGTCAAGGGCGCCCCGGTGTGGTTCAACAAAGACGCCGCGTTTCCAGGTAGGTTAGACACCTGCTTCTCCCCAATAGA<br>GGGGGGGGACCCAAACGACAGGGGGCGCCCCAGAGGCTAAGGTCGGCCACGCCACTCGCGGGTGGGCTCGTGTTACAG<br>CACACCAGCCCGTTCTTTTCCCCCCCTCCCACCCTTAGTCAGACTCTGTTACTTACCCGTCCGACCACCAACTGCCCC<br>CTTATCTAAGGGCCGGCTGGAAGACCGCCAGGGGGTCGGCCGGTGTCGCTGTAACCCCCCACGCCAATGACCCACGTA<br>CTCCAAGAAGGCATGTGTCCCACCCCGCCTGTGTTTTTGTGCCTGGCTCTCTATGCTTGGGTCTTACTGCCTGGGGGG<br>GGGGAGTGCGGGGGAGGGGGGGTGTGGAAGGAAATGCACGGCGCGTGTGTACCCCCCCTAAAGTTGTTCCTAAAGCGA<br>GGATATGGAGGAGTGGCGGGTGCCGGGGGACCGGGGTGATCTCTGGCACGCGGGGGTGGGAAGGGTCGGGGGAGGGGG<br>GATGGGGTACCGGCCCACCTGGCCGACGCGGGTGCGCGTGCCTCTGCACACCAACCCCACGTCCCCCGGCGGTCTCTA<br>AGAAGCACCGCCCCCCCTCCTTCATACCACCGAGCATGCCTGGGTGTGGGTTGGTAACCAACACGCCCATCCCCTCGT<br>CTCCTGTGATTCTCTGGCTGCACCGCATTCTTGTTTTCTAACTATGTTCCTGTTTCTGTCTCCCCCCCCCCCCACCCCT<br>CCGCCCCACCCCCCAACACCCACGTCTGTGGTGTGGCCGACCCCCTTTTGGGCGCCCCGTCCCGCCCCGCCACCCCTC<br>CCGTCCTTTGTTGCCCTATAGTGTAGTTAACCCCCCCCGCCCTTTGTGGCGGCCAGAGGCCAGGTCAGTCCGGGCGGG |

-continued

| SEQUENCES |
| --- |
| CAGGCGCTCGCGGAAACTTAACACCCACACCCAACCCACTGTGGTTCTGGCTCCATGCCAATGGCAGGATGCTTTCGG<br>GGATCGGTGGTCAGGCAGCCCGGGCCGCGGCTCTGTGGTTAACACCAGAGCCTGCCCAACATGGCACCCCCACTCCCA<br>CGCACCCCCACTCCCACGCACCCCCACTCCCACGCACCCCCACTCCCACGCACCCCCACTCCCACGCACCCCCACTCC<br>CACGCACCCCCACTCCCACGCACCCCCACTCCCACGCACCCCCACTCCCACGCACCCCCGAGATCCATCCAACACAGA<br>CAGGGAAAAGATACAAAAGTAAACCTTTATTTCCCAATAGACAGCAAAAATCCCCTGAGTTTTTATTAGGGCCAACA<br>CTAAAGACCCGCTGGTGTGTGGTGCCCGTGTCTTTCACTTTTCCCCTCCCCGACACGGATTGGCTGGTGTAGTGGGCG<br>CGGCCAGAGACCACCCAGCGCCCGACCCCCCCCTCCCCACAAACACGGGGGGCGTCCCTTATTGTTTTCCCTCGTCCC<br>GGGTCGACGCCCCCTGCTCCCCGGACCACGGGTGCCGAGACCGCAGGCTGCGGAAGTCCAGGGCGCCCACTAGGGTGC<br>CCTGGTCGAACAGCATGTTCCCCACGGGGGTCATCCAGAGGCTGTTCCACTCCGACGCGGGGGCCGTCGGGTACTCGG<br>GGGGCATCACGTGGTTACCCGCGGTCTCGGGGAGCAGGGTGCGGCGGCTCCAGCCGGGGACCGCGGCCCGCAGCCGGG<br>TCGCCATGTTTCCCGTCTGGTCCACCAGGACCACGTACGCCCCGATGTTCCCCGTCTCCATGTCCAGGATGGGCAGGC<br>AGTCCCCCGTGATCGTCTTGTTCACGTAAGGCGACAGGGCGACCACGCTAGAGACCCCCGAGATGGGCAGGTAGCGCG<br>TGAGGCCGCCCGCGGGGGCGGCCCCGGAAGTCTCCGCGTGGCGCGTCTTCCGGGCACACTTCCTCGGCCCCCGCGGCC<br>CAGAAGCAGCGCGGGGGCCGAGGGAGGTTTCCTCTTGTCTCCCTCCCAGGGCACCGACGGCCCCGCCCGAGGAGGCGG<br>AAGCGGAGGAGGACGCGGCCCCGGCGGCGGAAGAGGCGGCCCCCGCGGGAGTCGGGGCCGAGGAGGAAGAGGCAGAGG<br>AGGAAGAGGCGGAGGCCGCCGAGGACGTCAGGGGGGTCCCGGGCCCACCCTGGCCGCGCCCCCCCGGCCCTGAGTCGG<br>AGGGGGGGTGCGTCGCCGCCCTCTTGGCCCCTGCCGGCGCGAGGGGGGGACGCGTGGACTGGGGGGAGGGGTTTTCCT<br>GGCCCGACCCGCGCCTCTTCCTCGGACGCACCGCCGCCTCCTGCTCGACAGAGGCGGCGGAGGGGAGCGGGGGGGCGC<br>CGGAGGGGGCGGCGCCGCGGGAGGGCCCGTGTCCACCCTCCACGCCCGGCCCCCCCGAGCCGCGCGCCACCGTCGCAC<br>GCGCCCGGCACAGACTCTGTTCTTGGTTCGCGGCCTGAGCCAGGGACGAGTGCGACTGGGGCACACGGCGCGCGTCCG<br>CGGGGCGGGCGGCCGGCTCCGCCCCGGGGGCCGGGGCGCGGGGGCCGGGCCCCGGAGGCGGCGCTCGCACGCACGGGG<br>CCACGGCCGCGCGGGGGCGCGCGGGTCCCGACGCGGCCGAGGACGCGGTGGGCCCGGGGCGGGGGGCGGAGCCTGGCA<br>TGGGCGCCGCGGGGGGCCTGTGGGGAGAGGCCGGGGGGGAGTCGCTGATCACTATGGGGTCTCTGTTGTTTGCAAGGG<br>GGGCGGGTCTGTTGACAAGGGGGCCCGTCCGGCCCCTCGGCCGCCCCGCCTCCGCTTCAACAACCCCAACCCCAACCC<br>CAACCCCCCCGGAGGGGCCAGACGCCCCCCGCGGCGCCGCGGCTCGCGACTGGCGGGAGCCGCCGCCGCCGCTGCTGT<br>TGGTGGTGGTGTTGGTGTTACTGCTGCCGTGTGGCCCGATGGGCGCCGAGGGGGGCGCTGTCCGAGCCGCGGCCGGCT<br>GGGGGGCTGCGTGAGACGCCCCGCCCGTCACGGGGGGCGCGGCGGCGCCTCTGCGTGGGGGGGCGCGGGGCGTCCGGC<br>GGGGGGCGGGCGGTACGTAGTCTGCTGCAAGAGACAACGGGGGGCGCGATCAGGTTACGCCCCCTCCCAGGCCCTCCC<br>TTTCCGCGCCCGCCCGCCTATTCCTCCCTCCCCCCTCCTCCTCCTCCTCCCCCAGGGTCCTCGCCGCCCCCCGCCTCA<br>CCGTCGTCCAGGTCGTCGTCATCCTCGTCCGTGGTGGGCTCAGGGTGGGTGGGCGACAGGGCCCTCACCGTGTGCCCC<br>CCCAGGGTCAGGTACCGCGGGGCGAACCGCTGATTGCCCGTCCAGATAAAGTCCACGGCCGTGCCCGCCCTGACGGCC<br>TCCTCGGCCTCCATGCGGGTCTGGGGGTCGTTCACGATCGGGATGGTGCTGAACGACCCGCTGGGCGTCACGCCCACT<br>ATCAGGTACACCAGCTTGGCGTTGCACAGCGGGCAGGTGTTGCGCAATTGCATCCAGGTTTTCATGCACGGGATGCAG<br>AAGCGGTGCATGCACGGGAAGGTGTCGCAGCGCAGGTGGGGCGCGATCTCATCCGTGCACACGGCGCACACGTCGCCC<br>TCGTCGCTCCCCCCGTCCTCTCGAGGGGGGGCGCCCCCGCAACTGCCGGGGTCTTCCTCGCGGGGGGGGCTCCCCCC<br>GAGACCGCCCCCCCATCCACGCCCTGCGGCCCCAGCAGCCCCGTCTCGAACAGTTCCGTGTCCGTGCTGTCCGCCTCG<br>GAGGCGGAGTCGTCGTCATGGTGGTCGGCGTCCCCCCGCCCCCCCACTTCGGTCTCCGCCTCAGAGTCGCTGCTGTCC<br>GGCAGGTCTCGGTCGCAGGGAAACACCCAGACATCCGGGGCGGGCTAAGGGGAAAAAAGGGGGGCGGGTAAGAATGGG<br>GGGATTTCCCGCGTCAATCAGCGCCCACGAGTTCCCCCTCTCCCCCCCCCGCCTCACAAAGTCCTGCCCCCCTGCTGG<br>CCTCGGAAGAGGGGGGAGAAAGGGGTCTGCAACCAAAGGTGGTCTGGGTCCGTCCTTTGGATCCCGACCCCTCTTCTT<br>CCCTCTTCTCCCGCCCTCCAGACGCACCGGAGTCGGGGGTCCCACGGCGTCCCCCAAATATGGCGGGCGGCTCCTCCC<br>CACCCCCCTAGATGCGTGTGAGTAAGGGGGCCCTGCGTATGAGTCAGTGGGGACCACGCCCCCTAACACGGCGACCCC<br>GGTCCTTGTGTGTTTGTTGTGGGGGCGTGTCTCTGTGTATGAGTCAGGGGGTCCCACGGCGACCCCGGGCCCTGCGTC<br>TGAGTCAAAGGGGCCATGTGTATGTGTTGGGGGGTCTGTATATATAAAGTCAGGGGGTCACATGGCGACCCCCAACAG<br>GGCGACCCCGGTCCCTGTATATATATAGGGTCAGGGGGTTCCGCGCCCCCTAACATGGCGCCCCCGGTCCCTGTATATAT<br>AGTGTCACGGGGTTCCACGCCCCCTAACATGGCGCCCGCCCGGCTCCCGTGTATGAGTGGGGGTCCCCCAACATGGCG<br>GCCGGTTCCAGTGTAAGGGTCGGGGGTCCCCCAACATGGCGCCCCCCAATATGGCGCCCCCCAATATGGCGCCCCAGA<br>CATGGCGCCCGGCCCCTCACCTCGCGCTGGGGGCGGCCCTCAGGCCGGCGGGTACTCGCTCCGGGGCGGGGCTCCATG<br>GGGGTCGTATGCGGCTGGAGGGTCGCGGACGGAGGGTCCCTGGGGGTCGCAACGTAGGCGGGGCTTCTGTGGTGATGC<br>GGAGAGGGGGCGGCCCGAGTCTGCCTGGCTGCTGCGTCTCGCTCCGAGTGCCGAGGTGCAAATGCGACCAGACTGTCG<br>GGCCAGGGCTAACTTATACCCCACGCCTTTCCCCTCCCCAAAGGGGCGGCAGTGACGATTCCCCCAATGGCCGCGCGT<br>CCCAGGGGAGGCAGGCCCACCGCGGGGCGGCCCCGTCCCCGGGGACCAACCCGGCGCCCCCAAAGAATATCATTAGCA<br>TGCACGGCCCGGCCCCCGATTTGGGGGACCAACCCGGTGTCCCCCAAAGAACCCCATTAGCATGCCCCTCCCACCGAC<br>GCAACAGGGGCTTGGCCTGCGTCGGTGCCCCGGGGCTTCCCGCCTTCCCGAAGAAACTCATTACCATACCCGGAACCC<br>CAGGGGACCAATGCGGGTTCATTGAGCGACCCGCGGGCCAATGCGCGAGGGGCCGTGTGTTCCGCCAAAAAAGCAATT<br>AGCATAACCCGGAACCCCAGGGGAGTGGTTACGCGCGGCGCGGGAGGCGGGGAATACCGGGGTTGCCCATTAAGGGCC<br>GCGGGAATTGCCGGAAGCGGGAAGGGCGGCCGGGGCCGCCCATTAATGAGTTTCTAATTACCATACCGGGAAGCGGAA<br>CAAGGGTTACCTGGGACTGTGCGGTTGGGACGGCGCCCGTGGGCCCGGGCGGCCGGGGGCGGCGGGGGCCGCGATGGC<br>GGCGGCGGCGGGCCATGGAGACAGAGAGCGTGCCGGGGTGGTAGAGTTTGACAGGCAAGCATGTGCGTGCAGAGGCGA<br>GTAGTGCTTGCCTGTCTAACTCGCTCGTCTCGGCCGCGGGGGGCCCGGGCTGCCGCCGCCGCGCTTTAAAGGGCCGCG<br>CGCGACCCCCGGGGGGTGTGTTTTGGGGGGGGCCCGTTTTCGCTCCTCCCCCCGCTCCTCCCCCCGCTCCTCCCCCCG<br>CTCCTCCCCCCGCTCCTCCCCCCGCTCCTCCCCCCGCTCCTCCCCCCGCTCCTCCCCCCGCTCCTCCCCCCGCTCCTC<br>CCCCCGCTCCTCCCCCCGCTCCTCCCCCCGCTCCTCCCCCCGCTCCTCCCCCCGCTCCTCCCCCCGCTCCTCCCCCCG<br>CTCCTCCCCCCGCTCCTCCCCCCGCTCCCGCGGCCCCGCCCCCAACGCCCGCCGCGCGCGCGCACGCCGCCCGGACCG<br>CCGCCCGCCTTTTTTGCGCGCGCCCCGCCCGCGGGGGGCCCGGGCTGCCACAGGTGTAACAACACACACGGCTCATCC<br>ACACGTCACACGTCACGTCATCCACCACACCTGCCCACCAACACAACTCACAGCGACAACTCACCGCGCAACAACTCC<br>TGTTCCTCATCCACACGTCACCGCGCACCCCCCGCTCCTCCAGACGTCCCCCAGCGCAACACGCCGCTCCTGCTACAC<br>ACCACCGCCCCCTCCCCAGCCCCAGCCCTCCCCAGCCCCAGCCCTCCCCAGCCCCAGCCCTCCCCGGCCCCAGCCCTC<br>CCCGGCCCCAGCCCTCCCCGGCCCCAGCCCTCCCCGGCCCCAGCCCTCCCCGGCCCCAGCCCTCCCCGCCGCGTCCCG<br>CGCTCCCTCGGGGGGGTTCGGGCATCTCTACCTCAGTGCCGCCAATCTCAGGTCAGAGATCCAAACCCTCCGGGGGCG<br>CCCGCGCACCACCACCGCCCCTCGCCCCCTCCCGCCCCTCGCCCCCTCCCGCCCCTCGCCCCCTCCCGCCCCTCGCCC<br>CCTCCCGCCCCTCGCCCCCTCCCGCCCCTCGCCCCCTCCCGCCCCTCGCCCCCTCCCGCCCCTCGCCCCCTCCCGCCC<br>CTCGCCCCCTCCCGCCCCTCGCCCCCTCCCGCCCCTCGCCCCCTCCCGCCCCTCGCCCCCTCCCGCCCCTCGCCCCCT<br>CCCGCCCCTCGCCCCCTCCCGCCCCTCGCCCCCTCCCGCCCCTCGCCCCCTCCCGCCCCTCGCCCCCTCCCGCCCCTC<br>GCCCCCTCCCGCCCCTCGCCCCCTCCCGCCCCTCAAATAAACAACGCTACTGCAAAACTAAATCAGGTCGTTGTCGTT<br>TATTGTGTCTTCGGGTTTCGCAAGCGCCCCGCCCCGTCCCGGCCCGTTACAGCACCCCGTCCCCCTCGAACGCGCCGC<br>CGTCGTCGTCGTCCCAGGCGCCTTCCCAGTCCACAACTTCCCGTCGCGGGGGCGTGGCCAAGCCCGCCTCCGCCCCCA |

-continued

| SEQUENCES |
|---|
| GCACCTCCACGGCCCCCGCCGCCGCCAGCACGGTGCCGCTGCGGCCCGTGGCCGAGGCCCAGCGAATCCCGGGCAACG<br>CCGGCGGCAGGGCCCCCGGGCCGTCGTCGYCGCCGCGCAGCACCAGCGGGGGGGCGTCGTCGTCGGGCTCCAGCAGGG<br>CGCGGGCGCAAAAGTCCCTCCGCGGCCCGCGCCACCGGGCCGGGCCGGCGCGCACCGCCTCGCGCCCCAGCGCCACGT<br>ACACGGGCCGCAGCGGCGCGCCCAGGCCCCAGCGCGCGCAGGCGCGGTGCGAGTGGGCCTCCTCCTCGCAGAAGTCCG<br>GCGCGCCGGGCGCCATGGCGTCGGTGGTCCCCGAGGCCGCCGCCCGGCCGTCCAGCGCCGGCAGCACGGCCCGGCGGT<br>ACTCGCGCGGGGACATGGGCACCGGCGTGTCCGGGCCGAAGCGCGTGCGCACGCGGTAGCGCACGTTGCCGCCGCGGC<br>ACAGGCGCAGCGGCGGCGCGTCGGGGTACAGGCGCGCGTGCGCGGCCTCCACGCGCGCGAAGACCCCCGGGCCGAACA<br>CGCGGCCCGGGGCCAGCACCGTGCGGCGCAGGTCCCGCGCCGCCGGCCAGCGCACGGCGCACTGCACGGCGGGCAGCA<br>GGTCGCACGCCAGGTAGGCGTGCTGCCGCGACACCGCGGGCCCGTCGGCGGGCCAGTCGCAGGCGCGCACGGTGTTGA<br>CCACGATGAGCCGCCGGTCGCCGGCGCTGGCGAGCAGCCCCAGAAACTCCACGGCCCCGGCGAAGGCCAGGTCCCGCG<br>TGGACAGCAGCAGCACGCCCTGCGCGCCCAGCGCCGACACGTCGGGGGCGCCGGTCCAGTTGCCCGCCCAGGCGGCCG<br>TGTCCGGCCCGCACAGCCGGTTGGCCAGGGCCGCCAGCAGGCAGGACAGCCCGCCGCGCTCGGCGGACCACTCCGGCG<br>GCCCCCCCGAGGCCCCGCCGCCGGCCAGGTCCTCGCCCGGCAGCGGCGAGTACAGCACCACCACGCGCACGTCCTCGG<br>GGTCGGGGATCTGGCGCATCCAGGCCGCCATGCGGCGCAGCGGGCCCGAGGCGCGCAGGGGGCCAAAGAGGCGGCCCC<br>CGGCGGCCCCGTGGGGGTGGGGGTTATCGTCGTCGTCGCCGCCGCCGCACGCGGCCTGGGCGGCGGGGGCGGGCCCGG<br>CGCACCGCGCGGCGATCGAGGCCAGGGCCCGCGGGTCAAACATGAGGGCCGGTCGCCAGGGGACGGGGAACAGCGGGT<br>GGTCCGTGAGCTCGGCCACGGCGCGCGGGGAGCAGTAGGCCTCCAGGGCGGCGGCCGCGGGCGCCGCCGTGTGGCTGG<br>GCCCCGGGGGCTGCCGCCGCCAGCCGCCCAGGGGGTCGGGGCCCTCGGCGGGCCGGCGCGACACGGCCACGGGGCGCG<br>GGCGGGCCTGCGCCGCGGCGGCCCGGGGCGCCGCGGGCTGGGCGGGGGCGGGCTCGGGCCCCGGGGGCGTGGAGGGGG<br>GCGCGGGCGCGGGGAGGGGGGCGCGGGCGTCCGAGCCGGGGGCGTCCGCGCCGCTCTTCTTCGTCTTCGGGGGTCGCG<br>GGCCGCCGCCTCCGGGCGGCCGGGCCGGGCCGGGACTCTTGCGCTTGCGCCCCTCCCGCGGCGCGGCGGAGGCGGCGG<br>CGGCCGCCAGCGCGTCGGCGGCGTCCGGTGCGCTGGCGGCCGCCGCCAGCAGGGGGCGCAGGCTCTGGTTCTCAAACA<br>GCAGGTCCGCGGCGGCGGCGGCCGCGGAGCTCGGCAGGCGCGGGTCCCGCGGCAGCGCGGGGCCCAGGGCCCCGGCGA<br>CCAGGCTCACGGCGCGCACGGCGGCCACGGCGGCCTCGCTGCCGCCGGCCACGCGCAGGTCCCCGCGCAGGCGCATGA<br>GCACCAGCGCGTCGCGCACGAACCGCAGCTCGCGCAGCCACGCGCGCAGGCGGGGCGCGTCGGCGTGCGGCGGCGGCG<br>GGGAAGCGGGGCCCGCGGGTCCCTCCGGCCGCGGGGGGCTGGCGGGCCGGGCCCCGGCCAGCCCCGGGACGGCCGCCA<br>GGTCGCCGTCGAAGCCCTCGGCCAGCGCCTCCAGGATCCCGCGGCAGGCGGCCAGGCACTCCACGGCCACGCGGCCGG<br>CCTGGGCGCGGCGCCCGGCGTCGTCGTCGGCGTCGGCGTGGCGGGCGGCGTCGGGGTCGTCGCCCCCCGCGGGGGAGG<br>CGGGCGCGGCGGACAGCCGCCCCAGGGCGGCGAGGATCCCCGCGGCGCCGTACCCGGCGGGCACCGCGCGCTCGCCCG<br>GTGCGGCGACGACGGCGGCGGCGACCCCCTCGTCATCTGCGCCGGCGCCGGGGCTCCCCGCGGCCCCCGTCAGCGCCG<br>CGTTCTCGCGCGCCAACAGGGGCGCGTAGGCGCGGCGCAGGCTGGTCAGCAGGAAGCCCTTCTGCGCGCGGTCGTATC<br>GGCGGCTCATGGCCACGGCGGCCGCCGCGTGCGCCAGGCCCCAGCCGAAGCGGCCGGCCGCCATGGCGTAGCCCAGGT<br>GGGGCACGGCCCGCGCCACGCTGCCGGTGATGAAGGAGCTGCTGTTGCGCGCGGCGCCCGAGATCCGGAAGCAGGCCT<br>GGTCCAGCGCCACGTCCCCGGGGACCACGCGCGGGTTCTGGAGCCACCCCATGGCCTCCGCGTCCGGGGTGTACAGCA<br>GCCGCGTGATCAGGGCGTACTGCTGCGCGGCGTCGCCCAGCTCGGGCGCCCACACGGCCGCCGGGGCGCCCGAGGCCT<br>CGAACCGGCGTCGCGCCTCCTCCGCCTCGGGCGCCCCCAGAGGCCCGGGCGGCTGTCGCCCAGGCCGCCGTACAGCA<br>CCCGCCCCGGGGGCGGGGGCCCGGCGCCGGGCCACGGCTCCCCGCTGACGTACCCGTCGCGATAGCGCGCGTAGAAGG<br>CGCCGGAGGCCGCGTCGGCGTCCAGCTCGACCCGCCGGGGCTGCCCGGCCGTGAAGCGGCCCGTGGCGTCGCGGCCGG<br>CCACCGCCGCGCGGGCCCGGCGGCGCTCGATGCGGCCCGCGGAGGCCGCGGGGGTCCTCGCCGCCGCCCGGGGCTTGG<br>GCGCGGCCTCGGAGAGGGGGGGTGGCCCGGGCGGGGGCGGCGTCCGCCCGGGGGCTTCCGGCGCCGCGCTCGACGGAC<br>CCCGCCCGACGGCCCGCGCCTCGCGTGCGCGGTCGGCCGCGTCGTTGCCGTCGTCGTCCTCGTCCTCGTCGGACGACG<br>AGGACGAAGAGGATGCGGACGACGAGGACGAGGACCCGGAGTCCGACGAGGTCGATGACGCCGATGGCCGCCGCCGGC<br>CGTGACGACGTCTCCGCGGCGGCTGGGCCGGCGGGCGCGGCGACAGGCGGTCCGTGGGGTCCGGATACGCGCCGCGTA<br>GCGGGGCCTCCCGTGCGCGGCCCCGGGCCGGGGCCCGGTCGCCGGCGGCGTCGGCTGCGTCGTCGTACTCGTCCCCGT<br>CATCGTCGTCGGCTCGAAAGGCGGGGGTCCGGGGCGGCGAGGCCGCGGGGTCGGGCGTCGGGATCGTCCGGACGGCCT<br>CCTCTACCATGGAGGCCAGCAGGGCCAGCTGTCGCGGCGAGACGGCGTCCCCGGCGTCCTCGCCGGCGTCGGTGCCCG<br>CCGCGGGGGCCCTCCCGTCCCGCCGGGCGTCGTCGAGGTCGTGGGGGTGGTCGGGGTCGTGGTCGGGGTCGTCCCCGC<br>CCTCCTCCGTCTCCGCGCCCCACCCGAGGGCCCCCCGCTCGTCGCGGTCTGGGCTCGGGGTGGGCGGCGGCCCGTCGG<br>TGGGGCCCGGGGAGCCGGGGCGCTGCTTGTTCTCCGACGCCATCGCCGATGCGGGGCGATCCTCCGGGGATACGGCTG<br>CGACGGCGGACGTAGCACGGTAGGTCACCTACGGACTCTCGATGGGGAGGGGGCGAGACCCACGGACCCCGACGACCC<br>CCGCCGTCGACGCGGAACTAGCGCGGACCGGTCGATGCTTGGGTGGGAAAAAGGACAGGGACGGCCGATCCCCCTCCC<br>GCGCTTCGTCCGCGTATCGGCGTCCCGGCGCGGCGAGCGTCTGACGGTCTGTCTCTGGCGGTCCCGCGTCGGGTCGTG<br>GATCCGTGTCGGCAGCCGCGCTCCGTGTGGACGATCGGGGCGTCCTCGGGCTCATATAGTCCCAGGGGCCGGCGGGAA<br>GGAGGAGCAGCGGAGGCCGCCGGCCCCCCGCCCCCCAGGCGGGCCCGCCCCGAACGGAATTCCATTATGCACGACCCC<br>GCCCCGACGCCGGCACGCCGGGGGCCCGTGGCCGCGGCCCGTTGGTCGAACCCCCGGCCCCGCCCATCCGCGCCATCT<br>GCCATGGGCGGGGCGCGAGGGCGGGTGGGCCCGCGCCCCGCCCCGCATGGCATCTCATTACCGCCCGATCCGGTGGTT<br>TCCGCTTCCGTTCCGCATGCTAACGAGGAACGGGCCGGGGGCGGGGCCCGGGCCCCGACTTCCCGGTTCGGCGGTAAT<br>GAGATACGAGCCCCGCGCGCCCGTTGGCCGTCCCCGGGCCCCCGGTCCCGCCCGCCGGACGTTGGGACCAACGGGACG<br>GCGGGCGGCCCAAGGGCCGCCCGCCTTGCCGCCCCCCCATTGGCCGGCGGGCGGGACCGCCCCAAGGGGGCGGGGCCG<br>CCGGGTAAAAGAAGTGAGAACGCGAAGCGTTCGCACTTCGTCCCAATATATATATATTATTAGGGCGAAGTGCGAGCA<br>CTGGCGCCGTGCCCGACTCCGCGCCGGCCCCGGGGGCGGGCCCGGGCGGCGGGGGGCGGGTCTCTCCGGCGCACATAA<br>AGGCCCGGCGCGACCGACGCCCGCAGACGGCGCCGGCCACGAACGACGGGAGCGGCTGCGGAGCACGCGGACCGGGAG<br>CGGGACTCGCAGAGGGCCGTCGGAGCGGACGGCGTCGGCATCGCGACGCCCCGGCTCGGGATCGGGATCGCATCGGAA<br>AGGGACACGCGGACAAGACCCACCCACCCCACCCACGAAACACAGGGGACGCACCCCGGGGGCCTCCGACGACAGAAA<br>CCCACCGGTCCGCCTTTGTGCACGGGTAAGCACCTTGGGTGGGCGGAGGAGGGGGGACACGGGGGCGGAGGAGGGGGG<br>ACACGGGGGCGGAGGAGGGGGGACGCGGGGGCGGAGGAGGGGGGACGCGGGGGCGGAGGAGGGGGGACACGGGGGCGG<br>AGGAGGGGGCTCACCCGCGTTCGTGCCTTCCCGCAGGAGGAACGTCCTCGTCGAGGCGACCGGCGGCGACCGTTGCGT<br>GGACCGCTTCCTGCTCGTCGGGCGGGGGGAAGCCACTGTGGTCCTCCGGGACGTTTTCTGGATGGCCGACATTTCCCC<br>AGGCGCTTTTGCGCCTTGTGTAAAAGCGCGGCGTCCCGCTCTCCGATCCCCGCCCCTGGGCACGCGCAAGCGCAAGCG<br>CCCTTCCCGCCCCCTCTCATCGGAGTCTGAGGTAGAATCCGATACAGCCTTGGAGTCTGAGGTCGAATCCGAGACAGC<br>ATCGGATTCGACCGAGTCTGGGGACCAGGATGAAGCCCCCCGCATCGGTGGCCGTAGGGCCCCCCGGAGGCTTGGGGG<br>GCGGTTTTTTCTGGACATGTCGGCGGAATCCACCACGGGGACGGAAACGGATGCGTCGGTGTCGGACGACCCCGACGA<br>CACATCCGACTGGTCTTATGACGACATTCCCCCACGACCCAAGCGGGCCCGGGTAAACCTGCGGCTCACGAGCTCTCC<br>CGATCGGCGGGATGGGGTTATTTTTCCTAAGATGGGGCGGGTCCGGTCTACCCGGGAAACGCAGCCCCGGGCCCCCAC<br>CCCGTCGGCCCCAAGCCCAAATGCAATGCTACGGCGCTCGGTGCGCCAGGCCCAGAGGCGGAGCAGCGCACGATGGAC<br>CCCCGACCTGGGCTACATGCGCCAGTGTATCAATCAGCTGTTTCGGGTCCTGCGGGTCGCCCGGGACCCCCACGGCAG<br>TGCCAACCGCCTGCGCCACCTGATACGCGACTGTTACCTGATGGGATACTGCCGAGCCCGTCTGGCCCCGCGCACGTG |

-continued

| SEQUENCES |
| --- |
| GTGCCGTTTGCTGCAGGTGTCCGGCGGAACCTGGGGCATGCACCTGCGCAACACCATACGGGAGGTGGAGGCTCGATT<br>CGACGCCACCGCGGAACCCGTGTGCAAGCTTCCTTGTTTGGAGACCAGACGGTACGGCCCGGAGTGTGATCTTAGTAA<br>TCTCGAGATTCATCTCAGCGCGACAAGCGATGATGAAATCTCCGATGCCACCGATCTGGAGGCCGCCGGTTCGGACCA<br>CACGCTCGCGTCCCAGTCCGACACGGAGGATGCCCCCTCCCCCGTTACGCTGGAAACCCCAGAACCCCGCGGGTCCCT<br>CGCTGTGCGTCTGGAGGATGAGTTTGGGGAGTTTGACTGGACCCCCCAGGAGGGCTCCCAGCCCTGGCTGTCTGCGGT<br>CGTGGCCGATACCAGCTCCGTGGAACGCCCGGGCCCATCCGATTCTGGGGCGGGTCGCGCCGCAGAAGACCGCAAGTG<br>TCTGGACGGCTGCCGGAAAATGCGCTTCTCCACCGCCTGCCCCTATCCGTGCAGCGACACGTTTCTCCGGCCGTGAGT<br>CCGGTCGCCCCGACCCCCTTGTATGTCCCCAAAATAAAAGACCAAAATCAAAGCGTTTGTCCCAGCGTCTTAATGGCG<br>GGAAGGGCGGAGAGAAACAGACCACGCGTACATGGGGGGTGTTTGGGGGTTTATTGACATCGGGGCTACAGGGTGGTA<br>ACCGGATAGCAGATGTGAGGAAGTCTGGGCCGTTCGCCGCGAACGGCGATCAGAGGGTCCGTTTCTTGCGGACCACGG<br>CCCGGTGATGTGGGTTGTTCGTCTGGGATCTCGGGCATGCCCATACACGCACAACACGGACGCCGCACCGGATGGGAC<br>GTCGTAAGGGGGCCTGGGGTAGCTGGGTGGGGTTTGTGCAGAGCAATCAGGGACCGCAGCCAGCGCATACAATCGCGC<br>TCCCGTCCGTTTGTCCCGGGCAGTACCACGCCGTACTGGTATTCGTACCGGCTGAGCAGGGTCTCCAGGGGGTGGTTG<br>GGGGCCGCGGGGAACGGGGTCCACGCCACGGTCCACTCGGGCAAAAACCGAGTCGGCACGGCCCACGGTTCTCCCACC<br>CACGCGTCTGGGGTCTTGATGGCGATAAATCTTACCCCGAGCCGGATTTTTTGGGCGTATTCGAGAAACGGCACACAC<br>AGATCCGCCGCGCCTACCACCCACAAGTGGTAGAGGCGAGGGGGGCTGGGTTGGTCTCGGTGCAGCAGTCGGAAGCAC<br>GCCACGGCGTCCACGACCTCGGTGCTCTCCAAGGGGCTGTCCTCCGCAAACAGGCCCGTGGTGGTGTTTGGGGGGCAG<br>CGACAGGACCTAGTGCGCACGATCGGGCGGGTGGGTTTGGGTAAGTCCATCAGCGGCTCGGCCAACCGTCGAAGGTTG<br>GCCGGACGAACGACGACCGGGGTACCCAGGGGTTCTGATGCCAAAATGCGGCACTGCCTAAGCAGGAAGCTCCACAGG<br>GCCGGGCTTGCGTCGACGGAAGTCCGGGGCAGGGCGTTGTTCTGGTCAAGGAGGGTCATTACGTTGACGACAACAACG<br>CCCATGTTGGTATATTACAGGCCCGTGTCCGATTTGGGGCACTTGCAGATTTGTAAGGCCACGCACGGCGGGGAGACA<br>GGCCGACGCGGGGGCTGCTCTAAAAATTTAAGGGCCCTACGGTCCACAGACCCGCCTTCCCGGGGGGGCCCTTGGAGC<br>GACCGGCAGCGGAGGCGTCCGGGGGAGGGGAGGGTGATTTACGGGGGGGTAGGTCAGGGGGTGGGTCGTCAAACTGCC<br>GCTCCTTAAAACCCCGGGGCCCGTCGTTCGGGGTGCTCGTTGGTTGGCACTCACGGTGCGGCGAATGGCCTGTCGTAA<br>GTTTTGTCGCGTTTACGGGGGACAGGGCAGGAGGAAGGAGGAGGCCGTCCCGCCGGAGACAAAGCCGTCCCGGGTGTT<br>TCCTCATGGCCCCTTTTATACCCCAGCCGAGGACGCGTGCCTGGACTCCCCGCCCCCGGAGACCCCCAAACCTTCCCA<br>CACCACACCACCCGGCGATGCCGAGCGCCTGTGTCATCTGCAGGAGATCCTGGCCCAGATGTACGGAAACCAGGACTA<br>CCCCATAGAGGACGACCCCAGCGCGGATGCCGCGGACGATGTCGACGAGGACGCCCCGGACGACGTGGCCTATCCGGA<br>GGAATACGCAGAGGAGCTTTTTCTGCCCGGGGACGCGCCCGGTCCCCTTATCGGGGCCAACGACCACATCCCTCCCCC<br>GTGTGGCGCATCTCCCCCCGGTATACGACGACGCAGCCGGGATGAGATTGGGGCCACGGGATTTACCGCGGAAGAACT<br>GGACGCCATGGACAGGGAGGCGGCTCGAGCCATCAGCCGCGGCGGCAAGCCCCCCTCGACCATGGCCAAGCTGGTGAC<br>TGGCATGGGCTTTACGATCCACGGAGCGCTCACCCCAGGATCGGAGGGGTGTGTCTTTGACAGCAGCCACCCAGATTA<br>CCCCCAACGGGTAATCGTGAAGGCGGGGTGGTACACGAGCACGAGCCACGAGGCGCGACTGCTGAGGCGACTGGACCA<br>CCCCGCGATCCTGCCCCTCCTGGACCTGCATGTCGTCTCCGGGGTCACGTGTCTGGTCCTCCCCAAGTACCAGGCCGA<br>CCTGTATACCTATCTGAGTAGGCGCCTGAACCCGCTGGGACGCCCGCAGATCGCAGCGGTCTCCCGGCAGCTCCTAAG<br>CGCCGTTGACTACATTCACCGCCAGGGCATTATCCACCGCGACATTAAGACCGAAAATATTTTTATTAACACCCCCGA<br>GGACATTTGCCTGGGGGACTTTGGTGCCGCGTGCTTCGTGCAGGGTTCCCGATCAAGCCCCTTCCCCTACGGAATCGC<br>CGGAACCATCGACACCAACGCCCCCGAGGTCCTGGCCGGGGATCCGTATACCACCACCGTCGACATTTGGAGCGCCGG<br>TCTGGTGATCTTCGAGACTGCCGTCCACAACGCGTCCTTGTTCTCGGCCCCCCGCGGCCCCAAAAGGGGCCCGTGCGA<br>CAGTCAGATCACCCGCATCATCCGACAGGCCCAGGTCCACGTTGACGAGTTTTCCCCGCATCCAGAATCGCGCCTCAC<br>CTCGCGCTACCGCTCCCGCGCGGCCGGGAACAATCGCCCGCCGTACACCCGACCGGCCTGGACCCGCTACTACAAGAT<br>GGACATAGACGTCGAATATCTGGTTTGCAAAGCCCTCACCTTCGACGGCGCGCTTCGCCCCAGCGCCGCAGAGCTGCT<br>TTGTTTGCCGCTGTTTCAACAGAAATGACCGCCCCCAGGGGGCGGTGCTGTTTGCGGGTTGGCACAAAAAGACCCCGA<br>CCCGCGTCTGTGGTGTTTTTGGCATCATGTCGCCGGGCGCCATGCGTGCCGTTGTTCCCATTATCCCATTCCTTTTGG<br>TTCTTGTCGGTGTATCGGGGGTTCCCACCAACGTCTCCTCCACCACCCAACCCCAACTCCAGACCACCGGTCGTCCCT<br>CGCATGAAGCCCCCAACATGACCCAGACCGGCACCACCGACTCTCCCACCGCCATCAGCCTTACCACGCCCGACCACA<br>CACCCCCCATGCCAAGTATCGGACTGGAGGAGGAGGAAGAGGAGGAGGGGGCCGGGGACGGCGAACATCTTGAGGGGG<br>GAGATGGGACCCGTGACACCCTACCCCAGTCCCCGGGCCCAGCCTTCCCGTTGGCTGAGGACGTCGAGAAGGACAAAC<br>CCAACCGTCCCGTAGTCCCATCCCCCGATCCCAACAACTCCCCCGCGCGCCCCGAGACCAGTCGCCCGAAGACACCCC<br>CCACCATTATCGGGCCGCTGGCAACTCGCCCCACGACCCGACTCACCTCAAAGGGACGACCCTTGGTTCCGACGCCTC<br>AACATACCCCGCTGTTCTCGTTCCTCACTGCCTCCCCCGCCCTGGACACCCTCTTCGTCGTCAGCACCGTCATCCACA<br>CCTTATCGTTTTTGTGTATTGGTGCGATGGCGACACACCTGTGTGGCGGTTGGTCCAGACGCGGGCGACGCACACACC<br>CTAGCGTGCGTTACGTGTGCCTGCCGTCCGAACGCGGGTAGGGTATGGGGCGGGGGATGGGGAGAGCCCACACGCGGA<br>AAGCAAGAACAATAAAGGCGGTGGTATCTAGTTGATATGCATCTCTGGGTGTTTTTGGGGTGTGGCGGACGCGGGGCG<br>GTCATTGGACGGGGTGCAGTTAAATACATGCCCGGGACCCATGAAGCATGCGCGACTTCCGGGCCTCGGAACCCACCC<br>GAAACGGCCAACGGACGTCTGAGCCAGGCCTGGCTATCCGGAGAAACAGCACACGACTTGGCGTTCTGTGTGTCGCGA<br>TGTCTCTGCGCGCAGTCTGGCATCTGGGGCTTTTGGGAAGCCTCGTGGGGGCTGTTCTTGCCGCCACCCATCGGGGAC<br>CTGCGGCCAACACAACGGACCCCTTAACACACGCCCCAGTGTCCCCTCACCCCAGCCCCCTGGGGGGCTTTGCCGTCC<br>CCCTCGTAGTCGGTGGGCTGTGCGCCGTAGTCCTGGGGGCGGCGTGTCTGTTTGAGCTCCTGCGTCGTACGTGCCGCG<br>GGTGGGGGCGTTACCATCCCTACATGGACCCAGTTGTCGTATAATTCCCCCCCCCCCCCCCTTCTCCGCATGGGTGAT<br>GTCGGGTCCAAACTCCCGACACCACCAGCTGGCATGGTATAAATCACCGGTGCGCCCCCCAAACCATGTCCGGCAGGG<br>GGATGGGGGGGCGAATGCGGAGGGCACCCAACAACACCGGGCTAACCAGGAAATCCGTGGCCCCGGCCCCCAATAAAG<br>ATCGCGGTAGCCCGGCCGTGTGACACTATCGTCCATACCGACCACACCGACGAATCCCCTAAGGGGGAGGGGCCATTT<br>TACGAGGAGGAGGGGTATAACAAAGTCTGTCTTTAAAAAGCAGGGGTTAGGGAGTTGTTCGGTCATAAGCTTCAGCGC<br>GAACGACCAACTACCCCGATCATCAGTTATCCTTAAGGTCTCTTTTGTGTGGTGCGTTCCGGTATGGGGGGGGCTGCC<br>GCCAGGTTGGGGGCCGTGATTTTGTTTGTCGTCATAGTGGGCCTCCATGGGGTCCGCGGCAAATATGCCTTGGCGGAT<br>GCCTCTCTCAAGATGGCCGACCCCAATCGCTTTCGCGGCAAAGACCTTCCGGTCCTGGACCAGCTGACCGACCCTCCG<br>GGGGTCCGGCGCGTGTACCACATCCAGGCGGGCCTACCGGACCCGTTCCAGCCCCCCAGCCTCCCGATCACGGTTTAC<br>TACGCCGTGTTGGAGCGCGCCTGCCGCAGCGTGCTCCTAAACGCACCGTCGGAGGCCCCCCAGATTGTCCGCGGGGCC<br>TCCGAAGACGTCCGGAAACAACCCTACAACCTGACCATCGCTTGGTTTCGGATGGGAGGCAACTGTGCTATCCCCATC<br>ACGGTCATGGAGTACACCGAATGCTCCTACAACAAGTCTCTGGGGGCCTGTCCCATCCGAACGCAGCCCCGCTGGAAC<br>TACTATGACAGCTTCAGCGCCGTCAGCGAGGATAACCTGGGGTTCCTGATGCACGCCCCCGCGTTTGAGACCGCCGGC<br>ACGTACCTGCGGCTCGTGAAGATAAACGACTGGACGGAGATTACACAGTTTATCCTGGAGCACCGAGCCAAGGGCTCC<br>TGTAAGTACGCCCTCCCGCTGCGCATCCCCCCGTCAGCCTGCCTGTCCCCCCAGGCCTACCAGCAGGGGGTGACGGTG<br>GACAGCATCGGGATGCTGCCCCGCTTCATCCCCGAGAACCAGCGCACCGTCGCCGTATACAGCTTGAAGATCGCCGGG<br>TGGCACGGGCCCAAGGCCCCATACACGAGCACCCTGCTGCCCCCGGAGCTGTCCGAGACCCCCAACGCCACGCAGCCA<br>GAACTCGCCCCGGAAGACCCCGAGGATTCGGCCCTCTTGGAGGACCCCGTGGGGACGGTGGCGCCGCAAATCCCACCA |

-continued

| SEQUENCES |
|---|
| AACTGGCACATACCGTCGATCCAGGACGCCGCGACGCCTTACCATCCCCCGGCCACCCCGAACAACATGGGCCTGATC<br>GCCGGCGCGGTGGGCGGCAGTCTCCTGGCAGCCCTGGTCATTTGCGGAATTGTGTACTGGATGCGCCGCCGCACTCAA<br>AAAGCCCCAAAGCGCATACGCCTCCCCCACATCCGGGAAGACGACCAGCCGTCCTCGCACCAGCCCTTGTTTTACTAG<br>ATACCCCCCCTTAATGGGTGCGGGGGGGTCAGGTCTGCGGGGTTGGGATGGGACCTTAACTCCATATAAAGCGAGTCT<br>GGAAGGGGGGAAAGGCGGACAGTCGATAAGTCGGTAGCGGGGGACGCGCACCTGTTCCGCCTGTCGCACCCACAGCTT<br>TTTTTGCGAACCGTCCCGTTCCGGGATGCCGTGCCGCCCGTTGCAGGGCCTGGTGCTCGTGGGCCTCTGGGTCTGTGC<br>CACCAGCCTGGTTGTCCGTGGCCCCACGGTCAGTCTGGTATCAAACTCATTTGTGGACGCCGGGGCCTTGGGGCCCGA<br>CGGCGTAGTGGAGGAAGACCTGCTTATTCTCGGGGAGCTTCGCTTTGTGGGGGACCAGGTCCCCCACACCACCTACTA<br>CGATGGGGTCGTAGAGCTGTGGCACTACCCCATGGGACACAAATGCCCACGGGTCGTGCATGTCGTCACGGTGACCGC<br>GTGCCCACGTCGCCCCGCCGTGGCTTTCGCCCTGTGTCGCGCGACCGACAGCACTCACAGCCCCGCATATCCCACCCT<br>GGAGCTGAATCTGGCCCAACAGCCGCTTTTGCGGGTCCGGAGGGCGACGCGTGACTATGCCGGGGTGTACGTGTTACG<br>CGTATGGGTCGGGGACGCACCAAACGCCAGCCTGTTTGTCCTGGGGATGGCCATAGCCGCCGAAGGGACTCTGGCGTA<br>CAACGGCTCGGCCCATGGCTCCTGCGACCCGAAACTGCTTCCGTATTCGGCCCCGCGTCTGGCCCCGGCGAGCGTATA<br>CCAACCCGCCCCTAACCCGGCCTCCACCCCCTCGACCACCACCTCCACCCCCTCGACCACCATCCCCGCTCCCTCGAC<br>CACCATCCCCGCTCCCCAAGCATCGACCACACCCTTCCCCACGGGAGACCCAAAACCCCAACCTCACGGGGTCAACCA<br>CGAACCCCCATCGAATGCCACGCGAGCGACCCGCGACTCGCGATACGCGCTAACGGTGACCCAGATAATCCAGATAGC<br>CATCCCCGCGTCCATTATAGCCCTGGTGTTTCTGGGGAGCTGTATTTGCTTTATACACAGATGTCAACGCCGCTACCG<br>ACGCTCCCGCCGCCCGATTTACAACCCCCAGATACCCACTGGCATCTCATGCGCGGTGAACGAAGCGGCCATGGCCCG<br>CCTCGGAGCCGAGCTCAAATCGCATCCGAGCACCCCCCCCAAATCCCGGCGCCGGTCGTCACGCACACCAATGCCCTC<br>CCTGACGGCCATCGCCGAAGAGTCGGAGCCCGCGGGGGCGGCTGGGCTTCCGACGCCCCCCGTGGACCCCACGACATC<br>CACCCCAACGCCTCCCCTGTTGGTATAGGTCCACGGCCACTGGCCGGGGGCACCACATAACCGACCGCAGTCACTGAG<br>TTGGGAATAAACCGGTATTATTTACCTATATACGTGTATGTCCATTTCTTCCCCCCCCCCCCGGAAACCAAAGAAGGA<br>AACAAAGAATGGATGGGAGGAGTTCAGGAAACCGGGGAGAGGGCCCGCGGCGCATTTAAGGCGTTGTTGTGTTGACTT<br>TGGCTCTTCTGGCGGGTTGGTGCGGTGCTGTTTGTTGGGCTCCCATTTTACCCGAAGATCGGCTGCTATCCCCGGGAC<br>ATGGATCGCGGGGCGGTGGTGGGGTTTCTTCTCGGTGTTTGTGTTGTATCGTGCTTGGCGGGAACGCCCAAAACGTCC<br>TGGAGACGGGTGAGTGTCGGCGAGGACGTTTCGTTGCTTCCAGCTCCGGGGCCTACGGGGCGCGGCCCGACCCAGAAA<br>CTACTATGGGCCGTGGAACCCCTGGATGGGTGCGGCCCCTTACACCCGTCGTGGGTCTCGCTGATGCCCCCCAAGCAG<br>GTGCCCGAGACGGTCGTGGATGCGGCGTGCATGCGCGCTCCGGTCCCGCTGGCGATGGCGTACGCCCCCCCGGCCCCA<br>TCTGCGACCGGGGGTCTACGGACGGACTTCGTGTGGCAGGAGCGCGCGGCCGTGGTTAACCGGAGTCTGGTTATTTAC<br>GGGGTCCGAGAGACGGACAGCGGCCTGTATACCCTGTCTGTGGGCGACATAAAGGACCCGGCTCGCCAAGTGGCCTCG<br>GTGGTCCTGGTGGTGCAACCGGCCCCAGTTCCGACCCCACCCCCGACCCCAGCCGATTACGACGAGGATGACAATGAC<br>GAGGGCGAGGACGAAAGTCTAGCCGGCACTCCCGCCAGCGGGACCCCCCGGCTCCCGCCTCCCCCCGCCCCCCCGAGG<br>TCTTGGCCCAGCGCCCCCGAAGTCTCACACGTGCGTGGGGTGACCGTGCGTATGGAGACTCCGGAAGCTATCCTGTTT<br>TCCCCCGGGGAGGCGTTTAGCACGAACGTCTCCATCCATGCCATCGCCCACGACGACCAGACCTACACCATGGACGTC<br>GTCTGGTTGAGGTTCGACGTGCCGACCTCGTGTGCCGAGATGCGAATATACGAATCGTGTCTGTATCACCCGCAGCTC<br>CCAGAGTGTCTGTCCCCGGCCGACGCTCCGTGCGCCGCGAGTACGTGGACGTCTCGCCTGGCCGTCCGCAGCTACGCG<br>GGGTGTTCCAGAACAAACCCCCCGCCGCGCTGTTCGGCCGAGGCTCACATGGAGCCCTTCCCGGGGCTGGCGTGGCAG<br>GCGGCCTCCGTCAATCTGGAGTTCCGGGACGCGTCCCCACAACACTCCGGCCTGTATCTGTGCGTGGTGTACGTCAAC<br>GACCATATTCACGCATGGGGCCACATTACCATCAGCACCGCGGCGCAGTACCGGAACGCGGTGGTGGAACAGCCCCTC<br>CCACAGCGCGGCGCGGATTTGGCCGAGCCCACCCACCCGCACGTCGGGGCCCCTCCCCACGCGCCCCCAACCCACGGC<br>GCCCTGCGGTTAGGGGCGGTGATGGGGGCCGCCCTGCTGCTGTCTGCGCTGGGGTTGTCGGTGTGGGCGTGTATGACC<br>TGTTGGCGCAGGCGTGCCTGGCGGGCGGTTAAAAGCAGGGCCTCGGGTAAGGGGCCCACGTACATTCGCGTGGCCGAC<br>AGCGAGCTGTACGCGGACTGGAGCTCGGACAGCGAGGGAGAACGCGACCAGGTCCCGTGGCTGGCCCCCCCGGAGAGA<br>CCCGACTCTCCCTCCACCAATGGATCCGGCTTTGAGATCTTATCACCAACGGCTCCGTCTGTATACCCCCGTAGCGAT<br>GGGCATCAATCTCGCCGCCAGCTCACAACCTTTGGATCCGGAAGGCCCGATCGCCGTTACTCCCAGGCCTCCGATTCG<br>TCCGTCTTCTGGTAAGGCGCCCCATCCCGAGGCCCCACGTCGGTCGCCGAACTGGGCGACCGCCGGCGAGGTGGACGT<br>CGGAGACGAGCTAATCGCGATTTCCGACGAACGCGGACCCCCCCGACATGACCGCCCGCCCCTCGCCACGTCGACCGC<br>GCCCTCGCCACACCCGCGACCCCCGGGCTACACGGCCGTTGTCTCCCCGATGGCCCTCCAGGCTGTCGACGCCCCCTC<br>CCTGTTTGTCGCCTGGCTGGCCGCTCGGTGGCTCCGGGGGGCTTCCGGCCTGGGGGCCGTCCTGTGTGGGATTGCGTG<br>GTATGTGACGTCAATTGCCCGAGGCGCATAAAGGGCCGGTGGTCCGCCTAGCCGCAGCAAATTAAAAATCGTGAGTCA<br>CTGCGACCGCAACTTCCCACCCGGAGCTTTCTTCCGGCCTCGATGACGTCCCGGCTCTCCGATCCCAACTCCTCAGCG<br>CGATCCGACATGTCCGTGCCGCTTTATCCCACGGCCTCGCCAGTTTCGGTCGAAGCCTACTACTCGGAAAGCGAAGAC<br>GAGGCGGCCAACGACTTCCTCGTACGCATGGGCCGCCAACAGTCGGTATTAAGGCGTCGACGCAGACGCACCCGCTGC<br>GTCGGCATGGTGATCGCCTGTCTCCTCGTGGCCGTTCTGTCGGGCGGATTTGGGGCGCTCCTGATGTGGCTGCTCCGC<br>TAAAAGACCGCATCGACACGCGCGTCCTTCTTGTCGTCTCTCTTCCCCCCCATCACCCCGCAATTTGCACCCAGCCTT<br>TAACTACATTAAATTGGGTTCGATTGGCAATGTTGTCTCCCGGTTGATTTTTGGGTGGGTGGGGAGTGGGTGGGTGGG<br>GAGTGGGTGGGTGGGGAGTGGGTGGGTGGGGAGTGGGTGGGTGGGGAGTGGGTGGGTGGGGAGTGGGTGGGTGGGGAG<br>TGGGTGGGTGGGGAGTGGGTGGGTGGGGAGTGGGTGGGTGGGGAGTGGCAAGGAAGAAACAAGCCCGACCACCAGACA<br>GAAAATGTAACCATACCCAAACCGACTCTGGGGGCTGTTTGTGGGGTCGGAACCATAGGATGAACAAACCACCCCGTA<br>CCTCCCGCACCCTTGGGTGCGGTGGCTCATCGGCATCTGTCCGGTATGGGTTGTTCCCCACCCCACTTGCGTTCGGACG<br>TCTTAGAATCATGGCGGTTTTCTATGCCGACATCGGTTTTCTCCCCCGCAATAAGACACGATGCGATAAAATCTGTTT<br>GTGAAATTTATTAAGGGTACAAATTGCCCTAGCACAGGGGTGGGGTTAGGGCCGGGTCCCCACACCCAAACGCACCAA<br>ACAGATGCAGGCAGTGGGTCGAGTACAGCCCCGCGTACGAACACGTCGATGCGTGTGTCAGACAGCACCAGAAAGCAC<br>AGGCCATCAACAGGTCGTGCATATGTCGGTGGGTTTGGACGCGGGGGGCCATGGTGGTGATAAAGTTAATGGCCGCCG<br>TCCGCCAGGGCCACAGGGGCGACGTCTCTTGGTTGGCCCGGAGCCACTGGGTGTGGACCAGCCGCGCGTGGCGGCCCA<br>ACATGGCCCCTGTAGCCGGGGGCGGGGATCGCGCACGTTTGCAGCGCACATGCGAGACACCTCGACCACGGTTCGGA<br>AGAAGGCCCGGTGGTCCGCGGGCAACATCACCAGGTCGCAAGCGCCCGGGCGTCCAGAGGGTAGAGCCCTGAGTCAT<br>CCGAGGTTGGCTCATCGCCCGGGTCATGCCGCAAGTGCGTGTGGGTTGGGCTTCCGGTGGGCGGGACGCGAACCGCGG<br>TGTGGAGCCCTACGCGGGCCCGAGCGTACGCTCCATCTTGTGGGGAGAAGGGGTCTGGGCTCGCCAGGGGGGCATACT<br>TGCCCGGGCTATACAGACCCGCGAGCCGTACGTGGTTCGCGGGGGGTGCGTGGGGTCCGGGGCTCCCGGGGAGGCCGG<br>GGCTCCCGGGGAGGCCGGGGCTCCCACCGGGGTTGTCGTGGATCCCTGGGGTCACGCGGTACCCTGGGGTCTCTGGGA<br>GCTCGCGGTACTCTGGGTTCCCTAGGTTCTCGGGGTGGTCGCAGAACCCGGGGCTCCCGGGGAACACGCGGTGTCCTG<br>GGGATTGTTGGCGGTCGGACGGCTTCAGATGGCTTCGAGATCGTAGTGTCCGCACCGACTCGTAGTAGACCCGAATCT<br>CCACATTGCCCCGCCGCTTGATCATTATCACCCCGTTGCGGGGGTCCGGAGATCATGCGCGGGTGTCCTCGAGGTGCG<br>TGAACACCTCTGGGGTGCATGCCGGCGGACGGCACGCCTTTTAAGTAAACATCTGGGTCGCCCGGCCCAACTGGGGCC<br>GGGGGTTGGGTCTGGCTCATCTCGAGAGCCACGGGGGGAACCACCCTCCGCCCAGAAACTTGGGCGATGGTCGTACCC<br>GGGACTCAACGGGTTACCGGATTACGGGGACTGTCGGTCACGGTCCCGCCGGTTCTTCGATGTGCCACACCCAAGGAT |

-continued

| SEQUENCES |
| --- |
| GCGTTGGGGGCGATTTTGGGCAGCAGCCCGGGAGAGCGCAGCAGAGGACGCTCCGGGTCGTGCATGGCGGTTTTGGCT<br>GCCTCCCGGTCCTCACGCCCCCTTTTATTGATCTCATCGCGTACGTCGGCGTACGTCCTGGGCCCAACCCGCATGTTG<br>TCCAGGAAGGTGTCCGCCATTTCCAGGGCCCACGACATGCTCCCCCCGACGAGCAGGAAGCGGTCCACGCAACGGTC<br>GCCGCCGGTCGCCTCGACGAGGACGTTCCTCCTGCGGGAAGGCACGAACGCGGGTGAGCCCCCTCCTCCGCCCCCGTG<br>TCCCCCCTCCTCCGCCCCCGCGTCCCCCCTCCTCCGCCCCCGCGTCCCCCCTCCTCCGCCCCCGCGTCCCCCCTCCTC<br>CGCCCCCGCGTCCCCCCTCCTCCGCCCCCGCGTCCCCCCTCCTCCGCCCCCGTGTCCCCCCTCCTCCGCCCACCCAAG<br>GTGCTTACCCGTGCACAAAGGCGGACCGGTGGGTTTCTGTCGTCGGAGGCCCCCGGGGTGCGTCCCCTGTGTTTCGTG<br>GGTGGGGTGGGTGGGTCTTTCCGCGTGTCCCTTTCCGATGCGATCCCGATCCCGAGCCGGGGCGTCGCGATGCCGACG<br>CCGTCCGCTCCGACGGCCCTCTGCGAGTCCCGCTCCCGGTCCGCGTGCTCCGCAGCCGCTCCCGTCGTTCGTGGCCGG<br>CGCCGTCTGCGGGCGTCGGTCGCGCCGGGCCTTTATGTGCGCCGGAGAGACCCGCCCCCCGCCGCCCGGGCCCGCCCC<br>CGGGGCCGGCGCGGAGTCGGGCACGGCGCCAGTGCTCGCACTTCGCCCTAATAATATATATATATTGGGACGAAGTGC<br>GAACGCTTCGCGTTCTCACTTCTTTTACCCGGCGGCCCCGCCCCCTTGGGGCGGTCCCGCCCGCCGGCCAATGGGGGG<br>GCGGCAAGGCGGGCGGCCCTTGGGCCGCCCGCCGTCCCGTTGGTCCCAACGTCCGGCGGGCGGACCGGGGGCCCGGG<br>GACGGCCAACGGGCGCGCGGGGCTCGTATCTCATTACCGCCGAACCGGGAAGTCGGGGCCCGGGCCCCGCCCCCGGCC<br>CGTTCCTCGTTAGCATGCGGAACGGAAGCGGAAACCACCGGATCGGGCGGTAATGAGATGCCATGCGGGGCGGGGCGC<br>GGGCCCACCCGCCCTCGCGCCCCGCCCATGGCAGATGGCGCGGATGGGCGGGGCCGGGGGTTCGACCAACGGGCCGCG<br>GCCACGGGCCCCCGGCGTGCCGGCGTCGGGGCGGGGTCGTGCATAATGGAATTCCGTTCGGGGCGGGCCCGCCTGGGG<br>GGCGGGGGGCCGGCGGCCTCCGCTGCTCCTCCTTCCCGCCGGCCCCTGGGACTATATGAGCCCGAGGACGCCCCGATC<br>GTCCACACGGAGCGCGGCTGCCGACACGGATCCACGACCCGACGCGGGACCGCCAGAGACAGACCGTCAGACGCTCGC<br>CGCGCCGGGACGCCGATACGCGGACGAAGCGCGGGAGGGGGATCGGCCGTCCCTGTCCTTTTTCCCACCCAAGCATCG<br>ACCGGTCCGCGCTAGTTCCGCGTCGACGGCGGGGGTCGTCGGGGTCCGTGGGTCTCGCCCCCTCCCCATCGAGAGTCC<br>GTAGGTGACCTACCGTGCTACGTCCGCCGTCGCAGCCGTATCCCCGGAGGATCGCCCCGCATCGGCGATGGCGTCGGA<br>GAACAAGCAGCGCCCCGGCTCCCCGGGCCCCACCGACGGGCCGCCGCCCACCCCGAGCCCAGACCGCGACGAGCGGGG<br>GGCCCTCGGGTGGGGCGCGGAGACGGAGGAGGGCGGGGACGACCCCGACCACGACCCCGACCACCCCCACGACCTCGA<br>CGACGCCCGGCGGGACGGGAGGGCCCCCGCGGCGGGCACCGACGCCGGCGAGGACGCCGGGGACGCCGTCTCGCCGCG<br>ACAGCTGGCCCTGCTGGCCTCCATGGTAGAGGAGGCCGTCCGGACGATCCCGACGCCCGACCCCGCGGCCTCGCCGCC<br>CCGGACCCCCGCCTTTCGAGCCGACGACGATGACGGGGACGAGTACGACGACGCAGCCGACGCCGCCGGCGACCGGGC<br>CCCGGCCCGGGGCCGCGCACGGGAGGCCCCGCTACGCGGCGCGTATCCGGACCCCACGGACCGCCTGTCGCCGCGCCC<br>GCCGGCCCAGCCGCCGCGGAGACGTCGTCACGGCCGGCGGCGGCCATCGGCGTCATCGACCTCGTCGGACTCCGGGTC<br>CTCGTCCTCGTCGTCCGCATCCTCTTCGTCCTCGTCGTCCGACGAGGACGAGGACGACGACGGCAACGACGCGGCCGA<br>CCGCGCACGCGAGGCGCGGGCCGTCGGGCGGGGTCCGTCGAGCGCGGCGCCGGAAGCCCCCGGGCGGACGCCGCCCCC<br>GCCCGGGCCACCCCCCCTCTCCGAGGCCGCGCCCAAGCCCCGGGCGGCGGCGAGGACCCCCGCGGCCTCCGCGGGCCG<br>CATCGAGCGCCGCCGGGCCCGCGCGGCGGTGGCCGGCCGCGACGCCACGGGCCGCTTCACGGCCGGGCAGCCCCGGCG<br>GGTCGAGCTGGACGCCGACGCGGCCTCCGGCGCCTTCTACGCGCGCTATCGCGACGGGTACGTCAGCGGGGAGCCGTG<br>GCCCGGCGCCGGGCCCCCGCCCCCGGGGCGGGTGCTGTACGGCGCGGCCTGGGCGACAGCCGCCCGGGCCTCTGGGGGGC<br>GCCCGAGGCGGAGGAGGCGCGACGCCGGTTCGAGGCCTCGGGCGCCCCGGCGGCCGTGTGGGCGCCCGAGCTGGGCGA<br>CGCCGCGCAGCAGTACGCCCTGATCACGCGGCTGCTGTACACCCCGGACGCGGAGGCCATGGGGTGGCTCCAGAACCC<br>GCGCGTGGTCCCCGGGGACGTGGCGCTGGACCAGGCCTGCTTCCGGATCTCGGGCGCCGCGCGCAACAGCAGCTCCTT<br>CATCACCGGCAGCGTGGCGCGGGCCGTGCCCCACCTGGGCTACGCCATGGCGGCCGGCCGCTTCGGCTGGGGCCTGGC<br>GCACGCGGCGGCCGCCGTGGCCATGAGCCGCCGATACGACCGCGCGCAGAAGGGCTTCCTGCTGACCAGCCTGCGCCG<br>CGCCTACGCGCCCCTGTTGGCGCGCGAGAACGCGGCGCTGACGGGGGCCGCGGGGAGCCCCGGCGCCGGCGCAGATGA<br>CGAGGGGGTCGCCGCCGCCGCCGCCGCCGCACCGGGCGAGCGCGCGGTGCCCGCCGGGTACGGCGCCGCGGGGATCCT<br>CGCCGCCCTGGGGCGGCTGTCCGCCGCGCCCGCCTCCCCCGCGGGGGGCGACGACCCCGACGCCGCCCGCCACGCCGA<br>CGCCGACGACGACGCCGGGCGCCGCGCCCAGGCCGGCCGCGTGGCCGTGGAGTGCCTGGCCGCCTGCCGCGGGATCCT<br>GGAGGCGCTGGCCGAGGGCTTCGACGGCGACCTGGCGGCCGTCCCGGGGCTGGCCGGGGCCCGGCCCGCCAGCCCCCC<br>GCGGCCGGAGGGACCCGCGGGCCCCGCTTCCCCGCCGCCGCCGCACGCCGACGCGCCCCGCCTGCGCGCGTGGCTGCG<br>CGAGCTGCGGTTCGTGCGCGACGCGCTGGTGCTCATGCGCCTGCGCGGGGACCTGCGCGTGGCCGGCGGCAGCGAGGC<br>CGCCGTGGCCGCCGTGCGCGCCGTGAGCCTGGTCGCCGGGGCCCTGGGCCCCGCGCTGCCGCGGGACCCGCGCCTGCC<br>GAGCTCCGCGGCCGCCGCCGCCGCGGACCTGCTGTTTGAGAACCAGAGCCTGCGCCCCCTGCTGGCGGCGGCGGCCAG<br>CGCACCGGACGCCGCCGACGCGCTGGCGGCCGCCGCCGCCTCCGCCGCGCCGCGGGAGGGGCGCAAGCGCAAGAGTCC<br>CGGCCCGGCCCGGCCGCCCGGAGGCGGCGGCCCGCGACCCCCGAAGACGAAGAAGAGCGGCGCGGACGCCCCCGGCTC<br>GGACGCCCGCGCCCCCTCCCCGCGCCCGCGCCCCCTCCACGCCCCCGGGGCCCGAGCCCGCCCCCGCCCAGCCCGC<br>GGCGCCCCGGGCCGCCGCGGCGCAGGCCCGCCCGCGCCCCGTGGCCGTGTCGCGCCGGCCCGCCGAGGGCCCCGACCC<br>CCTGGGCGGCTGGCGGCGGCAGCCCCCGGGGCCCAGCCACACGGCGGCGCCCGCGGCCGCCGCCCTGGAGGCCTACTG<br>CTCCCCGCGCGCCGTGGCCGAGCTCACGGACCACCCGCTGTTCCCCGTCCCCTGGCGACCGGCCCTCATGTTTGACCC<br>GCGGGCCCTGGCCTCGATCGCCGCGCGGTGCGCCGGGCCCGCCCCCGCCGCCCAGGCCGCGTGCGGCGGCGGCGACGA<br>CGACGATAACCCCCACCCCCACGGGGCCGCCGGGGGCCGCCTCTTTGGCCCCCTGCGCGCCTCGGGCCCGCTGCGCCG<br>CATGGCGGCCTGGATGCGCCAGATCCCCGACCCCGAGGACGTGCGCGTGGTGGTGCTGTACTCGCCGCTGCCGGGCGA<br>GGACCTGGCCGGCGGCGGGGCCTCGGGGGGGCCGCCGGAGTGGTCCGCCGAGCGCGGCGGGCTGTCCTGCCTGCTGGC<br>GGCCCTGGCCAACCGGCTGTGCGGGCCGGACACGGCCGCCTGGGCGGGCAACTGGACCGGCGCCCCCGACGTGTCGGC<br>GCTGGGCGCGCAGGGCGTGCTGCTGCTGTCCACGCGGGACCTGGCCTTCGCCGGGGCCGTGGAGTTTCTGGGGCTGCT<br>CGCCAGCGCCGGCGACCGGCGGCTCATCGTGGTCAACACCGTGCGCGCCTGCGACTGGCCCGCCGACGGGCCCGCGGT<br>GTCGCGGCAGCACGCCTACCTGGCGTGCGACCTGCTGCCCGCCGTGCAGTGCGCCGTGCGCTGGCCGGCGGCGCGGGA<br>CCTGCGCCGCACGGTGCTGGCCCCGGGCCGCGTGTTCGGCCCGGGGGTCTTCGCGCGCGTGGAGGCCGCGCACGCGCG<br>CCTGTACCCCGACGCGCCGCCGCTGCGCCTGTGCCGCGGCGGCAACGTGCGCTACCGCGTGCGCACGCGCTTCGGCCC<br>GGACACGCCGGTGCCCATGTCCCCGCGCGAGTACCGCCGGGCCGTGCTGCCGGCGCTGGACGGCCGGGCGGCGGCCTC<br>GGGGACCACCGACGCCATGGCGCCCGGCGCGCCGGACTTCTGCGAGGAGGAGGCCCACTCGCACCGCGCCTGCGCGCG<br>CTGGGGCCTGGGCGCGCCGCTGCGGCCCGTGTACGTGGCGCTGGGGCGCGAGGCGGTGCGCGCCGGCCCGGCCCGGTG<br>GCGCGGGCCGCGGAGGGACTTTTGCGCCCGCGCCCTGCTGGAGCCCGACGACGACGCCCCCCCGCTGGTGCTGCGCGG<br>CGACGACGACGGCCCGGGGGCCCTGCCGCCGGCGTTGCCCGGGATTCGCTGGGCCTCGGCCACGGGCCGCAGCGGCAC<br>CGTGCTGGCGGCGGCGGGGGCCGTGGAGGTGCTGGGGGCGGAGGCGGGCTTGGCCACGCCCCCGCGACGGGAAGTTGT<br>GGACTGGGAAGGCGCCTGGGACGACGACGACGGCGGCGCGTTCGAGGGGGACGGGGTGCTGTAACGGGCCGGGACGGG<br>GCGGGGCGCTTGCGAAACCCGAAGACACAATAAACGGCAACAACCTGATTTAGTTTTGCAGTAGCGTTGTTTATTTGA<br>GGGGCGGGAGGGGGCGAGGGGCGGGAGGGGGCGAGGGGCGGGAGGGGGCGAGGGGCGGGAGGGGGCGAGGGGCGGGAG<br>GGGGCGAGGGGCGGGAGGGGGCGAGGGGCGGGAGGGGGCGAGGGGCGGGAGGGGGCGAGGGGCGGGAGGGGGCGAGGG<br>GCGGGAGGGGGCGAGGGGCGGGAGGGGGCGAGGGGCGGGAGGGGGCGAGGGGCGGGAGGGGGCGAGGGGCGGGAGGGG<br>GCGAGGGGCGGGAGGGGGCGAGGGGCGGGAGGGGGCGAGGGGCGGGAGGGGGCGAGGGGCGGGAGGGGGCGAGGGGCG |

-continued

| SEQUENCES |
|---|
| GGAGGGGGCGAGGGGCGGTGGTGGTGCGCGGGCGCCCCCGGAGGGTTTGGATCTCTGACCTGAGATTGGCGGCACTGA<br>GGTAGAGATGCCCGAACCCCCCCGAGGGAGCGCGGGACGCGCCGGGGAGGGCTGGGGCCGGGGAGGGCTGGGGCCGGG<br>GAGGGCTGGGGCCGGGGAGGGCTGGGGCCGGGGAGGGCTGGGGCCGGGGAGGGCTGGGGCTGGGGAGGGCTGGGGCTG<br>GGGAGGGCTGGGGCTGGTGGTGTGTGACAGGAGCGGCGTGTTGCGCTGGGGGACGTCTGGAGGAGCGGGGGGTGCGCG<br>GTGACGTGTGGATGAGGAACAGGAGTTGTTGCGCGGTGAGTTGTCGCTGTGAGTTGTGTTGGTGGGCAGGTGTGGTGG<br>ATGACGTGACGTGTGACGTGTGGATGAGGCGTGCTCTGTTGGTTTCACCTGTGGCAGCCCGGGCCCCCCGCGGGCGGG<br>GCGGCGCGCAAAAAAGGCGGGCGGCGGTCCGGGCGGCGTGCGCGCGCGCGGCGGGCGTTGGGGGCGGGGCCGCGGGAG<br>CGGGGGGAGGAGCGGGGGGAGGAGCGGGGGGAGGAGCGRRGGGAGGAGCGGGGGGAGGAGCGGGGGGAGGAGCGGGGG<br>GAGGAGCGGGGGGAGGAGCGGGGGGAGGAGCGGGGGGAGGAGCGGGGGGAGGAGCGGGGGGAGGAGCGGGGGGAGGAG<br>CGGGGGGAGGAGCGGGGGGAGGAGCGGGGGGAGGAGCGGGGGGAGGAGCGGGGGGAGGAGCGAAAACGGGCCCCCCCC<br>SAAACACACCCCCCGGGGGTCGCGCGCGGCCCTTTAAAGCGGTGGCGGCGCAGCCCGGGCCCCCCGCGGGCGCGCGCG<br>CGCGCAAAAAAGGCGGGCGGCGGTCCGGGCGGCGTGCGCGCGCGCGGCGGGCGTGGGGGGCGGGGCCGCGGGAGCGGG<br>GGGAGGAGCGGGGGGAGGAGCGGGGGGAGGAGCGGGGGGAGGAGCGGGGGGAGGAGCGGGGGGAGGAGCGGGGGGAGG<br>AGCGGGGGGAGGAGCGGGGGGAGGAGCGGGGGGAGGAGCGGGGGGAGGAGCGGGGGGAGGAGCGGGGGGAGGAGCGGG<br>GGGAGGAGCGGGGGGAGGAGCGGGGGGAGGAGCGGGGGGAGGAGCGGGGGGAGGAGCGAAAACGGGCCCCCCCCAAAA<br>CACACCCCCCGGGGGTCGCGCGCGGCCCTTTAAAGCGGGCGGCGGCAGCCCGGGCCCCCCGCGGCCGAGACGAGCGAG<br>TTAGACAGGCAAGCACTACTCGCCTCTGCACGCACATGCTTGCCTGTCAAACTCTACCACCCCGGCACGCTCTCTGTC<br>TCCATGGCCCGCCGCCGCCGCCATCGCGGCCCCCGCCGCCCCCGGCCGCCCGGGCCCACGGGCGCCGTCCCAACCGCA<br>CAGTCCCAGGTAACCCTTGTTCCGCTTCCCGGTATGGTAATTAGAAACTCATTAATGGGCGGCCCCGGCCGCCCTTCC<br>CGCTTCCGGCAATTCCCGCGGCCCTTAATGGGCAACCCCGGTATTCCCCGCCTCCCGCGCCGCGCGTAACCACTCCCC<br>TGGGGTTCCGGGTTATGCTAATTGCTTTTTTGGCGGAACACACGGCCCCTCGCGCATTGGCCCGCGGGTCGCTCAATG<br>AACCCGCATTGGTCCCCTGGGGTTCCGGGTATGGTAATGAGTTTCTTCGGGAAGGCGGGAAGCCCCGGGGCACCGACG<br>CAGGCCAAGCCCCTGTTGCGTCGGTGGGAGGGGCATGCTAATGGGGTTCTTTGGGGGACACCGGGTTGGTCCCCCAAA<br>TCGGGGGCCGGGCCGTGCATGCTAATGATATTCTTTGGGGGCGCCGGGTTGGTCCCCGGGGACGGGGCCGCCCCGCGG<br>TGGGCCTGCCTCCCCTGGGACGCGCGGCCATTGGGGGAATCGTCACTGCCGCCCCTTTGGGGAGGGGAAAGGCGTGGG<br>GTATAAGTTAGCCCTGGCCCGACAGTCTGGTCGCATTTGCACCTCGGCACTCGGAGCGAGACGCAGCAGCCAGGCAGA<br>CTCGGGCCGCCCCCTCTCCGCATCACCACAGAAGCCCCGCCTACGTTGCGACCCCCAGGGACCCTCCGTCCGCGACCC<br>TCCAGCCGCATACGACCCCCATGGAGCCCCGCCCCGGAGCGAGTACCCGCCGGCCTGAGGGCCGCCCCCAGCGCGAGG<br>TGAGGGGCCGGGCGCCATGTCTGGGGCGCCATATTGGGGGGCGCCATATTGGGGGGCGCCATGTTGGGGGACCCCCGA<br>CCCTTACACTGGAACCGGCCGCCATGTTGGGGGACCCCCACTCATACACGGGAGCCGGGCGCCATGTTGGGGCGCCAT<br>GTTAGGGGGCGTGGAACCCCGTGACACTATATATACAGGGACCGGGGGCGCCATGTTAGGGGGCGCGGAACCCCCTGA<br>CCCTATATATACAGGGACCGGGGTCGCCCTGTTGGGGGTCGCCATGTGACCCCCTGACTTTATATATACAGACCCCCC<br>AACACATACACATGGCCCCTTTGACTCAGACGCAGGGCCCGGGGTCGCCGTGGGACCCCCTGACTCATACACAGAGAC<br>ACGCCCCCACAACAAACACACAAGGACCGGGGTCGCCGTGTTAGGGGGCGTGGTCCCCACTGACTCATACGCAGGGCC<br>CCCTTACTCACACGCATCTAGGGGGGTGGGGAGGAGCCGCCCGCCATATTTGGGGGACGCCGTGGGACCCCCGACTCC<br>GGTGCGTCTGGAGGGCGGGAGAAGAGGGAAGAAGAGGGGTCGGGATCCAAAGGACGGACCCAGACCACCTTTGGTTGC<br>AGACCCCTTTCTCCCCCCTCTTCCGAGGCCAGCAGGGGGGCAGGACTTTGTGAGGCGGGGGGGGGAGAGGGGGAACTC<br>GTGGGCGCTGATTGACGCGGGAAATCCCCCCATTCTTACCCGCCCCCCTTTTTTCCCCTTAGCCCGCCCCGGATGTCT<br>GGGTGTTTCCCTGCGACCGAGACCTGCCGGACAGCAGCGACTCTGAGGCGGAGACCGAAGTGGGGGGGCGGGGGACG<br>CCGACCACCATGACGACGACTCCGCCTCCGAGGCGGACAGCACGGACACGGAACTGTTCGAGACGGGGCTGCTGGGGC<br>CGCAGGGCGTGGATGGGGGGGCGGTCTCGGGGGGGAGCCCCCCCCGCGAGGAAGACCCCGGCAGTTGCGGGGGCGCCC<br>CCCCTCGAGAGGACGGGGGGAGCGACGAGGGCGACGTGTGCGCCGTGTGCACGGATGAGATCGCGCCCCACCTGCGCT<br>GCGACACCTTCCCGTGCATGCACCGCTTCTGCATCCCGTGCATGAAAACCTGGATGCAATTGCGCAACACCTGCCCGC<br>TGTGCAACGCCAAGCTGGTGTACCTGATAGTGGGCGTGACGCCCAGCGGGTCGTTCAGCACCATCCCGATCGTGAACG<br>ACCCCCAGACCCGCATGGAGGCCGAGGAGGCCGTCAGGGCGGGCACGGCCGTGGACTTTATCTGGACGGGCAATCAGC<br>GGTTCGCCCCGCGGTACCTGACCCTGGGGGGGCACACGGTGAGGGCCCTGTCGCCCACCCACCCTGAGCCCACCACGG<br>ACGAGGATGACGACGACCTGGACGACGGTGAGGCGGGGGGGCGGCGAGGACCCTGGGGGAGGAGGAGGAGGAGGGGGG<br>AGGGAGGAATAGGCGGGCGGGGGAGGAAAGGGAGGGCCTGGGAGGGGGCGTAACCTGATCGCGCCCCCCGTTGTCTCT<br>TGCAGCAGACTACGTACCGCCCGCCCCCCGCCGGACGCCCCGCGCCCCCCCACGCAGAGGCGCCGCCGCGCCCCCCGT<br>GACGGGCGGGGCGTCTCACGCAGCCCCCCAGCCGGCCGCGGCTCGGACAGCGCCCCCCTCGGCGCCCATCGGGCCACA<br>CGGCAGCAGTAACACCAACACCACCACCAACAGCAGCGGCGGCGGCGGCTCCCGCCAGTCGCGAGCCGCGGCGCCGCG<br>GGGGGCGTCTGGCCCCTCCGGGGGGGTTGGGGTTGGGGTTGGGGTTGTTGAAGCGGAGGCGGGGCGGCCGAGGGGCCG<br>GACGGGCCCCCTTGTCAACAGACCCGCCCCCCTTGCAAACAACAGAGACCCCATAGTGATCAGCGACTCCCCCCCGGC<br>CTCTCCCCACAGGCCCCCCGCGGCGCCCATGCCAGGCTCCGCCCCCCGCCCCGGGCCCACCGCGTCCTCGGCCGCGTC<br>GGGACCCGCGCGCCCCCGCGCGGCCGTGGCCCCGTGCGTGCGAGCGCCGCCTCCGGGGCCCGGCCCCCGCGCCCCGGC<br>CCCCGGGGCGGAGCCGGCCGCCCGCCCCGCGGACGCGCGCCGTGTGCCCCAGTCGCACTCGTCCCTGGCTCAGGCCGC<br>GAACCAAGAACAGAGTCTGTGCCGGGCGCGTGCGACGGTGGCGCGCGGCTCGGGGGGGCCGGGCGTGGAGGGTGGACA<br>CGGGCCCTCCCGCGGCGCCGCCCCCTCCGGCGCCCCCCCGCTCCCCTCCGCCGCCTCTGTCGAGCAGGAGGCGGCGGT<br>GCGTCCGAGGAAGAGGCGCGGGTCGGGCCAGGAAAACCCCTCCCCCCAGTCCACGCGTCCCCCCCTCGCGCCGGCAGG<br>GGCCAAGAGGGCGGCGACGCACCCCCCCCTCCGACTCAGGGCCGGGGGGGCGCGGCCAGGGTGGGCCCGGGACCCCCCT<br>GACGTCCTCGGCGGCCTCCGCCTCTTCCTCCTCTGCCTCTTCCTCCTCGGCCCCGACTCCCGCGGGGGCCGCCTCTTC<br>CGCCGCCGGGGCCGCGTCCTCCTCCGCTTCCGCCTCCTCGGGCGGGGCCGTCGGTGCCCTGGGAGGGAGACAAGAGGA<br>AACCTCCCTCGGCCCCCGCGCTGCTTCTGGGCCGCGGGGGCCGAGGAAGTGTGCCCGGAAGACGCGCCACGCGGAGAC<br>TTCCGGGGCCGCCCCCGCGGGCGGCCTCACGCGCTACCTGCCCATCTCGGGGGTCTCTAGCGTGGTCGCCCTGTCGCC<br>TTACGTGAACAAGACGATCACGGGGGACTGCCTGCCCATCCTGGACATGGAGACGGGGAACATCGGGGCGTACGTGGT<br>CCTGGTGGACCAGACGGGAAACATGGCGACCCGGCTGCGGGCCGCGGTCCCCGGCTGGAGCCGCCGCACCCTGCTCCC<br>CGAGACCGCGGGTAACCACGTGATGCCCCCCGAGTACCCGACGGCCCCCGCGTCGGAGTGGAACAGCCTCTGGATGAC<br>CCCCGTGGGGAACATGCTGTTCGACCAGGGCACCCTAGTGGGCGCCCTGGACTTCCGCAGCCTGCGGTCTCGGCACCC<br>GTGGTCCGGGGAGCAGGGGGCGTCGACCCGGGACGAGGGAAAACAATAAGGGACGCCCCCCGTGTTTGTGGGGAGGGG<br>GGGGTCGGGCGCTGGGTGGTCTCTGGCCGCGCCCACTACACCAGCCAATCCGTGTCGGGGAGGGGAAAAGTGAAAGAC<br>ACGGGCACCACACACCAGCGGGTCTTTAGTGTTGGCCCTAATAAAAAACTCAGGGGATTTTTGCTGTCTATTGGGAAA<br>TAAAGGTTTACTTTTGTATCTTTTCCCTGTCTGTGTTGGATGGATCTCGGGGGTGCGTGGGAGTGGGGGTGCGTGGGA<br>GTGGGGGTGCGTGGGAGTGGGGGTGCGTGGGAGTGGGGGTGCGTGGGAGTGGGGGTGCGTGGGAGTGGGGGTGCGTGG<br>GAGTGGGGGTGCGTGGGAGTGGGGGTGCGTGGGAGTGGGGGTGCCATGTTGGGCAGGCTCTGGTGTTAACCACAGAGC<br>CGCGGCCCGGGCTGCCTGACCACCGATCCCCGAAAGCATCCTGCCATTGGCATGGAGCCAGAACCACAGTGGGTTGGG<br>TGTGGGTGTTAAGTTTCCGCGAGCGCCTGCCCGCCCGGACTGACCTGGCCTCTGGCCGCCACAAAGGGCGGGGGGGGT<br>TAACTACACTATAGGGCAACAAAGGACGGAGGGGTGGCGGGGCGGGACGGGGCGCCCAAAAGGGGGTCGGCCACACC |

-continued

| SEQUENCES |
| --- |
| ACAGACGTGGGTGTTGGGGGGTGGGGCGGAGGGGTGGGGGGGGGGAGACAGAAACAGGAACATAGTTAGAAAACAAG<br>AATGCGGTGCAGCCAGAGAATCACAGGAGACGAGGGGATGGGCGTGTTGGTTACCAACCCACACCCAGGCATGCTCGG<br>TGGTATGAAGGAGGGGGGGCGGTGCTTCTTAGAGACCGCCGGGGGACGTGGGGTTGGTGTGCAGAGGCACGCGCACCC<br>GCGCGGCCAGGTGGGCCGGTACCCCATCCCCCCTCCCCCGACCCTTCCCACCCCCGCGTGCCAGAGATCACCCCGGTC<br>CCCCGGCACCCGCCACTCCTCCATATCCTCGCTTTAGGAACAACTTTAGGGGGGGTACACACGCGCCGTGCATTTCCT<br>TCCACACCCCCCCTCCCCCGCACTCCCCCCCCCCCGGCAGTAAGACCCAAGCATAGAGAGCCAGGCACAAAAACACAG<br>GCGGGGTGGGACACATGCCTTCTTGGAGTACGTGGGTCATTGGCGTGGGGGGTTACAGCGACACCGGCCGACCCCCTG<br>GCGGTCTTCCAGCCGGCCCTTAGATAAGGGGGCAGTTGGTGGTCGGACGGGTAAGTAACAGAGTCTGACTAAGGGTGG<br>GAGGGGGGGAAAAGAACGGGCTGGTGTGCTGTAACACGAGCCCACCCGCGAGTGGCGTGGCCGACCTTAGCCTCTGGG<br>GCGCCCCCTGTCGTTTGGGTCCCCCCCCTCTATTGGGGAGAAGCAGGTGTCTAACCTACCTGGAAACGCGGCGTCTTT<br>GTTGAACCACACCGGGGCGCCCTTGACGAGTGGGATAACGGGGGAGGAAGGGAGGGAGGAGGGTACTGGGGGTGAAGA<br>AGGGGGGGGGGAGAAGCGAGAACAGGAAAGGCGACGGAGCCCGACAAAACACCGAGAAAAAAAAAACCACAGCGCATG<br>CGCCGGGCCGTTGTGGGGCCCCGGGCCGGGGCCCCTTGGGTCCGCCGGGGCCCCGGGCCGGGCCGCCACGGGGGCCGG<br>CCGTTGGCGGTAACCCCGATTGTTTATCTCAGGCCCCGGGCCGGGAACCCGGAAAAGCCTCCGGGGGGCCTTTTTCGC<br>GTCGCGTGCCGGCGAGCGGGCCCGGACGGGGCCCGGACCGCCGCGGTCGGGGGCCCCCTCGTCCCGGGCCGTACGCGG<br>CCTTCGCCCCGTGAGGGGACAGACGAACGAAACATTCCGGCGACGGAACGAAAAACACCCCAGACGGGTTAAAGAAAC<br>AGAAACCGCAACCCCCCCCACCCCCGAAACGGGGAAAACAAAAAACAGACCAGCGGCCGGCCGGCGCTTAGGGGGAGG<br>ATGTCGCCGACGCCCCTTGGCCGCCCCGGCTGCAGGGGGGCCCGGAGAGCCGCGGCACCCGGACGCGCCCGGAAAGTC<br>TTTCGCACCACCCGCGATCGGCACGGCCGCGCCCCCGCTTTTATAAAGGCTCAGATGACGCAGCAAAAACAGGCCACA<br>GCACCACGTGGGTAGGTGATGTAATTTTATTTTCCTCGTCTGCGGCCTAATGGATTTCCGGGCGCGGTGCCCCTGTCT<br>GCAGAGCACTTAACGGATTGATATCTCGCGGGCACGCGCGCCCTTAATGGACCGGCGCGGGGCGGGGGGCCGGATACC<br>CACACGGGCGGGGGGGGGGTGTCGCGGGCCGTCTGCTGGCCCGCGGCCACATAAACAATGACTCTGGGCCTTTCTGCC<br>TCTGCCGCTTGTGTGTGCGCGCGCCGGCTCTGCGGTGTCGGCGGCGGCTGCGGCGGCTGCGGCGGCCGCCGTGTTCGG<br>TCTCGGTAGCCGGCCGGCGGGTGGACTCGCGGGGGGCCGGAGGGTGGAAGGCAGGGGGGTGTAGGATGGGTATCAGGA<br>CTTCCACTTCCCGTCCTTCCATCCCCCGTTCCCCTCGGTTGTTCCTCGCCCCCCCCAACACCCCGCCGCTTTCCGTTG<br>GGGTTGTTATTGTTGTCGGGATCGTGCGGGCCGGGGGTCGCCGGGGCAGGGGCGGGGGCGTGGGCGGGGGTGCTCGTC<br>GATCGACCGGGCTCAGTGGGGGCGTGGGGTGGGTGGGAGAAGGCGAGGAGACTGGGGTGGGGGTGTCGGTGGGTGGTT<br>GTTTTTTGTGGTTGTTTTTGTGGCTGTTCCCGTCCCCCGTCACCCCCCTCCCTCCGTCCCCTCCGTCCCCCCGTCGCG<br>GGTGTTTGTGTTTGTTTATTCCGACATCGGTTTATTTAAATAAACACAGCCGTTCTGCGTGTCTGTTCTTGCGTGTGG<br>CTGGGGGCTTATATGTGGGGTCCCGGGGGCGGGATGGGGTTTAGCGGCGGGGGGCGGCGCGCCGGACGGGGCGCTGGA<br>GATAACGGCCCCCGGGGAACGGGGGACCGGGGCTGGGTCTCCCGAGGTGGGTGGGTGGGCGGCGGTGGCCGGGCCGGG<br>CCGGGCCGGGCCGGGCCGGGTGGGCGGGGTTTGGAAAAACGAGGAGGAGGAGGAGAAGGAGGGGGGGGGGGAGACGGG<br>GGGAAAGCAAGGACACGGCCCGGGGGGTGGGAGCGCGGGCCGGGCCGCTCGTAAGAGCCGCGACCCGGCCACCGGGGA<br>GCGTTGTCGCCGTCGGTCTGCCGGCCCCCGTCCCTCCCTTTTTTGACCAACCAGCGCCCCCCCCCCCCCTCACCACCA<br>TTCCTACTACCACCACCACCACCACCACCGACACCTCCCGCGCACCCCCGCCCACATCCCCCCCCAACCCGCACCACG<br>AGCACGGGTTGGGGGTAGCAGGGGATCAAAGGGGGGCAAGGCCGGCGGGGCGGTTCGGGGGGGGGGGGGGGGGGCGGG<br>AGACCGAGTAGGCCCCGCCCATCCGCGGCCCCTCCCGGCAGCCACGCCCCCCAGCGTCGGGTGTCACGGGGAAAGAGC<br>AGAGGGGAGAGGGGAGAGGGGGGAGAGGGGAGAGGGGGGAGAGGGGAGAGGGGGGAGAGGGGAGAGGGGGGGAGA<br>GGGGAGAGGGGGGGAGAGGGGAGAGGGGGGGAGAGGGGAGAGGGGGGGAGAGGGGAGAGGGGGGGAGAGGGGAGAGGG<br>GGGGAGGGGGAGAGAGGGGAGAGGGGGTATATAAACCAACGAAAAGCGCGGGAACGGGGATACGGGGCTTGTGTGGCA<br>CGACGTCGTGGTTGTGTTACTGGGCAAACACTTGGGGACTGTAGGTTTCTGTGGGTGCCGACCCTAGGCGCTATGGGG<br>ATTTTGGGTTGGGTCGGGCTTATTGCCGTTGGGGTTTTGTGTGTGCGGGGGGGCTTGTCTTCAACCGAATATGTTATT<br>CGGAGTCGGGTGGCTCGAGAGGTGGGGGATATATTAAAGGTGCCTTGTGTGCCGCTCCCGTCTGACGATCTTGATTGG<br>CGTTACGAGACCCCCTCGGCTATAAACTATGCTTTGATAGACGGTATATTTTTGCGTTATCACTGTCCCGGATTGGAC<br>ACGGTCTTGTGGGATAGGCATGCCCAGAAGGCATATTGGGTTAACCCCTTTTTATTTGTGGCGGGTTTTTTGGAGGAC<br>TTGAGTCACCCCGCGTTTCCTGCCAACACCCAGGAAACAGAAACGCGCTTGGCCCTTTATAAAGAGATACGCCAGGCG<br>CTGGACAGTCGCAAGCAGGCCGCCAGCCACACACCTGTGAAGGCTGGGTGTGTGAACTTTGACTATTCGCGCACCCGC<br>CGCTGTGTAGGGCGACAGGATTTGGGACCTACCAACGGAACGTCTGGACGGACCCCGGTTCTGCCGCCGGACGATGAA<br>GCGGGCCTGCAGCCGAAGCCCCTCACCACGCCGCCGCCCATCATCGCCACGTTGGACCCCACCCCGCGACGGGACGCC<br>GCCGCAAAAAGCAGACGCCGACGACCCCACTCCCGGCGCATCTAATGATGCCGCGACGGAAACCCGTCCGGGTTCGGG<br>GGGCGAACCGGCCGCCTGTCGCTCGTCAGGGCCGGCGGGCGCTCCTCGCCGCCCTAGAGGCTGTCCCGCTGGTGTGAC<br>GTTTTCCTCGTCCGCGCCCCCCGACCCTCCCATGGATTTAACAAACGGGGGGGTGTCGCCTGTGGCGACCTCGGCGCC<br>TCTGGACTGGACCACGTTTCGGCGTGTGTTTCTGATCGACGACGCGTGGCGGCCCCTGTTGGAGCCTGAGCTGGCGAA<br>CCCCTTAACCGCCCACCTCCTGACCGAATATAATCGTCGGTGCCAGACCGAAGAGGTGCTGCCGCCGCGGGAGGATGT<br>GTTTTCATGGACTCGTTATTGCACCCCCGACGAGGTGCGCGTGGTTATCATCGGCCAGGACCCATATCACCACCCCGG<br>CCAGGCGCACGGACTTGCGTTTAGCGTGCGCGCGAACGTGCCGCCTCCCCTGAGTCTTCGGAATGTCTTGGCGGCCGT<br>CAAGAACTGTTATCCCGAGGCACGGATGAGCGGCCACGGTTGCCTGGAAAAGTGGGCGCGGGACGGCGTCCTGTTACT<br>AAACACGACCCTGACCGTCAAGCGCGGGGCGGCGGCGTCCCACTCTAGAATCGGTTGGGACCGCTTCGTGGGCGGAGT<br>TATCCGCCGGTTGGCCGCGCGCCGCCCCGGCCTGGTGTTTATGCTCTGGGGCGCACATGCCCAGAATGCCATCAGGCC<br>GGACCCTCGGGTCCATTGCGTCCTCAAGTTTTCGCACCCGTCGCCCCTCTCCAAGGTTCCGTTCGGAACATGCCAGCA<br>TTTCCTCGTGGCGAATCGATATCTCGAGACCCGGTCGATTTCACCCATCGACTGGTCGGTTTGAAAGGCATCGACGTC<br>CGGGGTTTTCGTCTGTGGGGGCTTTTGGGTATTTCCGATGAATAAAGACGGTTAATGGTTAAACCTCTGGTCTCATAC<br>GGGTCGGTGATGTCGGGCGTCGGGGGAGAGGGAGTTCCCTCTGTGCTTGCGATTCTAGCCTCGTGGGGCTGGACGTTC<br>GACACGCCAAACCACGAGTCAGGGATATCGCCAGATACGACTCCCGCAGATTCCATTCGGGGGGCCGCTGTGGCCTCA<br>CCTGACCAACCTTTACACGGGGGCCCGGAACGGGAGGCCACAGCGCCGTCTTTCTCCCCAACGCGCGCGGATGACGGC<br>CCGCCCTGTACCGACGGGCCCTACGTGACGTTTGATACCCTGTTTATGGTGTCGTCGATCGACGAATTAGGGCGTCGC<br>CAGCTCACGGACACCATCCGCAAGGACCTGCGGTTGTCGCTGGCCAAGTTTAGCATTGCGTGCACCAAGACCTCCTCG<br>TTTTCGGGAAACGCCCCGCGCCACCACAGACGCGGGGCGTTCCAGCGCGGCACGCGGGCGCCGCGCAGCAACAAAAGC<br>CTTCAGATGTTTGTGTTGTGCAAACGCACCCACGCCGCTCGAGTGCGAGAGCAGCTTCGGGTCGTTATTCAGTCCCGC<br>AAGCCGCGCAAGTATTACACGTGATCTTCGGACGGGCGGCTCTGCCCCGCCGTCCCCGTGTTCGTCCACGAGTTCGTC<br>TCGTCCGAGCCAATGCGCCTCCACCGAGATAACGTCATGCTGGCCTCGGGGGCCGAGTAACCGCCCCCCCGCGCCACC<br>CTCACTGCCCGTCGCGCGTGTTTGATGTTAATAAATAACGCATAAATTTGGCTGGTTGTTTGTTGTCTTTAATGGACC<br>GCCCGCAAGGGGGGGGKGGCATTTCAGTGTCGGGTGACGAGCGCGATCCGGCCGGGATCCTAGGACCCCAAAAGTTTG<br>TCTGCGTATTCCAGGGCGGGGCTCAGTTGAATCTCCCGCAGCACCTCTACCAGCAGGTCCGCGGTGGGCTGGAGAAAC<br>TCGGCCGTCCCGGGGCAGGCGGTCGTCGGGGGTGGAGGCGCGGCGCCCACCCCGTGTGCCGCGCCTGGCGTCTCCTCT<br>GGGGGCGACCCGTAAATGGTTGCAGTGATGTAAATGGTGTCCGCGGTCCAGACCACGGTCAAAATGCCGGCCGTGGCG<br>CTCCGGGCGCTTTCGCCGCGCGAGGAGCTGACCCAGGAGTCGAACGGATACGCGTACATATGGGCGTCCCACCCGCGT |

-continued

| SEQUENCES |
|---|
| TCGAGCTTCTGGTTGCTGTCCCGGCCTATAAAGCGGTAGGCACAAAATTCGGCGCGACAGTCGATAATCACCAACAGC |
| CCAATGGGGGTGTGTTGGATAACAACGCCTCCGCGCGGCAGGCGGTCCTGGCGCTCCCGGCCCCGTACCATGATCGCG |
| CGGGTGCCGTACTCAAAAACATGCACCACCTGCGCGGCGTCGGGCAGTGCGCTGGTCAGCGAGGCCCTGGCGTGGCAT |
| AGGCTATACGCGATGGTCGTCTGTGGATTGGACATCTCGCGGTGGGTAGTGAGTCCCCCGGGCCGGGTTCGGTGGAAC |
| TGTAAGGGGACGGCGGGTTAATATACAATGACCACGTTCGGATCGCGCAGAGCCGATAGTATGTGCTTACTAATGACG |
| TCATCGCGCTCGTGGCGCTCCCGGAGCGGATTTAAGTTCATGCGAAGGAATTCGGAGGAGGTGGTGCGGGACATGGCC |
| ACGTACGCGCTGTTGAGGCGCAGGTTGCCGGGCGTAAAGCAGATGGCGACCTTGTCCAGGCTAAGGCCCTGGGAGCGC |
| GTGATGGTCATGGCAAGCTTGGAGCTGATGCCGTAGTCGGCGTTTATGGCCATGGCCAGCTCCGTAGAGTCAATGGAC |
| TCGACAAACTCGCTGATGTTGGTGTTGACGACGGACATGAAGCCGTGTTGGTCCCGCAAGACCACGTAAGGCAGGGGG |
| GCCTCTTCCAGTAACTCGGCCACGTTGGCCGTCGCGTGCCGCCTCCGCAGCTCGTCCGCAAAGGCAAACACCCGTGCG |
| TACGTGTATCCCATGAGCGTATAATTGTCCGTCTGCAGGGCGACGGACATCAGCCCCCCGCGCGGCGAGCCGGTCAGC |
| ATCTCGCAGCCCCGGAAGATAACGTTGTCCACGTACGTGCTAAAGGGGGCGCCTTCAAATGCCTCCCCAAAGAGCTCT |
| TGGAGGATTCGGAATCTCCCGAGGAAGGCCCGCTTCAGCAGCGCAAACTGGGTGTGAACGGCGGCGGTGGTCTCCGGT |
| TCCCCGGGGGTGTAGTGGCAGTAAAACACGTCGAGCTGTTGTTCGTCCAGCCCCGCGAAAATAACGTCGAGGTCGTCG |
| TCGGGAAAATCGTCCGGGCCCCCGTCCCGCGGCCCCAGTTGCTTAAAATCAAACGCACGCTCGCCGGGGGCGCCTGCG |
| TCGGCCATTACCGACGCCTGCGTCGGCACCCCCGAAGATTTGGGGCGCAGAGACAGAATCTCCGCCGTTAGTTCTCCC |
| ATGCGGGCGTAGGCGAGGGTCCTCTGGGTCGCATCCAGGCCCGGGCGCTGCAGAAAGTTGTAAAAGGAGATAAGCCCG |
| CTAAATATGAGCCGCGACAGGAACCTGTAGGCAAACTCCACCGAAGTCTCCCCCTGAGTCTTTACAAAGCTGTCGTCA |
| CGCAACACTGCCTCGAAGGCCCGGAACGTCCCACTAAACCCAAAAACCAGTTTTCGCAGGCGCGCGGTTACCGCGATC |
| TGGCTGTTGAGGACGTAAGTGACGTCGTTGCGGGCCACGACCAGCTGCTGTTTGCTGTGCACCTCGCAGCGCATGTGC |
| CCCGCGTCCTGGTCCTGGCTCTGCGAGTAGTTGGTGATGCGGCTGGCGTTGGCCGTGAGCCACTTTTCAATAGTCAGG |
| CCGGGCTGGTGTGTCAGCCGTCGGTATTCGTCAAACTCCTTGACCGACACGAACGTAAGCACGGGGAGGGTGAACACG |
| ACAAACTCCCCCTCACGGGTCACCTTCAGGTAGGCGTGGAGCTTGGCCATGTACGCGCTCACCTCTTTGTGGGAGGAG |
| AACAACCGCGTCCAGCCGGGGAGGTTGGCGGGGTTGGTGATGTAGTTTTCCGGGACGACGAAGCGATCCACGAACTGC |
| ATGTGCTCCTCGGTGATGGGTAGGCCGTACTCCAGCACCTTCATGAGGTTACCGAACTCGTGCTCGATGCACCGTTTG |
| TTGTTAATAAAAATGGCCCAGCTATACGAGAGGCGGGCGTACTCCCGCAGCGTGCGGTTGCAGATGAGGTACGTGAGC |
| ACGTTCTCGCTCTGGCGGACGGAACACCGCAGTTTCTGGTGCTCGAAGGTCGACTCCAGGGACGCCGTCTGTGTCGGC |
| GAGCCCACACACACCAACACGGGCCGCAGGCGGGCCGCGTACTGGGGGGTGTGGTACAGGGCGTTAATCATCCACCAG |
| CAATACACCACGGCCGTGAGGAGGTGACGCCCAAGGAGCCCGGCCTCGTCGATGACGATCACGTTGCTGCGGGTAAAG |
| GCCGGCAGCGCCCCGTGGGTGGCCGGGGCCAACCGCGTCAGGGCGCCCTCGGCCAACCCCAGGGTCCGTTCCAGGGCG |
| GCCAGGGCGCGAAACTCGTTCCGCGACTCCTCGCCCCCGGAGGCGGCCAGGGTGCGCTTCGTGAGGTCCAAAATCACC |
| TCCCAGTAGTACGTCAGATCTCGTCGCTGCAGGTCCTCCAGCGAGGCGGGGTTGCTGGTCAGGGTGTACGGGTACTGC |
| CCCAGTTGGGCCTGGACGTGATTCCCGCGAAACCCAAATTCATGAAAGATGGTGTTGATGGGTCGGCTGAGAAAGGCG |
| CCCGAGAGTTTGGCGTACATGTTTTGGGCCGCAATGCGCGTGGCGCCCGTCACCACACAGTCCAAGACCTCGTTGATT |
| GTCTGCACGCACGTGCTCTTTCCGGAGCCAGCGTTGCCGGTGATAAGATACACCGCGAACGGAAACTCCCTGAGGGGC |
| AGGCCTGCGGGGGACTCTAAGGCCGCCACGTCCCGGAACCACTGCAGACGGGGCACTTGCGCTCCGTCGAGCTGTTGT |
| TGCGAGAGCTCTCGGATGCGCTTAAGGATTGGCTGCACCCCGTGCATAGACGTAAAATTTAAAAAGGCCTCGGCCCTC |
| CCTGGAACGGCTGGTCGGTCCCCGGGTTGCTGAAGGTGCGGCGGGCCGGGTCTCTGTCCGTCTAGCTGGCGCTCCCCG |
| CCGGCCGCCGCCATGACCGCACCACGCTCGCGGGCCCCCACTACGCATGCGCGGGGGGACACGGAAGCGCTGTGCTCC |
| CCCGAGGACGGCTGGGTAAAGGTTCACCCCACCCCCGGTACGATGCTGTTCCGCGAGATTCTCCACGGGCAGCTGGGG |
| TATACCGAGGGCCAGGGGGTGTACAACGTCGTCCGGTCCAGCGAGGCGACCACCCGGCAGCTGCAGGCGGCGATCTTT |
| CACGCGCTCCTCAACGCCACCACTTACCGGGACCTCGAGGCGGACTGGCTCGGCCACGTGGCGGCCCGCGGTCTGCAG |
| CCCCAACGGCTGGTTCGCCGGTACAGGAACGCCCGGGAGGCGGATATCGCCGGGGTGGCCGAGCGGGTGTTCGACACG |
| TGGCGGAACACGCTTAGGACGACGCTGCTGGACTTTGCCCACGGGTTGGTCGCCTGCTTTGCGCCGGGCGGCCCGAGC |
| GGCCCGTCAAGCTTCCCCAAATATATCGACTGGCTGACGTGCCTGGGGCTGGTCCCCATATTACGCAAGCGACAAGAA |
| GGGGGTGTGACGCAGGGTCTGAGGGCGTTTCTCAAGCAGCACCCGCTGACCCGCCAGCTGGCCACGGTCGCGGAGGCC |
| GCGGAGCGCGCCGGCCCCGGGTTTTTGAGCTGGCGCTGGCCTTCGACTCCACGCGCGTGGCGGACTACGACCGCGTG |
| TATATTTACTACAACCACCGCCGGGGCGACTGGCTCGTGCGAGACCCCATCAGCGGGCAGCGCGGAGAATGTCTGGTG |
| CTGTGGCCTCCCTTGTGGACCGGGGACCGTCTGGTCTTCGATTCGCCCGTACAGCGGCTGTTTCCCGAGATCGTCGCG |
| TGTCACTCCCTCCGGGAACACGCGCACGTCTGCCGGCTGCGCAATACCGCGTCCGTCAAGGTGCTGCTGGGGCGCAAG |
| AGCGACAGCGAGCGCGGGGTGGCCGGCGCCGCGCGGGTCGTTAACAAGGTGTTGGGGGAGGACGACGAGACCAAGGCC |
| GGGTCGGCCGCCTCGCGCCTCGTGCGGCTTATCATCAACATGAAGGGCATGCGCCACGTAGGCGACATTAACGACACT |
| GTGCGTGCCTACCTCGACGAGGCCGGGGGGCACCTGATAGACGCCCCGGCCGTCGACGGTACCCTCCCGGGATTCGGC |
| AAGGGCGGAAACAGCCGCGGGTCTGCGGGCCAGGACCAGGGGGGGCGGGCGCCGCAGCTTCGCCAGGCCTTCCGCACG |
| GCCGTGGTTAACAACATCAACGGCGTGTTGGAGGGCTATATAAATAACCTGTTTGGAACCATCGAGCGCCTGCGCGAG |
| ACCAACGCGGGCCTGGCGACCCAGTTGCAGGAGCGCGACCGCGAGCTCCGGCGCGCAACATCGGGGGCCCTGGAGCGC |
| CAGCAGCGCGCGGCCGACCTGGCGGCCGAGTCCGTGACCGGGGGATGCGGCAGCCGCCCTGCGGGGGCGGACCTGCTC |
| CGGGCCGACTATGACATTATCGACGTCAGCAAGTCCATGGACGACGACACGTACGTCGCCAACAGTTTTCAGTACCCG |
| TACATCCCTTCGTACGCCCAGGACCTGGAGCGCCTGTCGCGCCTCTGGGAGCACGAGCTGGTGCGCTGTTTCAAAATT |
| CTGTGTCACCGCAACAACCAGGGCCAAGAGACGTCGATCTCGTACTCCAGCGGGGCGATCGCCGCATTCGTCGCCCCC |
| TACTTTGAGTCAGTGCTTCGGGCCCCCCGGGTAGGCGCGCCATCACGGGCTCCGATGTCATCCTGGGGGAGGAGGAGT |
| TATGGGATGCGGTGTTTAAGAAAACCCGCCTGCAAACGTACCTGACAGACATCGCGGCCCTGTTCGTCGCGGACGTCC |
| AGCACGCAGCGCTGCCCCCGCCCCCCTCCCCGGTCGGCGCCGATTTCCGGCCCGGCGCGTCCCCGCGGGGCCGGTCCA |
| GATCGCGGTCGCCCGGAAGAACTGCGCGAGGCGCGCCGGACCAGGGCGGGGGCATCGGGCACCGGGATGGCCGCCGCG |
| ACGGCCGACGATGAGGGGTCGGCCGCCACCATCCTCAAACAGGCCATCGCCGGGGACCGCAGCCTGGTCGAGGCGGCC |
| GAGGCGATTAGCCAGCAGACGCTGCTCCGCCTGGCCTGCGAGGTGCGCCAGGTCGGCGACCGCCAGCCGCGGTTTACC |
| GCCACCAGCATCGCGCGCGTCGACGTCGCGCCTGGGTGCCGGTTGCGGTTCGTTCTGGACGGGAGTCCCGAGGACGCC |
| TATGTGACGTCGGAGGATTACTTTAAGCGCTGCTGCGGCCAGTCCAGTTATCGCGGCTTCGCGGTGGCGGTCCTGACG |
| GCCAACGAGGACCACGTGCACAGCCTGGCCGTGCCCCCCCTCGTTCTGCTGCACCGGTTCTCCCTGTTCAACCCCAGG |
| GACCTCCTGGACTTTGAGCTTGCCTGTCTGCTGATGTACCTGGAGAACTGCCCCCGAAGCCACGCCACCCCGTCGACC |
| TTTGCCAAGGTTCTGGCGTGGCTCGGGGTCGCGGGTCGCCGCACGTCCCCATTCGAACGCGTTCGCTGCCTTTTCCTC |
| CGCAGTTGCCACTGGGTCCTAAACACACTCATGTTCATGGTGCACGTAAAACCGTTCGACGACGAGTTCGTCCTGCCC |
| CACTGGTACATGGCCCGGTACCTGCTGGCCAACAACCCGCCCCCCGTTCTCTCGGCCCTGTTCTGTGCCACCCCGACA |
| AGCTCCTCATTCCGGCTGCCGGGGCCGCCCCCCCGCTCCGACTGCGTGGCCTATAACCCCGCCGGGATCATGGGGAGC |
| TGCTGGGCGTCGGAGGAGGTGCGCGCGCCTCTGGTCTATTGGTGGCTTTCGGAGACCCCAAAACGACAGACGTCGTCG |
| CTGTTTTATCAGTTTTGTTGAATTTTAGGAAATAAACCCGGTTTTGTTTCTGTGGCCTCCCGACGGATGCGCGTGTCC |
| TTACTCCGTCTTGGTGGGTGGGTGGCTGTGTATGGCGTCCCATCTGTGCGGGGAGGGGGGCAAGTCGGCACGTATTCG |

-continued

| SEQUENCES |
|---|
| GACAGACTCAAGCACACACGGGGGAGCGCTCTTGTCTCAGGGCAATGTTTTTATTGGTCAAACTCAGGCAAACAGAAA<br>CGACATCTTGTCGTCAAAGGGATACACAAACTTCCCCCCCTCGCCCCATACTCCCGCCAGCACCCCGGTAAACACCAA<br>CTCAATCTCGCGCAGGATTTCGCGCAGGTGATGAGCGCAGTCCACGGGGGGGAGCACAAGGGGCCGCGGGTATAGATC<br>GACGGGGACGCCGACCGACTCCCCGCCTCCGGGACAGACACGCACGACGCGCCGCCAGTAGTGCTCTGCGTCCAGCAA<br>GGCGCCGCCGCGGAAGGCAGTGGGGGGCAAGGGGTCGCTGGCCTCAAAGGGGGACACCCGAACGCTCCAGTACTCCGC<br>GTCCAACCGTTTATTAAACGCGTCCAAGATAAGGCGGTCGCAGGCGTCCTCCATAAGGCCCCGGGCCGTGAGTGCGTC<br>CTCCTCCGGCACGCCTGCCGTTGTCAGGCCCAGGACCCGTCGCAGCGTGTCGCGTACGACCCCGGCCGCCGTGGTGTA<br>CGCGGGCCCGCGGAGAGGAAATCCCCCAAGATGGTCAGTGTTGTCGCGGGAGTTCCAGAACCACACTCCCGCCTGGCT<br>CCAGGCGACTGCGTGGGTGTAGACGCCCTCGAGGGCCAGGCACAGTGGGTGCCGCAGCCGGAGGCCGTTGGCCCTAAG<br>CACGGCTCCCACGGCCGTCTCGATGGCCCGCCGGGCGTCCTCGATCACCCCGGAAGCCGCATCCGCGTCTTGGGGGTC<br>CACGTTAAAGACACCCCAGAACGCACCCCCATCGCCCCCGCAGACCGCGAACTTCACCGAGCTGGCCGTCTCCTCGAT<br>CTGCAGGCAGACGGCGGCCATTACCCCACCCAGGAGCTGCCGCAGCGCAGGGCAGGTGTTGCACGTGTCCGGGACCAG<br>GCGCTCCAAGACGGCCCCGGCCCAGGGCTCTGAGGGAGCGGCCACCACCAGCGCGTCCAGTCTTGCTAGGCCCGTCCG<br>GCCGTGGGGGTCCGCCAGCCCGCTCCCCCCGAGGTCGGCCAGGGCCGCCAGGAGCTGGGCGCGAAGTCCGGGGAAGCA<br>AAACCGCGCCGTCCAGACGGGCCCGACGGCCGCGGGCGGGTCTAACAGTTGGATGATTTTAGTGGCGGGATGCCACCG<br>CGCCACCGCCTCCCGCACTGCGGGCAGGAGGCATCCGGCTGCCGCCGAGGCCACGCCGGGCCAGGCTCGCGGGGGGAG<br>GACGACCCTGACCCCCACCGCGGGCCAGGCCCCCAGGAGCGCGGCGTAAGCGGCCGCGGCCCCGCGCACCAGGTCCCG<br>TGCCGACTCGGCCGTGGCCGGCACGGTGAACGTGGGCCAACCCGGAAACCCCAGGACGGCAAAGTACGGGACGGGTCC<br>CCCCCGGACCTCAAACTCGGGCCCCAGAAAGGCAAAGACGGGGGCCAGGGCCCCGGGGGCGGCGTGGACCGTGGTATG<br>CCACTGCCGGAAAAGGGCGACGAGCGCCGGCGCGGAGAACTTCTCGCCGGCGCTTACAAAGTAGTCGTAATCGCGGGG<br>CAGCAGCACCCGTGCCGTGACTCGTTGTGGGTGCCCGCGTGGCCGCAGGCCCACCTCGCACACCTCGACCAGGTCCCC<br>GAACGCGCCCTCCTTCTTGATCGGCGGAAACGCAAGAGTCTGGTATTCGCGCGCAAATAGCGCGGTTCCGGTGGTGAT<br>GTTAACGGTCAGCGAAGCGGTGGACGCGCACTGGGGGGTGTCGCGAATGGCCGCCAGGCGCGCCCACGCCAGCCGCGC<br>GTCGGGATGCTCGGCAACGCGCGCCGCCAGGGCCATAGGGTCGATGTCAATGTTGGCCTCCGCGACCAGGAGAGCGGC<br>GCGAGGGGCGGCGGGCGGGCCCCACGACGCTCTCTCAACTTTCACCACCAGTCCCGTGCGTGGGTCCGAGCCGATACG<br>CAGCGGGGCGAACAGGGCCACCGGCCCGGTCTGGTGCTCCAGGGCCGCCAGGACGCACGCGTACAGCGCCCGCCACAG<br>AGTCGGGTTCTCCAGGGGCTCCAGCGGGGAGGCGGCCGGCGTCGTCGCGGCGCGGGCGGCCGCCACGACGGCCTGGAC<br>GGAGACGTCCGCGGAGCCGTAGAAATCCCGCAGCTCCGTCGCGGTGACGGAGACCTCCGCAAAGCGCGCGCGACCCTC<br>CCCTGCGGCGTTGCGACATACAAAATACACCAGGGCGTGGAAGTACTCGCGAGCGCGGGGGGGCAGCCATACCGCGTA<br>AAGGGTAATGGCGCTGACGCTCTCCTCCACCCACACGATATCTGCGGTGTCCATCGCACGGCCCCTAAGGATCACGGG<br>CGGTCTGTGGGTCCCATGCTGCCGTGCCTGGCCGGGCCCGGTGGGTTGCGGAAACCGGTGACGGGGGGGGGCGGTTT<br>TTGGGGTTGGGGTGGAAACGGCCCGGGTCCGGGGGCCAACTTGGCCCCTCGGTGCGTTCCGGCAACAGCGCCGCCGG<br>TCCGCGGACGACCACGTACCGAACGAGTGCGGTCCCGAGACTTATAGGGTGCTAAAGTTCACCGCCCCCTGCATCATG<br>GGCCAGGCCTCGGTGGGGAGCTCCGACAGCGCCGCCTCCAGGATGATGTCAGCGTTGGGGTTGGCGCTGGATGAGTGC<br>GTGCGCAAACAGCGCCCCCACGCGGGCACGCGTAGCTTGAAGCGCGCGCCCGCAAACTCCCGCTTGTGGGCCATAAGC<br>AGGGCGTACAGCTGCCTGTGGGTCCGGCAGGCGCTGTGGTCGATGTGGTGGGCGTCCAACAACCCCACGATTGTCTGT<br>TTGGTGAGGTTTTTAACGCGCCCCGCCCCGGGAAACGTCTGCGTGCTTTTGGCCATCTGCACGCCAAACAGTTCGCCC<br>CAGATTATCTTGAACAGCGCCACCGCGTGGTCCGTCTCACTAACGGACCCGCGCGGGGGACAGCCGCTTAGGGCGTCG<br>GCGACGCGCTTGACGGCTTCCTCCGAGAGCAGAAGTCCGTCGGTTACGTTACAGTGGCCCAGTTCGAACACCAGCTGC<br>ATGTAGCGGTCGTAGTGGGGGGTCAGCAGGTCCAGCACGTCATCGGGGCCGAAGGTCCTCCCAGATCCCCCGGCCGCC<br>GAGTCCCAATGCAGGCGCGCGGCCATGGTGCTGCACAGGCACAACAGCTCCCAGACAGGGGTTACGTTCAGGGTGGGG<br>GGCAGGGCCACGAGCTCCAGCTCTCCGGTGACGTTGATCGTGGGGATGACGCCCGTGGCGTAGTGGTCATAGATCCGC<br>CGAAATATGGCGCTGCTGCGGGTGGCCATGGGAACGCGGAGACAGGCCTCCAGCAACGCCAGGTAAATAAACCGCGTG<br>CGTCCCATCAGGCTGTTGAGGTTGCGCATGAGCGCGACAATTTCCGCCGGCGCGACATCGGACCGGAGGTATTTTTCG<br>ACGAAAAGACCCACCTCCTCCGTCTCGGCGGCCTGGGCCGGCAGCGACGCCTCGGGATCCCGGCACCGCAGCTCCCGT<br>AGATCGCGCTGGGCCCTGAGGGCGTCGAAATGTACGCCCCGCAAAAACAGACAGAAGTCCTTTGGGGTCAGGGTATCG<br>TCGTGTCCCCAGAAGCGCACGCGTATGCAGTTTAGGGTCAGCAGCATGTGAAGGATGTTAAGGCTGTCCGAGAGACAC<br>GCCAGCGTGCATCTCTCAAAGTAGTGTTTGTAACGGAATTTGTTGTAGATGCGCGACCCCCGCCCCAGCGACGTGTCG<br>CATGCCGACGCGTCACAGCGCCCCTTGAACCGGCGACACAGCAGGTTTGTGACCTGGGAGAACTGCGCGGGCCACTGG<br>CCGCAGGAACTGACCACGTGGTTCAGGAGCATGGGCGTAAAGACGGGCTCCGAGCGCGCCCCGGAGCCGTCCATGTAA<br>ATCAGTAGCTCCCCCTTGCGGAGGGTGCGCACCCGTCCCAGGGACTGGTACACGGACACCATGTCCGGTCCGTAGTTC<br>ATGGGTTTCACGTAGGCGAACATGCCATCAAAGTGCAGGGGATCGAAGCTGAGGCCCACGGTTACGACCGTCGTGTAT<br>ATAACCACGCGGTATTGGCCCCACGTGGTCACGTCCCCGAGGGGGGTGAGCGAGTGAAGCAACAGCACGCGGTCCGTA<br>AACTGACGGCAGAACCGGGCCACGATCTCCGCGAAGGAGACCGTCGACGAAAAAATGCAGATGTTATCGCCCCCGCCA<br>AGGCGCGCTTCCAGCTCCCCAAAGAACGTGGCCCCCCGGGCGTCCGGAGAGGCGTCCGGAGACGGGCCGCTCGGCGGC<br>CCGGGCGGGCGCAGGGCAGCCTGCAGGAGCTCGGTCCCCAGACGCGGGAGAAACAGGCACCGGCGCGCCGAAAACCCG<br>GGCATGGCGTACTCGCCGACCACCACATGCACGTTTTTTCGCCCCGGAGACCGCACAGGAAGTCCACCAACTGCGCG<br>TTGGCGGTTGCGTCCATGGCGATGATCCGAGGACATGTGCGCAGCAGGCGTAGCATTAACGCATCCACGCGGCCCAGT<br>TGCTGCATCGTTGGCGAATAGAGCTGGCCCAGCGTCGACATAACCTCGTCCAGAACGAGGACGTCGTAGTTGTTCAGA<br>AGGTTGGGGCCCACGCGATGAAGGCTTTCCACCTGGACGATAAGTCGGTGGAAGGGGCGGTCGTTCATAATGTAATTG<br>GTGGATGAGAAGTAGGTGACAAAGTCGACCAGGCCTGACTCAGCGAACCGCGTCGCCAGGGTCTGGGTAAAACTCCGA<br>CGACAGGAGACGACGAGCACACTCGTGTCCGGAGAGTGGATCGCTTCCCGCAGCCAGCGGATCAGCGCGGTAGTTTTT<br>CCCGACCCCATTGGCGCGCGGACCACAGTCACGCACCTGGCCGTCGGGGCGCTCGCGTTGGGGAAGGTGACGGGTCCG<br>TGCTGCTGCCGCTCGATCGTTGTTTTCGGGTGAACCCGGGGCACCCATTCGGCCAAATCCCCCCCGTATAACATCCGC<br>GCTAGCGATACGCTCGACGTGTACTGTTCGCACTCGTCGTCCCCAATGGGACGCCCGGCCCCCAGAGGATCCCCCGAC<br>TCCGCGCCCCCCACGAAAGGCATGACCGGGGCGCGGACGGCGTGGTGGGTCTGGTGTGTGCAGGTGGCGACGTTTGTG<br>GTCTCTGCGGTCTGCGTCACGGGGCTCCTCGTCCTGGCCTCTGTGTTCCGGGCACGGTTTCCCTGCTTTTACGCCACG<br>GCGAGCTCTTATGCCGGGGTTAACTCCACGGCCGAGGTGCGCGGGGGTGTAGCCGTGCCCCTCAGGTTGGACACGCAG<br>AGCCTTGTGGGCACTTATGTAATCACGGCCGTATTGTTGTTGGCCGCGGCCGTGTATGCCGTGGTCGGCGCCGTGACC<br>TCCCGCTACGACCGCGCCCTGGACGCGGGCCGCCGTCTGGCTGCGGCCCGCATGGCCATGCCGCACGCCACGCTGATC<br>GCCGGAAACGTCTGCTCTTGGTTGCTGCAGATCACCGTCCTGCTGCTGGCCCATCGCATCAGCCAGCTGGCCCACCTG<br>GTTTACGTCCTGCACTTTGCGTGTCTGGTGTATTTTGCGGCCCATTTTTGCACCAGGGGGGTCCTGAGCGGGACGTAT<br>CTGCGTCAGGTGCACGGCCTGATGGAGCTGGCCCCGACCCATCATCGCGTCGTCGGCCCGGCTCGCGCCGTGCTGACA<br>AACGCCTTGCTGTTGGGCGTCTTCCTGTGCACGGCCGACGCCGCGGTATCCCTGAATACCATCGCCGCGTTCAACTTT<br>AATTTTTCGGCCCCGGGCATGCTCATCTGCCTGACCGTGCTGTTCGCCATTCTCGTCGTATCGCTGTTGTTGGTGGTC<br>GAGGGGGTGTTGTGTCACTACGTGCGCGTGTTGGTGGGCCCCCACCTGGGGGCCGTTGCCGCCACGGGCATCGTCGGC<br>CTGGCCTGCGAGCACTATTACACCAACGGCTACTACGTGGTGGAGACGCAGTGGCCGGGGGCACAGACGGGAGTGCGC |

-continued

| SEQUENCES |
| --- |
| GTCGCCCTCGCCCTGGTCGCCGCCTTTGCCCTCGGCATGGCCGTGCTCCGCTGCACCCGCGCCTATCTGTATCACAGG<br>CGGCACCACACCAAATTTTTTATGCGCATGCGCGACACGCGACACCGCGCACATTCCGCCCTCAAGCGCGTACGCAGT<br>TCCATGCGCGGATCGCGAGACGGCCGCCACAGGCCCGCGCCCGGCAGCCCGCCCGGGATTCCCGAATATGCGGAAGAC<br>CCCTACGCGATCTCATACGGCGGCCAGCTCGACCGGTACGGAGATTCCGACGGGGAGCCGATTTACGACGAGGTGGCG<br>GACGACCAAACCGACGTATTGTACGCCAAGATACAACACCCGCGGCACCTGCCCGACGACGAGCCCATCTATGACACC<br>GTTGGGGGGTACGACCCCGAGCCCGCCGAGGACCCCGTGTACAGCACCGTCCGCCGTTGGTAGCTGTTTGGTTCCGTT<br>TTAATAAACCGTTTGTGTTTAACCCGACCGTGGTGTATGTCTGGTGTGTGGCGTCCGATCCCGTTACTATCACCGTCC<br>CCCCCCCCCCTCAACCCCGGCGATTGTGGGTTTTTTAAAAACGACACGCGTGCGACCGTATACAGAACATTATTTTGG<br>TTTTTATTCGCTATCGGACATGGGGGGTGGAAACTGGGTGGCGGGGCAGGCGCCTCCGGGGGTCCGCCGGTGAGTGTG<br>GCGCGAGGGGGGGTCCGACGAACGCAGGCGCGGTCTCCCCGGGGCCCGCGTAACCACGCGCATATCCGGGGGCACGTA<br>GAAATTACCTTCCTCTTCGGACTCGATATCCACGACGTCAAAGTCGTGGGCGGTCAGCGAGACGACCTCCCCGTCGTC<br>GGTGATGAGGACGTTGTTTCGGCAGCAGCAGGGCCGGGCCCCGGAGAACGAGAGGCCCATAGCTCGGCGAGCGTGTCG<br>TCGAACGCCAGGCGGCTGCTTCGCTGGATGGCCTTATAGATCTCCGGATCGATGCGGACGGGGGTAATGATCAGGGCG<br>ATCGGAACGGCCTGGTTCGGGAGAATGGACGCCTTGCTGGGTCCTGCGGCCCCGAGAGCCCCGGCGCCGTCCTCCAGG<br>CGGAACGTTACGCCCTCCTCCGCGCTGGTGCGGTGCCTGCCGATAAACGTCACCAGATGCGGGTGGGGGGGCAGTCG<br>GGGAAGTGGCTGTCGAGCACGTAGCCCTGCACCAAGATCTGCTTAAAGTTCGGGTGGCGGGGGTTCGCGAAGACGGGC<br>TCGCGGCGGACCAGATCCCCGGAGCTCCAGGACACGGGGGAGATGGTGTGGCGTCCGAGGTCGGGGGCGCCAAACAGA<br>AGCACCTCCGAGACAACGCCGCTATTTAACTCCACCAAGGCCCGATCCGCGGCGGAGCACCGCCTTTTTTCGCCCGAG<br>GCGTGGGCCTCTGACCAGGCCTGGTCTTGCGTGACGAGAGCCTCCTCCGGGCCGGGGACGCGCCCGGGCGCGAAGTAT<br>CGCACGCTGGGCTTCGGGATCGACCGGATAAATGCCCGGAACGCCTCCGGGGACCGGTGTGCCATCAAGTCCTCGTAC<br>GCGGAGGCCGTGGGGTCGCTGGGGTCCATGGGGTCGAAAGCGTACTTGGCCCGGCATTTGACCTCGTAAAAGGCCAGG<br>GGGGTCTTGGGGACTGGGGCCAGGTAGCCGTGAATGTCCCGAGGACAGACGAGAATATCCAGGGACGCCCCGACCATC<br>CCCGTGTGACCGTCCATGAGGACCCCACACGTATGCACGTTCTCTTCGGCGAGGTCGCTGGGTTCGTGGAAGATAAAG<br>CGCCGCGTGTCGGCGCCGGCCTCGCCGCCGTCGTCCGCGCGGCCCACGCAGTAGCGAAACAGCAGGCTTCGGGCCGTC<br>GGCTCGTTCACCCGCCCGAACATCACCGCCGAAGACTGTACATCCGGTCGCAGGCTGGCGTTGTGCTTCAGCCACTGG<br>GGCGAGAAACACGGACCCTGGGGGCCCCAGCGGAGGGTGGATGCGGTCGTGAGGCCCCGCCGGAGCAGGGCCCATAGC<br>TGGCAGTCGGCCTGGTTTTGCGTGGCCGCCTCGTAAAACCCCATGAGGGGCCGGGGCGCCACGGCGTCCGCGGCGGCC<br>GGGGGGGCGCGGCGCGTCAGGCGCCATAGGTGCCGGCCGAGTCCGCGGTCCACCATACCCGCCTCCTCGAGGACCACG<br>GCCAGGGAACACAGATAATCCAGGCGGGCCCAGAGGGGACCGATGGCCAGAGGGGCGCGGACGCCGCGCAGCAACCCG<br>CGCAGGTGGCGCTCGAACGTCTCGGCTAGTATATGGGAGGGCAGCGCGTTGGGGATCACCGACGCCGACCACATAGAG<br>TCAAGGTCCGGGGAGTCGGGATCGGCGTCCGGGTCGCGGGCGTGGGTGCCCCCAGGAGATAGCGGAATGTCCGGGGTC<br>GGAGGCCCGGAGGCGTCAGAAAGTGCCGGCGACGCGGCCCGGGGCTTTTCGTCTGCGGTGTCGGTGGCGTGCTGATCA<br>CGTGGGGGGTTATCGGGCGAATGGGAGCTCGGGTCCACAGCTGACGTCGTCTGGGGTGGGGGGGGCAGGGGACGGAAG<br>GTGGTTGTCAGCGGAAGACTGTTAGGGCGGGGGCGCTTGGGGGGGCTGTCGGGGCCACGAGGGGTGTCCTCGGCCAGG<br>GCCCAGGGACGCTTAGTCACGGTGCGTCCCGGCGGACATGCTGGGCCTACCGTGGACTCCATTTCCGAGACGACGTGG<br>GGGGAGCGGTGGTTGAGCGCGCCGCCGGGTGAACGCTGATTCTCACGACAGCGCGTGCCGCGCGCACGGGTTGGTGTG<br>ATACAGGCGGGACACCAGCACCAGGAGAGGCTTAAGCTCGGGAGGCAGCGCCACCGACGACAGTATCGCCTTGTGTGT<br>GTGCTGGTAATTTATACACCGATCCGTAAACGCGCGCCGAATCTTGGGATTGCGGAGGTGGCGCCGGATGCCCTCTGG<br>GACGTCATACGCCAGGCCGTGGGTGTTGGTCTCGGCCGAGTTGACAAACAGGGCTGGGTGCAGCACGCAGCGATAGGC<br>GAGCAGGGCCAGGGCGAAGTCCGGCGACAGCTGGTTGTTGAAATACTGGTAACCGGGAAACCGGGTCACGGGTACGCC<br>CAGGCTCGGGGCGACGTACACGCTAACCACCAACTCCAGCAGCGTCTGGCCCAGGGCGTACAGGTCAACCGCTAGCCC<br>GACGTCGTGCTTCAGGCGGTGGTTGGTAAATTCGGCCCGTTCGTTGTTAAGGTATTTCACCAACAGCTCCGGGGGCTG<br>GTTATACCCGTGACCCACCAGGGTGTGAAAGTTGGCTGTGGTTAGGGCGGTGGGCATGCCAAACATCCGGGGGGACTT<br>GAGGTCCGGCTCCTGGAGGCAAAACTGCCCCCGGGCGATCGTGGAGTTGGAGTTGAGGGTGACGAGGCTAAAGTCGGC<br>GAGGACGGCCCGCCGGAGCGAGACGGCGTCCGACCGCAGCATGACGAGGATGTTGGCGCACTTGATATCCAGGTGGCT<br>GATCCCGCAGGTGGTGTTTAAAAACACAACGGCACGGGCCAGCTCCGTGAAGCACTGGTGGAGGGCCGTCGAGACCGA<br>GGGGTTTGTTGTGCGCAGGGACGCCAGTTGGCCGATATACTTACCGAGGTCCATGTCGTACGCGGGGAACACTATCTG<br>TCGTTGTTGCAGCGAGAACCCGAGGGGCGCGATGAAGCCGCGGATGTTGTGGGTGCGGCCGGCGCGTAGAGCGCACTC<br>CCCGACCAACAGGGTCGCGATGAGCTCAACGGCAAACCACTCCTTTTCCTTTATGGTCTTAACGGCAAGCTTATGTTC<br>GCGAATCAGTTGGACTTCGCCGTATCCCCCAGACCCCCCGAAGCTTCGGGCCCCGGGGATCTCGAGGGTCGTGTAGTG<br>TAGGGCGGGGTTGATGGCGAACACGGGGCTGCATAGCTTGCGGATGCGCGTGAGGGTGAGGATGTGCGAGGGGGACGA<br>GGGGGGTGCGGTTAACGCCGCCTGGGATCTGCGCAGGGGCGGGCGGTTCAGTTTGGCCGCCGTACCGGGCGCCTCGGG<br>GGACGCGCGGCGATGAGACGAGCGGCTCATTCGCCATCGGGATAGTCCCGCGCGAAGCCGCTCGCGGAGGCCGGATCG<br>GTGGCGGCACCCGTGGGAGGAGCGGGAGACGGCGGCGTTCTGGAGAGAGGGGCCGCTGGGGCGCCCGGAGGCCCCATG<br>GGGGTTGGAGTGTATGTAGGATGCGAGCCAATCCTTGAAGGACCGTTGGCGTGCACCTTGGGGGCTGAGGTTAGCTGC<br>CACATGACCAGCAGGTCGCTGTCTGCGGGACTCATCCATCCTTCGGCCAGGTCGCCGTCTCCCCACAGAGAAGCGTTG<br>GTCGCTGCCTCCTCGAGTTGCTCCTCCTGGTCCGCAAGACGATCGTCCACGGCGTCCAGGCGCTCACCAAGCGCCGGA<br>TCGAGGTACCGTCGGTGTGCGGTTAGAAAGTCACGACGCGCCGCTTGCTCCTCCACGCGAATTTTAACACAGGTCGCG<br>CGCTGTCGCATCATCTCTAAGCGCGCGCGGACTTTAGCCGCGCCTCCAATTCCAAGTGGGCCGCCTTTGCAGCCATA<br>AAGGCGCCAACAAACCGAGGATCTTGGGTGCTGACGCCCTCCCGGTGCAGCTGCAGGGTCTGGTCCTTGTAAATCTCG<br>GCTCGGAGGTGCGTCTCGGCCAGGCGTCGGCGCAGGGCCGCGTGGGCGGCATCTCGGTCCATTCCGCCACCCTGCGGG<br>CGACCCGGGGGTGCTCTGATAGTCTCGCGTGCCCAAGGCCCGTGATCGGGGTACTTCGCCGCCGCGACCCGCCACCCG<br>GTGTGCGCGATGTTTGGTCAGCAGCTGGCGTCCGACGTCCAGCAGTACCTGGAGCGCCTCGAGAAACAGAGGCAACTT<br>AAGGTGGGCGCGGACGAGGCGTCGGCGGGCCTCACAATGGGCGGCGATGCCCTACGAGTGCCCTTTTTAGATTTCGCG<br>ACCGCGACCCCCAAGCGCCACCAGACCGTGGTCCCGGGCGTCGGGACGCTCCACGACTGCTGCGAGCACTCGCCGCTC<br>TTCTCGGCCGTGGCGCGGCGGCTGCTGTTTAATAGCCTGGTGCCGGCGCAACTAAAGGGGCGTGATTTCGGGGGCGAC<br>CACACGGCCAAGCTGGAATTCCTGGCCCCCGAGTTGGTACGGGCGGTGGCGCGACTGCGGTTTAAGGAGTGCGCGCCG<br>GCGGACGTGGTGCCTCAGCGTAACGCCTACTATAGCGTTCTGAACACGTTTCAGGCCCTCCACCGCTCCGAAGCCTTT<br>CGCCAGCTGGTGCACTTTGTGCGGGACTTTGCCCAGCTGCTTAAACCTCCTTCCGGGCCTCCAGCCTCACGGAGACCA<br>CGGGCCCCCCCAAAAAACGGGCCAAGGTGGACGTGGCCACCCACGGCCGGACGTACGGCACGCTGGAGCTGTTCCAAA<br>AAATGATCCTTATGCACGCCACCTACTTTCTGGCCGCCGTGCTCCTCGGGGACCACGCGGAGCAGGTCAACACGTTCC<br>TGCGTCTCGTGTTTGAGATCCCCCTGTTTAGCGACGCGGCCGTGCGCCACTTCCGCCAGCGCGCCACCGTGTTTCTCG<br>TCCCCCGGCGCCACGGCAAGACCTGGTTTCTGGTGCCCCTCATCGCGCTGTCGCTGGCCTCCTTTCGGGGGATCAAGA<br>TCGGCTACACGGCGCACATCCGCAAGGCGACCGAGCCGGTGTTTGAGGAGATCGACGCCTGCCTGCGGGGCTGGTTCG<br>GTTCGGCCCGAGTGGACCACGTTAAAGGGGAAACCATCTCCTTCTCGTTTCCGGACGGGTCGCGCAGTACCATCGTGT<br>TTGCCTCCAGCCACAACACAAACGTAAGTCCTCTTTTCTTTCGCATGGCTCTCCCAAGGGGCCCCGGGTCGACCCGAC<br>CCACACCCACCCACCCACATACACACACAACCAGACGCGGGAGGAAAGTCTGCCCCGTGGGCACTGATTTTTATTCGG |

-continued

| SEQUENCES |
| --- |
| GATCGCTTGAGGAGGCCCGGGCAACGGCCCGGGCAACGGTGGGGCAACTCGTAGCAAATAGGCGACTGATGTACGAAG<br>AGAAGACACACAGGCGCCACCCGGCGCTGGTCGGGGGGATGTTGTCCGCGCCGCACCGTCCCCCGACGACCTCTTGCA<br>GACGGTCCGTGATGCAAGGACGGCGGGGGCCTGCAGCAGGGTGACCGTATCCACGGGATGGCCAAAGAGAAGCGGAC<br>ACAGGCTAGCATCCCCCTGGACCGCCAGGGTACACTGGGCCATCTTGGCCCACAGACACGGGGCGACGCAGGGACAGG<br>ACTCCGTTACGACGGAGGAGAGCCACAGTGCGTTGGCGGAATCGATGTGGGGCGGCGGGGCGCAGGACTCGCAGCCCC<br>CCGGGTGGTTAGTGATCCTGGCCAGGAGCCATCCCAGATGGCGGGCCCTGCTTCCCGGTGGACAGAGCGACCCCAGGT<br>CGCTGTCCATGGCCCAGCAGTAGATCTGGCCGCTGGGGAGGTGCCACCAGGCCCCCGGGCCCAAGGCGCAGCACGCGC<br>CCGGCTCCGGGGGGGTCTTCGCGGGGACCAGATACGCGCCATCCAGCTCGCCGACCACTGGCTCCTCCGCGAGCTGTT<br>CGGTGGTTGGGTCGGGGTTTCCTCCGGGGGGGTGGCCGCCCGTATGCGGGCGAACGTGAGGGTGCACAGGAGCGGGG<br>TCAGGGGGTGCGTCACGCTCCGGAGGTGGACGATCGCGCAGTAGCGGCGCTCGCGGTTAAAGAAAAAGAGGGCAAAGA<br>AGGTGTTCGGGGGCAACCGCAGCGCCTTGGGGCGCGTCAGATACAGAAAAATCTCGCAGAAGAGGGCGCGCCCGGGGT<br>CTGGGTTAGGAAGGGCCACCTGACACAGAGGCTCGGTGAGGACCGTTAGACACCGAAAGATCTTGAGCCGCTCGTCCG<br>CCCGAACGACGCGCCACACAAAGACGGAGTTGACAATGCGCGCGATAGAGTCGACGTCCGTCCCCAGGTCGTCGACTC<br>TGTCGCGCGTGCCGCGAGCTCCGGCCCGGGAATCCGGCCGGGGCAAGGTCCCCGGGGGACCAGGCGGCGCCAGGGGCC<br>GCCGGGGTCCCAGCTGCGCCATGCCGGGGGCGGGGGGAGGGCAAACCCCAGAGGCGGGGGCCAACGGCGCGGGGAGGA<br>GTGGATGGGCGAGGTGGCCGGGGGAAGGCGCCCGCTAGCGAGAACGGCCGTTCCCGGACGACACCTTGCGACAAAACC<br>TAAGGACAGCGGCCCGCGCGACGGGGTCCGAGAGGCTAAGGTAGGCCGCGATGTTAATGGTGAACGCAAAGCCGCCGG<br>GAAAGACAACTATGCCACAGAGGCGGCGATTAAACCCCAGGCAGAGGTAGGCGTAGCTTTCCCCGGGCAGGTATTGCT<br>CGCAGACCCTGCGTGGGGCTGTGGAGGGGACGGCCTCCATGAAGCGACATTTACTCTGCTCGCGTTTACTGACGTCAC<br>CATCCATCGCCACGGCGATTGGACGATTGTTAAGCCGCAGCGTGTCTCCGCTTGTGCTGTAGTAGTCAAAAACGTAAT<br>GGCCGTCGGAGTCGGCAAAGCGGGCCGGGAGGTCGTCGCCGAGCGGGACGACCCGCCGCCCCCGACCGCCCCGTCCCC<br>CCAGGTGTGCCAGGACGGCCAGGGCATACGCGGTGTGAAAAAAGGCGTCGGGGGCGGTCCCCTCGACGGCGCGCATCA<br>GGTTCTCGAGGAGAATGGGGAAGCGCCTGGTCACCTCCCCCAGCCACGCGCGTTGGTCGGGGCCAAAGTCATAGCGCA<br>GGCGCTGTGAGATTCGCGGGCCGCCCTGAAGCGCGGCCCGGATGGCCTGGCCCAGGGCCCGGAGGCACGCCAGATGTA<br>TGCGCGCGGTAAAGGCGACCTCGGCGGCGATGTCAAAGGGCGGCAGGACGGGGCGCGGGTGGCGCAGGGGCACCTCGA<br>GCGCGGGAAAGCGGAGCAGCAGCTCCGCCTGCCCAGCGGGAGACAGCTGGTGGGGGCGCACGACGCGTTCTGCGGCGC<br>AGGCCTCGGTCAGGGCCGTGGCCAGCGCCGAGGACAGCAGCGGAGGGCGGGCGCGTCGCCCGCCCCACGCCACTGAGT<br>TCTCGTAGGAGACGACGACGAAGCGCTGCTTGGTTCCGTAGTGGTGGCGCAGGACCACGGAGATAGAACGACGGCTCC<br>ACAGCCAGTCCGGCCGGTCGCCGCCGCCGGCCAGGGCTTCCCATCCGCGATCCAACCACTCGACCAGCGACCGCGGCTTTG<br>TGGTACCAGGGGTAAGGGTTAGAACGTCGTTCAGGATGTCCTCGCCCCCGGGCCCGTGGGGCGCTGGGGCCACAAAGC<br>GGCCCCCGCCGGGGGGCTCCAGACCCGCCAGCACCGCATCTGCGTCAGCCGCCCCCATGGCGCCCCCGCTGACGGCCT<br>GGTGAACCAGGGCGCCCTGGCGGAGCCCCGATGCAACGCCACAGGCCGCACGCCCGGTCCGAGCGCGGACCGGGTGGC<br>GGCGGGTGACGTCCTGCACTGCCCGCTGAACCAACGCGAGGATCTCCTCGTTCTCCTGTGCGATGGACACGTCCTGGG<br>CCGCGGTCGTGTCGCCGCCGGGGGCCGTCAGCTGCTCCTCCGGGGAGATGGGGGGGTCGGACGCCCCGACGATGGGCG<br>GGTCTGCGGGCGCCCCCGCGTGGGGCCGGGCCAAGGGCTGCGGACGCGGGGACGCGCTTTCCCCCAGACCCATGGACA<br>GGTGGGCCGCGGCCTCCTTCGCGGCCGGCGGGGCGGCGGCGCCAAGCAGAGCGACGTAGCGGCACAAATGCCGACAGA<br>CGCGCATGATGCGCGTGCTGTCGGCCGCGTAGCGCGTGTTGGGGGGGACGAGCTCGTCGTAACTAAACAGAATCACGC<br>GGGCACAGCTCGCCCCCGAGCCCACGCGAGGCGCAGCGCCGCCACGGCGTACGGGTCATAGACGCCCTGCGCGTCAC<br>ACACCACGGGCAGGGAGACGAACAACCCCCCGGCGCTGGACGCACGCGGAAGGAGGCCAGGGTGTGCCGGCACGACGG<br>GGGCCAGAAGCTCCCCCACCGCATCCGCGGGCACGTAGGCGGCAAACGCCGTGCACCACGGGGTACAGTCGCCGGTGG<br>CATGAGCCCGAGTCTGGATTTCGACCTGGAAGTTTGCGGCCGTCCCGAGTCCGGGGCGGCCGCGCATCAGGGCGGCCA<br>GAGGGATTCCCGCGGCCGCCAGGCACTCGCTGGATATGATGACGTGAACCAAAGACGAGGGCCGACCCGGGCCGTGGC<br>CGAGATCGTACTGGACCTCGTTGGCCAAGTGCGCGTTCATGGTTCGGGGTGGGTGTGGGTGTGTAGGCGATGCGGGTC<br>CCCCGAGTCCGCGGGAAGGGCGTGGGTTTGGCGCGCGTATGCGTATTCGCCAACGGAGGCGTGCGTGCTTATGCGCGG<br>CGCGTTTCTTCTGTCTCCAGGGAATCCGAGGCCAGGACTTTAACCTGCTCTTTGTCGACGAGGCCAACTTTATTCGCC<br>CGGATGCGGTCCAGACGATTATGGGCTTTCTCAACCAGGCCAACTGCAAGATTATCTTCGTGTCGTCCACCAACACCG<br>GGAAGGCCAGTACGAGCTTTTTGTACAACCTCCGCGGGGCCGCCGACGAGCTTCTCAACGTGGTGACCTATATATGCG<br>ATGATCACATGCCGAGGGTGGTGACGCACACAAACGCCACGGCCTGTTCTTGTTATATCCTCAACAAGCCCGTTTTCA<br>TCACGATGGACGGGGCGGTTCGCCGGACCGCCGATTTGTTTCTGGCCGATTCCTTCATGCAGGAGATCATCGGGGGCC<br>AGGCCAGGGAGACCGGCGACGACCGGCCCGTTCTGACCAAGTCTGCGGGGGAGCGGTTTCTGTTGTACCGCCCCTCGA<br>CCACCACCAACAGCGGCCTCATGGCCCCCGATTTGTACGTGTACGTGGATCCCGCGTTCACGGCCAACACCCGAGCCT<br>CCGGGACCGGCGTCGCTGTCGTCGGGCGGTACCGCGACGATTATATCATCTTTGCCCTGGAGCACTTTTTTCTCCGCG<br>CGCTCACGGGCTCGGCCCCCGCCGACATCGCCCGCTGCGTCGTCCACAGTCTGACGCAGGTCCTGGCCCTGCATCCCG<br>GGGCGTTTCGCGGCGTCCGGGTGGCGGTCGAGGGAAATAGCAGCCAGGACTCGGCCGTCGCCATCGCCACGCACGTGC<br>ACACAGAGATGCACCGCCTACTGGCCTCGGAGGGGGCCGACGCGGGCTCGGGCCCCGAGCTTCTCTTCTACCACTGCG<br>AGCCTCCCGGGAGCGCGGTGCTGTACCCCTTTTTCCTGCTCAACAAACAGAAGACGCCCGCCTTTGAACACTTTATTA<br>AAAAGTTTAACTCCGGGGGCGTCATGGCCTCCCAGGAGATCGTTTCCGCGACGGTGCGCCTGCAGACCGACCCGGTCG<br>AGTATCTGCTCGAGCAGCTGAATAACCTCACCGAAACCGTCTCCCCCAACACTGACGTCCGTACGTATTCCGGAAAAC<br>GGAACGGCGCCTCGGATGACCTTATGGTCGCCGTCATTATGGCCATCTACCTTGCGGCCCAGGCCGGACCTCCGCACA<br>CATTCGCTCCCATCACACGCGTTTCGTGAGCGCCCAATAAACACACCCAGGTATGCTACGCACGACCACGGTGTCGCC<br>TGTTAAGGGGGGGGAAGGGGGTGTTGGCGGGAAGCGTGGGAACACGGGGGATTCTCTCACGACCGGCACCAGTACCAC<br>CCCCCTGTGAACACAGAAACCCAACCCAAATCCCATAAACATACGACACACAGGCATATTTTGGAATTTCTTGGGTTT<br>TTATTTATTTAGGTATGCTGGGGTTTCTCCCTGGATGCCCACCCCCCACCCCCCCGTGGGTCTAGCCGGGCCTTAGGG<br>ATAGCGTATAACGGGGGCCATGTCTCCGGACCGCACAACGGCCGCGCCGTCAAAGGTGCACACCCGAACCACGGGAGC<br>CAGGGCCAAGGTGTCTCCTAGTTGGCCCGCGTGGGTCAGCCAGGCGACGAGCGCCTCGTAAAGCGGCAGCCTTCGCTC<br>TCCATCCTGCACCAGGGCCGGGGCTTCGGGGTGAATGAGCTGGGCGGCCTCCCGCGTGACACTCTGCATCTGCAGGAG<br>AGCGTTCACGTACCCGTCCTGGGCACTTAGCGCAAAGAGCCGGGGGATTAGCGTAAGGATGATGGTGGTTCCCTCCGT<br>GATCGAGTAAACCATGTTAAGGACCAGCGATCGCAGCTCGGCGTTTACGGGACCGAGTTGTTGGACGTCCGCCAGCAG<br>CGAGAGGCGACTCCCGTTGTAGTACAGCACGTTGAGGTCTGGCAGCCCTCCGGGGTTTCTGGGGCTGGGGTTCAGGTC<br>CCGGATGCCCCTGGCCACGAGCCGCGCCACGATTTCGCGCGCCAGGGGCGATGGAAGCGGAACGGGAAACCGCAACGT<br>GAGGTCCAGCGAATCCAGGCGCACGTCCGTCGCTTGGCCCTCGAACACGGGCGGGACGAGGCTGATGGGGTCCCCGTT<br>ACAGAGATCTACGGGGGAGGTGTTGCGAAGGTTAACGGTGCCGGCGTGGGTGAGGCCCACGTCCAGGGGGCAGGCGAC<br>GATTCGCGTGGGAAGCACCCGGGTGATGACCGCGGGGAAGCGCCTTCGGTACGCCAGCAACAACCCCAACGTGTCGGG<br>ACTGACGCCTCCGGAGACGAAGGATTCGTGCGCCACGTCGGCCAGCGTCAGTTGCCGGCGGATGGTCGGCAGGAATAC<br>CACCCGCCCTTCGCAGCGCTGCAGCGCCGCCGCATCGGGGCGCGAGATGCCCGAGGGTATCGCGATGTCAGTTTCAAA<br>GCCGTCCGCCAGCATGGCGCCGATCCACGCGGCAGGGAGTGCAGTGGTGGTTCGGGTGGCGGGAGGAGCGCGGTGGGG<br>GTCAGCGGCGTAGCAGAGACGGGCGACCAACCTCGCATAGGACGGGGGGTGGGTCTTAGGGGGTTGGGAGGCGACAGG |

-continued

| SEQUENCES |
|---|
| GACCCCAGAGCATGCGCGGGGAGGTCTGTCGGGCCCAGACGCACCGAGAGCGAATCCGTCCACGGAGTCCCGGTCTGG |
| GTTTTATGGGGCCCGGCCCTCGGAATCGCGGCTTGTCGGCGGGGACAAAGGGGGCGGGGCTAGGGGGCTTGCGGAAAC |
| AGAAGACGCGTGGGATAAAAGAATCGCACTACCCCAAGGAAGGGCGGGGCGGTTTATTACAGAGCCAGTCCCTTGAGC |
| GGGGATGCGTCATAGACGAGATACTGCGCGAAGTGGGTCTCCCGCGCGTGGGCTTCCCCGTTGCGGGCGCTGCGGAGG |
| AGGGCGGGGTCGCTGGCGCAGGTGAGCGGGTAGGCCTCCTGAAACAGGCCACACGGGTCCTCCACGAGTTCGCGGCAC |
| CCCGGGGGGCGCTTAAACTGTACGTCGCTGGCGGCGGTGGCCGTGGACACCGCCGAACCCGTCTCCACGATCAGGCGC |
| TCCAGGCAGCGATGTTTGGCGGCGATGTCGGCCGACGTAAAGAACTTAAAGCAGGGGCTGAGCACCGGCGAGGCCCCG |
| TTGAGGTGGTAGGCCCCGTTATAGAGCAGGTCCCCGTACGAAAATCGCTGCGACGCCCACGGGTTGGCCGTGGCCGCA |
| AAGGCCCGGGACGGGTCGCTCTGGCCGTGGTCGTACATGAGGGCGGTGACATCCCCCTCCTTGTCCCCCGCGTAAACG |
| CCCCCGGCGGCGCGTCCCCGGGGGTTGCAGGGCCGGCGGAAGTAGTTGACGTCGGTCGACACGGGGGTGGCGATAAAC |
| TCACACACGGCGTCCTGGCCGTGGTCCATCCCTGCGCGCCGCGGCACCTGGGCGCACCCGAACACGGGGACGGGCTGG |
| GCCGGCCCCAGGCGGTTTCCCGCCACGACCGCGTTCCGCAGGTACACGGCTGCCGCGTTGTCCAGGAGAGGGGGAGCC |
| CCGCGGCCCAGGTAAAAGTTTTGGGGAAGGTTGCCCATGTCGGTGACGGGGTTGCGGACGGTTGCCGTGGCCACGACG |
| GCGGTGTAGCCCACGCCCAGGTCCACGTTCCCGCGCGGCTGGGTGAGCGTGAAGTTTACCCCCCCGCCAGTTTCGTGC |
| CGGGCCACCTGGAGCTGGCCCAGGAAGTACGCCTCCGACGCGCGCTCCGAGAACAGCATGTTCTCAGTCACAAAGCGG |
| TCCTGTCGGACGACGGTGAACCCAAACCCGGGATGGAGGCCCGTCTTGAGCTGATGATGCAAGGCCACGGGACTGATC |
| TTGAAGTACCCCGCCATGAGCGCGTAGGTCAGCGCGTTCTCCCCGGCCGCGCTCTCGCGGACGTGCTGCACGACGGGC |
| TGTCGGATCGACGAAAAGTAGTTGGCCCCCAGAGCCGGGGGGACCAGGGGGACCTGCCGCGACAGGTCGCGCAGGGCC |
| GGGGGGAAATTGGGCGCGTTCGCCACGTGGTCGGCCCCGGCGAACAGCGCGTTGACGGGAAGGGGGTAAAAATAGTCG |
| CCATTTTGGATGGTATGGTCCAGATGCTGGGGGGCCATCAGCAGGATTCCGGCGTGCAACGCCCCGTCGAATATGCGC |
| ATGTTGGTGGTGGACGCGGTGTTGGCGCCCGCGTCGGGCGCCGCCGAGCAGAGCAGCGCCGTTGTGCGTTCGGCCATG |
| TTGTGGGCCAGCACCTGCAGCGTGAGCATGGCGGGCCCGTCCACTACCACGCGCCCGTTGTGAAACATGGCGTTGACC |
| GTGTTGGCCACCAGATTGGCCGGGTGCAGGGGGTGCGCGGGGTCCGTCACGGGGTCGCTGGGGCACTCCTCGCCGGGG |
| GCGATCTCCGGGACCACCATGTTCTGCAGGGTGGCGTATACGCGGTCGAAGCGAACCCCCGCGGTGCAGCAGCGGCCC |
| CGCGAGAAGGCGGGCACCATCACGTAGTAGTAAATCTTGTGGTGCACGGTCCAGTCCGCCCCCCGGTGCGGCCGGTCA |
| TCCGCGGCGTCCGCGGCTCGGGCCTGGGTGTTGTGCAGCAGCTGGCCGTCGTTGCGGTTGAAGTCCGCGGTCGCCACG |
| TTACATGCCGCCGCGTACACGGGGTCGTGGCCCCCCGCGCTAACCCGGCAGTCGCGATGGCGGTCCAGGGCCGCGCGC |
| CGCATCAGGGCGTCACAGTCCCACACGAGGGGTGGCAGCAGCGCCGGGTCTCGCATTAGGTGATTCAGCTCGGCTTGC |
| GCCTGCCCGCCCAGCTCCGGGCCGGTCAGGGTAAAGTCATCAACCAGCTGGGCCAGGGCCTCGACGTGCGCCACCAGG |
| TCCCGGTACACGGCCATGCACTCCTCGGGAAGGTCTCCCCCGAGGTAGGTCACGACGTACGAGACCAGCGAGTAGTCG |
| TTCACGAACGCCGCGCACCGCGTGTTGTTCCAGTAGCTGGTGATGCACTGGACAACGAGCCGGGCCAGGGCGCAGAAG |
| ACGTGCTCGCTGCCGTGTATGGCGGCCTGCAGCAGGTAAAACACCGCCGGGTAGTTGCGGTCGTCGAACGCCCCGCGA |
| ACGGCGGCGATGGTGGCGGGGGCCATGGCGTGGCGTCCCACCCCCAGCTCCAGGCCCCGGGCGTCCCGGAACGCCGCC |
| GGACATAGCGCCAGGGGCAAGTTGCCGTTCACCACGCGCCAGGTGGCCTGGATCTCCCCCGGGCCGGCCGGGGGAACG |
| TCCCCCCCCGGCAGCTCCACGTCGGCCACCCCCACGAAGAAGTCGAACGCGGGGTGCAGCTCAAGAGCCAGGTTGGCG |
| TTGTCGGGCTGCATAAACTGCTCCGGGGTCATCTGGCCTTCCGCGACCCATCGGACCCGCCCGTGGGCCAGGCGCTGC |
| CCCCAGGCGTTCAAAAACAGCTGCTGCATGTCTGCGGCGGGGCCGGCCGGGGCCGCCACGTACGCCCCGTACGGATTG |
| GCGGCTTCGACGGGGTCGCGGTTAAGGCCCCCGACCGCCGCGTCAACGTTCATCAGCGAAGGGTGGCACACGGTCCCG |
| ATCGCGTGTTCCAGAGACAGGCGCAGCACCTGGCGGTCCTTCCCCCAAAAAAACAGCTGGCGGGGCGGGAAGGCGCGG |
| GGATCCGGGTGGCCGGGGGCGGGGACTAGGTCCCCGGCGTGCGCGGCAAACCGTTCCATGACCGGATTGAACAGGCCC |
| AGGGGCAGGACGAACGTCAGGTCCATGGCGCCCACCAGGGGGTAGGGAACGTTGGTGGCGGCGTAGATGCGCTTCTCC |
| AGGGCCTCCAGAAAGACCAGCTTCTCGCCGATGGACACCAGATCCGCGCGCACGCGCGTCGTCTGGGGGGCGCTCTCG |
| AGCTCGTCCAGCGTCTGCCGGTTCAGGTCGAGCTGCTCCTCCTGCATCTCCAGCAGGTGGCGGCCCACGTCGTCCAGA |
| CTTCGCACGGCCTTGCCCATCACGAGCGCCGTGACCAGGTTGGCCCCGTTCAGGACCATCTCGCCGTACGTCACCGGC |
| ACGTCGGCTTCGGTGTCCTCCACTTTCAGGAAGGACTGCAGGAGGCGCTGTTTGATCGGGGCTGTGGTGACTAGCACC |
| CCGTCGACCGGCCGCCCGCGCGTGTCGGCATGCGTCAGACGGGGCACGGCCACGGAGGGCTGCGTGGCCGTGGTGAGG |
| TCCACGAGCCAGGCCTCGACGGCCTCCCGGCGGTGGCCCGCCTTGCCCAGGAAAAAGCTCGTCTCGCAGAAGCTTCGC |
| TTTAGCTCGGCGACCAGGGTCGCCCGGGCCACCCTGGTGGCCAGGCGGCCGTTGTCCAGGTATCGTTGCATCGGCAAC |
| AACAAAGCCAGGGGCGGCGCCTTTTCCAGCAGCACGTGCAGCATCTGGTCGGCCGTGCCGCGCTCAAACGCCCCGAGG |
| ACGGCCTGGACGTTGCGAGCGAGCTGTTGGATGGCGCGCAACTGGCGATGCGCGCTGATACCCGTCCCGTCCAGGGCC |
| TCCCCCGTGAGCAGGGCGATGGCCTCGGTGGCCAGGCTGAAGGCGGCGTTCAGGGCCCGGCGGTCGATAATCTTGGTC |
| ATGTAATTGTGTGTGGGTTGCTCGATGGGGTGCGGGCCGTCGCGGGCAATCAGCGGCTGGTGGACCTCGAACTGTACG |
| CGCCCCTCGTTCATGTAGGCCAGCTCCGGAAACTTGGTACACACGCACGCCACCGACAACCCGAGCTCCAGAAAGCGC |
| ACGAGCGACAGGGTGTTGCAATACGACCCCAGCAGGGCGTCGAACTCGACGTCGTACAGGCTGTTTGCATCGGAGCGC |
| ACGCGGGAAAAAAAATCGAACAGGCGTCGATGCGACGCCACCTCGATCGTGCTAAGGAGGGACCCGGTCGGCACCATG |
| GCCGCGGCATACCGGTATCCCGGAGGGTCGCGGTTGGGAGCGGCCATAGGGTCGCGTGGAGATCGGCTGTCTCTAGCG |
| ATATTGGCCCGGGGAGGCTAAGATCCACCCCAACGCCCGGCCACCCGTGTACGTGCCCGACGGCCCAAGGTCCACCGA |
| AAGACACGACGGACCCGGACCCAAAGAGGCGGGGGATGCTGTGTGAGAGGCCGGGTGTCGGTCGGGGGGGAAAGGCAC |
| CGGGAGAAGGCTGCGGCCTCGTTCCAGGAGAACCCAGTGTCCCCAACAGACCCGGGGACGTGGGATCCCCGGCCTTAT |
| ATACCCCCCCCCCCGCCCCACCCCCGTTAGAACGCGACGGGTGCATTCAAGATGGCCCTGGTCCAAAAGCGTGCCAGG |
| AAGAAATTGGCAGAGGCGGCAAAGCTGTCCGCCGCCGCCACCCACATCGAGGCCCCGGCCACACAGGCTATCCCCAGG |
| GCCCGTGTGCGCAGGGGATCGGTGGGTGGCAGCATTTGGTTGGTGGCGATAAAGTGGAAAAGCCCGTCCGGACTGAAG |
| GTCTCGTGGGCGGCGGCGAACAAGGCACACAGGGCCGTGCCTCCCAAAAACATGGACATCCCCCAAAACACGGGCGCC |
| GACAACGGCAGACGATCCCTCTTGATGTTAACGTACAGGAGGAGCGCCCGCACCGCCCACGTAACGTAGTAGCCGACG |
| ATGGCGGCCAGGATACAGGCCGGCGCCACCACCCTTCCGGTCAGCCCGTAATACATGCCCGCTGCCACCATCTCCAAC |
| GGCTTCAGGACCAAAAACGACCAAAGGAACAGAATCACGCGCTTTGAAAAGACCGGCTGGGTATGGGGCGGAAGACGC |
| GAGTATGCCGAACTGACAAAAAAATCAGAGGTGCCGTACGAGGACAATGAAAACTGTTCCTCCAGCGGCAGTTCTCCC |
| TCCTCCCCCCCGAAGGCGGCCTCGTCGACCAGATCTCGATCCACCAGAGGAAGGTCATCCCGCATGGTCATGGGGTGT |
| GCGGTGGAGGTGGGGAGACCGAAACCGCAAAGGGTCGCTTACGTCAGCAGGATCCCGAGATCAAAGACACCCGGGTTC |
| TTGCACAAACACCACCCGGGTTGCATCCGCGGAGGCGAGTGTTTTGATAAGGCCGTTCCGCGCCTTGATATAACCTTT |
| GATGTTGACCACAAAACCCGGAATTTACGCCTACGCCCCAATGCCCACGCAAGATGAGGTAGGTAACCCCCCCGTGGG |
| TGTGACGTTGCGTTTAGTTCATTGGAGGCCAAGGGGAAAAATGGGGTGGGGAGGAAACGGAAAACCCAGTAGGCCGTG |
| TCGGGAACACGCCCGGGGTTGTCCTCAAAAGGCAGGGTCCATACTACGGAAGCCGTCGTTGTATTCGAGACCTGCCTG |
| TGCGACGCACGTCGGGGTTGCCTGTGTCCGGTTCGGCCCCCACCGCGTGCGGCACGCACGAGGACGAGTCCGCGTGCT |
| TTATTGGCGTTCCAAGCGTTGCCCTCCAGTTTCTGTTGTCGGTGTTCCCCCATACCCACGCCCACATCCACCGTAGGG |
| GGCCTCTGGGCCGTGTTACGTCGCCGCCCGCGATGGAGCTTAGCTACGCCACCACCATGCACTACCGGGACGTTGTGT |
| TTTACGTCACAACGGACCGAAACCGGGCCTACTTTGTGTGCGGGGGGTGTGTTTATTCCGTGGGGCGGCCGTGTGCCT |

-continued

| SEQUENCES |
|---|
| CGCAGCCCGGGGAGATTGCCAAGTTTGGTCTGGTCGTTCGAGGGACAGGCCCAGACGACCGCGTGGTCGCCAACTATG<br>TACGAAGCGAACTCCGACAACGCGGCCTGCAGGACGTGCGTCCCATTGGGGAGGACGAGGTGTTTCTGGACAGCGTGT<br>GTCTTCTAAACCCGAACGTGAGCTCCGAGCTGGATGTGATTAACACGAACGACGTGGAAGTGCTGGACGAATGTCTGG<br>CCGAGTACTGCACCTCGCTGCGAACCAGCCCGGGTGTGCTAATATCCGGGCTGCGCGTGCGGGCGCAAGACAGAATCA<br>TCGAGTTGTTTGAACACCCAACGATAGTCAACGTTTCCTCGCACTTTGTGTATACCCCGTCCCCATACGTGTTCGCCC<br>TGGCCCAGGCGCACCTCCCCCGGCTCCCGAGCTCGCTGGAGGCCCTGGTGAGCGGCCTGTTTGACGGCATCCCCGCCC<br>CACGCCAGCCACTTGACGCCCACAACCCGCGCACGGATGTGGTTATCACGGGCCGCCGCGCCCCACGACCCATCGCCG<br>GGTCGGGGGCGGGGTCGGGGGGCGCGGGCGCCAAGCGGGCCACCGTCAGCGAGTTCGTGCAAGTCAAACACATTGACC<br>GCGTGGGCCCCGCTGGCGTTTCGCCGGCGCCTCCGCCAAACAACACCGACTCGAGTTCCCTGGTGCCCGGGGCCCAGG<br>ATTCCGCCCCGCCCGGCCCCACGCTAAGGGAGCTGTGGTGGGTGTTTTATGCCGCAGACCGGGCGCTGGAGGAGCCCC<br>GCGCCGACTCTGGCCTCACCCGCGAGGAGGTACGTGCCGTACGTGGGTTCCGGGAGCAGGCGTGGAAACTGTTTGGCT<br>CCGCGGGGGCCCCGCGGGCGTTTATCGGGGCCGCGTTGGGCCTGAGCCCCCTCCAAAAGCTGGCCGTTTACTACTATA<br>TCATCCACCGAGAGAGGCGCCTGTCCCCCTTCCCCGCGCTAGTCCGGCTCGTAGGCCGGTACACACAGCGCCACGGCC<br>TGTACGTCCCTCGGCCCGACGACCCAGTCTTGGCCGATGCCATCAACGGGCTGGTTCGCGACGCGCTGGCGGCCGGAA<br>CCACAGCCGAGCAGCTCCTCATGTTCGACCTTCTCCCCCCAAAGGACGTGCCGGTGGGAAGCGACGTGCAGGCCGACA<br>GCACCGCTCTGCTGCGCTTTATAGAATCGCAACGTCTCGCCGTCCCCGGGGGGGTGATCTCCCCCGAGCACGTCGCGT<br>ACCTTGGTGCGTTCCTGAGCGTGCTGTACGCTGGCCGCGGGCGCATGTCCGCAGCAACGCACACCGCGCGGCTGACAG<br>GGGTGACCTCCCTGGTGCTAGCGGTGGGTGACGTGGACCGTCTTTCCGCGTTTGACCGCGGAGCGGCGGGCGCGGCCA<br>GCCGCACGCGGGCCGCCGGGTACCTGGATGTGCTTCTTACCGTTCGTCTCGCTCGCTCCAAACACGGACAGTCTGTGT<br>AACAGACCCCAATAAACGTATGTCGCTACCACACCCTTGTGTGTCAATGGACGCCTCTCCGGGGGGGAGAGGGAAAAC<br>AAAGAGGGGCTGGGGGAGCGGCACCACTGGGGCCTGAACAAACAAACCACAGACACGGTTACAGTTTATTCGGTCGGG<br>CGGATAAACGGCCGAAGCCACGCCCCCTTTATTCGCGTCTCCAAAAAAACGGGACACTTGTCCGGAGAACCTTTAGGA<br>TGCCAGCCAGGGCGGCGGTAATCATAACCACGCCCAGCGCAGAGGCGGCCAGAAACCCGGGCGCAATTGCGGCCACGG<br>GCTGCGTGTCAAAGGCTAGCAAATGAATGACGGTTCCGTTTGGAAATAGCAACAAGGCCGTGGACGGCACGTCGCTCG<br>AAAACACGCTCGGGGCGCCCTCCGTCGGCCCGGCGGCGATTTGCTGCTGTGTGTTGTCCGTATCCACCAGCAACACAG<br>ACATGACCTCCCCGGCTGGGGTGTAGCGCATAAACACGGCCCCCACGAGCCCCAGGTCGCGCTGGTTTTGGGTGCGCA<br>CCAGCCGCTTGGACTCGATATCCCGGGTGGAGCCTTCGCATGTCGCGGTGAGGTAGGTTAGGAACAGTGGGCGTCGGA<br>CGTCGACGCCGGTGAGCTTGTAGCCGATCCCCCGGGGCAGAGGGGAGTGGGTGACGACGTAGCTGGCGTTGTGGGTGA<br>TGGGTACCAGGATCCGTGGCTCGACGTTGGCAGACTGCCCCCCGCACCGATGTGAGGCCTCAGGGACGAAGGCGCGGA<br>TCAGGGCGTTGTAGTGTGCCCAGCGCGTCAGGGTCGAGGCGAGGCCGTGGGTCTGCTGGGCCAGGACTTCGACCGGGG<br>TCTCGGATCGGGTGGCTTGAGCCAGCGCGTCCAGGATAAACACGCTCTCGTCTAGATCAAAGCGCAGGGAGGCCGCGC<br>ATGGCGAAAAGTGGTCCGGAAGCCAAAAGAGGGTTTTCTGGTGGTCGGCCCGGGCCAGCGCGGTCCGGAGGTCGGCGT<br>TGGTCGCTGCGGCGACGTCGGACGTACACAGGGCCGATGCTATCAGAAGGCTCCGGCGGGCGCGTTCCCGCTGCACCG<br>CCGAGGGGACGCCCGCCAAGAACGGCTGCCGGAGGACAGCCGAGGCGTAAAATAGCGCCCGGTGGACGACCGGGGTGG<br>TCAGCACGCGGCCCCCTAGAAACTCGGCATACAGGGCGTCGATGAGATGGGCTGCGCTGGGCGCCACTGCGTCGTACG<br>CCGAGGGGCTATCCAGCACGAAGGCCAGCTGATAGCCCAGCGCGTGTAATGCCAAGCTCTGTTCGCGCTCCAGAATCT<br>CGGCCACCAGGTGCTGGAGCCGAGCCTCTAGCTGCAGGCGGGCCGTGGGATCCAAGACTGACACATTAAAAAACACAG<br>AATCCGCGGCACAGCCCGCGGCCCCGCGGGCGGCCAACCCGGCAAGCGCGCGCGAGTGGGCCAAAAAGCCTAGCAGGT<br>CGGAGAGGCAGACCGCGCCGTTTGCGTGGGCGGCGTTCACGAAAGCAAAACCCGACGTCGCGAGCAGCCCCGTTAGGC<br>GCCAGAAGAGAGGGGGGCGCGGGCCCTGCTCGGCGCCCGCGTCCCCCGAGAAAAACTCCGCGTATGCCCGCGACAGGA<br>ACTGGGCGTAGTTCGTGCCCTCCTCCGGGTAGCCGCCCACGCGGCGGAGGGCGTCCAGCGCGGAGCCGTTGTCGGCCC<br>GCGTCAGGGACCCTAGGACAAAGACCCGATACCGGGGGCCGCCCGGGGGCCCGGGAAGAGCCCCCGGGGGGTTTTCGT<br>CCGCGGGGTCCCCGACCCGATCTAGCGTCTGGCCCGCGGGGACCACCATCACTTCCACCGGAGGGCTGTCGTGCATGG<br>ATATCACGAGCCCCATGAATTCCCGCCCGTAGCGCGCGCGCACCAGCGCGGCATCGCACCCGAGCACCAGCTCCCCCG<br>TCGTCCAGATGCCCACGGGCCACGTCGAGGCCGACGGGGAGAAATACACGTACCTACCTGGGGATCTCAACAGGCCCC<br>GGGTGGCCAACCAGGTCGTGGACGCGTTGTGCAGGTGCGTGATGTCCAGCTCCGTCGTCGGGTGCCGCCGGGCCCCAA<br>CCGGCGGTCGGGGGGCGGTGTATCACGCGGCCCGCTTGGGTGGCTCGCCGTCGCCACGTTGTCTCCCCGCGGGAACG<br>TCAGGGCCTCGGGGTCAGGGACGGCCGAAAACGTTACCCAGGCCCGGGAACGCAGCAACACGGAGGCGACTGGATTGT<br>ACAAGAGACCCTTAAGGGGGGCGACCGAGGGGGGAGGCTGGGCGGTCGGCTCGACCGTGGTGGGGGCGGGCAGGCTCG<br>CGTTCGGGGGCCGGCCGAGCAGGTAGGTCTTCGGGATGTAAAGCAGCTGGCCGGGGTCCCGCGGAAACTCGGCCGTGG<br>TGACCAATACAAAACAAAAGCGCTCCTCGTACCAGCGAAGAAGGGGCAGAGATGCCGTAGTCAGGTTTAGTTCGTCCG<br>GCGGCGCCAGAAATCCGCGCGGTGGTTTTTGGGGGTCGGGGGTGTTTGGCAGCCACAGACGCCCGGTGTTTGTGTCGC<br>GCCAGTACATGCGGTCCATGCCCAGGCCATCCAAAAACCATGGGTCTGTCTGCTCAGTCCAGTCGTGGACCTGACCCC<br>ACGCAACGCCCAAAATAATAACCCCCACGAACCATAAACCATTCCCCATGGGGGACCCCGTCCCTAACCCACGGGGCC<br>CGTGGCTATGGCAGGGCTTGCCGCCCCGACGTTGGCTGCGAGCCCTGGGCCTTCACCCGAACTTGGGGGGTGGGGTGG<br>GGAAAAGGAAGAAACGCGGGCGTATTGGCCCCAATGGGGTCTCGGTGGGGTATCGACAGAGTGCCAGCCCTGGGACCG<br>AACCCCGCGTTTATGAACAAACGACCCAACACCCGTGCGTTTTATTCTGTCTTTTTATTGCCGTCATAGCGCGGGTTC<br>CTTCCGGTATTGTCTCCTTCCGTGTTTCAGTTAGCCTCCCCCATCTCCCGGGCAAACGTGCGCGCCAGGTCGCAGATC<br>GTCGGTATGGAGCCGGGGGTGGTGACGTGGGTCTGGACCATCCCGGAGGTAAGTTGCAGCAGGGCGTCCCGGCAGCCG<br>GCGGGCGATTGGTCGTAATCCAGGATAAAGACGTGCATGGGACGGAGGCGTTTGGCCAAGACGTCCAAGGCCCAGGCA<br>AACACGTTGTACAGGTCGCCGTTGGGGGCCAGCAACTCGGGGGCCCGAAACAGGGTAAATAACGTGTCCCCGATATGG<br>GGTCGTGGGCCCGCGTTGCTCTGGGGCTCGGCACCCTGGGGCGGCACGGCCGTCCCCGAAAGCTGTCCCCAATCCTCC<br>CGCCACGACCCGCCGCCCTGCAGATACCGCACCGTATTGGCAAGCAGCCCGTAAACGCGGCGAATCGCGGCCAGCATA<br>GCCAGGTCAAGCCGCTCGCCGGGGCGCTGGCGTTTGGCCAGGCGGTCGATGTGTCTGTCCTCCGGAAGGGCCCCCAAC<br>ACGATGTTTGTGCCGGGCAAGGTCGGCGGATGAGGGCCACGAACGCCAGCACGGCCTGGGGGGTCATGCTGCCCATA<br>AGGTATCGCGCGGCCGGGTAGCACAGGAGGGCGGCGATGGGATGGCGGTCGAAGATGAGGGTGAGGGCCGGGGGCGGG<br>GCATGTGAGCTCCCAGCCTCCCCCCCGATATGAGGAGCCAGAACGGCGTCGGTCACGGCATAAGGCATGCCCATTGTT<br>ATCTGGGCGCTTGTCATTACCACCGCCGCGTCCCCGGCCGATATCTCACCCTGGTCGAGGCGGTGTTGTGTGGTGTAG<br>ATGTTCGCGATTGTCTCGGAAGCCCCCAGCACCTGCCAGTAAGTCATCGGCTCGGGTACGTAGACGATATCGTCGCGC<br>GAACCCAGGGCCACCAGCAGTTGCGTGGTGGTGGTTTTCCCCATCCCGTGAGGACCGTCTATATAAACCCGCAGTAGC<br>GTGGGCATTTTCTGCTCCAGGCGGACTTCCGTGGCTTCTTGCTGCCGGCGAGGGCGCAACGCCGTACGTCGGTTGCTA<br>TGGCCGCGAGAACGCGCAGCCTGGTCGAACGCAGACGCGTGTTGATGGCAGGGGTACGAAGCCATACGCGCTTCTACA<br>AGGCGCTTGCCGAAGAGGTGCGGGAGTTTCACGCCACCAAGATCTGCGGCACGCTGTTGACGCTGTTAAGCGGGTCGC<br>TGCAGGGTCGCTCGGTGTTCGAGGCCACACGCGTCACCTTAATATGCGAAGTGGACCTGGGACCGCGCCGCCCCGACT<br>GCATCTGCGTGTTCGAATTCGCCAATGACAAGACGCTGGGCGGGGTTTGTGTCATCATAGAACTAAAGACATGCAAAT<br>ATATTTCTTCCGGGGACACCGCCAGCAAACGCGAGCAACGGGCCACGGGGATGAAGCAGCTGCGCCACTCCCTGAAGC<br>TCCTGCAGTCCCTCGCGCCTCCGGGTGACAAGATAGTGTACCTGTGCCCCGTCCTGGTGTTTGTCGCCCAACGGACGC |

-continued

| SEQUENCES |
| --- |
| TCCGCGTCAGCCGCGTGACCCGGCTCGTCCCGCAGAAGGTCTCCGGTAATATCACCGCAGTCGTGCGGATGCTCCAGA |
| GCCTGTCCACGTATACGGTCCCCATGGAGCCTAGGACCCAGCGAGCCCGTCGCCGCCGCGGCGGCGCCGCCCGGGGGT |
| CTGCGAGCAGACCGAAAAGGTCACACTCTGGGGCGCGCGACCCGCCCGAGTCAGCGGCCCGCCAATTACCACCCGCCG |
| ACCAAACCCCCGCCTCCACGGAGGGCGGGGGGGTGCTTAAGAGGATCGCGGCGCTCTTCTGCGTGCCCGTGGCCACCA |
| AGACCAAACCCCGAGCCGCCTCCGAATGAGAGTGTTTCGTTCCTTCCCCCTCCCCCGCGTCAGACAAACCCTAACCA |
| CCGCTTAAGCGGCCCCCGCGAGGTCCGAAGACTCATTTGGATCGGCGGGAGCCACCCGACAACAGCCCCCGGGTTTT |
| CCCACGCCAGACGCCGGTCCGCTGTGCCATCGCGCCCCCTCATCCCACCCCCCATCTTGTCCCCAAATAAAACAAGGT |
| CTGGTAATTAGGACAACGACCGCAGTTCTCGTGTGTTATTTTCGCTCTCCGCCTCTCGCAGATGGACCCGTACTGCCC |
| ATTTGACGCTCTGGACGTCTGGGAACACAGGCGCTTCATAGTCGCCGATTCCCGAAACTTCATCACCCCCGAGTTCCC |
| CCGGGACTTTTGGATGTCGCCCGTCTTTAACCTCCCCCGGGAGACGGCGGCGGAGCAGGTGGTCGTCCTACAGGCCCA |
| GCGCACAGCGGCTGCCGCTGCCCTGGAGAACGCCGCCATGCAGGCGGCCGAGCTCCCCGTCGATATCGAGCGCCGGTT |
| ACGCCCGATCGAACGGAACGTGCACAAGATCGCAGGCGCCCTGGAGGCGCTGGAGACGGCGGCGGCCGCCGCCGAAGA |
| GGCGGATGCCGCGCGCGGGGATGAGCCGGCGGGTGGGGGCGACGGGGGGGCGCCCCCGAGTCTGGCCGTCGCGGAGAT |
| GGAGGTCCAGATCGTGCGCAACGACCCGCCGCTACGATACGACACCAACCTCCCCGTGGATCTGCTACACATGGTGTA |
| CGCGGGCCGCGGGGCGACCGGATCGTCGGGGGTGGTGTTCGGGACCTGGTACCGCACTATCCAGGACCGCACCATCAC |
| GGACTTTCCCCTGACCACCCGCAGTGCCGACTTTCGGGACGGCCGTATGTCCAAGACCTTCATGACGGCGCTGGTACT |
| GTCCCTGCAGTCGTGCGGCCGGCTGTATGTGGGCCAGCGCCACTATTCCGCCTTCGAGTGCGCCGTGTTGTGTCTCTA |
| CCTGCTGTACCGAAACACGCACGGGGCCGCCGACGATAGCGACCGCGCTCCGGTCACGTTCGGGGATCTGCTGGGCCG |
| GCTGCCCCGCTACCTGGCGTGCCTGGCCGCGGTGATCGGGACCGAGGGCGGCCGGCCACAGTACCGCTACCGCGACGA |
| CAAGCTCCCCAAGACGCAGTTCGCGGCCGGCGGGGGCCGCTACGAACACGGAGCGCTGGCGTCGCACATCGTGATCGC |
| CACGCTGATGCACCACGGGGTGCTCCCGGCGGCCCCGGGGGACGTCCCCGGGACGCGAGCACCCACGTTAACCCCGA |
| CGGCGTGGCGCACCACGACGACATAAACCGCGCCGCCGCCGCGTTCCTCAGCCGGGGCCACAACCTATTCCTGTGGGA |
| GGACCAGACTCTGCTGCGGGCAACCGCGAACACCATAACGGCCCTGGGCGTTATCCAGCGGCTCCTCGCGAACGGCAA |
| CGTGTACGCGGACCGCCTCAACAACCGCCTGCAGCTGGGCATGCTGATCCCCGGAGCCGTCCCTTCGGAGGCCATCAC |
| CCGTGGGGCCTCCGGGTCCGACTCGGGGGCCATCAAGAGCGGAGACAACAATCTGGAGGCGCTATGTGCCAATTACGT |
| GCTTCCGCTGTACCGGGCCGACCCGGCGGTCGAGCTGACCCAGCTGTTTCCCGGCCTGGCCGCCCTGTGTCTTGACGC |
| CCAGGCGGGGCGGCCGGTCGGGTCGACGCGGCGGGTGGTGGATATGTCATCGGGGGCCCGCCAGGCGGCGCTGGTGCG |
| CCTCACCGCCCTGGAACTCATCAACCGCACCCGCACAAACCCCACCCCCGTGGGGGAGGTTATCCACGCCCACGACGC |
| CCTGGCGATCCAATACGAACAGGGGCTTGGCCTGCTGGCGCAGCAGGCACGCATTGGCTTGGGCTCCAACACCAAGCG |
| TTTCTCCGCGTTCAACGTTAGCAGCGACTACGACATGTTGTACTTTTTATGTCTGGGGTTCATTCCACAGTACCTGTC |
| GGCGGTTTAGTGGGTGGTGGGCGAGGGGGGAGGGGGCATTAGGGAGAAAGAACAAGAGCCTCCGTTGGGTTTTCTTTG |
| TGCCTGTACTCAAAAGGTCATACCCCGTAAACGGCGGGCTCCAGTCCCGGCCCGGCGGTTGGCGTGAACGCAACGGCG |
| GGAGCTGGGTTAGCGTTAGTTTAGCATTCGCTCTCGCCTTTCCGCCCGCCCCCCGACCGTTGCGCCTTTTTTTTTT |
| CGTCCACCAAAGTCTCTGTGGGTGCGCGCATGACAGCCGATGCCCCGGGAGACCGGATGGAGGAGCCCCTGCCAGACA |
| GGGCCGTGCCCATTTACGTGGCTGGGTTTTTGGCCCTGTATGACAGCGGGGACTCGGGCGAGTTGGCATTGGATCCGG |
| ATACGGTGCGTGCGGCCCTGCCTCCGGATAACCCACTCCCGATTAACGTGGACCACCGCGCTGGCTGCGAGGTGGGGC |
| GGGTGCTGGCCGTGGTCGACGACCCCCGCGGGCCGTTTTTTGTGGGACTGATCGCCTGCGTGCAACTGGAGCGCGTCC |
| TCGAGACGGCCGCCAGCGCTGCGATTTTCGAGCGCCGCGGGCCGCCGCTCTCCCGGGAGGAGCGCCTGTTGTACCTGA |
| TCACCAACTACCTGCCCTCGGTCTCCCTGGCCACAAAACGCCTGGGGGGCGAGGCGCACCCCGATCGCACGCTGTTCG |
| CGCACGTCGCGCTGTGCGCGATCGGGCGGCGCCTCGGCACTATCGTCACCTACGACACCGGTCTCGACGCCGCCATCG |
| CGCCCTTTCGCCACCTGTCGCCGGCGTCTCGCGAGGGGGCGCGGCGACTGGCCGCCGAGGCCGAGCTCGCGCTGTCCG |
| GACGCACCTGGGCGCCCGGCGTGGAGGCGCTGACCCACACGCTGCTTTCCACCGCCGTTAACAACATGATGCTGCGGG |
| ACCGCTGGAGCCTGGTGGCCGAGCGGCGGCGGCAGGCCGGGATCGCCGGACACACCTACCTCCAGGCGAGCGAAAAAT |
| TCAAAATGTGGGGGGCGGAGCCTGTTTCCGCGCCGGCGCGCGGGTATAAGAACGGGGCCCCGGAGTCCACGGACATAC |
| CGCCCGGCTCGATCGCTGCCGCGCCGCAGGGTGACCGGTGCCCAATCGTCCGTCAGTGCGGGGTCGCCTCGCCCCCGG |
| TACTGCCCCCCATGAACCCCGTTCCGGCATCGGGCACCCCGGCCCCCGCGCCGCCCGGCGACGGGAGCTACCTGTGGA |
| TCCCGGCCTCCCATTACAACCAGCTCGTCGCCGGCCACGCCGCGCCCCAACCCCAGCCGCATTCCGCGTTTGGTTTCC |
| CGGCTGCGGCGGGGGCCGTGGCCTATGGGCCTCACGGCGCGGGTCTTTCCCAGCATTACCCTCCCCACGTCGCCCATC |
| AGTATCCCGGGGTGCTGTTCTCGGGACCCAGCCCACTCGAGGCGCAGATAGCCGCGTTGGTGGGGGCCATAGCCGCGG |
| ACCGCCAGGCGGGCGGTCAGACGGCCGCGGGAGACCCTGGGGTCCGGGGGTCGGGAAAGCGTCGCCGGTACGAGGCGG |
| GGCCGTCGGAGTCCTACTGCGACCAGGACGAACCGGACGCGGACTACCCGTACTACCCCGGGGAGGCTCGAGGCGGGC |
| CGCGCGGGGTCGACTCTCGGCGCGCGGCCCGCCAGTCTCCCGGGACCAACGAGACCATCACGGCGCTGATGGGGGCGG |
| TGACGTCTCTGCAGCAGGAACTGGCGCACATGCGGGCTCGGACCAGCGCCCCCTATGGAATGTACACGCCGGTGGCGC |
| ACTATCGCCCTCAGGTGGGGGAGCCGGAACCAACAACGACCCACCCGGCCCTTTGTCCCCCGGAGGCCGTGTATCGCC |
| CCCCACCACACAGCGCCCCCTACGGTCCTCCCCAGGGTCCGGCGTCCCATGCCCCCACTCCCCCGTATGCCCCAGCTG |
| CCTGCCCGCCAGGCCCGCCACCGCCCCCATGTCCTTCCACCCAGACGCGCGCCCCTCTACCGACGGAGCCCGCGTTCC |
| CCCCCGCCGCCACCGGATCCCAACCGGAGGCATCCAACGCGGAGGCCGGGGCCCTTGTCAACGCCAGCAGCGCAGCAC |
| ACGTGGACGTTGACACGGCCCGCGCCGCCGATTTGTTCGTCTCTCAGATGATGGGGGCCCGCTGATTCGCCCCGGTCT |
| TTGGTACCATGGGATGTCTTACTGTATATCTTTTTAAATAAACCAGGTAATACCAAATAAGACCCATTGGTGTATGTT |
| CTTTTTTTATTGGGAGGCGCGGGTAGGCGGGTAGCTTTACAATGCAAAAACCTTCGACGTGGAGGAAGGCGTGGGGGG |
| GGGGAATCGGCACTGACCAAGGGGGTCCGTTTTGTCACGGGAAAGGAAAGAGGAAACAGGCCGCGGACACCCGGGGGA |
| GTTTATGTGTTCCCTTTTCTTTCTTCCCACACACACAAAAGGCGTACCAAACAAACAAACCAAAAGATGCACATGCGG |
| TTTAACACCCGTGGTTTTTATTTACAACAAACCCCCCGTCACAGGTCGTCCTCGTCGGCGTCACCGTCTTTGTTGGGA |
| ACTTGGGTGTAGTTGGTGTTGCGGCGCTTGCGCATGACCATGTCGGTGACCTTGGCGCTGAGCAGCGCGCTCGTGCCC |
| TTCTTCTTGGCCTTGTGTTCCGTGCGCTCCATGGCAGACACCAGGGCCATGTACCGTATCATCTCCCGGGCCTCGGCT |
| AGCTTGGCCTCGTCAAAGTCGCCGCCCTCCTCGCCCTCCCCGGACGCGTCCGGGTTGGTGGGGTTCTTGAGCTCCTTG |
| GTGGTTAGCGGGTACAGGGCCTTCATGGGGTTGCTCTGCAGCCGCATGACGTAGCGAAAGGCGAAGAAAGCCGCCGCC |
| AGGCCGGCCAGGACCAACAGACCCACGGCCAGCGCCCCAAAGGGGTTGGACATGAAGGAGGACACGCCCGACACGGCC |
| GATACCACGCCGCCCACGATGCCCATCACCACCTTGCCGACCGCGCGCCCCAGGTCGCCCATCCCCTCGAAGAACGCG |
| CCCAGGCCCGCGAACATGGCGGCGTTGGCGTCGGCGTGGATGACCGTGTCGATGTCGGCGAAGCGCAGGTCGTGCAGC |
| TGGTTGCGGCGCTGGACCTCCGTGTAGTCCAGCAGGCCGCTGTCCTTGATCTCGTGGCGGGTGTACACCTCCAGGGGG |
| ACAAACTCGTGATCCTCCAGCATGGTGATGTTGAGGTCGATGAAGGTGCTGACGGTGGTGATGTCGGCGCGGCTCAGC |
| TGGTGGGAGTACGCGTACTCCTCGAAGTACACGTAGCCCCCGCCGAAGGTGAAGTAGCGCCGGTGTCCCACGGTGCAC |
| GGCTCGATCGCATCGCGCGTCAGCCGCAGCTCGTTGTTCTCCCCCAGCTGCCCCTCGACCAACGGGCCCTGGTCTTCG |
| TACCGAAAGCTGACCAGGGGGCGGCTGTAGCAGGCCCCGGGCCGCGAGCTGATGCGCATCGAGTTTTGGACGATCACG |
| TTGTCCGCGGCGACCGGCACGCACGTGGAGACGGCCATCACGTCGCCGAGCATCCGCGCGCTCACCCGCCGGCCCACG |
| GTGGCCGAGGCGATGGCGTTGGGGTTCAGCTTGCGGGCCTCGTTCCACAGGGTCAGCTCGTGATTCTGCAGCTCGCAC |

-continued

| SEQUENCES |
| --- |
| CACGCGATGGCAACGCGGCCCAACATATCGTTGACATGGCGCTGTATGTGGTTGTACGTAAACTGCAGCCGGGCGAAC<br>TCGATGGAGGAGGTGGTCTTGATGCGCTCCACGGACGCGTTGGCGCTGGCCCCGGGCGGCGGGGGCGTGGGGTTTGGG<br>GGCTTGCGGCTCTGCTCTCGGAGGTGTTCCCGCACGTACAGCTCCGCGAGCGTGTTGCTGAGAAGGGGCTGGTACGCG<br>ATCAGAAAACCCCCATTGGCCAGGTAGTACTGCGGCTGGCCCACCTTGATGTGCGTCGCGTTGTACCTGCGGGCGAAG<br>ATGCGGTCCATGGCGTCGCGGGCGTCCTTGCCGATGCAGTCCCCCAGGTCCACGCGCGAGAGCGGGTACTCGGTCAGG<br>TTGGTGGTGAAGGTGGTGGATATGGCGTCGGAGGAGAATCGGAAGGAGCCGCCGTACTCGGAGCGCAGCATCTCGTCC<br>ACCTCCTGCCACTTGGTCATGGTGCAGACCGACGGGCGCTTTGGCACCCAGTCCCAGGCCACGGTGAACTTGGGGGTC<br>GTGAGCAGGTTCCGGGTGGTCGGCGCCGTGGCCCGGGCCTTGGTGGTGAGGTCGCGCGCGTAGAAGCCGTCAACCTGC<br>TTGAAGCGGTCGGCGGCGTAGCTGGTGTGTTCGGTGTGCGACCCCTCCCGGTAGCCGTAAAACGGGGACATGTACACA<br>AAGTCGCCAGTCGCCAGCACAAACTCGTCGTACGGGTACACCGAGCGCGCGTCCACCTCCTCGACGATGCAGTTTACC<br>GTCGTCCCGTACCGGTGGAACGCCTCCACCCGCGAGGGGTTGTACTTGAGGTCGGTGGTGTGCCAGCCCCGGCTCGTG<br>CGGGTCGCGGCGTTGGCCGGTTTCAGCTCCATGTCGGTCTCGTGGTCGTCCCGGTGAAACGCGGTGGTCTCCAGGTTG<br>TTGCGCACGTACTTGGCCGTGGACCGACAGACCCCCTTGGCGTTGATCTTGTCGATCACCTCCTCGAAGGGGACGGGG<br>GCGCGGTCCTCAAAGATCCCCATAAACTGGGAGTAGCGGTGGCCGAACCACACCTGCGAAACGGTGACGTCTTTGTAG<br>TACATGGTGGCCTTGAACTTGTACGGGGCGATGTTCTCCTTGAAGACCACCGCGATGCCCTCCGTGTAGTTCTGACCC<br>TCGGGCCGGGTCGGGCAGCGGCGCGGCTGCTCGAACTGCACCACCGTGGCGCCCGTGGGGGGTGGGCACACGTAAAAG<br>TTTGCATCGGTGTTCTCCGCCTTGATGTCCCGCAGGTGCTCGCGCAGGGTGGCGTGGCCCGCGGCGACGGTCGCGTTG<br>TCGCCGGCGGGGCGCGGCGGCGGTGGGGGTTTCGGTTTTTTGTTCTTCTTCGGTTTCGTGTCCCCCGTTGGGGCGGGG<br>CCAGGGGCGGGCGGCGCCGGAGTGGCAGGTCCCCCGTTCGCCGCCTGGGTCGCGGCCGCGACCCCAGGCGTGCCGGGG<br>GAACTCGGAGCCGCCGACGCCACCAGGACCCCCAGCGTCAACCCCAAGAGCGCCCATACGACGAACCACCGGCACCCC<br>CGCGCGGGGGCGCCCTGGCGCATGGCGGGACTACGGGGCCCGTCGTGCCCCCCGTCAGGTAGCCTGGGGGCGAGGTG<br>CTGGAGGACCGAGTAGAGGATCGAGAAAACGTCTCGGTCGTAGACCACGACCGACCGGGGGCCGATACAGCCGTCGGG<br>GGCGCTCTCGACGATGGCCACCAGCGGACAGTCGGAGTCGTACGTGAGATATACGCCGGGCGGGTAACGGTAACGACC<br>TTCGGAGGTCGGGCGGCTGCAGTCCGGGCGGCGCAACTCGAGCTCCCCGCACCGGTAGACCGAGGCAAAGAGTGTGGT<br>GGCGATAATCAGCTCGCGAATATATCGCCAGGCGGCGCGCTGAGTGGGCGTTATTCCGGAAATGCCGTCAAAACAGTA<br>AAACCTCTGAAATTCGCTGACGGCCCAATCAGCACCCGAGCCCCCCGCCCCCATGATGAACCGGGCGAGCTCCTCCTT<br>CAGGTGCGGCAGGAGCCCCACGTTCTCGACGCTGTAATACAGCGCGGTGTTGGGGGGCTGGGCGAAGCTGTGGGTGGA<br>GTGATCAAAGAGGGGCCCGTTGACGAGCTCGAAGAAGCGATGGGTGATGCTGGGGAGCAGGGCCGGGTCCACCTGGTG<br>TCGCAGGAGAGACGCTCGCATGAACCGGTGCGCGTCGAACACGCCCGGCGCCGAGCGGTTGTCGATGACCGTGCCCGC<br>GCCCGCCGTCAGGGCGCAGAAGCGCGCGCGCGCCGCAAAGCCGTTGGCGACCGCGGCGAACGTCGCGGGCAGCACCTC<br>GCCGTGGACGCTGACCCGCAGCATCTTCTCGAGCTCCCCGCGCTGCTCGCGGACGCAGCGCCCCAGGCTGGCCAACGA<br>CCGCTTCGTCAGGCGGTCCGCGTACAGCCGCCGTCGCTCCCGCACGTCCGCGGCCGCTTGCGTGGCGATGTCCCCCCA<br>CGTCTCGGGCCCCTGCCCCCGGGCCGCGGCGACGGTCTTCGTCCTCGCCCCCGCCCCCGGGAGCTCCCAACCCCCG<br>TGCCCCTTCCTCTACGGCGACACGGTCCCCGTCGTCGGGGCCCGCGCCGCCCCTTGGGCGCGTCCGCCGCGCCCCC<br>CGCCCCCATGCGCGCCAGCACGCGACGCAGCGCCTCCTCGTCGCACTGTTCGGGGCTGACGAGGCGCCGCAAGAGCGG<br>CGTCGTCAGGTGGTGGTCGTAGCACGCGCGGATGAGCGCCTCGATCTGATCGTCGGGTGACGTGGCCTGACCGCCGAT<br>TATTAGGGCGTCCACCATATCCAGCGCCGCCAGGTGGCTCCCGAACGCGCGATCGAAATGCTCCGCCCGCCGCCCGAA<br>CAGCGCCAGTTCCACGGCCACCGCGGCGGTCTCCTGCTGCAACTCGCGCCGCGCCAGCGCGGTCAGGTTGCTGGCAAA<br>CGCGTCCATGGTGGTCTGGCCGGCGCGGTCGCCGGACGCGAGCCAGAATCGCAATTCGCTGATGGCGTACAGGCCGGG<br>CGTGGTGGCCTGAAACACGTCGTGCGCCTCCAGCAGGGCGTCGGCCTCCTTGCGGACCGAGTCGTTCTCGGGCGACGG<br>GTGGGGCTGCCCGTCGCCCCCCGCGGTCCGGGCCAGCGCATGGTCCAACACGGAGAGCGCCCGCGCGCGGTCGGCGTC<br>CGACAGCCCGGCGGCGTGGGGCAGGTACCGCCGCAGCTCGTTGGCGTCCAGCCGCACCTGCGCCTGCTGGGTGACGTG<br>GTTACAGATACGGTCCGCCAGGCGGCGGGCGATCGTCGCCCCCTGGTTCGCCGTCACACACAGTTCCTCGAAACAGAC<br>CGCGCAGGGGTGGGACGGGTCGCTAAGCTCCGGGGGGACGATAAGGCCCGACCCCACCGCCCCCACCATAAACTCCCG<br>AACGCGCTCCAGCGCGGCGGTGGCGCCGCGCGAGGGGGTGATGAGGTGGCAGTAGTTTAGCTGCTTTAGAAAGTTCTC<br>GACGTCGTGCAGGAAACACAGCTCCATATGGACGGTCCCGCCATACGTATCCAGCCTGACCCGTTGGTGATACGGACA<br>GGGTCGGGCCAGGCCCATGGTCTCCGTGAAAAACACCGCGACGTCTCCCGCGGTCGCGAACGTCTCCAGGCTGCCCAG<br>GAGCCGCTCGCCCTCGCGCCACGCGTACTCTAGCAGCAACTCCAGGGTGACCGACAGCGGGGTGAGAAAGGCCCCGGC<br>CTGGGCCTCCAGGCCCGGCCTCAGACGACGCCGCAGCGCCCGCACCTGAAGCGCGTTCAGCTTCAGTTGGGGGAGCTT<br>CCCCCGTCCGATGTGGGGGTCGCACCGCCGGAGCAGCTCTATCTGAAACACATAGGTCTGCACCTGTCCGAGCAGGGC<br>TAACAACTTTTGACGGGCCACGGTGGGCTCGGACACCGGGGCGGCCATCTCGCGGCGCCGATCTGTACCGCGGCCGGA<br>GTATGCGGTGGACCGAGGCGGTCCGTACGCTACCCGGCGTCTGGCTGAGCCCCGGGGTCCCCCTATTCGGGGCGGCCT<br>CCCGCGGGCCCGCCGACCGGCAAGCCGGGAGTCGGCGGCGCGTGCGTTTCTGTTCTATTCCCAGACACCGCGGAGAGG<br>AATCACGGCCCGCCCAGAGATATAGACACGGAACACAAACAAGCACGGATGTCGTAGCAATAATTTATTTTACACACA<br>TTCCCCGCCCCGCCCTAGGTTCCCCCACCCCCCAACCCCTCACAGCATATCCAACGTCAGGTCTCCCTTTTTGTCGGG<br>GGGCCCCTCCCCAAACGGGTCATCCCCGTGGAACGCCCGTTTGCGGCCGGCAAATGCCGGTCCCGGGGCCCCCGGGCC<br>GCCGAACGGCGTCGCGTTGTCGTCCTCGCAGCCAAAATCCCCAAAGTTAAACACCTCCCCGACGTTGCCGAGTTGGCT<br>GACTAGGGCCTCGGCCTCGTGCGCCACCTCCAGGGCCGCGTCCGTCGACCACTCGCCGTTGCCGCGCTCCAGGGCACG<br>TGCGGTCAGCTCCATCATCTCCTCGCTTAGGTACTCGTCCTCCAGGAGCGCCAGCCAGTCCTCGATCTGCAGCTGTTG<br>GGTGCGGGGCCCCAGGCTTTTCACGGTCGCCACGAACACGCTACTGGCGACGGCCGCCCCGCCCTCGGAGATAATGCC<br>CCGGAGCTGCTCGCACAGCGAGCTTTCGTGCGCTCCGCCGCCGAGGCTCGAGGCCGCGCACACAAACCCGGCCCGGGG<br>ACAGGCCAGGACGAACTTGCGGGTGCGGTCAAAAATAAGGAGCGGGCACGCGTTTTTGCCGCCCATCAGGCTGGCCCA<br>GTTCCCGGCCTGAAACACACGGTCGTTGCCGGCCATGCCGTAGTATTTGCTGATGCTCAACCCCAACACGACCATGGG<br>GCGTGCCGCCATGACGGGCCGCAGCAGGTTGCAGCTGGCGAACATGGAGGTCCACGCGCCCGGATGCGCGTCCACGGC<br>GTCCATCAGCGCGCGGGCCCCGGCCTCCAGGCCCGCCCCGCCCTGCGCGGACCACGCGGCCGCCGCCTGCACGCTGGG<br>GGGACGGCGGGACCCCGCGATGATGGCCGTGAGGGTGTTGATGAAGTACGTCGAGTGATCGCAGTACCGCAGAATCTG<br>GTTTGCCATGTAGTACATCGCCAGCTCGCTCACGTTGTTGGGGGCCAGGTTAATAAAGTTGATCGCGCCGTAGTCCAG<br>GGAAAACTTTTTAATGAACGCGATGGTCTCGATGTCCTCGCGCGACAGGAGCCGGGCGGGAAGCTGGTTGCGTTGGAG<br>GGCCGTCCAGAACCACTGCGGGTTCGGCTGGTTGGACCCCGGGGGCTTGCCGTTGGGGAAGATGGCCGCGTGGAACTG<br>CTTCAGCAGAAAGCCCAGCGGTCCGAGGAGGATGTCCACGCGCTTGTCGGGCTTCTGGTAGGCGCTCTGGAGGCTGGC<br>GACCCGCGCCTTGGCGGCCTCGGACGCGTTGGCGCTCGCGCCCGCGAACAACACGCGGCTCTTGACGCGCAGCTCCTT<br>GGGAAACCCCAGGGTCACGCGGGCAACGTCGCCCTCGAAGCTGCTCTCGGCGGGGGCCGTCTGGCCGGCCGTCAGGCT<br>GGGGGCGCAGATAGCCGCACCCTCCGAGAGCGCGACCGTCAGCGTTTTGGCCGACAGAAACCCGTTGTTAAACATGTC<br>CATCACGCGCCGCCGCAGCACCGGTTGGAATTGATTGCGAAAGTTGCGCCCCTCGACCGACTGCCCGGCGAACACCCC<br>GTGGCACTGGCTCAGGGCCAGGTCCTGGTACACGGCGAGGTTGGATCGCCGCCCGAGAAGCTGAAGCAGGGGGCACGG<br>CCCGCACGCGTACGGGTCCAGCGTCAGGGACATGGCGTGGTTGGCCTCGCCCAGACCGTCGCGAAACTTGAAGTTCCT<br>CCCCTCCACCAGGTTGCGCATCAGCTGCTCCACCTCGCGGTCCACGACCTGCCTGACGTTGTTCACCACCGTATGCAG |

-continued

| SEQUENCES |
|---|
| GGCCTCGCGGTTGGTGATGATGGTCTCCAGCCGCCCCATGGCCGTGGGGACCGCCTGGTCCACGTACTGCAGGGTCTC<br>GAGTTCGGCCATGACGCGCTCGGTCGCCGCGCGGTACGTCTCCTGCATGATGGTCCGGGCGGTCTCGGATCCGTCCGC<br>GCGCTTCAGGGCCGAGAAGGCGGCGTAGTTTCCCAGCACGTCGCAGTCGCTGTACATGCTGTTCATGGTCCCGAAGAC<br>GCCGATGGCTCCGCGGGCGGCGCTGGCGAACTTGGGATGGCGCGCCCGGAGGCGCATGAGCGTCGTGTGTACGCAGGC<br>GTGGCGCGTGTCGAAGGTGCACAGGTTACAGGGCACGTCGGTCTGGTTGGAGTCCGCGACGTATCGAAACACGTCCAT<br>CTCCTGGCGCCCGACGATCACGCCGCCGTCGCAGCGCTCCAGGTAAAACAGCATCTTGGCCAGCAGCGCCGGGGAAAA<br>CCCACACAACATGGCCAGGTGCTCGCCGGCAAATTCCTGGGTTCCGCCGACGAGGGGCGCGGTGGGCCGACCCTCGAA<br>CCCGGGCACCACGTGTCCCTCGCGGTCCACCTGTGGGTTGGCCGCCACGTGGGTCCCGGGCACGAGGAAGAAGCGGTA<br>AAAGGAGGGTTTGCTGTGGTCCTTTGGGTCCGCCGGGCCGGCGTCGTCCACCTCGGTGAGATGGAGGGCCGAGTTGGT<br>GCTAAATACCATGGCCCCCACGAGTCCCGCGGCGCGCGCCAGGTACGCCCCGACGGCGTTGGCGCGGGCCGCGGCCGT<br>GTCCTGGCCCTCGAACAGCGGCCACGCGGAGATGTCGGTGGGCGGCTCGTCAAAGACGGCCATCGACACGATAGACTC<br>GAGGGCCAGGGCGGCATCTCCGGCCATGACGGAGGCCAGGCGCTGTTCGAACCCGCCCGCAGGGCCCTTGCCGCCGCC<br>GTCACGCCCGCCCCGCGGGGTCTTACCCTGGCTGGCTTCGAAGGCCGTGAACGTAATGTCGGCGGGGAGGGCGGCGCC<br>CTCGTGGTTTTCGTCAAACGCCAGGTGGGCGGCCGCGCGGGCCACGGCGTCCACGTTTCGGCATCGCAGTGCCACGGC<br>GGCGGGTCCCACGACCGCCTCGAACAGGAGGCGGTGGAGGGGGCGGTTAAAAAACGGAAGCGGGTAGGTAAAATTCTC<br>CCCGATAGATCGGTGGTTGGCGTTGAACGGCTCTGCGATGACACGGCTAAAATCCGGCATGAACAGCTGCAACGGGTA<br>CACGGGTATGCGGTGCACCTCCGCCCCGCCTATGGTTACCTTGTCCGAGCCTCCCAGGTGCAGAAAGGTGTTGTTGAT<br>GCACACGGCCTCCTTGAAGCCCTCGGTAACGACCAGATACAGGAGGGCGCGGTCCGGGTCCAGGCCGAGGCGCTCACA<br>CAGCGCCTCCCCCGTCGTCTCGTGTTTGAGGTCGCCGGGCCGGGGGGTGTAGTCCGAAAAGCCAAAATGGCGGCGTGC<br>CCGCTCGCAGAGTCGCGTCAGGTTCGGGGCCTGGGTGCTGGGGTCCAGGTGCCGGCCGCCGTGAAAGACGTACACGGA<br>CGAGCTGTAGTGCGAGGGCGTCAGTTTCAGGGACACCGCGGTACCCCCGAGCCCCGTCGTGCGAGAACCCACGACCAC<br>GGCCACGTTGGCCTCAAAGCCGCTCTCCACGGTCAGGCCCACGACCAGGGGCGCCACGGCGACGTCGGCATCGCCGCT<br>GCGCGCCGACAGTAACGCCAGAAGCTCGATGCCTTCGGACGGACACGCGCGAGCGTACACGTATCCCAGGGGCCCGGG<br>GGGGACCTTGATGGTGGTTGCCGTCTTGGGCTTTGTCTCCATGTCCTTCTGTCAATCGGTCCGCGAACGGAGGTAATC<br>CCGGCACGACGACGGACGCCCGACAAGGTATGTCTCCCGAGCGTCAAAATCCGGGGGGGGGCGGCGACGGTCAAGGGG<br>AGGGTTGGAGACCGGGGTTGGGGAATGAATCCCTACCCTTCACCGACAACCCCCCGGGTAATCACGGGGTGCCGATGA<br>ACCCCGGCGGCCGGCAACGCGGGGTCCCTGCGAGAGGCACAGATGCTTACGGTCAGGTGCTCCGGGTCGGGTGCGTCT<br>GGTATGCGGTTGGTATATGTACACTTTACCTGGGGGCGTGCCTGGCCGCCCCAGCCCCTCCCACGCCCCGCGCGTCAT<br>CAGCCGGTGGGCGTGGCCGCTATTATAAAAAAAGTGAGAACGCGAAGCGTTCGCACTTTGTCCTAATAATATATATAT<br>TATTAGGACAAAGTGCGAACGCTTCGCGTTCTCACTTTTTTTATAATAGCGCCCACGCCCACCGGCTACGTCACGCTC<br>CTGTCGGCCGCCGGCGGTCCATAAGCCCGGCCGGCCGGGCCGACGCGAATAAACCGGGCCGCCGGCCGGGGCGCCGCG<br>CAGCAGCTCGCCGCCCGGATCCGCCAGACAAACAAGGCCCTTGCACATGCCGGCCCGGGCGAGCCTGGGGGTCCGGTA<br>ATTTTGCCATCCCACCCAAGCGGCTTTTTGGGTTTTTCTCTTCCCCCCTCCCCACATCCCCCCTCTTTAGGGGTTCGG<br>GTGGTAACAACCGCGATGTTTTCCGGTGGCGGCGGCCCGCTGTCCCCCGGAGGAAAGTCGGCGGCCAGGGCGGCGTCC<br>GGGTTTTTTGCGCCCGCCGGCCCTCGCGGAGCCGGCCGGGGACCCCCGCCTTGCTTGAGGCAAAACTTTTACAACCCC<br>TACCTCGCCCCAGTCGGGACGCAACAGAAGCCGACCGGGCCAACCCAGCGCCATACGTACTATAGCGAATGCGATGAA<br>TTTCGATTCATCGCCCCGCGGGTGCTGGACGAGGATGCCCCCCCGGAGAAGCGCGCCGGGGTGCACGACGGTCACCTC<br>AAGCGCGCCCCCAAGGTGTACTGCGGGGGGGACGAGCGCGACGTCCTCCGCGTCGGGTCGGGCGGCTTCTGGCCGCGG<br>CGCTCGCGCCTGTGGGGCGGCGTGGACCACGCCCCGGCGGGGTTCAACCCCACCGTCACCGTCTTTCACGTGTACGAC<br>ATCCTGGAGAACGTGGAGCACGCGTACGCATGCGCGCGGCCCAGTTCCACGCGCGGTTTATGGACGCCATCACACCGA<br>CGGGGACCGTCATCACGCTCCTGGGCCTGACTCCGGAAGGCCACCGGGTGGCCGTTCACGTTTACGGCACGCGGCAGT<br>ACTTTTACATGAACAAGGAGGAGGTCGACAGGCACCTACAATGCCGCGCCCCACGAGATCTCTGCGAGCGCATGGCCG<br>CGGCCCTGCGCGAGTCCCCGGGCGCGTCGTTCCGCGGCATTTCCGCGGACCACTTCGAGGCGGAGGTGGTGGAGCGCA<br>CCGACGTGTACTACTACGAGACGCGCCCCGCTCTGTTTTACCGCGTCTACGTCCGAAGCGGGCGCGTGCTGTCGTACC<br>TGTGCGACAACTTCTGCCCGGCCATCAAGAAGTACGAGGGTGGGGTCGACGCCACCACCCGGTTCATCCTGGACAACC<br>CCGGGTTCGTCACCTTCGGCTGGTACCGTCTCAAACCGGGCCGGAACAACACGCTAGCCCAGCCGGCGGCCCCGATGG<br>CCTTCGGGACATCCAGCGACGTCGAGTTTAACTGTACGGCGGACAACCTGGCCATCGAGGGGGGCATGAGCGACCTAC<br>CGGCATACAAGCTCATGTGCTTCGATATCGAATGCAAGGCGGGGGGGGAGGACGAGCTGGCCTTTCCGGTGGCCGGGC<br>ACCCGGAGGACCTGGTCATCCAGATATCCTGTCTGCTCTACGACCTGTCCACCACCGCCCTGGAGCACGTCCTCCTGT<br>TTTCGCTCGGTTCCTGCGACCTCCCCGAATCCCACCTGAACGAGCTGGCGGCCAGGGGCCTGCCCACGCCCGTGGTTC<br>TGGAATTCGACAGCGAATTCGAGATGCTGTTGGCCTTCATGACCCTTGTGAAACAGTACGGCCCCGAGTTCGTGACCG<br>GGTACAACATCATCAACTTCGACTGGCCCTTCTTGCTGGCCAAGCTGACGGACATTTACAAGGTCCCCCTGGACGGGT<br>ACGGCCGCATGAACGGCCGGGGCGTGTTTCGCGTGTGGGACATAGGCCAGAGCCACTTCCAGAAGCGCAGCAAGATAA<br>AGGTGAACGGCATGGTGAACATCGACATGTACGGGATTATAACCGACAAGATCAAGCTCTCGAGCTACAAGCTCAACG<br>CCGTGGCCGAAGCCGTCCTGAAGGACAAGAAGAAGGACCTGAGCTATCGCGACATCCCCGCCTACTACGCCGCCGGGC<br>CCACGCAACGCGGGGTGATCGGCGAGTACTGCATACAGGATTCCCTGCTGGTGGGCCAGCTGTTTTTTAAGTTTTTGC<br>CCCATCTGGAGCTCTCGGCCGTCGCGCGCTTGGCGGGTATTAACATCACCCGCACCATCTACGACGGCCAGCAGATCC<br>GCGTCTTTACGTGCCTGCTGCGCCTGGCCGACCAGAAGGGCTTTATTCTGCCGGACACCCAGGGGCGATTTAGGGGCG<br>CCGGGGGGGAGGCGCCCAAGCGTCCGGCCGCAGCCCGGGAGGACGAGGAGCGGCCAGAGGAGGAGGGGGAGGACGAGG<br>ACGAACGCGAGGAGGGCGGGGGCGAGCGGGAGCCGGAGGGCGCGCGGGAGACCGCCGGCCGGCACGTGGGGTACCAGG<br>GGGCCAGGGTCCTTGACCCCACTTCCGGGTTTCATGTGAACCCCGTGGTGGTGTTCGACTTTGCCAGCCTGTACCCCA<br>GCATCATCCAGGCCCACAACCTGTGCTTCAGCACGCTCTCCCTGAGGGCCGACGCAGTGGCGCACCTGGAGGCGGGCA<br>AGGACTACCTGGAGATCGAGGTGGGGGGGCGACGGCTGTTCTTCGTCAAGGCTCACGTGCGAGAGAGCCTCCTCAGCA<br>TCCTCCTGCGGGACTGGCTCGCCATGCGAAAGCAGATCCGCTCGCGGATTCCCCAGAGCAGCCCCGAGGAGGCCGTGC<br>TCCTGGACAAGCAACAGGCCGCCATCAAGGTCGTGTGTAACTCGGTTTACGGGTTCACGGGAGTGCAGCACGGACTCC<br>TGCCGTGCCTGCACGTTGCCGCGACGGTGACGACCATCGGCCGCGAGATGCTGCTCGCGACCCGCGAGTACGTCCACG<br>CGCGCTGGGCGGCCTTCGAACAGCTCCTGGCCGATTTCCCGGAGGCGGCCGACATGCGCGCCCCCGGGCCCTATTCCA<br>TGCGCATCATCTACGGGGACACGGACTCCATCTTTGTGCTGTGCCGCGGCCTCACGGCCGCCGGGCTGACGGCCGTGG<br>GCGACAAGATGGCGAGCCACATCTCGCGCGCGCTGTTTCTGTCCCCCATCAAACTCGAGTGCGAAAAGACGTTCACCA<br>AGCTGCTGCTGATCGCCAAGAAAAAGTACATCGGCGTCATCTACGGGGGTAAGATGCTCATCAAGGGCGTGGATCTGG<br>TGCGCAAAAACAACTGCGCGTTTATCAACCGCACCTCCAGGGCCCTGGTCGACCTGCTGTTTTACGACGATACCGTAT<br>CCGGAGCGGCCGCCGCGTTAGCCGAGCGCCCCGCAGAGGAGTGGCTGGCGCGACCCCTGCCCGAGGGACTGCAGGCGT<br>TCGGGGCCGTCCTCGTAGACGCCCATCGGCGCATCACCGACCCGGAGAGGGACATCCAGGACTTTGTCCTCACCGCCG<br>AACTGAGCAGACACCCGCGCGCGTACACCAACAAGCGCCTGGCCCACCTGACGGTGTATTACAAGCTCATGGCCCGCC<br>GCGCGCAGGTCCCGTCCATCAAGGACCGGATCCCGTACGTGATCGTGGCCCAGACCCGCGAGGTAGAGGAGACGGTCG<br>CGCGGCTGGCCGCCCTCCGCGAGCTCGACGCCGCCGCCCCAGGGGACGAGCCCGCCCCCCCCGCGGCCCTGCCCTCCC<br>CGGCCAAGCGCCCCCGGGAGACGCCGTTGCATGCCGACCCCCCGGGAGGCGCGTCCAAGCCCCGCAAGCTGCTGGTGT |

-continued

| SEQUENCES |
|---|
| CCGAGCTGGCCGAGGATCCCGCATACGCCATTGCCCACGGCGTCGCCCTGAACACGGACTATTACTTCTCCCACCTGT<br>TGGGGGCGGCGTGCGTGACATTCAAGGCCCTGTTTGGGAATAACGCCAAGATCACCGAGAGTCTGTTAAAAAGGTTTA<br>TTCCCGAAGTGTGGCACCCCCCGGACGACGTGGCCGCGCGGCTCCGGGCCGCAGGGTTCGGGGCGGTGGGTGCCGGCG<br>CTACGGCGGAGGAAACTCGTCGAATGTTGCATAGAGCCTTTGATACTCTAGCATGAGCCCCCCGTCGAAGCTGATGTC<br>CCTCATTTTACAATAAATGTCTGCGGCCGACACGGTCGGAATCTCCGCGTCCGTGGGTTTCTCTGCGTTGCGCCGGAC<br>CACGAGCACAAACGTGCTCTGCCACACGTGGGCGACGAACCGGTACCCCGGGCACGCGGTGAGCATCCGGTCTATGAG<br>CCGGTAGTGCAGGTGGGCGGACGTGCCGGGAAAGATGACGTACAGCATGTGGCCCCCGTAAGTGGGGTCCGGGTAAAA<br>CAACAGCCGCGGGTCGCACGCCCCGCCTCCGCGCAGGATCGTGTGGACGAAAAAAAGCTCGGGTTGGCCAAGAATCCC<br>GGCCAAGAGGTCCTGGAGGGGGGCGTTGTGGCGGTCGGCCAACACGACCAAGGAGGCCAGGAAGGCGCGATGCTCGAA<br>TATCGTGTTGATCTGCTGCACGAAGGCCAGGATTAGGGCCTCGCGGCTGGTGGCGGCGAACCGCCCGTCTCCCGCGTT<br>GCACGCGGGACAGCAACCCCCGATGCCTAGGTAGTAGCCCATCCCGGAGAGGGTCAGGCAGTTGTCGGCCACGGTCTG<br>GTCCAGACAGAAGGGCAGCGAGACGGGAGTGGTCTTCACCAGGGGCACCGAGAGCGAGCGCACGATGGCGATCTCCTC<br>GGAGGGCGTCTGGGCGAGGGCGGCGAAAAGGCCCCGATAGCGCTGGCGCTCGTGTAAACACAGCTCCTGTTTGCGGGC<br>GTGAGGCGGCAGGCTCTTCCGGGAGGCCCGACGCACCACGCCCAGAGTCCCGCCGGCCGCAGAGGAGCGCGACCGCCG<br>GCGCTCCTTGCCGTGATAGGGCCCGGGCCGGGAGCCGCGGCGATGGGGGTCGGTGTCATACATAGGTACACAGGGTGT<br>GCTCCAGGGACAGGAGCGAGATCGAGTGGCGTCTAAGCAGCGCGCCCGCCTCACGGACAAATGTGGCGAGCGCGGTGG<br>GCTTTGGTACAAATACCTGATACGTCTTGAAGGTGTAGATGAGGGCACGCAACGCTATGCAGACACGCCCCTCGAACT<br>CGTTCCCGCAGGCCAGTTTGGCCTTGTGGAGCAGCAGCTCGTCGGGATGGGTGGCGGGGGGATGGCCGAACAGAACCC<br>AGGGGTCAACCTCCATCTCCGTAATGGCGCACATGGGGTCACAGAACATGTGCTTAAAGATGGCCTCGGGCCCCGCGG<br>CCCGAAGCAGGCTCACAAACCGGCCCCCGTCCCCGGGCTGCGTCTCGGGGTCAGCCTCGAGCTGGTCGACGACGGGTA<br>CGATACAGTCGAAGAGGCTCGTGTTGTTTTCCGAGTAGCGGACCACGGAGGCCCGGAGTCTGCGCAGGGCCAGCCAGT<br>AAGCACGCACCAGTAACAGGTTACACAGCAGGCATTCTCCGCCGGTGCGCCCGCGCCCCCGGCCGTGTTTCAGCACGG<br>TGGCCATCAGAGGGCCCAGGTCGAGGTCGGGCTGGGCATCGGGTTCGGTAAACTGCGCAAAGCGCGGAGCCACGTCGC<br>GCGTGCGTGCCCCGCGATGCGCTTCCCAGGACTGGCGGACCGTGGCGCGACGGGCCTCCGCGGCAGCGCGCAGCTGGG<br>GCCCCGACTCCCAGACGGCGGGGGTGCCGGCGAGGAGCAGCAGGACCAGATCCGCGTACGCCCACGTATCCGGCGACT<br>CCTCCGGCTCGCGGTCCCCGGCGACCGTCTCGAATTCCCCGTTGCGAGCGGCGGCGCGCGTACAGCAGCTGTCCCCGC<br>CCCCGCGCCGACCCTCCGTGCAGTCCAGGAGACGGGCGCAATCCTTCCAGTTCATCAGCGCGGTGGTGAGCGACGGCT<br>GCGTGCCGGATCCCGCCGACCCCGCCCCCTCCTCGCCCCCGGAGGCCAAGGTTCCGATGAGGGCCCGGGTGGCAGACT<br>GCGCCAGGAACGAGTAGTTGGAGTACTGCACCTTGGCGGCTCCCGGGGAGGGCGAGGGCTTGGGTTGCTTCTGGGCAT<br>GCCGCCCGGGCACCCCGCCGTCGGTACGGAAGCAGCAGTGGAGAAAAAAGTGCCGGTGGATGTCGTTTATGGTGAGGG<br>CAAAGCGTGCGAAGGAGCCGACCAGGGTCGCCTTCTTGGTGCGCAGAAAGTGGCGGTCCATGACGTACACAAACTCGA<br>ACGCGGCCACGAAGATGCTAGCGGCGCAGTGGGGCGCCCCCAGGCATTTGGCACAGAGAAACGCGTAATCGGCCACCC<br>ACTGAGGCGAGAGGCGGTAGGTTTGCTTGTACAGCTCGATGGTGCGGCAGACCAGACAGGGCCGGTCCAGCGCGAAGG<br>TGTCGATGGCCGCCGCGGAAAAGGGCCCGGTGTCCAAAAGCCCCTCCCCACAGGGATCCGGGGGCGGGTTGCGGGGTC<br>CTCCGCGCCCGCCCGAACCCCCTCCGTCGCCCGCCCCCCCGCGGGCCCTTGAGGGGGCGGTGACCACGTCGGCGGCGA<br>CGTCCTCGTCGAGCGTACCGACGGGCGGCACACCTATCACGTGACTGGCCGTCAGGAGCTCGGCGCAGAGAGCCTCGT<br>TAAGAGCCAGGAGGCTGGGATCGAAGGCCACATACGCGCGCTCGAACGCCCCCGCCTTCCAGCTGCTGCCGGGGGACT<br>CTTCGCACACCGCGACGCTCGCCAGGACCCCGGGGGGCGAAGTTGCCATGGCTGGGCGGGAGGGGCGCACGCGCCAGC<br>GAACTTTACGGGACACAATCCCCGACTGCGCGCTGCGGTCCCAGACCCTGGAGAGTCTAGACGCGCGCTACGTCTCGC<br>GAGACGGCGCGCATGACGCGGCCGTCTGGTTCGAGGATATGACCCCCGCCGAGCTGGAGGTTGTCTTCCCGACTACGG<br>ACGCCAAGCTGAACTACCTGTCGCGGACGCAGCGGCTGGCCTCCCTCCTGACGTACGCCGGGCCTATAAAAGCGCCCG<br>ACGACGCCGCCGCCCCGCAGACCCCGGACACCGCGTGTGTGCACGGCGAGCTGCTCGCCCGCAAGCGGGAAAGATTCG<br>CGGCGGTCATTAACCGGTTCCTGGACCTGCACCAGATTCTGCGGGGCTGACGCGCGTGCTGTTGGGCGGGACGGTTCG<br>CGAACCCTTTGGTGGGTTTACGCGGGCACGCACGCTCCCATCGCGGGCGCCATGGCGGGACTGGGCAAGCCCTACACC<br>GGCCACCCAGGTGACGCCTTCGAGGGTCTCGTTCAGCGAATTCGGCTTATCGTCCCATCTACGTTGCGGGGCGGGGAC<br>GGGGAGGCGGGCCCCTACTCTCCCTCCAGCCTCCCCTCCAGGTGCGCCTTTCAGTTTCATGGCCATGACGGGTCCGAC<br>GAGTCGTTTCCCATCGAGTATGTACTGCGGCTTATGAACGACTGGGCCGAGGTCCCGTGCAACCCTTACCTGCGCATA<br>CAGAACACCGGCGTGTCGGTGCTGTTTCAGGGGTTTTTCATCGCCCACACAACGCCCCCGGGGGCGCGATTACGCCA<br>GAGCGGACCAATGTGATCCTGGGGTCCACCGAGACGACGGGGTTGTCCCTCGGCGACCTGGACACCATCAAGGGGCGG<br>CTCGGCCTGGATGCCCGGCCGATGATGGCCAGCATGTGGATCAGCTGCTTTGTGCGCATGCCCCGCGTGCAGCTCGCG<br>TTTCGGTTCATGGGCCCCGAAGATGCCGGACGGACGAGACGGATCCTGTGCCGCGCCGCCGAGCAGGCTATTACCCGT<br>CGCCGCCGAACCCGGCGGTCCCGGGAGGCGTACGGGGCCGAGGCCGGGCTGGGGGTGGCCGGAACGGGTTTCCGGGCC<br>AGGGGGGACGGTTTTGGCCCGCTCCCCTTGTTAACCCAAGGGCCCTCCCGCCCGTGGCACCAGGCCCTGCGGGGTCTT<br>AAGCACCTACGGATTGGCCCCCCCGCGCTCGTTTTGGCGGCGGGACTCGTCCTGGGGGCCGCTATTTGGTGGGTGGTT<br>GGTGCTGGCGCGCGCCTATAAAAAAGGACGCACCGCCGCCCTAATCGCCAGTGCGTTCCGGACGCCTTCGCCCCACAC<br>AGCCCTCCCGACCGACACCCCCATATCGCTTCCCGACCTCCGGTCCCGATGGCGTCCCGCAATTTCACCGCCCCAACA<br>CCGTTACCACCGATAGCGTCCGGGCGCTTGGCATGCGCGGGCTCGTCTTGGCCACCAATAACTCTCAGTTTATCATGG<br>ATAACAACCACCCACACCCCCAGGGCACCCAAGGGGCCGTGCGGGAGTTTCTCCGCGGTCAGGCGGCGGCACTGACGG<br>ACCTTGGTCTGGCCCACGCAAACAACACGTTTACCCCGCAGCCTATGTTCGCGGGCGACGCACCGGCCGCCTGGTTGC<br>GGCCCGCGTTTGGCCTGCGGCGCACCTATTCACCTTTTGTCGTTCGAGAACCTTCGACGCCCGGGACCCCGTGAGGCC<br>CAGGGAGTTCCTTCTGGGGTGTTTTAATCAATAAAAGACCACACCAACGCACGAGCCTTGCGTTTAATGTCGTGTTTA<br>TTCAAGGGAGTGGGATAGGGTTCGACGGTTCGAAACTTAACACACCAAATAATCGAGCGCGTCTAGCCCAGTAACATG<br>CGCACGTGATGTAGGCTGGTCAGCACGGCGTCGCTGTGATGAAGCAGCGCCCGGCGGGTCCGCTGTAACTGCTGTTGT<br>AGGCGGTAACAGGCGCGGATCAGCACCGCCAGGGCGCTACGACCGGTGCGTTGCACGTAGCGTCGCGACAGAACTGCG<br>TTTGCCGATACGGGCGGGGGGCCGAATTGTAAGCGCGTCACCTCTTGGGAGTCATCGGCGGATAACGCACTGAATGGT<br>TCGTTGGTTATGGGGGAGTGTGGTTCCCCAGGGAGTGGGTCGAACGCCTCGGCCTCGGAATCCGAGAGGAACAACGAG<br>GTGGCGTCGGAGTCTTCGTCGTCAGAGACATACAGGGTCTGAAGCAGCGACACGGGCGGGGGGGTAGCGTCGATGTGT<br>AGCGCGAGGGAGGATGCCCACGAAGACACCCCAGACAAGGAGCTGCCCGTGCGTGGATTTGTGGAAGACGCGGAAGCC<br>GGGACGGATGGGCGGTTTTGCGGTGCCCGGAACCGAACCGCCGGATACTCCCCGGGTGCTACATGCCCGTTTTGGGGC<br>TGGGGTTGGGGCTGGGGTTGGGGCTGGGGTTGGGGCTGGGGTTGGGGCTGGGGTTGGGGCTGGGGTTGGGGTTGGGGT<br>TGGGGCTGGGGTTGGGGTTGGGGCTGGGGCTGGGGCTGGGGCTGGGGCTGGGGCTGGGGCTGGGGCTGGGGCTGGGGC<br>TGGGGCTGGGGCTGGGGCTGGGGCTGGGGCTGGGGTTGGGGCTGGGGCGCGGACAGGCGGCTGACGGTCAAATGCCCC<br>CGGGGGCGCGCAGATGTGGTGGGCGTGGCCACCGGCTGCCGTGTAGTGGGGCGGCGGGAAACCGGGCCTCCGGGCGTA<br>ACACCGCCCTCCAGCGTCAAGTATGTGGGGGGCGGGCCTGACGTCGGGGGCGGGGTGACGGGTTGGACCGCGGGAGGC<br>GGGGGAGAGGGACCTGCGGGAGAGGATGAGGTCGGCTCGGCCGGGTTGCGGCCTAAAACAGGGGCCGTGGGGTCGGCG<br>GGGTCCCAGGGTGAAGGGAGGGATTCCCGCGATTCGGACAGCGACGCGACAGCGGGGCGCGTAAGGCGCCGCTGCGGC<br>CCGCCTACGGGAACCCTGGGGGGGGTTGGCGCGGGACCCGAGGTTAGCGGGGGGCGGCGGTTTTCGCCCCCCGGGCAAA |

-continued

| SEQUENCES |
|---|
| ACCGTGCCGGTTGCGACCGGGGGCGGAACGGGATCGATAGGGAGAGCGGGAGAAGCCTGGCCGGCGGACTGGGGACCG<br>AGCGGGAGGGGCACACCAGACACCAAAGCGTGGGGCGCTGGCTCTGGGGGTTTGGGAGGGGCCGGGGGGCGCGCGAAA<br>TCGGTAACCGGGGCGACCGTGTCGGGGAGGGCAGGCGGCCGCCAACCCTGGGTGGTCGCGGAAGCCTGGGTGGCGCGC<br>GCCAGGGAGCGTGCCCGGCGGTGTCGGCGCGCGCGCGACCCGGACGAAGAAGCGGTAGAAGCGCGGGAGGAGGCGGGG<br>GGGCGGGGGGCGGTGGCATCGGGGGGCGCCGGGGAACTTTGGGGGGACGGCAAGCGCCGGAAGTCGTCGCGGGGGCCC<br>ACGGGCGCCGGCCGCGTGCTTTCGGCCGGGACGCCCGGTCGTGCTTCGCGAGCCGTGACTGCCGGCCCAGGGGGCCGC<br>GGTGCACACTGGGACGTGGGGACGGACTGATCGGCGGTGGGCGAAAGGGGGTCCGGGGCAAGGAGGGGCGCGGGGCCG<br>CCGGAGTCGTCAGACGCGAGCTCCTCCAGGCCGTGAATCCATGCCCACATGCGAGGGGGGACGGGCTCGCCGGGGGTG<br>GCGTCGGTGAATAGCGTGGGGGCCAGGCTTCCGGGCCCCAACGAGCCCTCCGCCCCAACAAGGTCCGCCGGGCCGGGG<br>GTCGGGTTCGGGACCGAGGGGCTCTGGTCGTCGGGGGCGCGCTGGTACACCGGATGCCCCGGGAATAGCTCCCCCGAC<br>AGGAGGGAGGCGTCGAACGGCCGCCCGAGGATAGCTCGCGCGAGGAAGGGGTCCTCGTCGGTGGCGCTCGCGGCGAGG<br>ACGTCCTCGCCGCCCACCACAAACGGGAGCTCCTCGGTGGCCTCGCTGCCAACAAACCGCACGTCGGGGGGGCCGGGG<br>GGGTCCGGGTTTTCCCACAACACCGCGACCGGGGTCATGGAGATGTCCACGAGCACCAGGCACGGCGGGCCCCGGGCG<br>AGGGGCCGCTCGGCGATGAGCGCGGACAGGCGCGGGAGCTGTGCCGCCAGACACGCGTTTTCGATCGGGTTAAGGTCG<br>GCGTGCAGGAGGCGGACGGCCCACGTCTCGATGTCGGACGACACGGCATCGCGCAAGGCGGCGTCCGGCCCGCGAGCG<br>CGTGAGTCAAACAGCGTGAGGCACAGCTCCAGTTCCGACTCGCGGGAAAAGGCCGTGGTGTTGCGGAGCGCCACGACG<br>ACGGGCGCGCCCAGGAGCACTGCCGCCAGCACCAGGTCCATGGCCGTAACGCGCGCCGCGGGGGTGCGGTGGGTGGCG<br>GCGGCCGGCACGGCGACGTGCTGGCCCGTGGGCCGGTAGAGGGCGTTGGGGGGAGCGGGGGGTGACGCCTCGCGCCCC<br>CCCGAGGGGCTCAGCGTCTGCCCAGATTCCAGACGCGCGGTCAGAAGGGCGTCGAAACTGTCATACTCTGTGTAGTCG<br>TCCGGAAACATGCAGGTCCAAAGAGCGGCCAGCGCGGTGCTTGGGAGACACATGCGCCCGAGGACGCTCACCGCCGCC<br>AGCGCCTGGGCGGGACTCAGCTTTCCCAGCGCGGCGCCGCGCTCGGTTCCCAGCTCGGGGACCGAGCGCCAGGGCGCC<br>AGGGGGTCGGTTTCGGACAACTTGCCGCGGCGCCAGTCTGCCAGCCGCGTGCCGAACATGAGGCCCCGGGTCGGAGGG<br>CCTCCGGCCGAAAACGCTGGCAGCACGCGGATGCGGGCGTCTGGATGCGGGGTCAGGCGCTGCACGAATAGCATGGAA<br>TCTGCTGCGTTCTGAAACGCACGGGGGAGGGTGAGATGCATGTACTCGTGTTGGCGGACCAGATCCAGGCGCCAAAAG<br>GTGTAAATGTGTTCCGGGGAGCTGGCCACCAGCGCCACCAGCACGTCGTTCTCGTTAAAGGAAACGCGGTGCCTAGTG<br>GAGCTCTGGGGTCCGAGCGGCGGCCCCGGGGCCGCCGCGTCACCCCCCCATTCCAGCTGGGCCCAGCGACACCCAAAC<br>TCGCGCGTGAGAGTGGTCGCGACGAGGGCGACGTAGAGCTCGGCCGCCGCATCCATCGAGGCCCCCCATCTCGCCTGG<br>CGGTGGCGCACAAAGCGTCCGAAGAGCTGAAAGTTGGCGGCCTGGGCGTCGCTGAGGGCCAGCTGAAACCGGTTGATG<br>ACGGTGAGGACGTACATGGCCGTGACGGTCGAGGCCGACTCCAGGGTGTCCGTCGGAAGCGGGGGGCGAATGCATGCC<br>GCCTCGGGACACATCAGCAGCGCGCCGAGCTTGTCGGTCACGGCCGGGAAGCAGAGCGCGTACTGCAGTGGCGTTCCA<br>TCCGGGACCAAAAAGCTGGGGGCGAACGGCCTATCCAGCGTACTGGTGGCCTCGCGCAGCACCAGGGGCCCCGGGCCT<br>CCGCTCACTCGCAGGTACGCCTCGCCCCGGCGGCGCAGCATCTGCGGGTCGGCCTCTTGGCCGGGTGGGGCGGACGCC<br>CGGGCGCGGGCGTCTAGGGCGCGAAGATCCACGAGCAGGGGCGCGGGCGCGGCCGCCGCGCCCGCGCCCGTCTGGCCT<br>GTGGCCTTGGCGTACGCGCTATATAAGCCCATGCGGCGTTGGATGAGCTCCCGCGCGCCCCGGAACTCCTCCACCGCC<br>CATGGGGCCAGGTCCCCGGCCACCGCGTCCAATTCCGCCAACAGGCCCCCCAGGGTGTCAAAGTTCATCTCCCAGGCC<br>ACCCTTGGCACCACCTCGTCCCGCAGCCGGGCGCTCAGGTCGGCGTGTTGGGCCACGCGCCCCCCGAGCTCCTCCACG<br>GCCCCGGCCCGCTCGGCGCTCTTGGCGCCCAGGACGCCCTGGTACTTGGCGGGAAGGCGCTCGTAGTCCCGCTGGGCT<br>CGCAGCCCCGACACAGTGTTGGTGGTGTCCTGCAGGGCGCGAAGCTGCTCGCATGCCGCGCGAAATCCCTCGGGCGAT<br>TTCCAGGCCCCCCCGCGAACGCGGCCGAAGCGACCCCATACCTCGTCCCACTCCGCCTCGGCCTCCTCGAAAGACCTC<br>CGCAGGGCCTCGACGCGGCGACGGGTGTCGAAGAGCGACTGCAGGCGCGCGCCCTGTCGCGTCAGGAGGCCCGGGCCG<br>TCGCCGCTGGCCGCGCTTAGCGGGTGCGTCTCAAAGGTGCGCTGGGCATGTTCCAACCAGGCGACCGCCTGCACGTCG<br>AGCTCGCGCGCCTTCTCCGTCTGGTCCAACAGAATCTCGACCTGATCCGCGATCTCCTCCGCCGAGCGCGCCTGGTCC<br>AGCGTCTTGGCCACGGTCGCCGGGACGGCAACCACCTTCAGCAGGGTCTTCAGATTGGCCAGACCCTCGGCCTCGAGC<br>TGGGCCCGGCGCTCGCGCGCGGCCAGCACCTCCCGCAACCCCGCCGTGACCCGCTCGGTGGCTTCGGCGCGCTGCTGT<br>TTGGCGCGCACCACGGCGTCCTTGGTATCGGCCAGGTCCTGTCGGGTCACGAATGCGACGTAGTCGGCGTACGCCGTG<br>TCCTTCACGGGGCTCTGGTCCACGCGCTCCAGCGCCGCCACACACGCCACCAGCGCGTCCTCGCTCGGGCAGGGCAGG<br>GTGACCCCTGCCCGGACAAGCTCGGCGGCCGCCGCCGGGTCGTTGCGCACCGCGGATATCTCCTCCGCGGCGGCGGCC<br>AGGTCCAGCGCCACGCTTCCGATCGCGCGCCGCGCGTCGGCCCGGAGGGCGTCCAGGCGATCGCGGATATCCACGTAC<br>TCGGCGTAGCCCTTTTGAAAAAACGGCACGTACTGGCGCAGGGCCGGCACGCCCCCCAAGTCTTCCGACAGGTGTAGG<br>ACGGCCTCGTGGTAGTCGATAAACCCGTCGTTCACCTGGGCCCGCTCCAGCAGCCCCCCCGCGAGCCGCAGAAGCCGC<br>GCCAGGGGCTCGGTGTCCACCCGAAACATGTCGGCGTACGTGTCGGCCGCGGCCCCGAAGGCCGCGCTCCAGTCGATG<br>CGGTGAATGGCTGCGAGCGGGGGAGCATGGGGTGGCGCTGGTTCTCGGGGGTGTATGGGTTAAACGCAAGGGCCGTC<br>TCCAGGGCAAGGGTCACCGCCTTGGCGTTGGTTCCCAGCGCCTGCTCGGCCCGCTTTCGGAAGTCCCGGGGGTTGTAG<br>CCGTGCGTGCCCGCCAGCGCCTGCAGGCGACGGAGCTCGACCACGTCAAACTCGGCACCGCTTTCCACGCGGTCCAGC<br>ACGGCCTCCACGTCGGCGGCCCAGCGCTCGTGGCTACTGCGGGCGCGCTGGGCCGCCATCTTCTCTCTGAGGTCGGCG<br>GTGGCGGCCTCAAGTTCGTCGGCGCGGCGTCGCGTGGCGCCGATGACCTTTCCCAGCTCCTGCAGGGCGCGCCCGCTG<br>GGGGAGTGGTCCCCGGCCGTCCCTTCGGCGTGCAACAGGCCCCCGAACCTGCCCTCGTGGCCCGCGAGGCTTTCCCGC<br>GCGCCGGTGGTCGCGCGCGTCGCGGCCTGGATCAGGGAGGCATGCTCTCCCTCCGGTTGGTTGGCGGCCCGGCGCACC<br>TGGACGACAAGGTCGGCGGCAGCCGACCCTAAGGTCGTGAGCTGGGCGATGGCCCCCCGCGCGTCCAGGGCCAACCGA<br>GTCGCCTTGACGTATCCCGCGGCGCTGTCGGCCATGGCCGCTAGGAAGGCCAGGGGGGAGGCCGGGTCGCTGGCGGCC<br>GCGCCCAGGGCCGTCACTGCGTCGACCAGGACGCGGTGCGCCCGCACGGCCGCATCCACCGTCGACGCGGGGTCTGCC<br>GTCGCGACGGCGGCGCTGCCGGCGTTGATGGCGTTCGAGACGGCGTGGGCTATGATCGGGGCGTGATCGGCGAAGAAC<br>TGCAAGAGAAACGGAGTCTCGGGGGCGTTGGCGAACAGGTTCTTCAGCACCACCACGAAGCTGGGATGCAAGCCGGAC<br>AGAGCCGTCGCCGTGTCCGGAGTCGGGTGCTCCAGGGCATCTCGGTACTGCCCCAGCAGCCCCCACATGTCCGCCCGC<br>AGCGCCGCCGTAACCTCCGGGGGCGCCCCCGAACGGCCTCGGGGAGGTCCGACCAGCCCGCCGGCAGGGAGGCCCGC<br>AGGGTCGTCAGGACGGCCGGACAGGCCTTTAGCCCCACAAAGTCAGGGAGGGGCCGCAGGACCCCCTGGAGTTTGTGC<br>AAGAACTTCTCCCGGGCGTCGCGGGCCACCTTCGCCCGCTCCCGCGCTCCCTCGAGCATTGCCTCCAGGGAGCGCGCG<br>CGCTCCCGCAAACGGGCACGCGCATCGGGGGCGAGCTCTGCCGTCAGCTTGGCGGCATCCATGGCCCGCGCCTGCCGC<br>AGCGCTTCCTCGGCCATGCGCGTGGCCTCTGGCGACAGCCCGCCGTCGTCGGGGTAGGGCGACGCGCCGGGCGCAGGA<br>ACAAAGGCCGCGTCGCTGTCCAGCTGCTGGCCCAGGGCCGCATCTAGGGCGTCGAAGCGCCGCAGCTCGGCCAGACCC<br>GAGCTGCGGCGCGCCTGCTGGTCGTTAATGTCGCGGATGCTGCGCGCCAGCTCGTCCAGCGGCTTGCGTTCTATCAGC<br>CCTTGGTTGGCGGCGTCCGTCAGGACGGAGAGCCAGGCCGCCAGGTCCTCGGGGGCGTCCAGCGTCTGGCCCCGCTGT<br>ATCAGATCCCGCAACAGGATGGCCGTGGGGCTGGTCGCGATCGGGGGCGGGGCGGGAATGGCGGCGCTCTGCGCGATG<br>TCCCGCGTGTGCTGGTCGAAGACAGGCAGGGACTCTAGCAGCTGGACCACGGGCACGACGGCGGCCGAAGCCACGTGA<br>AACCGGCGGTCGTTGTTGTCGCTGGCCTGCAGAGCCTTGGCGCTGTATACGGCCCCCCGGTAAAAGTACTCCTTAACC<br>GCGCCCTCGATCGCCCGACGGGCCTGGGTCCGCACCTCCTCCAGCCGAACCTGAACGGCCTCGGGGCCCAGGGGGGGT<br>GGGCGCGGAGCCCCCTGCGGGGCCGCCCCGGCCGGGGCGGGCATTACGCCGAGGGGCCCGGCGTGCTGTGAGACCGCG |

-continued

| SEQUENCES |
|---|
| TCGACCCCGCGAGCGAGGGCGTCGAGGGCCTCGCGCATCTGGCGATCCTCCGCCTCCACCCTAATCTCTTCGCCACGG<br>GCAAATTTGGCCAGAGCCTGGACTCTATACAGAAGCGGTTCTGGGTGCGTCGGGGTGGCGGGGGCAAAAAGGGTGTCC<br>GGGTGGGCCTGCGAGCGCTCCAGAAGCCACTCGCCGAGGCGTGTATACAGATTGGCCGGCGGGGCCGCGCGAAGCTGC<br>AGCTCCAGGTCCGCGAGTTCCCCGTAAAAGGCGTCCGTCTCCCGAATGACATCCCTAGCCACAAGGATCAGCTTCGCC<br>AGCGCCAGGCGACCGATCAGAGAGTTTTCGTCCAGCACGTGCTGGACGAGGGGCAGATGGGCGGCCACGTCGGCCAGG<br>CTCAGGCGCGTGGAGGCCAGAAAGTCCCCCACGGCCGTTTTCCGGGGCAGCATGCTCAGGGTAAACTCCAGCAGGGCG<br>GCGGCCGGGCCGGCCACCCCGGCCTGGGTGTGCGTCCGGGCCCCGTTCTCGATGAGAAAGGCGAGGACGCGTTCAAAG<br>AAAAAAATAACACAGAGCTCCAGCAGCCCCGGAGAAGCCGGATACGGCGACCGTAAGGCGCTGATGGTGAGCCGCGAA<br>CACGCGGCGACCTCGCGGGCCAGGGCGGCGGAGCACGCGGTGAACTTAACCGCCGTGGCGGCCACGTTTGGGTGGGCC<br>TCGAACAGCTGGGCAAGGTCTGCGCCCGGGGGCTCGGGTGAGCGGCGAGTCTTCAGCGCCTCGAGGGCCTGCGAGGAC<br>GCCGGAACCGTGGGCCCGTCGTCCTCGCCCGCCTCGGCGACCGGCGGCCCGGCCGGGTCGGGGGGTGCCGAGGCGAGG<br>ACAGGCTCCGGAACGGAGGCGGGGACCGCGGCCCCGACGGGGGTTTTGCCTTTGGGGGTGGATTTCTTCTTGGTTTTG<br>GCAGGGGGGGCCGAGCGTTTCGTTTTCTCCCCCGAAGTCAGGTCTTCGACGCTGGAAGGCGGAGTCCAGGTGGGTCGG<br>CGGCGCTTGGGAAGGCCGGCCGAGTAGCGTGCCCGGTGCCGACCAACCGGGACGACGCCCATCTCCAGGACCCGCATG<br>TCGTCGTCATCTTCTTCGGCCGCCTCTGCGGCGGGGGGCTTGGGGGCGGAGGGAGGCGGTGGTGGGATCGCGGAGGGT<br>GGGTCGGCGGAGGGTGGGTCGGCGGAGGGGGGATCCGTGGGTGGGGTACCCTTCAGGGCCACCGCCCATACATCGTCG<br>GGCGCCCGATTCGGGCGCTTGGCCTCTGGTTTTGCCGACGGACCGGCCGTCCCCCGGGATGTCTCGGAGGCCCTGTCG<br>TCGCGACGGGCCCGGGTCGGTGGCGGCGACTGGGCGGCTGTGGGCGGGTGGGGCCCCGTGCCCCCTACCCCCTCCCGG<br>GGGCCCACGCCGACGCAGGGCTCCCCCAGGCCCGCGATCTCGCCCCGCAGGGGGTGCGTGATGGCCACGCGCCGTTCG<br>CTGAACGCTTCGTCCTGCAGGTAAGTCTCGCTGGCCCCGTAAAGATGCAGAGCCGCGGCCGTCAAGTCCGCAGGAGCC<br>GCGGGTTCCGGGCCCGACGGCACGAAAAACACCATGGCTCCCGCCCACCGTACGTCCGGGCGATCGCGGGTGTAATAC<br>GTCAGGTATGGATACATGTCCCCCGCCCGCACTTTGGCGATGAACGCGGGGGTGCCCTCCGGAAGGCCGTGCGGGTCA<br>AAAAGGTATGCGGTGTCGCCGTCCCTGAACAACCCCATCCCTAGGGGGCCAATGGTTAGGAGCGTGTACGACAGGGGG<br>CGCAGGGCCCACGGGCCGGCGAAGAACGTGTGTGCGGGGCATTGTGTCTCCAGCAGGCCCGCCGCGGGCTCCCCGAAG<br>AAGCCCACCTCGCCGTATACGCGCGAGAAGACACAGCGCAGTCCGCCGCGCGCCCCTGGGTACTCGAGGAAGTTGGGG<br>AGCTCGACGATCGAACACATGCGCGGCGGCCCAGGGCCCGCGGTCGCGCGCGTCCACTCGCCCCCCTCGACCAAACAA<br>CCCTCGATGGCCTCCGCGGACAGAACGTCGCGAGGGCCCACATCAAATATGAGGCTGAGAAAGGACAGCGACGAGCGC<br>ATGCACGATACCGACCCCCCCGGCTCCAGGTCGGGCGCGAACTGGTTCCGAGCACCGGTGACCACGATGTCGCGATCC<br>CCCCCGCGTTCCATCGTGGAGTGCGGTGGGGTGCCCGCGATCATATGTGCCCTACTGGCCAGAGACCCGGCCTGTTTA<br>TGGACCGGACCCCCGGGGTTAGTGTTGTTTCCGCCACCCATGCCCCCGTACCATGGCCCCGGTTCCCCTGATTAGGCT<br>ACGAGTCGCGGTGATCGCTTCCCAAAAACCGAGCTGCGTTTGTCTGTCTTGATCTTTCCCCCCCCCCCCGCCCGCCCG<br>CACACCATAACACCGAGAACAACACACGGGGGTGGGCGTAACATAATAAAGCTTTATTGGTAACTAGTTAACGGCAAG<br>TCCGTGGGTGGCGCGACGGTGTCCTCCGGGCTCATCTCGTCGTCCTCGACGGGGGTGTTGGAATGAGGCGCCCCCTCG<br>CGGTCCGCCTGGCGTGGGCCGTGCCCATAGGCCTCCGGCTTCTGTGCGTCCATGGGCATAGGCGCGGGGAGACTGTTT<br>CCGGCGTCGCGGACCTCCAGGTCCCTGGGAGACTCCGGTCCGGCTAACGGACGAAACGCGGAAGCGCGAAACACGCCG<br>TCGGTGACCCGCAGGAGCTCGTTCATCAGTAACCAATCCATACTCAGCGTAACGGCCAGCCCCTGGCGAGACAGATCC<br>ACGGAATCCGGAACCGCGGTCGTCTGGCCCAGGGGGCCGAGGCTGTAGTCCCCCCAGGCCCCTAGGTCGCGACGGCTC<br>GTAAGCACGACGCGGTCGGCCGCGGGGCTTTGCGGGGGGGCGTCCTCGGGCGCATGCGCCATTACCTCTCGGATGGCC<br>GCGGCGCGCTGGTCGGCCGAGCTGACCAAGGGCGCCACGACCACGGCGCGCTCCGTCTGCAGGCCCTTCCACGTGTCG<br>TGGAGTTCCTGGACAAACTCGGCCACGGGCTCGGGTCCCGCGGCCGCGCGCGCGGCTTGATAGCAGGCCGAGAGACGC<br>CGCCAGCGCGCTAGAAACTGACCCATGAAGCAAAACCCGGGGACCTGGTCTCCCGACAGCAGCTTCGACGCCCGGGCG<br>TGAATGCCGGACACGACGGACAGAAACCCGTGAATTTCGCGCCGGACCACGGCCAGCACGTTGTCCTCGTGCGACACC<br>TGGGCCGCCAGCTCGTCGCACACCCCCAGGTGCGCCGTGGTTTCGGTGATGACGGAACGCAGGCTCGCGAGGGACGCG<br>ACCAGCGCGCGCTTGGCGTCGTGATACATGCTGCAGTACTGACTCACCGCGTCCCCCATGGCCTCGGGGGGCCAGGGC<br>CCCAGGCGGTCGGGCGTGTCCCCGACCACCGCATACAGGCGGCGCCCGTCGCTCTCGAACCGACACTCGAAAAAGGCG<br>GAGAGCGTGCGCATGTGCAGCCGCAGCAGCACGATGGCGTCCTCCAGTTGGCGAATCAGGGGGTCTGCGCGCTCGGCG<br>AGGTCCTGCAGCACCCCCCGGGCGGCCAGGGCGTACATGCTAATCAACAGGAGGCTGGTGCCCACCTCGGGGGGCGGG<br>GGGGGCTGCAGCTGGACCAGGGGCCGCAGCTGCTCGACGGCACCCCTGGAGATCACGTACAGCTCCCGGAGCAGCTGC<br>TCTATGTTGTCGGCCATCTGCATAGTGGGGCCGAGGCCGCCCCGGGCGGCCGGTTCGAGGAGGGTAATCAGCGCGCCC<br>AGTTTGGTGCGATGGCCCTCGACCGTGGGGAGATAGCCCAGCCCAAAGTCCCGGGCCCAGGCCAACACACGCAGGGCG<br>AACTCGACCGGGCGTGGAAGGTAGGCCGCGCTACACGTGGCCCTCAACGCGTCCCCGACCACCAGGGCCAGAACGTAG<br>GGGACGAAGCCCGGGTCGGCGAGGACGTTGGGGTGAATGCCCTCGAGGGCGGGGAAGCGGATCTGGGTCGCCGCGGCC<br>AGGTGGACAGAGGGGGCGTGGCTGGGCTGCCCGACGGGGAGAAGCGCGGACAGCGGCGTGGCCGGGGTGGTGGGGGTG<br>ATGTCCCAGTGGGTCTGACCATACACGTCGATCCAGATGAGCGCCGTCTCGCGGAGAAGGCTGGGTTGACCGGAACTA<br>AAGCGGCGCTCGGCCGTCTCAAACTCCCCCACGAGCGCCCGCCGCAGGCTCGCCAGATGTTCCGTCGGCACGGCCGGA<br>CCCATGATACGCGCCAGCGTCTGGCTCAGAACGCCCCCCGACAGGCCGACCGCCTCGCAGAGCCGCCCGTGCGTGTGC<br>TCGCTGGCGCCCTGGACCCGCCTGAAAGTTTTTACGTAGTTGGCATAGTACCCGTATTCCCGCGCCAGACCAAACACG<br>TTCGACCCCGCGAGGGCAATGCACCCAAAGAGCTGCTGGACTTCGCCGAGTCCGTGGCCGGCGGGCGTCCGCGCGGGG<br>ACGCCCGCCGCCAGAAACCCCTCCAGGGCCGAAAGGTAGTGCGTGCAGTGCGAGGGCGTGAACCCAGCGTCGATCAGG<br>GTGTTGATCACCACGGAGGGCGAATTGGTATTCTGGATCAACGTCCACGTCTGCTGCAGCAGAGCCAACAGCCGCTGC<br>TGGGCGCCGGCGGAGGGCTGCTCCCCGAGCTGCAGCAGGCTGGAGACGGCAGGCTGGAAGACTGCCAGTGCCGACGAA<br>CTCAGGAACGGCACGTCGGGATCAAACACGGCCACGTCCGTCCGCACGCGCGCCATTAGCGTCCCCGGGGGCGCACAG<br>GCCGAGCGCGGGCTGACGCGGCTGAGGGCCGTCGACACGCGCACCTCCTCGCGGCTGCGAACCATCTTGTTGGCCTCC<br>AGTGGCGGAATCATTATGGCCGGGTCGATCTCCCGCACGGTGTGCTGAAACTGCGCCAACAGGGGCGGCGGGACCACA<br>GCCCCCCGCTCGGGGGTCGTCAGGTACTCGTCCACCAGGGCCAACGTAAAGAGGGCCCGTGTGAGGGGAGTGAGGGTC<br>GCGTCGTCTATGCGCTGGAGGTGCGCCGAGAACAGCGTCACCCGATTACTCACCAGGGCCAAGAACCGGAGGCCCTCT<br>TGCACGAACGGGGCGGGGAAGAGCAGGCTGTACGCCGGGGTGGTAAGGTTCGCGCTGGGCTGCCCCAACGGGACCGGC<br>GCCATCTTGAGCGACGTCTCCCCAAGGGCCTCGATGGAGGTCCGCGGGCTCATGGCCAAGCAGCTCTTGGTGACGGTT<br>TGCCAGCGGTCTATCCACTCCACGGCGCACTGGCGGACGCGGACCGGCCCCAGGGCCGCCGCGGTCGCAGGCCGGCGG<br>AATCCAGCGCATGGGACGTGTCGGAGCCGGTGACCGCGAGGATGGTGTCCTTGATGACCTCCATCTCCCGGAAGGCCT<br>GGTCGGGGGCCTCGGGGAGAGCCACCACCAAGCGGTGTACGAGCAACCCGGGGAGGTTCTCGGCCAAGAGCGCCGTCT<br>CCGGAAGCCCGTGGGCCCGGTGGAACGCGCACAGGTGTTCCAGCAGCGGCCGCCAGCATGCCCGCGCGTCTGCCGGGG<br>CGATGGCCGTTCCCGACAACAGAAACGCCGCCATGGCGGCGCGCAGCTTGGCCGTGGCCAGAAACGCCGGGTCGTCCG<br>CCCCGTTTGCCGTCTCGGCCGTGGGGGTTGGCGGTTGGCGAAGGCCGGCTAGGCTCGCCAATAGGCGCTGCATAGGTC<br>CGTCCGAGGGCGGACCGGCGGGTGAGGTCGTGACGACGGGGGCCTCGGACGGGAGACCGCGGTCTGCCATGACGCCCG<br>GCTCGCGTGGGTGGGGGACAGCGTAGACCAACGACGAGACCGGGCGGGAATGACTGTCGTGCGCTGTAGGGAGCGGCG<br>AATTATCGATCCCCTGCGGCCCTCCAGGAACCCCGCAGGCGTTGCGAGTACCCCGCGTCTTCGCGGGGTGTTATACGG |

-continued

SEQUENCES

CCACTTAAGTCCCGGCATCCCGTTCGCGGACCCAGGCCCGGGGGATTGTCCGGATGTGCGGGCAGCCCGGACGGCGTG
GGTTGCGGACTTTCTGCGGGGCGGCCCAAATGGCCCTTTAAACGTGTGTATACGGACGCGCCGGGCCAGTCGGCCAAC
ACAACCCACCGGAGGCGGTAGCCGCGTTTGGCTGTGGGGTGGGTGGTTCCGCCTTGTGTGAGTGTCCTTTCGACCCCC
CCCCCCCCCCTCCCCCGGGTCTTGCTAGGTCGCGATCTGTGGTCGCAATGAAGACCAATCCGCTACCCGCAACCCCTT
CCGTGTGGGGCGGGAGTACCGTGGAACTCCCCCCCACCACACGCGATACCGCGGGGCAGGGCCTGCTTCGGCGCGTCC
TGCGCCCCCCGATCTCTCGCCGCGACGGCCCAGTGCTCCCCAGGGGGTCGGGACCCCGGAGGGCGGCCAGCACGCTGT
GGTTGCTTGGCCTGGACGGCACAGACGCGCCCCCTGGGGCGCTGACCCCCAACGACGATACCGAACAGGCCCTGGACA
AGATCCTGCGGGGCACCATGCGCGGGGGGGCGGCCCTGATCGGCTCCCCGCGCCATCATCTAACCCGCCAAGTGATCC
TGACGGATCTGTGCCAACCCAACGCGGATCGTGCCGGGACGCTGCTTCTGGCGCTGCGGCACCCCGCCGACCTGCCTC
ACCTGGCCCACCAGCGCGCCCCGCCAGGCCGGCAGACCGAGCGGCTGGGCGAGGCCTGGGGCCAGCTGATGGAGGCGA
CCGCCCTGGGGTCGGGGCGAGCCGAGAGCGGGTGCACGCGCGCGGGCCTCGTGTCGTTTAACTTCCTGGTGGCGGCGT
GTGCCGCCTCGTACGACGCGCGCGACGCCGCCGATGCGGTACGGGCCCACGTCACGGCCAACTACCGCGGGACGCGGG
TGGGGGCGCGCCTGGATCGTTTTTCCGAGTGTCTGCGCGCCATGGTTCACACGCACGTCTTCCCCCACGAGGTCATGC
GGTTTTTCGGGGGGCTGGTGTCGTGGGTCACCCAGGACGAGCTAGCGAGCGTCACCGCCGTGTGCGCCGGGCCCCAGG
AGGCGGCGCACACCGGCCACCCGGGCCGGCCCCGCTCGGCCGTGATCCTCCCGGCGTGTGCGTTCGTGGACCTGGACG
CCGAGCTGGGGCTGGGGGGCCCGGGCGCGGCGTTTCTGTACCTGGTATTCACTTACCGCCAGCGCCGGGACCAGGAGC
TGTGTTGTGTGTACGTGATCAAGAGCCAGCTCCCCCCGCGCGGGTTGGAGCCGGCCCTGGAGCGGCTGTTTGGGCGCC
TCCGGATCACCAACACGATTCACGGCACCGAGGACATGACGCCCCCGGCCCCAAACCGAAACCCCGACTTCCCCCTCG
CGGGCCTGGCCGCCAATCCCCAAACCCCGCGTTGCTCGGCTGGCCAGGTCACGAACCCCCAGTTCGCCGACAGGCTGT
ACCGCTGGCAGCCGGACCTTCGGGGGCGCCCCACCGCACGCACCTGTACGTACGCCGCCTTTGCAGAGCTCGGCATGA
TGCCCGAGGATAGTCCCCGCTGCCTGCACCGCACCGAGCGCTTTGGGGCGGTCAGCGTCCCCGTTGTTATTCTGGAAG
GCGTGGTGTGGCGCCCCGGCGAGTGGCGGGCATGCGCGTGAGCGTAGCAAACGCCCCGCCCACACAACGCTCCGCCCC
CAACCCCTTCCCCGCTGTCACTCGTGGTTCGTTGACCCGGACGTCCGCCAAATAAAGCCACTGAAACCCGAAACGCGA
GTGTTGTAACGTCCTTTGGGCGGGAGGAAGCCCGTATAGCATACATTATACGAAGTTATAGCGCGAAGTTCCTATTCT
CTAGAAAGTATAGGAACTTCGAATTGGTCGACGGATCCAACCGCGGAAGACCCAGGCCGCCTCGGGTGTAACGTTAGA
CCGAGTTCGCCGGGCCGGCTCCGCGGGCCAGGGCCCGGGCACGGGCCTCGGGCCCCAGGCACGGCCCGATGACCGCCT
CGGCCTCCGCCACCCGGCGCCGGAACCGAGCCCGGTCGGCCCGCTCGCGGGCCCACGAGCCGCGGCGCGCCAGGCGGG
CGGCCGAGGCCCAGACCACCAGGTGGCGCACCCGGACGTGGGGCGAGAAGCGCACCCGCGTGGGGGTCGCGGGGGTCG
CGGGGGTCGCGGGGGGCTTCGGCGCCCCCTCCCCGCCCGCGCGTCGCAGGCGCAGGCGCGCCAGGTGCTCTGCGGTGA
CGCGCAGGCGGAGGGCGAGGCGCGGCGGAAGGCGGAAGGGGCGTGAGGGGGGGTGGGAGGGGTTAGCCCCGCCCCCCG
GGCCCGCGCCGGGCGGTGGGGGCCGGGGCCGGGGGGCGGCGGCGGTGGGCCGGGCCTCTGGCGCCGGCTCGGGCGGGG
GGCTGTCCGGCCAGTCGTCGTCATCGTCGTCGTCGGACGCGGACTCGGGAACGTGGAGCCACTGGCGCAGCAGCAGCG
AACAAGAAGGCGGGGGCCCACTGGCGGGGGGCGGCGGCGGGGCGGCCGCGGGCGCGCTCCTGACCACGGGTTCCGAGT
TGGGCGTGGAGGTTACCTGGGACTGTGCGGTTGGGACGGCGCCCGTGGGCCCGGGCGGCCGGGGGCGGCGGGGGCCGC
GATGGCGGCGGCGGCGGGCCATGATCAAGCTCATGGCGCCGCGCTCTGCTTCTGGAAGGCTGCGCTCCGCGGCGTGGA
TGCTCCGGGGAAAGTTGCGCTCCGCGGCAGGGATGCTCCTGGGAAGGTTGCGCTCCGCGGCAGGGATGCTCTGGGGAA
GGCTGGTCCTGGCCGAGGATCGGGAACGCGCCGCTCGCTCTGCTTCTCTTGTCTTCGCTTGTCTCTGGATGGAACCAG
ATTTGGTTCTGAGTAGCTGTCAGCGTCTGGTGACCTGCTCGCCGCCCTGCGCCTTTAAGGAGTCTTCACCGGCCCCGC
CCACTCTCCGCTGGGCCAATCAGCGAGCCGGAGGAGGCCTTGGGGCCAGGAATCTTCCAGCAGTTTCGCGTCTGGTGG
AGCTTCCCCGCCTCCCTTGAGTAATCGGAGTTGTGGGTTCCGCCCTTGTCCAGAACTCTCCAGAGGTTTCTGGGGTTC
ACTGGAGAGTACGGATTCCTGAGGGGGAGGGTGTGGGGAAGTGCTGGTGCTACTAGTGACACTGTTGCTATGGCGACG
CATTACTAAGGCCTGTGTGGAATGGACAAGAAAGATCACCTCTAGCTCGGTGTTGTGTACAGTTTGTTGTGATTTGTG
GGGTTTCGCCAACTCGCACAGTTCTGAATATGGGGGTTAAAGGCTAAAACTTAAGGGCTAAAACTTCTCCCCGCCAAG
TTTAGGAGACCCAGGGAGATGCCTGGGGGCGTGTCCGGTGACGTGATCCTCTCCAATCGCGTTACAATGGCAGTGCTG
CCTCTGACCTCATGGACTAATTTAGGAACTAGAGGCTCTGTCCCAGCACAGGCTCAAAGTTGCCGGGAGGGGCGGGGT
GGGGGGTGGGGGGGACCCCGGCTGCTCAGTTTGGATGTTCCTGGAGCTCGGTACCCGCGATCGCCCCTAGAGGATCTA
CTAGTCATATGGATAAGCCTGGGAACCTCGTCCAGGTGTCTGCAACCGAGAGTTCTCAGCCTCCAGCAGAGTCCTGGT
GGGGAGTGGGGAGATAGGGTCAGCTCCAGCTGAGGTAGCATGTCCTGCCACTGCAGGATCAATCTCTATTGTGACCAT
TGTCATATAAAAGCCACACAGTCATATACCCACAGATATATACTTAGCCAACCCATATTTGAGACACAGGGAGACCCC
ACATGCAGATTCCCACAGTCGGAGGCAGGGCCAAATGAATTGCTAACACTTATATCAGACTCCTCAGATCAGTCTCCG
CCTCCCCACCCAAGGCCAAGGCCGATGACCTCATCCTCTGGGAGGGAGGCCGATTCTCATGCTAATTATTGCCTTTTG
TCCACACTACCATCTGGAGGGCCTAAGAAGGGAGGGCTCCTCAGGGGAAGTGGGAATTCTCAGGCTGTTCCCAGGGGA
TGGCTCTCTCTCTGCCCCCAGAGCTGGTAACAGACAAAAGCAAATGAATTCAGCTCCCCTTCTCCAAATCCTTTTCAG
ACCTCAAACGCCAGTGGTTACATTCCTCAGAGCTGCCTGGACCCTTCCCCTCAGAGGACTGACTGGGGCTAAAGCCCT
CATCTCAGGATCACAAACTCTTCAGGGATCGGATCTCGGCCCGGGCTAGCACGCGTAAGAGCTCGGTACCTATCGATA
GAGAAATGTTCTGGCACCTGCACTTGCACTGGGGACAGCCTATTTTGCTAGTTTGTTTTGTTTCGTTTTGTTTTGATG
GAGAGCGTATGTTAGTACTATCGATTCACACAAAAAACCAACACACAGATGTAATGAAAATAAAGATATTTTATTGCG
GCGATCCGGAACCCTTAAT (SEQ ID NO: 1)

SEQ ID NO: 2 Nestin Promoter aaccctgaag agtttgtgat cctgagatga gggctttagc cccagtcagt cctctgaggg 60
gaagggtcca ggcagctctg aggaatgtaa ccactggcgt ttgaggtctg aaaaggattt 120
ggagaagggg agctgaattc atttgctttt gtctgttacc agctctgggg gcagagagag 180
agccatcccc tgggaacagc ctgagaattc ccacttcccc tgaggagccc tcccttctta 240
ggccctccag atggtagtgt ggacaaaagg caataattag catgagaatc ggcctccctc 300
ccagaggatg aggtcatcgg ccttggcctt gggtggggag gcggagactg atctgaggag 360
tctgatataa gtgttagcaa ttcatttggc cctgcctccg actgtgggaa tctgcatgtg 420
gggtctccct gtgtctcaaa tatgggttgg ctaagtatat atctgtgggt atatgactgt 480
gtggctttta tatgacaatg gtcacaatag agattgatcc tgcagtggca ggacatgcta 540

-continued

| SEQUENCES | |
|---|---|
| cctcagctgg agctgaccct atctccccac tccccaccag gactctgctg gaggctgaga | 600 |
| actctcggtt gcagacacct ggacgaggtt caggcttatc atatgactag tagatcctct | 660 |
| aggggcgatc gcgggtaccg agctccagga acatccaaac tgagcagccg gggtcccccc | 720 |
| caccccccac cccgcccctc ccggcaactt tgagcctgtg ctgggacaga gcctctagtt | 780 |
| cctaaattag tccatgaggt cagaggcagc actgccattg taacgcgatt ggagaggatc | 840 |
| acgtcaccgg acacgccccc aggcatctcc ctgggtctcc taaacttggc ggggagaagt | 900 |
| tttagccctt aagttttagc ctttaacccc catattcaga actgtgcgag ttggcgaaac | 960 |
| cccacaaatc acaacaaact gtacacaaca ccgagctaga ggtgatcttt cttgtccatt | 1020 |
| ccacacaggc cttagtaatg cgtcgccata gcaacagtgt cactagtagc accagcactt | 1080 |
| ccccacaccc tccccctcag gaatccgtac tctccagtga accccagaaa cctctggaga | 1140 |
| gttctggaca agggcggaac ccacaactcc gattactcaa gggaggcggg gaagctccac | 1200 |
| cagacgcgaa actgctggaa gattcctggc cccaaggcct cctccggctc gctgattggc | 1260 |
| ccagcggaga gtgggcgggg ccggtgaaga ctccttaaag gcgcagggcg gcgagcaggt | 1320 |
| caccagacgc tgacagctac tcagaaccaa atctggttcc atccagagac aagcgaagac | 1380 |
| aagagaagca gagcgagcgg cgcgttcccg atcctcggcc aggaccagcc ttccccagag | 1440 |
| catccctgcc gcggagcgca accttcccag gagcatccct gccgcggagc gcaactttcc | 1500 |
| ccggagcatc cacgccgcgg agcgcagcct tccagaagca | 1540 (SEQ ID NO: 2) |

| UL39 Sequences ribonucleotide reductase subunit 1 [Human *herpesvirus* 1] | |
|---|---|
| LOCUS | NP_044641 1137 aa linear VRL 24-AUG-2010 |
| DEFINITION | ribonucleotide reductase subunit 1 [Human *herpesvirus* 1]. |
| ACCESSION | NP_044641 |
| VERSION | NP_044641.1 GI:9629420 |
| DBLINK | BioProject: PRJNA15217 |
| DBSOURCE REFSEQ: | accession NC_001806.1 |
| KEYWORDS | RefSeq. |
| SOURCE | Human *herpesvirus* 1 (*Herpes* simplex virus 1) |
| ORGANISM | Human *herpesvirus* 1<br>Viruses; dsDNA viruses, no RNA stage; *Helpesvirales*; *Herpesviridae*; *Alphahelpesvirinae*; *Simplexvirus*. |
| REFERENCE | 1 (residues 1 to 1137) |
| AUTHORS | McGeoch,D.J., Dallymple,M.A., Davison,A.J., Dolan,A., Frame,M.C., McNab,D., Perry,L.J., Scott,J.E. and Taylor,P. |
| TITLE | The complete DNA sequence of the long unique region in the genome of *herpes* simplex virus type 1 |
| JOURNAL | J. Gen. Virol. 69 (PT 7), 1531-1574 (1988) |
| PUBMED | 2839594 |
| REFERENCE | 2 (residues 1 to 1137) |
| CONSRTM | NCBI Genome Project |
| TITLE | Direct Submission |
| JOURNAL | Submitted (01-AUG-2000) National Center for Biotechnology Information, NIH, Bethesda, MD 20894, USA |

-continued

| SEQUENCES |
|---|

| | |
|---|---|
| REFERENCE | 3 (residues 1 to 1137) |
| AUTHORS | McGeoch,D.J. |
| TITLE | Direct Submission |
| JOURNAL | Submitted (17-JAN-1989) McGeoch D.J., MRC Virology Institute, Institute of Virology, Church Street, Glasgow Gil 5JR, GB |
| COMMENT PROVISIONAL REFSEQ: | This record has not yet been subject to final NCBI review. The reference sequence was derived from CAA32314. CURATION: The original gene nomenclature has been retained. Genes presumably inherited from the common ancestor of alpha-, beta- and gammaherpesviruses (core genes) and non-core genes presumably inherited from the ancestor of alphaherpesviruses (alpha genes) are indicated. Initiation codons are assigned with as much confidence as is possible for each protein-coding region. A standard protein nomenclature has been applied so that orthologs have the same name in all herpesviruses. Protein information may have been propagated from other herpesvirus species.<br>Method: conceptual translation. |
| FEATURES | Location/Qualifiers |
| source | 1..1137<br>/organism = "Human *herpesvirus* 1"<br>/strain = "17"<br>/host = "*Homo sapiens*"<br>/db_xref = "taxon: 10298"<br>/acronym = "HHV-1"<br>/acronym = "HSV-1" |
| Protein | 1..1137<br>/product = "ribonucleotide reductase subunit 1"<br>/EC_number = "1.17.4.1"<br>/function = "nucleotide metabolism"<br>/note = translation initiation factor-associated protein (N-terminal region)"<br>/calculated_mol_wt = 123920 |
| Region | 491..576<br>/region_name = "Ribonuc_redigN"<br>/note = "Ribonucleotide reductase, all-alpha domain; pfam00317"<br>/db_xref = "CDD:249765" |
| Region | 537..1113<br>/region_name = "RNR_PFL"<br>/note = "Ribonucleotide reductase and Pyruvate formate lyase; c109939"<br>/db_xref = "CDD:245211" |
| Region | 580..1113<br>/region_name = "Ribonuc_red_lgC"<br>/note = "Ribonucleotide reductase, barrel domain; pfam02867"<br>/db_xref = "CDD:251578" |
| CDS | 1..1137<br>/gene = "UL39"<br>/locus_tag = "HHV1gp057"<br>/coded_by = "NC_001806.1:86444..89857"<br>/db_xref = "GOA:P08543"<br>/db_xref = "InterPro:IPR000788"<br>/db_xref = "InterPro:IPR003010"<br>/db_xref = "UniProtKB/Swiss-Prot:P08543"<br>/db_xref = "GeneID:2703361" |
| ORIGIN | |
| 1 | masrpaassp vearapvggq eaggpsaatq geaagaplah ghhvycqrvn gvmvlsdktp |
| 61 | gsasyrisdn nfvqcgsnct miidgdvvrg rpqdpgaaas papfvavtni gagsdggtav |
| 121 | vafggtprrs agtstgtqta dvptealggp pppprftlgg gccscrdtrr rsavfggegd |
| 181 | pvgpaefvsd drssdsdsdd sedtdsetls hassdvsgga tyddaldsds ssddslqidg |

-continued

SEQUENCES

```
 241       pvcrpwsndt apldvcpgtp gpgadaggps avdphaptpe agaglaadpa varddaegls
 301       dprprlgtgt aypvpleltp enaeavarfl gdavnrepal mleyfcrcar eetkrvpprt
 361       fgspprlted dfgllnyalv emqrlcldvp pvppnaympy ylreyvtrlv ngfkplvsrs
 421       arlyrilgvl vhlrirtrea sfeewlrske vaklfglter lreheaqlvi laqaldhydc
 481       lihstphtlv erglqsalky eefylkrfgg hymesvfqmy triagflacr atrgmrhial
 541       gregswwemf kfffhrlydh qivpstpaml nlgtrnyyts scylvnpqat tnkatlrait
 601       snvsailarn ggiglcvqaf ndsgpgtasv mpalkvldsl vaahnkesar ptgacvylep
 661       whtdvravlr mkgvlageea qrcdnifsal wmpdlffkrl irhldgeknv twtlfdrdts
 721       msladfhgee feklyqhlev mgfgeqipiq elaygivrsa attgspfvmf kdavnrhyiy
 781       dtqgaaiags nlcteivhpa skrssgvcnl gsvnlarcvs rqtfdfgrlr davqacvlmv
 841       nimidstlqp tpqctrgndn lrsmgigmqg lhtaclklgl dlesaefqdl nkhiaevmll
 901       samktsnalc vrgarpfnhf krsmyragrf hwerfpdarp ryegewemlr qsmmkhglrn
 961       sqfvalmpta asaqisdvse gfaplftnlf skvtrdgetl rpntlllkel ertfsgkrll
1021       evmdsldakq wsvaqalpcl epthplrrfk tafdydqkll idlcadrapy vdhsqsmtly
1081       vtekadgtlp astlvrllvh aykrglktgm yyckvrkatn sgvfggddni vcmscal (SEQ ID NO: 3)
```

Nestin 2$^{nd}$ intron sequence SEQ ID NO: 4

```
aaccctgaag agtttgtgat cctgagatga gggctttagc cccagtcagt cctctgaggg       60
gaagggtcca ggcagctctg aggaatgtaa ccactggcgt ttgaggtctg aaaaggattt      120
ggagaagggg agctgaattc atttgctttt gtctgttacc agctctgggg gcagagagag      180
agccatcccc tgggaacagc ctgagaattc ccacttcccc tgaggagccc tcccttctta      240
ggccctccag atggtagtgt ggacaaaagg caataattag catgagaatc ggcctccctc      300
ccagaggatg aggtcatcgg ccttggcctt gggtggggag gcggagactg atctgaggag      360
tctgatataa gtgttagcaa ttcatttggc cctgcctccg actgtgggaa tctgcatgtg      420
gggtctccct gtgtctcaaa tatgggttgg ctaagtatat atctgtgggt atatgactgt      480
gtggctttta tatgacaatg gtcacaatag agattgatcc tgcagtggca ggacatgcta      540
cctcagctgg agctgaccct atctccccac tccccaccag gactctgctg gaggctgaga      600
actctcggtt gcagacacct ggacgaggtt                                      630 (SEQ ID NO: 4)
```

hsp68: heat shock protein 68 SEQ ID NO: 5

```
caggcttatc atatgactag tagatcctct aggggcgatc gcgggtaccg agctccagga       60
acatccaaac tgagcagccg gggtccccc cacccccac cccgcccctc ccggcaactt      120
tgagcctgtg ctgggacaga gcctctagtt cctaaattag tccatgaggt cagaggcagc      180
actgccattg taacgcgatt ggagaggatc acgtcaccgg acacgccccc aggcatctcc      240
ctgggtctcc taaacttggc ggggagaagt tttagccctt aagttttagc ctttaacccc      300
catattcaga actgtgcgag ttggcgaaac cccacaaatc acaacaaact gtacacaaca      360
ccgagctaga ggtgatcttt cttgtccatt ccacacaggc cttagtaatg cgtcgccata      420
gcaacagtgt cactagtagc accagcactt ccccacaccc tccccctcag gaatccgtac      480
tctccagtga accccagaaa cctctggaga gttctggaca agggcggaac ccacaactcc      540
gattactcaa gggaggcggg gaagctccac cagacgcgaa actgctggaa gattcctggc      600
cccaaggcct cctccggctc gctgattggc ccagcggaga gtgggcgggg ccggtgaaga      660
```

-continued

| SEQUENCES | |
|---|---|
| ctccttaaag gcgcagggcg gcgagcaggt caccagacgc tgacagctac tcagaaccaa | 720 |
| atctggttcc atccagagac aagcgaagac aagagaagca gagcgagcgg cgcgttcccg | 780 |
| atcctcggcc aggaccagcc ttccccagag catccctgcc gcggagcgca accttcccag | 840 |
| gagcatccct gccgcggagc gcaactttcc ccggagcatc cacgccgcgg agcgcagcct | 900 |
| tccagaagca | 910 (SEQ ID NO: 5) |

Genome sequence of UL39 is (nts. 86217..90988) of NC_001806.1 (SEQ ID NO: 6)

86217 acaa caggtgggtg ctttggaaac ttgccggtcg ccgtgctcct gtgagcttgc gtccctcccc 86281 ggtttccttt gcgctcccgc cttccggacc tgctctcgcc tatcttcttt ggctctcggt 86341 gcgattcgtc aggcagcggc cttgtcgaat ctcgacccca ccactcgccg gacccgccga 86401 cgtcccctct cgagcccgcc gaaacccgcc gcgtctgttg aaatggccag ccgcccagcc 86461 gcatcctctc ccgtcgaagc gcgggccccg gttgggggac aggaggccgg cggccccagc 86521 gcagccaccc agggggaggc cgccggggcc cctctcgccc acggccacca cgtgtactgc 86581 cagcgagtca atggcgtgat ggtgctttcc gacaagacgc ccgggtccgc gtcctaccgc 86641 atcagcgata gcaactttgt ccaatgtggt tccaactgca ccatgatcat cgacggagac 86701 gtggtgcgcg ggcgccccca ggacccgggg gccgcggcat cccccgctcc cttcgttgcg 86761 gtgacaaaca tcggagccgg cagcgacggc gggaccgccg tcgtggcatt cgggggaacc 86821 ccacgtcgct cggcggggac gtctaccggt acccagacgg ccgacgtccc caccgaggcc 86881 cttgggggcc cccctcctcc tccccgcttc accctgggtg gcggctgttg ttcctgtcgc 86941 gacacacggc gccgctctgc ggtattcggg ggggaggggg atccagtcgg ccccgcggag 87001 ttcgtctcgg acgaccggtc gtccgattcc gactcggatg actcggagga cacggactcg 87061 gagacgctgt cacacgcctc ctcggacgtg tccggcgggg ccacgtacga cgacgccctt 87121 gactccgatt cgtcatcgga tgactccctg cagatagatg gccccgtgtg tcgcccgtgg 87181 agcaatgaca ccgcgcccct ggatgtttgc cccgggaccc ccggcccggg cgccgacgcc 87241 ggtggtccct cagcggtaga cccacacgcg ccgacgccag aggccggcgc tggtcttgcg 87301 gccgatcccg ccgtggcccg ggacgacgcg gaggggcttt cggacccccg gccacgtctg 87361 ggaacgggca cggcctaccc cgtccccctg gaactcacgc ccgagaacgc ggaggccgtg 87421 gcgcgctttc tgggagatgc cgtgaaccgc gaacccgcgc tcatgctgga gtacttttgc 87481 cggtgcgccc gcgaggaaac caagcgtgtc ccccccagga cattcggcag ccccccctcgc 87541 ctcacggagg acgactttgg gcttctcaac tacgcgctcg tggagatgca gcgcctgtgt 87601 ctggacgttc ctccggtccc gccgaacgca tacatgccct attatctcag ggagtatgtg 87661 acgcggctgg tcaacgggtt caagccgctg gtgagccggt ccgctcgcct ttaccgcatc 87721 ctgggggttc tggtgcacct gcggatccgg acccgggagg cctcctttga ggagtggctg 87781 cgatccaagg aagtggccct ggattttggc ctgacggaaa ggcttcgcga gcacgaagcc 87841 cagctggtga tcctggccca ggctctggac cattacgact gtctgatcca cagcacaccg 87901 cacacgctgg tcgagcgggg gctgcaatcg gccctgaagt atgaggagtt ttacctaaag 88961 cgttttggcg ggcactacat ggagtccgtc ttccagatgt acacccgcat cgccggcttt 88021 ttggcctgcc gggccacgcg cggcatgcgc cacatcgccc tggggcgaga ggggtcgtgg 88081 tgggaaatgt tcaagttctt tttccaccgc ctctacgacc accagatcgt accgtcgacc 88141 cccgccatgc tgaacctggg gacccgcaac tactacacct ccagctgcta cctggtaaac -continued

| SEQUENCES | |
|---|---|
| 88201 | ccccaggcca ccacaaacaa ggcgaccctg cgggccatca ccagcaacgt cagtgccatc |
| 88261 | ctcgcccgca acgggggcat cgggctatgc gtgcaggcgt ttaacgactc cggccccggg |
| 88321 | accgccagcg tcatgcccgc cctcaaggtc cttgactcgc tggtggcggc gcacaacaaa |
| 88381 | gagagcgcgc gtccgaccgg cgcgtgcgtg tacctggagc cgtggcacac cgacgtgcgg |
| 88441 | gccgtgctcc ggatgaaggg ggtcctcgcc ggcgaagagg cccagcgctg cgacaatatc |
| 88501 | ttcagcgccc tctggatgcc agacctgttt ttcaagcgcc tgattcgcca cctggacggc |
| 88561 | gagaagaacg tcacatggac cctgttcgac cgggacacca gcatgtcgct cgccgacttt |
| 88621 | cacggggagg agttcgagaa gctctaccag cacctcgagg tcatggggtt cggcgagcag |
| 88681 | atacccatcc aggagctggc ctatggcatt gtgcgcagtg cggccacgac cgggagcccc |
| 88741 | ttcgtcatgt tcaaagacgc ggtgaaccgc cactacatct acgacaccca gggggcggcc |
| 88801 | atcgccggct ccaacctctg caccgagatc gtccatccgg cctccaagcg atccagtggg |
| 88861 | gtctgcaacc tgggaagcgt gaatctggcc cgatgcgtct ccaggcagac gtttgacttt |
| 88921 | gggcggctcc gcgacgccgt gcaggcgtgc gtgctgatgg tgaacatcat gatcgacagc |
| 88981 | acgctacaac ccacgcccca gtgcacccgc ggcaacgaca acctgcggtc catgggaatc |
| 89041 | ggcatgcagg gcctgcacac ggcctgcctg aagctggggc tggatctgga gtctgccgaa |
| 89101 | tttcaggacc tgaacaaaca catcgccgag gtgatgctgc tgtcggcgat gaagaccagc |
| 89161 | aacgcgctgt gcgttcgcgg ggcccgtccc ttcaaccact ttaagcgcag catgtatcgc |
| 89221 | gccggccgct ttcactggga gcgctttccg gacgcccggc cgcggtacga gggcgagtgg |
| 89281 | gagatgctac gccagagcat gatgaaacac ggcctgcgca acagccagtt tgtcgcgctg |
| 89341 | atgcccaccg ccgcctcggc gcagatctcg gacgtcagcg agggctttgc ccccctgttc |
| 89401 | accaacctgt tcagcaaggt gacccgggac ggcgagacgc tgcgccccaa cacgctcctg |
| 89461 | ctaaaggaac tggaacgcac gtttagcggg aagcgcctcc tggaggtgat ggacagtctc |
| 89521 | gacgccaagc agtggtccgt ggcgcaggcg ctcccgtgcc tggagcccac ccaccccctc |
| 89581 | cggcgattca agaccgcgtt tgactacgac cagaagttgc tgatcgacct gtgtgcggac |
| 89641 | cgcgcccccct acgtcgacca tagccaatcc atgaccctgt atgtcacgga gaaggcggac |
| 89701 | gggaccctcc cagcctccac cctggtccgc cttctggtcc acgcatataa gcgcggacta |
| 89761 | aaaacaggga tgtactactg caaggttcgc aaggcgacca acagcggggt ctttggcggc |
| 89821 | gacgacaaca ttgtctgcat gagctgcgcg ctgtgaccga caaacccct ccgcgccagg |
| 89881 | cccgccgcca ctgtcgtcgc cgtcccacgc tctcccctgc tgccatggat tccgcggccc |
| 89941 | cagccctctc ccccgctctg acggccctta cgggccagag cgcgacggcg gacctggcga |
| 90001 | tccagattcc aaagtgcccc gaccccgaga ggtacttcta cacctcccag tgtcccgaca |
| 90061 | ttaaccacct gcgctccctc agcatcctta accgctggct ggaaaccgag cttgttttcg |
| 90121 | tgggggacga ggaggacgtc tccaagcttt ccgagggcga gctcagcttt taccgcttcc |
| 90181 | tcttcgcttt cctgtcggcc gccgacgacc tggttacgga aaacctgggc ggcctctccg |
| 90241 | gcctgtttga gcagaaggac attctccact actacgtgga gcaggaatgc atcgaagtcg |
| 90301 | tacactcgcg cgtgtacaac atcatccagc tggtgctttt ccacaacaac gaccaggcgc |
| 90361 | gccgcgagta cgtggccggt accatcaacc acccggccat ccgcgccaag gtggactggt |
| 90421 | tggaagcgcg ggtgcgggaa tgcgcctccg ttccggaaaa gttcattctc atgatcctca |
| 90481 | tcgagggcat ctttttttgcc gcctcgtttg ccgccatcgc ctaccttcgc accaacaacc |

-continued

SEQUENCES 90541 ttctgcgggt cacctgccag tcaaacgacc tcatcagccg ggacgaggcc gtgcacacga 90601 cggcctcgtg ttacatctac aacaactacc tcggcgggca cgccaagccc ccgcccgacc 90661 gcgtgtacgg gctgttccgc caggcggtcg agatcgagat cggatttatc cgatcccagg 90721 cgccgacgga cagccatatc ctgagcccgg cggcgctggc ggccatcgaa aactacgtgc 90781 gattcagcgc ggatcgcctg ttgggcctta tccacatgaa gccactgttt tccgccccac 90841 cccccgacgc cagctttccg ctgagcctca tgtccaccga caaacacacc aattttttcg 90901 agtgtcgcag cacctcctac gccggggcgg tcgtcaacga tctgtgagtg tcgcggcgcg 90988 cttctacccg tgtttgccca taataaac >del-seq of fHSV Quik-1 (SEQ ID NO: 7)
aataaagccactgaaacccgaaacgcgagtgttgtaacgtcctttgggcgggaggaagccacaaaatgca
aatgggatacatggaaggaacacaccccccgtgactcaggacatcggtgtgtccttttgggtttcactgaa
actggcccgcgccccacccctgcgcgatgtggataaaaagccagcgcgggtggtttagggtaccacaggt
gggtgctttggaaacttgccggtcgccgtgctcctgtgagcttgcgtccctccccggtttcctttgcgct
cccgccttccggacctgctctcgcctactcttctttggctctcggtgcgattcgtcaggcagcggccttg
tcgaatctcgaccccaccactcgccggacccgccgacgtcccctcagcttgcatgcctgcaggtcgagcc
cgccgaaacccgccgcgtctgttgaaatggccagccgccccgccgcatcctctcccgtcgaagcgcgggc
cccggttgggggacaggaggccggcggccccagcgcagccacccaggggggaggccgccggggcccctctc
gcccgcggccaccacgtgtactgccagcgagtcaatggcgtgatggtgctttccgacaagacgcccgggt
ccgcgtcctaccgcatcagcgatagcaactttgtccaatgtggttccaactgcaccatgatcatagacgg
agacgtggtgcgcgggcgcccccaggacccgggggccgcggcatcccccgctcccttcgttgcggtgaca
aacatcggagccggcagcgacggcgggaccgccgtcgtggcattcgggggaaccccacgtcgctcggcgg
ggacgtctaccggtacccagacgaccgacgtccccaccgaggcccttggggggccccctcctcctccccg
cttcaccctgggtggcggctgttgttcctgtcgcgacacacggcgccgctctgcggtattcggggggggag
ggggatcgatccatcgccaccatggtgagcaagggcgaggagctgttcaccggggtggtgcccatcctgg
tcgagctggacggcgacgtaaacggccacaagttcagcgtgtccggcgagggcgagggcgatgccaccta
cggcaagctgaccctgaagttcatctgcaccaccggcaagctgcccgtgccctggcccaccctcgtgacc
accctgacctacggcgtgcagtgcttcagccgctaccccgaccacatgaagcagcacgacttcttcaagt
ccgccatgcccgaaggctacgtccaggagcgcaccatcttcttcaaggacgacggcaactacaagacccg
cgccgaggtgaagttcgagggcgacaccctggtgaaccgcatcgagctgaagggcatcgacttcaaggag
gacggcaacatcctggggcacaagctggagtacaactacaacagccacaacgtctatatcatggccgaca
agcagaagaacggcatcaaggtgaacttcaagatccgccacaacatcgaggacggcagcgtgcagctcgc
cgaccactaccagcagaacacccccatcggcgacggccccgtgctgctgcccgacaaccactacctgagc
acccagtccgccctgagcaaagaccccaacgagaagcgcgatcacatggtcctgctggagttcgtgaccg
ccgccgggatcactctcggcatggacgagctgtacaagtaaagcggccgatcc (SEQ ID NO: 7)

>PCR-del-GFP-FRT-Gm-F&R (SEQ ID NO: 08)
aataaagccactgaaacccgaaacgcgagtgttgtaacgtcctttgggcgggaggaagcccgtatagcat
acattatacgaagttatagcgcgaagttcctattctctagaaagtataggaacttcaagctttaaacttt
tgccattctcaccggattcagtcgtcactcatggtgatttctcacttgataaccttatttttgacgaggg
gaaattaggccgggaagccgatctcggcttgaacgaattgttaggtggcggtacttgggtcgatatcaaa
gtgcatcacttcttcccgtatgcccaactttgtatagagagccactgcgggatcgtcaccgtaatctgct
tgcacgtagatcacataagcaccaagcgcgttggcctcatgcttgaggagattgatgagcgcggtggcaa
tgccctgcctccggtgctcgccggagactgcgagatcatagatatagatctcactacgcggctgctcaaa
cttgggcagaacgtaagccgcgagagcgccaacaaccgcttcttggtcgaaggcagcaagcgcgatgaat
gtcttactacggagcaagttcccgaggtaatcggagtccggctgatgttgggagtaggtggctacgtctc
cgaactcacgaccgaaaagatcaagagcagcccgcatggatttgacttggtcagggccgagcctacatgt
gcgaatgatgcccatacttgagccacctaactttgttttagggcgactgccctgctgcgtaacatcgttg
ctgctgcgtaacatcgttgctgctccataacatcaaacatcgacccacggcgtaacgcgcttgctgcttg
gatgcccgaggcatagactgtacaaaaaaacagtcataacaagccatgaaaaccgccactgcgccgttac
caccgctgcgttcggtcaaggttctggaccagttgcgtgagcgcatacgctacttgcattacagtttacg
aaccgaacaggcttatgtcaactgggttcgtgccttcatccgtttccacggtgtgcgtcacccggcaacc
ttgggcagcagcgaagtcgaggcatttctgtcctggctggcgaacgagcgcaaggtttcggtctccacgc
atcgtcaggcattggcggccttgctgttcttctacggcaaggtgctgtgaccgccgccgggatcactctc
ggcatggacgagctgtacaagtaaagcggccgatcc (SEQ ID NO: 8)

What is claimed is:

1. A tumor-selective oncolytic herpes viral vector, comprising:

(a) a deletion in both copies of the gene encoding γ34.5, and (b) an insertion of at least one copy of the HSV γ34.5 gene under the transcriptional control of a Nestin promoter; and (c) a deletion of the gene that encodes for the HSV viral protein ICP6, wherein the tumor-selective oncolytic herpes viral vector does not express green fluorescent protein;

wherein the vector does not contain UL39 nucleic acid regulatory sequences; and wherein the vector lacks an ICP6-GFP expression cassette.

2. The tumor-selective oncolytic herpes viral vector of claim 1, wherein the at least one copy of the γ34.5 gene under the transcriptional control of a nestin promoter is inserted into a deleted locus comprising a nucleic acid sequence that encodes for the large subunit of ribonucleotide reductase ICP6.

3. The tumor-selective oncolytic herpes viral vector of claim 1, wherein the nestin promoter comprises SEQ ID NO: 2.

4. The tumor-selective oncolytic herpes viral vector of claim 1, wherein the vector comprises the sequence of SEQ ID NO: 1.

5. A method of killing intracranial tumor cells in a subject, the method comprising administering the tumor-selective oncolytic herpes viral vector of claim 1 by intratumoral injection to a subject in need thereof, thereby killing intracranial tumor cells in the subject.

6. The method of claim 5, wherein the tumor cells comprise a glioblastoma cell.

7. The method of claim 5, wherein the tumor cells comprise a cancer stem cell.

8. The method of claim 5, wherein the subject is a mammal.

9. The method of claim 5, wherein the subject is a human.

* * * * *

UNITED STATES PATENT AND TRADEMARK OFFICE

CERTIFICATE OF CORRECTION

PATENT NO. : 10,806,761 B2
APPLICATION NO. : 15/571749
DATED : October 20, 2020
INVENTOR(S) : Nakashima et al.

It is certified that error appears in the above-identified patent and that said Letters Patent is hereby corrected as shown below:

In the Specification

At Column 1, Line 13:
Insert the following heading and paragraph:
--GOVERNMENT SUPPORT
This invention was made with government support under NS061811 awarded by the National Institutes of Health. The government has certain rights in the invention.--

Signed and Sealed this
Twenty-sixth Day of March, 2024

Katherine Kelly Vidal

Katherine Kelly Vidal
*Director of the United States Patent and Trademark Office*